US012692274B2

(12) United States Patent
Barberis et al.

(10) Patent No.: US 12,692,274 B2
(45) Date of Patent: Jul. 28, 2026

(54) TETRAHYDROISOQUINOLINE DERIVATIVES FOR THE TREATMENT OF RED BLOOD DISORDERS AND INFLAMMATORY DISEASES

(71) Applicant: Sanofi, Paris (FR)

(72) Inventors: Claude Barberis, Waltham (MA); George Karageorge, Waltham (MA); John Jurcak, Waltham (MA); Kristen Terranova, Waltham (MA)

(73) Assignee: Sanofi, Paris (FR)

( * ) Notice: Subject to any disclaimer, the term of this patent is extended or adjusted under 35 U.S.C. 154(b) by 579 days.

(21) Appl. No.: 18/026,069

(22) PCT Filed: Sep. 14, 2021

(86) PCT No.: PCT/US2021/050212
§ 371 (c)(1),
(2) Date: Mar. 13, 2023

(87) PCT Pub. No.: WO2022/056448
PCT Pub. Date: Mar. 17, 2022

(65) Prior Publication Data

US 2023/0357270 A1 Nov. 9, 2023

Related U.S. Application Data

(60) Provisional application No. 63/229,338, filed on Aug. 4, 2021, provisional application No. 63/078,118, filed on Sep. 14, 2020.

(51) Int. Cl.

| | |
|---|---|
| ***C07D 471/08*** | (2006.01) |
| ***A61K 31/4748*** | (2006.01) |
| ***A61P 3/00*** | (2006.01) |
| ***A61P 7/06*** | (2006.01) |
| ***A61P 29/00*** | (2006.01) |
| ***A61P 37/00*** | (2006.01) |
| ***C07D 471/18*** | (2006.01) |
| ***C07D 471/22*** | (2006.01) |
| ***C07D 491/22*** | (2006.01) |
| ***C07D 498/18*** | (2006.01) |
| ***C07D 498/22*** | (2006.01) |

(52) U.S. Cl.
CPC ......... *C07D 498/18* (2013.01); *C07D 471/18* (2013.01); *C07D 471/22* (2013.01); *C07D 498/22* (2013.01)

(58) Field of Classification Search
CPC .. C07D 471/08; C07D 471/18; C07D 471/22; C07D 491/22; C07D 498/18; C07D 498/22; A61K 31/4748; A61P 3/00; A61P 7/06; A61P 29/00; A61P 37/00
See application file for complete search history.

(56) References Cited

U.S. PATENT DOCUMENTS 11,518,763 B2 * 12/2022 Matsumoto ............. A61P 11/00

FOREIGN PATENT DOCUMENTS

| | | | |
|---|---|---|---|
| JP | 2017-503786 | A | 2/2017 |
| WO | 2015/092713 | A1 | 6/2015 |
| WO | 2018/125880 | A1 | 7/2018 |
| WO | 2018/140738 | A1 | 8/2018 |
| WO | WO 2018/140876 | A1 | 8/2018 |
| WO | 2018/181345 | A1 | 10/2018 |
| WO | WO 2020/116660 | A1 | 6/2020 |
| WO | 2022/056448 | A1 | 3/2022 |

OTHER PUBLICATIONS

Kanwugu et al., Activation of Nrf2 Pathway as a Protective Mechanism Against Oxidative Stress-Induced Diseases: Potential of Astaxanthin, Archives of Biochemistry and Biophysics, vol. 741, 109601 (Year: 2023).*
International Search Report and Written Opinion for PCT/US2021/050212 dated Jan. 26, 2022, 17 pages.
Foster, A.B. (Dec. 1984). "Deuterium Isotope Effects in Studies of Drug Metabolism," Trends Pharmacol. Sci. 5(12):524-527.
International Preliminary Report on Patentability date of completion Dec. 13, 2022, for Patent Application No. PCT/US2021/050212 filed on Sep. 14, 2021, 8 pages.

* cited by examiner

*Primary Examiner* — Brenda L Coleman
(74) *Attorney, Agent, or Firm* — MORRISON & FOERSTER LLP

(57) ABSTRACT

Provided herein are compounds and compositions thereof for activating nuclear factor erythroid 2-related factor 2 (Nrf2) for treating red blood cell diseases and inflammatory diseases.

20 Claims, No Drawings

TETRAHYDROISOQUINOLINE DERIVATIVES FOR THE TREATMENT OF RED BLOOD DISORDERS AND INFLAMMATORY DISEASES

CROSS-REFERENCE TO RELATED APPLICATIONS

This application is a U.S. National Stage Application under 35 U.S.C. § 371 of International Application No. PCT/US2021/050212, filed Sep. 14, 2021, which claims the benefit under 35 U.S.C. § 119(e) of U.S. Provisional Application No. 63/078,118, filed Sep. 14, 2020, and U.S. Provisional Application No. 63/229,338, filed Aug. 4, 2021, each of which is hereby incorporated by reference in its entirety.

FIELD

The present disclosure relates generally to compounds, compositions, and method for treating red blood cell and inflammatory diseases.

BACKGROUND

Nuclear factor erythroid 2-related factor 2 (Nrf2), also known as nuclear factor erythroid-derived 2-like 2, is a transcription factor that in humans is encoded by the NFE2L2 gene. Nrf2 is a basic leucine zipper (bZIP) protein that regulates the expression of antioxidant proteins that protect against oxidative damage triggered by injury and inflammation. Nrf2 lies at the center of a complex regulatory network and performs a vital role in the regulation of metabolism, inflammation, autophagy, proteostasis, mitochondrial physiology, and immune responses.

Red blood cell (RBC) disorders are conditions that affect red blood cells, the cells of blood that carry oxygen from the lungs to all parts of the body. There are many different types of red blood cell disorders, including: anemia and hemoglobinopathies (e.g. sickle cell disease and thalassemia). Inflammatory diseases include, but are not limited to, asthma, rheumatoid arthritis, ulcerative colitis and Crohn's disease. There is currently a large unmet medical need for safe and effective oral therapies for the treatment of red blood cell and inflammatory diseases. Nrf2 activators stimulate proteins that protect against oxidative damage to mitigate inflammation and treat red blood cell diseases.

Accordingly, in one aspect, provided herein are compounds which activate Nrf2 for use in treating red blood cell diseases.

Accordingly, in another aspect, provided herein are compounds which activate Nrf2 for use in treating inflammatory diseases.

SUMMARY

Embodiment 1. A compound of Formula (I):

(I)

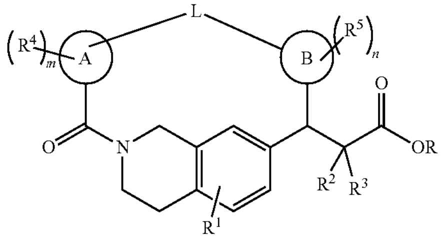

or a pharmaceutically acceptable salt thereof, wherein:

R is H or $C_{1-6}$ alkyl optionally substituted with —OH, $C_{1-6}$ alkyloxy, or $C_{1-6}$ aryl;

$R^1$ is H or $C_{1-6}$ alkyl;

$R^2$ is H or $C_{1-6}$ alkyl;

$R^3$ is H or $C_{1-6}$ alkyl;

Ring B is $C_{5-12}$ arylene or $C_{3-12}$ heteroarylene containing 1 to 4 heteroatoms independently selected from N and O;

n is 0, 1, 2, or 3;

each $R^5$ is independently halo, $C_{1-6}$ alkyl, or $C_{1-6}$ alkyloxy;

Ring A is $C_{5-12}$ arylene or $C_{3-12}$ heteroarylene containing 1-2 heteroatoms independently selected from N and O;

m is 1, 2, 3, or 4;

each $R^4$ is independently H, halo, $C_{1-6}$ alkyl, or $C_{1-6}$ alkoxy, wherein the $C_{1-6}$ alkyl and $C_{1-6}$ alkoxy groups are optionally substituted with 1-3 groups independently selected from halo, $C_{1-6}$ alkyloxy, amido, and N,N-dimethylamido groups; and L is $C_{4-8}$ alkylene, $C_{4-8}$ alkenylene, $C_{4-8}$ heteroalkylene, or $C_{4-8}$ heteroalkenylene, each of which is optionally substituted with 1 or 4 groups independently selected from halo and $C_{1-6}$ alkyl, and wherein the heteroalkylene and heteroalkenylene comprise 1 to 4 oxygen atoms.

Embodiment 1a(i). A compound of Formula (I):

(I)

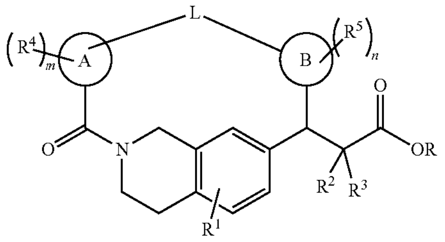

or a pharmaceutically acceptable salt thereof, wherein:

R is H or $C_{1-6}$ alkyl optionally substituted with —OH, $C_{1-6}$ alkyloxy, or $C_{1-6}$ aryl;

$R^1$ is H or $C_{1-6}$ alkyl;

$R^2$ is H or $C_{1-6}$ alkyl;

$R^3$ is H or $C_{1-6}$ alkyl;

Ring B is $C_{5-12}$ arylene or $C_{3-12}$ heteroarylene containing 1 to 4 heteroatoms independently selected from N and O, provided that Ring B is not

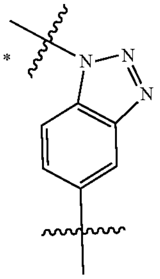 [SMILES: *c1ccc2c(c1)nnn2*]

wherein the * designates a bond to L;

n is 0, 1, 2, or 3;

each $R^5$ is independently halo, $C_{1-6}$ alkyl, or $C_{1-6}$ alkyloxy;

Ring A is $C_{5-12}$ arylene or $C_{3-12}$ heteroarylene containing 1-2 heteroatoms independently selected from N and O;

m is 1, 2, 3, or 4;

each $R^4$ is independently H, halo, $C_{1-6}$ alkyl, or $C_{1-6}$ alkoxy, wherein the $C_{1-6}$ alkyl and $C_{1-6}$ alkoxy groups are optionally substituted with 1-3 groups independently selected from halo, $C_{1-6}$ alkyloxy, amido, and N,N-dimethylamido groups; and L is $C_{4-8}$ alkylene, $C_{4-8}$ alkenylene, $C_{4-8}$ heteroalkylene, or $C_{4-8}$ heteroalkenylene, each of which is optionally substituted with 1 or 4 groups independently selected from halo and $C_{1-6}$ alkyl, and wherein the heteroalkylene and heteroalkenylene comprise 1 to 4 oxygen atoms.

Embodiment 1a(ii). A compound of Formula (I):

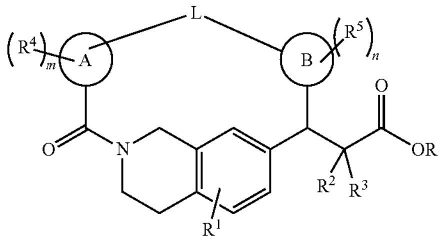

(I)

or a pharmaceutically acceptable salt thereof, wherein:

R is H or $C_{1-6}$ alkyl optionally substituted with one substituent selected from —OH, $C_{1-6}$ alkyloxy, or $C_{6-12}$ aryl;

$R^1$ is H or $C_{1-6}$ alkyl;

$R^2$ is H or $C_{1-6}$ alkyl;

$R^3$ is H or $C_{1-6}$ alkyl;

Ring B is $C_{6-12}$ arylene or $C_{3-12}$ heteroarylene containing 1 to 4 heteroatoms independently selected from N and O, provided that Ring B is not

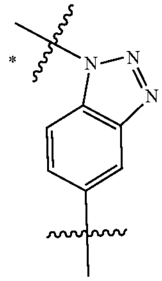 [SMILES: *c1ccc2c(c1)nnn2*]

wherein the * designates a bond to L;

n is 0, 1, 2, or 3;

each $R^5$ is independently halo, $C_{1-6}$ alkyl, or $C_{1-6}$ alkyloxy;

Ring A is $C_{6-12}$ arylene or $C_{3-12}$ heteroarylene containing 1-2 heteroatoms independently selected from N and O;

m is 1, 2, 3, or 4;

each $R^4$ is independently H, halo, $C_{1-6}$ alkyl, or $C_{1-6}$ alkoxy, wherein the $C_{1-6}$ alkyl and $C_{1-6}$ alkoxy groups are optionally substituted with 1-3 groups independently selected from halo, $C_{1-6}$ alkyloxy, amido, and N,N-dimethylamido groups; and L is $C_{4-8}$ alkylene, $C_{4-8}$ alkenylene, $C_{4-8}$ heteroalkylene, or $C_{4-8}$ heteroalkenylene, each of which is optionally substituted with 1 or 4 groups independently selected from halo and $C_{1-6}$ alkyl, and wherein the heteroalkylene and heteroalkenylene comprise 1 to 4 oxygen atoms.

Embodiment 1a(iii). A compound of Formula (I):

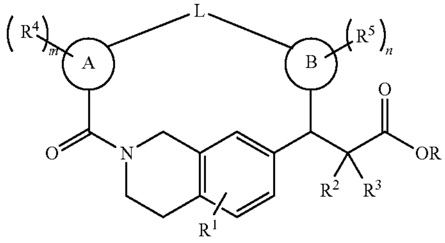

(I)

or a pharmaceutically acceptable salt thereof, wherein:

R is H or $C_{1-6}$ alkyl optionally substituted with one substituent selected from —OH, $C_{1-6}$ alkyloxy, or $C_{6-12}$ aryl;

$R^1$ is H or $C_{1-6}$ alkyl;

$R^2$ is H or $C_{1-6}$ alkyl;

$R^3$ is H or $C_{1-6}$ alkyl;

Ring B is $C_{6-12}$ arylene or $C_{3-12}$ heteroarylene containing 1 to 4 heteroatoms independently selected from N and O;

n is 0, 1, 2, or 3;

each $R^5$ is independently halo, $C_{1-6}$ alkyl, or $C_{1-6}$ alkyloxy;

Ring A is $C_{7-12}$ arylene or 7- to 12-membered heteroarylene containing 1-2 heteroatoms independently selected from N and O;

m is 1, 2, 3, or 4;

each $R^4$ is independently H, halo, $C_{1-6}$ alkyl, or $C_{1-6}$ alkoxy, wherein the $C_{1-6}$ alkyl and $C_{1-6}$ alkoxy groups are optionally substituted with 1-3 groups independently selected from halo, $C_{1-6}$ alkyloxy, amido, and N,N-dimethylamido groups; and L is $C_{4-8}$ alkylene, $C_{4-8}$ alkenylene, $C_{4-8}$ heteroalkylene, or $C_{4-8}$ heteroalkenylene, each of which is optionally substituted with 1 or 4 groups independently selected from halo and $C_{1-6}$ alkyl, and wherein the heteroalkylene and heteroalkenylene comprise 1 to 4 oxygen atoms.

Embodiment 1b. The compound of embodiment 1a(i) or 1a(ii) or 1(a)(iii), or a pharmaceutically acceptable salt thereof, wherein Ring B is not benzotriazole.

Embodiment 1c. The compound of embodiment 1a(i) or 1a(ii) or 1(a)(iii), wherein L is $C_{5-7}$ alkylene, $C_{5-7}$ alkenylene, $C_{5-7}$ heteroalkylene, or $C_{5-7}$ heteroalkenylene, each of which is optionally substituted with 1 or 4 groups independently selected from halo and $C_{1-6}$ alkyl, and wherein the heteroalkylene and heteroalkenylene comprise 1 to 2 oxygen atoms.

Embodiment 1d. The compound of embodiment 1a(i) or 1a(ii) or 1(a)(iii), or a pharmaceutically acceptable salt thereof, wherein L is $C_{4-8}$ alkylene which is optionally substituted with 1 or 4 groups independently selected from halo and $C_{1-6}$ alkyl.

Embodiment 1e. The compound of embodiment 1a(i) or 1a(ii) or 1(a)(iii), or a pharmaceutically acceptable salt thereof, wherein L is $C_6$ alkylene which is optionally substituted with 1 or 4 groups independently selected from halo and $C_{1-6}$ alkyl.

Embodiment 1f. The compound of embodiment 1a(i) or 1a(ii) or 1(a)(iii), or a pharmaceutically acceptable salt thereof, wherein L is $C_{4-8}$ alkenylene, each of which is optionally substituted with 1 or 4 groups independently selected from halo and $C_{1-6}$ alkyl.

Embodiment 1g. The compound of embodiment 1a(i) or 1a(ii) or 1(a)(iii), or a pharmaceutically acceptable salt thereof, wherein L is $C_{4-8}$ heteroalkylene, each of which is optionally substituted with 1 or 4 groups independently selected from halo and $C_{1-6}$ alkyl, and wherein the heteroalkylene comprise 1 to 4 oxygen atoms.

Embodiment 1h. The compound of embodiment 1a(i) or 1a(ii) or 1(a)(iii), or a pharmaceutically acceptable salt thereof, wherein L is $C_{4-8}$ heteroalkenylene, each of which is optionally substituted with 1 or 4 groups independently selected from halo and $C_{1-6}$ alkyl, and wherein the heteroalkenylene comprise 1 to 4 oxygen atoms.

Embodiment 1i. The compound of embodiment 1a(i) or 1a(ii) or 1(a)(iii), or a pharmaceutically acceptable salt thereof, wherein L is $C_{4-8}$ alkenylene or $C_{4-8}$ heteroalkenylene, and the $C_{4-8}$ alkenylene and $C_{4-8}$ heteroalkenylene comprise one point of unsaturation (i.e., one unsaturated bond).

Embodiment 2. The compound of embodiment 1(i) or 1a(ii) or 1(a)(iii), or a pharmaceutically acceptable salt thereof, wherein the compound of Formula (I) is a compound of Formula (IA):

(IA)

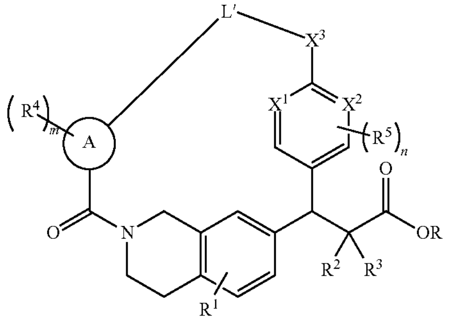

wherein:

L' is $C_{4-6}$ alkylene, $C_{4-6}$ alkenylene, $C_{4-6}$ heteroalkylene, or $C_{4-6}$ heteroalkenylene, each of which is optionally substituted with 1 or 2 groups independently selected from halo and $C_{1-6}$ alkyl, and wherein the heteroalkylene and heteroalkenylene comprise 1 or 2 oxygen atoms;

$X^3$ is $CH_2$ or O;

n is 0, 1, or 2; and $X^1$ and $X^2$ are independently CH or N.

Embodiment 2a(i). A compound of Formula (IC):

(IC)

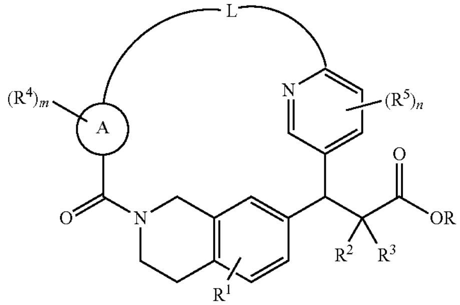

or a pharmaceutically acceptable salt thereof, wherein:

R is H or $C_{1-6}$ alkyl optionally substituted with —OH, $C_{1-6}$ alkyloxy, or $C_{1-6}$ aryl;

$R^1$ is H or $C_{1-6}$ alkyl;

$R^2$ is H or $C_{1-6}$ alkyl;

$R^3$ is H or $C_{1-6}$ alkyl;

n is 0, 1, 2, or 3;

each $R^5$ is independently halo, $C_{1-6}$ alkyl, or $C_{1-6}$ alkyloxy;

Ring A is $C_{5-12}$ arylene or $C_{3-12}$ heteroarylene containing 1-2 heteroatoms independently selected from N and O;

m is 1, 2, 3, or 4;

each $R^4$ is independently H, halo, $C_{1-6}$ alkyl, or $C_{1-6}$ alkoxy, wherein the $C_{1-6}$ alkyl and $C_{1-6}$ alkoxy groups are optionally substituted with 1-3 groups independently selected from halo, $C_{1-6}$ alkyloxy, amido, and N,N-dimethylamido groups; and L is $C_{4-8}$ alkylene, $C_{4-8}$ alkenylene, $C_{4-8}$ heteroalkylene, or $C_{4-8}$ heteroalkenylene, each of which is optionally substituted with 1 or 4 groups independently selected from halo and $C_{1-6}$ alkyl, and wherein the heteroalkylene and heteroalkenylene comprise 1 to 4 oxygen atoms.

Embodiment 2a(ii). A compound of Formula (IC):

(IC)

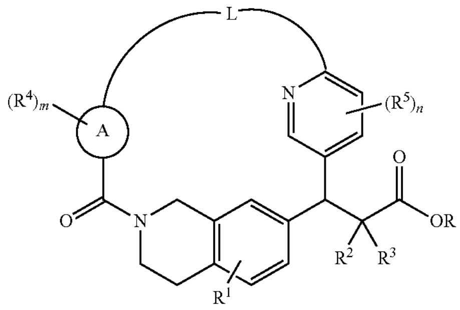

or a pharmaceutically acceptable salt thereof, wherein:

R is H or $C_{1-6}$ alkyl optionally substituted with one substituent selected from —OH, $C_{1-6}$ alkyloxy, and $C_{6-12}$ aryl;

$R^1$ is H or $C_{1-6}$ alkyl;

$R^2$ is H or $C_{1-6}$ alkyl;

$R^3$ is H or $C_{1-6}$ alkyl;

n is 0, 1, 2, or 3;

each $R^5$ is independently halo, $C_{1-6}$ alkyl, or $C_{1-6}$ alkyloxy;

Ring A is $C_{6-12}$ arylene or $C_{3-12}$ heteroarylene containing 1-2 heteroatoms independently selected from N and O;

m is 1, 2, 3, or 4;

each $R^4$ is independently H, halo, $C_{1-6}$ alkyl, or $C_{1-6}$ alkoxy, wherein the $C_{1-6}$ alkyl and $C_{1-6}$ alkoxy groups are optionally substituted with 1-3 groups independently selected from halo, $C_{1-6}$ alkyloxy, amido, and N,N-dimethylamido groups; and L is $C_{4-8}$ alkylene, $C_{4-8}$ alkenylene, $C_{4-8}$ heteroalkylene, or $C_{4-8}$ heteroalkenylene, each of which is optionally substituted with 1 or 4 groups independently selected from halo and $C_{1-6}$ alkyl, and wherein the heteroalkylene and heteroalkenylene comprise 1 to 4 oxygen atoms.

Embodiment 2b. The compound of embodiment 2a(i) or 2a(ii), wherein L is $C_{5-7}$ alkylene, $C_{5-7}$ alkenylene, $C_{5-7}$ heteroalkylene, or $C_{5-7}$ heteroalkenylene, each of which is optionally substituted with 1 or 4 groups independently selected from halo and $C_{1-6}$ alkyl, and wherein the heteroalkylene and heteroalkenylene comprise 1 to 2 oxygen atoms.

Embodiment 2c. The compound of embodiment 2a(i) or 2a(ii), or a pharmaceutically acceptable salt thereof, wherein L is $C_{4-8}$ alkylene which is optionally substituted with 1 or 4 groups independently selected from halo and $C_{1-6}$ alkyl.

Embodiment 2d. The compound of embodiment 2a(i) or 2a(ii), or a pharmaceutically acceptable salt thereof, wherein L is $C_6$ alkylene which is optionally substituted with 1 or 4 groups independently selected from halo and $C_{1-6}$ alkyl.

Embodiment 2e. The compound of embodiment 2a(i) or 2a(ii), or a pharmaceutically acceptable salt thereof, wherein L is $C_{4-8}$ alkenylene, each of which is optionally substituted with 1 or 4 groups independently selected from halo and $C_{1-6}$ alkyl.

Embodiment 2f. The compound of embodiment 2a(i) or 2a(ii), or a pharmaceutically acceptable salt thereof, where L is $C_{4-8}$ heteroalkylene, each of which is optionally substituted with 1 or 4 groups independently selected from halo and $C_{1-6}$ alkyl, and wherein the heteroalkylene comprise 1 to 4 oxygen atoms.

Embodiment 2g. The compound of embodiment 2a(i) or 2a(ii), or a pharmaceutically acceptable salt thereof, where L is $C_{4-8}$ heteroalkenylene, each of which is optionally substituted with 1 or 4 groups independently selected from halo and $C_{1-6}$ alkyl, and wherein the heteroalkenylene comprise 1 to 4 oxygen atoms.

Embodiment 2h. The compound of embodiment 2a(i) or 2a(ii), or a pharmaceutically acceptable salt thereof, where L is $C_{4-8}$ alkenylene or $C_{4-8}$ heteroalkenylene, and the $C_{4-8}$ alkenylene and $C_{4-8}$ heteroalkenylene comprise one point of unsaturation (i.e., one unsaturated bond).

Embodiment 3. The compound of embodiment 2, or a pharmaceutically acceptable salt thereof, wherein $X^3$ is $CH_2$.

Embodiment 4. The compound of embodiment 2, or a pharmaceutically acceptable salt thereof, wherein $X^3$ is O.

Embodiment 5. The compound of any one of embodiments 2 to 4, or a pharmaceutically acceptable salt thereof, wherein $X^1$ is N.

Embodiment 6. The compound of any one of embodiments 2 to 4, or a pharmaceutically acceptable salt thereof, wherein $X^1$ is CH.

Embodiment 7. The compound of any one of embodiments 2 to 4, or a pharmaceutically acceptable salt thereof, wherein $X^2$ is N.

Embodiment 8. The compound of any one of embodiments 2 to 4, or a pharmaceutically acceptable salt thereof, wherein $X^2$ is CH.

Embodiment 9. The compound of any one of embodiments 2 to 4, or a pharmaceutically acceptable salt thereof, wherein $X^1$ and $X^2$ are each N.

Embodiment 10. The compound of any one of embodiments 2 to 4, or a pharmaceutically acceptable salt thereof, wherein $X^1$ and $X^2$ are each CH.

Embodiment 11. The compound of any one of embodiments 2 to 4, or a pharmaceutically acceptable salt thereof, wherein one of $X^1$ and $X^2$ is CH and the other is N.

Embodiment 12. The compound of any one of embodiments 1 to 11, or a pharmaceutically acceptable salt thereof, wherein n is 2.

Embodiment 13. The compound of any one of embodiments 1 to 11, or a pharmaceutically acceptable salt thereof, wherein n is 1.

Embodiment 14. The compound of any one of embodiments 1 to 13, or a pharmaceutically acceptable salt thereof, wherein each $R^5$ is independently $C_{1-4}$ alkyl or $C_{1-4}$ alkyloxy.

Embodiment 15. The compound of any one of embodiments 1 to 14, or a pharmaceutically acceptable salt thereof, wherein each $R^5$ is independently methyl or methoxy.

Embodiment 16. The compound of any one of embodiments 1 to 11, or a pharmaceutically acceptable salt thereof, wherein n is 0.

Embodiment 17. The compound of any one of embodiments 2 to 16, or a pharmaceutically acceptable salt thereof, wherein L' is $C_{4-6}$ alkylene, $C_{4-6}$ alkenylene, $C_{4-6}$ heteroalkylene, or $C_{4-6}$ heteroalkenylene, wherein the heteroalkylene and heteroalkenylene comprise 1 or 2 oxygen atoms.

Embodiment 18. The compound of embodiment 17, or a pharmaceutically acceptable salt thereof, wherein the $C_{4-6}$ alkenylene or $C_{4-6}$ heteroalkenylene comprise one unsaturated bond.

Embodiment 19. The compound of any one of embodiments 2 to 3 and 5 to 18, or a pharmaceutically acceptable salt thereof, wherein $X^3$ is $CH_2$ and L' is $C_{4-6}$ alkenylene or $C_{4-6}$ heteroalkenylene containing one unsaturated bond.

Embodiment 20. The compound of any one of embodiments 2 and 4 to 18, or a pharmaceutically acceptable salt thereof, wherein $X^3$ is O and L' is $C_{4-6}$ alkenylene or $C_{4-6}$ heteroalkenylene containing one unsaturated bond.

Embodiment 21. The compound of any one of embodiments 2 to 3 and 5 to 18, or a pharmaceutically acceptable salt thereof, wherein $X^3$ is $CH_2$ and L' is $C_{4-6}$ alkylene or $C_{4-6}$ heteroalkylene, wherein $C_{4-6}$ heteroalkylene comprises 1 or 2 oxygen atoms.

Embodiment 22. The compound of any one of embodiments 2 and 4 to 18, or a pharmaceutically acceptable salt thereof, wherein $X^3$ is O and L' is $C_{4-6}$ alkylene or $C_{4-6}$ heteroalkylene, wherein the $C_{4-6}$ heteroalkylene comprises 1 oxygen atom.

Embodiment 23. The compound of any one of embodiments 2 and 4 to 18, or a pharmaceutically acceptable salt thereof, wherein $X^3$ is O and L' is $C_{4-6}$ alkylene.

Embodiment 24. The compound of any one of embodiments 2 to 3 and 5 to 18, or a pharmaceutically acceptable salt thereof, wherein $X^3$ is $CH_2$ and L' is $C_{4-6}$ alkylene.

Embodiment 25. The compound of embodiment 1, or a pharmaceutically acceptable salt thereof, wherein the compound of Formula (I) is a compound of Formula (IB):

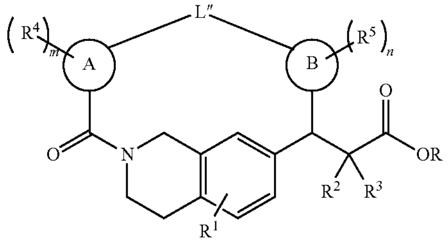

(IB)

wherein:

L" is $C_{4-6}$ alkylene, $C_{4-6}$ alkenylene, $C_{4-6}$ heteroalkylene, or $C_{4-6}$ heteroalkenylene, each of which is optionally substituted with 1 or 2 groups independently selected from halo and $C_{1-6}$ alkyl, and wherein the heteroalkylene and heteroalkenylene comprise 1 to 2 oxygen atoms;

Ring B" is selected from

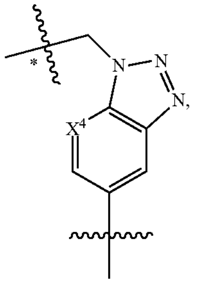 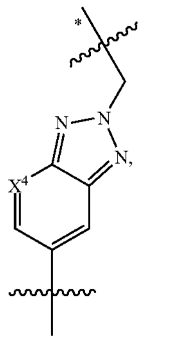

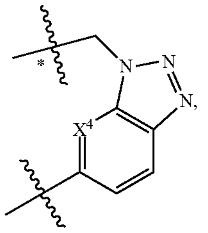 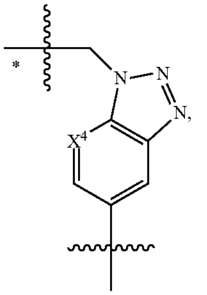

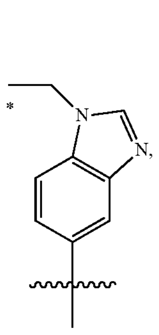 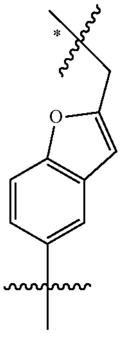 , and 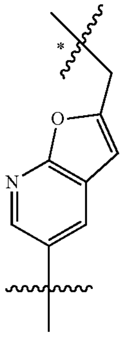 , wherein the * designates a bond to L"; $X^4$ is $CR^5$, CH, or N; Ring B" is substituted with —$(R^5)_n$ where n is 0, 1, 2, or 3; and each $R^5$ is independently halo, $C_{1-4}$ alkyl, or $C_{1-4}$ alkyloxy. It should be noted that Ring B" includes a methylene, which in Formula I is included within L.

Embodiment 25a. The compound of embodiment 25, or a pharmaceutically acceptable salt thereof, wherein Ring B" is selected from

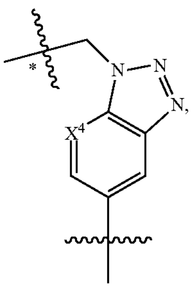 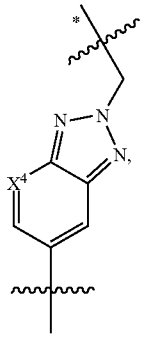

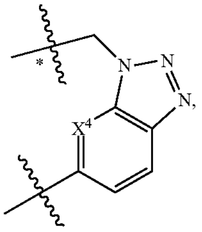 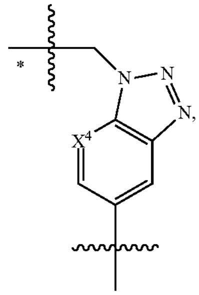

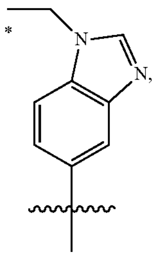 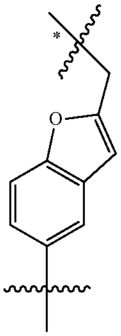 , and 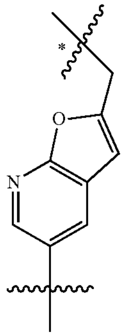 , wherein the * designates a bond to L"; $X^4$ is $CR^5$, CH, or N; Ring B" is substituted with —$(R^5)_n$ where n is 0, 1, 2, or 3; and each $R^5$ is independently halo, $C_{1-4}$ alkyl, or $C_{1-4}$ alkyloxy, provided that the ring is not

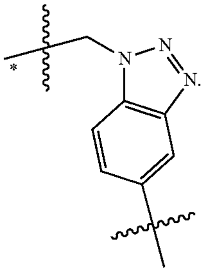 [SMILES: *Cn1nnc2cc(*)ccc21]

Embodiment 26. The compound of embodiment 25, or a pharmaceutically acceptable salt thereof, wherein Ring B" is

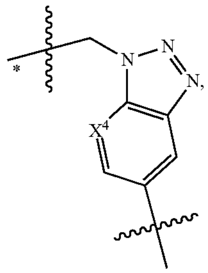

wherein the * designates a bond to L"; $X^4$ is N; Ring B is substituted with —$(R^5)_n$ where n is 0, 1, or 2; and each $R^5$ is independently halo, $C_{1-4}$ alkyl, or $C_{1-4}$ alkyloxy.

Embodiment 27. The compound of embodiment 25, or a pharmaceutically acceptable salt thereof, wherein $X^4$ is CH.

Embodiment 28. The compound of embodiment 25, or a pharmaceutically acceptable salt thereof, wherein $X^4$ is N.

Embodiment 29. The compound of embodiment 25, or a pharmaceutically acceptable salt thereof, wherein $X^4$ is $CR^5$.

Embodiment 30. The compound of any one of embodiments 25 to 29, or a pharmaceutically acceptable salt thereof, wherein n is 2.

Embodiment 31. The compound of any one of embodiments 25 to 29, or a pharmaceutically acceptable salt thereof, wherein n is 1.

Embodiment 32. The compound of any one of embodiments 25 to 31, or a pharmaceutically acceptable salt thereof, wherein each $R^5$ is independently $C_{1-4}$ alkyl or $C_{1-4}$ alkoxy.

Embodiment 33. The compound of any one of embodiments 25 to 32, or a pharmaceutically acceptable salt thereof, wherein each $R^5$ is independently methyl or methoxy.

Embodiment 34. The compound of any one of embodiments 25 to 29, or a pharmaceutically acceptable salt thereof, wherein n is 0.

Embodiment 35. The compound of any one of embodiments 25 to 34, or a pharmaceutically acceptable salt thereof, wherein L" is $C_{4-6}$ alkylene, $C_{4-6}$ alkenylene, $C_{4-6}$ heteroalkylene, or $C_{4-6}$ heteroalkenylene, wherein the heteroalkylene and heteroalkenylene comprise 1 to 2 oxygen atoms.

Embodiment 36. The compound of any one of embodiments 25 to 35, or a pharmaceutically acceptable salt thereof, wherein L" is $C_{4-6}$ alkenylene or $C_{4-6}$ heteroalkenylene, wherein the heteroalkenylene comprises 1 oxygen atom, and wherein the $C_{4-6}$ alkenylene and $C_{4-6}$ heteroalkylene comprise one unsaturated bond.

Embodiment 37. The compound of any one of embodiments 25 to 35, or a pharmaceutically acceptable salt thereof, wherein L" is $C_{4-6}$ alkylene or $C_{4-6}$ heteroalkylene, wherein the $C_{4-6}$ heteroalkylene comprises 1 or 2 oxygen atoms.

Embodiment 38. The compound of any one of embodiments 25 to 35, or a pharmaceutically acceptable salt thereof, wherein L" is $C_{4-6}$ alkylene.

Embodiment 39. The compound of any one of embodiments 25 to 38, or a pharmaceutically acceptable salt thereof, wherein each $R^5$ is independently halo, $C_{1-4}$ alkyl, or $C_{1-4}$ alkyloxy.

Embodiment 40. The compound of any one of embodiments 25 to 39, or a pharmaceutically acceptable salt thereof, wherein each $R^5$ is independently F, Cl, or methyl.

Embodiment 41. The compound of any one of embodiments 25 to 40, or a pharmaceutically acceptable salt thereof, wherein Ring A is phenylene, indolylene, pyrrolopyridinylene, pyridinylene, pyrazinylene, pyrimidinylene, pyridazinylene, naphthalenylene, quinolinylene, benzoimidazolylene, or benzofuranylene.

Embodiment 42. The compound of any one of embodiments 1 to 41, or a pharmaceutically acceptable salt thereof, wherein Ring A is

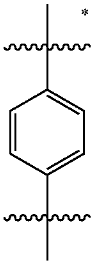,
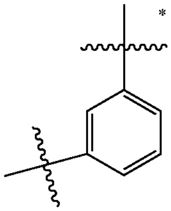,
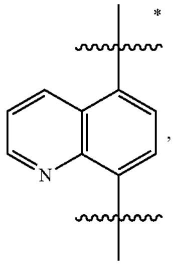,
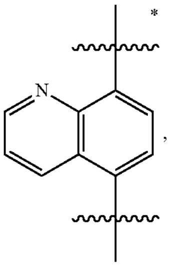,
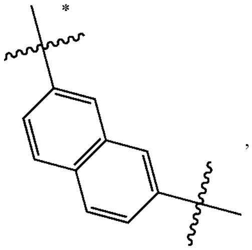,
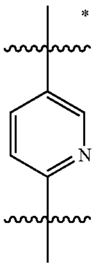,
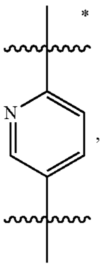,
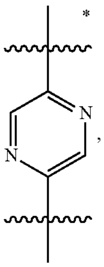,
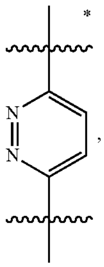,
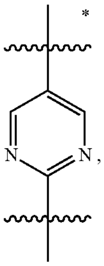,
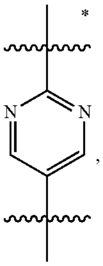,
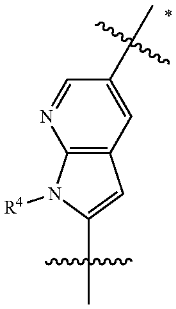,
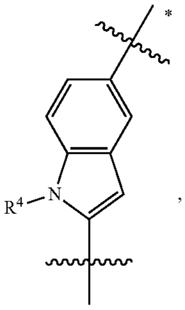,
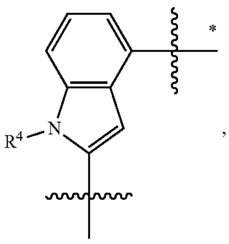, -continued

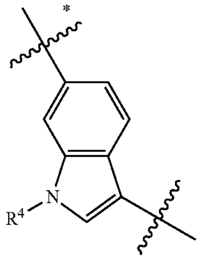, 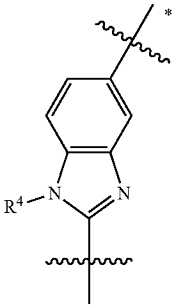,

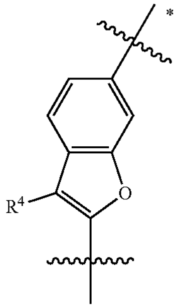, 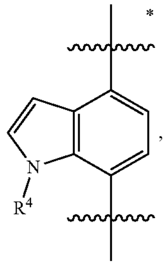,

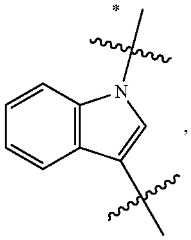, 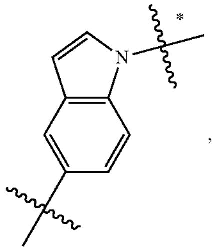, or

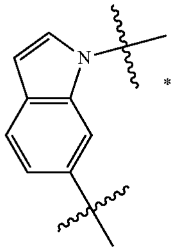, wherein the * designates a bond to L, L', or L", Ring A is substituted with —$(R^4)_m$ where m is 1, 2, 3, or 4; and each $R^4$ is independently H, halo, $C_{1-6}$ alkyl, or $C_{1-6}$ alkoxy, wherein the $C_{1-6}$ alkyl and $C_{1-6}$ alkoxy groups are optionally substituted with 1-3 groups independently selected from halo, $C_{1-6}$ alkyloxy, amido, and N,N-dimethylamido groups.

Embodiment 43. The compound of any one of embodiments 1 to 42, or a pharmaceutically acceptable salt thereof, wherein Ring A is

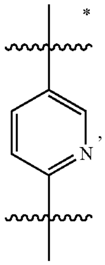, 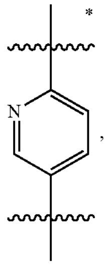, 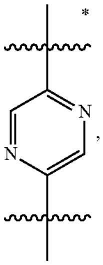, 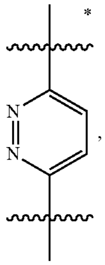,

-continued

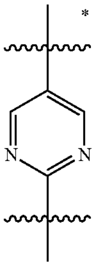, 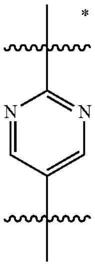, 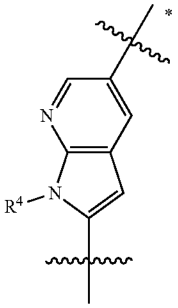,

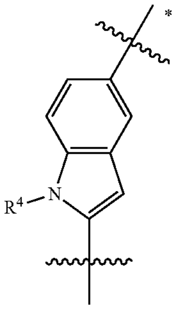, 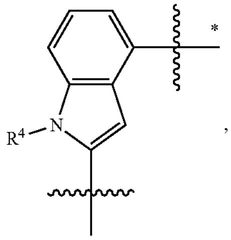,

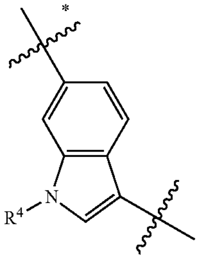, 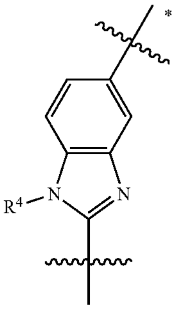,

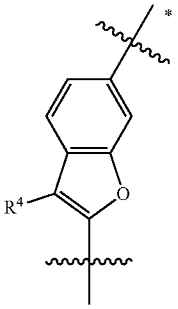, 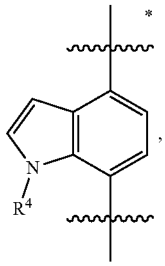,

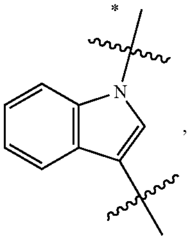, 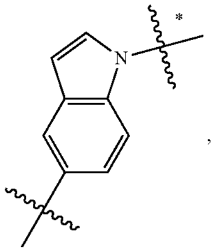, or

-continued

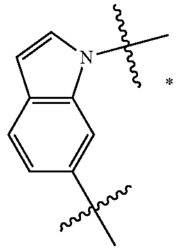

, wherein the * designates a bond to L, L', or L", Ring A is substituted with —$(R^4)_m$ where m is 1 or 2; and each $R^4$ is independently H, halo, $C_{1-4}$ alkyl, or $C_{1-4}$ alkoxy, wherein the $C_{1-4}$ alkyl and $C_{1-4}$ alkoxy groups are optionally substituted with 1-3 groups independently selected from halo, $C_{1-4}$ alkyloxy, amido, and N,N-dimethylamido groups.

Embodiment 44. The compound of any one of embodiments 1 to 42, or a pharmaceutically acceptable salt thereof, wherein Ring A is

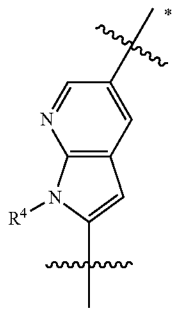

or

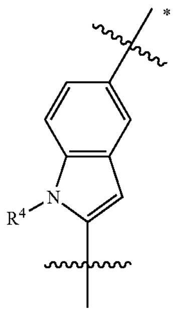

, wherein the * designates a bond to L, L', or L", Ring A is substituted with —$(R^4)_m$ where m is 1 or 2; and each $R^4$ is independently H, halo, $C_{1-4}$ alkyl, or $C_{1-4}$ alkoxy, wherein the $C_{1-4}$ alkyl and $C_{1-4}$ alkoxy groups are optionally substituted with 1-3 groups independently selected from halo, $C_{1-4}$ alkyloxy, amido, and N,N-dimethylamido groups.

Embodiment 45. The compound of any one of embodiments 1 to 42, or a pharmaceutically acceptable salt thereof, wherein Ring A is

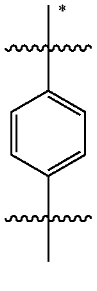

or

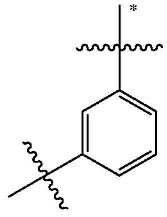

.

and wherein the * designates a bond to L, L', or L", Ring A is substituted with —$(R^4)_m$ where m is 1, 2, 3, or 4; and each $R^4$ is independently H, halo, $C_{1-4}$ alkyl, or $C_{1-4}$ alkoxy, wherein the $C_{1-4}$ alkyl and $C_{1-4}$ alkoxy groups are optionally substituted with 1-3 groups independently selected from halo, $C_{1-4}$ alkyloxy, amido, and N,N-dimethylamido groups.

Embodiment 46. The compound of any one of embodiments 1 to 45, or a pharmaceutically acceptable salt thereof, wherein each $R^4$ is independently selected from H, halo, $C_{1-4}$ alkyl, and $C_{1-4}$ alkoxy, wherein the $C_{1-4}$ alkyl and $C_{1-4}$ alkoxy groups are optionally substituted with 1-3 groups independently selected from halo, $C_{1-4}$ alkyloxy, amido, and N,N-dimethylamido.

Embodiment 47a. The compound of any one of embodiments 1 to 46, or a pharmaceutically acceptable salt thereof, wherein each $R^4$ is independently selected from H, halo, $C_{1-4}$ alkyl, and $C_{1-4}$ alkoxy, wherein each $C_{1-4}$ alkyl and $C_{1-4}$ alkoxy group is optionally substituted with 1-3 groups independently selected from F, Cl, methyl, methoxy, amido, and N,N-dimethylamido.

Embodiment 47b. The compound of any one of embodiments 1 to 46, or a pharmaceutically acceptable salt thereof, wherein each $R^4$ is independently selected from H, halo, $C_{1-4}$ alkyl, and $C_{1-4}$ alkoxy, wherein each $C_{1-4}$ alkyl and $C_{1-4}$ alkoxy group is optionally substituted with 1-3 groups independently selected from F, Cl, methoxy, amido, and N,N-dimethylamido.

Embodiment 48. The compound of any one of embodiments 1 to 47, or a pharmaceutically acceptable salt thereof, wherein each $R^4$ is independently selected from H, methyl, isobutyl, F, Cl, trifluoromethyl, methoxy, difluoromethoxy, trifluoromethoxy, N,N-dimethylamido, 3,3,3-trifluoropropyl, 2,2-difluoroethyl, 3-fluoropropyl, and methoxyethyl.

Embodiment 49. The compound of any one of embodiments 1 to 48, or a pharmaceutically acceptable salt thereof, wherein R is H, methyl, ethyl, 2-hydroxy-ethyl, or benzyl.

Embodiment 50. The compound of any one of embodiments 1 to 49, or a pharmaceutically acceptable salt thereof, wherein R is H.

Embodiment 51. The compound of any one of embodiments 1 to 50, or a pharmaceutically acceptable salt thereof, wherein $R^1$ is H or $C_{1-4}$ alkyl.

Embodiment 52. The compound of any one of embodiments 1 to 51, or a pharmaceutically acceptable salt thereof, wherein $R^1$ is H or methyl.

Embodiment 53. The compound of any one of embodiments 1 to 52, or a pharmaceutically acceptable salt thereof, wherein $R^1$ is H.

Embodiment 54. The compound of any one of embodiments 1 to 53, or a pharmaceutically acceptable salt thereof, wherein $R^2$ is H or $C_{1-4}$ alkyl.

Embodiment 55. The compound of any one of embodiments 1 to 54, or a pharmaceutically acceptable salt thereof, wherein $R^2$ is H or methyl.

Embodiment 56. The compound of any one of embodiments 1 to 55, or a pharmaceutically acceptable salt thereof, wherein $R^3$ is H or $C_{1-4}$ alkyl.

Embodiment 57. The compound of any one of embodiments 1 to 56, or a pharmaceutically acceptable salt thereof, wherein $R^3$ is H or methyl.

Embodiment 58. The compound of any one of embodiments 1 to 54 and 56, or a pharmaceutically acceptable salt thereof, wherein one of $R^2$ and $R^3$ is H and the other is $C_{1-4}$ alkyl.

Embodiment 59. The compound of any one of embodiments 1 to 58, or a pharmaceutically acceptable salt thereof, wherein one of $R^2$ and $R^3$ is H and the other is methyl.

Embodiment 60. The compound of any one of embodiments 1 to 57, or a pharmaceutically acceptable salt thereof, wherein $R^2$ and $R^3$ are each H.

Embodiment 6 The compound of any one of embodiments 1 to 57, or a pharmaceutically acceptable salt thereof, wherein $R^2$ and $R^3$ are each methyl.

Embodiment 62. A compound selected from the compounds in Table 1, or a pharmaceutically acceptable salt thereof.

Embodiment 63. A compound selected from the compounds in Table 2, or a pharmaceutically acceptable salt thereof.

Embodiment 63a. A compound selected from the compounds in Table 2a, or a pharmaceutically acceptable salt thereof.

Embodiment 63b. A compound selected from the compounds in Table 3, or a pharmaceutically acceptable salt thereof.

Embodiment 64. A pharmaceutical composition comprising the compound of any one of embodiments 1 to 63, or a pharmaceutically acceptable salt thereof, and a pharmaceutically acceptable excipient.

Embodiment 65. A method of activating Nrf2 comprising contacting an effective amount of the compound of any one of embodiments 1-63, or a pharmaceutically acceptable salt thereof, or the pharmaceutical composition of embodiment 64, with the Nrf2.

Embodiment 66. A method of treating sickle cell disease in a subject in need thereof, comprising administering to the subject a therapeutically effective amount of the compound of any one of embodiments 1-63, or a pharmaceutically acceptable salt thereof, or the pharmaceutical composition of embodiment 64.

DESCRIPTION

Definitions

The following description sets forth exemplary embodiments of the present technology. It should be recognized, however, that such description is not intended as a limitation on the scope of the present disclosure but is instead provided as a description of exemplary embodiments.

Unless defined otherwise, all technical and scientific terms used herein have the same meaning as is commonly understood by one of skill in the art to which the claimed subject matter belongs. It is to be understood that the foregoing general description and the following detailed description are exemplary and explanatory only and are not restrictive of any subject matter claimed. To the extent any material incorporated herein by reference is inconsistent with the express content of this disclosure, the express content controls. In this application, the use of the singular includes the plural unless specifically stated otherwise. It must be noted that, as used in the specification and the appended claims, the singular forms "a," "an" and "the" include plural referents unless the context clearly dictates otherwise. In this application, the use of "or" means "and/or" unless stated otherwise. Furthermore, use of the term "including" as well as other forms, such as "include," "includes," and "included," is not limiting.

Reference in the specification to "some embodiments," "an embodiment," "one embodiment" or "other embodiments" means that a particular feature, structure, or characteristic described in connection with the embodiments is included in at least some embodiments, but not necessarily all embodiments, of the disclosure.

As used herein, ranges and amounts can be expressed as "about" a particular value or range. About also includes the exact amount. Hence "about 5 μL" means "about 5 μL" and also "5 μL." Generally, the term "about" includes an amount that would be expected to be within experimental error, such as for example, within 15%, 10%, or 5%.

The section headings used herein are for organizational purposes only and are not to be construed as limiting the subject matter described.

A dash ("-") that is not between two letters or symbols is used to indicate a point of attachment for a substituent. For example, $-C(O)NH_2$ is attached through the carbon atom. A dash at the front or end of a chemical group is a matter of convenience; chemical groups may be depicted with or without one or more dashes without losing their ordinary meaning. A wavy line drawn through a line in a structure indicates a point of attachment of a group. Unless chemically or structurally required, no directionality or stereochemistry is indicated or implied by the order in which a chemical group is written or named.

The prefix "$C_{u-v}$" indicates that the following group has from u to v carbon atoms. For example, "$C_{1-6}$ alkyl" indicates that the alkyl group has from 1 to 6 carbon atoms.

Reference to "about" a value or parameter herein includes (and describes) embodiments that are directed to that value or parameter per se. In certain embodiments, the term "about" includes the indicated amount±10%. In certain embodiments, the term "about" includes the indicated amount±5%. In certain embodiments, the term "about" includes the indicated amount±1%. Also, to the term "about X" includes description of "X". Also, the singular forms "a" and "the" include plural references unless the context clearly dictates otherwise. Thus, e.g., reference to "the compound" includes a plurality of such compounds and reference to "the assay" includes reference to one or more assays and equivalents thereof known to those skilled in the art.

"Alkyl" refers to an unbranched or branched saturated hydrocarbon chain. As used herein, alkyl has 1 to 20 carbon atoms (i.e., $C_1$-$C_{20}$ alkyl), 1 to 10 carbon atoms (i.e., $C_1$-$C_{10}$ alkyl), 1 to 6 carbon atoms (i.e., $C_1$-$C_6$ alkyl) or 1 to 3 carbon atoms (i.e., $C_1$-$C_3$ alkyl). Examples of alkyl groups include methyl, ethyl, propyl, isopropyl, n-butyl, sec-butyl, isobutyl, tert-butyl, pentyl, 2-pentyl, isopentyl, neopentyl, hexyl, 2-hexyl, 3-hexyl and 3-methylpentyl. When an alkyl residue having a specific number of carbons is named by chemical name or identified by molecular formula, all positional isomers having that number of carbons may be encompassed; thus, for example, "butyl" includes n-butyl (i.e., $-(CH_2)_3CH_3$), isobutyl (i.e., $-CH_2CH(CH_3)_2$), sec-butyl (i.e., $-CH(CH_3)CH_2CH_3$), and tert-butyl (i.e., $-C(CH_3)_3$); and "propyl" includes n-propyl (i.e., $-(CH_2)_2CH_3$) and isopropyl (i.e., $-CH(CH_3)_2$).

"Alkenyl" refers to an alkyl group containing at least one carbon-carbon double bond and having from 2 to 20 carbon atoms (i.e., $C_{2-20}$ alkenyl), 2 to 8 carbon atoms (i.e., $C_{2-8}$ alkenyl), 2 to 6 carbon atoms (i.e., $C_{2-6}$ alkenyl), or 2 to 4 carbon atoms (i.e., $C_{2-4}$ alkenyl). Examples of alkenyl groups include ethenyl, propenyl, butadienyl (including 1,2-butadienyl and 1,3-butadienyl).

"Alkoxy" or "alkyloxy" refers to the group "alkyl-O—". Examples of alkoxy groups include methoxy, ethoxy, n-propoxy, iso-propoxy, n-butoxy, tert-butoxy, sec-butoxy, n-pentoxy, n-hexoxy, and 1,2-dimethylbutoxy.

"Amido" refers to both a "C-amido" group which refers to the group $-C(O)NR^yR^z$ and an "N-amido" group which refers to the group $-NR^yC(O)R^z$, wherein $R^y$ and $R^z$ are independently selected from the group consisting of hydrogen, alkyl, aryl, haloalkyl, or heteroaryl, each of which may be optionally substituted.

"Amino" refers to the group $-NR^yR^z$ wherein $R^y$ and $R^z$ are independently selected from the group consisting of hydrogen, alkyl, cycloalkyl, haloalkyl, aryl, or heteroaryl, each of which may be optionally substituted.

"Aryl" refers to an aromatic carbocyclic group having a single ring (e.g. monocyclic) or multiple rings (e.g. bicyclic or tricyclic) including fused systems. As used herein, aryl has 6 to 20 ring carbon atoms (i.e., $C_{6-20}$ aryl), 6 to 12 carbon ring atoms (i.e., $C_{6-12}$ aryl), or 6 to 10 carbon ring atoms (i.e., $C_{6-10}$ aryl). In certain embodiments, aryl has 6 to 18 carbon ring atoms (i.e., $C_{6-18}$ aryl). Examples of aryl groups include phenyl, naphthyl, fluorenyl, and anthryl. Aryl, however, does not encompass or overlap in any way with heteroaryl defined below. If one or more aryl groups are fused with a heteroaryl, the resulting ring system is heteroaryl. If one or more aryl groups are fused with a heterocyclyl, the resulting ring system is heterocyclyl.

"Halogen" or "halo" includes fluoro, chloro, bromo, and iodo.

"Heteroalkyl" refers to a monovalent alkyl group, and "heteroalkylene" refers to a divalent alkyl group, with one or more heteroatoms independently selected from nitrogen, oxygen, and sulfur. The terms "heteroalkyl" and "heteroalkylene" include unbranched or branched saturated chain having carbon and heteroatoms. Heteroatomic groups include, but are not limited to, —NR'—, —O—, —S—, —S(O)—, $—S(O)_2—$, and the like, where R' is H, alkyl, alkenyl, alkynyl, aryl, cycloalkyl, heteroalkyl, heteroaryl or heterocyclyl, each of which may be optionally substituted. Examples of heteroalkyl groups include $—OCH_3$, $—CH_2OCH_3$, $—SCH_3$, $—CH_2SCH_3$, $—NR'CH_3$, and $—CH_2NR'CH_3$, where R' is hydrogen, alkyl, aryl, arylalkyl, heteroalkyl, or heteroaryl, each of which may be optionally substituted. Examples of heteroalkylene groups include $—OCH_2—$, $—CH_2OCH_2—$, $—OCH_2CH_2O—$, $—OCH_2OCH_2—$, $—SCH_3$, $—CH_2SCH_2—$, $—NR'CH_2—$, and $—CH_2NR'CH_2—$, where R' is hydrogen, alkyl, aryl, arylalkyl, heteroalkyl, or heteroaryl, each of which may be optionally substituted. In certain embodiments, examples of heteroalkyl groups include $—CH_2SCH_3$, and $—CH_2NR'CH_3$, and examples of heteroalkylene groups include $—CH_2SCH_2—$, and $—CH_2NR'CH_2—$, where R' is hydrogen, alkyl, alkenyl, alkynyl, cycloalkyl, heterocyclyl, aryl, heteroalkyl, or heteroaryl; each of which may be optionally substituted, as defined herein. As used herein, heteroalkyl includes 1 to 10 carbon atoms, 1 to 8 carbon atoms, or 1 to 4 carbon atoms; and 1 to 3 heteroatoms, 1 to 2 heteroatoms, or 1 heteroatom. In certain embodiments, the term "heteroalkyl" requires that the point of attachment to the remainder of the molecule is through a carbon atom.

"Heteroalkenyl" refers to a monovalent heteroalkyl group and "heteroalkenylene" refers to a divalent heteroalkyl group, each containing at least one carbon-carbon double bond and having from 2 to 20 carbon atoms, 2 to 8 carbon atoms, 2 to 6 carbon atoms, or 2 to 4 carbon atoms and with one or more heteroatoms independently selected from nitrogen, oxygen, and sulfur. The terms "heteroalkenyl" and "heteroalkenylene" include unbranched or branched saturated chains having carbon and heteroatoms. Heteroatomic groups include, but are not limited to, —NR'—, —O—, —S—, —S(O)—, $—S(O)_2—$, and the like, where R' is H, alkyl, alkenyl, alkynyl, aryl, cycloalkyl, heteroalkyl, heteroaryl or heterocyclyl, each of which may be optionally substituted. Examples of heteroalkenyl groups include $—OCHCH_2$, $—CH_2OCHCH_2$, $—SCHCH_2$, $—CH_2SCHCH_2$, $—NR'CHCH_2$, and $—CH_2NR'CHCH_2$, and examples of heteroalkenylene groups include —OCHCH—, $—CH_2OCHCH—$, —SCHCH—, $—CH_2SCHCH—$, —NR'CHCH—, and $—CH_2NR'CHCH—$, where R' is hydrogen, alkyl, aryl, arylalkyl, heteroalkyl, or heteroaryl, each of which may be optionally substituted. As used herein, heteroalkenyl and heteroalkenylene includes 1 to 10 carbon atoms, 1 to 8 carbon atoms, or 1 to 4 carbon atoms; and 1 to 3 heteroatoms, 1 to 2 heteroatoms, or 1 heteroatom.

"Heteroaryl" refers to an aromatic group having a single ring, multiple rings, or multiple fused rings, with one or more ring heteroatoms independently selected from nitrogen, oxygen, and sulfur. As used herein, heteroaryl includes 1 to 20 ring carbon atoms (i.e., $C_{1-20}$ heteroaryl), 3 to 12 ring carbon atoms (i.e., $C_{3-12}$ heteroaryl), or 3 to 8 carbon ring atoms (i.e., $C_{3-8}$ heteroaryl); and 1 to 5 heteroatoms, 1 to 4 heteroatoms, 1 to 3 ring heteroatoms, 1 to 2 ring heteroatoms, or 1 ring heteroatom independently selected from nitrogen, oxygen, and sulfur. In certain embodiments, the term "heteroaryl" refers to a 5-14 membered ring system. In certain embodiments, heteroaryl includes 1 to 13 ring carbon atoms (i.e., $C_{1-13}$ heteroaryl). In certain embodiments, heteroaryl includes 1 to 6 heteroatoms. Examples of heteroaryl groups include pyrimidinyl, purinyl, pyridyl, pyridazinyl, benzothiazolyl, and pyrazolyl. Examples of the fused-heteroaryl rings include, but are not limited to, benzo[d]thiazolyl, quinolinyl, isoquinolinyl, benzo[b]thiophenyl, indazolyl, benzo[d]imidazolyl, pyrazolo[1,5-a]pyridinyl, and imidazo[1,5-a]pyridinyl, where the heteroaryl can be bound via either ring of the fused system. In certain embodiments, examples of heteroaryl groups include azepinyl, acridinyl, benzimidazolyl, benzothiazolyl, benzindolyl, benzodioxolyl, benzofuranyl, benzooxazolyl, benzothiazolyl, benzothiadiazolyl, benzo[b][1,4]dioxepinyl, 1,4-benzodioxanyl, benzonaphthofuranyl, benzoxazolyl, benzodioxolyl, benzodioxinyl, benzopyranyl, benzopyranonyl, benzofuranyl, benzofuranonyl, benzothienyl (benzothiophenyl), benzotriazolyl, benzo[4,6]imidazo[1,2-a]pyridinyl, carbazolyl, cinnolinyl, dibenzofuranyl, dibenzothiophenyl, furanyl, furanonyl, isothiazolyl, imidazolyl, indazolyl, indolyl, indazolyl, isoindolyl, indolinyl, isoindolinyl, isoquinolyl, indolizinyl, isoxazolyl, naphthyridinyl, oxadiazolyl, 2-oxoazepinyl, oxazolyl, oxiranyl, 1-oxidopyridinyl, 1-oxidopyrimidinyl, 1-oxidopyrazinyl, 1-oxidopyridazinyl, 1-phenyl-1H-pyrrolyl, phenazinyl, phenothiazinyl, phenoxazinyl, phthalazinyl, pteridinyl, purinyl, pyrrolyl, pyrazolyl, pyridinyl, pyrazinyl, pyrimidinyl, pyridazinyl, quinazolinyl, quinoxalinyl, quinolinyl, quinuclidinyl, isoquinolinyl, tetrahydroquinolinyl, thiazolyl, thiadiazolyl, triazolyl, tetrazolyl, triazinyl and thiophenyl (i.e., thienyl). Any aromatic ring, having a single or multiple fused rings, containing at least one heteroatom, is considered a heteroaryl regardless of the attachment to the remainder of the molecule (i.e., through any one of the fused rings). Heteroaryl does not encompass or overlap with aryl as defined above. The term "heteroarylene" refers to a divalent heteroaryl group, and examples of heteroarylenes include but are not limited to indolylene, pyrrolopyridinylene, pyridinylene, pyrazinylene, pyrimidinylene, pyridazinylene, quinolinylene, benzoimidazolylene, and benzofuranylene.

Certain commonly used alternative chemical names may be used. For example, a divalent group such as a divalent "alkyl" group, a divalent "phenyl" group, a divalent "heteroaryl" group, a divalent "heterocyclyl" group etc., may also be referred to as an "alkylene" group, an "phenylene" group, a "heteroarylene" group, or a "heterocyclylene" group, respectively.

The terms "optional" or "optionally" means that the subsequently described event or circumstance may or may not occur, and that the description includes instances where said event or circumstance occurs and instances in which it does not. Also, the term "optionally substituted" refers to any one or more hydrogen atoms on the designated atom or group may or may not be replaced by a moiety other than hydrogen.

The term "substituted" means that any one or more hydrogen atoms (e.g. 1 to 5 or 1 to 3) on the designated atom or group is replaced with one or more substituents other than hydrogen, provided that the designated atom's normal valence is not exceeded. The one or more substituents include, but are not limited to, alkyl, alkenyl, alkynyl, alkoxy, acyl, amino, amido, amidino, aryl, azido, carbamoyl, carboxyl, carboxyl ester, cyano, guanidino, halo, haloalkyl, haloalkoxy, heteroalkyl, heteroaryl, heterocyclyl, hydroxy, hydrazino, imino, oxo, nitro, alkylsulfinyl, sulfonic acid, alkylsulfonyl, thiocyanate, thiol, thione, or combinations thereof.

Polymers or similar indefinite structures arrived at by defining substituents with further substituents appended ad infinitum (e.g., a substituted aryl having a substituted alkyl which is itself substituted with a substituted aryl group, which is further substituted by a substituted heteroalkyl group, etc.) are not intended for inclusion herein. Unless otherwise noted, the maximum number of serial substitutions in compounds described herein is three. For example, serial substitutions of substituted aryl groups with two other substituted aryl groups are limited to ((substituted aryl) substituted aryl) substituted aryl. Similarly, the above definitions are not intended to include impermissible substitution patterns (e.g., methyl substituted with 5 fluorines or heteroaryl groups having two adjacent oxygen ring atoms). Such impermissible substitution patterns are well known to the skilled artisan. When used to modify a chemical group, the term "substituted" may describe other chemical groups defined herein. Unless specified otherwise, where a group is described as optionally substituted, any substituents of the group are themselves unsubstituted. For example, in certain embodiments, the term "substituted alkyl" refers to an alkyl group having one or more substituents including hydroxy, halo, alkoxy, acyl, oxo, amino, cycloalkyl, heterocyclyl, aryl, and heteroaryl. In other embodiments, the one or more substituents may be further substituted with halo, alkyl, haloalkyl, hydroxy, alkoxy, cycloalkyl, heterocyclyl, aryl, or heteroaryl, each of which is substituted. In other embodiments, the substituents may be further substituted with halo, alkyl, haloalkyl, alkoxy, hydroxy, cycloalkyl, heterocyclyl, aryl, or heteroaryl, each of which is unsubstituted.

In many cases, the compounds of this disclosure are capable of forming acid and/or base salts by virtue of the presence of amino and/or carboxyl groups or groups similar thereto.

The disclosure also includes "deuterated analogs" of compounds described herein in which from 1 to n hydrogens attached to a carbon atom is/are replaced by deuterium, in which n is the number of hydrogens in the molecule. Such compounds exhibit increased resistance to metabolism and are thus useful for increasing the half-life of any compound when administered to a mammal, particularly a human. See, for example, Foster, "Deuterium Isotope Effects in Studies of Drug Metabolism," Trends Pharmacol. Sci. 5(12):524-527 (1984). Such compounds are synthesized by means well known in the art, for example by employing starting materials in which one or more hydrogens have been replaced by deuterium.

Provided are also pharmaceutically acceptable salts, hydrates, solvates, tautomeric forms, and stereoisomers of the compounds described herein. "Pharmaceutically acceptable" or "physiologically acceptable" refer to compounds, salts, compositions, dosage forms and other materials which are useful in preparing a pharmaceutical composition that is suitable for veterinary or human pharmaceutical use.

The term "pharmaceutically acceptable salt" of a given compound refers to salts that retain the biological effectiveness and properties of the given compound, and which are not biologically or otherwise undesirable. "Pharmaceutically acceptable salts" or "physiologically acceptable salts" include, for example, salts with inorganic acids and salts with an organic acid. In addition, if the compounds described herein are obtained as an acid addition salt, the free base can be obtained by basifying a solution of the acid salt. Conversely, if the product is a free base, an addition salt, particularly a pharmaceutically acceptable addition salt, may be produced by dissolving the free base in a suitable organic solvent and treating the solution with an acid, in accordance with conventional procedures for preparing acid addition salts from base compounds. Those skilled in the art will recognize various synthetic methodologies that may be used to prepare nontoxic pharmaceutically acceptable addition salts. Pharmaceutically acceptable acid addition salts may be prepared from inorganic and organic acids. Salts derived from inorganic acids include hydrochloric acid, hydrobromic acid, sulfuric acid, nitric acid, phosphoric acid, and the like. Salts derived from organic acids include acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluene-sulfonic acid, salicylic acid, and the like. Likewise, pharmaceutically acceptable base addition salts can be prepared from inorganic and organic bases. Salts derived from inorganic bases include, by way of example only, sodium, potassium, lithium, ammonium, calcium and magnesium salts. Salts derived from organic bases include, but are not limited to, salts of primary, secondary and tertiary amines, such as alkyl amines (i.e., $NH_2$(alkyl)), dialkyl amines (i.e., HN(alkyl)$_2$), trialkyl amines (i.e., N(alkyl)$_3$), substituted alkyl amines (i.e., $NH_2$(substituted alkyl)), di(substituted alkyl) amines (i.e., HN(substituted alkyl)$_2$), tri (substituted alkyl) amines (i.e., N(substituted alkyl)$_3$), alkenyl amines (i.e., $NH_2$(alkenyl)), dialkenyl amines (i.e., HN(alkenyl)$_2$), trialkenyl amines (i.e., N(alkenyl)$_3$), substituted alkenyl amines (i.e., $NH_2$(substituted alkenyl)), di(substituted alkenyl) amines (i.e., HN(substituted alkenyl)$_2$), tri(substituted alkenyl) amines (i.e., N(substituted alkenyl)$_3$, mono-, di- or tri-cycloalkyl amines (i.e., $NH_2$(cycloalkyl), HN(cycloalkyl)$_2$, N(cycloalkyl)$_3$), mono-, di- or tri-arylamines (i.e., $NH_2$(aryl), HN(aryl)$_2$, N(aryl)$_3$), or mixed amines, etc. Specific examples of suitable amines include, by way of example only, isopropylamine, trimethyl amine, diethyl amine, tri(iso-propyl) amine, tri(n-propyl) amine, ethanolamine, 2-dimethylaminoethanol, piperazine, piperidine, morpholine, N-ethylpiperidine, and the like.

The term "hydrate" refers to the complex formed by the combining of a compound of Formula (I) and water.

A "solvate" refers to an association or complex of one or more solvent molecules and a compound of the disclosure. Examples of solvents that form solvates include, but are not limited to, water, isopropanol, ethanol, methanol, dimethylsulfoxide, ethylacetate, acetic acid, and ethanolamine.

Some of the compounds exist as tautomers. Tautomers are in equilibrium with one another. For example, amide containing compounds may exist in equilibrium with imidic acid tautomers. Regardless of which tautomer is shown, and regardless of the nature of the equilibrium among tautomers, the compounds are understood by one of ordinary skill in the art to comprise both amide and imidic acid tautomers. Thus, the amide containing compounds are understood to include their imidic acid tautomers. Likewise, the imidic acid containing compounds are understood to include their amide tautomers.

The compounds disclosed herein, or their pharmaceutically acceptable salts include an asymmetric center and may thus give rise to enantiomers, diastereomers, and other stereoisomeric forms that may be defined, in terms of absolute stereochemistry, as (R)- or (S)- or, as (D)- or (L)- for amino acids. The disclosure is meant to include all such possible isomers, as well as their racemic and optically pure forms. Optically active (+) and (−), (R)- and (S)-, or (D)- and (L)-isomers may be prepared using chiral synthons or chiral reagents, or resolved using conventional techniques, for example, chromatography and fractional crystallization. Conventional techniques for the preparation/isolation of individual enantiomers include chiral synthesis from a suitable optically pure precursor or resolution of the racemate (or the racemate of a salt or derivative) using, for example, chiral high pressure liquid chromatography (HPLC). When the compounds described herein contain olefinic double bonds or other centres of geometric asymmetry, and unless specified otherwise, it is intended that the compounds include both E and Z geometric isomers. Likewise, all tautomeric forms are also intended to be included.

"Stereoisomers" are isomers that differ only in the way the atoms are arranged in space and include enantiomers and diastereomers. In certain embodiments, a "stereoisomer" refers to a compound made up of the same atoms bonded by the same bonds but having different three-dimensional structures, which are not interchangeable. The present disclosure contemplates various stereoisomers and mixtures thereof and includes "enantiomers," which refers to two stereoisomers whose molecules are nonsuperimposeable mirror images of one another.

"Enantiomers" are a pair of stereoisomers that are non-superimposable mirror images of each other. A 1:1 mixture of a pair of enantiomers is a "racemic" mixture.

"Diastereoisomers" are stereoisomers that have at least two asymmetric atoms, but which are not mirror-images of each other.

The absolute stereochemistry is specified according to the Cahn Ingold Prelog R S system. When the compound is a pure enantiomer the stereochemistry at each chiral carbon may be specified by either R or S. Resolved compounds whose absolute configuration is unknown are designated (+) or (−) depending on the direction (dextro- or laevorotatary) that they rotate the plane of polarized light at the wavelength of the sodium D line.

As used herein, "pharmaceutically acceptable carrier" or "pharmaceutically acceptable excipient" or "excipient" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the active ingredient, its use in the therapeutic compositions is contemplated. Supplementary active ingredients can also be incorporated into the compositions.

"Effective amount" or dose of a compound or a compositions refers to that amount of the compound or the composition that results in an intended result as desired based on the disclosure herein. Effective amounts can be determined by standard pharmaceutical procedures in cell cultures or experimental animals including, without limitation, by determining the LD50 (the dose lethal to 50% of the population) and the ED50 (the dose therapeutically effective in 50% of the population).

"Therapeutically effective amount" or dose of a compound or a compositions refers to that amount of the compound or the composition that results in reduction or inhibition of symptoms or a prolongation of survival in a subject (i.e., a human patient). The results may require multiple doses of the compound or the composition.

"Treating" or "treatment" of a disease in a subject refers to 1) preventing the disease from occurring in a patient that is predisposed or does not yet display symptoms of the disease; 2) inhibiting the disease or arresting its development; or 3) ameliorating or causing regression of the disease. As used herein, "treatment" or "treating" is an approach for obtaining beneficial or desired results including clinical results. For the purposes of this disclosures, beneficial or desired results include, but are not limited to, one or more of the following: decreasing one or more symptoms resulting from the disease or disorder, diminishing the extent of the disease or disorder, stabilizing the disease or disorder (e.g., preventing or delaying the worsening of the disease or disorder), delaying the occurrence or recurrence of the disease or disorder, delay or slowing the progression of the disease or disorder, ameliorating the disease or disorder state, providing a remission (whether partial or total) of the disease or disorder, decreasing the dose of one or more other medications required to treat the disease or disorder, enhancing the effect of another medication used to treat the disease or disorder, delaying the progression of the disease or disorder, increasing the quality of life, and/or prolonging survival of a subject. Also encompassed by "treatment" is a reduction of pathological consequence of the disease or disorder. The methods of the disclosure contemplate any one or more of these aspects of treatment.

As used herein, the terms "individual(s)", "subject(s)" and "patient(s)" mean any mammal. Examples include, but are not limited to, mice, rats, hamsters, guinea pigs, pigs, rabbits, cats, dogs, goats, sheep, cows, and humans. In some embodiments, the mammal is a human.

Although various features of the disclosure may be described in the context of a single embodiment, the features may also be provided separately or in any suitable combination. Conversely, although the disclosure may be described herein in the context of separate embodiments for clarity, the disclosure may also be implemented in a single embodiment.

Compounds

In one aspect, provided herein is a compound of Formula (I)

(I)

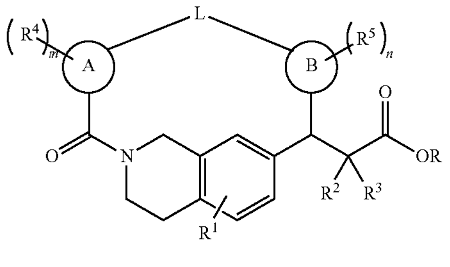

or a pharmaceutically acceptable salt thereof, wherein:

R is H or $C_{1-6}$ alkyl optionally substituted with benzyl;

$R^1$ is H or $C_{1-6}$ alkyl;

$R^2$ is H or $C_{1-6}$ alkyl;

$R^3$ is H or $C_{1-6}$ alkyl;

Ring B is $C_{5-12}$ arylene or $C_{3-12}$ heteroarylene containing 1 to 4 heteroatoms selected from N and O;

n is 0, 1, 2, or 3;

each $R^5$ is independently halo, $C_{1-6}$ alkyl, or $C_{1-6}$ alkyloxy;

Ring A is $C_{5-12}$ arylene or $C_{3-12}$ heteroarylene containing 1-2 heteroatoms selected from N and O;

m is 1, 2, 3, or 4;

each $R^4$ is independently H, halo, $C_{1-6}$ alkyl, or $C_{1-6}$ alkoxy, wherein the $C_{1-6}$ alkyl and $C_{1-6}$ alkoxy groups are optionally substituted with 1-3 groups independently selected from halo, $C_{1-6}$ alkyloxy, amido, and N,N-dimethylamido; and L is $C_{4-8}$ alkylene, $C_{4-8}$ alkenylene, $C_{4-8}$ heteroalkylene, or $C_{4-8}$ heteroalkenylene, each of which is optionally substituted with 1 or 4 groups independently selected from halo and $C_{1-6}$ alkyl, and wherein the heteroalkylene and heteroalkenylene comprise 1 to 4 oxygen atoms.

In some embodiments, provided herein is a compound of Formula (I), or a pharmaceutically acceptable salt thereof, wherein:

R is H or $C_{1-6}$ alkyl optionally substituted with phenyl;

$R^1$ is H or $C_{1-6}$ alkyl;

$R^2$ is H or $C_{1-6}$ alkyl;

$R^3$ is H or $C_{1-6}$ alkyl;

Ring B is $C_{6-12}$ arylene or $C_{3-12}$ heteroarylene containing 1 to 4 heteroatoms selected from N and O;

n is 0, 1, 2, or 3;

each $R^5$ is independently halo, $C_{1-6}$ alkyl, or $C_{1-6}$ alkyloxy;

Ring A is $C_{6-12}$ arylene or $C_{3-12}$ heteroarylene containing 1-2 heteroatoms selected from N and O;

m is 1, 2, 3, or 4;

each $R^4$ is independently H, halo, $C_{1-6}$ alkyl, or $C_{1-6}$ alkoxy, wherein the $C_{1-6}$ alkyl and $C_{1-6}$ alkoxy groups are optionally substituted with 1-3 groups independently selected from halo, $C_{1-6}$ alkyloxy, amido, and N,N-dimethylamido; and L is $C_{4-8}$ alkylene, $C_{4-8}$ alkenylene, $C_{4-8}$ heteroalkylene, or $C_{4-8}$ heteroalkenylene, each of which is optionally substituted with 1 or 4 groups independently selected from halo and $C_{1-6}$ alkyl, and wherein the heteroalkylene and heteroalkenylene comprise 1 to 4 oxygen atoms.

In some embodiments, provided is a compound of Formula (I):

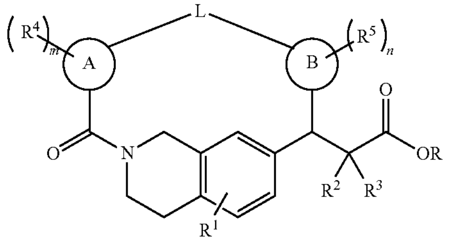

(I)

or a pharmaceutically acceptable salt thereof, wherein:

R is H or $C_{1-6}$ alkyl optionally substituted with —OH, $C_{1-6}$ alkyloxy, or $C_{1-6}$ aryl;

$R^1$ is H or $C_{1-6}$ alkyl;

$R^2$ is H or $C_{1-6}$ alkyl;

$R^3$ is H or $C_{1-6}$ alkyl;

Ring B is $C_{5-12}$ arylene or $C_{3-12}$ heteroarylene containing 1 to 4 heteroatoms independently selected from N and O, provided that Ring B is not

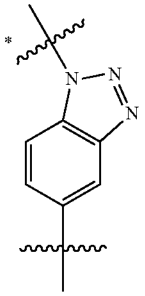 [SMILES: *c1ccc2c(c1)nnn2*]

wherein the * designates a bond to L;

n is 0, 1, 2, or 3;

each $R^5$ is independently halo, $C_{1-6}$ alkyl, or $C_{1-6}$ alkyloxy;

Ring A is $C_{5-12}$ arylene or $C_{3-12}$ heteroarylene containing 1-2 heteroatoms independently selected from N and O;

m is 1, 2, 3 or 4;

each $R^4$ is independently H, halo, $C_{1-6}$ alkyl, or $C_{1-6}$ alkoxy, wherein the $C_{1-6}$ alkyl and $C_{1-6}$ alkoxy groups are optionally substituted with 1-3 groups independently selected from halo, $C_{1-6}$ alkyloxy, amido, and N,N-dimethylamido groups; and L is $C_{4-8}$ alkylene, $C_{4-8}$ alkenylene, $C_{4-8}$ heteroalkylene, or $C_{4-8}$ heteroalkenylene, each of which is optionally substituted with 1 or 4 groups independently selected from halo and $C_{1-6}$ alkyl, and wherein the heteroalkylene and heteroalkenylene comprise 1 to 4 oxygen atoms.

In some embodiments, provided is a compound of Formula (I) or a pharmaceutically acceptable salt thereof, wherein:

R is H or $C_{1-6}$ alkyl optionally substituted with one substituent selected from —OH, $C_{1-6}$ alkyloxy, or $C_{6-12}$ aryl;

$R^1$ is H or $C_{1-6}$ alkyl;

$R^2$ is H or $C_{1-6}$ alkyl;

$R^3$ is H or $C_{1-6}$ alkyl;

Ring B is $C_{6-12}$ arylene or $C_{3-12}$ heteroarylene containing 1 to 4 heteroatoms independently selected from N and O, provided that Ring B is not

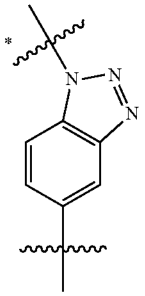 [SMILES: *c1ccc2c(c1)nnn2*]

wherein the * designates a bond to L;

n is 0, 1, 2, or 3;

each $R^5$ is independently halo, $C_{1-6}$ alkyl, or $C_{1-6}$ alkyloxy;

Ring A is $C_{6-12}$ arylene or $C_{3-12}$ heteroarylene containing 1-2 heteroatoms independently selected from N and O;

m is 1, 2, 3 or 4;

each $R^4$ is independently H, halo, $C_{1-6}$ alkyl, or $C_{1-6}$ alkoxy, wherein the $C_{1-6}$ alkyl and $C_{1-6}$ alkoxy groups are optionally substituted with 1-3 groups independently selected from halo, $C_{1-6}$ alkyloxy, amido, and N,N-dimethylamido groups; and L is $C_{4-8}$ alkylene, $C_{4-8}$ alkenylene, $C_{4-8}$ heteroalkylene, or $C_{4-8}$ heteroalkenylene, each of which is optionally substituted with 1 or 4 groups independently selected from halo and $C_{1-6}$ alkyl, and wherein the heteroalkylene and heteroalkenylene comprise 1 to 4 oxygen atoms.

In some embodiments, Ring B is not benzotriazole.

In some embodiments, L is $C_{5-7}$ alkylene, $C_{5-7}$ alkenylene, $C_{5-7}$ heteroalkylene, or $C_{5-7}$ heteroalkenylene, each of which is optionally substituted with 1 or 4 groups independently selected from halo and $C_{1-6}$ alkyl, and wherein the heteroalkylene and heteroalkenylene comprise 1 to 2 oxygen atoms. In some embodiments, L is $C_{5-7}$ alkylene, $C_{5-7}$ alkenylene, $C_{5-7}$ heteroalkylene, or $C_{5-7}$ heteroalkenylene, each of which is optionally substituted with 1 or 4 groups independently selected from halo and $C_{1-6}$ alkyl, and wherein the heteroalkylene and heteroalkenylene comprise 1 oxygen atom. In some embodiments, L is $C_{5-7}$ alkylene, $C_{5-7}$ alkenylene, $C_{5-7}$ heteroalkylene, or $C_{5-7}$ heteroalkenylene, each of which is optionally substituted with 1 or 4 groups independently selected from halo and $C_{1-6}$ alkyl, and wherein the heteroalkylene and heteroalkenylene comprise 2 oxygen atoms.

In some embodiments, L is $C_{4-8}$ alkenylene or $C_{4-8}$ heteroalkenylene, and the $C_{4-8}$ alkenylene and $C_{4-8}$ heteroalkenylene comprise one point of unsaturation (i.e., one unsaturated bond).

In some embodiments, L is selected from

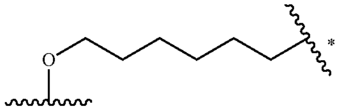
,
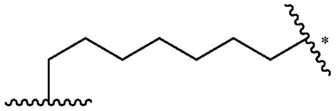
,
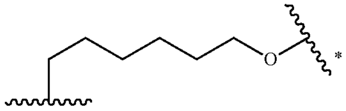
,
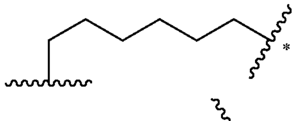
,
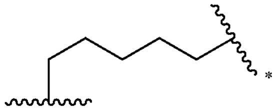
,
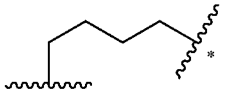
,
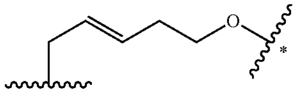
, -continued

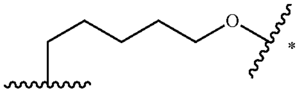
,
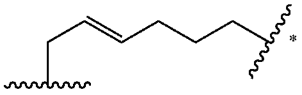
,
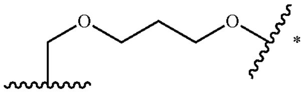
,
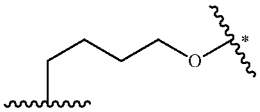
,
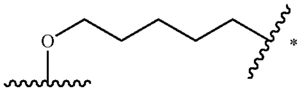
,
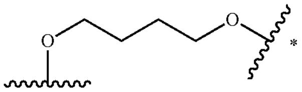
,
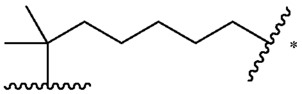
,
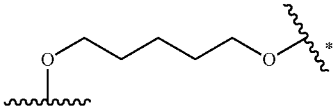
,
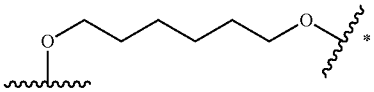
,
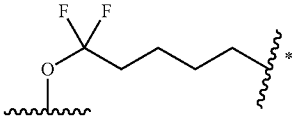
,
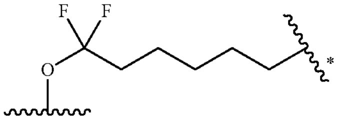
,
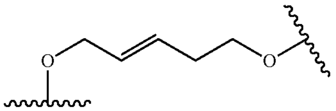
,
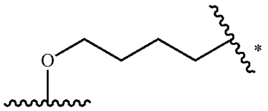
,
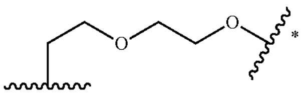
,
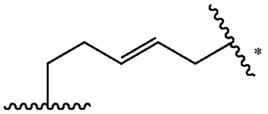
,
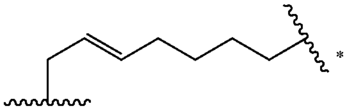
, -continued

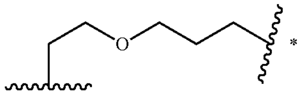
,

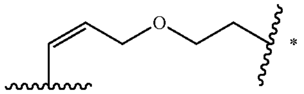
,

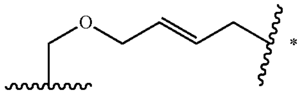
,

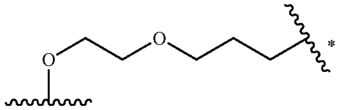
,

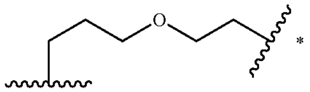
,

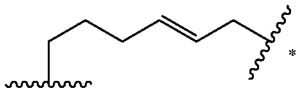
,

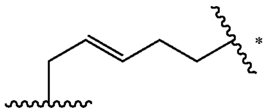
,

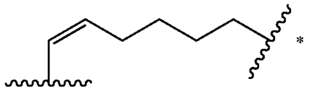
,

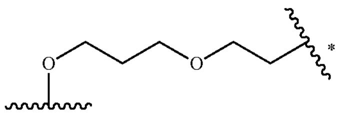
,

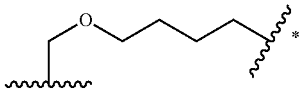
,

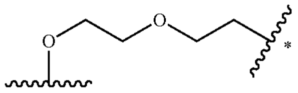
,

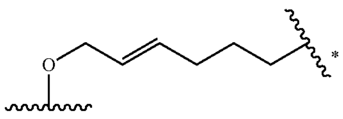
,

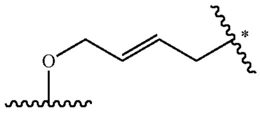
, and

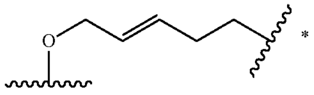
, the * designates a bond to ring B.

In some embodiments, the compound of Formula (I) is a compound of Formula (IA):

(IA)

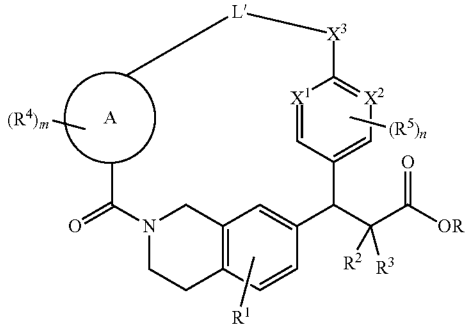

or a pharmaceutically acceptable salt thereof, wherein:

L' is $C_{4-6}$ alkylene, $C_{4-6}$ alkenylene, $C_{4-6}$ heteroalkylene, or $C_{4-6}$ heteroalkenylene, each of which is optionally substituted with 1 or 2 groups independently selected from halo and $C_{1-6}$ alkyl, and wherein the heteroalkylene and heteroalkenylene comprise 1 or 2 oxygen atoms;

$X^3$ is $CH_2$ or 0;

n is 0, 1, or 2;

each $X^1$ and $X^2$ is independently CH or N; and

Ring A, R, $R^1$, $R^2$, $R^3$, $R^4$, $R^5$, m, and n are as described for the compound of Formula (I).

In some embodiments, provided is a compound of Formula (IC)

(IC)

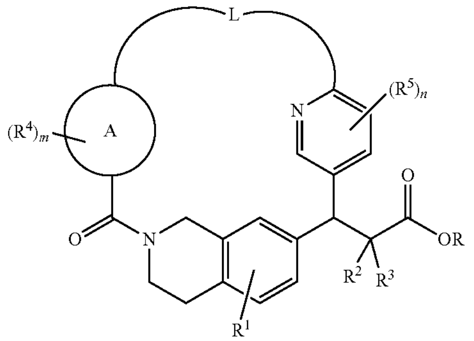

or a pharmaceutically acceptable salt thereof, wherein:

R is H or $C_{1-6}$ alkyl optionally substituted with —OH, $C_{1-6}$ alkyloxy, or $C_{1-6}$ aryl;

$R^1$ is H or $C_{1-6}$ alkyl;

$R^2$ is H or $C_{1-6}$ alkyl;

$R^3$ is H or $C_{1-6}$ alkyl;

n is 0, 1, 2, or 3;

each $R^5$ is independently halo, $C_{1-6}$ alkyl, or $C_{1-6}$ alkyloxy;

Ring A is $C_{5-12}$ arylene or $C_{3-12}$ heteroarylene containing 1-2 heteroatoms independently selected from N and O;

m is 1, 2, 3, or 4;

each $R^4$ is independently H, halo, $C_{1-6}$ alkyl, or $C_{1-6}$ alkoxy, wherein the $C_{1-6}$ alkyl and $C_{1-6}$ alkoxy groups are optionally substituted with 1-3 groups independently selected from halo, $C_{1-6}$ alkyloxy, amido, and N,N-dimethylamido groups; and L is $C_{4-8}$ alkylene, $C_{4-8}$ alkenylene, $C_{4-8}$ heteroalkylene, or $C_{4-8}$ heteroalkenylene, each of which is optionally substituted with 1 or 4 groups independently selected from halo and $C_{1-6}$ alkyl, and wherein the heteroalkylene and heteroalkenylene comprise 1 to 4 oxygen atoms.

In some embodiments, provided is a compound of Formula (IC) or a pharmaceutically acceptable salt thereof, wherein:

R is H or $C_{1-6}$ alkyl optionally substituted with one substituent selected from —OH, $C_{1-6}$ alkyloxy, and $C_{6-12}$ aryl;

$R^1$ is H or $C_{1-6}$ alkyl;

$R^2$ is H or $C_{1-6}$ alkyl;

$R^3$ is H or $C_{1-6}$ alkyl;

n is 0, 1, 2, or 3;

each $R^5$ is independently halo, $C_{1-6}$ alkyl, or $C_{1-6}$ alkyloxy;

Ring A is $C_{6-12}$ arylene or $C_{3-12}$ heteroarylene containing 1-2 heteroatoms independently selected from N and O;

m is 1, 2, 3, or 4;

each $R^4$ is independently H, halo, $C_{1-6}$ alkyl, or $C_{1-6}$ alkoxy, wherein the $C_{1-6}$ alkyl and $C_{1-6}$ alkoxy groups are optionally substituted with 1-3 groups independently selected from halo, $C_{1-6}$ alkyloxy, amido, and N,N-dimethylamido groups; and L is $C_{4-8}$ alkylene, $C_{4-8}$ alkenylene, $C_{4-8}$ heteroalkylene, or $C_{4-8}$ heteroalkenylene, each of which is optionally substituted with 1 or 4 groups independently selected from halo and $C_{1-6}$ alkyl, and wherein the heteroalkylene and heteroalkenylene comprise 1 to 4 oxygen atoms.

In some embodiments, $X^3$ is $CH_2$. In some embodiments, $X^3$ is O.

In some embodiments, $X^1$ is N. In some embodiments, $X^1$ is CH. In some embodiments, $X^2$ is N. In some embodiments, $X^2$ is CH. In some embodiments, $X^1$ and $X^2$ are each N. In some embodiments, $X^1$ and $X^2$ are each CH. In some embodiments, one of $X^1$ and $X^2$ is CH and the other is N.

In some embodiments, n is 2. In some embodiments, n is 1. In some embodiments, n is 0.

In some embodiments, each $R^5$ is independently $C_{1-4}$ alkyl or $C_{1-4}$ alkoxy. In some embodiments, each $R^5$ is independently methyl or methoxy.

In some embodiments, L' is $C_{4-6}$ alkylene, $C_{4-6}$ alkenylene, $C_{4-6}$ heteroalkylene, or $C_{4-6}$ heteroalkenylene, wherein heteroalkylene and heteroalkenylene comprise 1 or 2 oxygen atoms. In some embodiments, the $C_{4-6}$ alkenylene and $C_{4-6}$ heteroalkenylene comprise one point of unsaturation (i.e., one unsaturated bond).

In some embodiments, $X^3$ is $CH_2$ and L' is $C_{4-6}$ alkenylene or $C_{4-6}$ heteroalkenylene containing one point of unsaturation (i.e., one unsaturated bond).

In some embodiments, $X^3$ is O and L' is $C_{4-6}$ alkenylene or $C_{4-6}$ heteroalkenylene containing one point of unsaturation (i.e., one unsaturated bond). In some embodiments, $X^3$ is $CH_2$ and L' is $C_{4-6}$ alkylene or $C_{4-6}$ heteroalkylene, wherein the $C_{4-6}$ heteroalkylene comprises 1 or 2 oxygen atoms. In some embodiments, $X^3$ is O and L' is $C_{4-6}$ alkylene or $C_{4-6}$ heteroalkylene, wherein the $C_{4-6}$ heteroalkylene comprises 1 oxygen atom. In some embodiments, $X^3$ is O and L' is $C_{4-6}$ alkylene. In some embodiments, $X^3$ is $CH_2$ and L' is $C_{4-6}$ alkylene.

In some embodiments, the compound of Formula (I) is a compound of Formula (IB):

(IB)

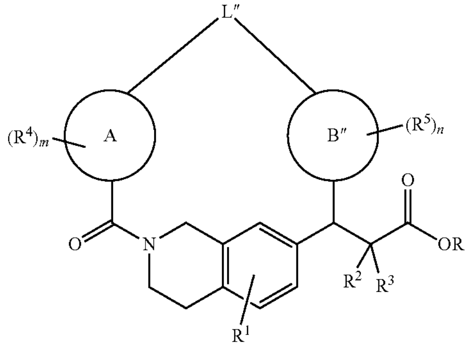

or a pharmaceutically acceptable salt thereof, wherein:

L" is $C_{4-6}$ alkylene, $C_{4-6}$ alkenylene, $C_{4-6}$ heteroalkylene, or $C_{4-6}$ heteroalkenylene, each of which is optionally substituted with 1 or 2 groups independently selected from halo and $C_{1-6}$ alkyl, and wherein the heteroalkylene and heteroalkenylene comprise 1 to 2 oxygen atoms;

Ring B" is selected from

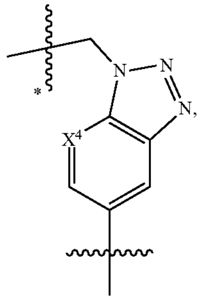

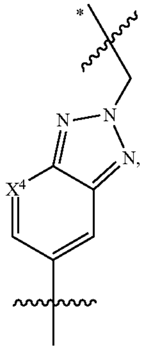

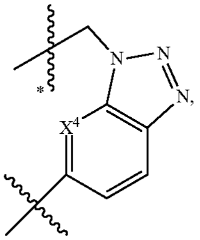

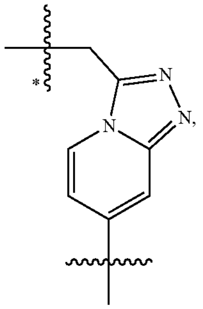

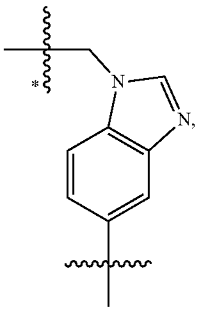

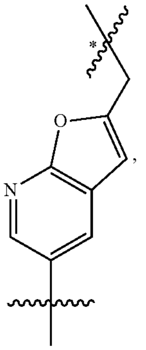

and

-continued

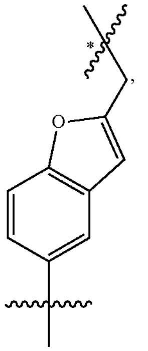

wherein the * designates a bond to L"; $X^4$ is $CR^5$, CH, or N; and

Ring A, R, $R^1$, $R^2$, $R^3$, $R^4$, $R^5$, m, and n are as described for the compound of Formula (I).

In some embodiments, Ring B" is selected from

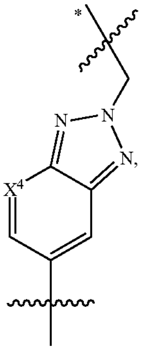
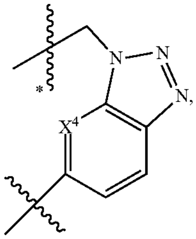

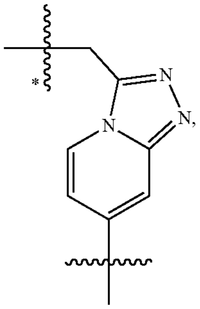
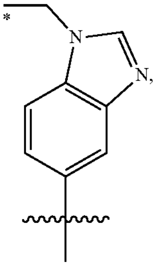

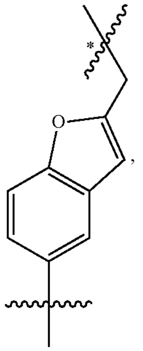
, and
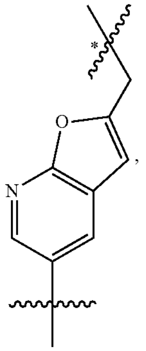

wherein the * designates a bond to L or L"; $X^4$ is $CR^5$, CH, or N—; Ring B or Ring B" is substituted with —$(R^5)_n$ where n is 0, 1, 2, or 3; and each $R^5$ is independently halo, $C_{1-4}$ alkyl, or $C_{1-4}$ alkyloxy.

In some embodiments, the ring is not

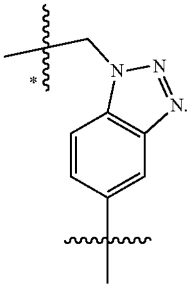 [SMILES: *Cn1nnc2cc(*)ccc21]

In some embodiments, Ring B" is

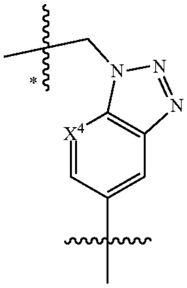

wherein the * designates a bond to L"; $X^4$ is $CR^5$, CH, or N; Ring B" is substituted with —$(R^5)_n$ where n is 0, 1, or 2; and each $R^5$ is independently halo, $C_{1-4}$ alkyl, or $C_{1-4}$ alkyloxy.

In some embodiments, Ring B" is

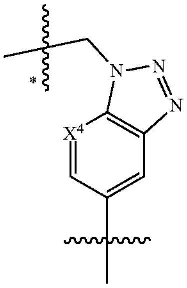

wherein the * designates a bond to L"; $X^4$ is N; Ring B" is substituted with —$(R^5)_n$ where n is 0, 1, or 2; and each $R^5$ is independently halo, $C_{1-4}$ alkyl, or $C_{1-4}$ alkyloxy.

In some embodiments, $X^4$ is CH. In some embodiments, $X^4$ is N. In some embodiments, $X^4$ is $CR^5$.

In some embodiments, n is 2. In some embodiments, n is 1. In some embodiments, n is 0.

In some embodiments, each $R^5$ is $C_{1-4}$ alkyl or $C_{1-4}$ alkoxy. In some embodiments, each $R^5$ is methyl or methoxy.

In some embodiments, L" is $C_{4-6}$ alkylene, $C_{4-6}$ alkenylene, $C_{4-6}$ heteroalkylene, or $C_{4-6}$ heteroalkenylene, wherein the heteroalkylene and heteroalkenylene comprise 1 to 2 oxygen atoms.

In some embodiments, L" is $C_{4-6}$ alkenylene or $C_{4-6}$ heteroalkenylene, wherein the heteroalkenylene comprises 1 oxygen atom, and wherein the $C_{4-6}$ alkenylene and $C_{4-6}$ heteroalkylene comprise one point of unsaturation (i.e., one unsaturated bond). In some embodiments, L" is $C_{4-6}$ alkylene or $C_{4-6}$ heteroalkylene, wherein each $C_{4-6}$ heteroalkylene comprises 1 or 2 oxygen atoms. In some embodiments, L" is $C_{4-6}$ alkylene.

In some embodiments, each $R^5$ is independently halo, $C_{1-4}$ alkyl, or $C_{1-4}$ alkoxy. In some embodiments, each $R^5$ is independently F, Cl, or methyl.

In some embodiments, Ring A is phenylene, indolylene, pyrrolopyridinylene, pyridinylene, pyrazinylene, pyrimidinylene, pyridazinylene, naphthalenylene, quinolinylene, benzoimidazolylene, or benzofuranylene.

In some embodiments of the compound of Formula (I), Formula (IA), and/or Formula (IB), Ring A is

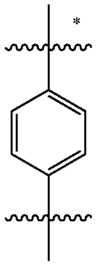
,
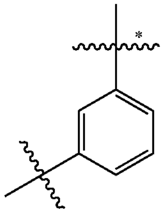
,
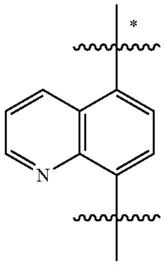
,
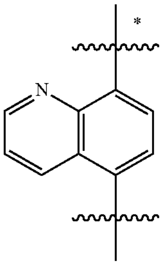
,
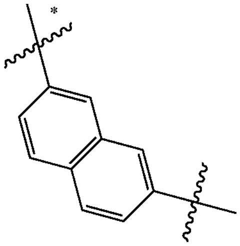
,
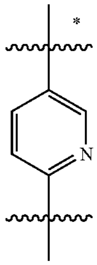
,
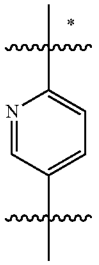
,
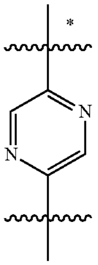
,
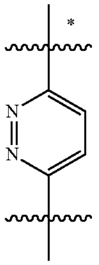
,
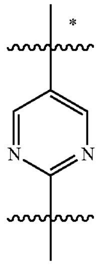
,
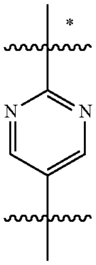
, -continued

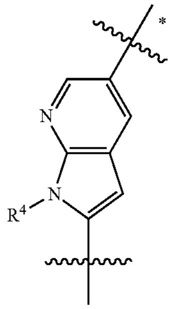
,
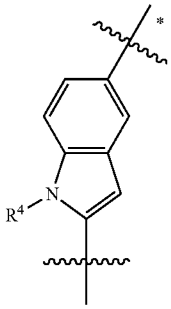
,
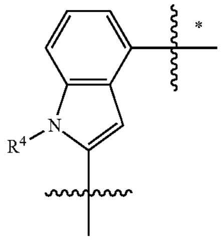
,
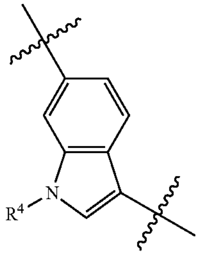
,
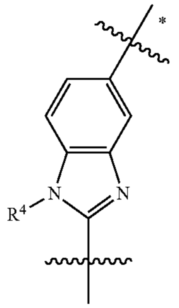
,
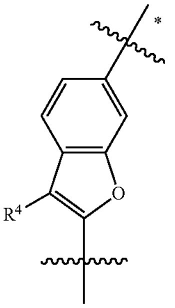
,
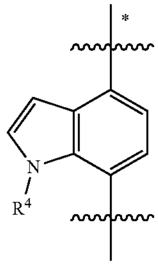
,
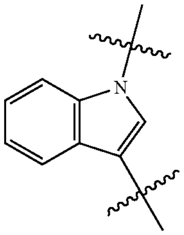
,
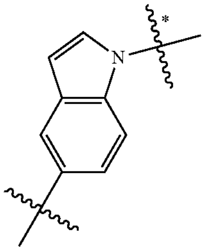
, or
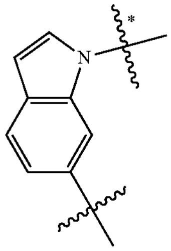
, wherein the * designates a bond to L, L', or L", Ring A is substituted with —$(R^4)_m$ where m is 1, 2, 3, or 4; and each $R^4$ is independently H, halo, $C_{1-6}$ alkyl, or $C_{1-6}$ alkoxy, wherein the $C_{1-6}$ alkyl and $C_{1-6}$ alkoxy groups are optionally substituted with 1-3 groups independently selected from halo, $C_{1-6}$ alkyloxy, amido, and N,N-dimethylamido groups.

In some embodiments of the compound of Formula (I), Formula (IA), and/or Formula (IB), wherein Ring A is

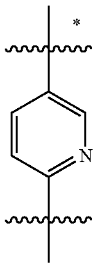,
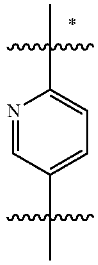,
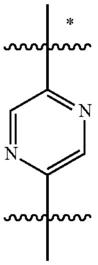,
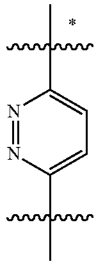,
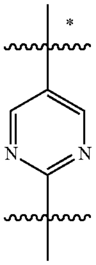,
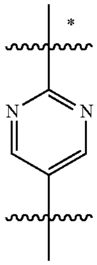,
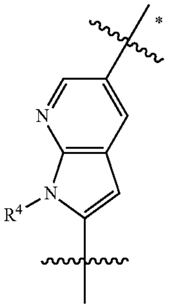,
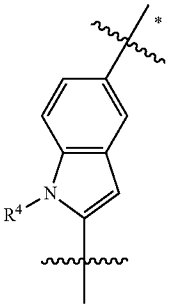,
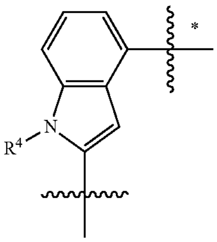,
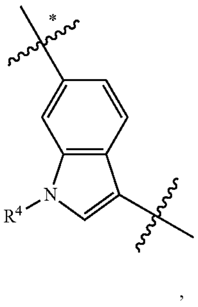,
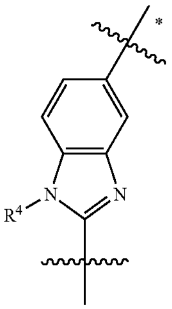,
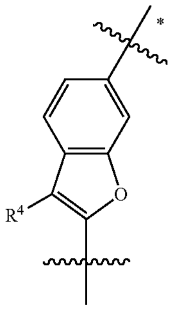,
-continued
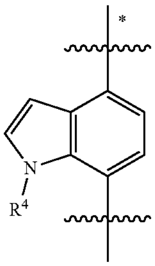,
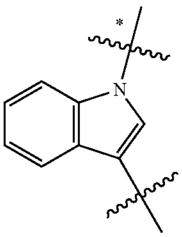,
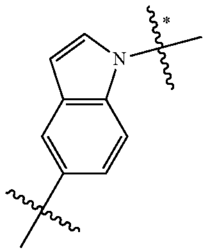, or
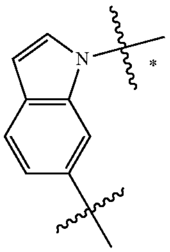,
wherein the * designates a bond to L, L', or L", Ring A is substituted with $—(R^4)_m$ where m is 1 or 2; and each $R^4$ is independently H, halo, $C_{1-4}$ alkyl, or $C_{1-4}$ alkoxy, wherein the $C_{1-4}$ alkyl and $C_{1-4}$ alkoxy groups are optionally substituted with 1-3 groups independently selected from halo, $C_{1-4}$ alkyloxy, amido, and N,N-dimethylamido groups.
In some embodiments, Ring A is
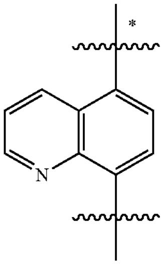,
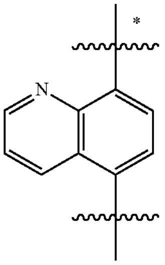,
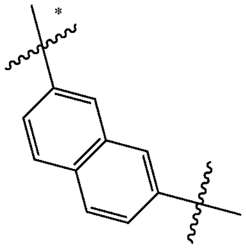,
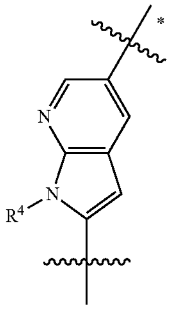,
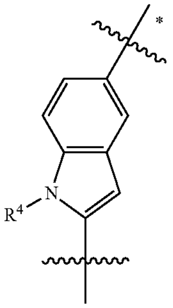,
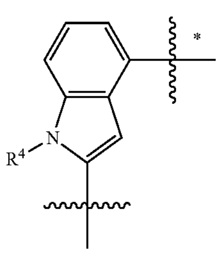, -continued

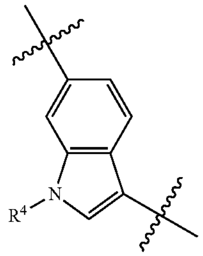

,

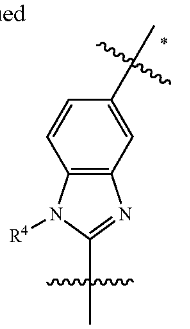

,

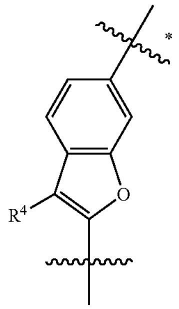

,

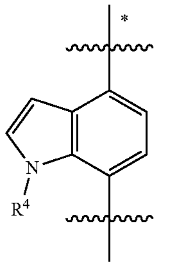

,

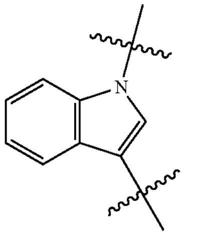

,

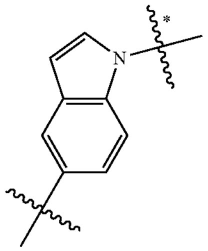

, or

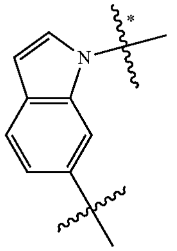

, wherein the * designates a bond to L, L', or L", Ring A is substituted with —$(R^4)_m$ where m is 1, 2, 3, or 4; and each $R^4$ is independently H, halo, $C_{1-6}$ alkyl, or $C_{1-6}$ alkoxy, wherein the $C_{1-6}$ alkyl and $C_{1-6}$ alkoxy groups are optionally substituted with 1-3 groups independently selected from halo, $C_{1-6}$ alkyloxy, amido, and N,N-dimethylamido groups.

In some embodiments of the compound of Formula (I), Formula (IA), and/or Formula (IB), wherein Ring A is

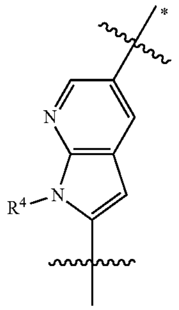

or

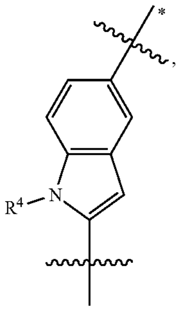

, wherein the * designates a bond to L, L', or L", Ring A is substituted with —$(R^4)_m$ where m is 1 or 2; and each $R^4$ is independently H, halo, $C_{1-4}$ alkyl, or $C_{1-4}$ alkoxy, wherein the $C_{1-4}$ alkyl and $C_{1-4}$ alkoxy groups are optionally substituted with 1-3 groups independently selected from halo, $C_{1-4}$ alkyloxy, amido, and N,N-dimethylamido groups.

In some embodiments of the compound of Formula (I), Formula (IA), and/or Formula (IB), Ring A is

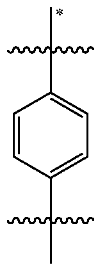

or

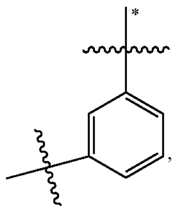

, wherein the * designates a bond to L, L' or L", Ring A is substituted with —$(R^4)_m$ where m is 1, 2, 3, or 4; and each $R^4$ is independently H, halo, $C_{1-4}$ alkyl, or $C_{1-4}$ alkoxy, wherein the $C_{1-4}$ alkyl and $C_{1-4}$ alkoxy groups are optionally substituted with 1-3 groups independently selected from halo, $C_{1-4}$ alkyloxy, amido, and N,N-dimethylamido groups.

In some embodiments, each $R^4$ is independently selected from H, halo, $C_{1-4}$ alkyl, $C_{1-4}$ alkoxy, wherein the $C_{1-4}$ alkyl and $C_{1-4}$ alkoxy groups are optionally substituted with 1-3 groups independently selected from halo, $C_{1-4}$ alkoxy, amido, and N,N-dimethylamido. In some embodiments, each $R^4$ is independently selected from H, halo, $C_{1-4}$ alkyl, $C_{1-4}$ alkoxy, wherein the $C_{1-4}$ alkyl and $C_{1-4}$ alkoxy groups are each optionally substituted with 1-3 groups independently selected from F, Cl, methyl, methoxy, amido, and N,N-dimethylamido. In some embodiments, each $R^4$ is independently selected from H, halo, $C_{1-4}$ alkyl, $C_{1-4}$ alkoxy, wherein the $C_{1-4}$ alkyl and $C_{1-4}$ alkoxy groups are each optionally substituted with 1-3 groups independently selected from F, Cl, methoxy, amido, and N,N-dimethylamido. In some embodiments, each $R^4$ is independently selected from H, methyl, isobutyl, F, Cl, trifluoromethyl, methoxy, difluoromethoxy, trifluoromethoxy, N,N-dimethylamido, 3,3,3-trifluoropropyl, 2,2-difluoroethyl, 3-fluoropropyl, methoxyethyl.

In some embodiments, R is H or $C_{1-4}$ alkyl optionally substituted with one substituent selected from —OH, $C_{1-6}$ alkyloxy, or $C_{6-12}$ aryl. In some embodiments, R is H or $C_{1-4}$ alkyl optionally substituted with one substituent selected from —OH, $C_{1-6}$ alkyloxy, or phenyl. In some embodiments, R is H, methyl, or benzyl. In some embodiments, R is H.

In some embodiments, $R^1$ is H or $C_{1-4}$ alkyl. In some embodiments, $R^1$ is H or methyl. In some embodiments, $R^1$ is H.

In some embodiments, $R^2$ is H or $C_{1-4}$ alkyl. In some embodiments, $R^2$ is H or methyl. In some embodiments, $R^3$ is H or $C_{1-4}$ alkyl. In some embodiments, $R^3$ is H or methyl. In some embodiments, one of $R^2$ and $R^3$ is H and the other is $C_{1-4}$ alkyl. In some embodiments, one of $R^2$ and $R^3$ is H and the other is methyl. In some embodiments, $R^2$ and $R^3$ are each H. In some embodiments, $R^2$ and $R^3$ are each methyl.

In some embodiments, disclosed herein are pharmaceutical compositions comprising a compound of Formula (I), or a pharmaceutically acceptable salt thereof, and a pharmaceutically acceptable excipient.

In the descriptions herein, it is understood that every description, variation, embodiment, or aspect of a moiety may be combined with every description, variation, embodiment, or aspect of other moieties the same as if each and every combination of descriptions is specifically and individually listed. For example, every description, variation, embodiment, or aspect provided herein with respect to L of Formula (I) may be combined with every description, variation, embodiment, or aspect of Ring A, Ring B, R, $R^1$, $R^2$, $R^3$, $R^4$, $R^5$, m, and n the same as if each and every combination were specifically and individually listed. It is also understood that all descriptions, variations, embodiments, or aspects of Formula (I), where applicable, apply equally to other formulae detailed herein, and are equally described, the same as if each and every description, variation, embodiment, or aspect were separately and individually listed for all formulae. For example, all descriptions, variations, embodiments, or aspects of Formula (I), where applicable, apply equally to any of the formulae as detailed herein, such as Formula (IA) or Formula (IB), and are equally described, the same as if each and every description, variation, embodiment, or aspect were separately and individually listed for all formulae.

In some embodiments, provided is a compound selected from the compounds in Table 1 or a pharmaceutically acceptable salt thereof. In some embodiments, provided is a compound selected from the compounds in Table 2 or a pharmaceutically acceptable salt thereof. Although certain compounds described in the present disclosure, including in Table 1, Table 2, Table 2a, and Table 3 are presented as specific stereoisomers and/or in a non-stereochemical form, it is understood that any or all stereochemical forms, including any enantiomeric or diastereomeric forms, and any tautomers or others form of any of the compounds of the present disclosure, including in Table 1, Table 2, Table 2a, and Table 3, are herein described. In some embodiments provided is a compound selected from the compounds in Table 2a or a pharmaceutically acceptable salt thereof. In some embodiments provided is a compound selected from the compounds in Table 3 or a pharmaceutically acceptable salt thereof. Although certain compounds described in the present disclosure, including in Table 3, are presented as specific stereoisomers and/or in a non-stereochemical form, it is understood that any or all stereochemical forms, including any enantiomeric or diastereomeric forms, and any tautomers or others form of any of the compounds of the present disclosure, including in Table 3, are herein described.

Also provided herein are the following compounds in Table 1, Table 2, Table 2a, and Table 3.

TABLE 1

| Compound No. | Compound |
|---|---|
| 404 | 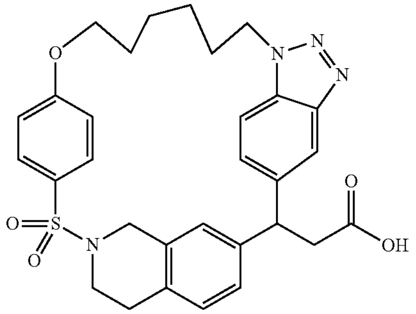 [SMILES: O=C(O)CC1c2ccc3c(c2)CN(CC3)S(=O)(=O)c2ccc(cc2)OCCCCCCn2nnc3cc1ccc32] |
| 405 | 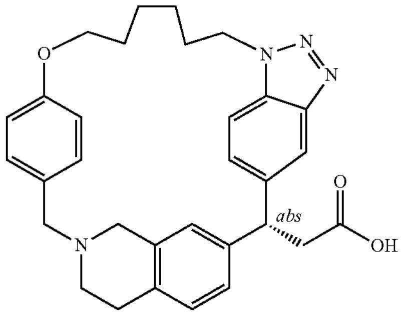 [SMILES: O=C(O)C[C@@H]1c2ccc3c(c2)CN(CC3)Cc2ccc(cc2)OCCCCCCn2nnc3cc1ccc32] |
| 406 | 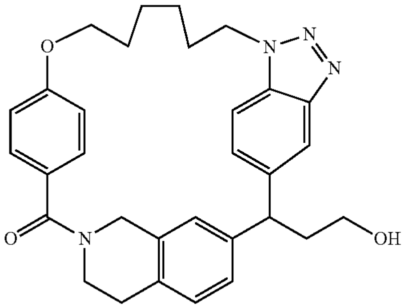 [SMILES: O=C1c2ccc(cc2)OCCCCCCn2nnc3cc(ccc32)C(CCO)c2ccc3c(c2)CN1CC3] |
| 407 | 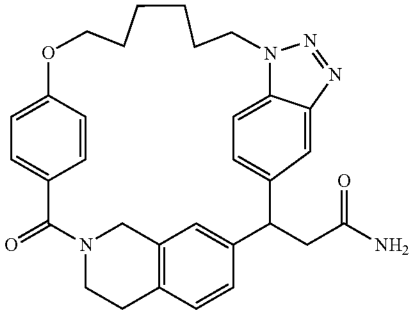 [SMILES: NC(=O)CC1c2ccc3c(c2)CN(CC3)C(=O)c2ccc(cc2)OCCCCCCn2nnc3cc1ccc32] |

or a pharmaceutically acceptable salt thereof.

TABLE 2
| Comp'd No | Structure |
| --- | --- |
| 1 | 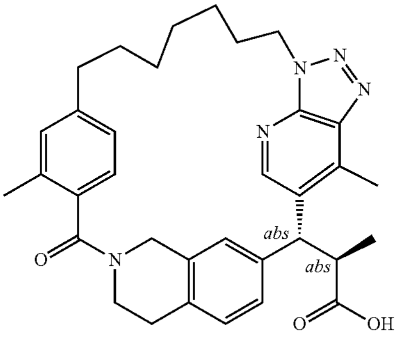 |
| 2 | 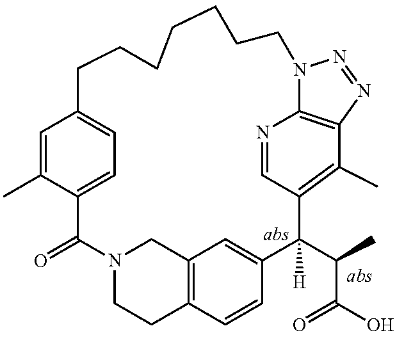 |
| 3 | 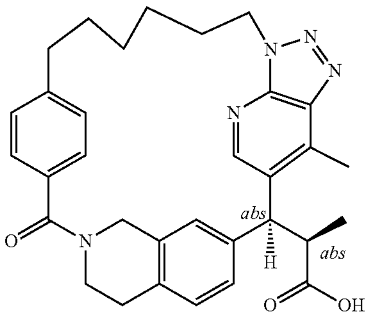 [SMILES: Cc1c2cnc3c1nnn3CCCCCCc1ccc(cc1)C(=O)N1CCc3ccc(cc3C1)[C@@H]2[C@@H](C)C(=O)O] |
| 4 | 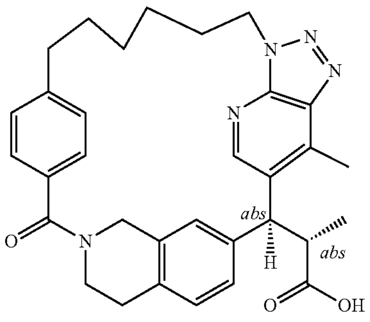 [SMILES: Cc1c2cnc3c1nnn3CCCCCCc1ccc(cc1)C(=O)N1CCc3ccc(cc3C1)[C@@H]2[C@H](C)C(=O)O] |
TABLE 2-continued
| Comp'd No | Structure |
| --- | --- |
| 5 | 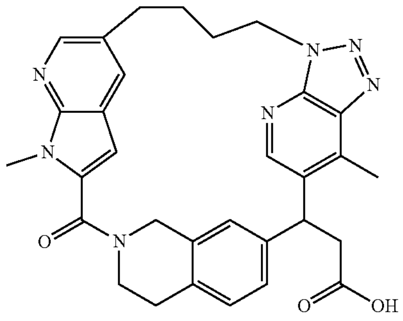 |
| 6 | 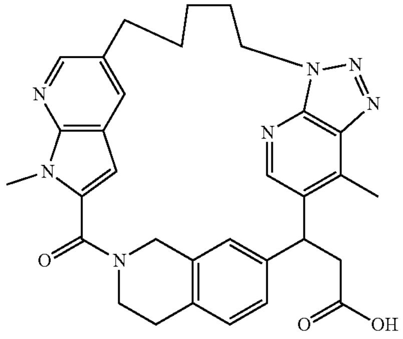 |
| 7 | 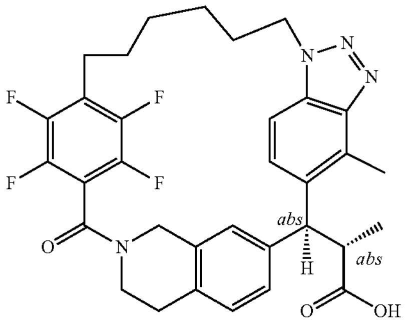 [SMILES: Cc1c2ccc3c1nnn3CCCCCCc1c(F)c(F)c(c(F)c1F)C(=O)N1CCc3ccc(cc3C1)[C@@H]2[C@H](C)C(=O)O] |
| 8 | 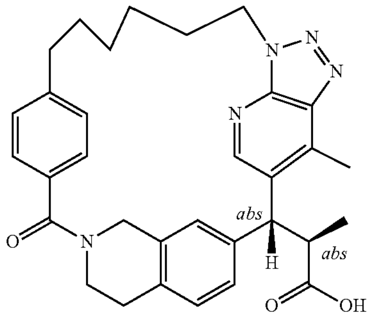 [SMILES: Cc1c2cnc3c1nnn3CCCCCCc1ccc(cc1)C(=O)N1CCc3ccc(cc3C1)[C@H]2[C@@H](C)C(=O)O] |

TABLE 2-continued
| Comp'd No | Structure |
|---|---|
| 9 | 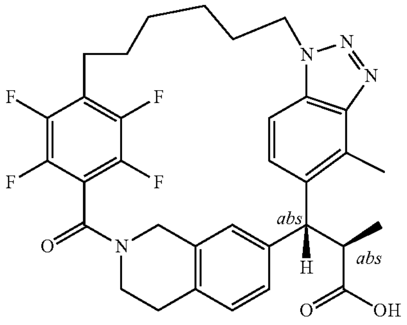 [SMILES: Cc1c2ccc3c1nnn3CCCCCCc1c(F)c(F)c(c(F)c1F)C(=O)N1CCc3ccc(cc3C1)[C@H]2[C@@H](C)C(=O)O] |
| 10 | 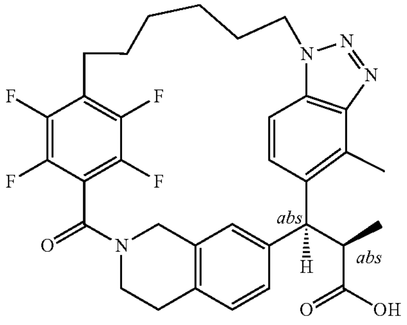 [SMILES: Cc1c2ccc3c1nnn3CCCCCCc1c(F)c(F)c(c(F)c1F)C(=O)N1CCc3ccc(cc3C1)[C@@H]2[C@@H](C)C(=O)O] |
| 11 | 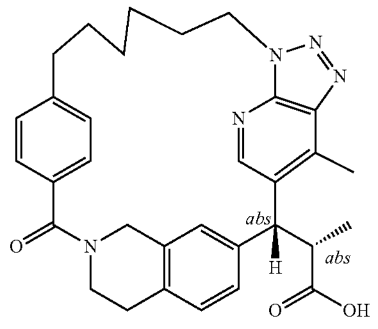 [SMILES: Cc1c2cnc3c1nnn3CCCCCCc1ccc(cc1)C(=O)N1CCc3ccc(cc3C1)[C@H]2[C@H](C)C(=O)O] |
| 12 | 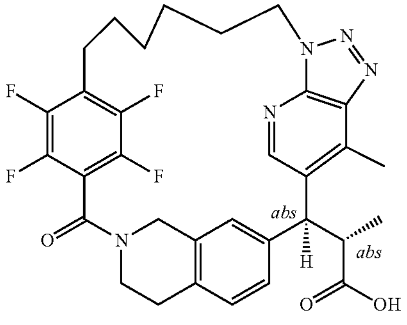 [SMILES: Cc1c2cnc3c1nnn3CCCCCCc1c(F)c(F)c(c(F)c1F)C(=O)N1CCc3ccc(cc3C1)[C@@H]2[C@H](C)C(=O)O] |
TABLE 2-continued
| Comp'd No | Structure |
|---|---|
| 13 | 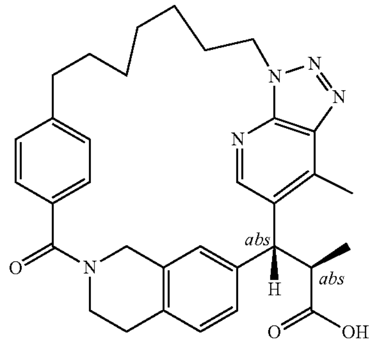 [SMILES: Cc1c2cnc3c1nnn3CCCCCCCc1ccc(cc1)C(=O)N1CCc3ccc(cc3C1)[C@H]2[C@@H](C)C(=O)O] |
| 14 | 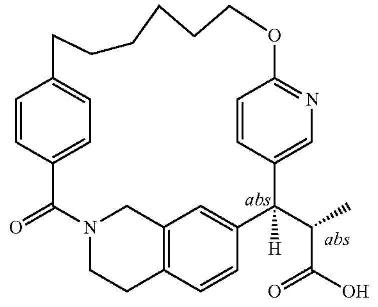 [SMILES: C[C@H](C(=O)O)[C@@H]1c2ccc(nc2)OCCCCCCc2ccc(cc2)C(=O)N2CCc3ccc1cc3C2] |
| 15 | 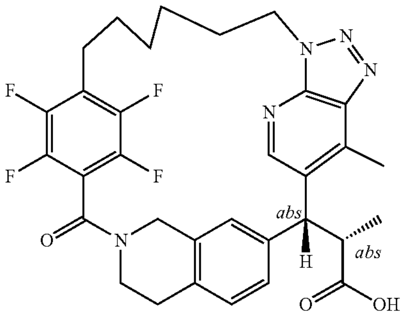 [SMILES: Cc1c2cnc3c1nnn3CCCCCCc1c(F)c(F)c(c(F)c1F)C(=O)N1CCc3ccc(cc3C1)[C@H]2[C@H](C)C(=O)O] |
| 16 | 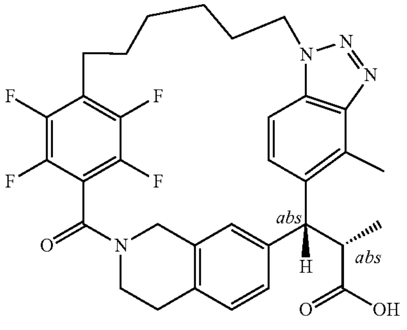 [SMILES: Cc1c2ccc3c1nnn3CCCCCCc1c(F)c(F)c(c(F)c1F)C(=O)N1CCc3ccc(cc3C1)[C@H]2[C@H](C)C(=O)O] |

TABLE 2-continued
| Comp'd No | Structure |
| --- | --- |
| 17 | 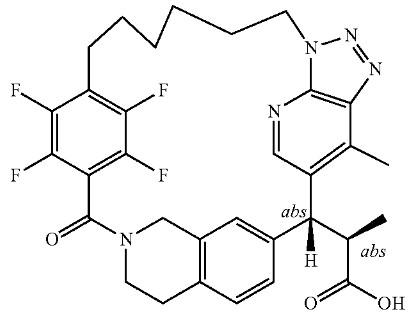 [SMILES: Cc1c2cnc3c1nnn3CCCCCCc1c(F)c(F)c(c(F)c1F)C(=O)N1CCc3ccc(cc3C1)[C@H]2[C@@H](C)C(=O)O] |
| 18 | 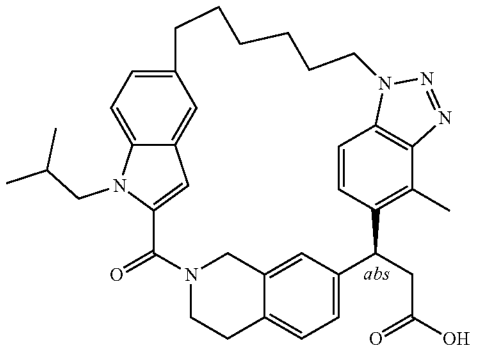 [SMILES: Cc1c2ccc3c1nnn3CCCCCCc1ccc3c(c1)cc(n3CC(C)C)C(=O)N1CCc3ccc(cc3C1)[C@@H]2CC(=O)O] |
| 19 | 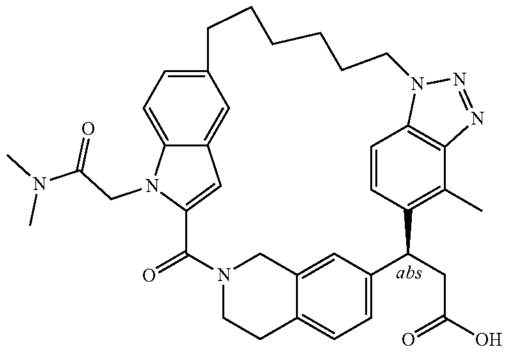 |
| 20 | 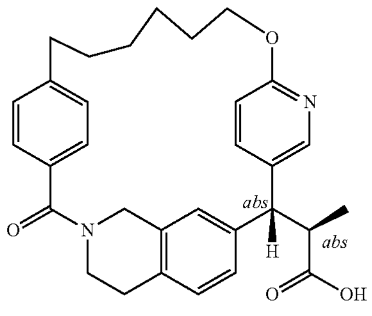 [SMILES: C[C@@H](C(=O)O)[C@H]1c2ccc(nc2)OCCCCCCc2ccc(cc2)C(=O)N2CCc3ccc1cc3C2] |
TABLE 2-continued
| Comp'd No | Structure |
| --- | --- |
| 21 | 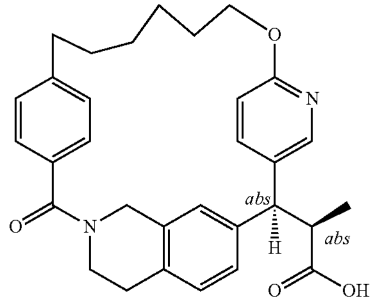 [SMILES: C[C@@H](C(=O)O)[C@@H]1c2ccc(nc2)OCCCCCCc2ccc(cc2)C(=O)N2CCc3ccc1cc3C2] |
| 22 | 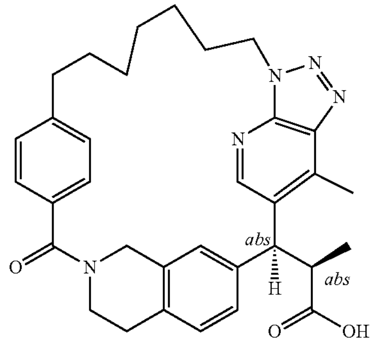 [SMILES: Cc1c2cnc3c1nnn3CCCCCCCc1ccc(cc1)C(=O)N1CCc3ccc(cc3C1)[C@@H]2[C@@H](C)C(=O)O] |
| 23 | 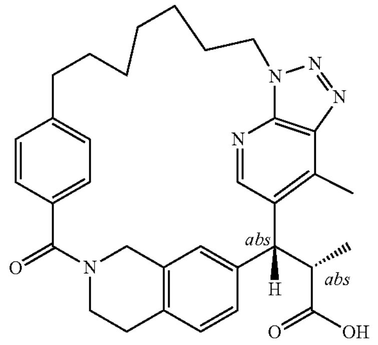 [SMILES: Cc1c2cnc3c1nnn3CCCCCCCc1ccc(cc1)C(=O)N1CCc3ccc(cc3C1)[C@H]2[C@H](C)C(=O)O] |
| 24 | 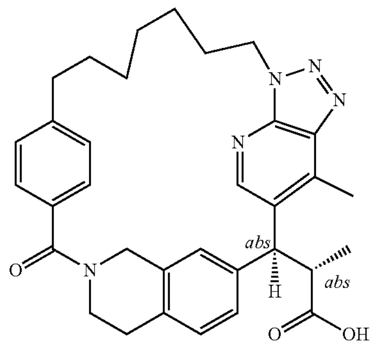 [SMILES: Cc1c2cnc3c1nnn3CCCCCCCc1ccc(cc1)C(=O)N1CCc3ccc(cc3C1)[C@@H]2[C@H](C)C(=O)O] |

TABLE 2-continued
| Comp'd No | Structure |
|---|---|
| 25 | 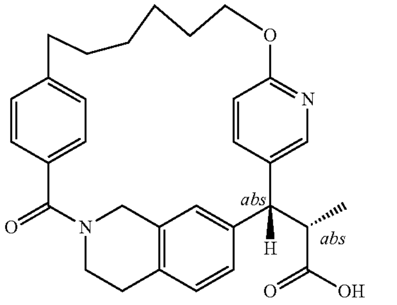 [SMILES: C[C@H](C(=O)O)[C@H]1c2ccc(nc2)OCCCCCCc2ccc(cc2)C(=O)N2CCc3ccc1cc3C2] |
| 26 | 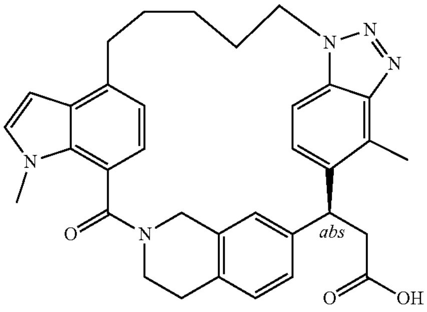 [SMILES: Cc1c2ccc3c1nnn3CCCCCc1ccc(c3c1ccn3C)C(=O)N1CCc3ccc(cc3C1)[C@@H]2CC(=O)O] |
| 27 | 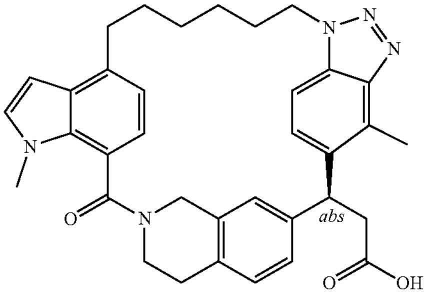 [SMILES: Cc1c2ccc3c1nnn3CCCCCCc1ccc(c3c1ccn3C)C(=O)N1CCc3ccc(cc3C1)[C@@H]2CC(=O)O] |
| 28 | 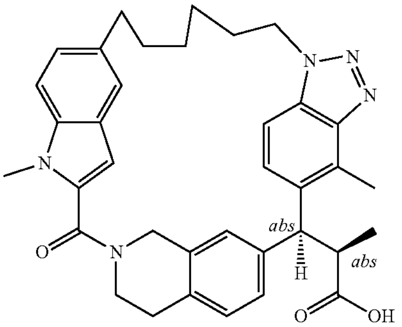 [SMILES: Cc1c2ccc3c1nnn3CCCCCCc1ccc3c(c1)cc(n3C)C(=O)N1CCc3ccc(cc3C1)[C@@H]2[C@@H](C)C(=O)O] |
| 29 | 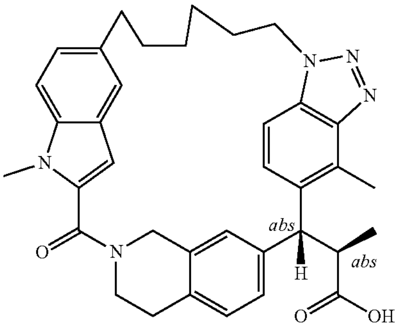 [SMILES: Cc1c2ccc3c1nnn3CCCCCCc1ccc3c(c1)cc(n3C)C(=O)N1CCc3ccc(cc3C1)[C@H]2[C@@H](C)C(=O)O] |
TABLE 2-continued
| Comp'd No | Structure |
|---|---|
| 30 | 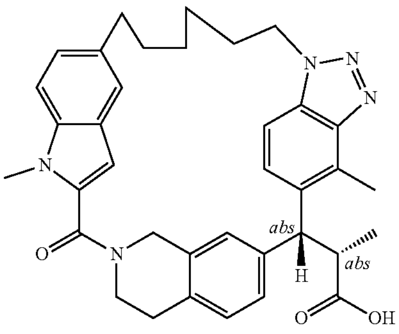 [SMILES: Cc1c2ccc3c1nnn3CCCCCCc1ccc3c(c1)cc(n3C)C(=O)N1CCc3ccc(cc3C1)[C@H]2[C@H](C)C(=O)O] |
| 31 | 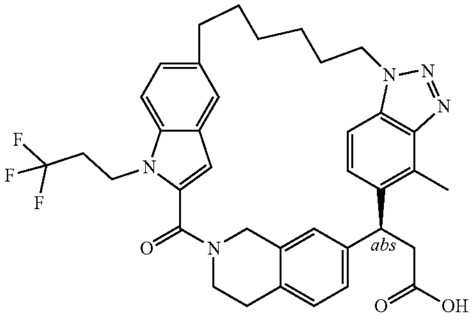 [SMILES: Cc1c2ccc3c1nnn3CCCCCCc1ccc3c(c1)cc(n3CCC(F)(F)F)C(=O)N1CCc3ccc(cc3C1)[C@@H]2CC(=O)O] |
| 32 | 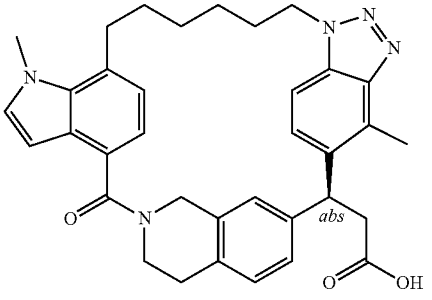 [SMILES: Cc1c2ccc3c1nnn3CCCCCCc1ccc(c3ccn(C)c13)C(=O)N1CCc3ccc(cc3C1)[C@@H]2CC(=O)O] |
| 33 | 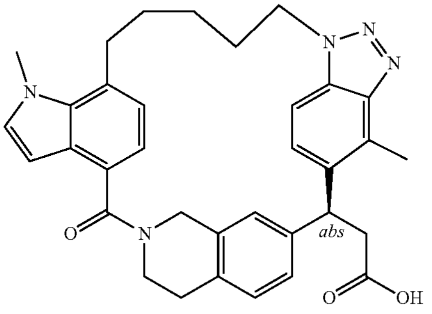 [SMILES: Cc1c2ccc3c1nnn3CCCCCc1ccc(c3ccn(C)c13)C(=O)N1CCc3ccc(cc3C1)[C@@H]2CC(=O)O] |

TABLE 2-continued
| Comp'd No | Structure |
| --- | --- |
| 34 | 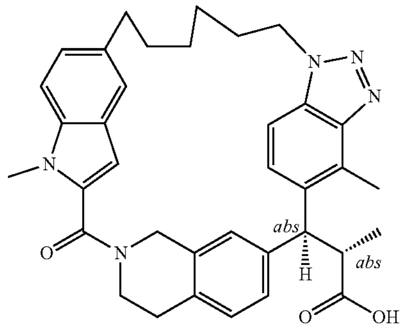 [SMILES: Cc1c2ccc3c1nnn3CCCCCCc1ccc3c(c1)cc(n3C)C(=O)N1CCc3ccc(cc3C1)[C@@H]2[C@H](C)C(=O)O] |
| 35 | 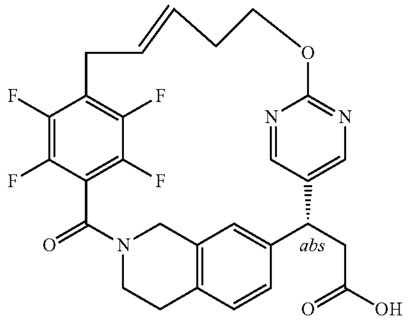 [SMILES: O=C(O)C[C@H]1c2cnc(nc2)OCC/C=C/Cc2c(F)c(F)c(c(F)c2F)C(=O)N2CCc3ccc1cc3C2] |
| 36 | 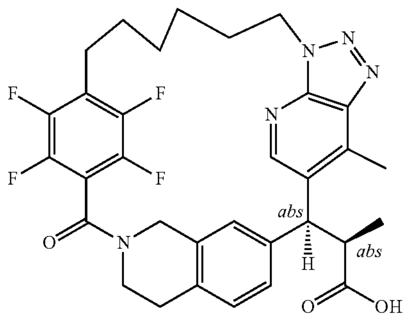 [SMILES: Cc1c2cnc3c1nnn3CCCCCCc1c(F)c(F)c(c(F)c1F)C(=O)N1CCc3ccc(cc3C1)[C@@H]2[C@@H](C)C(=O)O] |
| 37 | 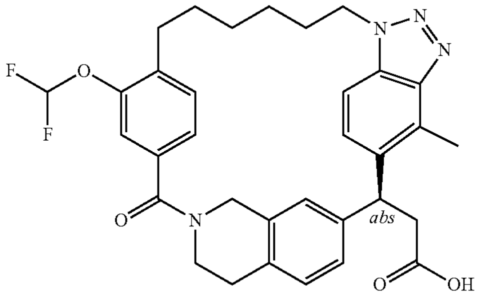 [SMILES: Cc1c2ccc3c1nnn3CCCCCCc1ccc(cc1OC(F)F)C(=O)N1CCc3ccc(cc3C1)[C@@H]2CC(=O)O] |
| 38 | 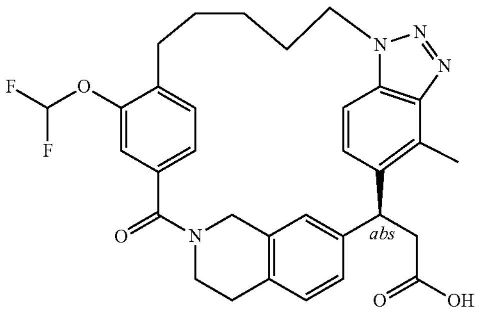 [SMILES: Cc1c2ccc3c1nnn3CCCCCc1ccc(cc1OC(F)F)C(=O)N1CCc3ccc(cc3C1)[C@@H]2CC(=O)O] |
TABLE 2-continued
| Comp'd No | Structure |
| --- | --- |
| 39 | 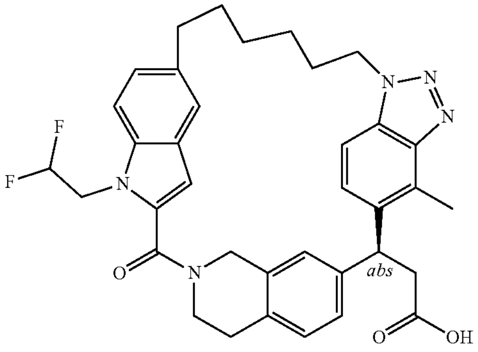 [SMILES: Cc1c2ccc3c1nnn3CCCCCCc1ccc3c(c1)cc(n3CC(F)F)C(=O)N1CCc3ccc(cc3C1)[C@@H]2CC(=O)O] |
| 40 | 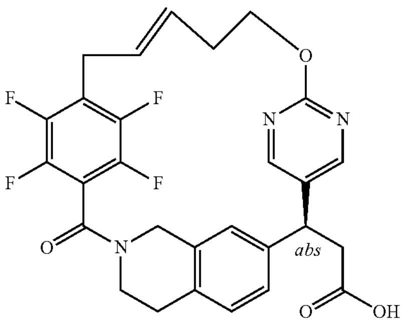 [SMILES: O=C(O)C[C@@H]1c2cnc(nc2)OCC/C=C/Cc2c(F)c(F)c(c(F)c2F)C(=O)N2CCc3ccc1cc3C2] |
| 41 | 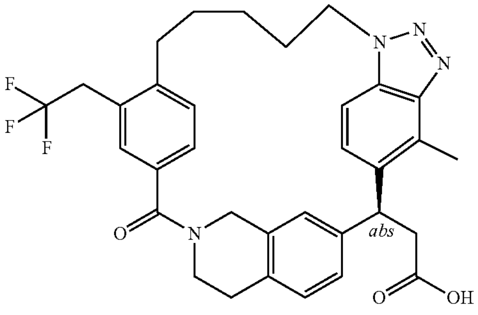 [SMILES: Cc1c2ccc3c1nnn3CCCCCc1ccc(cc1CC(F)(F)F)C(=O)N1CCc3ccc(cc3C1)[C@@H]2CC(=O)O] |
| 42 | 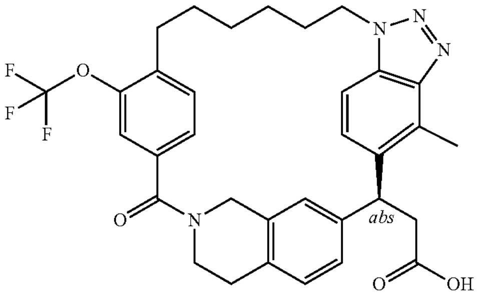 [SMILES: Cc1c2ccc3c1nnn3CCCCCCc1ccc(cc1OC(F)(F)F)C(=O)N1CCc3ccc(cc3C1)[C@@H]2CC(=O)O] |

TABLE 2-continued
| Comp'd No | Structure |
|---|---|
| 43 | 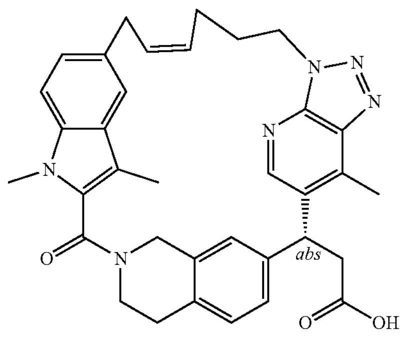 |
| 44 | 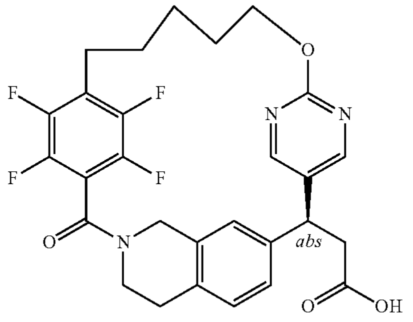 [SMILES: O=C(O)C[C@@H]1c2cnc(nc2)OCCCCCc2c(F)c(F)c(c(F)c2F)C(=O)N2CCc3ccc1cc3C2] |
| 45 | 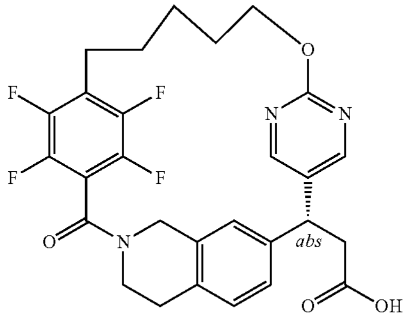 [SMILES: O=C(O)C[C@H]1c2cnc(nc2)OCCCCCc2c(F)c(F)c(c(F)c2F)C(=O)N2CCc3ccc1cc3C2] |
| 46 | 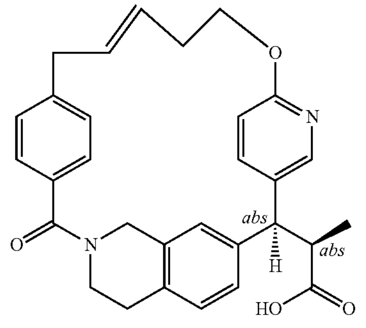 [SMILES: C[C@@H](C(=O)O)[C@@H]1c2ccc(nc2)OCC/C=C/Cc2ccc(cc2)C(=O)N2CCc3ccc1cc3C2] |
TABLE 2-continued
| Comp'd No | Structure |
|---|---|
| 47 | 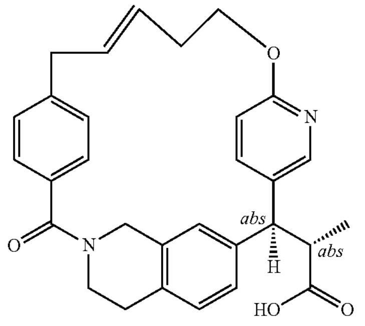 [SMILES: C[C@H](C(=O)O)[C@@H]1c2ccc(nc2)OCC/C=C/Cc2ccc(cc2)C(=O)N2CCc3ccc1cc3C2] |
| 48 | 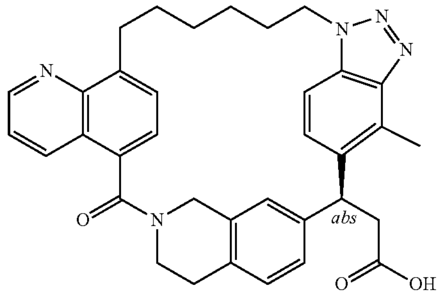 [SMILES: Cc1c2ccc3c1nnn3CCCCCCc1ccc(c3cccnc13)C(=O)N1CCc3ccc(cc3C1)[C@@H]2CC(=O)O] |
| 49 | 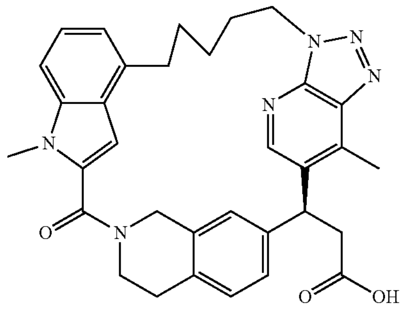 |
| 50 | 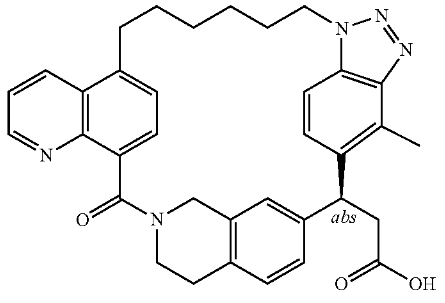 [SMILES: Cc1c2ccc3c1nnn3CCCCCCc1ccc(c3ncccc13)C(=O)N1CCc3ccc(cc3C1)[C@@H]2CC(=O)O] |
| 51 | 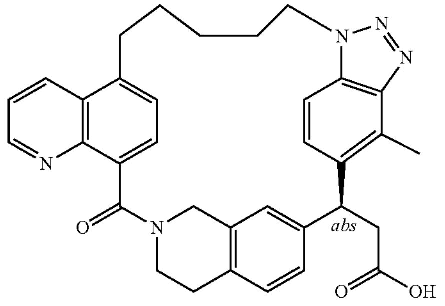 [SMILES: Cc1c2ccc3c1nnn3CCCCCc1ccc(c3ncccc13)C(=O)N1CCc3ccc(cc3C1)[C@@H]2CC(=O)O] |

TABLE 2-continued
| Comp'd No | Structure |
|---|---|
| 52 | 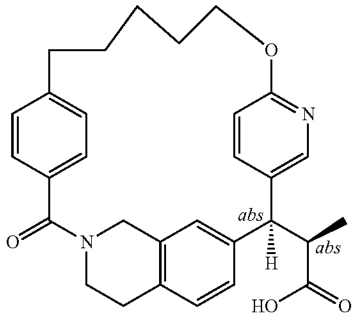 [SMILES: C[C@@H](C(=O)O)[C@@H]1c2ccc(nc2)OCCCCCc2ccc(cc2)C(=O)N2CCc3ccc1cc3C2] |
| 53 | 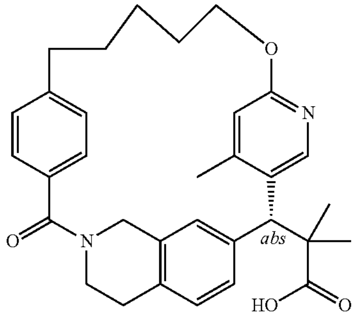 [SMILES: Cc1cc2ncc1[C@H](C(C)(C)C(=O)O)c1ccc3c(c1)CN(CC3)C(=O)c1ccc(cc1)CCCCCO2] |
| 54 | 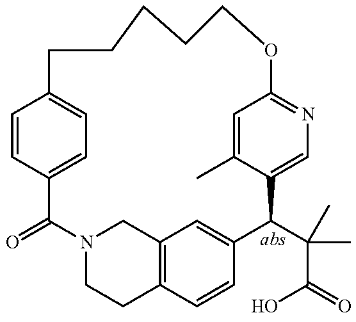 [SMILES: Cc1cc2ncc1[C@@H](C(C)(C)C(=O)O)c1ccc3c(c1)CN(CC3)C(=O)c1ccc(cc1)CCCCCO2] |
| 55 | 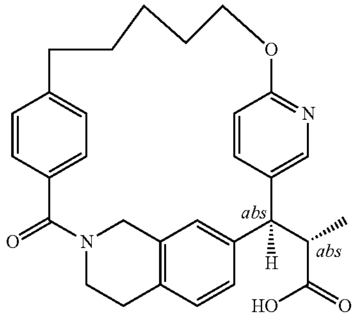 [SMILES: C[C@H](C(=O)O)[C@@H]1c2ccc(nc2)OCCCCCc2ccc(cc2)C(=O)N2CCc3ccc1cc3C2] |
TABLE 2-continued
| Comp'd No | Structure |
|---|---|
| 56 | 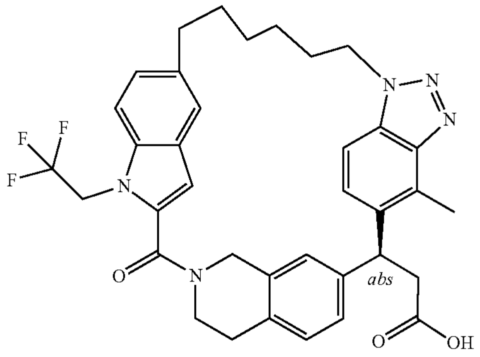 [SMILES: Cc1c2ccc3c1nnn3CCCCCCc1ccc3c(c1)cc(n3CC(F)(F)F)C(=O)N1CCc3ccc(cc3C1)[C@@H]2CC(=O)O] |
| 57 | 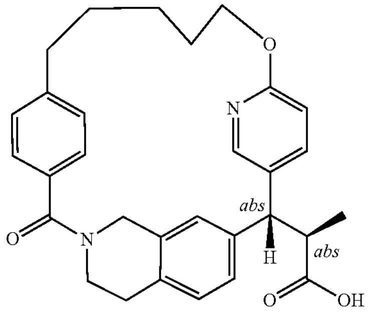 [SMILES: C[C@@H](C(=O)O)[C@H]1c2ccc(nc2)OCCCCCc2ccc(cc2)C(=O)N2CCc3ccc1cc3C2] |
| 58 | 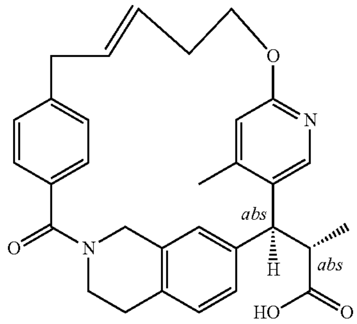 [SMILES: Cc1cc2ncc1[C@@H]([C@H](C)C(=O)O)c1ccc3c(c1)CN(CC3)C(=O)c1ccc(cc1)C/C=C/CCO2] |
| 59 | 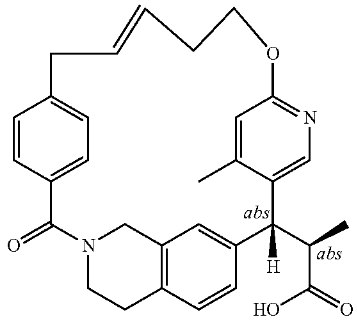 [SMILES: Cc1cc2ncc1[C@H]([C@@H](C)C(=O)O)c1ccc3c(c1)CN(CC3)C(=O)c1ccc(cc1)C/C=C/CCO2] |

TABLE 2-continued
| Comp'd No | Structure |
|---|---|
| 60 | 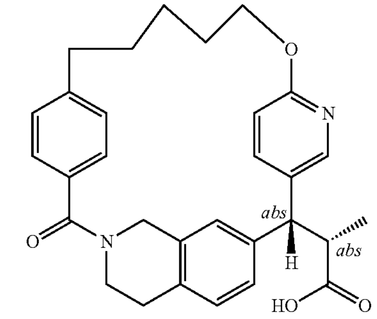 [SMILES: C[C@H](C(=O)O)[C@H]1c2ccc(nc2)OCCCCCc2ccc(cc2)C(=O)N2CCc3ccc1cc3C2] |
| 61 | 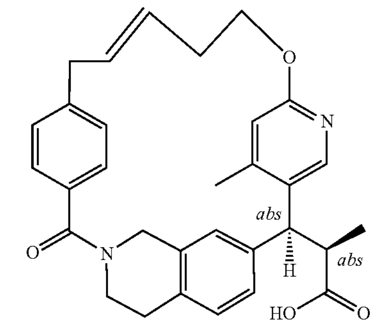 [SMILES: Cc1cc2ncc1[C@@H]([C@@H](C)C(=O)O)c1ccc3c(c1)CN(CC3)C(=O)c1ccc(cc1)C/C=C/CCO2] |
| 62 | 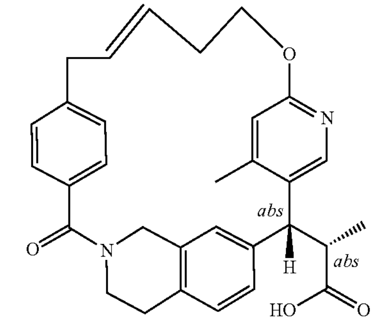 [SMILES: Cc1cc2ncc1[C@H]([C@H](C)C(=O)O)c1ccc3c(c1)CN(CC3)C(=O)c1ccc(cc1)C/C=C/CCO2] |
| 63 | 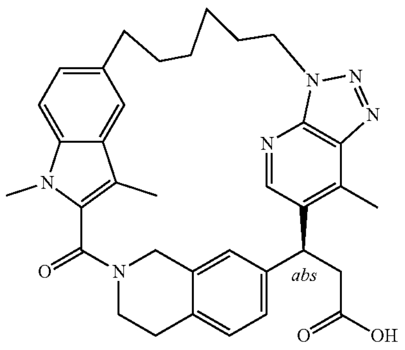 [SMILES: Cc1c2n(C)c3ccc(cc13)CCCCCCn1nnc3c(C)c(cnc31)[C@@H](CC(=O)O)c1ccc3c(c1)CN(CC3)C2=O] |
TABLE 2-continued
| Comp'd No | Structure |
|---|---|
| 64 | 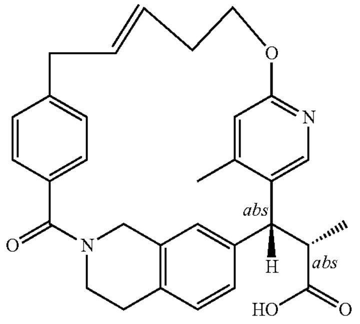 [SMILES: Cc1cc2ncc1[C@H]([C@H](C)C(=O)O)c1ccc3c(c1)CN(CC3)C(=O)c1ccc(cc1)C/C=C/CCO2] |
| 65 | 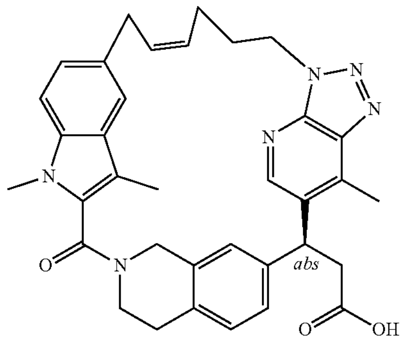 [SMILES: Cc1c2n(C)c3ccc(cc13)C/C=C\CCCn1nnc3c(C)c(cnc31)[C@@H](CC(=O)O)c1ccc3c(c1)CN(CC3)C2=O] |
| 66 | 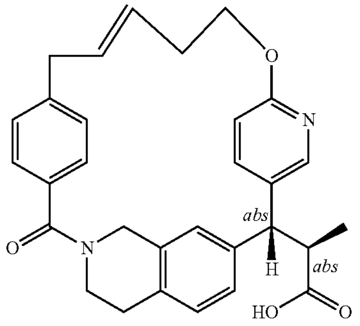 [SMILES: C[C@@H](C(=O)O)[C@H]1c2ccc(nc2)OCC/C=C/Cc2ccc(cc2)C(=O)N2CCc3ccc1cc3C2] |
| 67 | 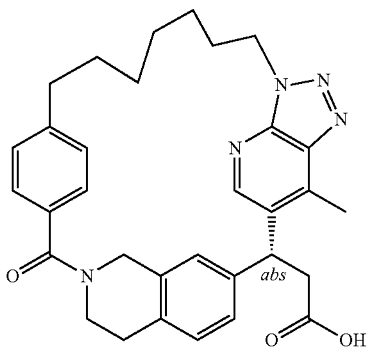 [SMILES: Cc1c2cnc3c1nnn3CCCCCCCc1ccc(cc1)C(=O)N1CCc3ccc(cc3C1)[C@H]2CC(=O)O] |

TABLE 2-continued
| Comp'd No | Structure |
| --- | --- |
| 68 | 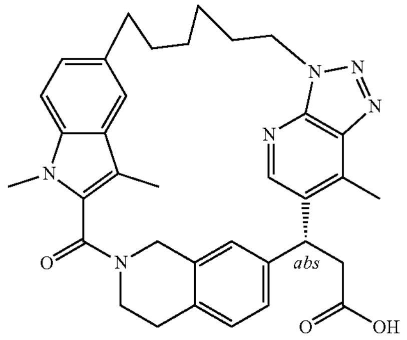 [SMILES: Cc1c2n(C)c3ccc(cc13)CCCCCCn1nnc3c(C)c(cnc31)[C@H](CC(=O)O)c1ccc3c(c1)CN(CC3)C2=O] |
| 69 | 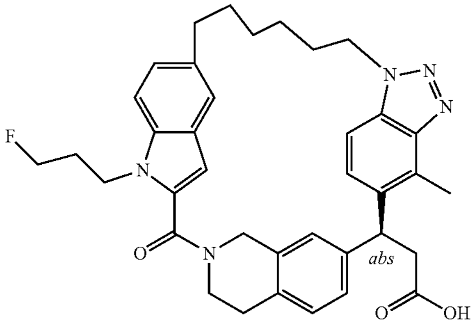 [SMILES: Cc1c2ccc3c1nnn3CCCCCCc1ccc3c(c1)cc(n3CCCF)C(=O)N1CCc3ccc(cc3C1)[C@@H]2CC(=O)O] |
| 70 | 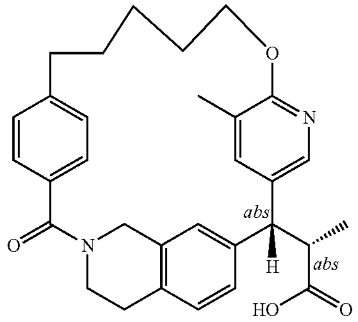 [SMILES: Cc1cc2cnc1OCCCCCc1ccc(cc1)C(=O)N1CCc3ccc(cc3C1)[C@H]2[C@H](C)C(=O)O] |
| 71 | 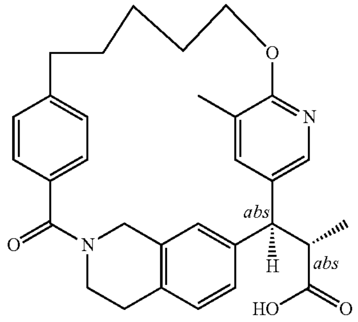 [SMILES: Cc1cc2cnc1OCCCCCc1ccc(cc1)C(=O)N1CCc3ccc(cc3C1)[C@@H]2[C@H](C)C(=O)O] |
TABLE 2-continued
| Comp'd No | Structure |
| --- | --- |
| 72 | 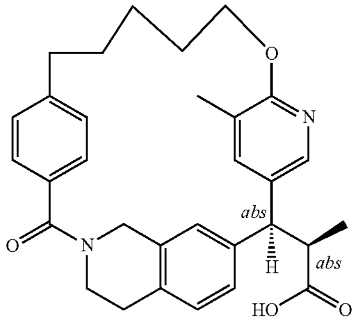 [SMILES: Cc1cc2cnc1OCCCCCc1ccc(cc1)C(=O)N1CCc3ccc(cc3C1)[C@@H]2[C@@H](C)C(=O)O] |
| 73 | 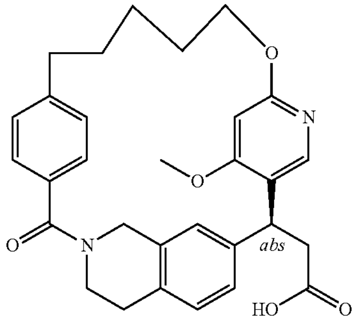 [SMILES: COc1cc2ncc1[C@@H](CC(=O)O)c1ccc3c(c1)CN(CC3)C(=O)c1ccc(cc1)CCCCCO2] |
| 74 | 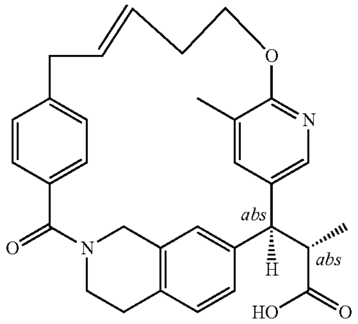 [SMILES: Cc1cc2cnc1OCC/C=C/Cc1ccc(cc1)C(=O)N1CCc3ccc(cc3C1)[C@@H]2[C@H](C)C(=O)O] |
| 75 | 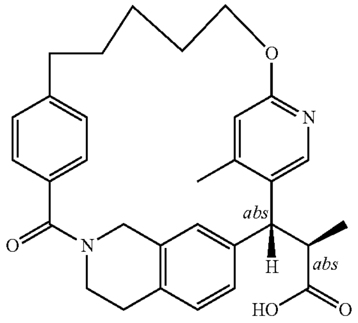 [SMILES: Cc1cc2ncc1[C@H]([C@@H](C)C(=O)O)c1ccc3c(c1)CN(CC3)C(=O)c1ccc(cc1)CCCCCO2] |

TABLE 2-continued
| Comp'd No | Structure |
|---|---|
| 76 | 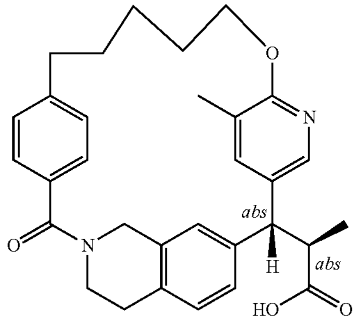 [SMILES: Cc1cc2cnc1OCCCCCc1ccc(cc1)C(=O)N1CCc3ccc(cc3C1)[C@H]2[C@@H](C)C(=O)O] |
| 77 | 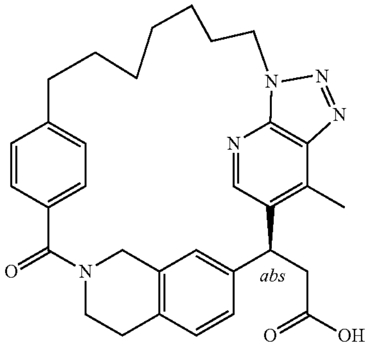 [SMILES: Cc1c2cnc3c1nnn3CCCCCCCc1ccc(cc1)C(=O)N1CCc3ccc(cc3C1)[C@@H]2CC(=O)O] |
| 78 | 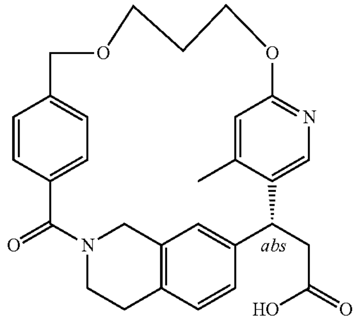 [SMILES: Cc1cc2ncc1[C@H](CC(=O)O)c1ccc3c(c1)CN(CC3)C(=O)c1ccc(cc1)COCCCO2] |
| 79 | 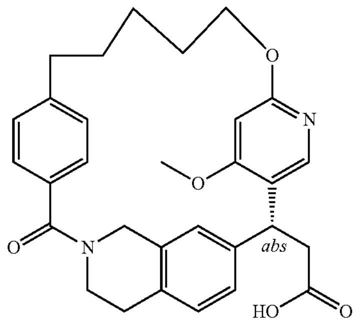 [SMILES: COc1cc2ncc1[C@H](CC(=O)O)c1ccc3c(c1)CN(CC3)C(=O)c1ccc(cc1)CCCCCO2] |
TABLE 2-continued
| Comp'd No | Structure |
|---|---|
| 80 | 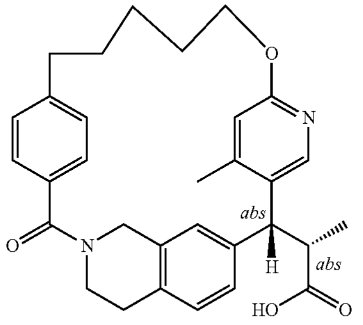 [SMILES: Cc1cc2ncc1[C@H]([C@H](C)C(=O)O)c1ccc3c(c1)CN(CC3)C(=O)c1ccc(cc1)CCCCCO2] |
| 81 | 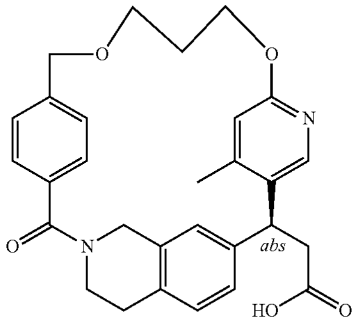 [SMILES: Cc1cc2ncc1[C@@H](CC(=O)O)c1ccc3c(c1)CN(CC3)C(=O)c1ccc(cc1)COCCCO2] |
| 82 | 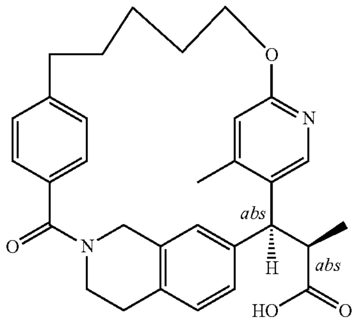 [SMILES: Cc1cc2ncc1[C@@H]([C@@H](C)C(=O)O)c1ccc3c(c1)CN(CC3)C(=O)c1ccc(cc1)CCCCCO2] |
| 83 | 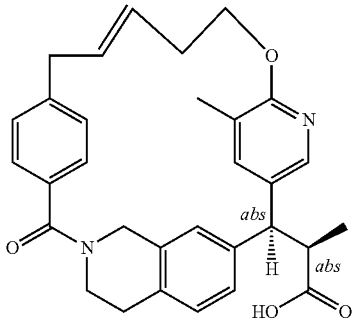 [SMILES: Cc1cc2cnc1OCC/C=C/Cc1ccc(cc1)C(=O)N1CCc3ccc(cc3C1)[C@@H]2[C@@H](C)C(=O)O] |

TABLE 2-continued
| Comp'd No | Structure |
|---|---|
| 84 | 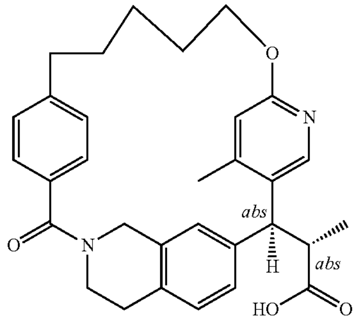 [SMILES: Cc1cc2ncc1[C@@H]([C@H](C)C(=O)O)c1ccc3c(c1)CN(CC3)C(=O)c1ccc(cc1)CCCCCO2] |
| 85 | 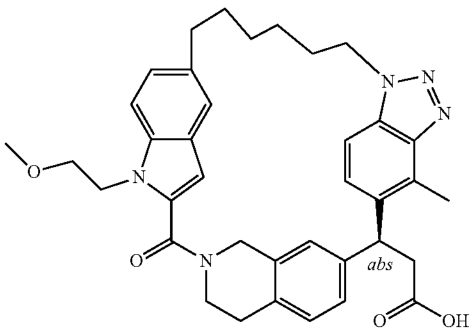 [SMILES: COCCn1c2cc3cc(ccc31)CCCCCCn1nnc3c(C)c(ccc31)[C@@H](CC(=O)O)c1ccc3c(c1)CN(CC3)C2=O] |
| 86 | 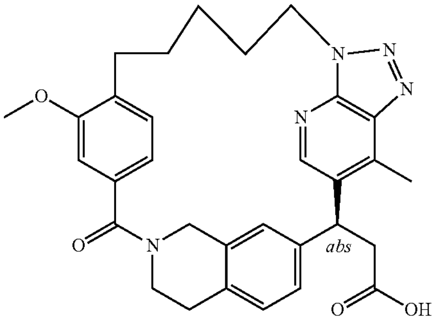 |
| 87 | 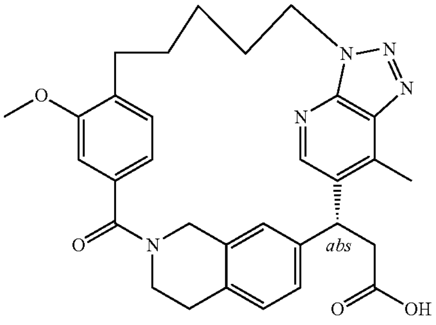 |
TABLE 2-continued
| Comp'd No | Structure |
|---|---|
| 88 | 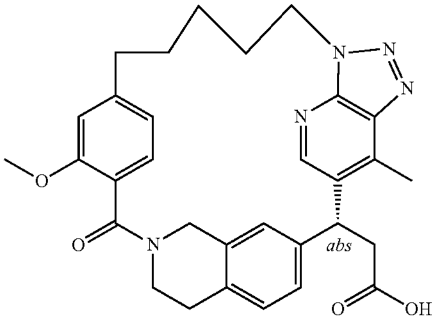 |
| 89 | 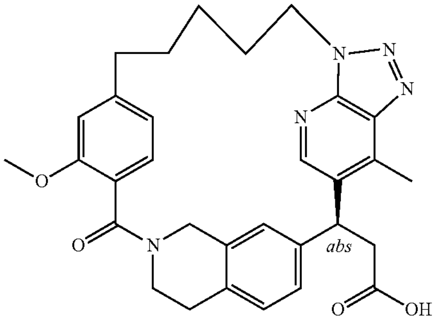 |
| 90 | 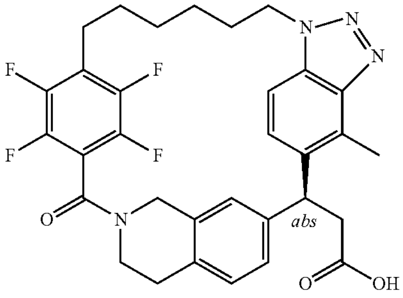 [SMILES: Cc1c2ccc3c1nnn3CCCCCCc1c(F)c(F)c(c(F)c1F)C(=O)N1CCc3ccc(cc3C1)[C@@H]2CC(=O)O] |
| 91 | 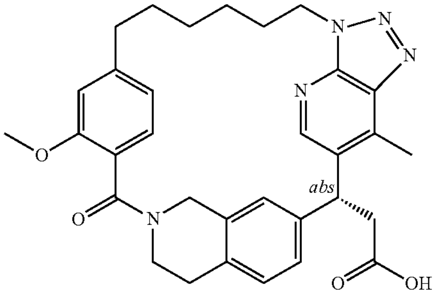 |
| 92 | 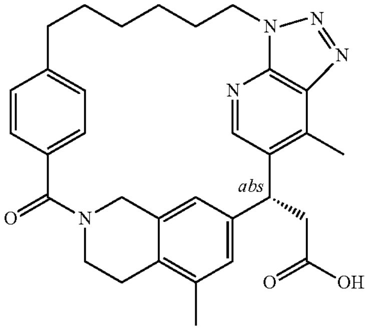 [SMILES: Cc1cc2cc3c1CCN(C3)C(=O)c1ccc(cc1)CCCCCCn1nnc3c(C)c(cnc31)[C@@H]2CC(=O)O] |

TABLE 2-continued
| Comp'd No | Structure |
|---|---|
| 93 | 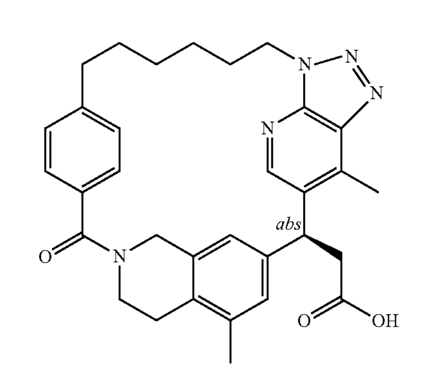 [SMILES: Cc1cc2cc3c1CCN(C3)C(=O)c1ccc(cc1)CCCCCCn1nnc3c(C)c(cnc31)[C@H]2CC(=O)O] |
| 94 | 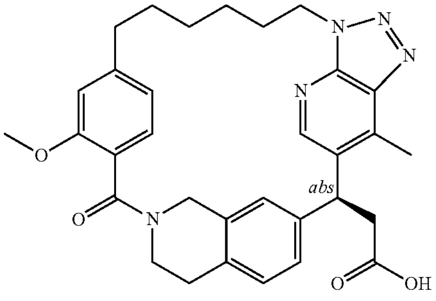 |
| 95 | 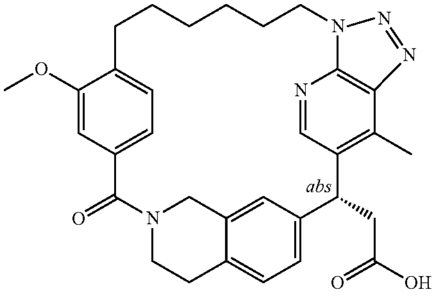 |
| 96 | 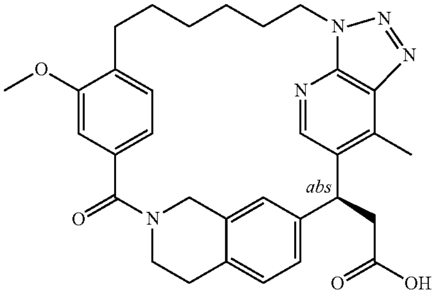 |
TABLE 2-continued
| Comp'd No | Structure |
|---|---|
| 97 | 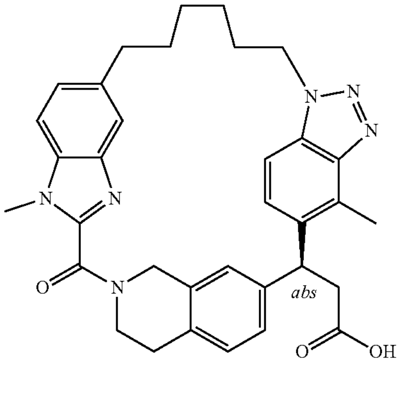 [SMILES: Cc1c2ccc3c1nnn3CCCCCCc1ccc3c(c1)nc(n3C)C(=O)N1CCc3ccc(cc3C1)[C@@H]2CC(=O)O] |
| 98 | 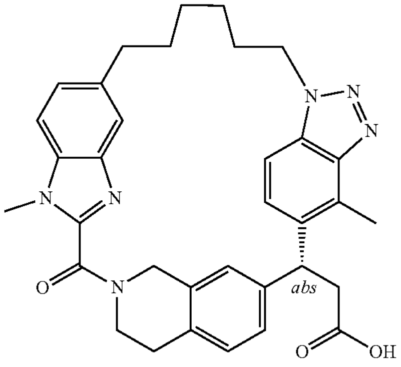 [SMILES: Cc1c2ccc3c1nnn3CCCCCCc1ccc3c(c1)nc(n3C)C(=O)N1CCc3ccc(cc3C1)[C@H]2CC(=O)O] |
| 99 | 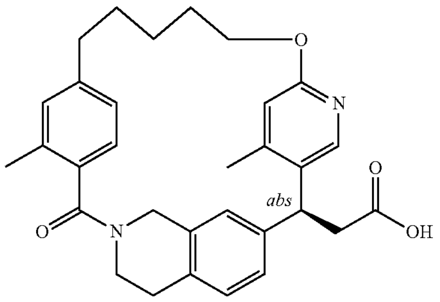 [SMILES: Cc1cc2ccc1C(=O)N1CCc3ccc(cc3C1)[C@H](CC(=O)O)c1cnc(cc1C)OCCCCC2] |
| 100 | 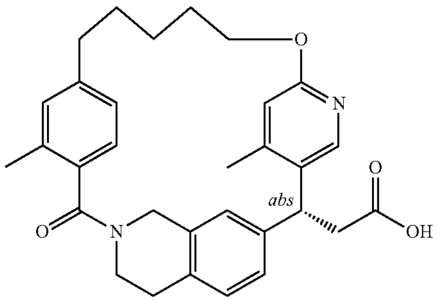 [SMILES: Cc1cc2ccc1C(=O)N1CCc3ccc(cc3C1)[C@@H](CC(=O)O)c1cnc(cc1C)OCCCCC2] |

TABLE 2-continued
| Comp'd No | Structure |
| --- | --- |
| 101 | 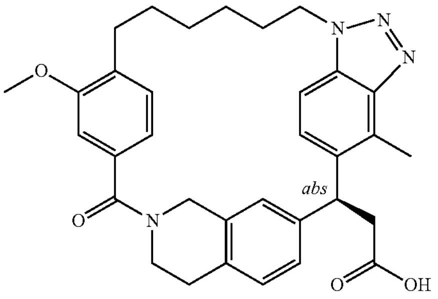 |
| 102 | 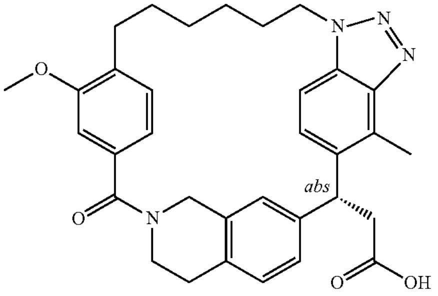 |
| 103 | 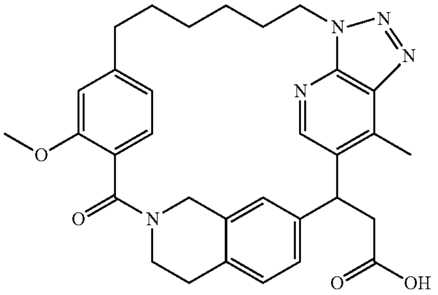 |
| 104 | 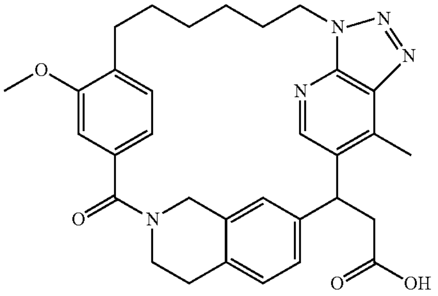 |
| 105 | 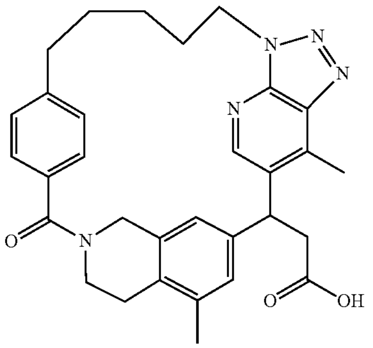 [SMILES: Cc1cc2cc3c1CCN(C3)C(=O)c1ccc(cc1)CCCCCn1nnc3c(C)c(cnc31)C2CC(=O)O] |
TABLE 2-continued
| Comp'd No | Structure |
| --- | --- |
| 106 | 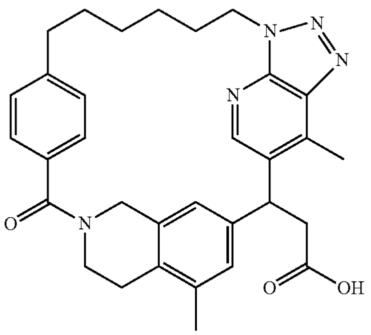 [SMILES: Cc1cc2cc3c1CCN(C3)C(=O)c1ccc(cc1)CCCCCCn1nnc3c(C)c(cnc31)C2CC(=O)O] |
| 107 | 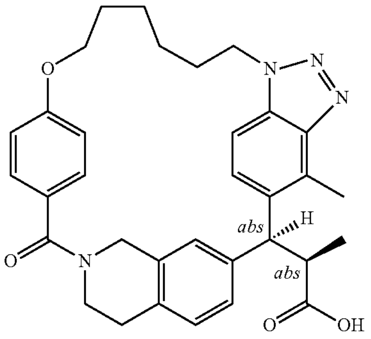 [SMILES: Cc1c2ccc3c1nnn3CCCCCCOc1ccc(cc1)C(=O)N1CCc3ccc(cc3C1)[C@@H]2[C@@H](C)C(=O)O] |
| 108 | 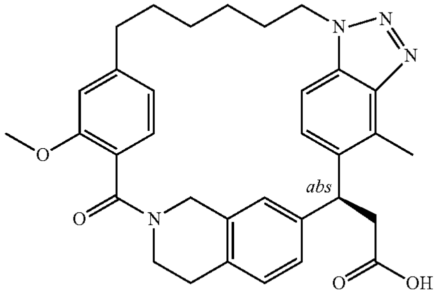 |
| 109 | 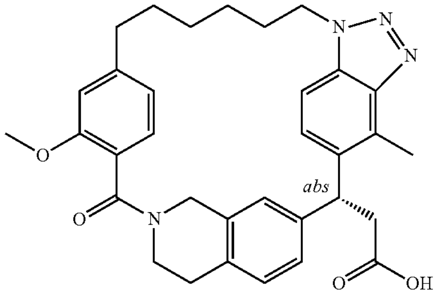 |

TABLE 2-continued
| Comp'd No | Structure |
|---|---|
| 110 | 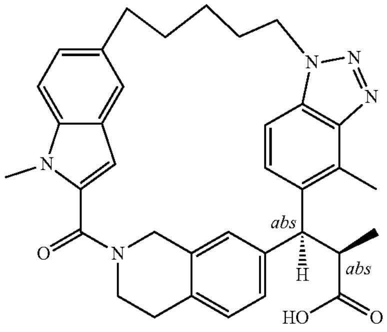 [SMILES: Cc1c2ccc3c1nnn3CCCCCc1ccc3c(c1)cc(n3C)C(=O)N1CCc3ccc(cc3C1)[C@@H]2[C@@H](C)C(=O)O] |
| 111 | 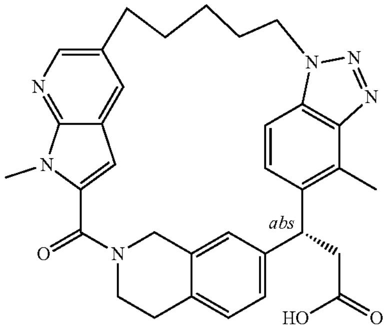 [SMILES: Cc1c2ccc3c1nnn3CCCCCc1cnc3c(c1)cc(n3C)C(=O)N1CCc3ccc(cc3C1)[C@H]2CC(=O)O] |
| 112 | 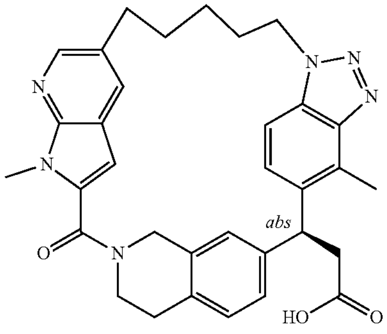 [SMILES: Cc1c2ccc3c1nnn3CCCCCc1cnc3c(c1)cc(n3C)C(=O)N1CCc3ccc(cc3C1)[C@@H]2CC(=O)O] |
| 113 | 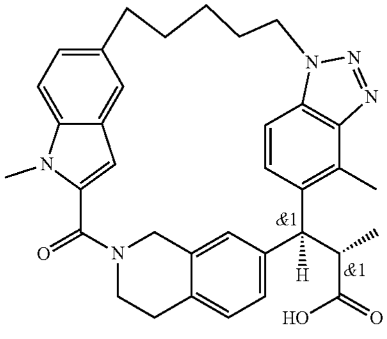 [SMILES: Cc1c2ccc3c1nnn3CCCCCc1ccc3c(c1)cc(n3C)C(=O)N1CCc3ccc(cc3C1)[C@@H]2[C@H](C)C(=O)O] |
TABLE 2-continued
| Comp'd No | Structure |
|---|---|
| 114 | 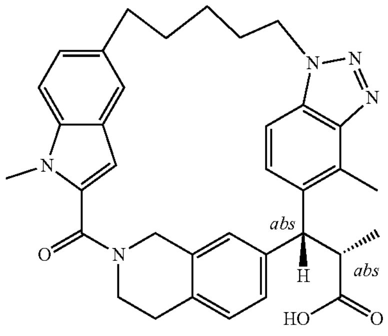 [SMILES: Cc1c2ccc3c1nnn3CCCCCc1ccc3c(c1)cc(n3C)C(=O)N1CCc3ccc(cc3C1)[C@H]2[C@H](C)C(=O)O] |
| 115 | 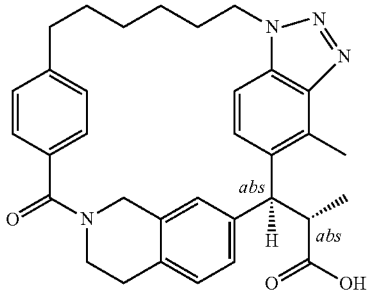 [SMILES: Cc1c2ccc3c1nnn3CCCCCCc1ccc(cc1)C(=O)N1CCc3ccc(cc3C1)[C@@H]2[C@H](C)C(=O)O] |
| 116 | 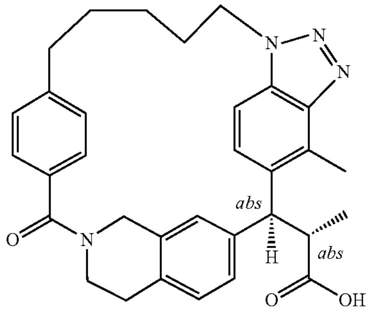 [SMILES: Cc1c2ccc3c1nnn3CCCCCc1ccc(cc1)C(=O)N1CCc3ccc(cc3C1)[C@@H]2[C@H](C)C(=O)O] |
| 117 | 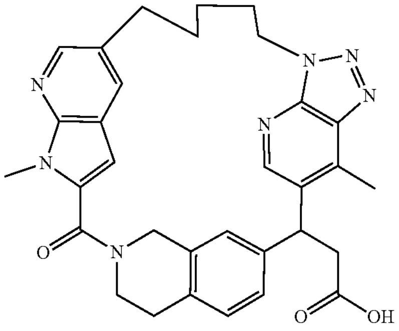 |
| 118 | 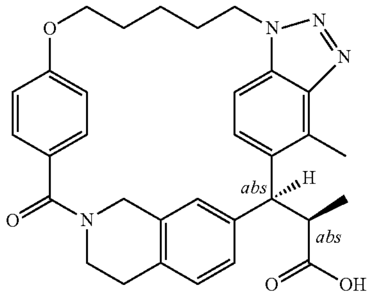 [SMILES: Cc1c2ccc3c1nnn3CCCCCOc1ccc(cc1)C(=O)N1CCc3ccc(cc3C1)[C@@H]2[C@@H](C)C(=O)O] |

TABLE 2-continued
| Comp'd No | Structure |
|---|---|
| 119 | 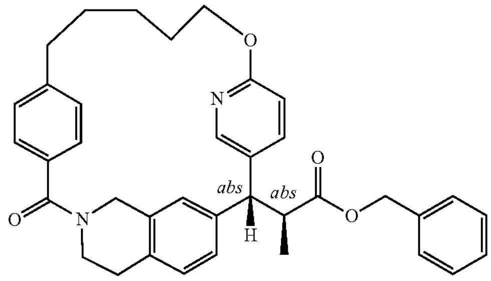 [SMILES: C[C@H](C(=O)OCc1ccccc1)[C@H]1c2ccc(nc2)OCCCCCc2ccc(cc2)C(=O)N2CCc3ccc1cc3C2] |
| 120 | 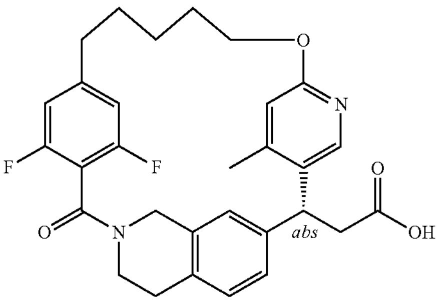 [SMILES: Cc1cc2ncc1[C@H](CC(=O)O)c1ccc3c(c1)CN(CC3)C(=O)c1c(F)cc(cc1F)CCCCCO2] |
| 121 | 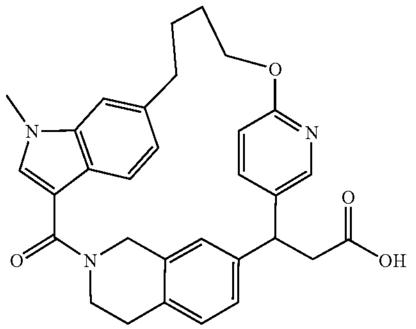 [SMILES: Cn1cc2c3ccc(cc31)CCCCOc1ccc(cn1)C(CC(=O)O)c1ccc3c(c1)CN(CC3)C2=O] |
| 122 | 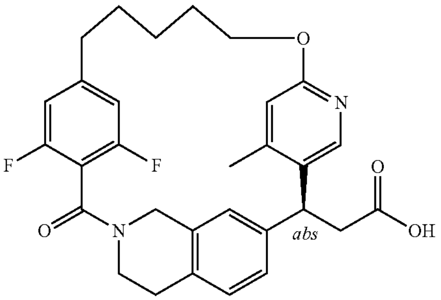 [SMILES: Cc1cc2ncc1[C@@H](CC(=O)O)c1ccc3c(c1)CN(CC3)C(=O)c1c(F)cc(cc1F)CCCCCO2] |
| 123 | 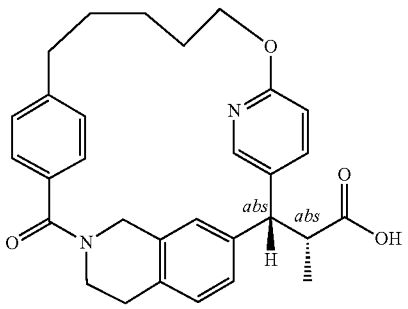 [SMILES: C[C@@H](C(=O)O)[C@H]1c2ccc(nc2)OCCCCCc2ccc(cc2)C(=O)N2CCc3ccc1cc3C2] |
TABLE 2-continued
| Comp'd No | Structure |
|---|---|
| 124 | 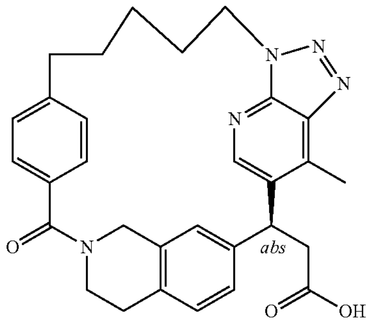 [SMILES: Cc1c2cnc3c1nnn3CCCCCc1ccc(cc1)C(=O)N1CCc3ccc(cc3C1)[C@@H]2CC(=O)O] |
| 125 | 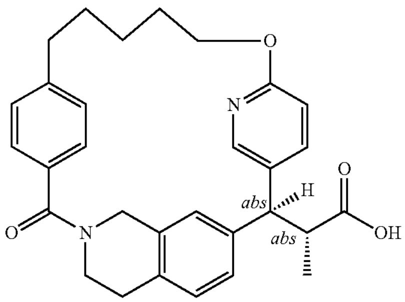 [SMILES: C[C@@H](C(=O)O)[C@@H]1c2ccc(nc2)OCCCCCc2ccc(cc2)C(=O)N2CCc3ccc1cc3C2] |
| 126 | 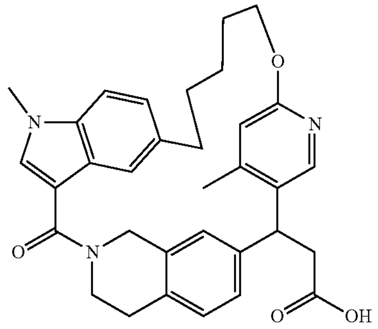 [SMILES: Cc1cc2ncc1C(CC(=O)O)c1ccc3c(c1)CN(CC3)C(=O)c1cn(C)c3ccc(cc13)CCCCCO2] |
| 127 | 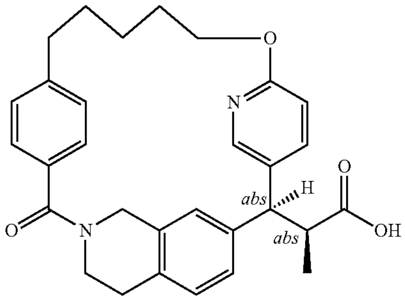 [SMILES: C[C@H](C(=O)O)[C@@H]1c2ccc(nc2)OCCCCCc2ccc(cc2)C(=O)N2CCc3ccc1cc3C2] |

TABLE 2-continued
| Comp'd No | Structure |
|---|---|
| 128 | 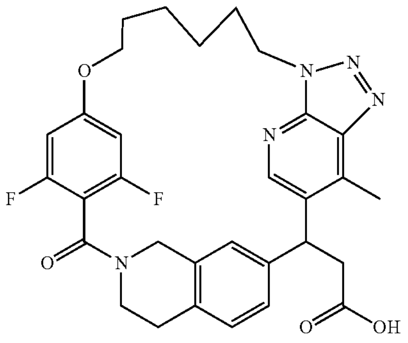 [SMILES: Cc1c2cnc3c1nnn3CCCCCCOc1cc(F)c(c(F)c1)C(=O)N1CCc3ccc(cc3C1)C2CC(=O)O] |
| 129 | 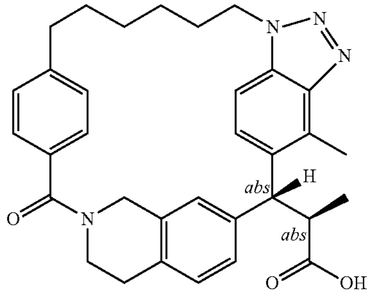 [SMILES: Cc1c2ccc3c1nnn3CCCCCCc1ccc(cc1)C(=O)N1CCc3ccc(cc3C1)[C@H]2[C@@H](C)C(=O)O] |
| 130 | 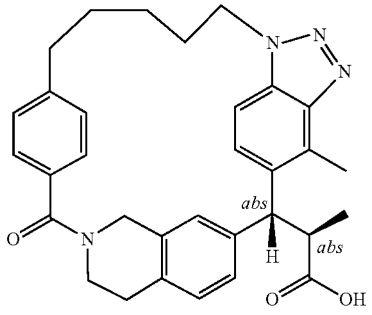 [SMILES: Cc1c2ccc3c1nnn3CCCCCc1ccc(cc1)C(=O)N1CCc3ccc(cc3C1)[C@H]2[C@@H](C)C(=O)O] |
| 131 | 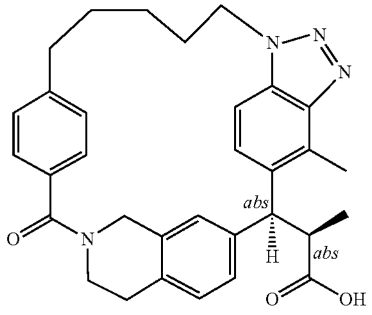 [SMILES: Cc1c2ccc3c1nnn3CCCCCc1ccc(cc1)C(=O)N1CCc3ccc(cc3C1)[C@@H]2[C@@H](C)C(=O)O] |
| 132 | 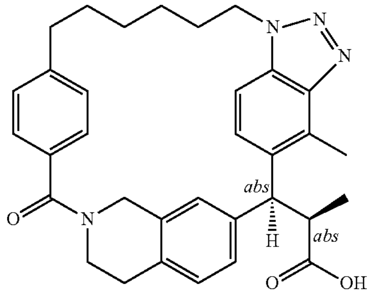 [SMILES: Cc1c2ccc3c1nnn3CCCCCCc1ccc(cc1)C(=O)N1CCc3ccc(cc3C1)[C@@H]2[C@@H](C)C(=O)O] |
TABLE 2-continued
| Comp'd No | Structure |
|---|---|
| 133 | 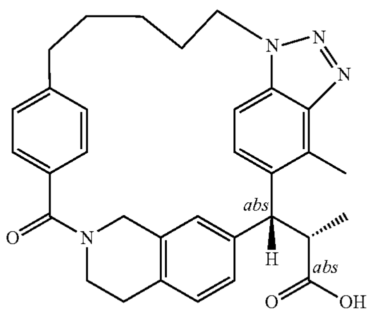 [SMILES: Cc1c2ccc3c1nnn3CCCCCc1ccc(cc1)C(=O)N1CCc3ccc(cc3C1)[C@H]2[C@H](C)C(=O)O] |
| 134 | 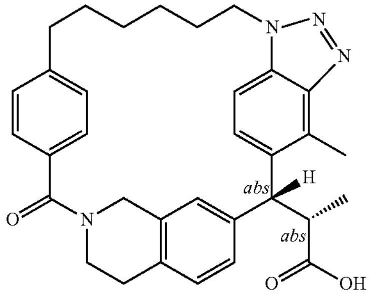 [SMILES: Cc1c2ccc3c1nnn3CCCCCCc1ccc(cc1)C(=O)N1CCc3ccc(cc3C1)[C@H]2[C@H](C)C(=O)O] |
| 135 | 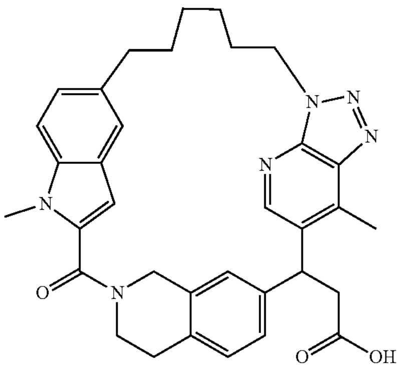 [SMILES: Cc1c2cnc3c1nnn3CCCCCCc1ccc3c(c1)cc(n3C)C(=O)N1CCc3ccc(cc3C1)C2CC(=O)O] |
| 136 | 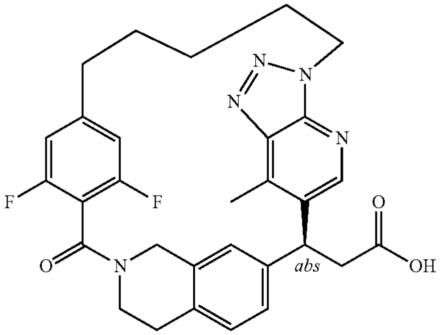 [SMILES: Cc1c2cnc3c1nnn3CCCCCc1cc(F)c(c(F)c1)C(=O)N1CCc3ccc(cc3C1)[C@@H]2CC(=O)O] |

TABLE 2-continued
| Comp'd No | Structure |
| --- | --- |
| 137 | 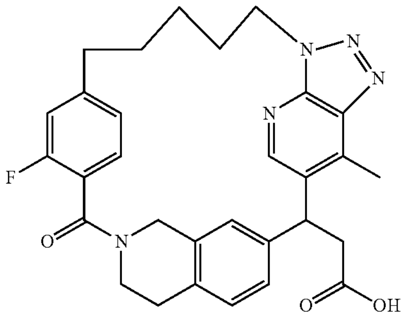 [SMILES: Cc1c2cnc3c1nnn3CCCCCc1ccc(c(F)c1)C(=O)N1CCc3ccc(cc3C1)C2CC(=O)O] |
| 138 | 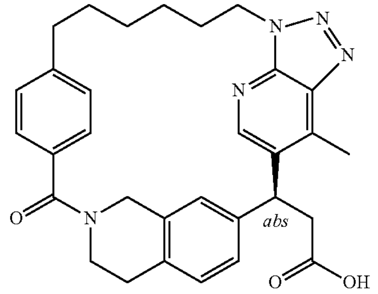 [SMILES: Cc1c2cnc3c1nnn3CCCCCCc1ccc(cc1)C(=O)N1CCc3ccc(cc3C1)[C@@H]2CC(=O)O] |
| 139 | 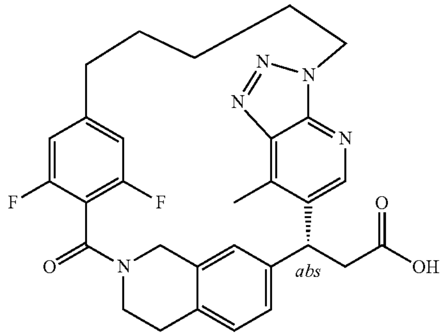 [SMILES: Cc1c2cnc3c1nnn3CCCCCc1cc(F)c(c(F)c1)C(=O)N1CCc3ccc(cc3C1)[C@H]2CC(=O)O] |
| 140 | 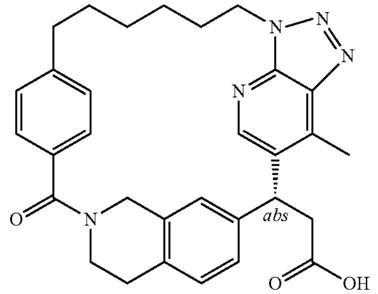 [SMILES: Cc1c2cnc3c1nnn3CCCCCCc1ccc(cc1)C(=O)N1CCc3ccc(cc3C1)[C@H]2CC(=O)O] |
| 141 | 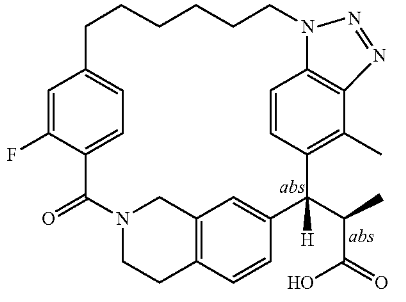 [SMILES: Cc1c2ccc3c1nnn3CCCCCCc1ccc(c(F)c1)C(=O)N1CCc3ccc(cc3C1)[C@H]2[C@@H](C)C(=O)O] |
| 142 | 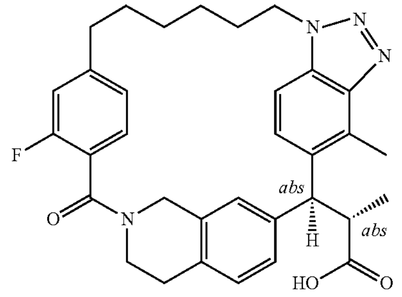 [SMILES: Cc1c2ccc3c1nnn3CCCCCCc1ccc(c(F)c1)C(=O)N1CCc3ccc(cc3C1)[C@@H]2[C@H](C)C(=O)O] |
| 143 | 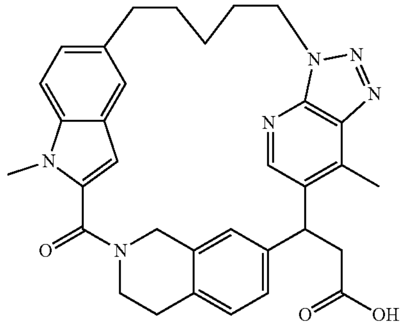 [SMILES: Cc1c2cnc3c1nnn3CCCCCc1ccc3c(c1)cc(n3C)C(=O)N1CCc3ccc(cc3C1)C2CC(=O)O] |
| 144 | 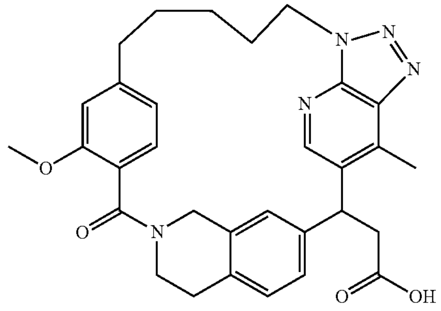 |
| 145 | 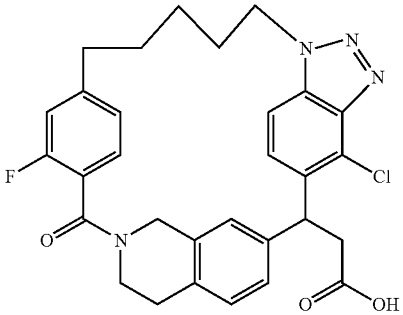 [SMILES: O=C(O)CC1c2ccc3c(c2)CN(CC3)C(=O)c2ccc(cc2F)CCCCCn2nnc3c(Cl)c1ccc32] |
| 146 | 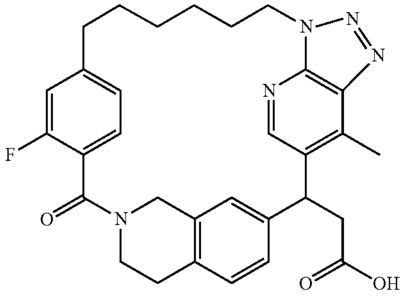 [SMILES: Cc1c2cnc3c1nnn3CCCCCCc1ccc(c(F)c1)C(=O)N1CCc3ccc(cc3C1)C2CC(=O)O] |

TABLE 2-continued
| Comp'd No | Structure |
| --- | --- |
| 147 | 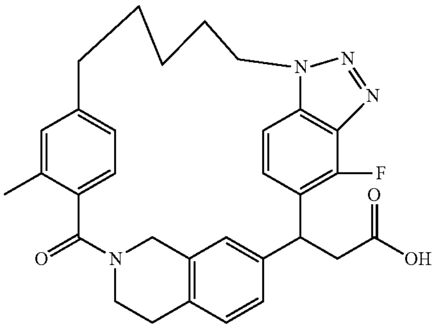 [SMILES: Cc1cc2ccc1C(=O)N1CCc3ccc(cc3C1)C(CC(=O)O)c1ccc3c(nnn3CCCCC2)c1F] |
| 148 | 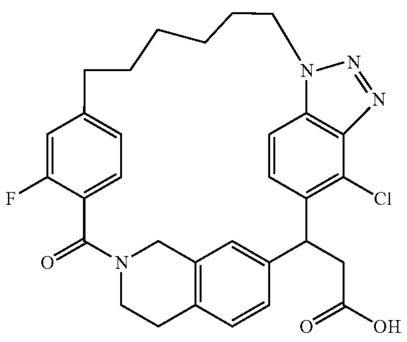 [SMILES: O=C(O)CC1c2ccc3c(c2)CN(CC3)C(=O)c2ccc(cc2F)CCCCCCn2nnc3c(Cl)c1ccc32] |
| 149 | 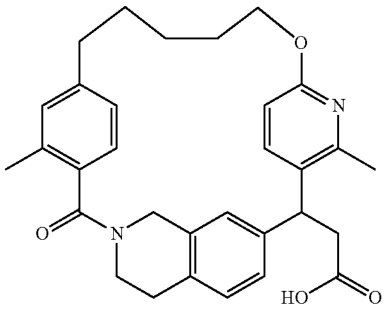 [SMILES: Cc1cc2ccc1C(=O)N1CCc3ccc(cc3C1)C(CC(=O)O)c1ccc(nc1C)OCCCCC2] |
| 150 | 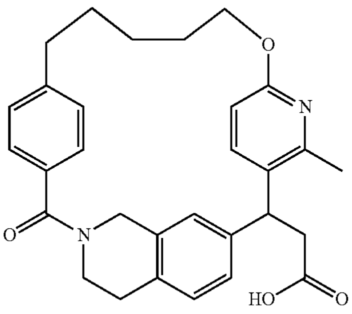 [SMILES: Cc1nc2ccc1C(CC(=O)O)c1ccc3c(c1)CN(CC3)C(=O)c1ccc(cc1)CCCCCO2] |
TABLE 2-continued
| Comp'd No | Structure |
| --- | --- |
| 151 | 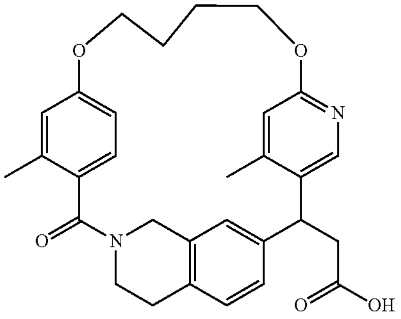 [SMILES: Cc1cc2ccc1C(=O)N1CCc3ccc(cc3C1)C(CC(=O)O)c1cnc(cc1C)OCCCCO2] |
| 152 | 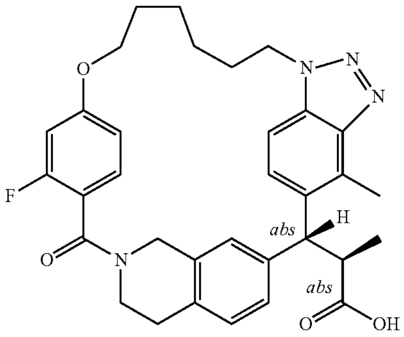 [SMILES: Cc1c2ccc3c1nnn3CCCCCCOc1ccc(c(F)c1)C(=O)N1CCc3ccc(cc3C1)[C@H]2[C@@H](C)C(=O)O] |
| 153 | 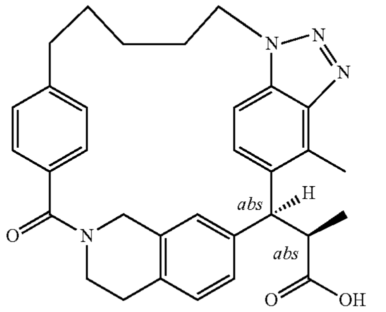 [SMILES: Cc1c2ccc3c1nnn3CCCCCc1ccc(cc1)C(=O)N1CCc3ccc(cc3C1)[C@@H]2[C@@H](C)C(=O)O] |
| 154 | 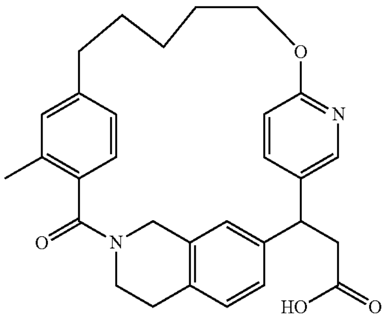 [SMILES: Cc1cc2ccc1C(=O)N1CCc3ccc(cc3C1)C(CC(=O)O)c1ccc(nc1)OCCCCC2] |

TABLE 2-continued
| Comp'd No | Structure |
|---|---|
| 155 | 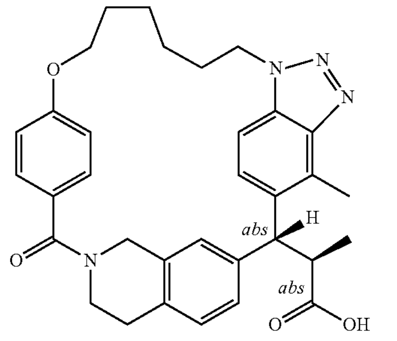 [SMILES: Cc1c2ccc3c1nnn3CCCCCCOc1ccc(cc1)C(=O)N1CCc3ccc(cc3C1)[C@H]2[C@@H](C)C(=O)O] |
| 156 | 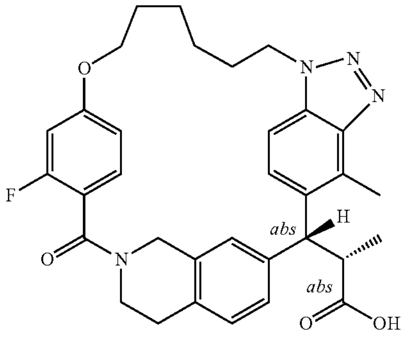 [SMILES: Cc1c2ccc3c1nnn3CCCCCCOc1ccc(c(F)c1)C(=O)N1CCc3ccc(cc3C1)[C@H]2[C@H](C)C(=O)O] |
| 157 | 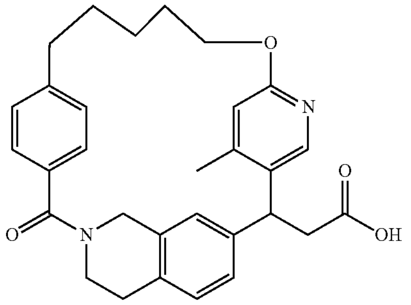 [SMILES: Cc1cc2ncc1C(CC(=O)O)c1ccc3c(c1)CN(CC3)C(=O)c1ccc(cc1)CCCCCO2] |
| 158 | 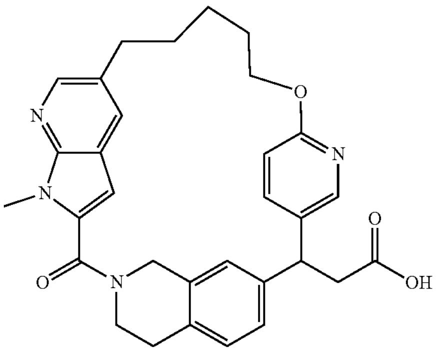 [SMILES: Cn1c2cc3cc(cnc31)CCCCCOc1ccc(cn1)C(CC(=O)O)c1ccc3c(c1)CN(CC3)C2=O] |
TABLE 2-continued
| Comp'd No | Structure |
|---|---|
| 159 | 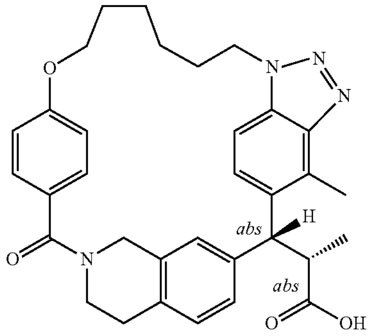 [SMILES: Cc1c2ccc3c1nnn3CCCCCCOc1ccc(cc1)C(=O)N1CCc3ccc(cc3C1)[C@H]2[C@H](C)C(=O)O] |
| 160 | 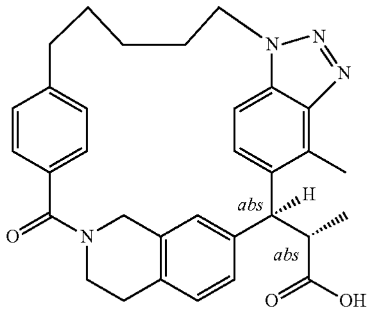 [SMILES: Cc1c2ccc3c1nnn3CCCCCc1ccc(cc1)C(=O)N1CCc3ccc(cc3C1)[C@@H]2[C@H](C)C(=O)O] |
| 161 | 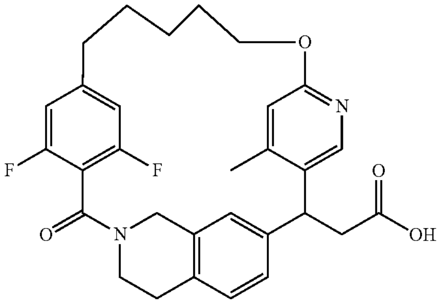 [SMILES: Cc1cc2ncc1C(CC(=O)O)c1ccc3c(c1)CN(CC3)C(=O)c1c(F)cc(cc1F)CCCCCO2] |
| 162 | 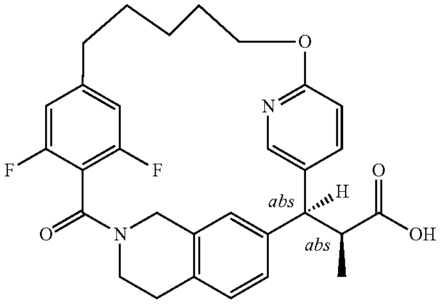 [SMILES: C[C@H](C(=O)O)[C@@H]1c2ccc(nc2)OCCCCCc2cc(F)c(c(F)c2)C(=O)N2CCc3ccc1cc3C2] |
| 163 | 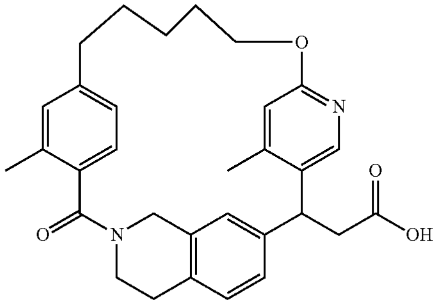 [SMILES: Cc1cc2ccc1C(=O)N1CCc3ccc(cc3C1)C(CC(=O)O)c1cnc(cc1C)OCCCCC2] |

TABLE 2-continued
| Comp'd No | Structure |
|---|---|
| 164 | 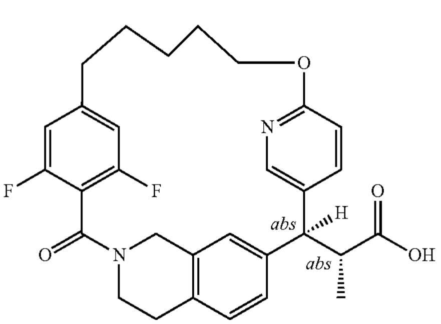 [SMILES: C[C@@H](C(=O)O)[C@@H]1c2ccc(nc2)OCCCCCc2cc(F)c(c(F)c2)C(=O)N2CCc3ccc1cc3C2] |
| 165 | 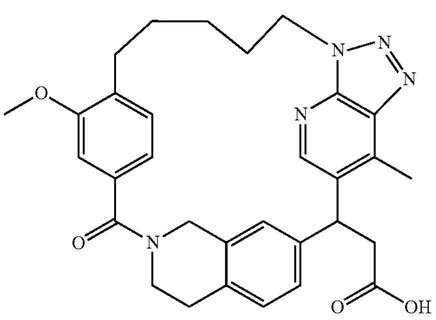 |
| 166 | 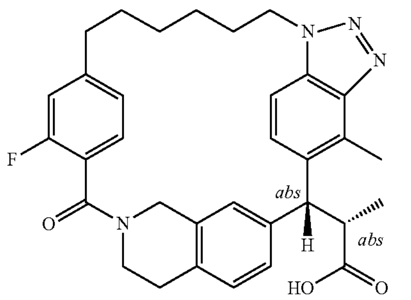 [SMILES: Cc1c2ccc3c1nnn3CCCCCCc1ccc(c(F)c1)C(=O)N1CCc3ccc(cc3C1)[C@H]2[C@H](C)C(=O)O] |
| 167 | 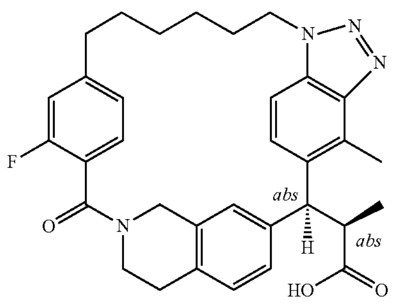 [SMILES: Cc1c2ccc3c1nnn3CCCCCCc1ccc(c(F)c1)C(=O)N1CCc3ccc(cc3C1)[C@@H]2[C@@H](C)C(=O)O] |
| 168 | 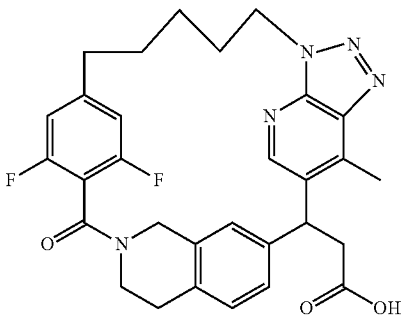 [SMILES: Cc1c2cnc3c1nnn3CCCCCc1cc(F)c(c(F)c1)C(=O)N1CCc3ccc(cc3C1)C2CC(=O)O] |
TABLE 2-continued
| Comp'd No | Structure |
|---|---|
| 169 | 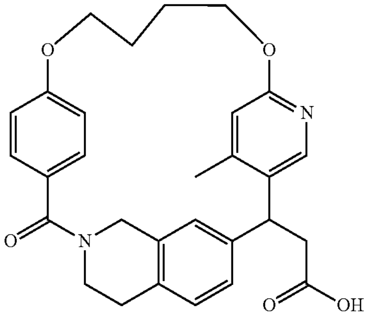 [SMILES: Cc1cc2ncc1C(CC(=O)O)c1ccc3c(c1)CN(CC3)C(=O)c1ccc(cc1)OCCCCO2] |
| 170 | 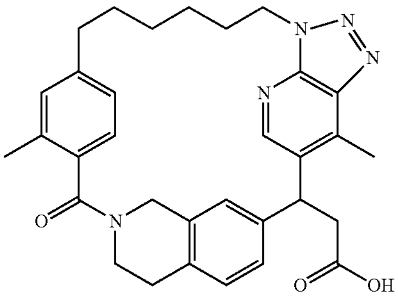 |
| 171 | 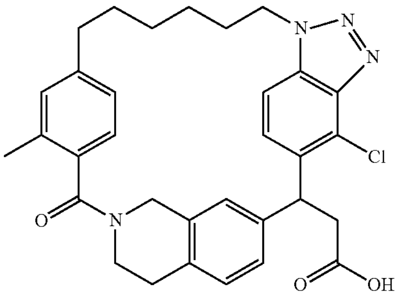 [SMILES: Cc1cc2ccc1C(=O)N1CCc3ccc(cc3C1)C(CC(=O)O)c1ccc3c(nnn3CCCCCC2)c1Cl] |
| 172 | 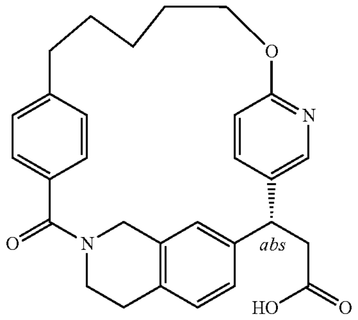 [SMILES: O=C(O)C[C@H]1c2ccc(nc2)OCCCCCc2ccc(cc2)C(=O)N2CCc3ccc1cc3C2] |
| 173 | 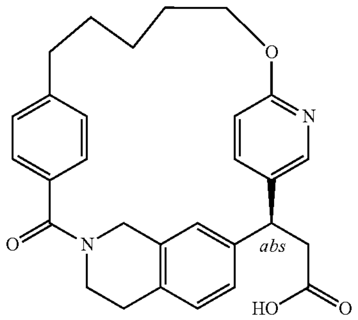 [SMILES: O=C(O)C[C@@H]1c2ccc(nc2)OCCCCCc2ccc(cc2)C(=O)N2CCc3ccc1cc3C2] |

TABLE 2-continued
| Comp'd No | Structure |
|---|---|
| 174 | 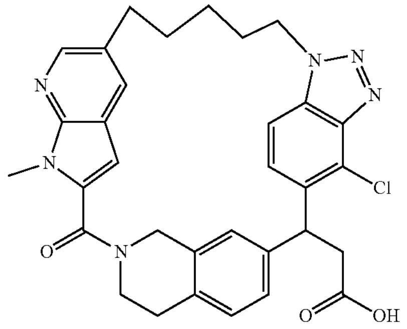 [SMILES: Cn1c2cc3cc(cnc31)CCCCCn1nnc3c(Cl)c(ccc31)C(CC(=O)O)c1ccc3c(c1)CN(CC3)C2=O] |
| 175 | 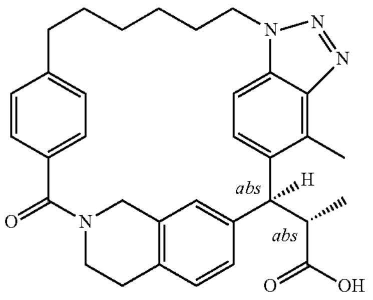 [SMILES: Cc1c2ccc3c1nnn3CCCCCCc1ccc(cc1)C(=O)N1CCc3ccc(cc3C1)[C@@H]2[C@H](C)C(=O)O] |
| 176 | 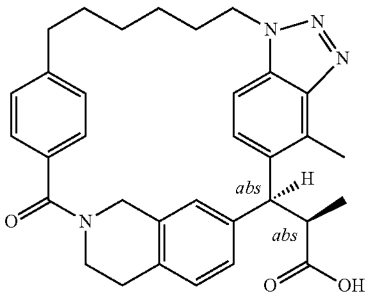 [SMILES: Cc1c2ccc3c1nnn3CCCCCCc1ccc(cc1)C(=O)N1CCc3ccc(cc3C1)[C@@H]2[C@@H](C)C(=O)O] |
| 177 | 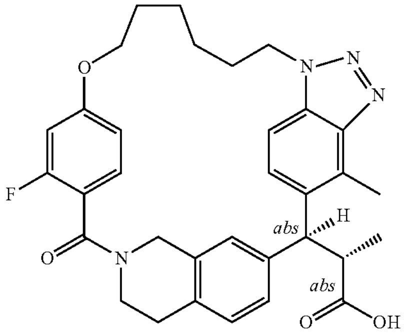 [SMILES: Cc1c2ccc3c1nnn3CCCCCCOc1ccc(c(F)c1)C(=O)N1CCc3ccc(cc3C1)[C@@H]2[C@H](C)C(=O)O] |
| 178 | 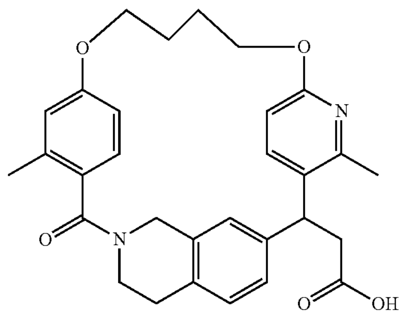 |
| 179 | 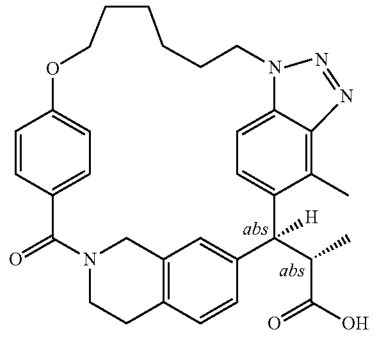 [SMILES: Cc1c2ccc3c1nnn3CCCCCCOc1ccc(cc1)C(=O)N1CCc3ccc(cc3C1)[C@@H]2[C@H](C)C(=O)O] |
| 180 | 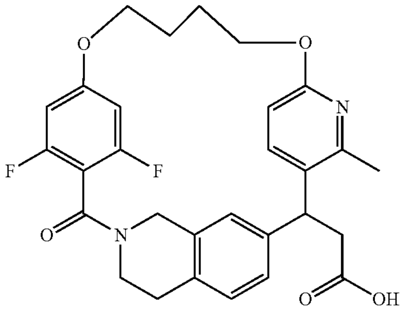 [SMILES: Cc1nc2ccc1C(CC(=O)O)c1ccc3c(c1)CN(CC3)C(=O)c1c(F)cc(cc1F)OCCCCO2] |
| 181 | 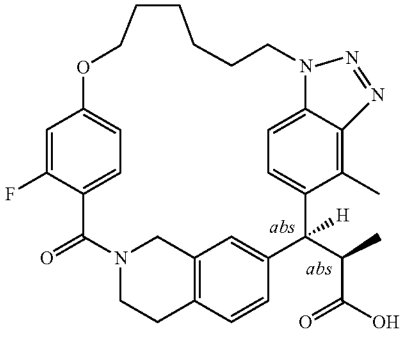 [SMILES: Cc1c2ccc3c1nnn3CCCCCCOc1ccc(c(F)c1)C(=O)N1CCc3ccc(cc3C1)[C@@H]2[C@@H](C)C(=O)O] |
| 182 | 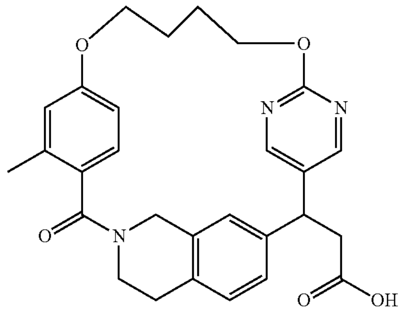 [SMILES: Cc1cc2ccc1C(=O)N1CCc3ccc(cc3C1)C(CC(=O)O)c1cnc(nc1)OCCCCO2] |

TABLE 2-continued
| Comp'd No | Structure |
|---|---|
| 183 | 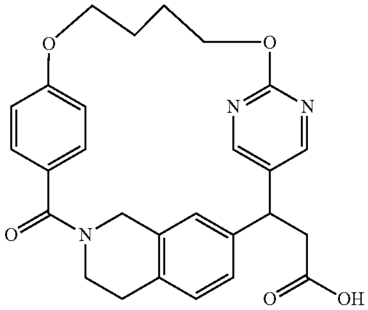 [SMILES: O=C(O)CC1c2cnc(nc2)OCCCCOc2ccc(cc2)C(=O)N2CCc3ccc1cc3C2] |
| 184 | 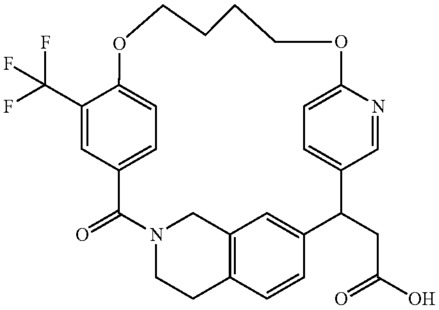 [SMILES: O=C(O)CC1c2ccc(nc2)OCCCCOc2ccc(cc2C(F)(F)F)C(=O)N2CCc3ccc1cc3C2] |
| 185 | 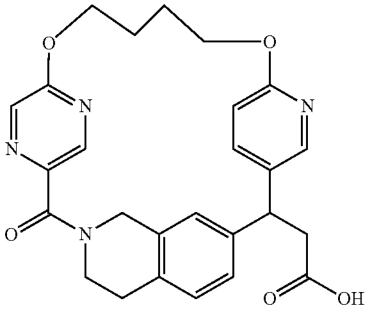 [SMILES: O=C(O)CC1c2ccc(nc2)OCCCCOc2cnc(cn2)C(=O)N2CCc3ccc1cc3C2] |
| 186 | 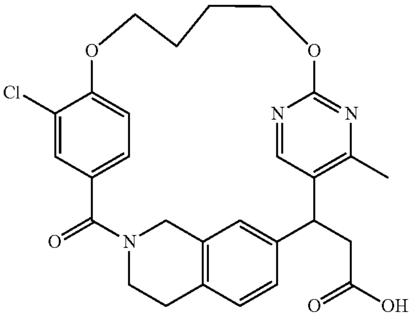 [SMILES: Cc1nc2ncc1C(CC(=O)O)c1ccc3c(c1)CN(CC3)C(=O)c1ccc(c(Cl)c1)OCCCCO2] |
| 187 | 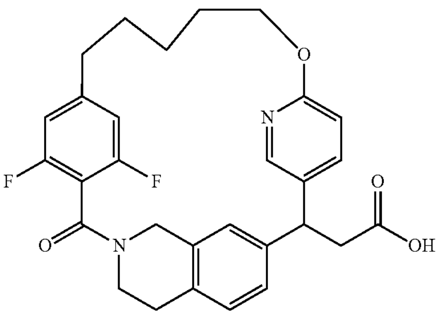 [SMILES: O=C(O)CC1c2ccc(nc2)OCCCCCc2cc(F)c(c(F)c2)C(=O)N2CCc3ccc1cc3C2] |
TABLE 2-continued
| Comp'd No | Structure |
|---|---|
| 188 | 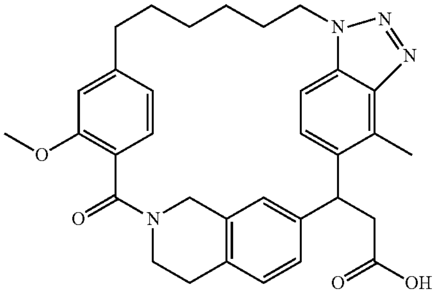 |
| 189 | 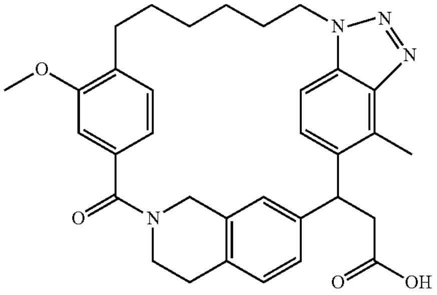 |
| 190 | 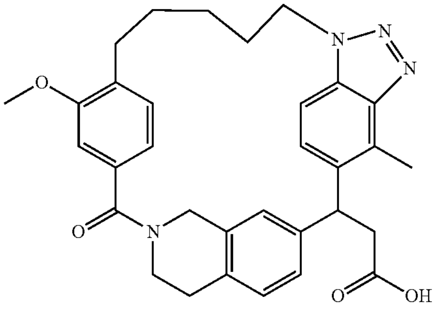 |
| 191 | 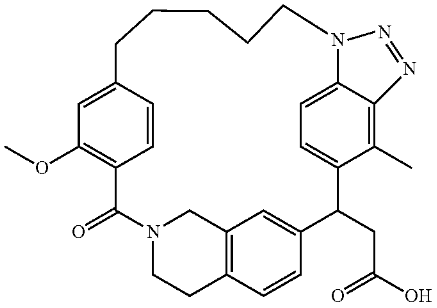 |

TABLE 2-continued
| Comp'd No | Structure |
| --- | --- |
| 192 | 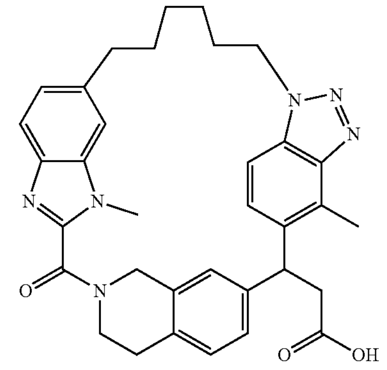 [SMILES: Cc1c2ccc3c1nnn3CCCCCCc1ccc3nc(n(C)c3c1)C(=O)N1CCc3ccc(cc3C1)C2CC(=O)O] |
| 193 | 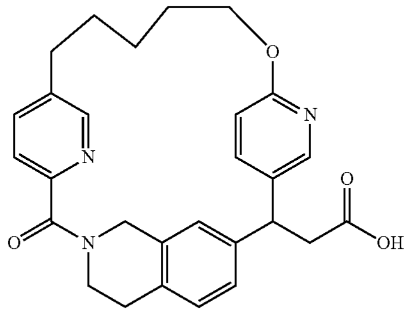 [SMILES: O=C(O)CC1c2ccc(nc2)OCCCCCc2ccc(nc2)C(=O)N2CCc3ccc1cc3C2] |
| 194 | 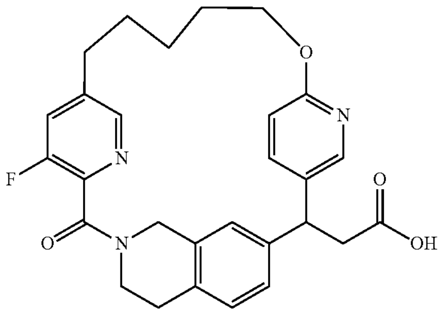 [SMILES: O=C(O)CC1c2ccc(nc2)OCCCCCc2cnc(c(F)c2)C(=O)N2CCc3ccc1cc3C2] |
| 195 | 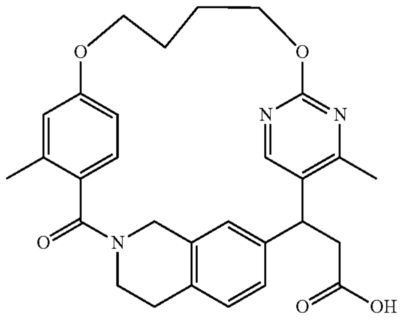 |
TABLE 2-continued
| Comp'd No | Structure |
| --- | --- |
| 196 | 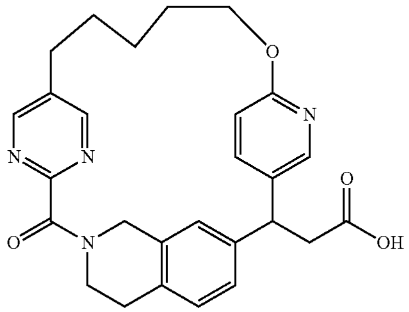 |
| 197 | 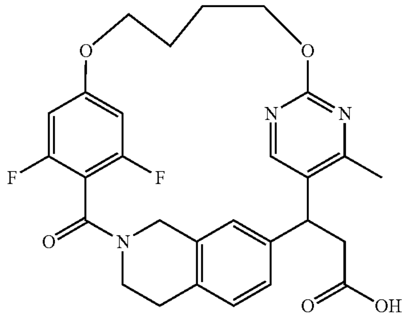 [SMILES: Cc1nc2ncc1C(CC(=O)O)c1ccc3c(c1)CN(CC3)C(=O)c1c(F)cc(cc1F)OCCCCO2] |
| 198 | 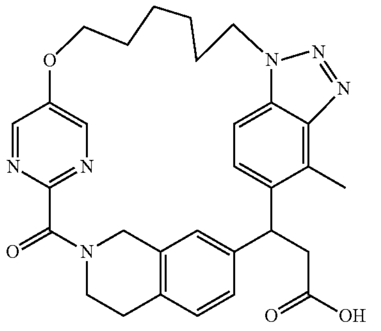 [SMILES: Cc1c2ccc3c1nnn3CCCCCCOc1cnc(nc1)C(=O)N1CCc3ccc(cc3C1)C2CC(=O)O] |
| 199 | 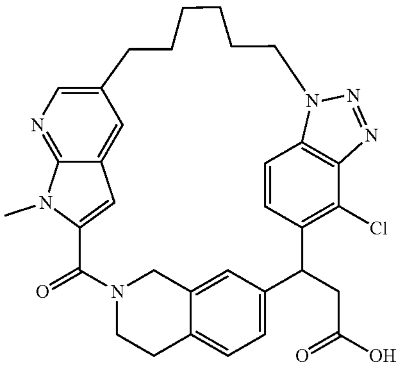 [SMILES: Cn1c2cc3cc(cnc31)CCCCCCn1nnc3c(Cl)c(ccc31)C(CC(=O)O)c1ccc3c(c1)CN(CC3)C2=O] |

TABLE 2-continued
| Comp'd No | Structure |
|---|---|
| 200 | 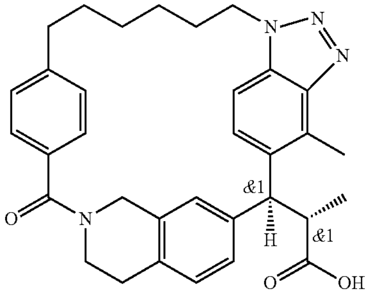 [SMILES: Cc1c2ccc3c1nnn3CCCCCCc1ccc(cc1)C(=O)N1CCc3ccc(cc3C1)[C@@H]2[C@H](C)C(=O)O] |
| 201 | 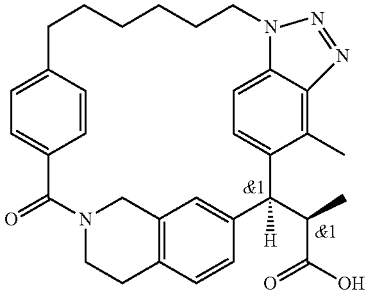 [SMILES: Cc1c2ccc3c1nnn3CCCCCCc1ccc(cc1)C(=O)N1CCc3ccc(cc3C1)[C@@H]2[C@@H](C)C(=O)O] |
| 202 | 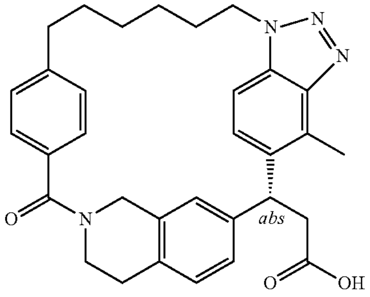 [SMILES: Cc1c2ccc3c1nnn3CCCCCCc1ccc(cc1)C(=O)N1CCc3ccc(cc3C1)[C@H]2CC(=O)O] |
| 203 | 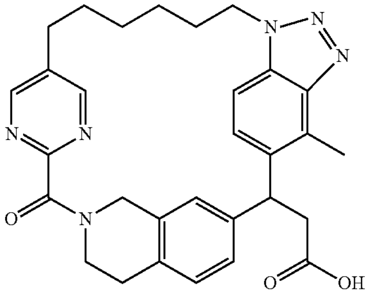 [SMILES: Cc1c2ccc3c1nnn3CCCCCCc1cnc(nc1)C(=O)N1CCc3ccc(cc3C1)C2CC(=O)O] |
| 204 | 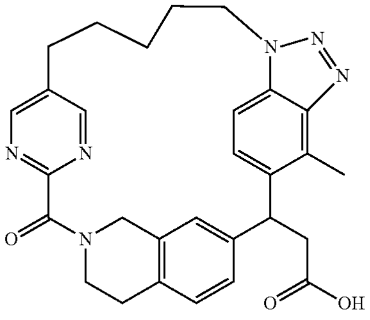 [SMILES: Cc1c2ccc3c1nnn3CCCCCc1cnc(nc1)C(=O)N1CCc3ccc(cc3C1)C2CC(=O)O] |
TABLE 2-continued
| Comp'd No | Structure |
|---|---|
| 205 | 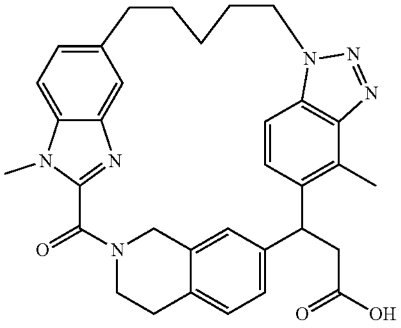 |
| 206 | 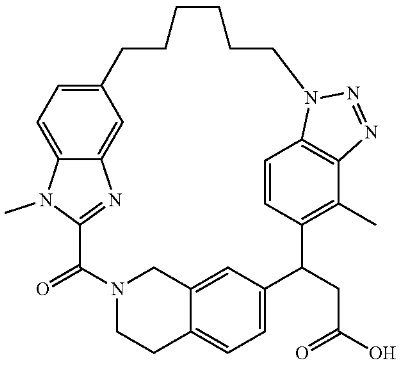 [SMILES: Cc1c2ccc3c1nnn3CCCCCCc1ccc3c(c1)nc(n3C)C(=O)N1CCc3ccc(cc3C1)C2CC(=O)O] |
| 207 | 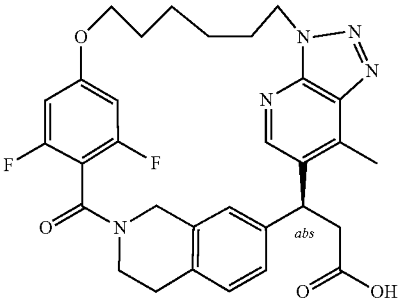 [SMILES: Cc1c2cnc3c1nnn3CCCCCCOc1cc(F)c(c(F)c1)C(=O)N1CCc3ccc(cc3C1)[C@@H]2CC(=O)O] |
| 208 | 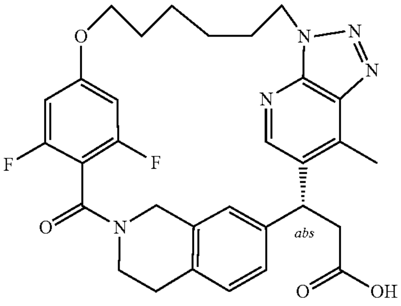 [SMILES: Cc1c2cnc3c1nnn3CCCCCCOc1cc(F)c(c(F)c1)C(=O)N1CCc3ccc(cc3C1)[C@H]2CC(=O)O] |

TABLE 2-continued
| Comp'd No | Structure |
| --- | --- |
| 209 | 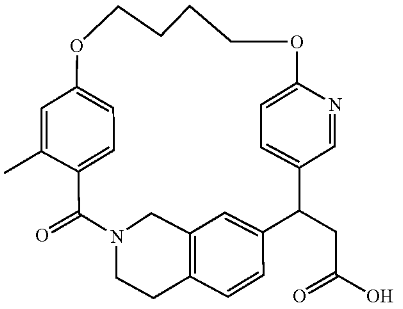 [SMILES: Cc1cc2ccc1C(=O)N1CCc3ccc(cc3C1)C(CC(=O)O)c1ccc(nc1)OCCCCO2] |
| 210 | 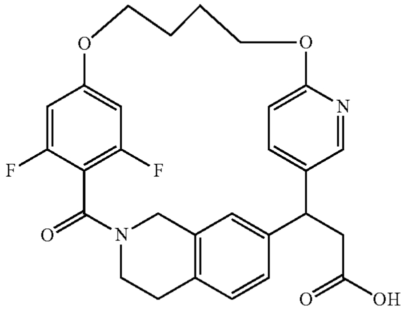 [SMILES: O=C(O)CC1c2ccc(nc2)OCCCCOc2cc(F)c(c(F)c2)C(=O)N2CCc3ccc1cc3C2] |
| 211 | 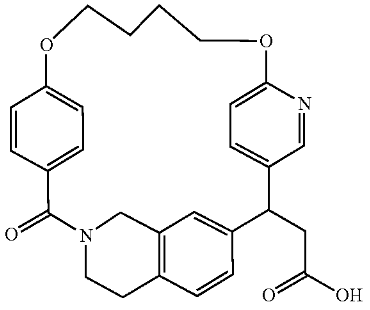 [SMILES: O=C(O)CC1c2ccc(nc2)OCCCCOc2ccc(cc2)C(=O)N2CCc3ccc1cc3C2] |
| 212 | 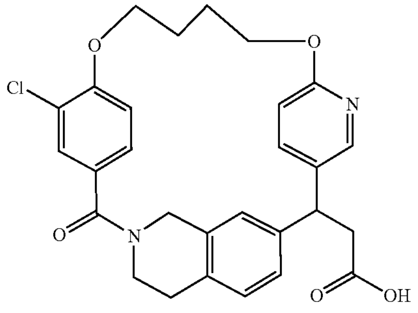 [SMILES: O=C(O)CC1c2ccc(nc2)OCCCCOc2ccc(cc2Cl)C(=O)N2CCc3ccc1cc3C2] |
| 213 | 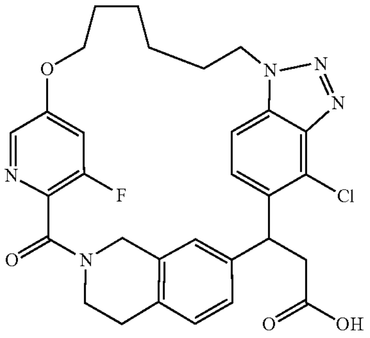 [SMILES: O=C(O)CC1c2ccc3c(c2)CN(CC3)C(=O)c2ncc(cc2F)OCCCCCCn2nnc3c(Cl)c1ccc32] |
TABLE 2-continued
| Comp'd No | Structure |
| --- | --- |
| 214 | 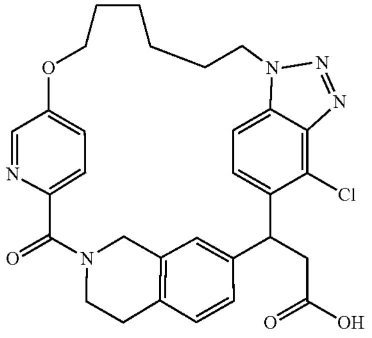 [SMILES: O=C(O)CC1c2ccc3c(c2)CN(CC3)C(=O)c2ccc(cn2)OCCCCCCn2nnc3c(Cl)c1ccc32] |
| 215 | 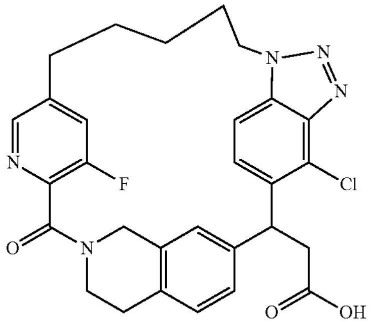 [SMILES: O=C(O)CC1c2ccc3c(c2)CN(CC3)C(=O)c2ncc(cc2F)CCCCCn2nnc3c(Cl)c1ccc32] |
| 216 | 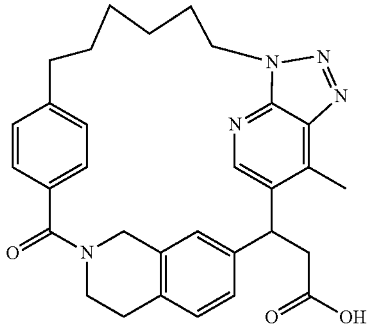 [SMILES: Cc1c2cnc3c1nnn3CCCCCCc1ccc(cc1)C(=O)N1CCc3ccc(cc3C1)C2CC(=O)O] |
| 217 | 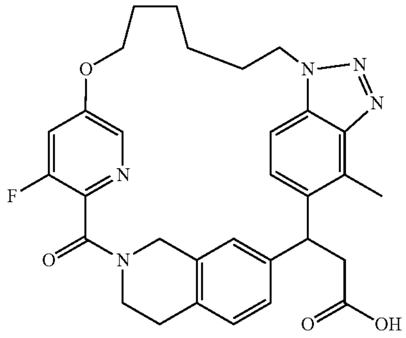 [SMILES: Cc1c2ccc3c1nnn3CCCCCCOc1cnc(c(F)c1)C(=O)N1CCc3ccc(cc3C1)C2CC(=O)O] |

TABLE 2-continued
| Comp'd No | Structure |
| --- | --- |
| 218 | 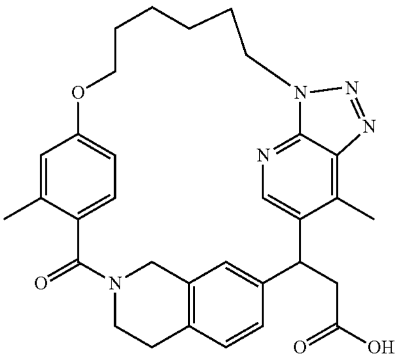 |
| 219 | 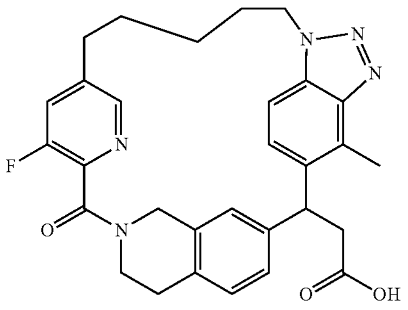 [SMILES: Cc1c2ccc3c1nnn3CCCCCc1cnc(c(F)c1)C(=O)N1CCc3ccc(cc3C1)C2CC(=O)O] |
| 220 | 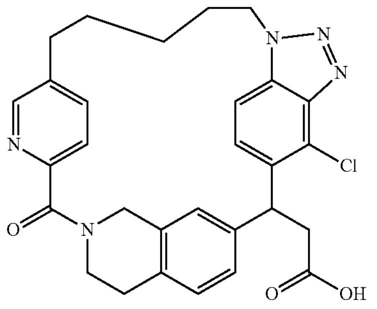 [SMILES: O=C(O)CC1c2ccc3c(c2)CN(CC3)C(=O)c2ccc(cn2)CCCCCn2nnc3c(Cl)c1ccc32] |
| 221 | 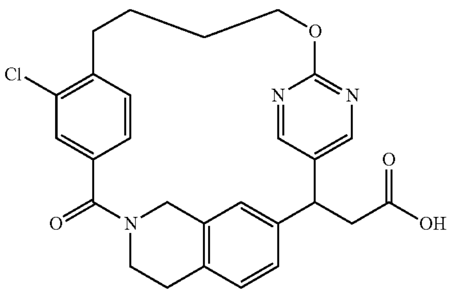 [SMILES: O=C(O)CC1c2cnc(nc2)OCCCCc2ccc(cc2Cl)C(=O)N2CCc3ccc1cc3C2] |
TABLE 2-continued
| Comp'd No | Structure |
| --- | --- |
| 222 | 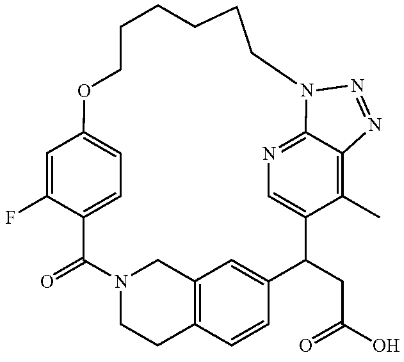 [SMILES: Cc1c2cnc3c1nnn3CCCCCCOc1ccc(c(F)c1)C(=O)N1CCc3ccc(cc3C1)C2CC(=O)O] |
| 223 | 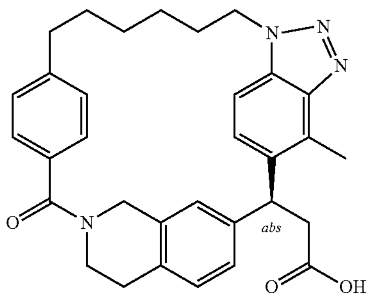 [SMILES: Cc1c2ccc3c1nnn3CCCCCCc1ccc(cc1)C(=O)N1CCc3ccc(cc3C1)[C@@H]2CC(=O)O] |
| 224 | 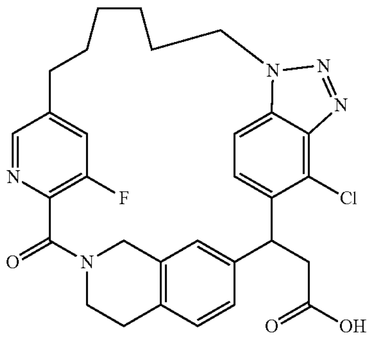 [SMILES: O=C(O)CC1c2ccc3c(c2)CN(CC3)C(=O)c2ncc(cc2F)CCCCCCn2nnc3c(Cl)c1ccc32] |
| 225 | 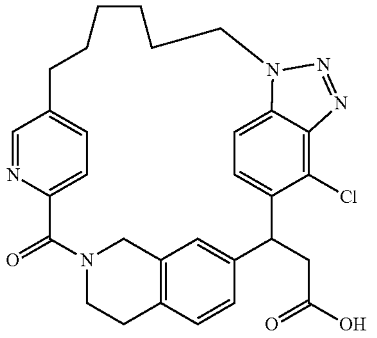 [SMILES: O=C(O)CC1c2ccc3c(c2)CN(CC3)C(=O)c2ccc(cn2)CCCCCCn2nnc3c(Cl)c1ccc32] |

TABLE 2-continued
| Comp'd No | Structure |
| --- | --- |
| 226 | 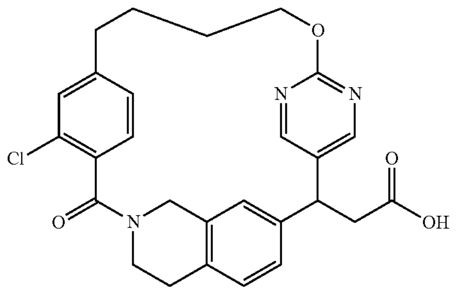 [SMILES: O=C(O)CC1c2cnc(nc2)OCCCCc2ccc(c(Cl)c2)C(=O)N2CCc3ccc1cc3C2] |
| 227 | 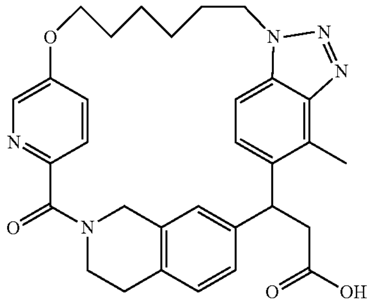 [SMILES: Cc1c2ccc3c1nnn3CCCCCCOc1ccc(nc1)C(=O)N1CCc3ccc(cc3C1)C2CC(=O)O] |
| 228 | 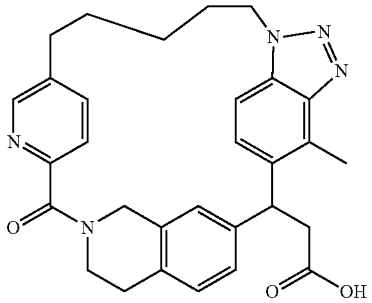 [SMILES: Cc1c2ccc3c1nnn3CCCCCc1ccc(nc1)C(=O)N1CCc3ccc(cc3C1)C2CC(=O)O] |
| 229 | 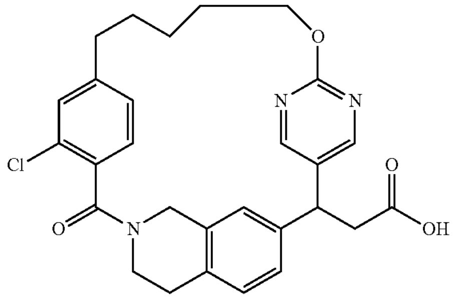 [SMILES: O=C(O)CC1c2cnc(nc2)OCCCCCc2ccc(c(Cl)c2)C(=O)N2CCc3ccc1cc3C2] |
| 230 | 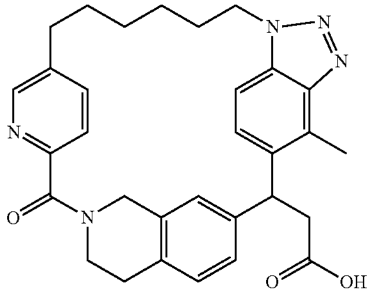 |
TABLE 2-continued
| Comp'd No | Structure |
| --- | --- |
| 231 | 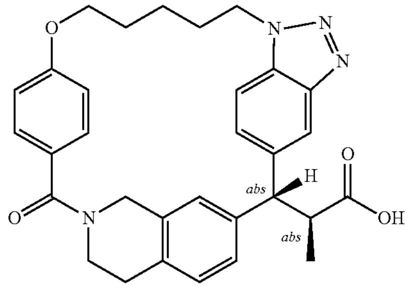 [SMILES: C[C@H](C(=O)O)[C@@H]1c2ccc3c(c2)CN(CC3)C(=O)c2ccc(cc2)OCCCCCn2nnc3cc1ccc32] |
| 232 | 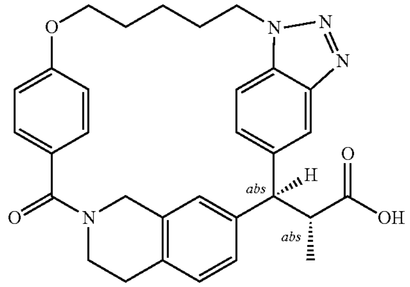 [SMILES: C[C@@H](C(=O)O)[C@H]1c2ccc3c(c2)CN(CC3)C(=O)c2ccc(cc2)OCCCCCn2nnc3cc1ccc32] |
| 233 | 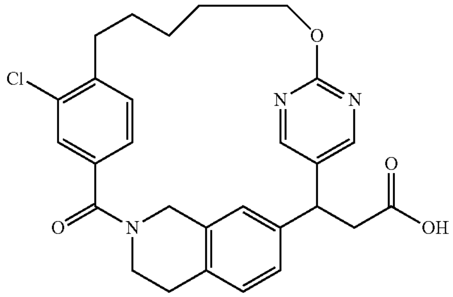 [SMILES: O=C(O)CC1c2cnc(nc2)OCCCCCc2ccc(cc2Cl)C(=O)N2CCc3ccc1cc3C2] |
| 234 | 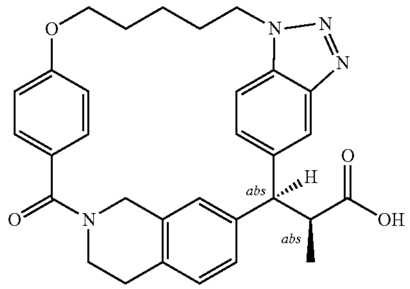 [SMILES: C[C@H](C(=O)O)[C@H]1c2ccc3c(c2)CN(CC3)C(=O)c2ccc(cc2)OCCCCCn2nnc3cc1ccc32] |
| 235 | 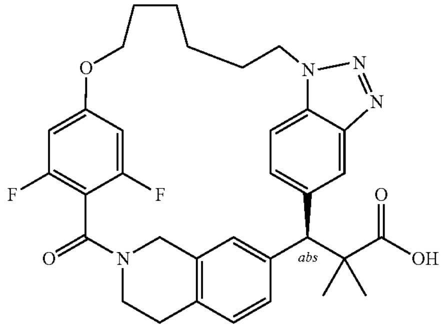 [SMILES: CC(C)(C(=O)O)[C@H]1c2ccc3c(c2)CN(CC3)C(=O)c2c(F)cc(cc2F)OCCCCCCn2nnc3cc1ccc32] |

TABLE 2-continued
| Comp'd No | Structure |
| --- | --- |
| 236 | 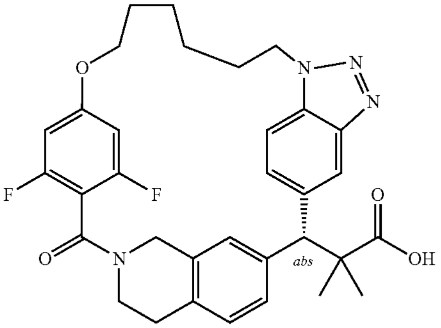 [SMILES: CC(C)(C(=O)O)[C@@H]1c2ccc3c(c2)CN(CC3)C(=O)c2c(F)cc(cc2F)OCCCCCCn2nnc3cc1ccc32] |
| 237 | 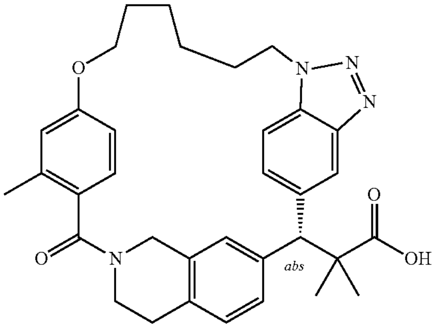 [SMILES: Cc1cc2ccc1C(=O)N1CCc3ccc(cc3C1)[C@@H](C(C)(C)C(=O)O)c1ccc3c(c1)nnn3CCCCCCO2] |
| 238 | 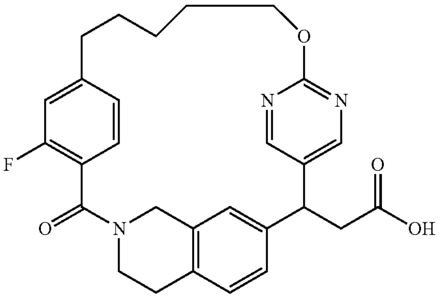 [SMILES: O=C(O)CC1c2cnc(nc2)OCCCCCc2ccc(c(F)c2)C(=O)N2CCc3ccc1cc3C2] |
| 239 | 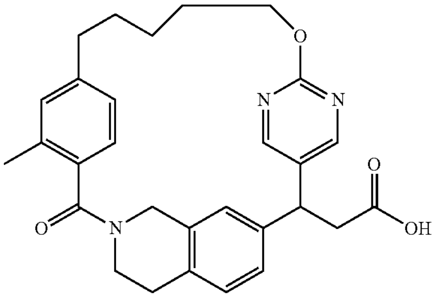 [SMILES: Cc1cc2ccc1C(=O)N1CCc3ccc(cc3C1)C(CC(=O)O)c1cnc(nc1)OCCCCC2] |
| 240 | 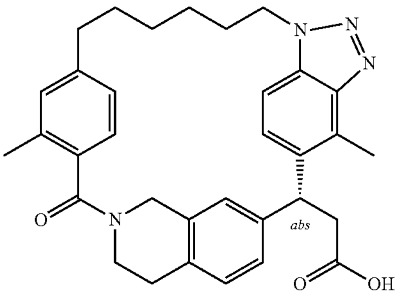 |
TABLE 2-continued
| Comp'd No | Structure |
| --- | --- |
| 241 | 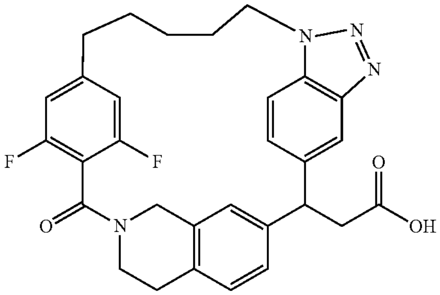 [SMILES: O=C(O)CC1c2ccc3c(c2)CN(CC3)C(=O)c2c(F)cc(cc2F)CCCCCn2nnc3cc1ccc32] |
| 242 | 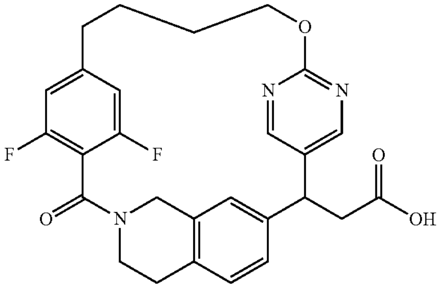 [SMILES: O=C(O)CC1c2cnc(nc2)OCCCCc2cc(F)c(c(F)c2)C(=O)N2CCc3ccc1cc3C2] |
| 243 | 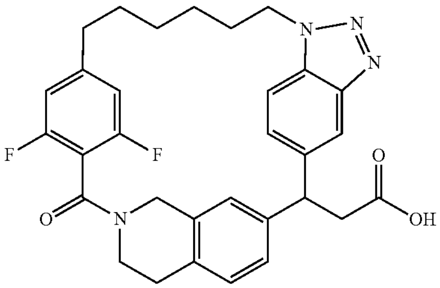 [SMILES: O=C(O)CC1c2ccc3c(c2)CN(CC3)C(=O)c2c(F)cc(cc2F)CCCCCCn2nnc3cc1ccc32] |
| 244 | 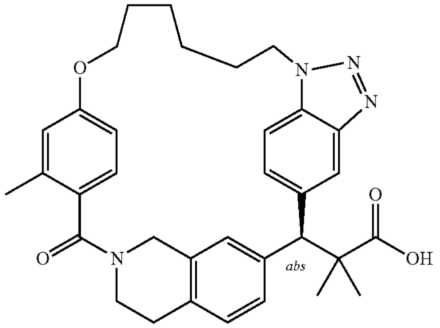 [SMILES: Cc1cc2ccc1C(=O)N1CCc3ccc(cc3C1)[C@H](C(C)(C)C(=O)O)c1ccc3c(c1)nnn3CCCCCCO2] |
| 245 | 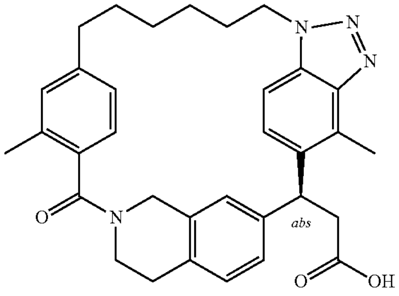 |

TABLE 2-continued
| Comp'd No | Structure |
|---|---|
| 246 | 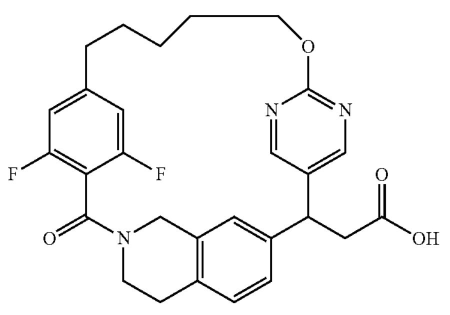 [SMILES: O=C(O)CC1c2cnc(nc2)OCCCCCc2cc(F)c(c(F)c2)C(=O)N2CCc3ccc1cc3C2] |
| 247 | 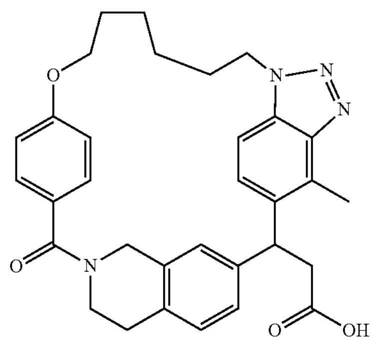 [SMILES: Cc1c2ccc3c1nnn3CCCCCCOc1ccc(cc1)C(=O)N1CCc3ccc(cc3C1)C2CC(=O)O] |
| 248 | 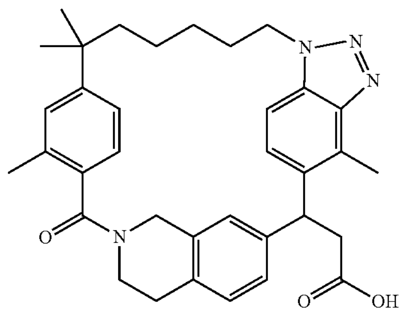 |
| 249 | 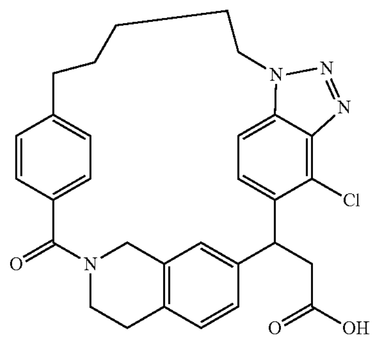 [SMILES: O=C(O)CC1c2ccc3c(c2)CN(CC3)C(=O)c2ccc(cc2)CCCCCn2nnc3c(Cl)c1ccc32] |
TABLE 2-continued
| Comp'd No | Structure |
|---|---|
| 250 | 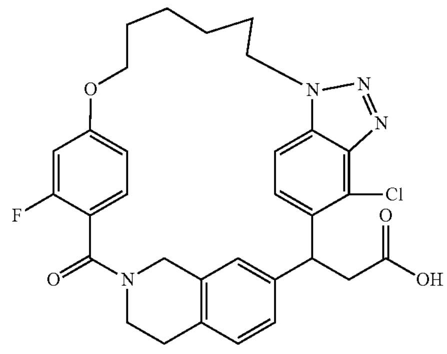 [SMILES: O=C(O)CC1c2ccc3c(c2)CN(CC3)C(=O)c2ccc(cc2F)OCCCCCCn2nnc3c(Cl)c1ccc32] |
| 251 | 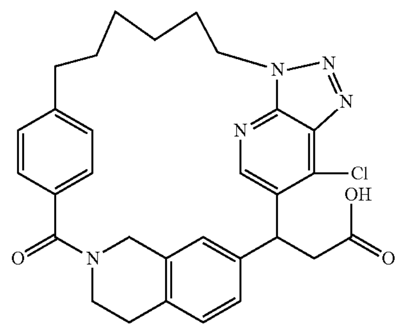 [SMILES: O=C(O)CC1c2ccc3c(c2)CN(CC3)C(=O)c2ccc(cc2)CCCCCCn2nnc3c(Cl)c1cnc32] |
| 252 | 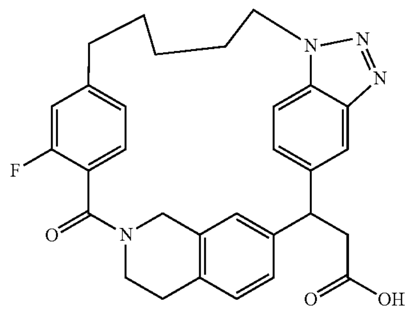 [SMILES: O=C(O)CC1c2ccc3c(c2)CN(CC3)C(=O)c2ccc(cc2F)CCCCCn2nnc3cc1ccc32] |
| 253 | 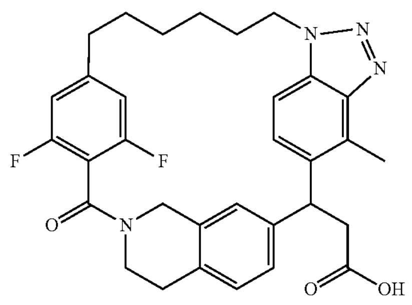 [SMILES: Cc1c2ccc3c1nnn3CCCCCCc1cc(F)c(c(F)c1)C(=O)N1CCc3ccc(cc3C1)C2CC(=O)O] |
| 254 | 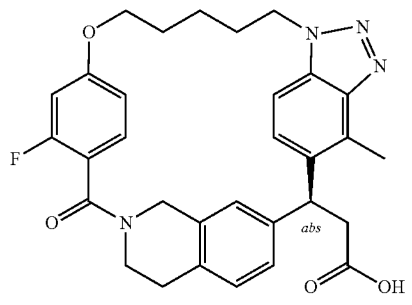 [SMILES: Cc1c2ccc3c1nnn3CCCCCOc1ccc(c(F)c1)C(=O)N1CCc3ccc(cc3C1)[C@@H]2CC(=O)O] |

TABLE 2-continued
| Comp'd No | Structure |
|---|---|
| 255 | 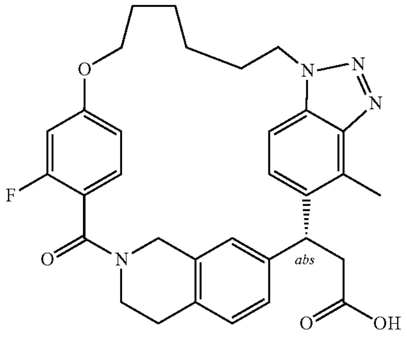 [SMILES: Cc1c2ccc3c1nnn3CCCCCCOc1ccc(c(F)c1)C(=O)N1CCc3ccc(cc3C1)[C@H]2CC(=O)O] |
| 256 | 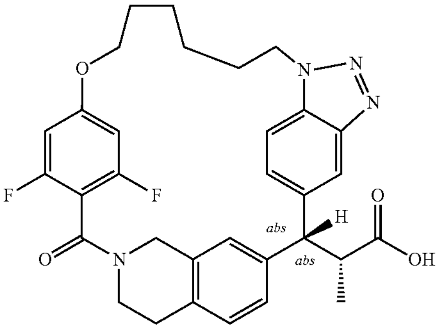 [SMILES: C[C@@H](C(=O)O)[C@@H]1c2ccc3c(c2)CN(CC3)C(=O)c2c(F)cc(cc2F)OCCCCCCn2nnc3cc1ccc32] |
| 257 | 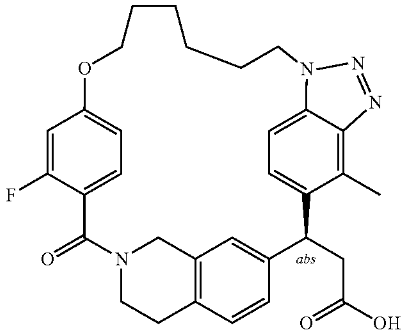 [SMILES: Cc1c2ccc3c1nnn3CCCCCCOc1ccc(c(F)c1)C(=O)N1CCc3ccc(cc3C1)[C@@H]2CC(=O)O] |
| 258 | 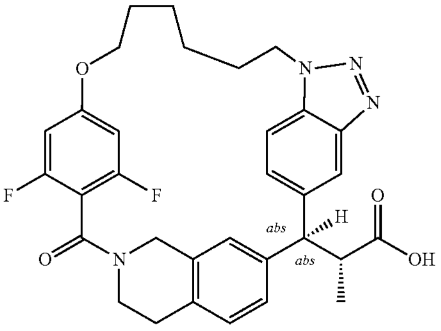 [SMILES: C[C@@H](C(=O)O)[C@H]1c2ccc3c(c2)CN(CC3)C(=O)c2c(F)cc(cc2F)OCCCCCCn2nnc3cc1ccc32] |
TABLE 2-continued
| Comp'd No | Structure |
|---|---|
| 259 | 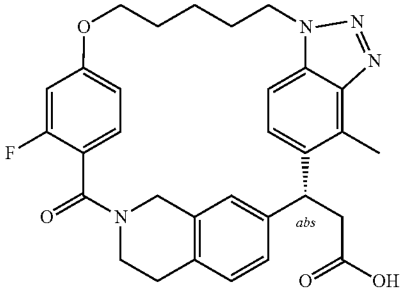 [SMILES: Cc1c2ccc3c1nnn3CCCCCOc1ccc(c(F)c1)C(=O)N1CCc3ccc(cc3C1)[C@H]2CC(=O)O] |
| 260 | 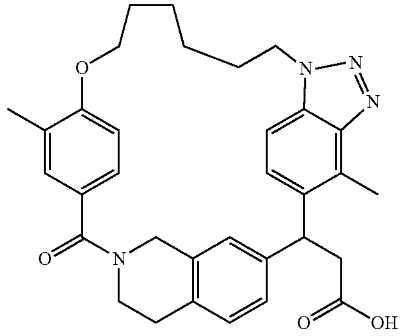 [SMILES: Cc1cc2ccc1OCCCCCCn1nnc3c(C)c(ccc31)C(CC(=O)O)c1ccc3c(c1)CN(CC3)C2=O] |
| 261 | 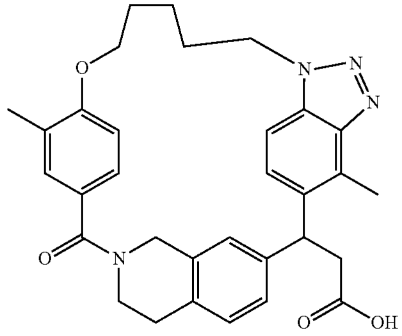 [SMILES: Cc1cc2ccc1OCCCCCn1nnc3c(C)c(ccc31)C(CC(=O)O)c1ccc3c(c1)CN(CC3)C2=O] |
| 262 | 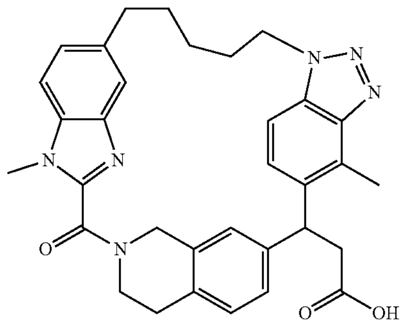 [SMILES: Cc1c2ccc3c1nnn3CCCCCc1ccc3c(c1)nc(n3C)C(=O)N1CCc3ccc(cc3C1)C2CC(=O)O] |

TABLE 2-continued
| Comp'd No | Structure |
|---|---|
| 263 | 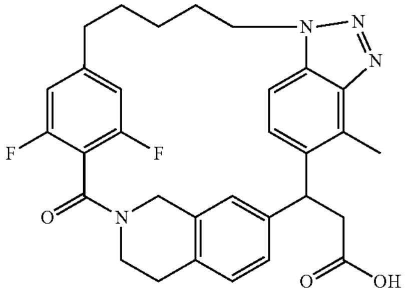 [SMILES: Cc1c2ccc3c1nnn3CCCCCc1cc(F)c(c(F)c1)C(=O)N1CCc3ccc(cc3C1)C2CC(=O)O] |
| 264 | 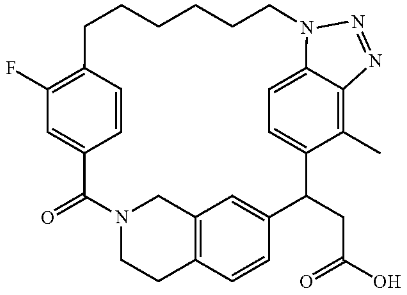 [SMILES: Cc1c2ccc3c1nnn3CCCCCCc1ccc(cc1F)C(=O)N1CCc3ccc(cc3C1)C2CC(=O)O] |
| 265 | 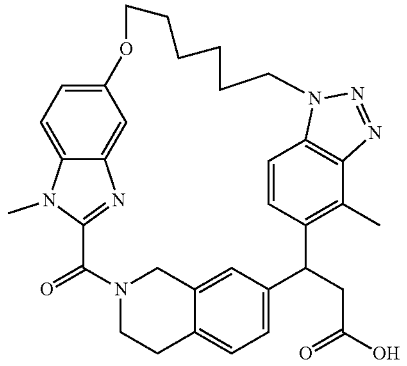 [SMILES: Cc1c2ccc3c1nnn3CCCCCCOc1ccc3c(c1)nc(n3C)C(=O)N1CCc3ccc(cc3C1)C2CC(=O)O] |
| 266 | 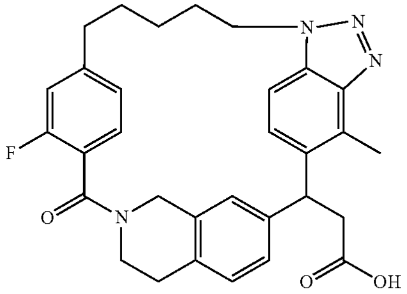 [SMILES: Cc1c2ccc3c1nnn3CCCCCc1ccc(c(F)c1)C(=O)N1CCc3ccc(cc3C1)C2CC(=O)O] |
| 267 | 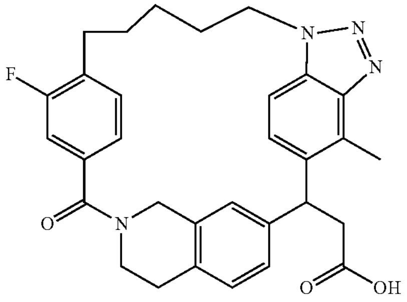 [SMILES: Cc1c2ccc3c1nnn3CCCCCc1ccc(cc1F)C(=O)N1CCc3ccc(cc3C1)C2CC(=O)O] |
TABLE 2-continued
| Comp'd No | Structure |
|---|---|
| 268 | 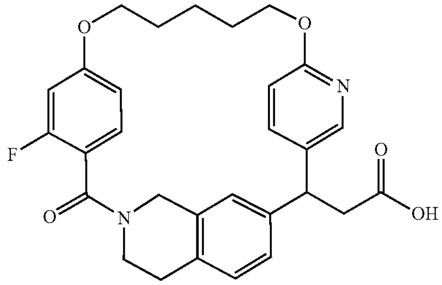 [SMILES: O=C(O)CC1c2ccc(nc2)OCCCCCOc2ccc(c(F)c2)C(=O)N2CCc3ccc1cc3C2] |
| 269 | 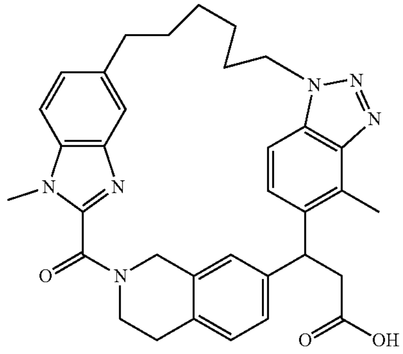 [SMILES: Cc1c2ccc3c1nnn3CCCCCCc1ccc3c(c1)nc(n3C)C(=O)N1CCc3ccc(cc3C1)C2CC(=O)O] |
| 270 | 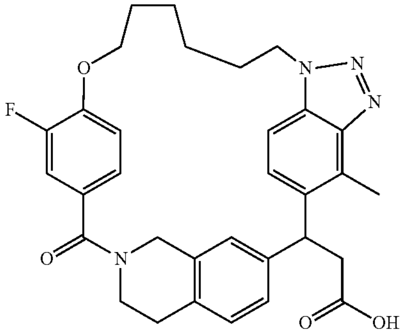 [SMILES: Cc1c2ccc3c1nnn3CCCCCCOc1ccc(cc1F)C(=O)N1CCc3ccc(cc3C1)C2CC(=O)O] |
| 271 | 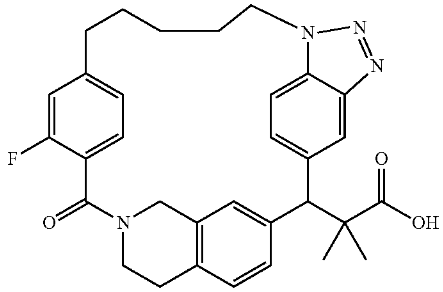 [SMILES: CC(C)(C(=O)O)C1c2ccc3c(c2)CN(CC3)C(=O)c2ccc(cc2F)CCCCCn2nnc3cc1ccc32] |
| 272 | 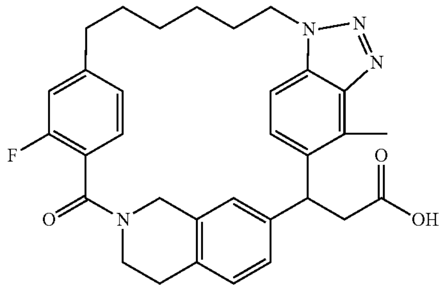 [SMILES: Cc1c2ccc3c1nnn3CCCCCCc1ccc(c(F)c1)C(=O)N1CCc3ccc(cc3C1)C2CC(=O)O] |

TABLE 2-continued
| Comp'd No | Structure |
|---|---|
| 273 | 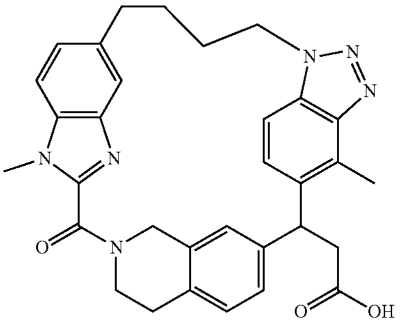 [SMILES: Cc1c2ccc3c1nnn3CCCCc1ccc3c(c1)nc(n3C)C(=O)N1CCc3ccc(cc3C1)C2CC(=O)O] |
| 274 | 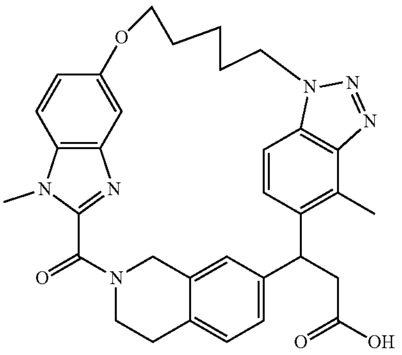 [SMILES: Cc1c2ccc3c1nnn3CCCCCOc1ccc3c(c1)nc(n3C)C(=O)N1CCc3ccc(cc3C1)C2CC(=O)O] |
| 275 | 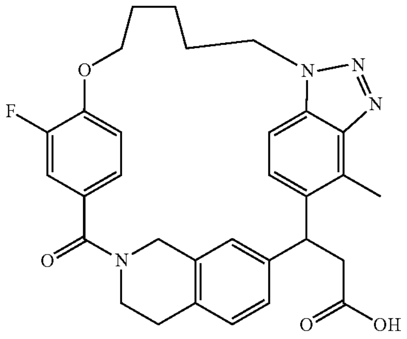 [SMILES: Cc1c2ccc3c1nnn3CCCCCOc1ccc(cc1F)C(=O)N1CCc3ccc(cc3C1)C2CC(=O)O] |
| 276 | 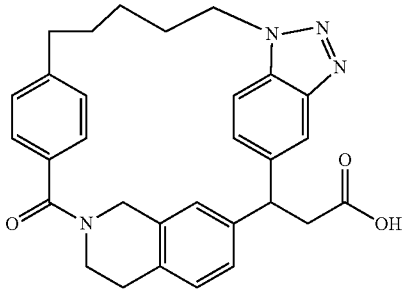 [SMILES: O=C(O)CC1c2ccc3c(c2)CN(CC3)C(=O)c2ccc(cc2)CCCCCn2nnc3cc1ccc32] |
TABLE 2-continued
| Comp'd No | Structure |
|---|---|
| 277 | 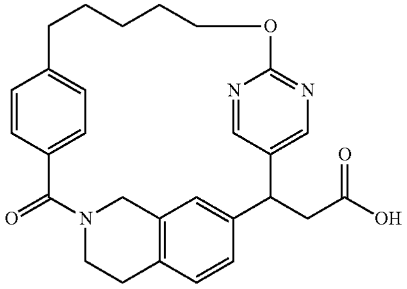 [SMILES: O=C(O)CC1c2cnc(nc2)OCCCCCc2ccc(cc2)C(=O)N2CCc3ccc1cc3C2] |
| 278 | 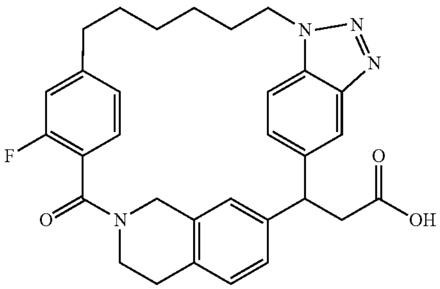 [SMILES: O=C(O)CC1c2ccc3c(c2)CN(CC3)C(=O)c2ccc(cc2F)CCCCCCn2nnc3cc1ccc32] |
| 279 | 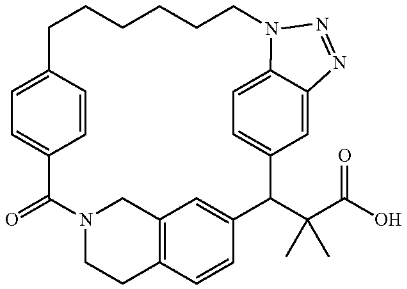 [SMILES: CC(C)(C(=O)O)C1c2ccc3c(c2)CN(CC3)C(=O)c2ccc(cc2)CCCCCCn2nnc3cc1ccc32] |
| 280 | 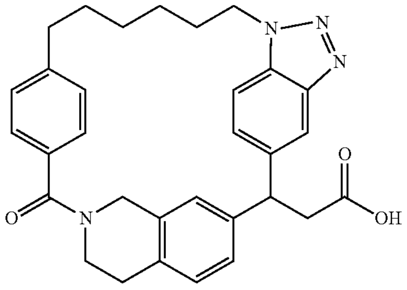 [SMILES: O=C(O)CC1c2ccc3c(c2)CN(CC3)C(=O)c2ccc(cc2)CCCCCCn2nnc3cc1ccc32] |
| 281 | 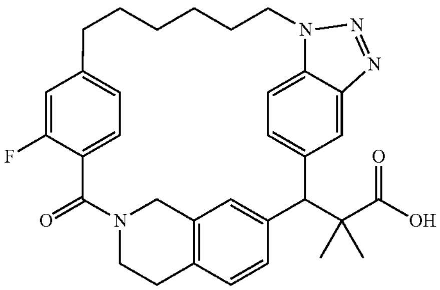 [SMILES: CC(C)(C(=O)O)C1c2ccc3c(c2)CN(CC3)C(=O)c2ccc(cc2F)CCCCCCn2nnc3cc1ccc32] |

TABLE 2-continued
| Comp'd No | Structure |
|---|---|
| 282 | 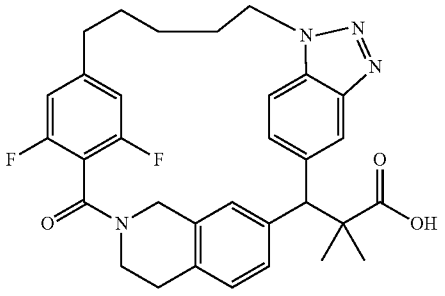 [SMILES: CC(C)(C(=O)O)C1c2ccc3c(c2)CN(CC3)C(=O)c2c(F)cc(cc2F)CCCCCn2nnc3cc1ccc32] |
| 283 | 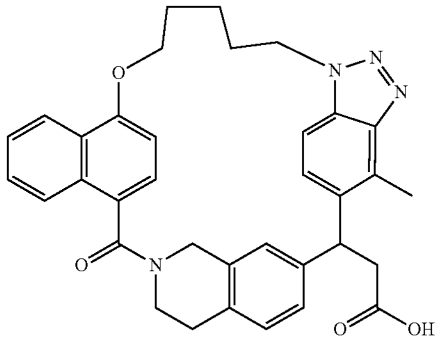 [SMILES: Cc1c2ccc3c1nnn3CCCCCOc1ccc(c3ccccc13)C(=O)N1CCc3ccc(cc3C1)C2CC(=O)O] |
| 284 | 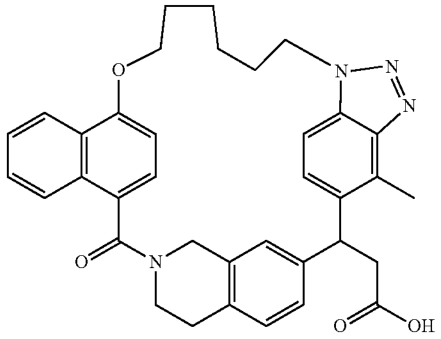 [SMILES: Cc1c2ccc3c1nnn3CCCCCCOc1ccc(c3ccccc13)C(=O)N1CCc3ccc(cc3C1)C2CC(=O)O] |
| 285 | 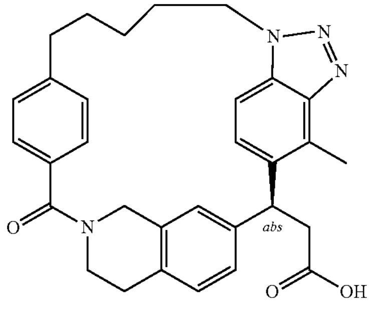 [SMILES: Cc1c2ccc3c1nnn3CCCCCc1ccc(cc1)C(=O)N1CCc3ccc(cc3C1)[C@@H]2CC(=O)O] |
TABLE 2-continued
| Comp'd No | Structure |
|---|---|
| 286 | 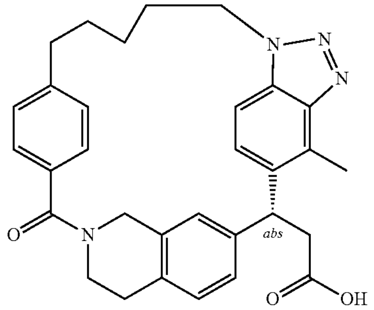 [SMILES: Cc1c2ccc3c1nnn3CCCCCc1ccc(cc1)C(=O)N1CCc3ccc(cc3C1)[C@H]2CC(=O)O] |
| 287 | 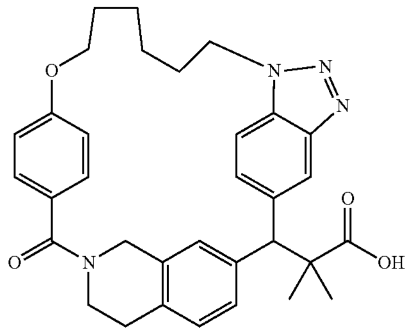 [SMILES: CC(C)(C(=O)O)C1c2ccc3c(c2)CN(CC3)C(=O)c2ccc(cc2)OCCCCCCn2nnc3cc1ccc32] |
| 288 | 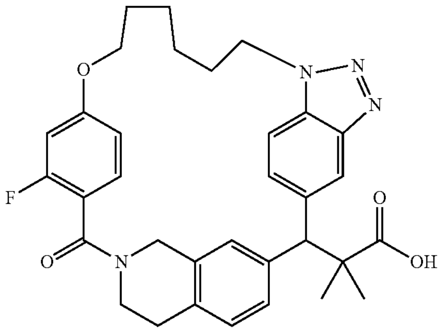 [SMILES: CC(C)(C(=O)O)C1c2ccc3c(c2)CN(CC3)C(=O)c2ccc(cc2F)OCCCCCCn2nnc3cc1ccc32] |
| 289 | 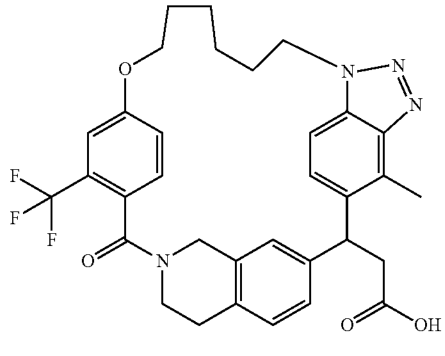 [SMILES: Cc1c2ccc3c1nnn3CCCCCCOc1ccc(c(C(F)(F)F)c1)C(=O)N1CCc3ccc(cc3C1)C2CC(=O)O] |

TABLE 2-continued
| Comp'd No | Structure |
|---|---|
| 290 | 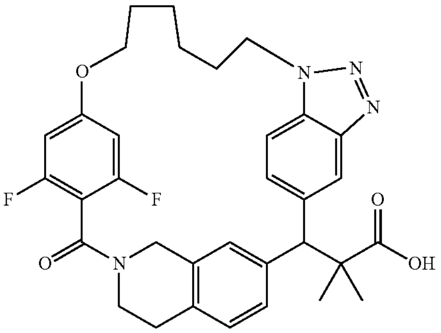 [SMILES: CC(C)(C(=O)O)C1c2ccc3c(c2)CN(CC3)C(=O)c2c(F)cc(cc2F)OCCCCCCn2nnc3cc1ccc32] |
| 291 | 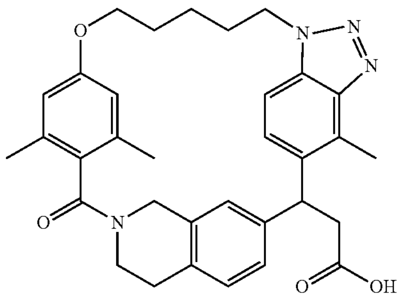 |
| 292 | 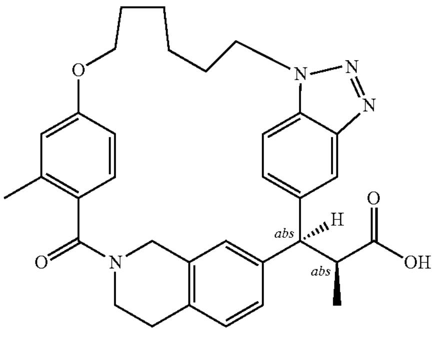 [SMILES: Cc1cc2ccc1C(=O)N1CCc3ccc(cc3C1)[C@H]([C@H](C)C(=O)O)c1ccc3c(c1)nnn3CCCCCCO2] |
| 293 | 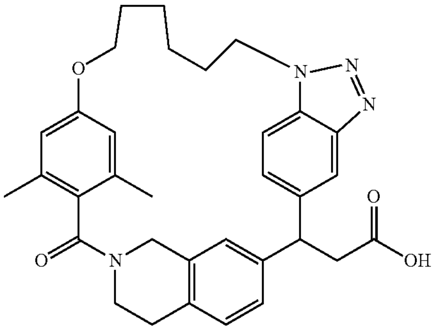 [SMILES: Cc1cc2cc(C)c1C(=O)N1CCc3ccc(cc3C1)C(CC(=O)O)c1ccc3c(c1)nnn3CCCCCCO2] |
TABLE 2-continued
| Comp'd No | Structure |
|---|---|
| 294 | 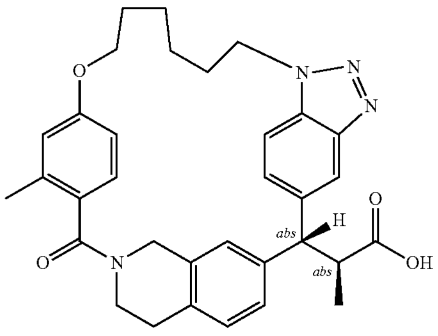 [SMILES: Cc1cc2ccc1C(=O)N1CCc3ccc(cc3C1)[C@@H]([C@H](C)C(=O)O)c1ccc3c(c1)nnn3CCCCCCO2] |
| 295 | 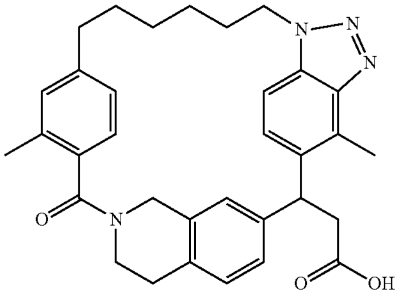 [SMILES: Cc1cc2ccc1C(=O)N1CCc3ccc(cc3C1)C(CC(=O)O)c1ccc3c(nnn3CCCCCC2)c1C] |
| 296 | 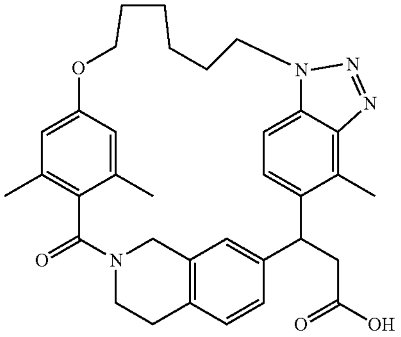 [SMILES: Cc1cc2cc(C)c1C(=O)N1CCc3ccc(cc3C1)C(CC(=O)O)c1ccc3c(nnn3CCCCCCO2)c1C] |
| 297 | 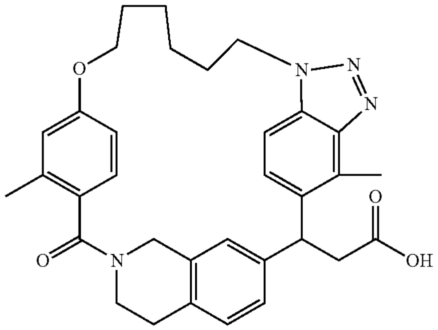 [SMILES: Cc1cc2ccc1C(=O)N1CCc3ccc(cc3C1)C(CC(=O)O)c1ccc3c(nnn3CCCCCCO2)c1C] |

TABLE 2-continued
| Comp'd No | Structure |
|---|---|
| 298 | 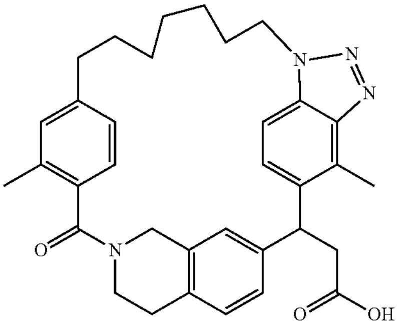 |
| 299 | 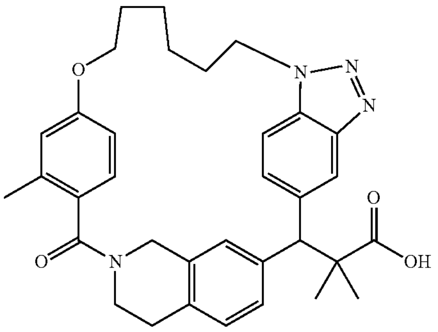 [SMILES: Cc1cc2ccc1C(=O)N1CCc3ccc(cc3C1)C(C(C)(C)C(=O)O)c1ccc3c(c1)nnn3CCCCCCO2] |
| 300 | 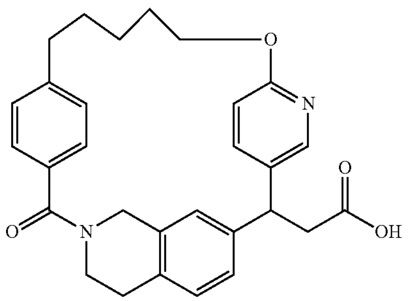 [SMILES: O=C(O)CC1c2ccc(nc2)OCCCCCc2ccc(cc2)C(=O)N2CCc3ccc1cc3C2] |
| 301 | 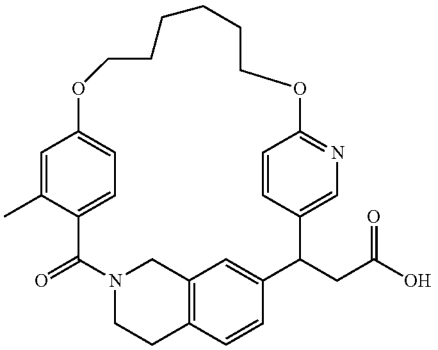 [SMILES: Cc1cc2ccc1C(=O)N1CCc3ccc(cc3C1)C(CC(=O)O)c1ccc(nc1)OCCCCCCO2] |
TABLE 2-continued
| Comp'd No | Structure |
|---|---|
| 302 | 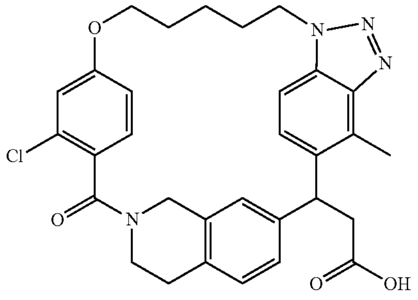 [SMILES: Cc1c2ccc3c1nnn3CCCCCOc1ccc(c(Cl)c1)C(=O)N1CCc3ccc(cc3C1)C2CC(=O)O] |
| 303 | 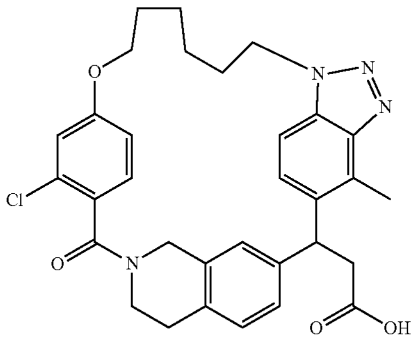 [SMILES: Cc1c2ccc3c1nnn3CCCCCCOc1ccc(c(Cl)c1)C(=O)N1CCc3ccc(cc3C1)C2CC(=O)O] |
| 304 | 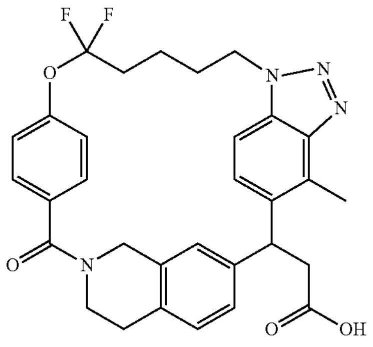 [SMILES: Cc1c2ccc3c1nnn3CCCCC(F)(F)Oc1ccc(cc1)C(=O)N1CCc3ccc(cc3C1)C2CC(=O)O] |
| 305 | 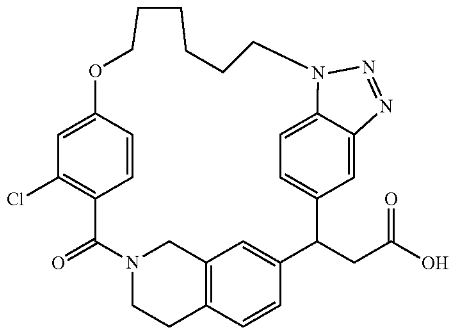 [SMILES: O=C(O)CC1c2ccc3c(c2)CN(CC3)C(=O)c2ccc(cc2Cl)OCCCCCCn2nnc3cc1ccc32] |

TABLE 2-continued
| Comp'd No | Structure |
|---|---|
| 306 | 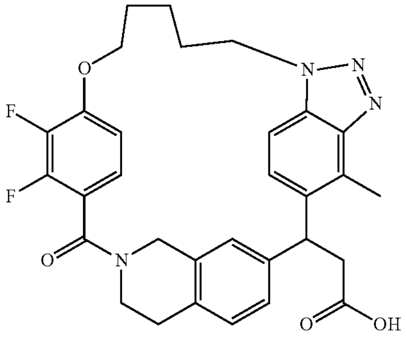 [SMILES: Cc1c2ccc3c1nnn3CCCCCOc1ccc(c(F)c1F)C(=O)N1CCc3ccc(cc3C1)C2CC(=O)O] |
| 307 | 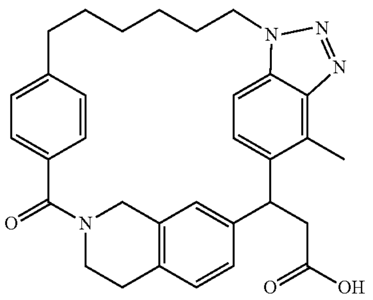 |
| 308 | 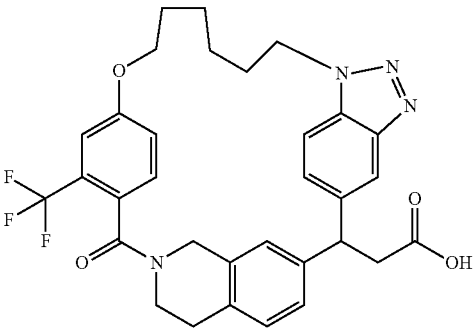 [SMILES: O=C(O)CC1c2ccc3c(c2)CN(CC3)C(=O)c2ccc(cc2C(F)(F)F)OCCCCCCn2nnc3cc1ccc32] |
| 309 | 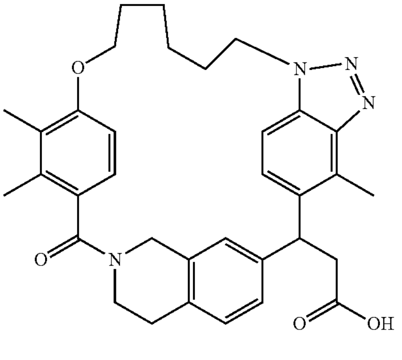 |
TABLE 2-continued
| Comp'd No | Structure |
|---|---|
| 310 | 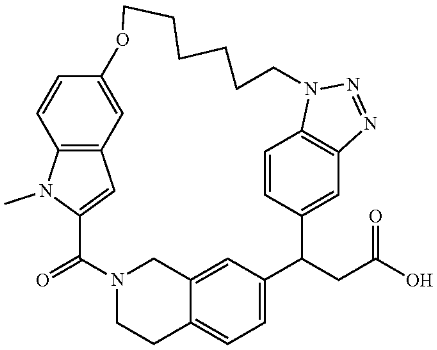 [SMILES: Cn1c2cc3cc(ccc31)OCCCCCCn1nnc3cc(ccc31)C(CC(=O)O)c1ccc3c(c1)CN(CC3)C2=O] |
| 311 | 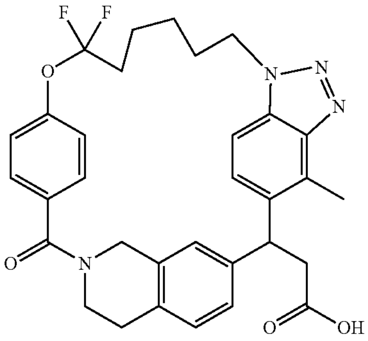 [SMILES: Cc1c2ccc3c1nnn3CCCCCC(F)(F)Oc1ccc(cc1)C(=O)N1CCc3ccc(cc3C1)C2CC(=O)O] |
| 312 | 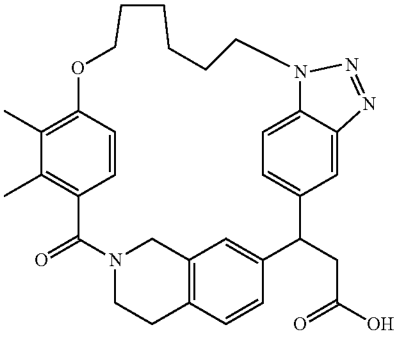 [SMILES: Cc1c2ccc(c1C)C(=O)N1CCc3ccc(cc3C1)C(CC(=O)O)c1ccc3c(c1)nnn3CCCCCCO2] |
| 313 | 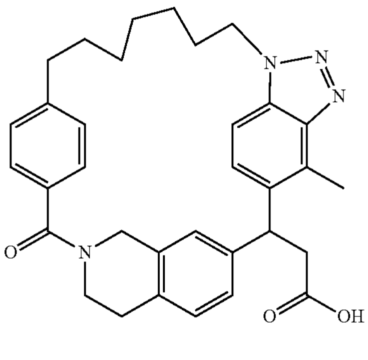 [SMILES: Cc1c2ccc3c1nnn3CCCCCCCc1ccc(cc1)C(=O)N1CCc3ccc(cc3C1)C2CC(=O)O] |

TABLE 2-continued
| Comp'd No | Structure |
|---|---|
| 314 | 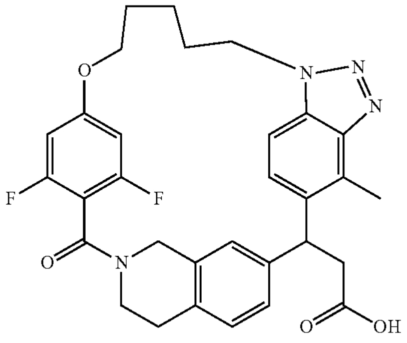 [SMILES: Cc1c2ccc3c1nnn3CCCCCOc1cc(F)c(c(F)c1)C(=O)N1CCc3ccc(cc3C1)C2CC(=O)O] |
| 315 | 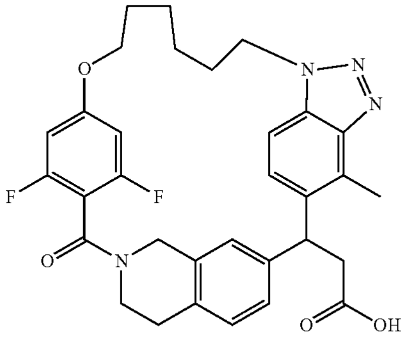 [SMILES: Cc1c2ccc3c1nnn3CCCCCCOc1cc(F)c(c(F)c1)C(=O)N1CCc3ccc(cc3C1)C2CC(=O)O] |
| 316 | 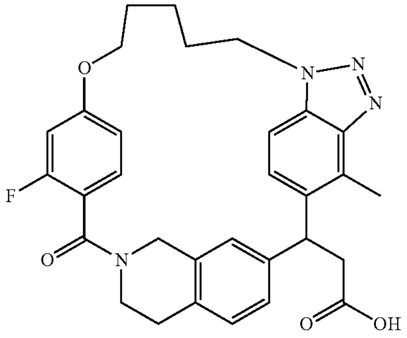 [SMILES: Cc1c2ccc3c1nnn3CCCCCOc1ccc(c(F)c1)C(=O)N1CCc3ccc(cc3C1)C2CC(=O)O] |
| 317 | 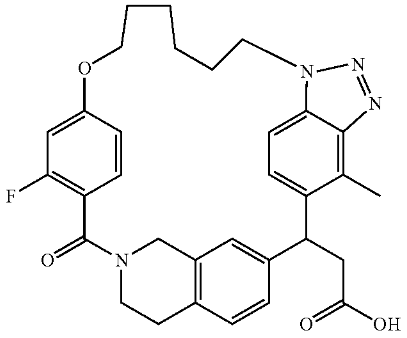 [SMILES: Cc1c2ccc3c1nnn3CCCCCCOc1ccc(c(F)c1)C(=O)N1CCc3ccc(cc3C1)C2CC(=O)O] |
TABLE 2-continued
| Comp'd No | Structure |
|---|---|
| 318 | 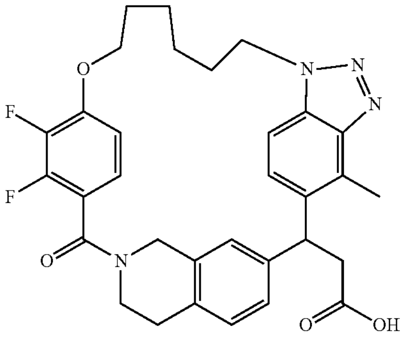 [SMILES: Cc1c2ccc3c1nnn3CCCCCCOc1ccc(c(F)c1F)C(=O)N1CCc3ccc(cc3C1)C2CC(=O)O] |
| 319 | 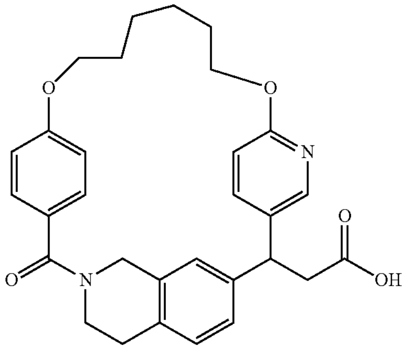 [SMILES: O=C(O)CC1c2ccc(nc2)OCCCCCCOc2ccc(cc2)C(=O)N2CCc3ccc1cc3C2] |
| 320 | 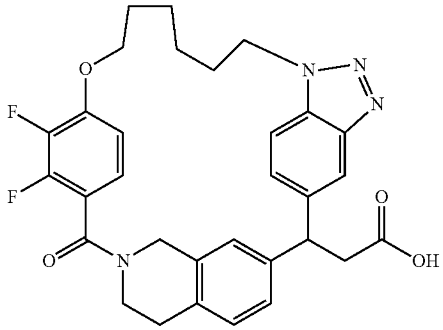 [SMILES: O=C(O)CC1c2ccc3c(c2)CN(CC3)C(=O)c2ccc(c(F)c2F)OCCCCCCn2nnc3cc1ccc32] |
| 321 | 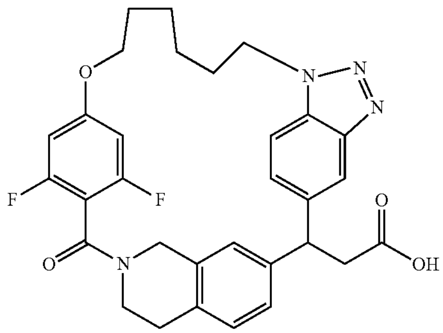 [SMILES: O=C(O)CC1c2ccc3c(c2)CN(CC3)C(=O)c2c(F)cc(cc2F)OCCCCCCn2nnc3cc1ccc32] |

TABLE 2-continued
| Comp'd No | Structure |
| --- | --- |
| 322 | 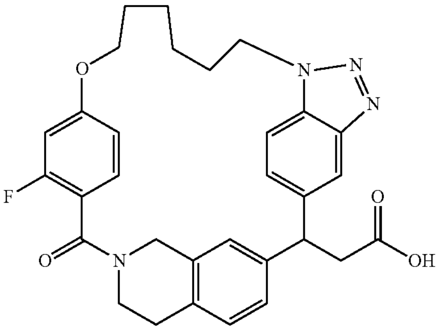 [SMILES: O=C(O)CC1c2ccc3c(c2)CN(CC3)C(=O)c2ccc(cc2F)OCCCCCCn2nnc3cc1ccc32] |
| 323 | 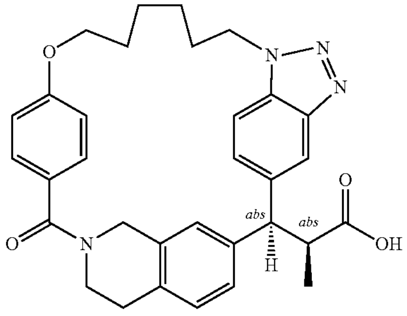 [SMILES: C[C@H](C(=O)O)[C@H]1c2ccc3c(c2)CN(CC3)C(=O)c2ccc(cc2)OCCCCCCn2nnc3cc1ccc32] |
| 324 | 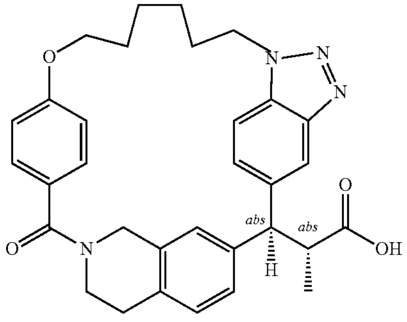 [SMILES: CCCCCCCOc1ccc(C(=O)N2CCc3ccc([C@@H](c4ccc5[nH]nnc5c4)[C@@H](C)C(=O)O)cc3C2)cc1] |
| 325 | 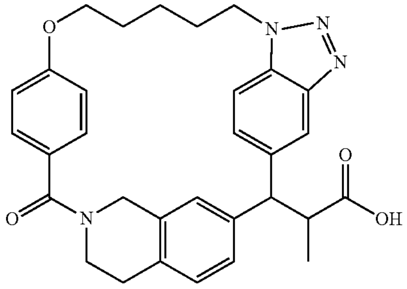 [SMILES: CC(C(=O)O)C1c2ccc3c(c2)CN(CC3)C(=O)c2ccc(cc2)OCCCCCn2nnc3cc1ccc32] |
TABLE 2-continued
| Comp'd No | Structure |
| --- | --- |
| 326 | 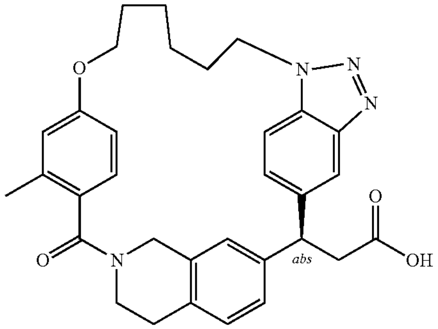 [SMILES: Cc1cc2ccc1C(=O)N1CCc3ccc(cc3C1)[C@H](CC(=O)O)c1ccc3c(c1)nnn3CCCCCCO2] |
| 327 | 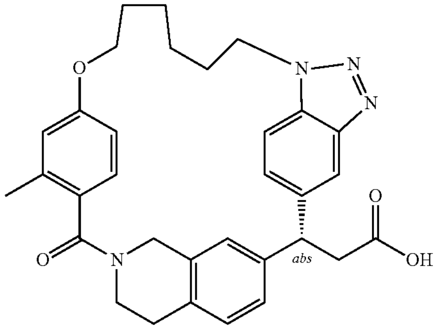 [SMILES: Cc1cc2ccc1C(=O)N1CCc3ccc(cc3C1)[C@@H](CC(=O)O)c1ccc3c(c1)nnn3CCCCCCO2] |
| 328 | 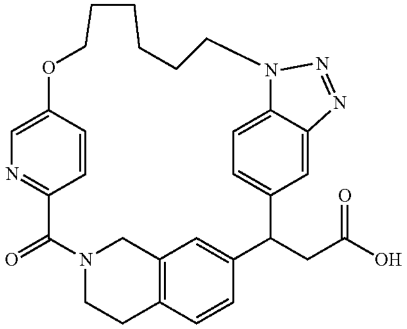 [SMILES: O=C(O)CC1c2ccc3c(c2)CN(CC3)C(=O)c2ccc(cn2)OCCCCCCn2nnc3cc1ccc32] |
| 329 | 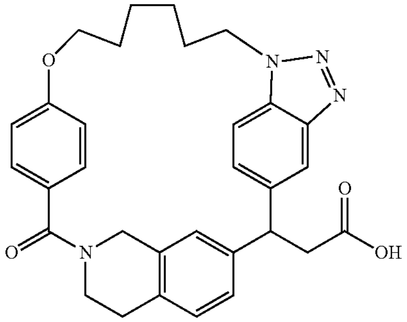 [SMILES: O=C(O)CC1c2ccc3c(c2)CN(CC3)C(=O)c2ccc(cc2)OCCCCCCn2nnc3cc1ccc32] |

TABLE 2-continued
| Comp'd No | Structure |
| --- | --- |
| 330 | 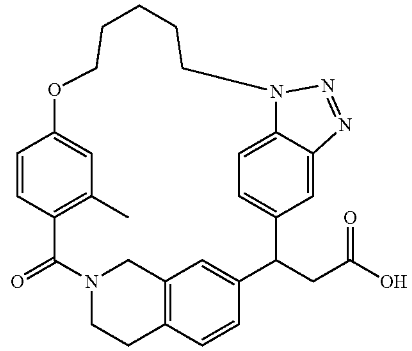 [SMILES: Cc1cc2ccc1C(=O)N1CCc3ccc(cc3C1)C(CC(=O)O)c1ccc3c(c1)nnn3CCCCCO2] |
| 331 | 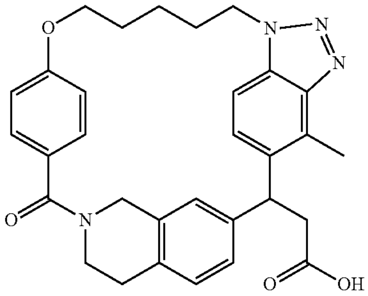 [SMILES: Cc1c2ccc3c1nnn3CCCCCOc1ccc(cc1)C(=O)N1CCc3ccc(cc3C1)C2CC(=O)O] |
| 332 | 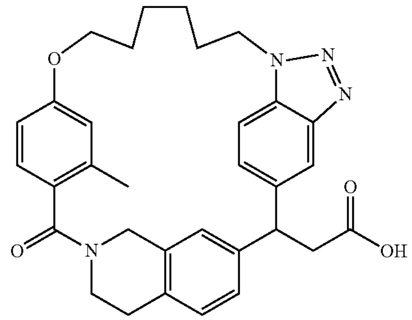 [SMILES: Cc1cc2ccc1C(=O)N1CCc3ccc(cc3C1)C(CC(=O)O)c1ccc3c(c1)nnn3CCCCCCO2] |
| 333 | 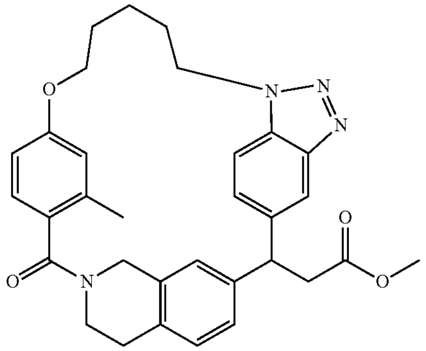 [SMILES: COC(=O)CC1c2ccc3c(c2)CN(CC3)C(=O)c2ccc(cc2C)OCCCCCn2nnc3cc1ccc32] |
TABLE 2-continued
| Comp'd No | Structure |
| --- | --- |
| 334 | 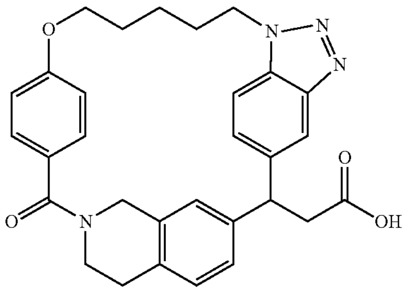 [SMILES: O=C(O)CC1c2ccc3c(c2)CN(CC3)C(=O)c2ccc(cc2)OCCCCCn2nnc3cc1ccc32] |
| 335 | 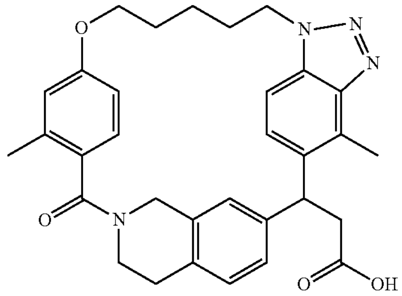 [SMILES: Cc1cc2ccc1C(=O)N1CCc3ccc(cc3C1)C(CC(=O)O)c1ccc3c(nnn3CCCCCO2)c1C] |
| 336 | 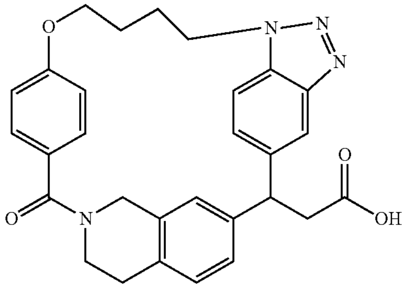 [SMILES: O=C(O)CC1c2ccc3c(c2)CN(CC3)C(=O)c2ccc(cc2)OCCCCn2nnc3cc1ccc32] |
| 337 | 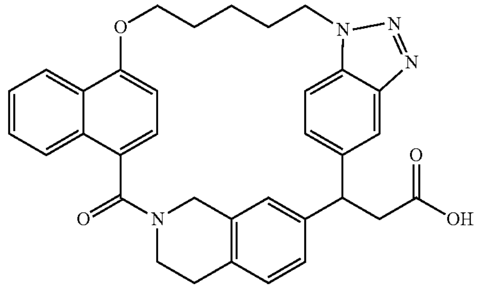 [SMILES: O=C(O)CC1c2ccc3c(c2)CN(CC3)C(=O)c2ccc(c3ccccc23)OCCCCCn2nnc3cc1ccc32] |
| 338 | 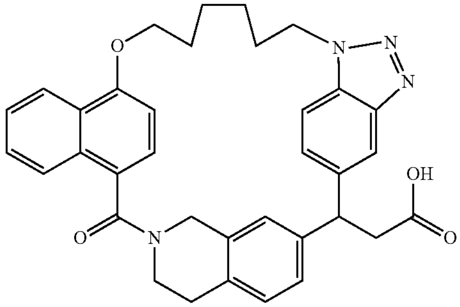 [SMILES: O=C(O)CC1c2ccc3c(c2)CN(CC3)C(=O)c2ccc(c3ccccc23)OCCCCCCn2nnc3cc1ccc32] |

TABLE 2-continued
| Comp'd No | Structure |
| --- | --- |
| 344 | 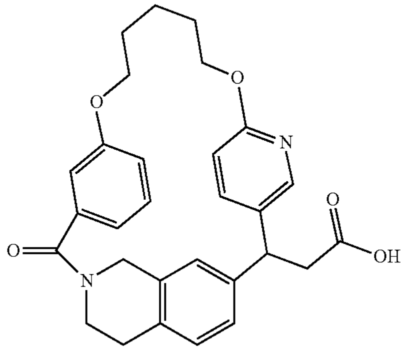 [SMILES: O=C(O)CC1c2ccc(nc2)OCCCCCOc2cccc(c2)C(=O)N2CCc3ccc1cc3C2] |
| 345 | 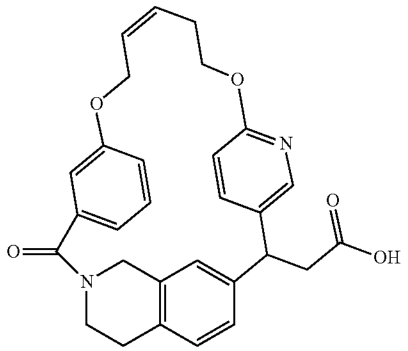 [SMILES: O=C(O)CC1c2ccc(nc2)OCC/C=C\COc2cccc(c2)C(=O)N2CCc3ccc1cc3C2] |
| 346 | 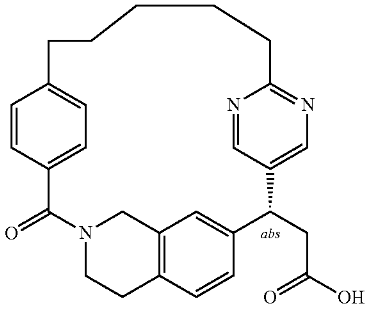 [SMILES: O=C(O)C[C@H]1c2cnc(nc2)CCCCCc2ccc(cc2)C(=O)N2CCc3ccc1cc3C2] |
| 347 | 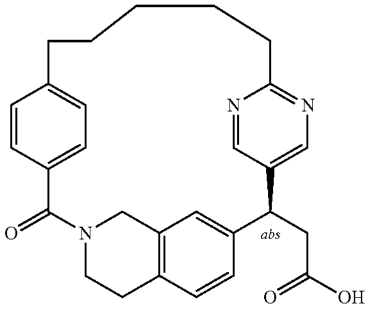 [SMILES: O=C(O)C[C@@H]1c2cnc(nc2)CCCCCc2ccc(cc2)C(=O)N2CCc3ccc1cc3C2] |
TABLE 2-continued
| Comp'd No | Structure |
| --- | --- |
| 348 | 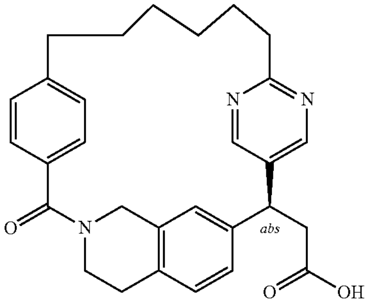 [SMILES: O=C(O)C[C@@H]1c2cnc(nc2)CCCCCCc2ccc(cc2)C(=O)N2CCc3ccc1cc3C2] |
| 349 | 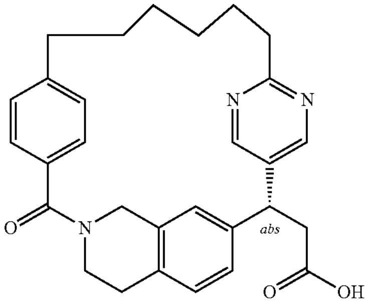 [SMILES: O=C(O)C[C@H]1c2cnc(nc2)CCCCCCc2ccc(cc2)C(=O)N2CCc3ccc1cc3C2] |
| 350 | 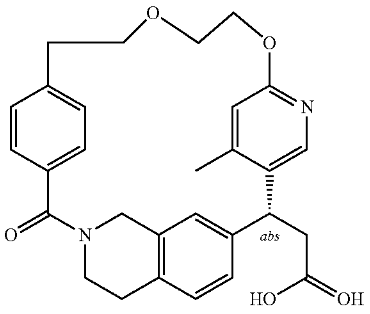 [SMILES: Cc1cc2ncc1[C@H](CC(=O)O)c1ccc3c(c1)CN(CC3)C(=O)c1ccc(cc1)CCOCCO2] |
| 351 | 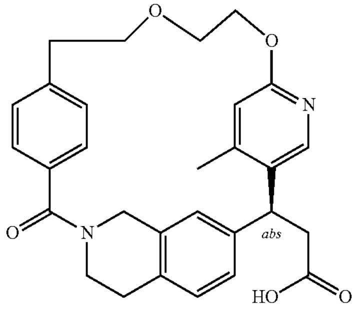 [SMILES: Cc1cc2ncc1[C@@H](CC(=O)O)c1ccc3c(c1)CN(CC3)C(=O)c1ccc(cc1)CCOCCO2] |
| 352 | 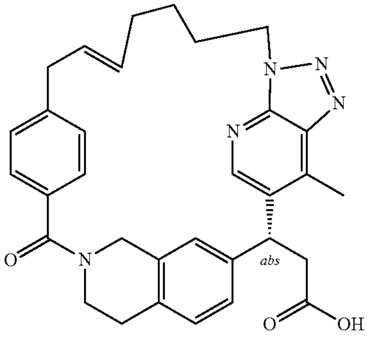 [SMILES: Cc1c2cnc3c1nnn3CCCC/C=C/Cc1ccc(cc1)C(=O)N1CCc3ccc(cc3C1)[C@H]2CC(=O)O] |

| Comp'd No | Structure |
| --- | --- |
| 353 | 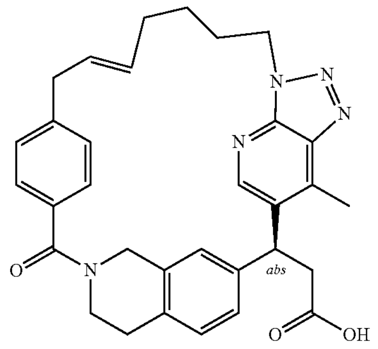 [SMILES: Cc1c2cnc3c1nnn3CCCC/C=C/Cc1ccc(cc1)C(=O)N1CCc3ccc(cc3C1)[C@@H]2CC(=O)O] |
| 354 | 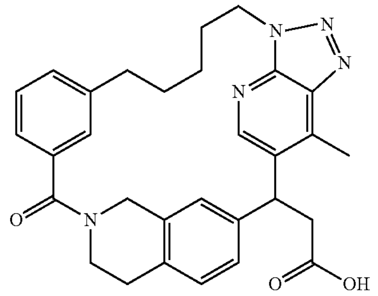 [SMILES: Cc1c2cnc3c1nnn3CCCCCc1cccc(c1)C(=O)N1CCc3ccc(cc3C1)C2CC(=O)O] |
| 355 | 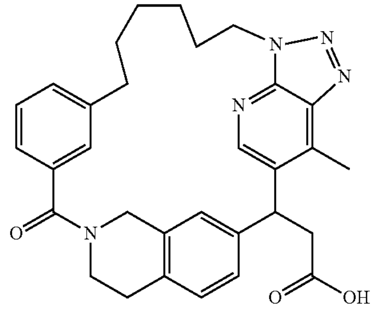 [SMILES: Cc1c2cnc3c1nnn3CCCCCCc1cccc(c1)C(=O)N1CCc3ccc(cc3C1)C2CC(=O)O] |
| 356 | 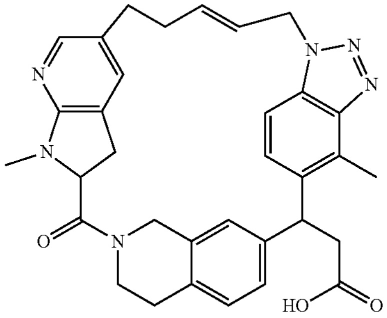 |
| Comp'd No | Structure |
| --- | --- |
| 357 | 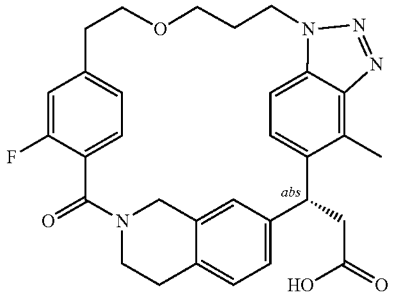 [SMILES: Cc1c2ccc3c1nnn3CCCOCCc1ccc(c(F)c1)C(=O)N1CCc3ccc(cc3C1)[C@H]2CC(=O)O] |
| 358 | 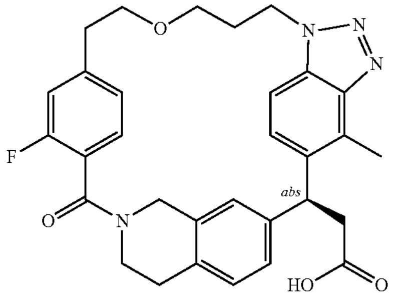 [SMILES: Cc1c2ccc3c1nnn3CCCOCCc1ccc(c(F)c1)C(=O)N1CCc3ccc(cc3C1)[C@@H]2CC(=O)O] |
| 359 | 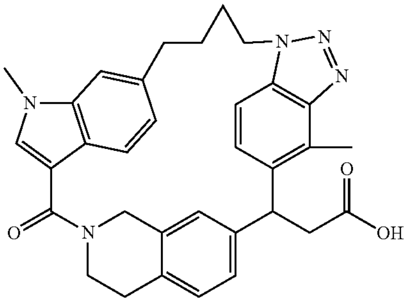 [SMILES: Cc1c2ccc3c1nnn3CCCCc1ccc3c(cn(C)c3c1)C(=O)N1CCc3ccc(cc3C1)C2CC(=O)O] |
| 360 | 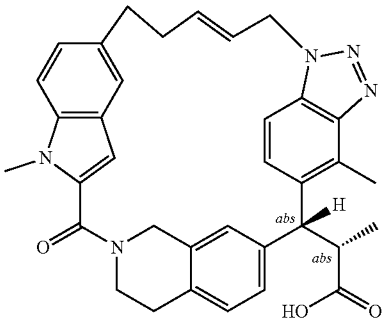 [SMILES: Cc1c2ccc3c1nnn3C/C=C/CCc1ccc3c(c1)cc(n3C)C(=O)N1CCc3ccc(cc3C1)[C@H]2[C@H](C)C(=O)O] |

TABLE 2-continued
| Comp'd No | Structure |
| --- | --- |
| 361 | 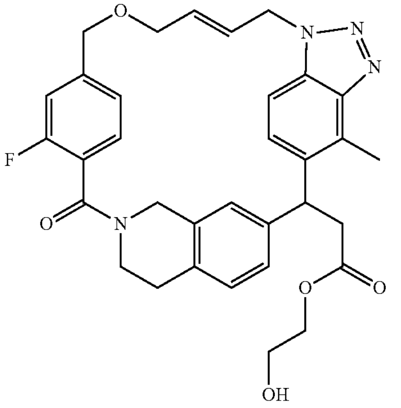 [SMILES: Cc1c2ccc3c1nnn3C/C=C/COCc1ccc(c(F)c1)C(=O)N1CCc3ccc(cc3C1)C2CC(=O)OCCO] |
| 362 | 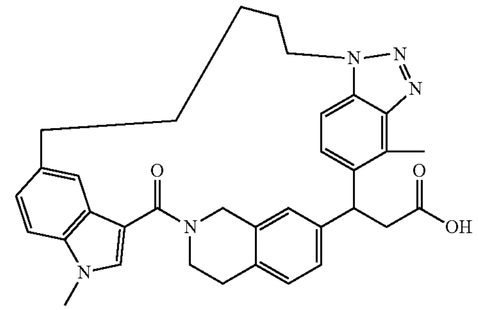 [SMILES: Cc1c2ccc3c1nnn3CCCCCc1ccc3c(c1)c(cn3C)C(=O)N1CCc3ccc(cc3C1)C2CC(=O)O] |
| 363 | 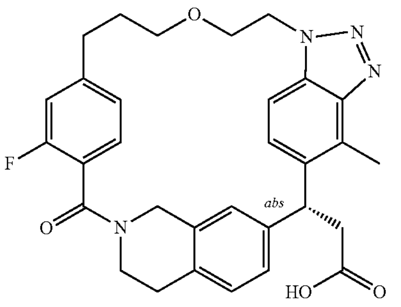 [SMILES: Cc1c2ccc3c1nnn3CCOCCCc1ccc(c(F)c1)C(=O)N1CCc3ccc(cc3C1)[C@H]2CC(=O)O] |
| 364 | 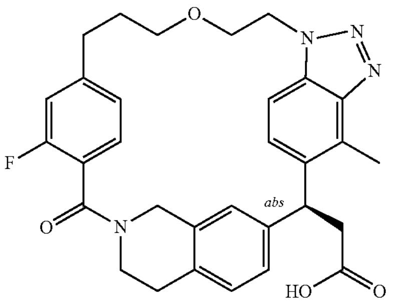 [SMILES: Cc1c2ccc3c1nnn3CCOCCCc1ccc(c(F)c1)C(=O)N1CCc3ccc(cc3C1)[C@@H]2CC(=O)O] |
TABLE 2-continued
| Comp'd No | Structure |
| --- | --- |
| 365 | 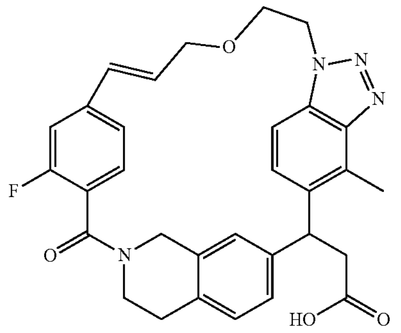 [SMILES: Cc1c2ccc3c1nnn3CCOC/C=C/c1ccc(c(F)c1)C(=O)N1CCc3ccc(cc3C1)C2CC(=O)O] |
| 366 | 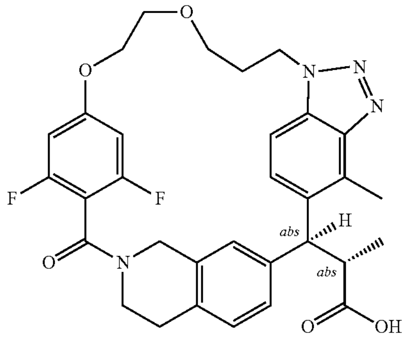 [SMILES: Cc1c2ccc3c1nnn3CCCOCCOc1cc(F)c(c(F)c1)C(=O)N1CCc3ccc(cc3C1)[C@@H]2[C@H](C)C(=O)O] |
| 367 | 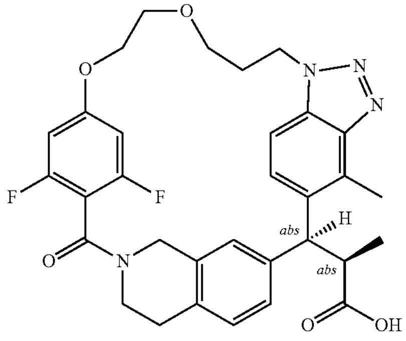 [SMILES: Cc1c2ccc3c1nnn3CCCOCCOc1cc(F)c(c(F)c1)C(=O)N1CCc3ccc(cc3C1)[C@@H]2[C@@H](C)C(=O)O] |
| 368 | 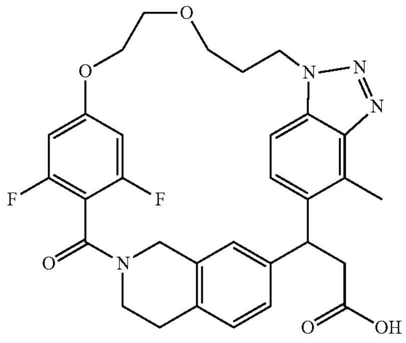 [SMILES: Cc1c2ccc3c1nnn3CCCOCCOc1cc(F)c(c(F)c1)C(=O)N1CCc3ccc(cc3C1)C2CC(=O)O] |

TABLE 2-continued
| Comp'd No | Structure |
|---|---|
| 369 | 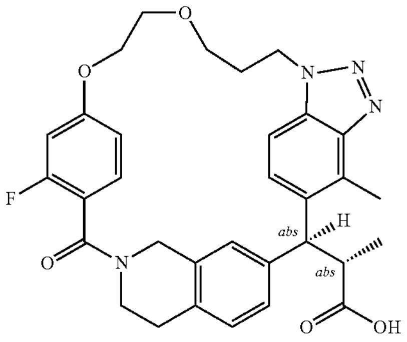 [SMILES: Cc1c2ccc3c1nnn3CCCOCCOc1ccc(c(F)c1)C(=O)N1CCc3ccc(cc3C1)[C@@H]2[C@H](C)C(=O)O] |
| 370 | 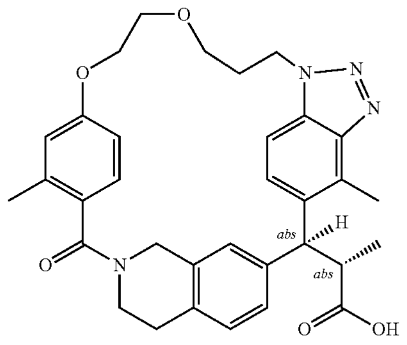 [SMILES: Cc1cc2ccc1C(=O)N1CCc3ccc(cc3C1)[C@H]([C@H](C)C(=O)O)c1ccc3c(nnn3CCCOCCO2)c1C] |
| 371 | 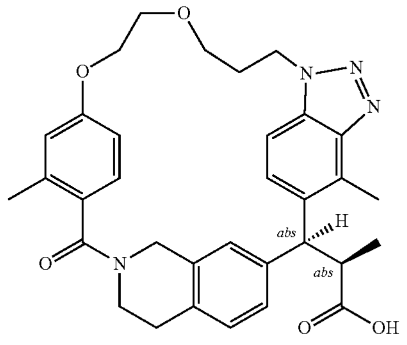 [SMILES: Cc1cc2ccc1C(=O)N1CCc3ccc(cc3C1)[C@H]([C@@H](C)C(=O)O)c1ccc3c(nnn3CCCOCCO2)c1C] |
| 372 | 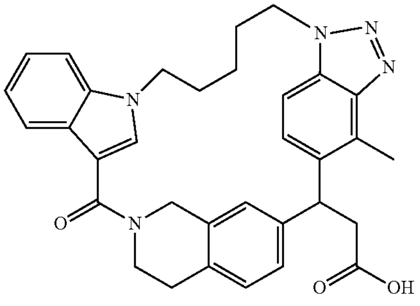 [SMILES: Cc1c2ccc3c1nnn3CCCCCn1cc(c3ccccc31)C(=O)N1CCc3ccc(cc3C1)C2CC(=O)O] |
TABLE 2-continued
| Comp'd No | Structure |
|---|---|
| 373 | 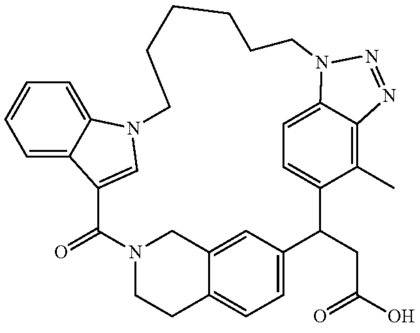 [SMILES: Cc1c2ccc3c1nnn3CCCCCCn1cc(c3ccccc31)C(=O)N1CCc3ccc(cc3C1)C2CC(=O)O] |
| 374 | 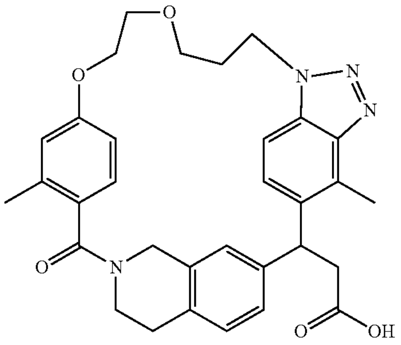 |
| 375 | 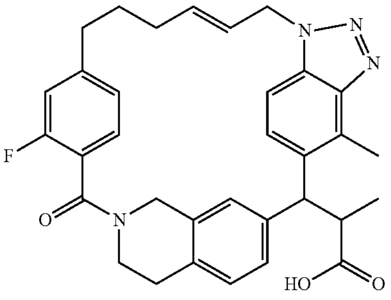 [SMILES: Cc1c2ccc3c1nnn3C/C=C/CCCc1ccc(c(F)c1)C(=O)N1CCc3ccc(cc3C1)C2C(C)C(=O)O] |
| 376 | 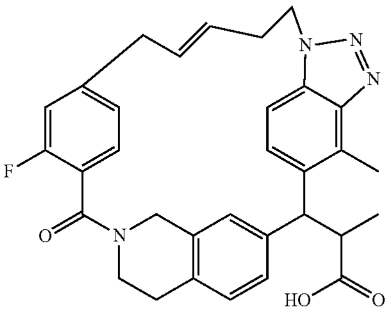 [SMILES: Cc1c2ccc3c1nnn3CC/C=C/Cc1ccc(c(F)c1)C(=O)N1CCc3ccc(cc3C1)C2C(C)C(=O)O] |

TABLE 2-continued
| Comp'd No | Structure |
| --- | --- |
| 377 | 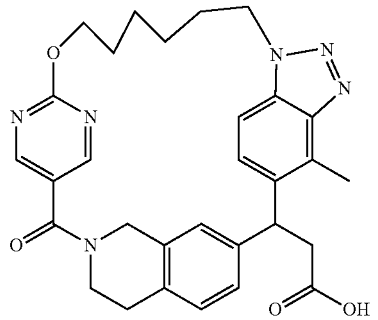 [SMILES: Cc1c2ccc3c1nnn3CCCCCCOc1ncc(cn1)C(=O)N1CCc3ccc(cc3C1)C2CC(=O)O] |
| 378 | 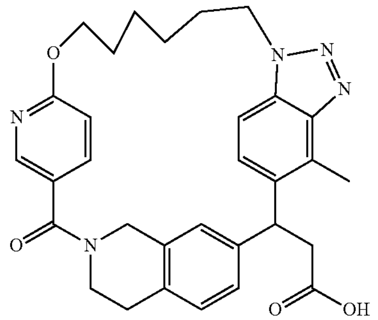 [SMILES: Cc1c2ccc3c1nnn3CCCCCCOc1ccc(cn1)C(=O)N1CCc3ccc(cc3C1)C2CC(=O)O] |
| 379 | 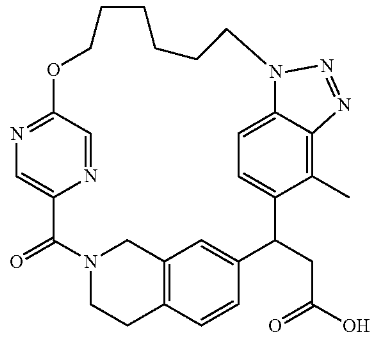 [SMILES: Cc1c2ccc3c1nnn3CCCCCCOc1cnc(cn1)C(=O)N1CCc3ccc(cc3C1)C2CC(=O)O] |
| 380 | 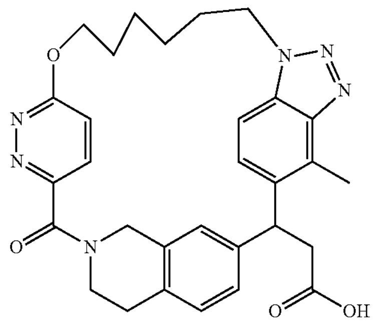 [SMILES: Cc1c2ccc3c1nnn3CCCCCCOc1ccc(nn1)C(=O)N1CCc3ccc(cc3C1)C2CC(=O)O] |
TABLE 2-continued
| Comp'd No | Structure |
| --- | --- |
| 381 | 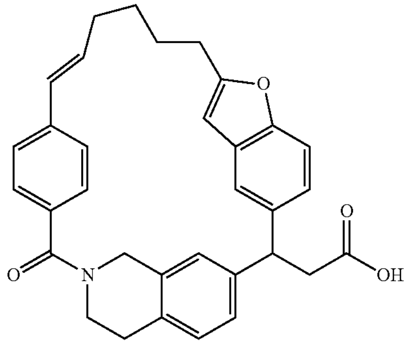 [SMILES: O=C(O)CC1c2ccc3c(c2)CN(CC3)C(=O)c2ccc(cc2)/C=C/CCCCc2cc3cc1ccc3o2] |
| 382 | 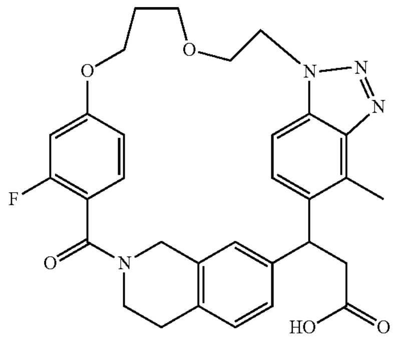 [SMILES: Cc1c2ccc3c1nnn3CCOCCCOc1ccc(c(F)c1)C(=O)N1CCc3ccc(cc3C1)C2CC(=O)O] |
| 383 | 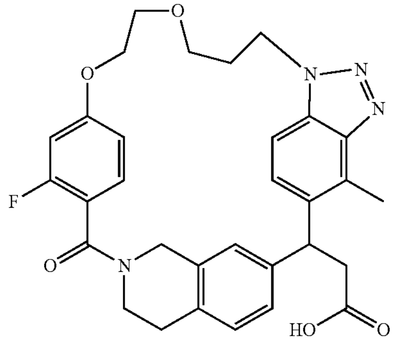 [SMILES: Cc1c2ccc3c1nnn3CCCOCCOc1ccc(c(F)c1)C(=O)N1CCc3ccc(cc3C1)C2CC(=O)O] |
| 384 | 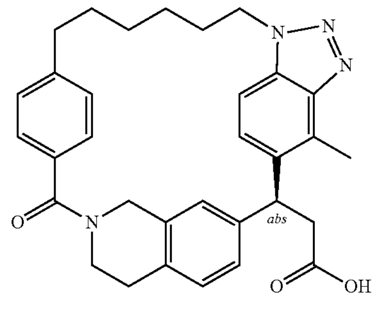 |

TABLE 2-continued
| Comp'd No | Structure |
| --- | --- |
| 385 | 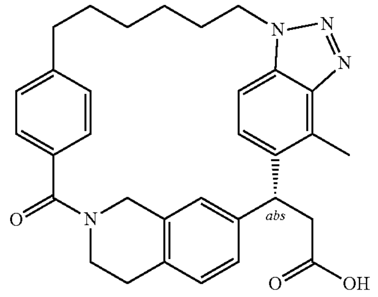 |
| 386 | 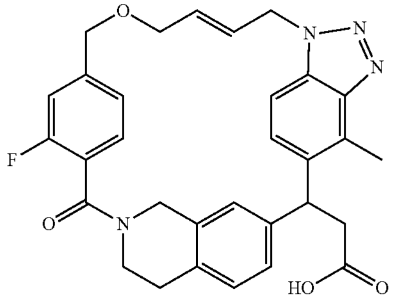 [SMILES: Cc1c2ccc3c1nnn3C/C=C/COCc1ccc(c(F)c1)C(=O)N1CCc3ccc(cc3C1)C2CC(=O)O] |
| 387 | 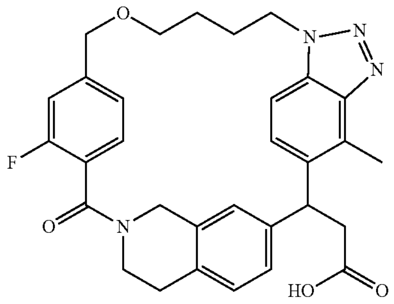 [SMILES: Cc1c2ccc3c1nnn3CCCCOCc1ccc(c(F)c1)C(=O)N1CCc3ccc(cc3C1)C2CC(=O)O] |
| 388 | 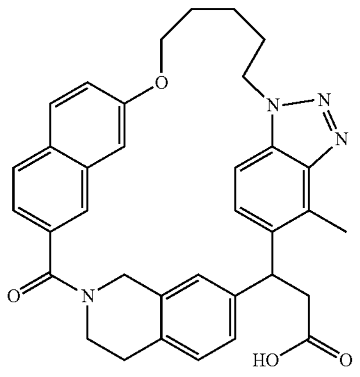 [SMILES: Cc1c2ccc3c1nnn3CCCCCOc1ccc3ccc(cc3c1)C(=O)N1CCc3ccc(cc3C1)C2CC(=O)O] |
TABLE 2-continued
| Comp'd No | Structure |
| --- | --- |
| 389 | 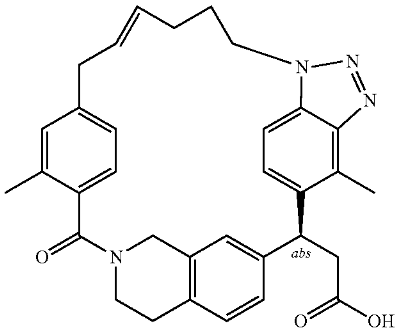 |
| 390 | 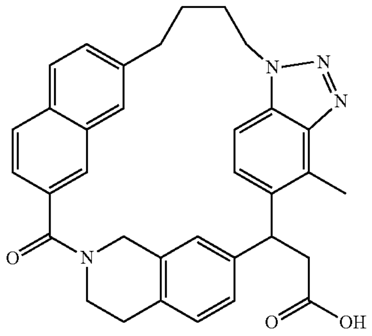 [SMILES: Cc1c2ccc3c1nnn3CCCCc1ccc3ccc(cc3c1)C(=O)N1CCc3ccc(cc3C1)C2CC(=O)O] |
| 391 | 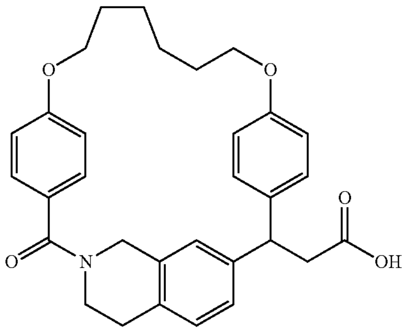 [SMILES: O=C(O)CC1c2ccc(cc2)OCCCCCCOc2ccc(cc2)C(=O)N2CCc3ccc1cc3C2] |
| 392 | 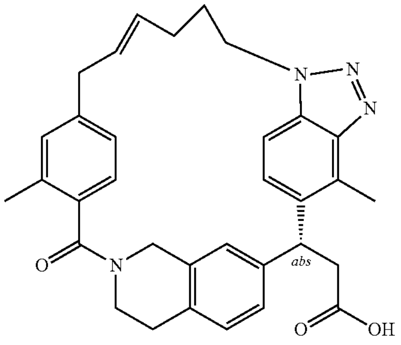 |

TABLE 2-continued
| Comp'd No | Structure |
|---|---|
| 393 | 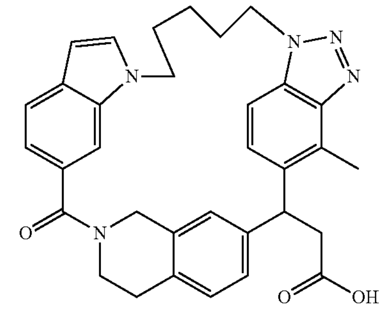 [SMILES: Cc1c2ccc3c1nnn3CCCCCn1ccc3ccc(cc31)C(=O)N1CCc3ccc(cc3C1)C2CC(=O)O] |
| 394 | 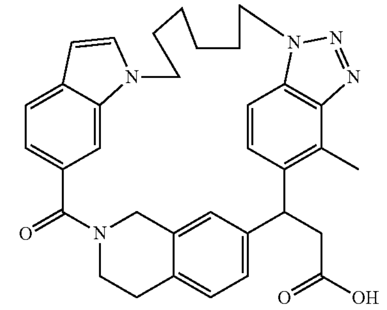 [SMILES: Cc1c2ccc3c1nnn3CCCCCCn1ccc3ccc(cc31)C(=O)N1CCc3ccc(cc3C1)C2CC(=O)O] |
| 395 | 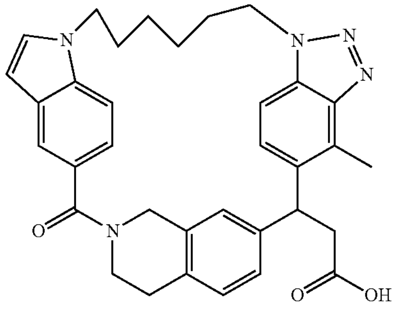 [SMILES: Cc1c2ccc3c1nnn3CCCCCCn1ccc3cc(ccc31)C(=O)N1CCc3ccc(cc3C1)C2CC(=O)O] |
| 396 | 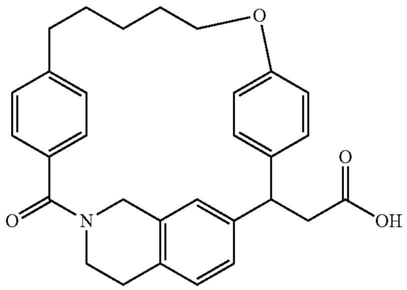 [SMILES: O=C(O)CC1c2ccc(cc2)OCCCCCc2ccc(cc2)C(=O)N2CCc3ccc1cc3C2] |
| 397 | 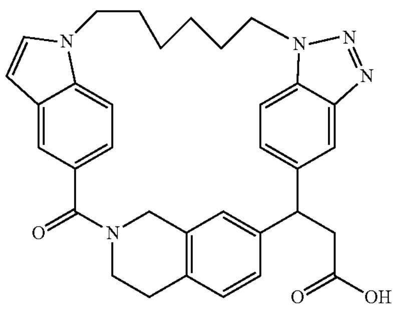 [SMILES: O=C(O)CC1c2ccc3c(c2)CN(CC3)C(=O)c2ccc3c(ccn3CCCCCCn3nnc4cc1ccc43)c2] |
TABLE 2-continued
| Comp'd No | Structure |
|---|---|
| 398 | 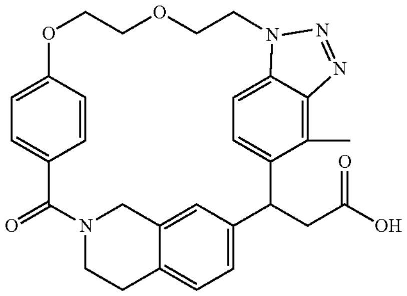 [SMILES: Cc1c2ccc3c1nnn3CCOCCOc1ccc(cc1)C(=O)N1CCc3ccc(cc3C1)C2CC(=O)O] |
| 399 | 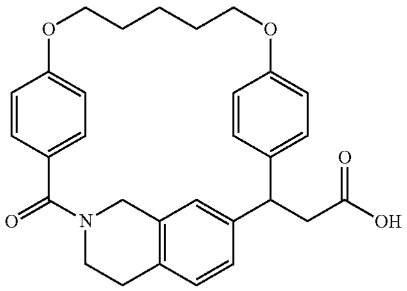 [SMILES: O=C(O)CC1c2ccc(cc2)OCCCCCOc2ccc(cc2)C(=O)N2CCc3ccc1cc3C2] |
| 400 | 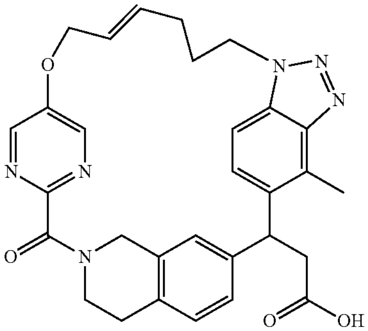 [SMILES: Cc1c2ccc3c1nnn3CCC/C=C/COc1cnc(nc1)C(=O)N1CCc3ccc(cc3C1)C2CC(=O)O] |
| 401 | 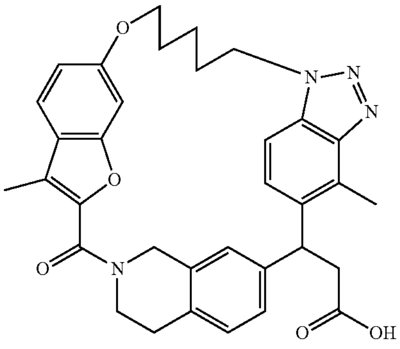 |

TABLE 2-continued
| Comp'd No | Structure |
| --- | --- |
| 402 | 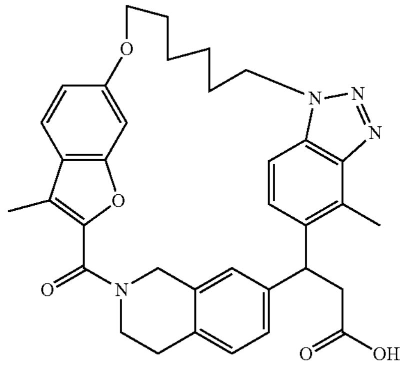 |
| 403 | 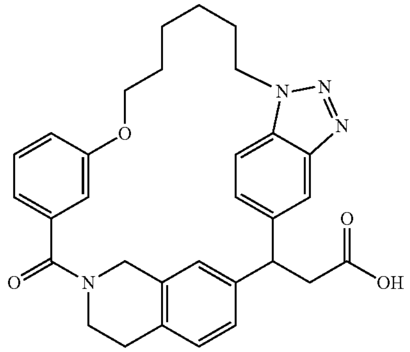 [SMILES: O=C(O)CC1c2ccc3c(c2)CN(CC3)C(=O)c2cccc(c2)OCCCCCCn2nnc3cc1ccc32] |
| 408 | 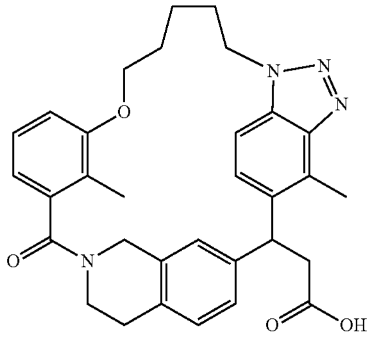 [SMILES: Cc1c2cccc1C(=O)N1CCc3ccc(cc3C1)C(CC(=O)O)c1ccc3c(nnn3CCCCCO2)c1C] |
| 409 | 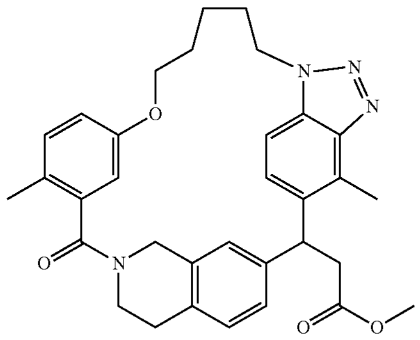 |
TABLE 2-continued
| Comp'd No | Structure |
| --- | --- |
| 410 | 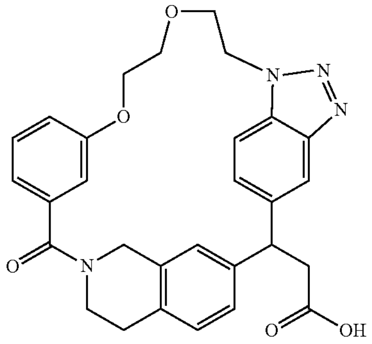 [SMILES: O=C(O)CC1c2ccc3c(c2)CN(CC3)C(=O)c2cccc(c2)OCCOCCn2nnc3cc1ccc32] |
| 411 | 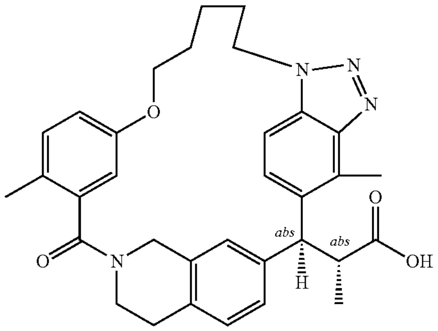 [SMILES: Cc1ccc2cc1C(=O)N1CCc3ccc(cc3C1)[C@H]([C@@H](C)C(=O)O)c1ccc3c(nnn3CCCCCO2)c1C] |
| 412 | 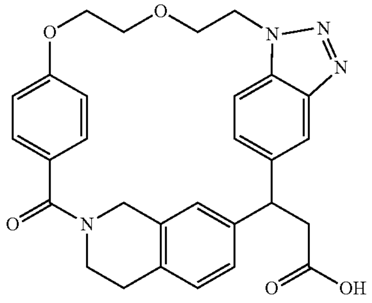 [SMILES: O=C(O)CC1c2ccc3c(c2)CN(CC3)C(=O)c2ccc(cc2)OCCOCCn2nnc3cc1ccc32] |
| 413 | 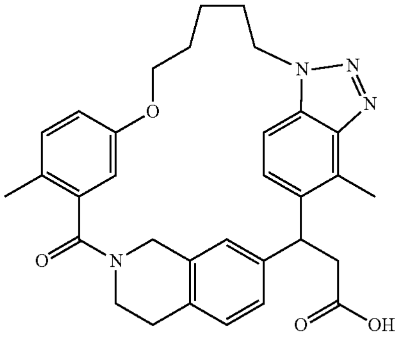 |

TABLE 2-continued
| Comp'd No | Structure |
|---|---|
| 414 | 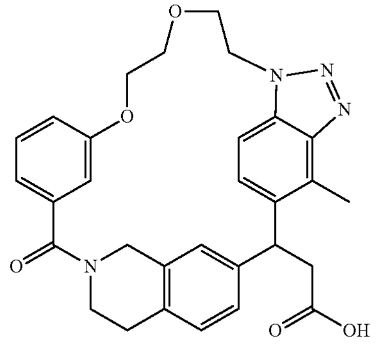 [SMILES: Cc1c2ccc3c1nnn3CCOCCOc1cccc(c1)C(=O)N1CCc3ccc(cc3C1)C2CC(=O)O] |
| 415 | 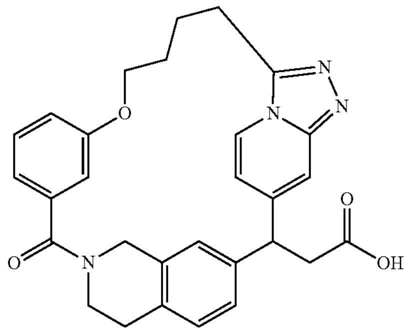 [SMILES: O=C(O)CC1c2ccc3c(c2)CN(CC3)C(=O)c2cccc(c2)OCCCCc2nnc3cc1ccn23] |
| 416 | 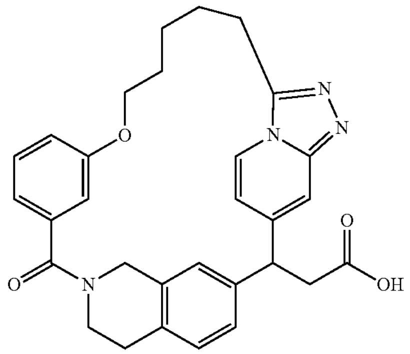 [SMILES: O=C(O)CC1c2ccc3c(c2)CN(CC3)C(=O)c2cccc(c2)OCCCCCc2nnc3cc1ccn23] |
| 417 | 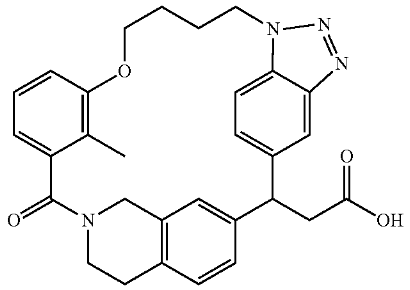 [SMILES: Cc1c2cccc1C(=O)N1CCc3ccc(cc3C1)C(CC(=O)O)c1ccc3c(c1)nnn3CCCCO2] |
TABLE 2-continued
| Comp'd No | Structure |
|---|---|
| 418 | 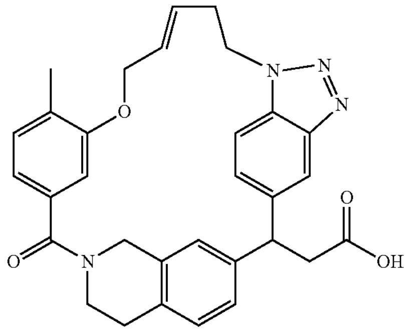 [SMILES: Cc1ccc2cc1OC/C=C/CCn1nnc3cc(ccc31)C(CC(=O)O)c1ccc3c(c1)CN(CC3)C2=O] |
| 419 | 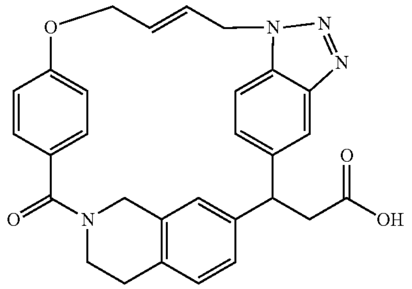 [SMILES: O=C(O)CC1c2ccc3c(c2)CN(CC3)C(=O)c2ccc(cc2)OC/C=C/Cn2nnc3cc1ccc32] |
| 420 | 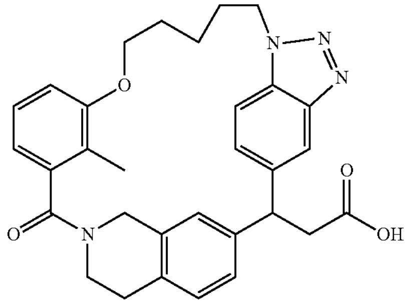 [SMILES: Cc1c2cccc1C(=O)N1CCc3ccc(cc3C1)C(CC(=O)O)c1ccc3c(c1)nnn3CCCCCO2] |
| 421 | 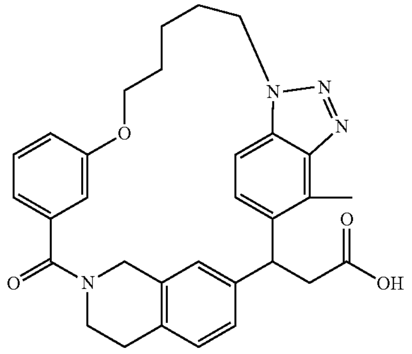 [SMILES: Cc1c2ccc3c1nnn3CCCCCOc1cccc(c1)C(=O)N1CCc3ccc(cc3C1)C2CC(=O)O] |

TABLE 2-continued
| Comp'd No | Structure |
|---|---|
| 422 | 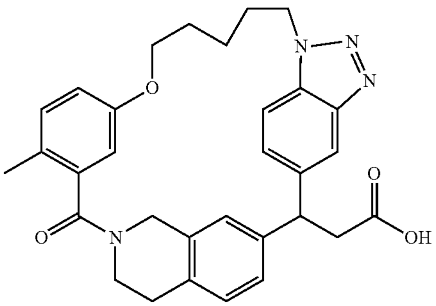 [SMILES: Cc1ccc2cc1C(=O)N1CCc3ccc(cc3C1)C(CC(=O)O)c1ccc3c(c1)nnn3CCCCCO2] |
| 423 | 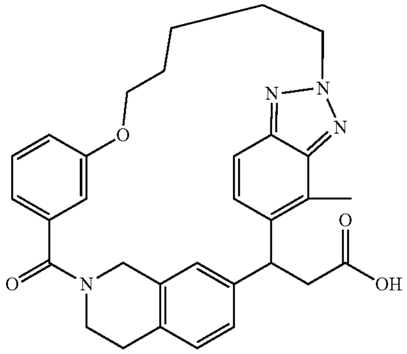 [SMILES: Cc1c2ccc3nn(nc13)CCCCCOc1cccc(c1)C(=O)N1CCc3ccc(cc3C1)C2CC(=O)O] |
| 424 | 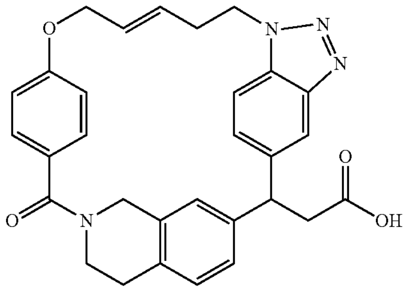 [SMILES: O=C(O)CC1c2ccc3c(c2)CN(CC3)C(=O)c2ccc(cc2)OC/C=C/CCn2nnc3cc1ccc32] |
| 425 | 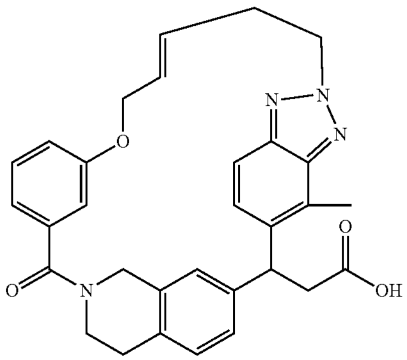 [SMILES: Cc1c2ccc3nn(nc13)CC/C=C/COc1cccc(c1)C(=O)N1CCc3ccc(cc3C1)C2CC(=O)O] |
| 426 | 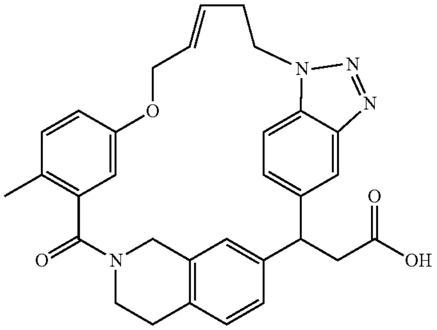 [SMILES: Cc1ccc2cc1C(=O)N1CCc3ccc(cc3C1)C(CC(=O)O)c1ccc3c(c1)nnn3CC/C=C/CO2] |
| 427 | 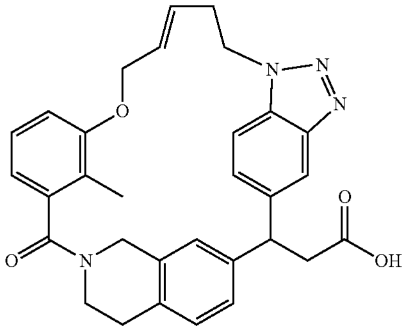 [SMILES: Cc1c2cccc1C(=O)N1CCc3ccc(cc3C1)C(CC(=O)O)c1ccc3c(c1)nnn3CC/C=C/CO2] |
| 428 | 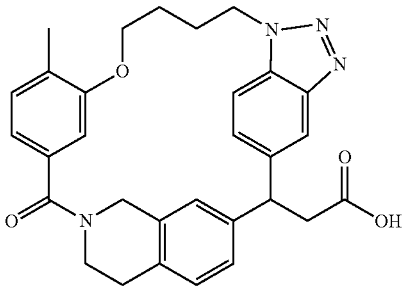 [SMILES: Cc1ccc2cc1OCCCCn1nnc3cc(ccc31)C(CC(=O)O)c1ccc3c(c1)CN(CC3)C2=O] |
| 429 | 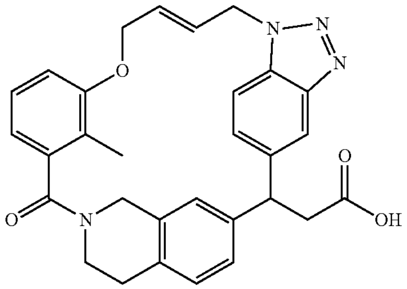 [SMILES: Cc1c2cccc1C(=O)N1CCc3ccc(cc3C1)C(CC(=O)O)c1ccc3c(c1)nnn3C/C=C/CO2] |
| 430 | 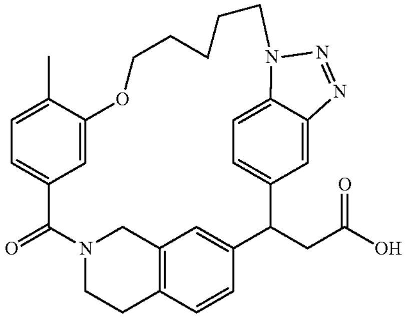 [SMILES: Cc1ccc2cc1OCCCCCn1nnc3cc(ccc31)C(CC(=O)O)c1ccc3c(c1)CN(CC3)C2=O] |

TABLE 2-continued
| Comp'd No | Structure |
|---|---|
| 431 | 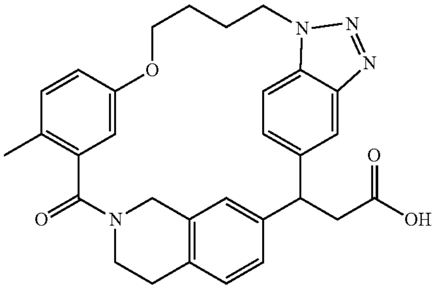 [SMILES: Cc1ccc2cc1C(=O)N1CCc3ccc(cc3C1)C(CC(=O)O)c1ccc3c(c1)nnn3CCCCO2] |
| 432 | 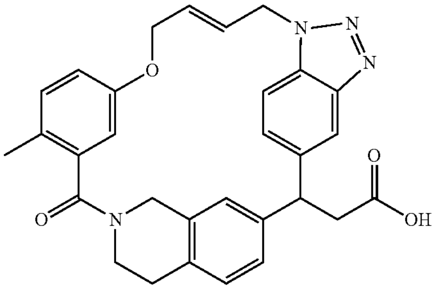 [SMILES: Cc1ccc2cc1C(=O)N1CCc3ccc(cc3C1)C(CC(=O)O)c1ccc3c(c1)nnn3C/C=C/CO2] |
| 433 | 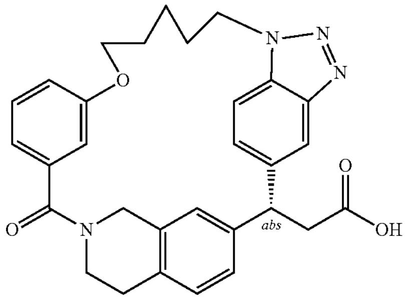 [SMILES: O=C(O)C[C@@H]1c2ccc3c(c2)CN(CC3)C(=O)c2cccc(c2)OCCCCCn2nnc3cc1ccc32] |
| 434 | 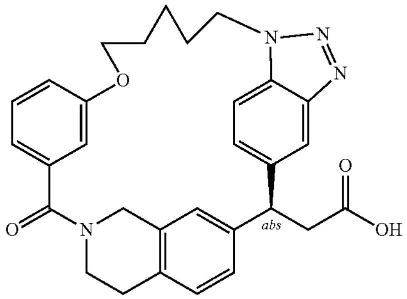 [SMILES: O=C(O)C[C@H]1c2ccc3c(c2)CN(CC3)C(=O)c2cccc(c2)OCCCCCn2nnc3cc1ccc32] |
| 435 | 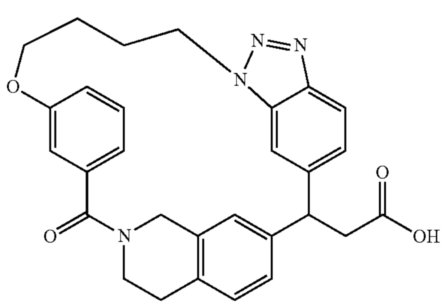 [SMILES: O=C(O)CC1c2ccc3c(c2)CN(CC3)C(=O)c2cccc(c2)OCCCCn2nnc3ccc1cc32] |
TABLE 2-continued
| Comp'd No | Structure |
|---|---|
| 436 | 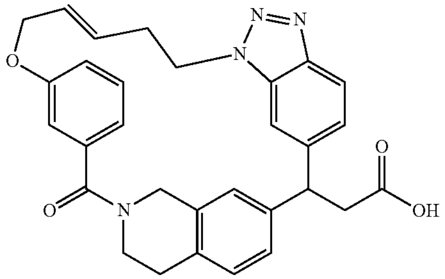 [SMILES: O=C(O)CC1c2ccc3c(c2)CN(CC3)C(=O)c2cccc(c2)OC/C=C/CCn2nnc3ccc1cc32] |
| 437 | 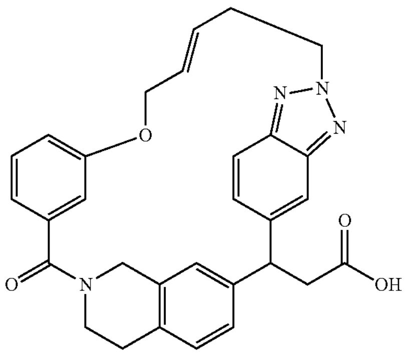 [SMILES: O=C(O)CC1c2ccc3c(c2)CN(CC3)C(=O)c2cccc(c2)OC/C=C/CCn2nc3ccc1cc3n2] |
| 438 | 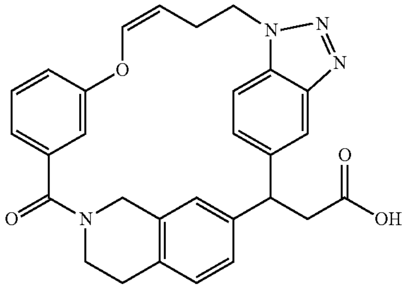 [SMILES: O=C(O)CC1c2ccc3c(c2)CN(CC3)C(=O)c2cccc(c2)O/C=C\CCn2nnc3cc1ccc32] |
| 439 | 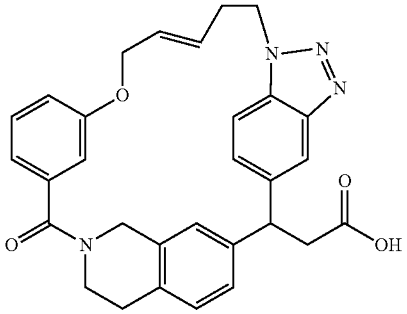 [SMILES: O=C(O)CC1c2ccc3c(c2)CN(CC3)C(=O)c2cccc(c2)OC/C=C/CCn2nnc3cc1ccc32] |

TABLE 2-continued
| Comp'd No | Structure |
|---|---|
| 440 | 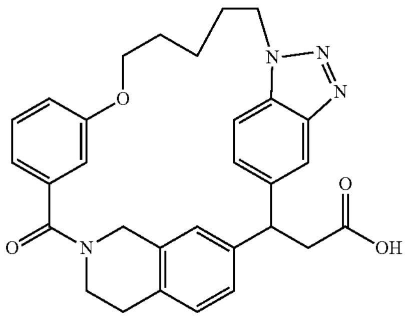 [SMILES: O=C(O)CC1c2ccc3c(c2)CN(CC3)C(=O)c2cccc(c2)OCCCCCn2nnc3cc1ccc32] |
or a pharmaceutically acceptable salt thereof.
TABLE 2a
| Comp'd No | Structure |
|---|---|
| 1 | 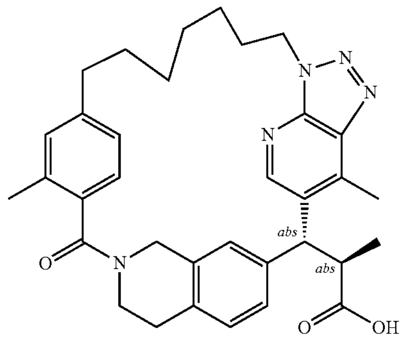 |
| 2 | 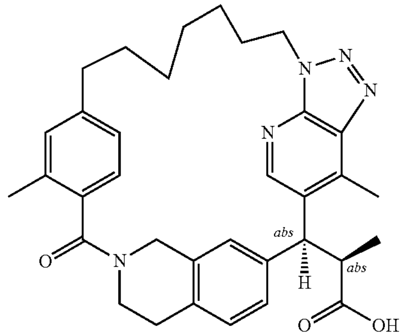 |
| 3 | 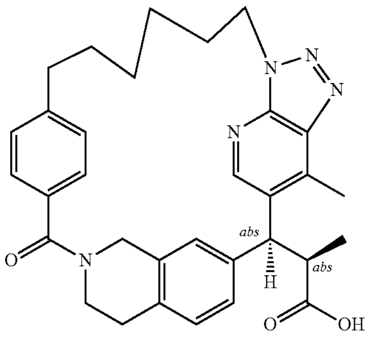 [SMILES: Cc1c2cnc3c1nnn3CCCCCCc1ccc(cc1)C(=O)N1CCc3ccc(cc3C1)[C@@H]2[C@@H](C)C(=O)O] |
TABLE 2a-continued
| Comp'd No | Structure |
|---|---|
| 4 | 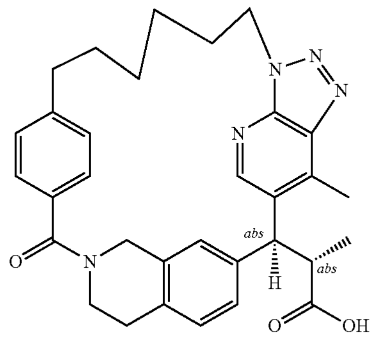 [SMILES: Cc1c2cnc3c1nnn3CCCCCCc1ccc(cc1)C(=O)N1CCc3ccc(cc3C1)[C@@H]2[C@H](C)C(=O)O] |
| 5 | 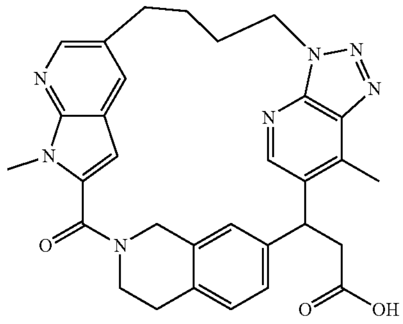 |
| 6 | 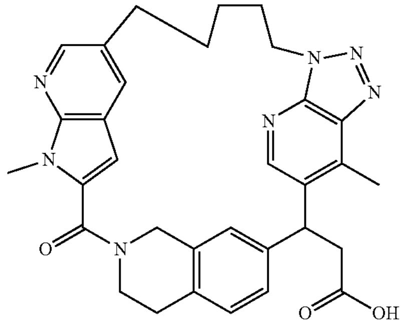 |
| 7 | 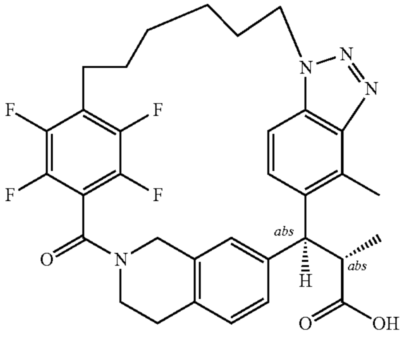 [SMILES: Cc1c2ccc3c1nnn3CCCCCCc1c(F)c(F)c(c(F)c1F)C(=O)N1CCc3ccc(cc3C1)[C@@H]2[C@H](C)C(=O)O] |

TABLE 2a-continued
| Comp'd No | Structure |
|---|---|
| 8 | 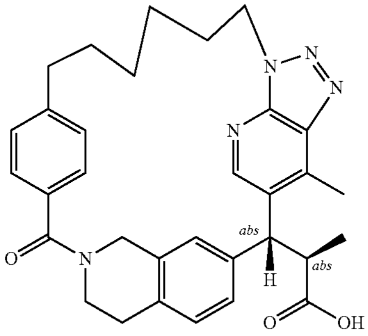 [SMILES: Cc1c2cnc3c1nnn3CCCCCCc1ccc(cc1)C(=O)N1CCc3ccc(cc3C1)[C@H]2[C@@H](C)C(=O)O] |
| 9 | 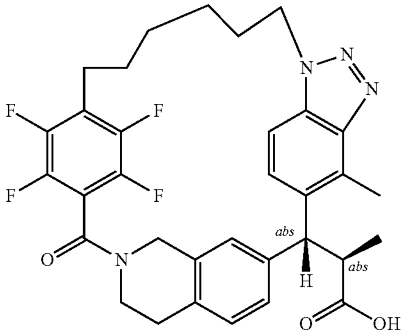 [SMILES: Cc1c2ccc3c1nnn3CCCCCCc1c(F)c(F)c(c(F)c1F)C(=O)N1CCc3ccc(cc3C1)[C@H]2[C@@H](C)C(=O)O] |
| 10 | 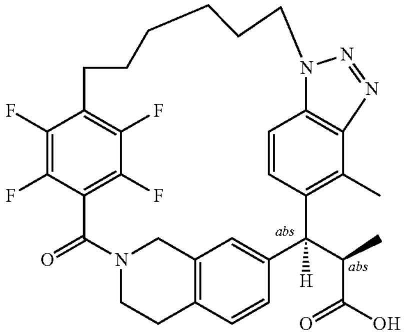 [SMILES: Cc1c2ccc3c1nnn3CCCCCCc1c(F)c(F)c(c(F)c1F)C(=O)N1CCc3ccc(cc3C1)[C@@H]2[C@@H](C)C(=O)O] |
| 11 | 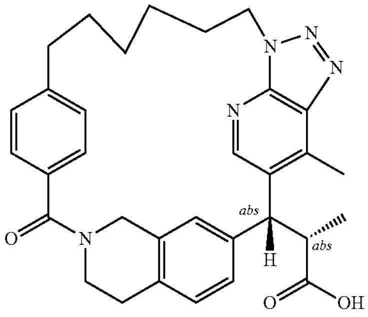 [SMILES: Cc1c2cnc3c1nnn3CCCCCCc1ccc(cc1)C(=O)N1CCc3ccc(cc3C1)[C@H]2[C@H](C)C(=O)O] |
TABLE 2a-continued
| Comp'd No | Structure |
|---|---|
| 12 | 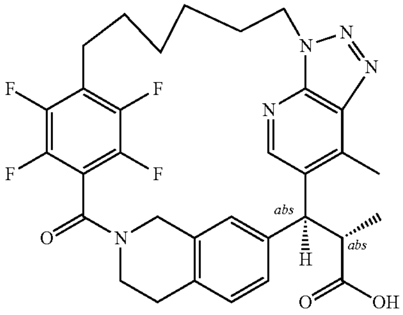 [SMILES: Cc1c2cnc3c1nnn3CCCCCCc1c(F)c(F)c(c(F)c1F)C(=O)N1CCc3ccc(cc3C1)[C@@H]2[C@H](C)C(=O)O] |
| 13 | 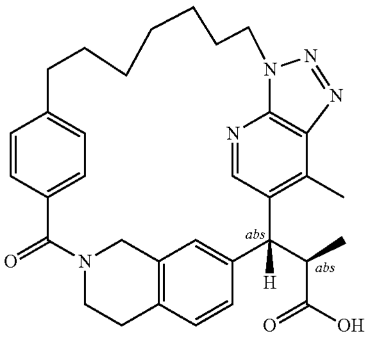 [SMILES: Cc1c2cnc3c1nnn3CCCCCCCc1ccc(cc1)C(=O)N1CCc3ccc(cc3C1)[C@H]2[C@@H](C)C(=O)O] |
| 14 | 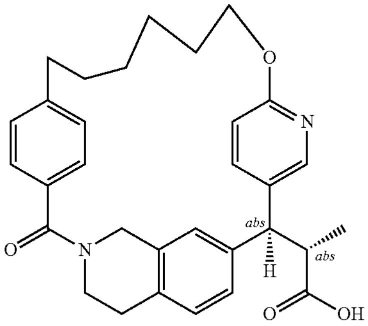 [SMILES: C[C@H](C(=O)O)[C@@H]1c2ccc(nc2)OCCCCCCc2ccc(cc2)C(=O)N2CCc3ccc1cc3C2] |
| 15 | 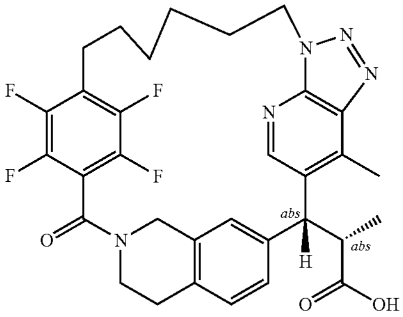 [SMILES: Cc1c2cnc3c1nnn3CCCCCCc1c(F)c(F)c(c(F)c1F)C(=O)N1CCc3ccc(cc3C1)[C@H]2[C@H](C)C(=O)O] |

TABLE 2a-continued
| Comp'd No | Structure |
| --- | --- |
| 16 | 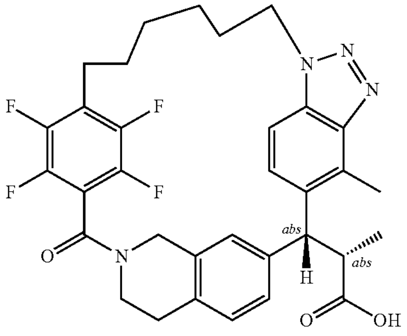 [SMILES: Cc1c2ccc3c1nnn3CCCCCCc1c(F)c(F)c(c(F)c1F)C(=O)N1CCc3ccc(cc3C1)[C@H]2[C@H](C)C(=O)O] |
| 17 | 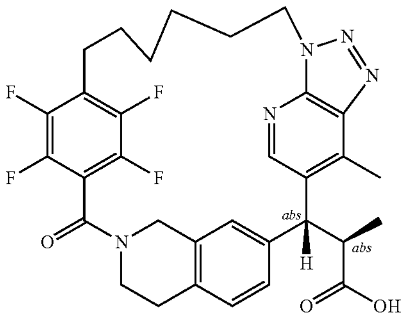 [SMILES: Cc1c2cnc3c1nnn3CCCCCCc1c(F)c(F)c(c(F)c1F)C(=O)N1CCc3ccc(cc3C1)[C@H]2[C@@H](C)C(=O)O] |
| 18 | 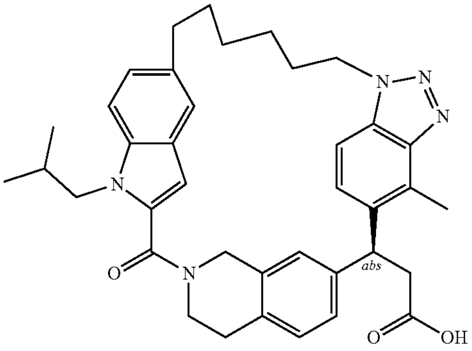 [SMILES: Cc1c2ccc3c1nnn3CCCCCCc1ccc3c(c1)cc(n3CC(C)C)C(=O)N1CCc3ccc(cc3C1)[C@@H]2CC(=O)O] |
| 19 | 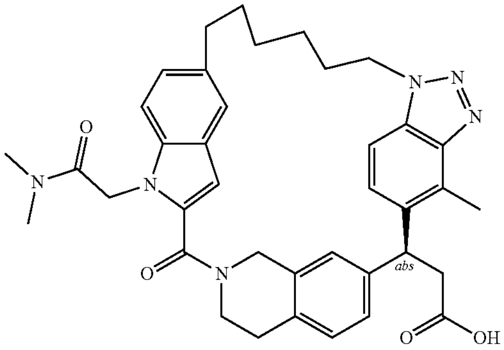 |
TABLE 2a-continued
| Comp'd No | Structure |
| --- | --- |
| 20 | 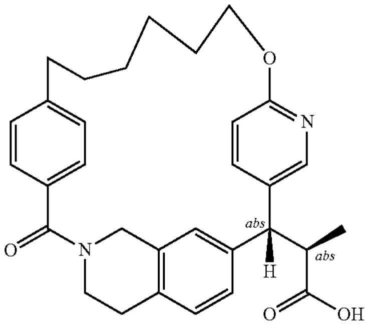 [SMILES: C[C@@H](C(=O)O)[C@H]1c2ccc(nc2)OCCCCCCc2ccc(cc2)C(=O)N2CCc3ccc1cc3C2] |
| 21 | 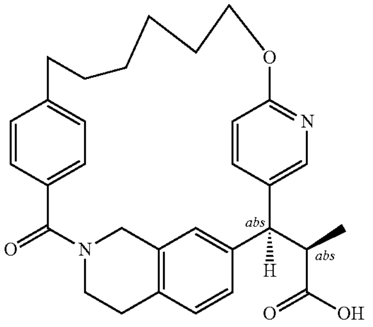 [SMILES: C[C@@H](C(=O)O)[C@@H]1c2ccc(nc2)OCCCCCCc2ccc(cc2)C(=O)N2CCc3ccc1cc3C2] |
| 22 | 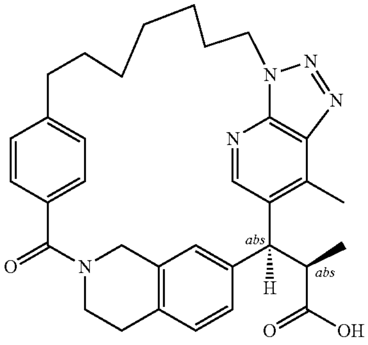 [SMILES: Cc1c2cnc3c1nnn3CCCCCCCc1ccc(cc1)C(=O)N1CCc3ccc(cc3C1)[C@@H]2[C@@H](C)C(=O)O] |
| 23 | 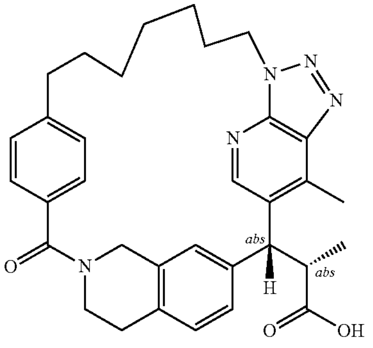 [SMILES: Cc1c2cnc3c1nnn3CCCCCCCc1ccc(cc1)C(=O)N1CCc3ccc(cc3C1)[C@H]2[C@H](C)C(=O)O] |

TABLE 2a-continued
| Comp'd No | Structure |
|---|---|
| 24 | 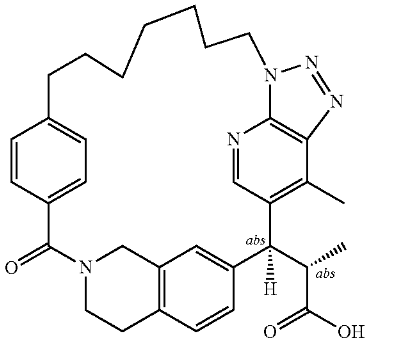 [SMILES: Cc1c2cnc3c1nnn3CCCCCCCc1ccc(cc1)C(=O)N1CCc3ccc(cc3C1)[C@@H]2[C@H](C)C(=O)O] |
| 25 | 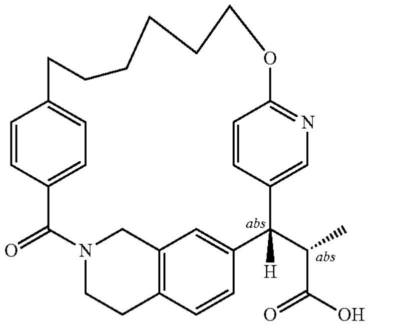 [SMILES: C[C@H](C(=O)O)[C@H]1c2ccc(nc2)OCCCCCCc2ccc(cc2)C(=O)N2CCc3ccc1cc3C2] |
| 26 | 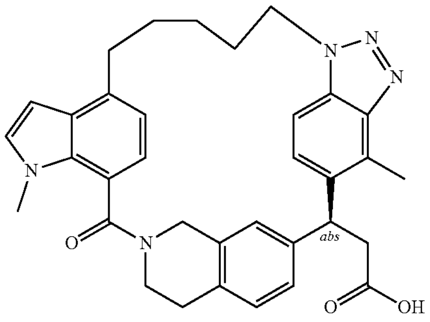 [SMILES: Cc1c2ccc3c1nnn3CCCCCc1ccc(c3c1ccn3C)C(=O)N1CCc3ccc(cc3C1)[C@@H]2CC(=O)O] |
| 27 | 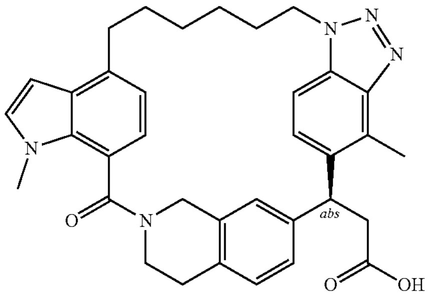 [SMILES: Cc1c2ccc3c1nnn3CCCCCCc1ccc(c3c1ccn3C)C(=O)N1CCc3ccc(cc3C1)[C@@H]2CC(=O)O] |
TABLE 2a-continued
| Comp'd No | Structure |
|---|---|
| 28 | 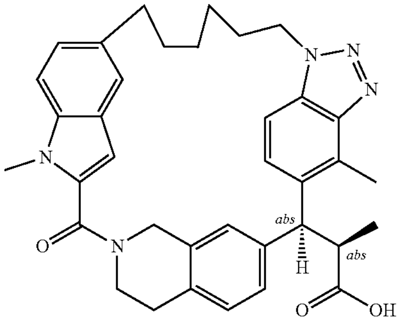 [SMILES: Cc1c2ccc3c1nnn3CCCCCCc1ccc3c(c1)cc(n3C)C(=O)N1CCc3ccc(cc3C1)[C@@H]2[C@@H](C)C(=O)O] |
| 29 | 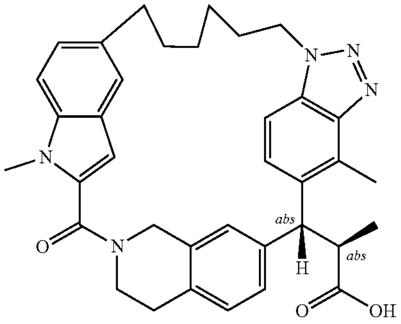 [SMILES: Cc1c2ccc3c1nnn3CCCCCCc1ccc3c(c1)cc(n3C)C(=O)N1CCc3ccc(cc3C1)[C@H]2[C@@H](C)C(=O)O] |
| 30 | 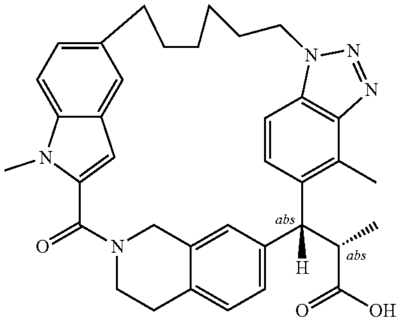 [SMILES: Cc1c2ccc3c1nnn3CCCCCCc1ccc3c(c1)cc(n3C)C(=O)N1CCc3ccc(cc3C1)[C@H]2[C@H](C)C(=O)O] |
| 31 | 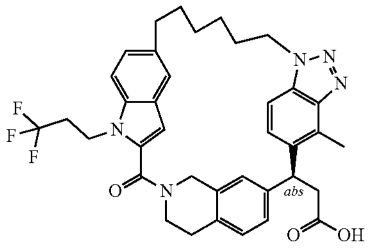 [SMILES: Cc1c2ccc3c1nnn3CCCCCCc1ccc3c(c1)cc(n3CCC(F)(F)F)C(=O)N1CCc3ccc(cc3C1)[C@@H]2CC(=O)O] |
| 32 | 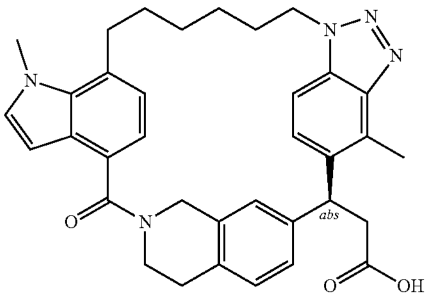 [SMILES: Cc1c2ccc3c1nnn3CCCCCCc1ccc(c3ccn(C)c13)C(=O)N1CCc3ccc(cc3C1)[C@@H]2CC(=O)O] |

TABLE 2a-continued
| Comp'd No | Structure |
|---|---|
| 33 | 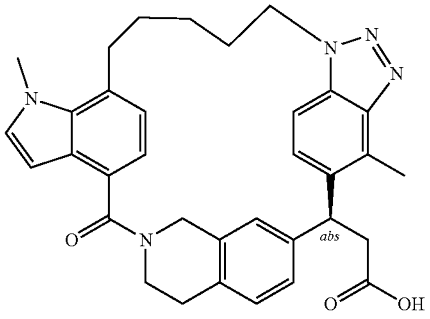 [SMILES: Cc1c2ccc3c1nnn3CCCCCc1ccc(c3ccn(C)c13)C(=O)N1CCc3ccc(cc3C1)[C@@H]2CC(=O)O] |
| 34 | 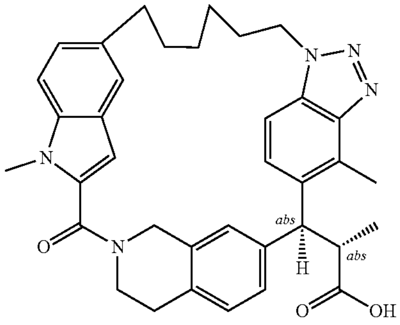 [SMILES: Cc1c2ccc3c1nnn3CCCCCCc1ccc3c(c1)cc(n3C)C(=O)N1CCc3ccc(cc3C1)[C@@H]2[C@H](C)C(=O)O] |
| 35 | 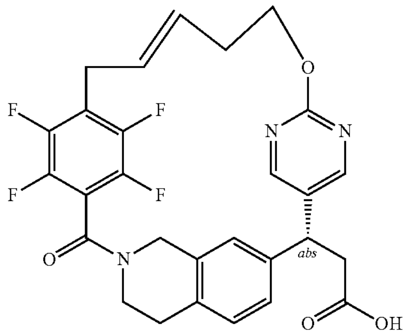 [SMILES: O=C(O)C[C@H]1c2cnc(nc2)OCC/C=C/Cc2c(F)c(F)c(c(F)c2F)C(=O)N2CCc3ccc1cc3C2] |
| 36 | 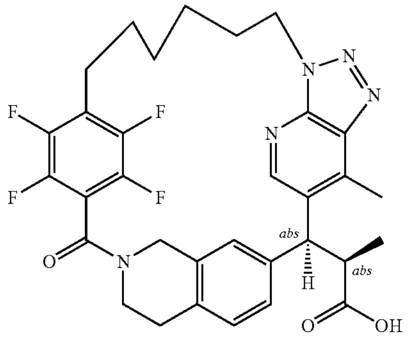 [SMILES: Cc1c2cnc3c1nnn3CCCCCCc1c(F)c(F)c(c(F)c1F)C(=O)N1CCc3ccc(cc3C1)[C@@H]2[C@@H](C)C(=O)O] |
TABLE 2a-continued
| Comp'd No | Structure |
|---|---|
| 37 | 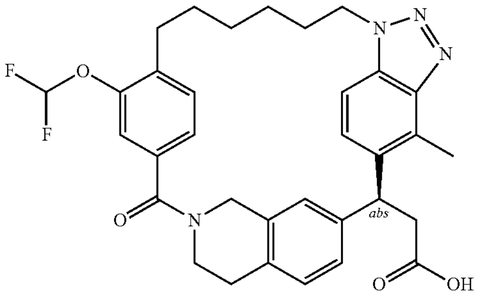 [SMILES: Cc1c2ccc3c1nnn3CCCCCCc1ccc(cc1OC(F)F)C(=O)N1CCc3ccc(cc3C1)[C@@H]2CC(=O)O] |
| 38 | 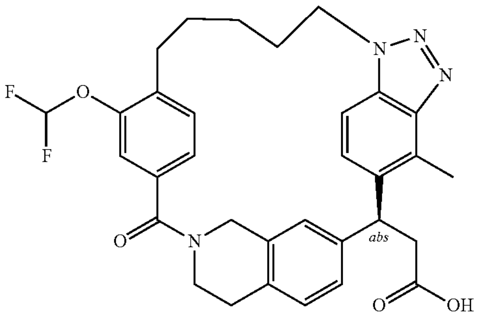 [SMILES: Cc1c2ccc3c1nnn3CCCCCc1ccc(cc1OC(F)F)C(=O)N1CCc3ccc(cc3C1)[C@@H]2CC(=O)O] |
| 39 | 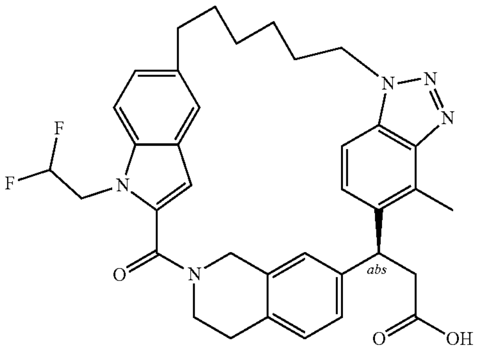 [SMILES: Cc1c2ccc3c1nnn3CCCCCCc1ccc3c(c1)cc(n3CC(F)F)C(=O)N1CCc3ccc(cc3C1)[C@@H]2CC(=O)O] |
| 40 | 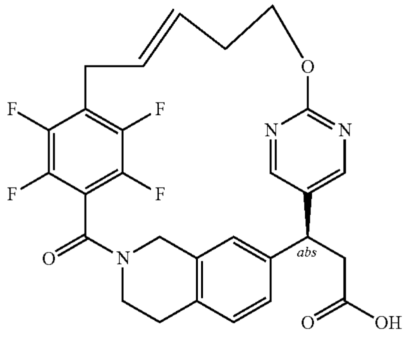 [SMILES: O=C(O)C[C@@H]1c2cnc(nc2)OCC/C=C/Cc2c(F)c(F)c(c(F)c2F)C(=O)N2CCc3ccc1cc3C2] |

TABLE 2a-continued
| Comp'd No | Structure |
|---|---|
| 41 | 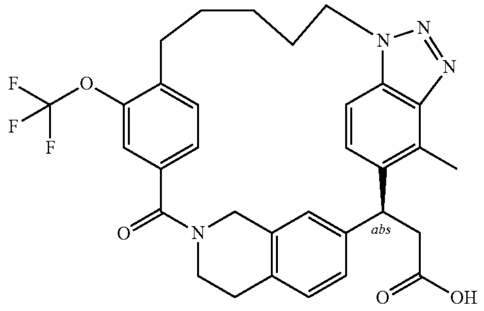 [SMILES: Cc1c2ccc3c1nnn3CCCCCc1ccc(cc1OC(F)(F)F)C(=O)N1CCc3ccc(cc3C1)[C@@H]2CC(=O)O] |
| 42 | 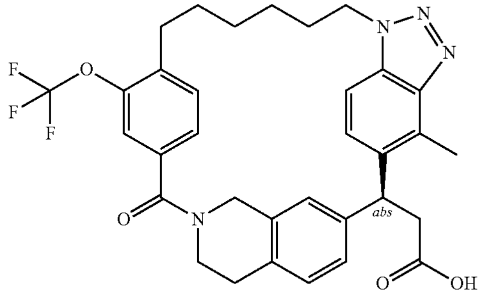 [SMILES: Cc1c2ccc3c1nnn3CCCCCCc1ccc(cc1OC(F)(F)F)C(=O)N1CCc3ccc(cc3C1)[C@@H]2CC(=O)O] |
| 43 | 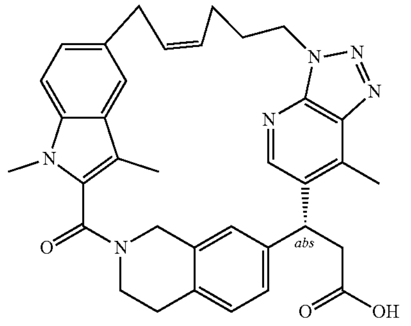 |
| 44 | 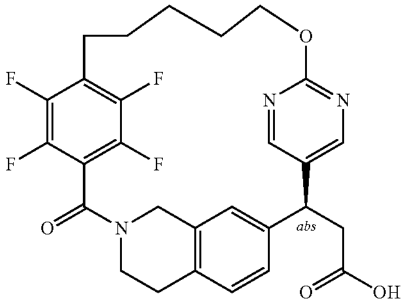 [SMILES: O=C(O)C[C@@H]1c2cnc(nc2)OCCCCCc2c(F)c(F)c(c(F)c2F)C(=O)N2CCc3ccc1cc3C2] |
| 45 | 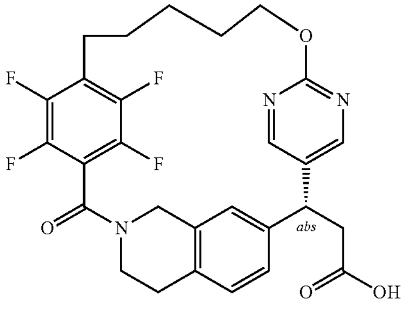 [SMILES: O=C(O)C[C@H]1c2cnc(nc2)OCCCCCc2c(F)c(F)c(c(F)c2F)C(=O)N2CCc3ccc1cc3C2] |
TABLE 2a-continued
| Comp'd No | Structure |
|---|---|
| 46 | 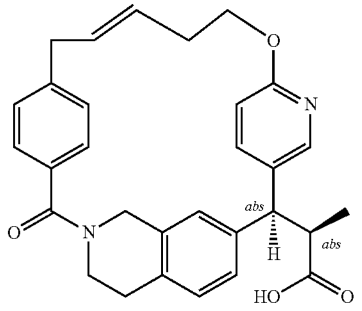 [SMILES: C[C@@H](C(=O)O)[C@@H]1c2ccc(nc2)OCC/C=C/Cc2ccc(cc2)C(=O)N2CCc3ccc1cc3C2] |
| 47 | 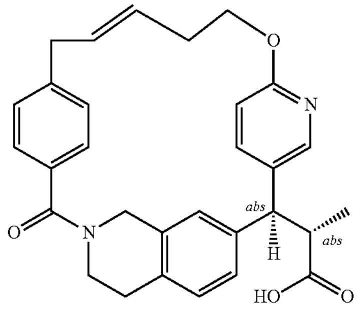 [SMILES: C[C@H](C(=O)O)[C@@H]1c2ccc(nc2)OCC/C=C/Cc2ccc(cc2)C(=O)N2CCc3ccc1cc3C2] |
| 48 | 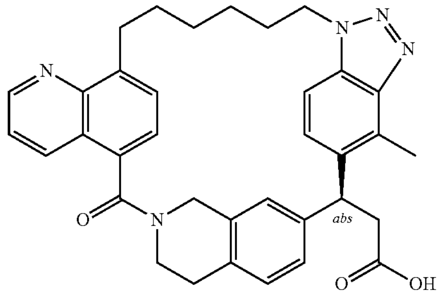 [SMILES: Cc1c2ccc3c1nnn3CCCCCCc1ccc(c3cccnc13)C(=O)N1CCc3ccc(cc3C1)[C@@H]2CC(=O)O] |
| 49 | 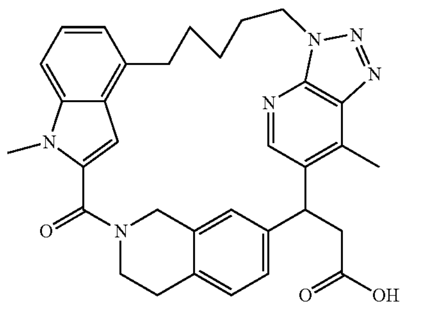 |
| 50 | 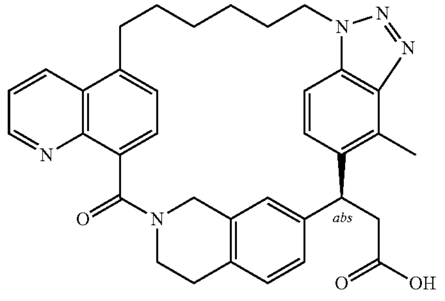 [SMILES: Cc1c2ccc3c1nnn3CCCCCCc1ccc(c3ncccc13)C(=O)N1CCc3ccc(cc3C1)[C@@H]2CC(=O)O] |

TABLE 2a-continued
| Comp'd No | Structure |
|---|---|
| 51 | 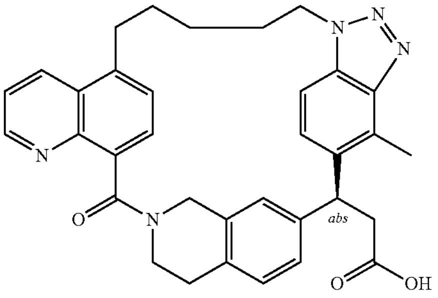 [SMILES: Cc1c2ccc3c1nnn3CCCCCc1ccc(c3ncccc13)C(=O)N1CCc3ccc(cc3C1)[C@@H]2CC(=O)O] |
| 52 | 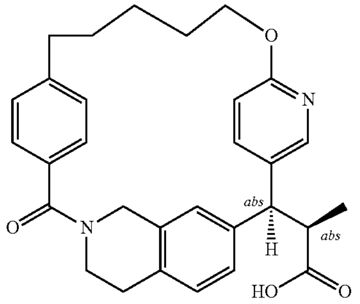 [SMILES: C[C@@H](C(=O)O)[C@@H]1c2ccc(nc2)OCCCCCc2ccc(cc2)C(=O)N2CCc3ccc1cc3C2] |
| 53 | 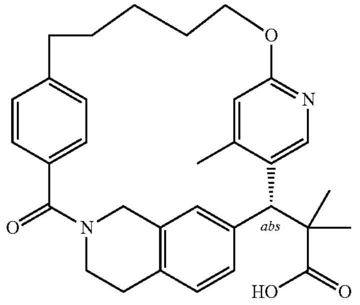 [SMILES: Cc1cc2ncc1[C@H](C(C)(C)C(=O)O)c1ccc3c(c1)CN(CC3)C(=O)c1ccc(cc1)CCCCCO2] |
| 54 | 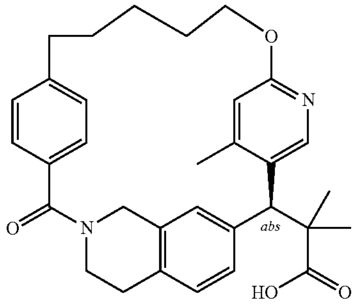 [SMILES: Cc1cc2ncc1[C@@H](C(C)(C)C(=O)O)c1ccc3c(c1)CN(CC3)C(=O)c1ccc(cc1)CCCCCO2] |
| 55 | 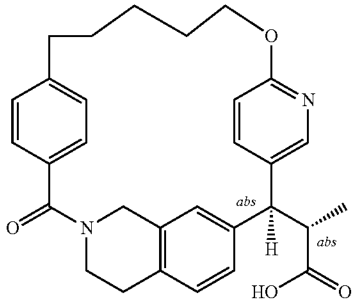 [SMILES: C[C@H](C(=O)O)[C@@H]1c2ccc(nc2)OCCCCCc2ccc(cc2)C(=O)N2CCc3ccc1cc3C2] |
TABLE 2a-continued
| Comp'd No | Structure |
|---|---|
| 56 | 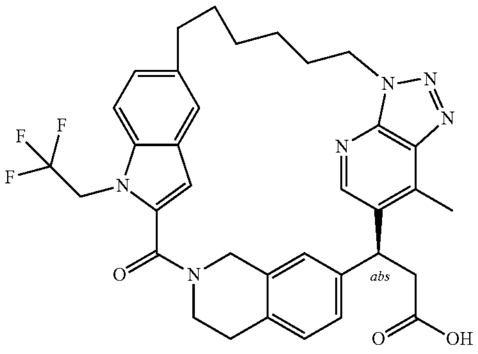 [SMILES: Cc1c2cnc3c1nnn3CCCCCCc1ccc3c(c1)cc(n3CC(F)(F)F)C(=O)N1CCc3ccc(cc3C1)[C@@H]2CC(=O)O] |
| 57 | 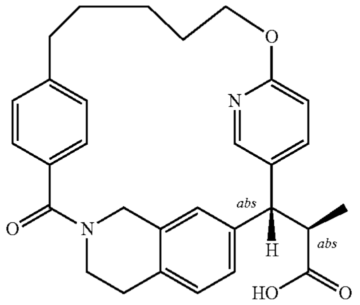 [SMILES: C[C@@H](C(=O)O)[C@H]1c2ccc(nc2)OCCCCCc2ccc(cc2)C(=O)N2CCc3ccc1cc3C2] |
| 58 | 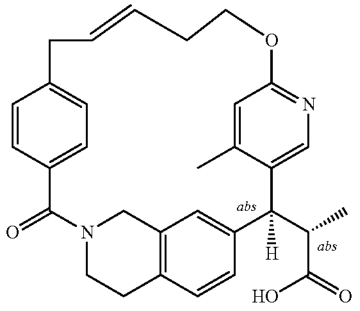 [SMILES: Cc1cc2ncc1[C@@H]([C@H](C)C(=O)O)c1ccc3c(c1)CN(CC3)C(=O)c1ccc(cc1)C/C=C/CCO2] |
| 59 | 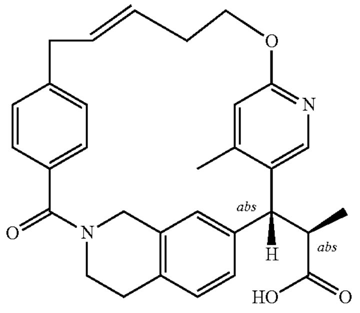 [SMILES: Cc1cc2ncc1[C@H]([C@@H](C)C(=O)O)c1ccc3c(c1)CN(CC3)C(=O)c1ccc(cc1)C/C=C/CCO2] |

TABLE 2a-continued
| Comp'd No | Structure |
|---|---|
| 60 | 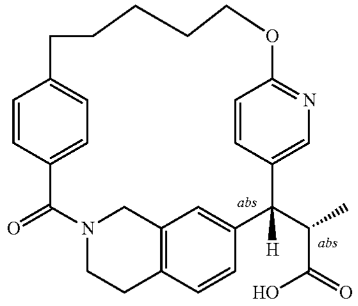 [SMILES: C[C@H](C(=O)O)[C@H]1c2ccc(nc2)OCCCCCc2ccc(cc2)C(=O)N2CCc3ccc1cc3C2] |
| 61 | 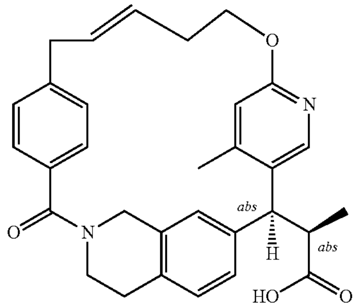 [SMILES: Cc1cc2ncc1[C@@H]([C@@H](C)C(=O)O)c1ccc3c(c1)CN(CC3)C(=O)c1ccc(cc1)C/C=C/CCO2] |
| 62 | 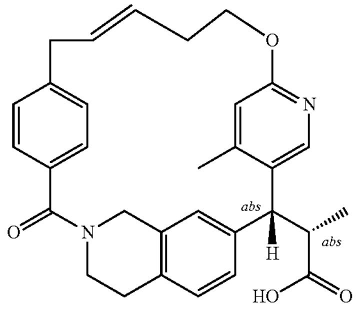 [SMILES: Cc1cc2ncc1[C@H]([C@H](C)C(=O)O)c1ccc3c(c1)CN(CC3)C(=O)c1ccc(cc1)C/C=C/CCO2] |
| 63 | 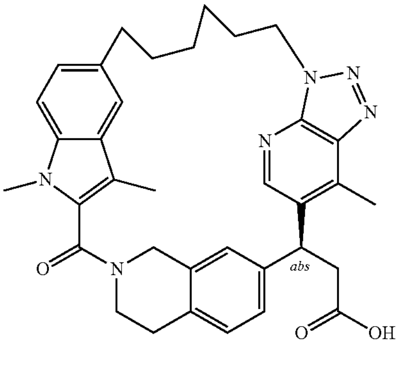 |
TABLE 2a-continued
| Comp'd No | Structure |
|---|---|
| 64 | 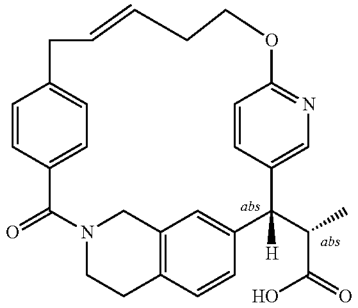 [SMILES: C[C@H](C(=O)O)[C@H]1c2ccc(nc2)OCC/C=C/Cc2ccc(cc2)C(=O)N2CCc3ccc1cc3C2] |
| 65 | 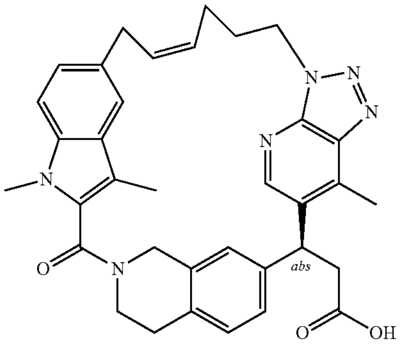 |
| 66 | 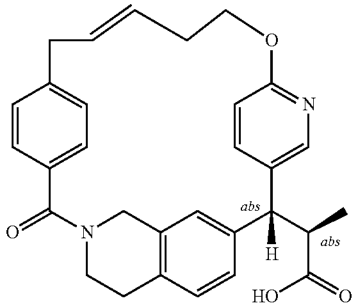 [SMILES: C[C@@H](C(=O)O)[C@H]1c2ccc(nc2)OCC/C=C/Cc2ccc(cc2)C(=O)N2CCc3ccc1cc3C2] |
| 67 | 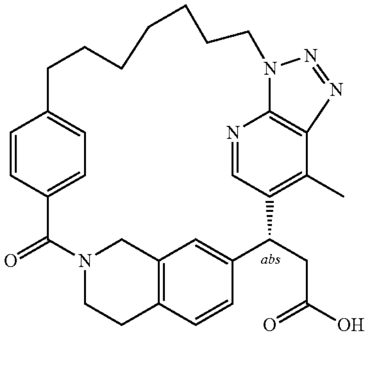 [SMILES: Cc1c2cnc3c1nnn3CCCCCCCc1ccc(cc1)C(=O)N1CCc3ccc(cc3C1)[C@H]2CC(=O)O] |

TABLE 2a-continued
| Comp'd No | Structure |
|---|---|
| 68 | 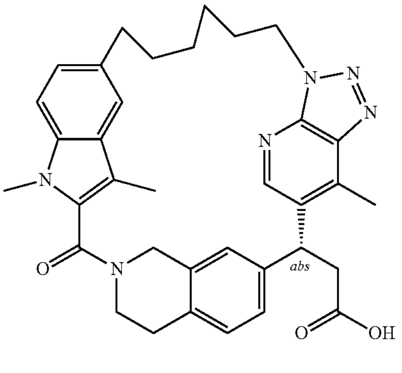 |
| 69 | 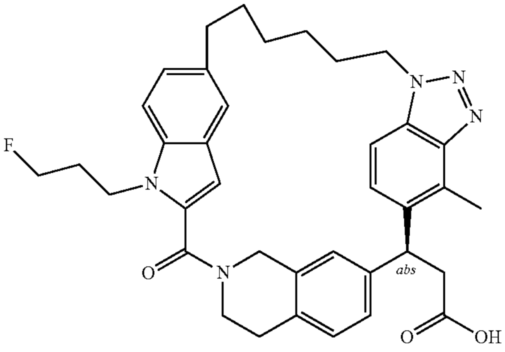 [SMILES: Cc1c2ccc3c1nnn3CCCCCCc1ccc3c(c1)cc(n3CCCF)C(=O)N1CCc3ccc(cc3C1)[C@@H]2CC(=O)O] |
| 70 | 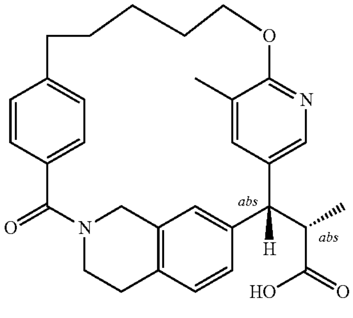 [SMILES: Cc1cc2cnc1OCCCCCc1ccc(cc1)C(=O)N1CCc3ccc(cc3C1)[C@H]2[C@H](C)C(=O)O] |
| 71 | 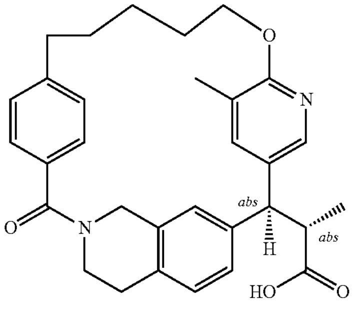 [SMILES: Cc1cc2cnc1OCCCCCc1ccc(cc1)C(=O)N1CCc3ccc(cc3C1)[C@@H]2[C@H](C)C(=O)O] |
TABLE 2a-continued
| Comp'd No | Structure |
|---|---|
| 72 | 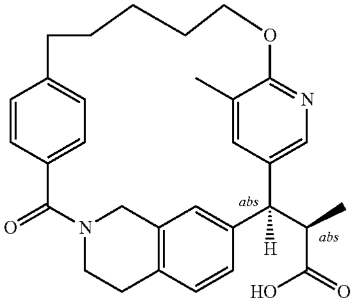 [SMILES: Cc1cc2cnc1OCCCCCc1ccc(cc1)C(=O)N1CCc3ccc(cc3C1)[C@@H]2[C@@H](C)C(=O)O] |
| 73 | 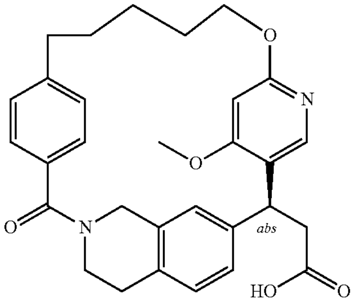 [SMILES: COc1cc2ncc1[C@@H](CC(=O)O)c1ccc3c(c1)CN(CC3)C(=O)c1ccc(cc1)CCCCCO2] |
| 74 | 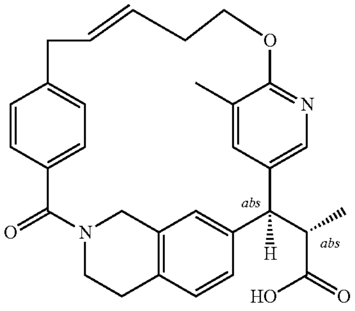 [SMILES: Cc1cc2cnc1OCC/C=C/Cc1ccc(cc1)C(=O)N1CCc3ccc(cc3C1)[C@@H]2[C@H](C)C(=O)O] |
| 75 | 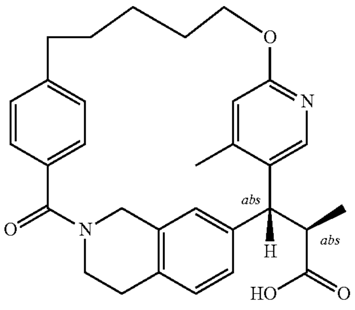 [SMILES: Cc1cc2ncc1[C@H]([C@@H](C)C(=O)O)c1ccc3c(c1)CN(CC3)C(=O)c1ccc(cc1)CCCCCO2] |
| 76 | 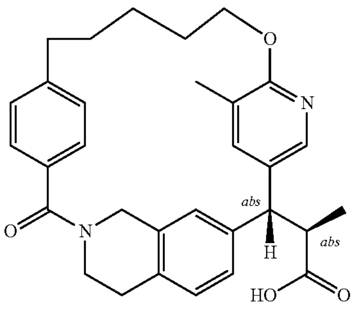 [SMILES: Cc1cc2cnc1OCCCCCc1ccc(cc1)C(=O)N1CCc3ccc(cc3C1)[C@H]2[C@@H](C)C(=O)O] |

TABLE 2a-continued
| Comp'd No | Structure |
|---|---|
| 77 | 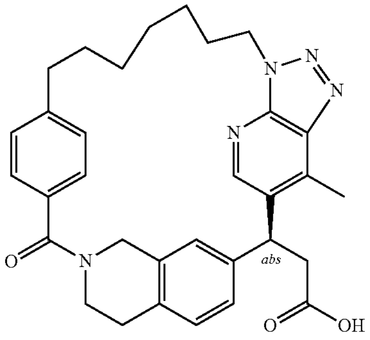 [SMILES: Cc1c2cnc3c1nnn3CCCCCCCc1ccc(cc1)C(=O)N1CCc3ccc(cc3C1)[C@@H]2CC(=O)O] |
| 78 | 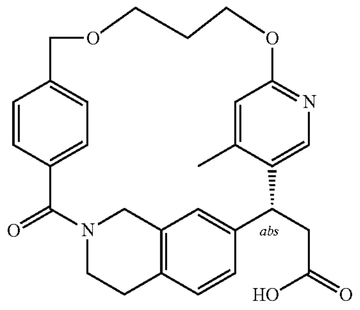 [SMILES: Cc1cc2ncc1[C@H](CC(=O)O)c1ccc3c(c1)CN(CC3)C(=O)c1ccc(cc1)COCCCO2] |
| 79 | 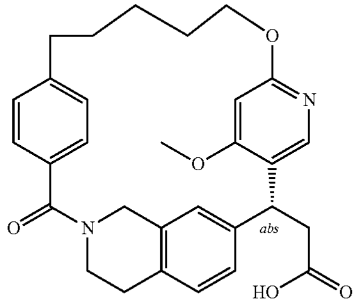 [SMILES: COc1cc2ncc1[C@H](CC(=O)O)c1ccc3c(c1)CN(CC3)C(=O)c1ccc(cc1)CCCCCO2] |
| 80 | 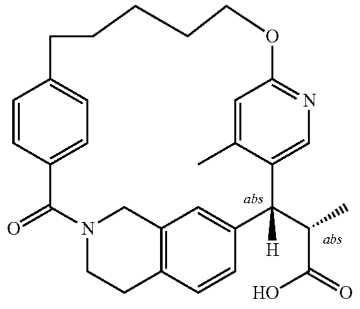 [SMILES: Cc1cc2ncc1[C@H]([C@H](C)C(=O)O)c1ccc3c(c1)CN(CC3)C(=O)c1ccc(cc1)CCCCCO2] |
| 81 | 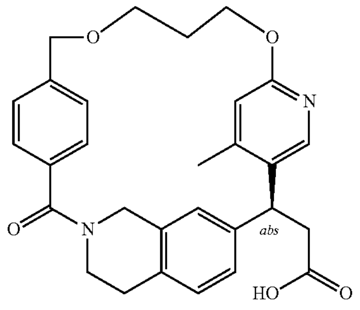 [SMILES: Cc1cc2ncc1[C@@H](CC(=O)O)c1ccc3c(c1)CN(CC3)C(=O)c1ccc(cc1)COCCCO2] |
TABLE 2a-continued
| Comp'd No | Structure |
|---|---|
| 82 | 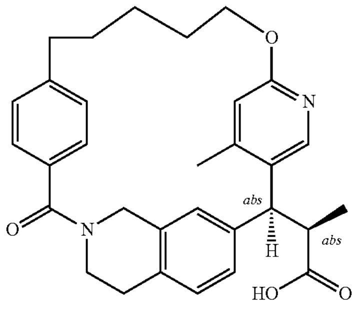 [SMILES: Cc1cc2ncc1[C@@H]([C@@H](C)C(=O)O)c1ccc3c(c1)CN(CC3)C(=O)c1ccc(cc1)CCCCCO2] |
| 83 | 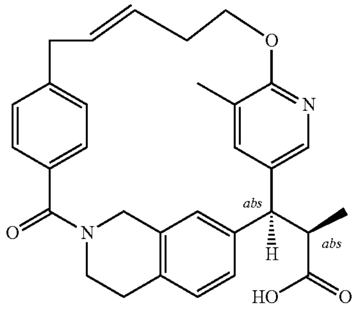 [SMILES: Cc1cc2cnc1OCC/C=C/Cc1ccc(cc1)C(=O)N1CCc3ccc(cc3C1)[C@@H]2[C@@H](C)C(=O)O] |
| 84 | 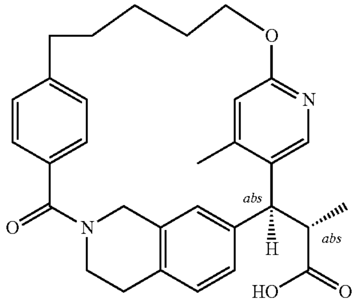 [SMILES: Cc1cc2ncc1[C@@H]([C@H](C)C(=O)O)c1ccc3c(c1)CN(CC3)C(=O)c1ccc(cc1)CCCCCO2] |
| 85 | 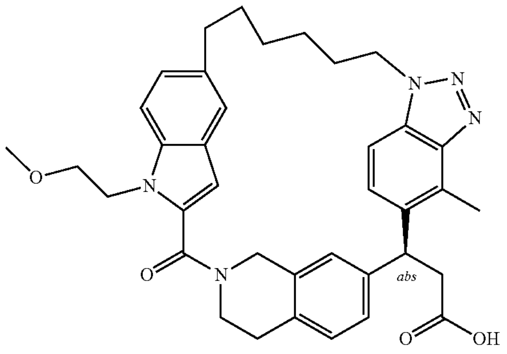 |

TABLE 2a-continued
| Comp'd No | Structure |
|---|---|
| 86 | 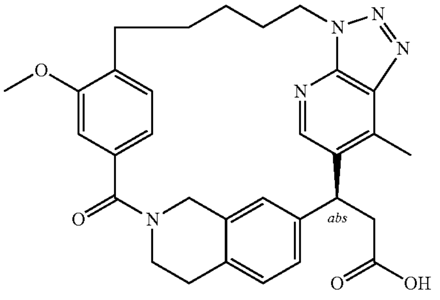 |
| 87 | 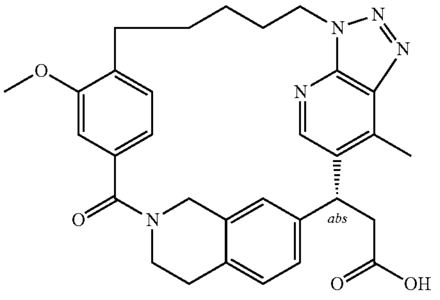 |
| 88 | 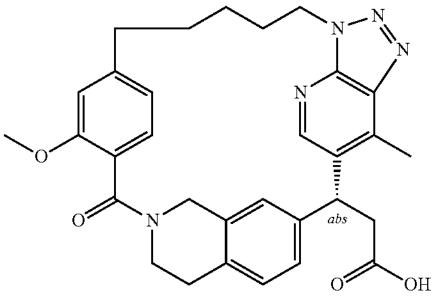 |
| 89 | 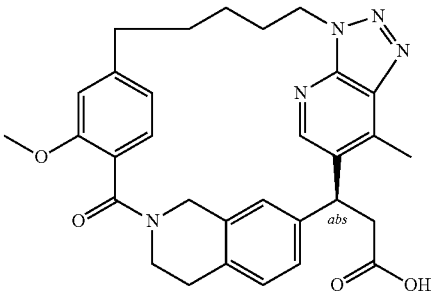 |
| 90 | 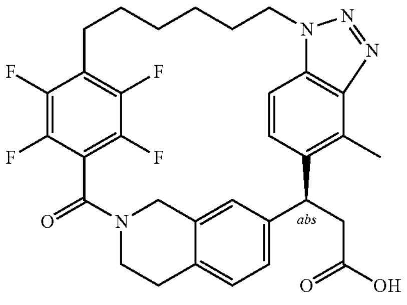 [SMILES: Cc1c2ccc3c1nnn3CCCCCCc1c(F)c(F)c(c(F)c1F)C(=O)N1CCc3ccc(cc3C1)[C@@H]2CC(=O)O] |
TABLE 2a-continued
| Comp'd No | Structure |
|---|---|
| 91 | 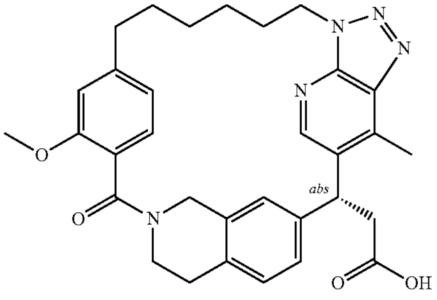 |
| 92 | 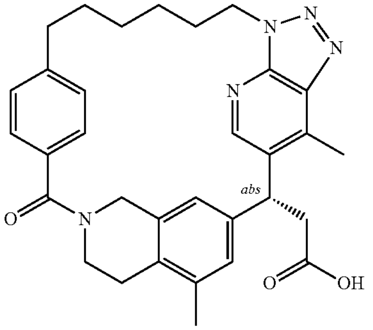 [SMILES: Cc1cc2cc3c1CCN(C3)C(=O)c1ccc(cc1)CCCCCCn1nnc3c(C)c(cnc31)[C@@H]2CC(=O)O] |
| 93 | 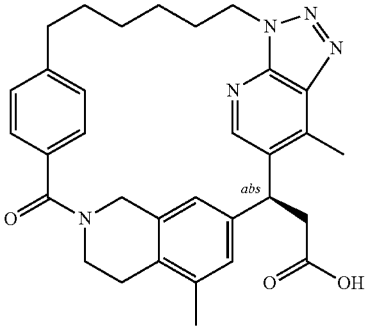 [SMILES: Cc1cc2cc3c1CCN(C3)C(=O)c1ccc(cc1)CCCCCCn1nnc3c(C)c(cnc31)[C@H]2CC(=O)O] |
| 94 | 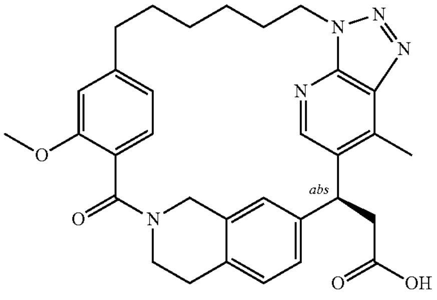 |
| 95 | 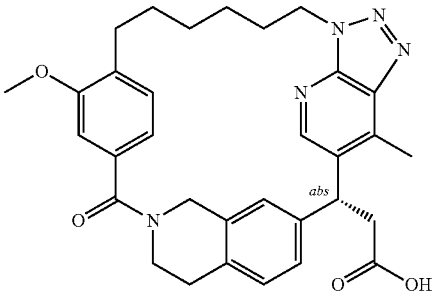 |

TABLE 2a-continued
| Comp'd No | Structure |
|---|---|
| 96 | 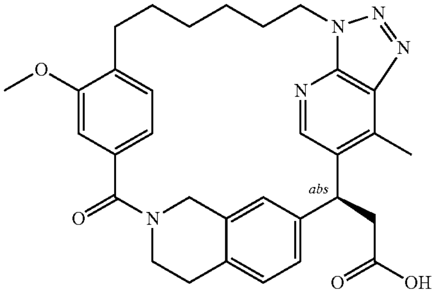 |
| 97 | 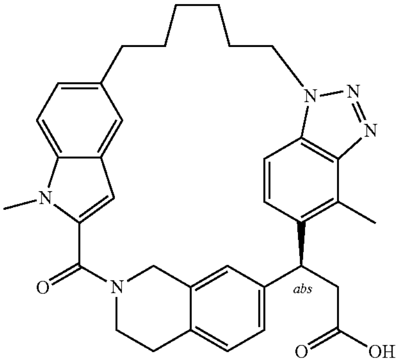 |
| 98 | 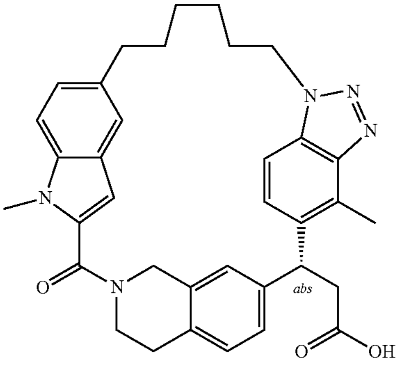 |
| 99 | 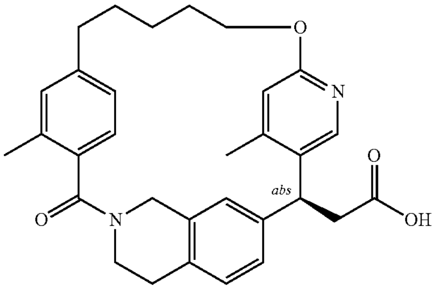 [SMILES: Cc1cc2ccc1C(=O)N1CCc3ccc(cc3C1)[C@H](CC(=O)O)c1cnc(cc1C)OCCCCC2] |
TABLE 2a-continued
| Comp'd No | Structure |
|---|---|
| 100 | 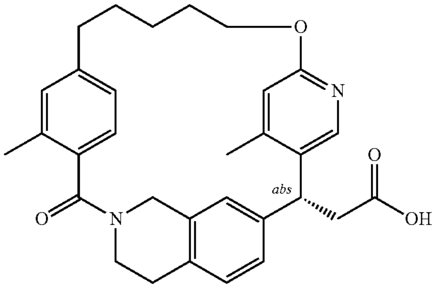 [SMILES: Cc1cc2ccc1C(=O)N1CCc3ccc(cc3C1)[C@@H](CC(=O)O)c1cnc(cc1C)OCCCCC2] |
| 101 | 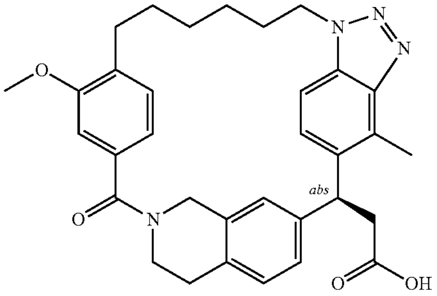 |
| 102 | 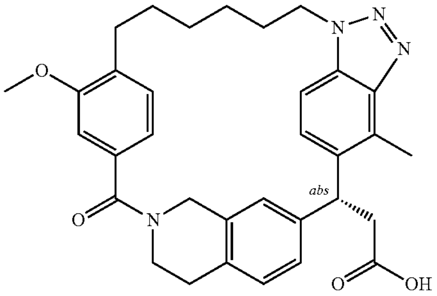 |
| 103 | 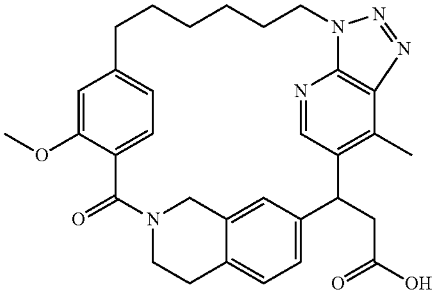 |
| 104 | 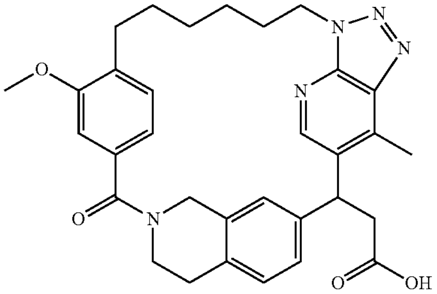 |

TABLE 2a-continued
| Comp'd No | Structure |
|---|---|
| 105 | 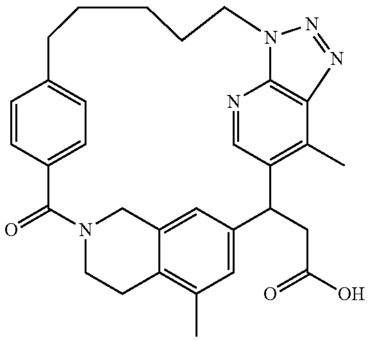 [SMILES: Cc1cc2cc3c1CCN(C3)C(=O)c1ccc(cc1)CCCCCn1nnc3c(C)c(cnc31)C2CC(=O)O] |
| 106 | 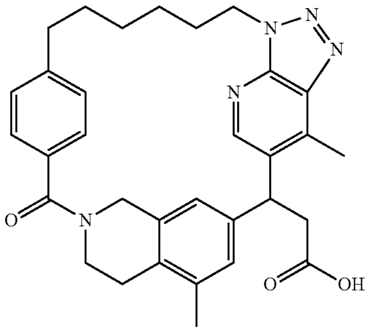 [SMILES: Cc1cc2cc3c1CCN(C3)C(=O)c1ccc(cc1)CCCCCCn1nnc3c(C)c(cnc31)C2CC(=O)O] |
| 107 | 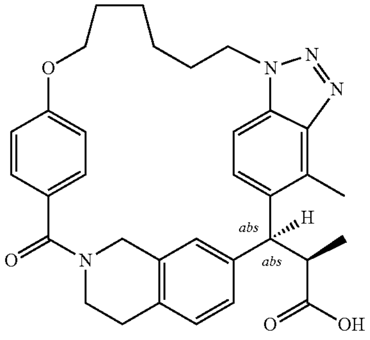 [SMILES: Cc1c2ccc3c1nnn3CCCCCCOc1ccc(cc1)C(=O)N1CCc3ccc(cc3C1)[C@@H]2[C@@H](C)C(=O)O] |
| 108 | 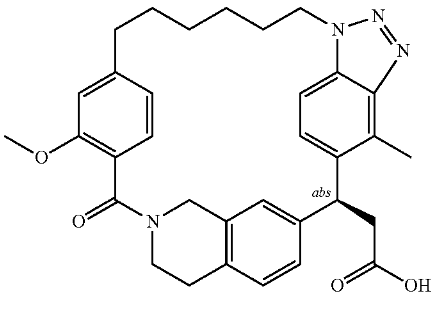 |
TABLE 2a-continued
| Comp'd No | Structure |
|---|---|
| 109 | 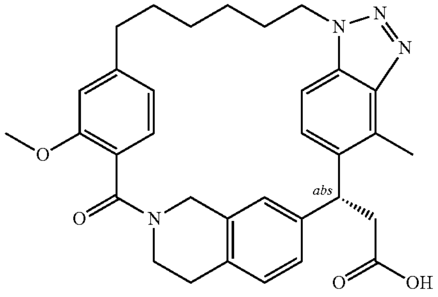 |
| 110 | 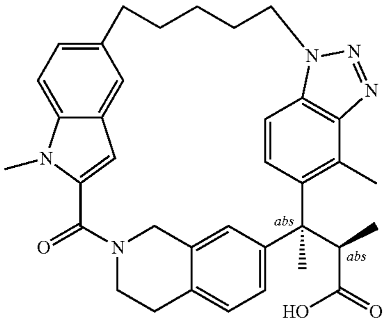 [SMILES: Cc1c2ccc3c1nnn3CCCCCc1ccc3c(c1)cc(n3C)C(=O)N1CCc3ccc(cc3C1)[C@]2(C)[C@@H](C)C(=O)O] |
| 111 | 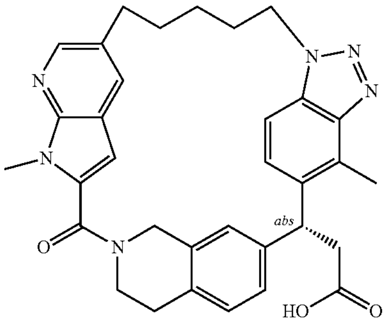 |
| 112 | 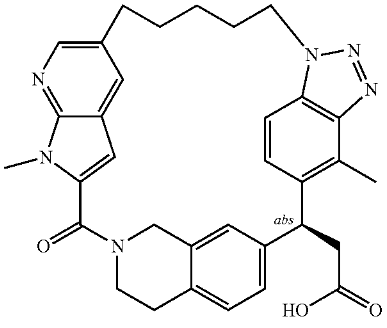 |

TABLE 2a-continued
| Comp'd No | Structure |
| --- | --- |
| 113 | 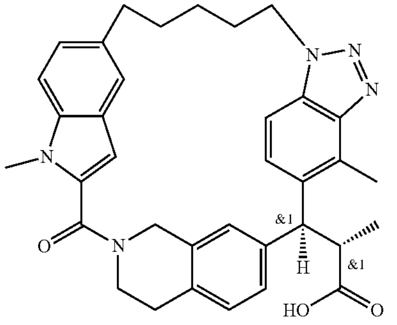 [SMILES: Cc1c2ccc3c1nnn3CCCCCc1ccc3c(c1)cc(n3C)C(=O)N1CCc3ccc(cc3C1)[C@@H]2[C@H](C)C(=O)O] |
| 114 | 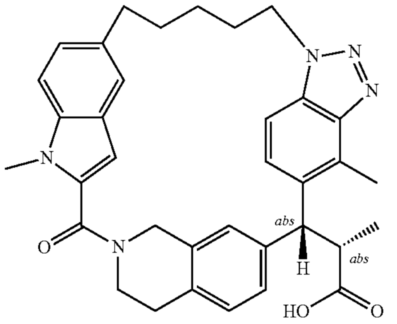 [SMILES: Cc1c2ccc3c1nnn3CCCCCc1ccc3c(c1)cc(n3C)C(=O)N1CCc3ccc(cc3C1)[C@H]2[C@H](C)C(=O)O] |
| 115 | 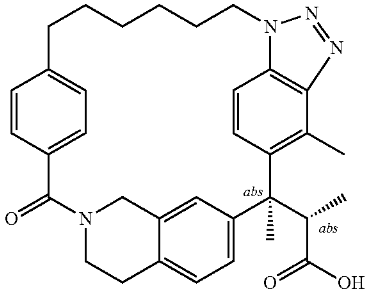 [SMILES: Cc1c2ccc3c1nnn3CCCCCCc1ccc(cc1)C(=O)N1CCc3ccc(cc3C1)[C@]2(C)[C@H](C)C(=O)O] |
| 117 | 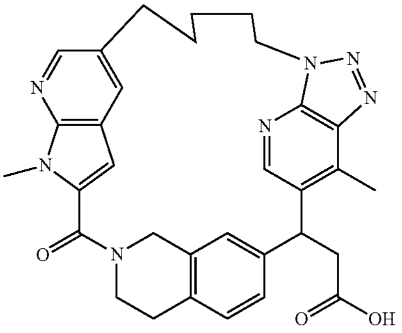 |
| 118 | 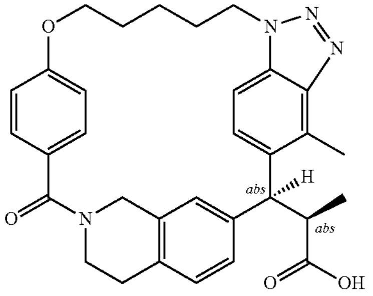 [SMILES: Cc1c2ccc3c1nnn3CCCCCOc1ccc(cc1)C(=O)N1CCc3ccc(cc3C1)[C@@H]2[C@@H](C)C(=O)O] |
TABLE 2a-continued
| Comp'd No | Structure |
| --- | --- |
| 119 | 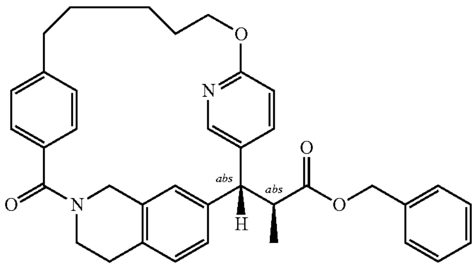 [SMILES: C[C@H](C(=O)OCc1ccccc1)[C@H]1c2ccc(nc2)OCCCCCc2ccc(cc2)C(=O)N2CCc3ccc1cc3C2] |
| 120 | 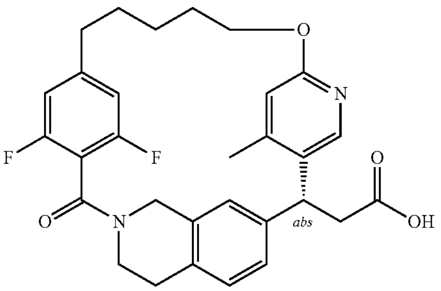 [SMILES: Cc1cc2ncc1[C@H](CC(=O)O)c1ccc3c(c1)CN(CC3)C(=O)c1c(F)cc(cc1F)CCCCCO2] |
| 121 | 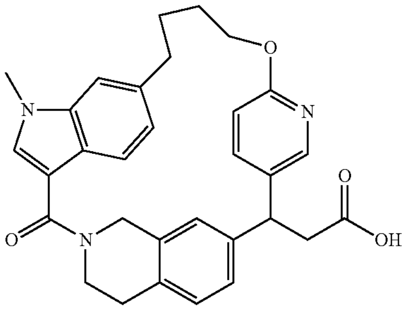 [SMILES: Cn1cc2c3ccc(cc31)CCCCOc1ccc(cn1)C(CC(=O)O)c1ccc3c(c1)CN(CC3)C2=O] |
| 122 | 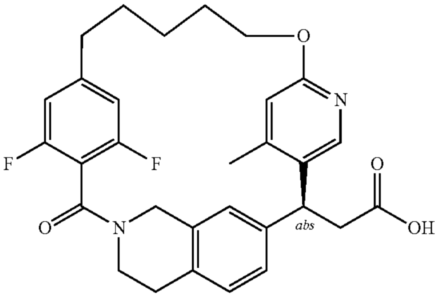 [SMILES: Cc1cc2ncc1[C@@H](CC(=O)O)c1ccc3c(c1)CN(CC3)C(=O)c1c(F)cc(cc1F)CCCCCO2] |
| 123 | 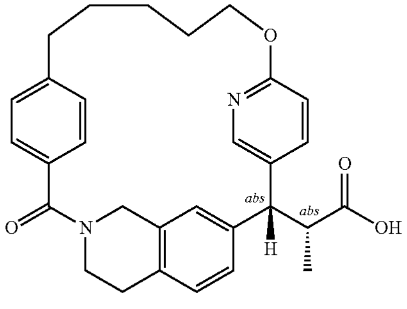 [SMILES: C[C@@H](C(=O)O)[C@H]1c2ccc(nc2)OCCCCCc2ccc(cc2)C(=O)N2CCc3ccc1cc3C2] |

TABLE 2a-continued
| Comp'd No | Structure |
|---|---|
| 124 | 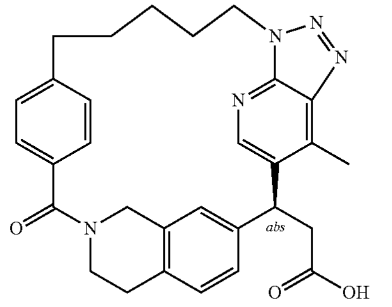 [SMILES: Cc1c2cnc3c1nnn3CCCCCc1ccc(cc1)C(=O)N1CCc3ccc(cc3C1)[C@@H]2CC(=O)O] |
| 125 | 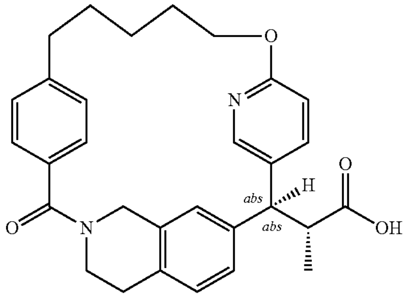 [SMILES: C[C@@H](C(=O)O)[C@@H]1c2ccc(nc2)OCCCCCc2ccc(cc2)C(=O)N2CCc3ccc1cc3C2] |
| 126 | 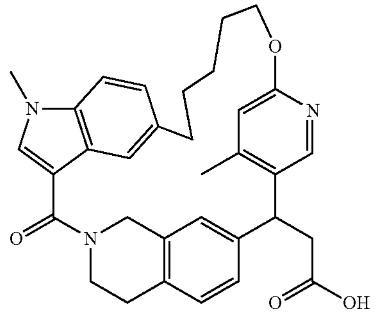 [SMILES: Cc1cc2ncc1C(CC(=O)O)c1ccc3c(c1)CN(CC3)C(=O)c1cn(C)c3ccc(cc13)CCCCCO2] |
| 127 | 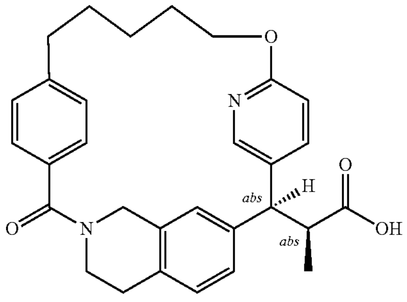 [SMILES: C[C@H](C(=O)O)[C@@H]1c2ccc(nc2)OCCCCCc2ccc(cc2)C(=O)N2CCc3ccc1cc3C2] |
| 128 | 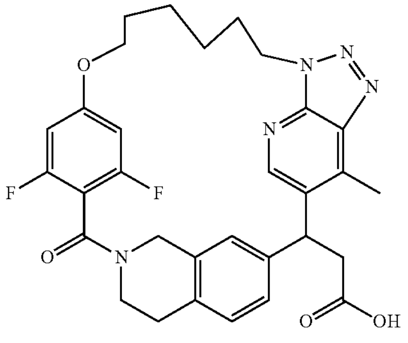 [SMILES: Cc1c2cnc3c1nnn3CCCCCCOc1cc(F)c(c(F)c1)C(=O)N1CCc3ccc(cc3C1)C2CC(=O)O] |
TABLE 2a-continued
| Comp'd No | Structure |
|---|---|
| 129 | 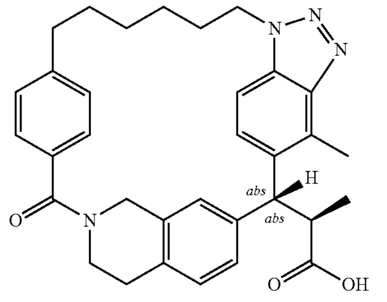 [SMILES: Cc1c2ccc3c1nnn3CCCCCCc1ccc(cc1)C(=O)N1CCc3ccc(cc3C1)[C@H]2[C@@H](C)C(=O)O] |
| 132 | 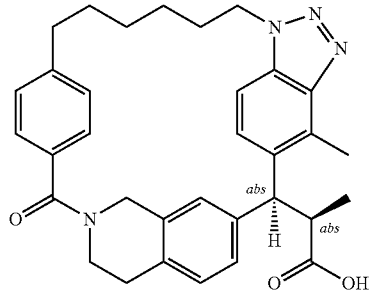 [SMILES: Cc1c2ccc3c1nnn3CCCCCCc1ccc(cc1)C(=O)N1CCc3ccc(cc3C1)[C@@H]2[C@@H](C)C(=O)O] |
| 134 | 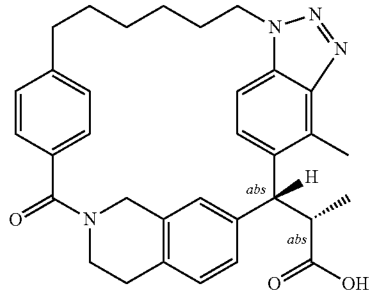 [SMILES: Cc1c2ccc3c1nnn3CCCCCCc1ccc(cc1)C(=O)N1CCc3ccc(cc3C1)[C@H]2[C@H](C)C(=O)O] |
| 135 | 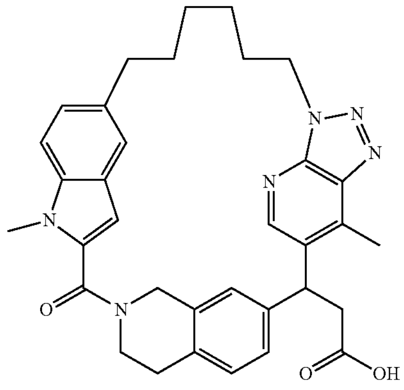 |

TABLE 2a-continued
| Comp'd No | Structure |
| --- | --- |
| 136 | 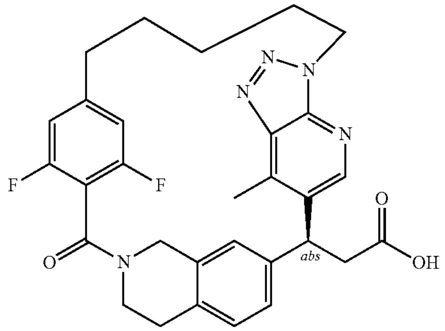 [SMILES: Cc1c2cnc3c1nnn3CCCCCc1cc(F)c(c(F)c1)C(=O)N1CCc3ccc(cc3C1)[C@@H]2CC(=O)O] |
| 137 | 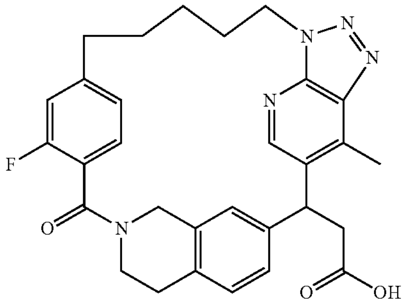 [SMILES: Cc1c2cnc3c1nnn3CCCCCc1ccc(c(F)c1)C(=O)N1CCc3ccc(cc3C1)C2CC(=O)O] |
| 138 | 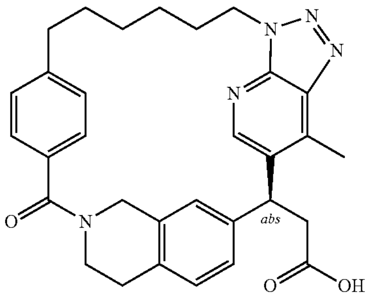 [SMILES: Cc1c2cnc3c1nnn3CCCCCCc1ccc(cc1)C(=O)N1CCc3ccc(cc3C1)[C@@H]2CC(=O)O] |
| 139 | 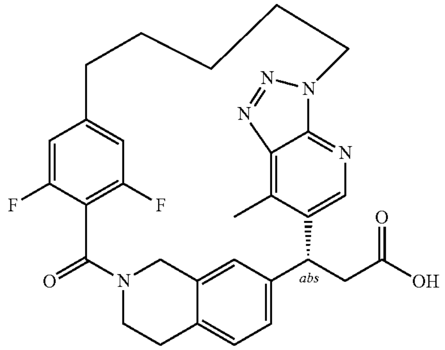 [SMILES: Cc1c2cnc3c1nnn3CCCCCc1cc(F)c(c(F)c1)C(=O)N1CCc3ccc(cc3C1)[C@H]2CC(=O)O] |
TABLE 2a-continued
| Comp'd No | Structure |
| --- | --- |
| 140 | 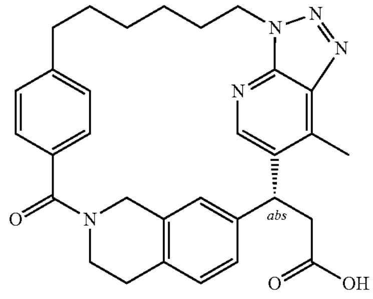 [SMILES: Cc1c2cnc3c1nnn3CCCCCCc1ccc(cc1)C(=O)N1CCc3ccc(cc3C1)[C@H]2CC(=O)O] |
| 141 | 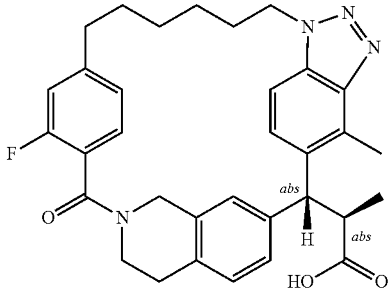 [SMILES: Cc1c2ccc3c1nnn3CCCCCCc1ccc(c(F)c1)C(=O)N1CCc3ccc(cc3C1)[C@H]2[C@@H](C)C(=O)O] |
| 142 | 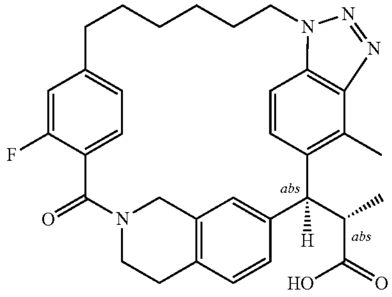 [SMILES: Cc1c2ccc3c1nnn3CCCCCCc1ccc(c(F)c1)C(=O)N1CCc3ccc(cc3C1)[C@@H]2[C@H](C)C(=O)O] |
| 143 | 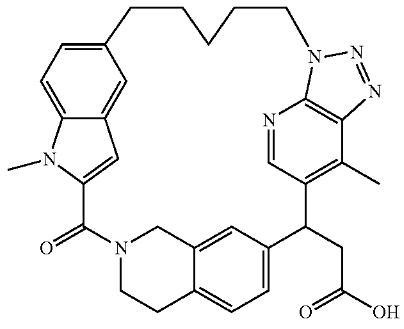 |
| 144 | 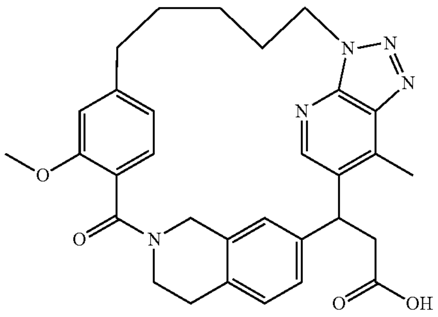 |

TABLE 2a-continued
| Comp'd No | Structure |
|---|---|
| 145 | 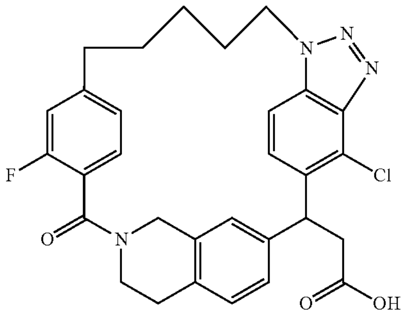 [SMILES: O=C(O)CC1c2ccc3c(c2)CN(CC3)C(=O)c2ccc(cc2F)CCCCCn2nnc3c(Cl)c1ccc32] |
| 146 | 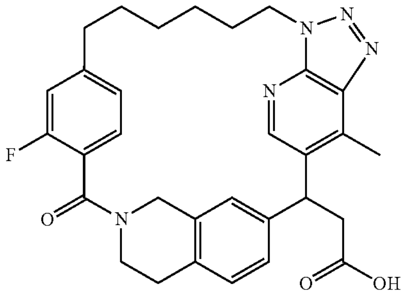 [SMILES: Cc1c2cnc3c1nnn3CCCCCCc1ccc(c(F)c1)C(=O)N1CCc3ccc(cc3C1)C2CC(=O)O] |
| 147 | 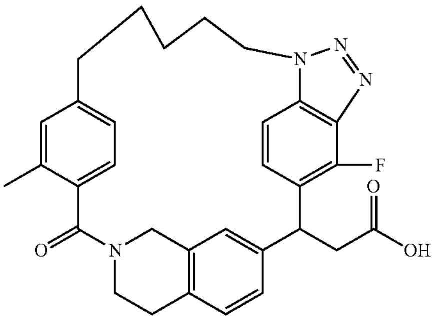 [SMILES: Cc1cc2ccc1C(=O)N1CCc3ccc(cc3C1)C(CC(=O)O)c1ccc3c(nnn3CCCCC2)c1F] |
| 148 | 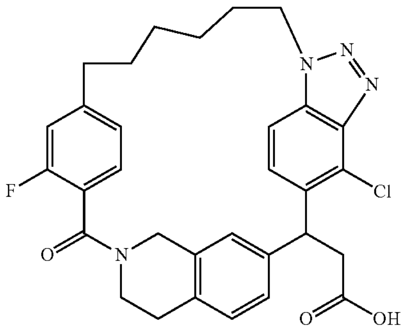 [SMILES: O=C(O)CC1c2ccc3c(c2)CN(CC3)C(=O)c2ccc(cc2F)CCCCCCn2nnc3c(Cl)c1ccc32] |
| 149 | 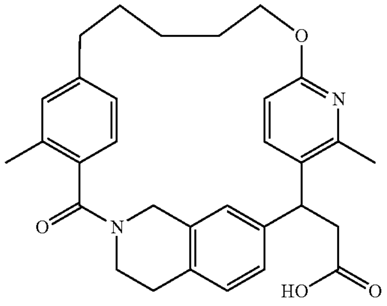 |
TABLE 2a-continued
| Comp'd No | Structure |
|---|---|
| 150 | 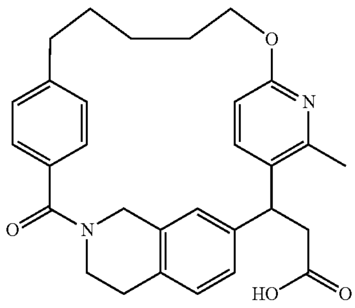 [SMILES: Cc1nc2ccc1C(CC(=O)O)c1ccc3c(c1)CN(CC3)C(=O)c1ccc(cc1)CCCCCO2] |
| 151 | 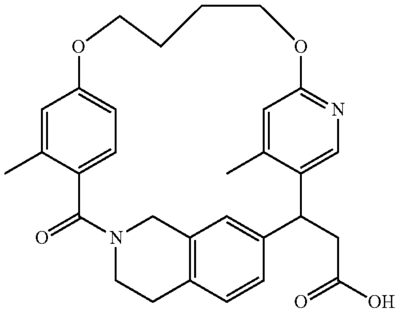 [SMILES: Cc1cc2ccc1C(=O)N1CCc3ccc(cc3C1)C(CC(=O)O)c1cnc(cc1C)OCCCCO2] |
| 152 | 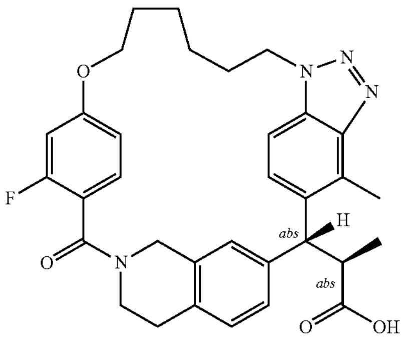 [SMILES: Cc1c2ccc3c1nnn3CCCCCCOc1ccc(c(F)c1)C(=O)N1CCc3ccc(cc3C1)[C@H]2[C@@H](C)C(=O)O] |
| 154 | 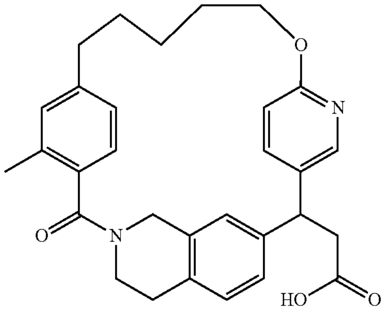 [SMILES: Cc1cc2ccc1C(=O)N1CCc3ccc(cc3C1)C(CC(=O)O)c1ccc(nc1)OCCCCC2] |

TABLE 2a-continued
| Comp'd No | Structure |
|---|---|
| 155 | 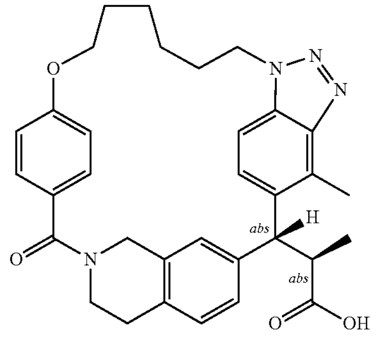 [SMILES: Cc1c2ccc3c1nnn3CCCCCCOc1ccc(cc1)C(=O)N1CCc3ccc(cc3C1)[C@H]2[C@@H](C)C(=O)O] |
| 156 | 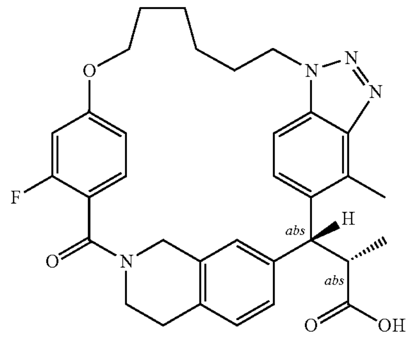 [SMILES: Cc1c2ccc3c1nnn3CCCCCCOc1ccc(c(F)c1)C(=O)N1CCc3ccc(cc3C1)[C@H]2[C@H](C)C(=O)O] |
| 157 | 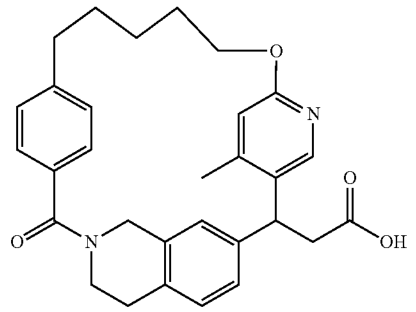 [SMILES: Cc1cc2ncc1C(CC(=O)O)c1ccc3c(c1)CN(CC3)C(=O)c1ccc(cc1)CCCCCO2] |
| 158 | 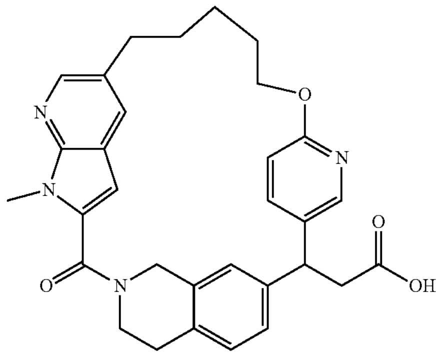 [SMILES: Cn1c2cc3cc(cnc31)CCCCCOc1ccc(cn1)C(CC(=O)O)c1ccc3c(c1)CN(CC3)C2=O] |
TABLE 2a-continued
| Comp'd No | Structure |
|---|---|
| 159 | 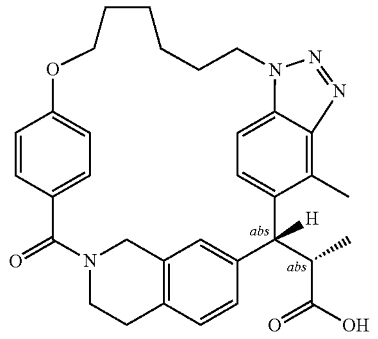 [SMILES: Cc1c2ccc3c1nnn3CCCCCCOc1ccc(cc1)C(=O)N1CCc3ccc(cc3C1)[C@H]2[C@H](C)C(=O)O] |
| 161 | 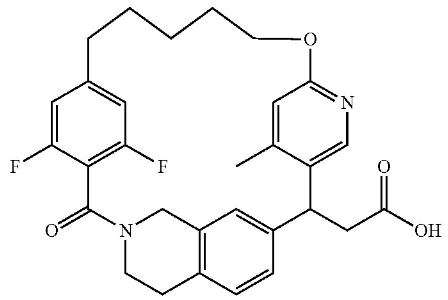 [SMILES: Cc1cc2ncc1C(CC(=O)O)c1ccc3c(c1)CN(CC3)C(=O)c1c(F)cc(cc1F)CCCCCO2] |
| 162 | 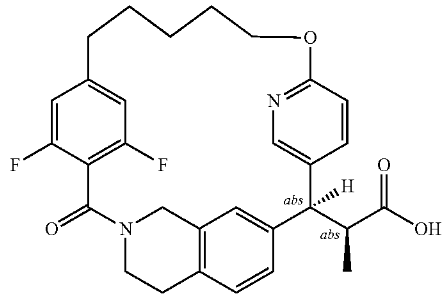 [SMILES: C[C@H](C(=O)O)[C@@H]1c2ccc(nc2)OCCCCCc2cc(F)c(c(F)c2)C(=O)N2CCc3ccc1cc3C2] |
| 163 | 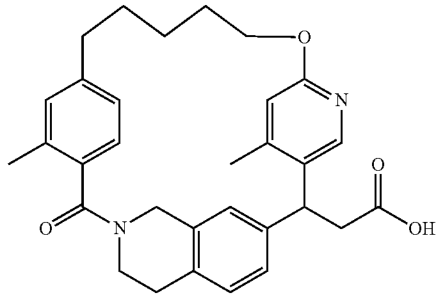 [SMILES: Cc1cc2ccc1C(=O)N1CCc3ccc(cc3C1)C(CC(=O)O)c1cnc(cc1C)OCCCCC2] |
| 164 | 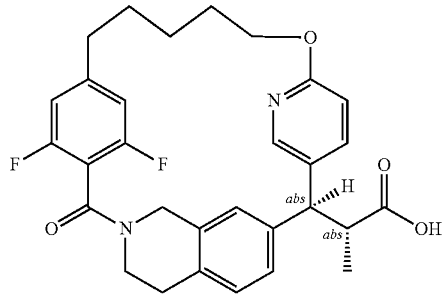 [SMILES: C[C@@H](C(=O)O)[C@@H]1c2ccc(nc2)OCCCCCc2cc(F)c(c(F)c2)C(=O)N2CCc3ccc1cc3C2] |

TABLE 2a-continued
| Comp'd No | Structure |
| --- | --- |
| 165 | 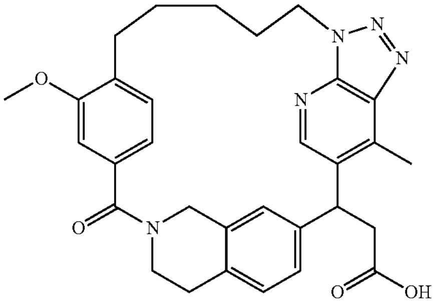 |
| 166 | 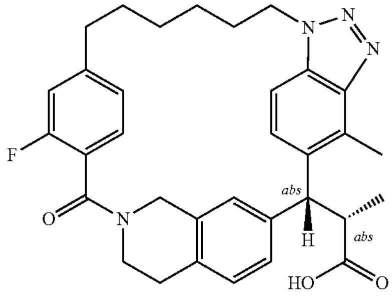 [SMILES: Cc1c2ccc3c1nnn3CCCCCCc1ccc(c(F)c1)C(=O)N1CCc3ccc(cc3C1)[C@H]2[C@H](C)C(=O)O] |
| 167 | 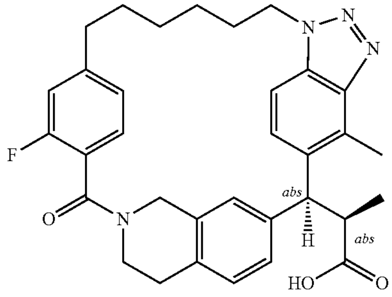 [SMILES: Cc1c2ccc3c1nnn3CCCCCCc1ccc(c(F)c1)C(=O)N1CCc3ccc(cc3C1)[C@@H]2[C@@H](C)C(=O)O] |
| 168 | 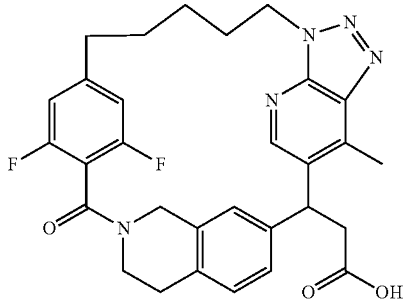 [SMILES: Cc1c2cnc3c1nnn3CCCCCc1cc(F)c(c(F)c1)C(=O)N1CCc3ccc(cc3C1)C2CC(=O)O] |
| 169 | 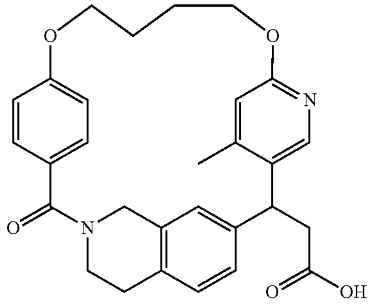 [SMILES: Cc1cc2ncc1C(CC(=O)O)c1ccc3c(c1)CN(CC3)C(=O)c1ccc(cc1)OCCCCO2] |
TABLE 2a-continued
| Comp'd No | Structure |
| --- | --- |
| 170 | 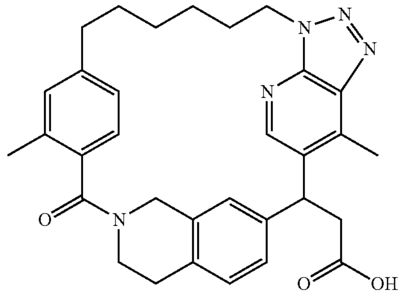 |
| 171 | 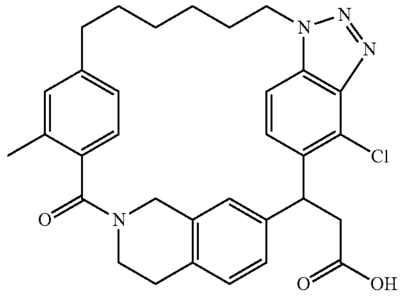 [SMILES: Cc1cc2ccc1C(=O)N1CCc3ccc(cc3C1)C(CC(=O)O)c1ccc3c(nnn3CCCCCC2)c1Cl] |
| 172 | 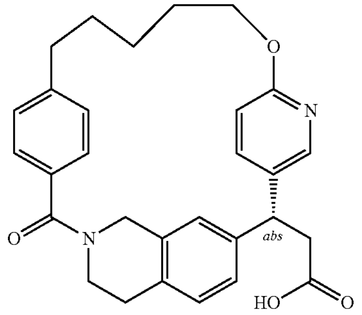 [SMILES: O=C(O)C[C@H]1c2ccc(nc2)OCCCCCc2ccc(cc2)C(=O)N2CCc3ccc1cc3C2] |
| 173 | 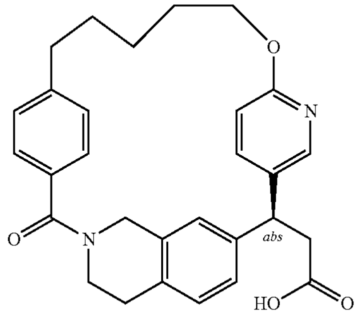 [SMILES: O=C(O)C[C@@H]1c2ccc(nc2)OCCCCCc2ccc(cc2)C(=O)N2CCc3ccc1cc3C2] |
| 174 | 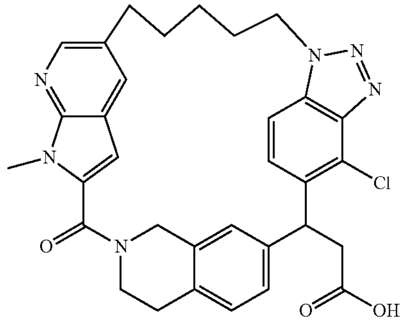 [SMILES: Cn1c2cc3cc(cnc31)CCCCCn1nnc3c(Cl)c(ccc31)C(CC(=O)O)c1ccc3c(c1)CN(CC3)C2=O] |

TABLE 2a-continued
| Comp'd No | Structure |
|---|---|
| 175 | 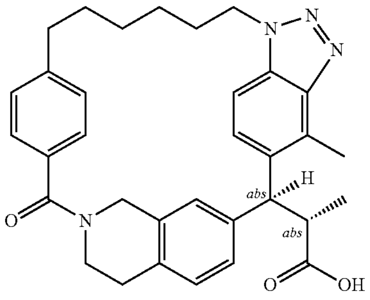 [SMILES: Cc1c2ccc3c1nnn3CCCCCCc1ccc(cc1)C(=O)N1CCc3ccc(cc3C1)[C@@H]2[C@H](C)C(=O)O] |
| 176 | 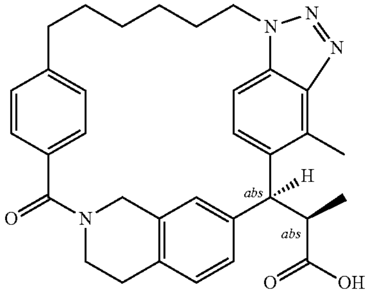 [SMILES: Cc1c2ccc3c1nnn3CCCCCCc1ccc(cc1)C(=O)N1CCc3ccc(cc3C1)[C@@H]2[C@@H](C)C(=O)O] |
| 177 | 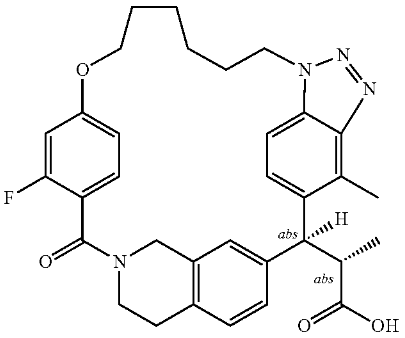 [SMILES: Cc1c2ccc3c1nnn3CCCCCCOc1ccc(c(F)c1)C(=O)N1CCc3ccc(cc3C1)[C@@H]2[C@H](C)C(=O)O] |
| 178 | 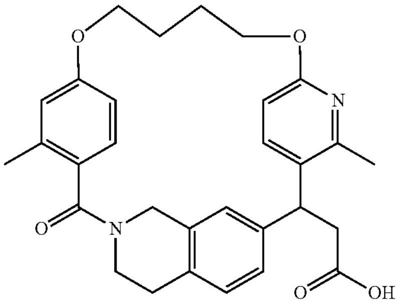 |
| 179 | 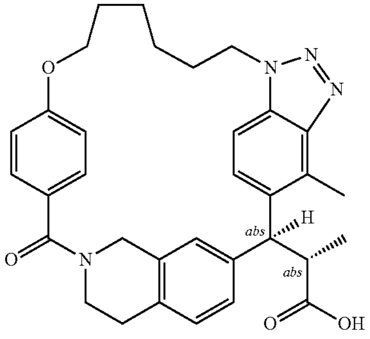 [SMILES: Cc1c2ccc3c1nnn3CCCCCCOc1ccc(cc1)C(=O)N1CCc3ccc(cc3C1)[C@@H]2[C@H](C)C(=O)O] |
| 180 | 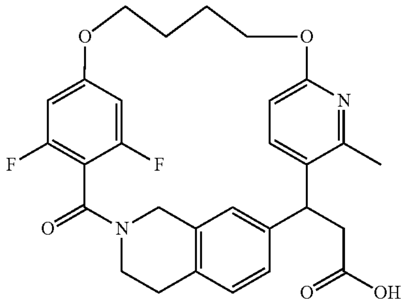 [SMILES: Cc1nc2ccc1C(CC(=O)O)c1ccc3c(c1)CN(CC3)C(=O)c1c(F)cc(cc1F)OCCCCO2] |
| 181 | 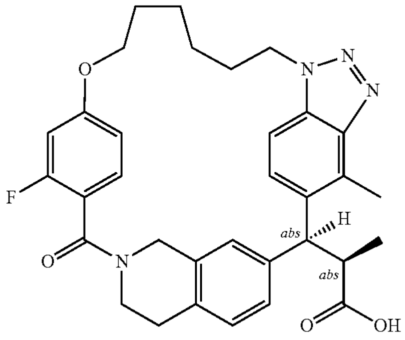 [SMILES: Cc1c2ccc3c1nnn3CCCCCCOc1ccc(c(F)c1)C(=O)N1CCc3ccc(cc3C1)[C@@H]2[C@@H](C)C(=O)O] |
| 182 | 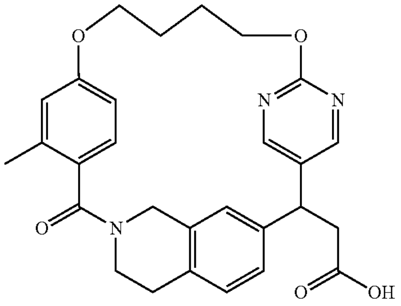 [SMILES: Cc1cc2ccc1C(=O)N1CCc3ccc(cc3C1)C(CC(=O)O)c1cnc(nc1)OCCCCO2] |
| 183 | 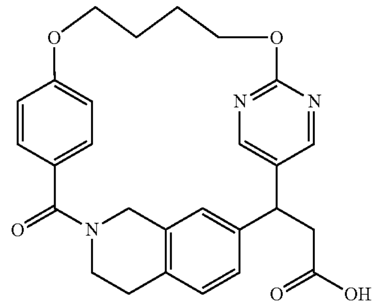 [SMILES: O=C(O)CC1c2cnc(nc2)OCCCCOc2ccc(cc2)C(=O)N2CCc3ccc1cc3C2] |

TABLE 2a-continued
| Comp'd No | Structure |
| --- | --- |
| 184 | 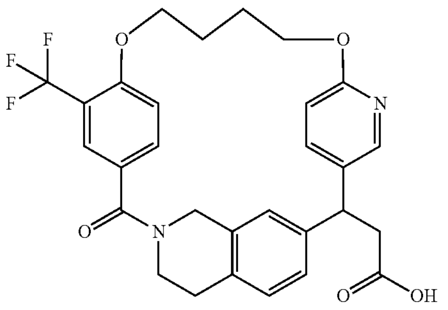 [SMILES: O=C(O)CC1c2ccc(nc2)OCCCCOc2ccc(cc2C(F)(F)F)C(=O)N2CCc3ccc1cc3C2] |
| 185 | 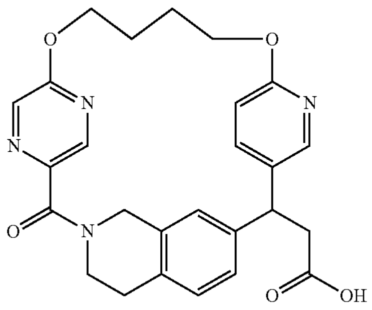 [SMILES: O=C(O)CC1c2ccc(nc2)OCCCCOc2cnc(cn2)C(=O)N2CCc3ccc1cc3C2] |
| 186 | 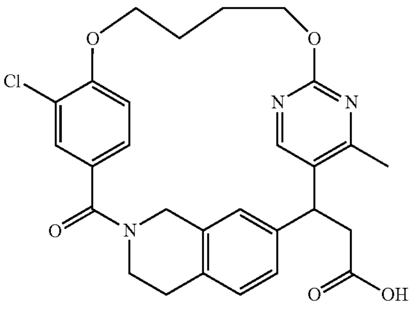 [SMILES: Cc1nc2ncc1C(CC(=O)O)c1ccc3c(c1)CN(CC3)C(=O)c1ccc(c(Cl)c1)OCCCCO2] |
| 187 | 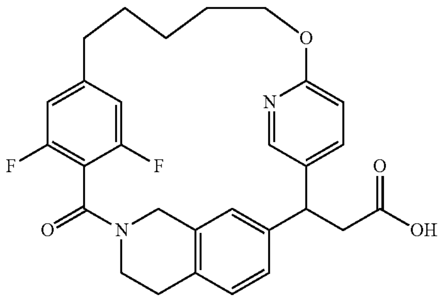 [SMILES: O=C(O)CC1c2ccc(nc2)OCCCCCc2cc(F)c(c(F)c2)C(=O)N2CCc3ccc1cc3C2] |
| 188 | 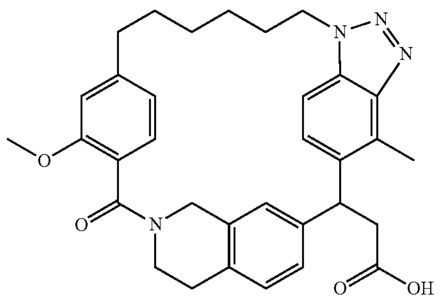 |
TABLE 2a-continued
| Comp'd No | Structure |
| --- | --- |
| 189 | 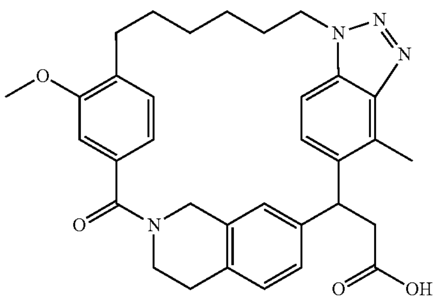 |
| 190 | 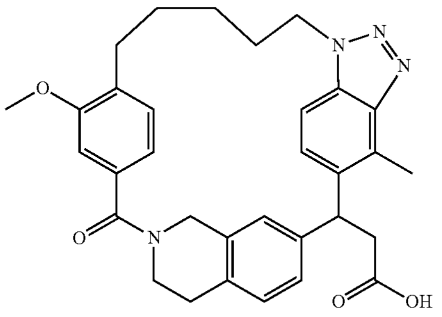 |
| 191 | 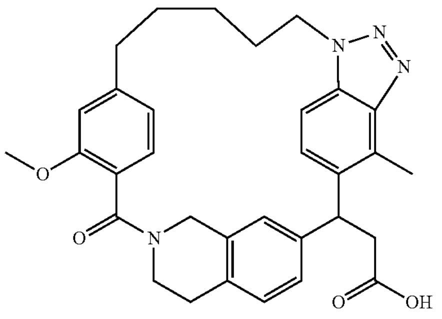 |
| 192 | 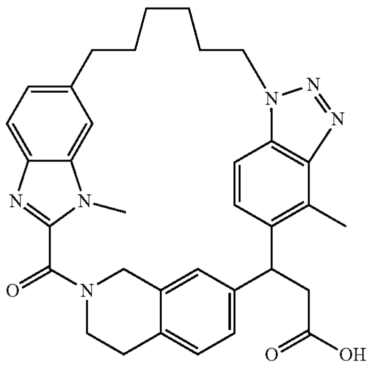 [SMILES: Cc1c2ccc3c1nnn3CCCCCCc1ccc3nc(n(C)c3c1)C(=O)N1CCc3ccc(cc3C1)C2CC(=O)O] |

TABLE 2a-continued
| Comp'd No | Structure |
| --- | --- |
| 193 | 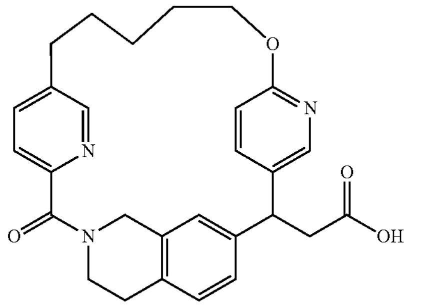 |
| 194 | 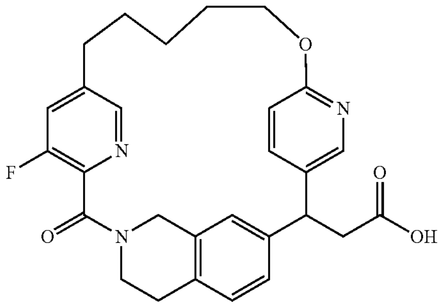 [SMILES: O=C(O)CC1c2ccc(nc2)OCCCCCc2cnc(c(F)c2)C(=O)N2CCc3ccc1cc3C2] |
| 195 | 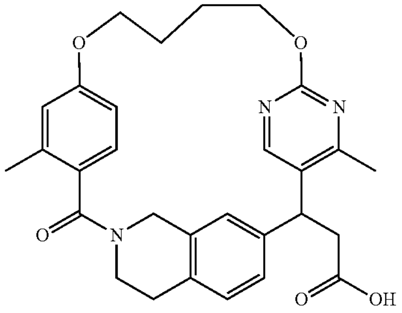 [SMILES: Cc1cc2ccc1C(=O)N1CCc3ccc(cc3C1)C(CC(=O)O)c1cnc(nc1C)OCCCCO2] |
| 196 | 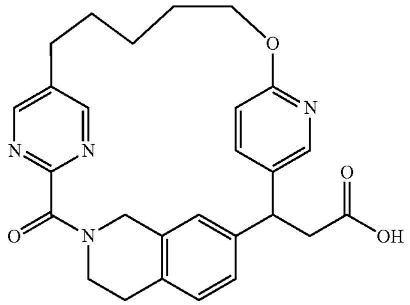 [SMILES: O=C(O)CC1c2ccc(nc2)OCCCCCc2cnc(nc2)C(=O)N2CCc3ccc1cc3C2] |
| 197 | 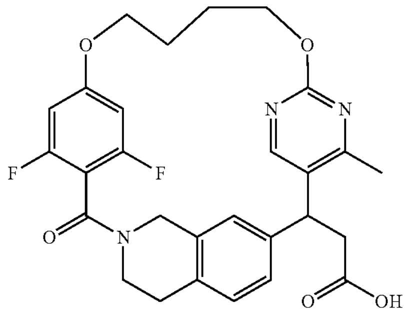 [SMILES: Cc1nc2ncc1C(CC(=O)O)c1ccc3c(c1)CN(CC3)C(=O)c1c(F)cc(cc1F)OCCCCO2] |
| 198 | 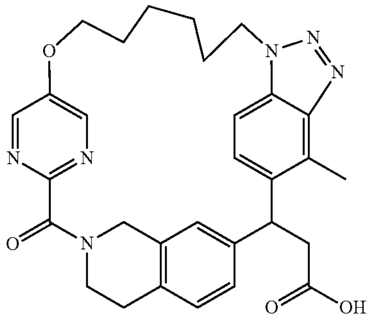 [SMILES: Cc1c2ccc3c1nnn3CCCCCCOc1cnc(nc1)C(=O)N1CCc3ccc(cc3C1)C2CC(=O)O] |
| 199 | 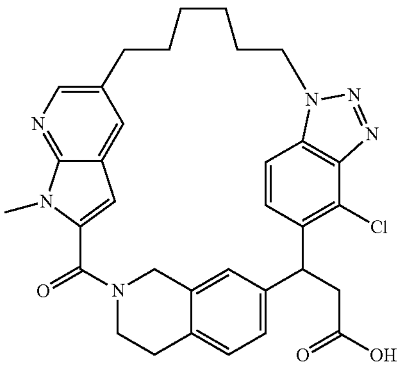 [SMILES: Cn1c2cc3cc(cnc31)CCCCCCn1nnc3c(Cl)c(ccc31)C(CC(=O)O)c1ccc3c(c1)CN(CC3)C2=O] |
| 200 | 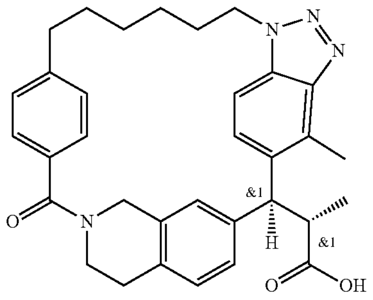 [SMILES: Cc1c2ccc3c1nnn3CCCCCCc1ccc(cc1)C(=O)N1CCc3ccc(cc3C1)[C@@H]2[C@H](C)C(=O)O] |
| 201 | 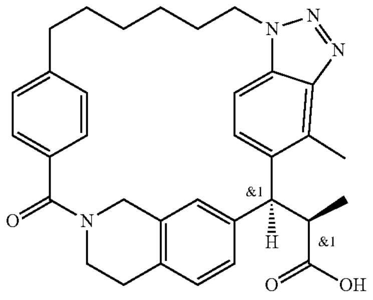 [SMILES: Cc1c2ccc3c1nnn3CCCCCCc1ccc(cc1)C(=O)N1CCc3ccc(cc3C1)[C@@H]2[C@@H](C)C(=O)O] |

TABLE 2a-continued
| Comp'd No | Structure |
| --- | --- |
| 203 | 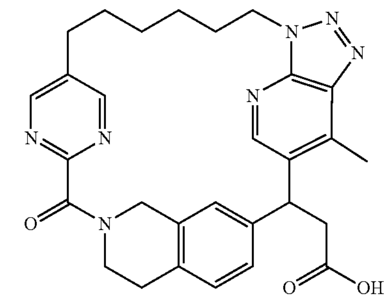 [SMILES: Cc1c2cnc3c1nnn3CCCCCCc1cnc(nc1)C(=O)N1CCc3ccc(cc3C1)C2CC(=O)O] |
| 204 | 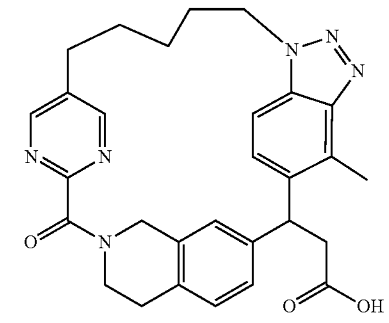 [SMILES: Cc1c2ccc3c1nnn3CCCCCc1cnc(nc1)C(=O)N1CCc3ccc(cc3C1)C2CC(=O)O] |
| 205 | 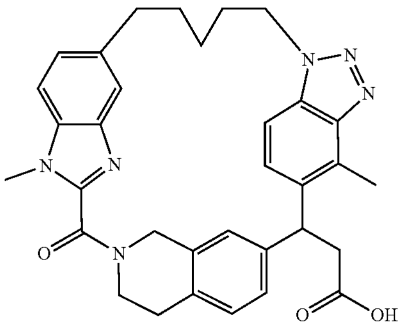 [SMILES: Cc1c2ccc3c1nnn3CCCCCc1ccc3c(c1)nc(n3C)C(=O)N1CCc3ccc(cc3C1)C2CC(=O)O] |
| 206 | 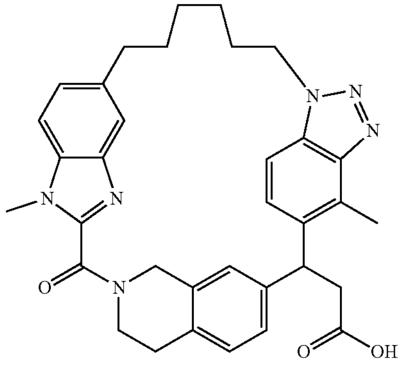 [SMILES: Cc1c2ccc3c1nnn3CCCCCCc1ccc3c(c1)nc(n3C)C(=O)N1CCc3ccc(cc3C1)C2CC(=O)O] |
TABLE 2a-continued
| Comp'd No | Structure |
| --- | --- |
| 207 | 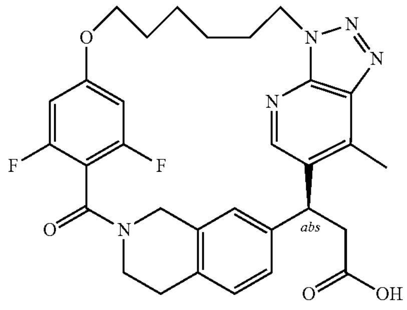 [SMILES: Cc1c2cnc3c1nnn3CCCCCCOc1cc(F)c(c(F)c1)C(=O)N1CCc3ccc(cc3C1)[C@@H]2CC(=O)O] |
| 208 | 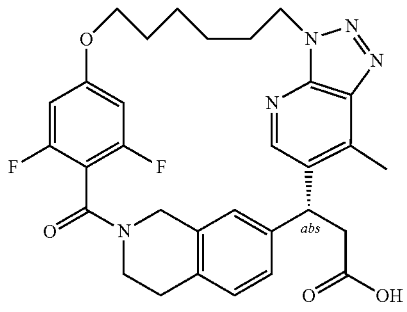 [SMILES: Cc1c2cnc3c1nnn3CCCCCCOc1cc(F)c(c(F)c1)C(=O)N1CCc3ccc(cc3C1)[C@H]2CC(=O)O] |
| 209 | 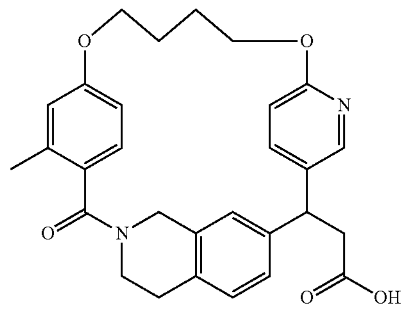 [SMILES: Cc1cc2ccc1C(=O)N1CCc3ccc(cc3C1)C(CC(=O)O)c1ccc(nc1)OCCCCO2] |
| 210 | 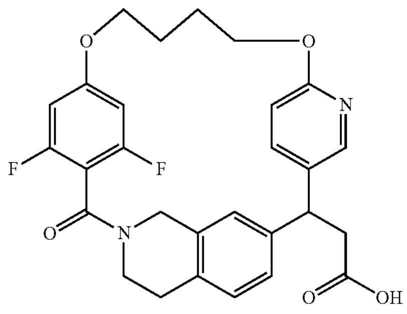 [SMILES: O=C(O)CC1c2ccc(nc2)OCCCCOc2cc(F)c(c(F)c2)C(=O)N2CCc3ccc1cc3C2] |

| Comp'd No | Structure |
|---|---|
| 211 | 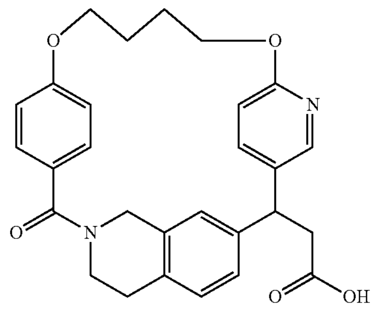 [SMILES: O=C(O)CC1c2ccc(nc2)OCCCCOc2ccc(cc2)C(=O)N2CCc3ccc1cc3C2] |
| 212 | 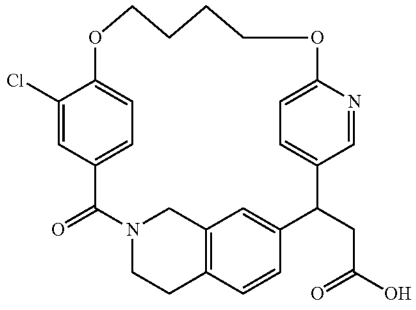 [SMILES: O=C(O)CC1c2ccc(nc2)OCCCCOc2ccc(cc2Cl)C(=O)N2CCc3ccc1cc3C2] |
| 213 | 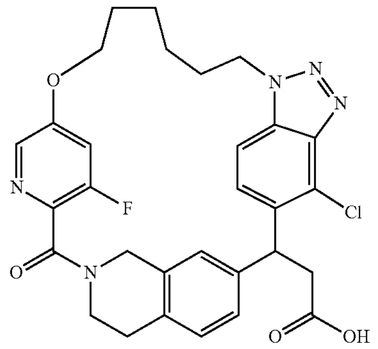 [SMILES: O=C(O)CC1c2ccc3c(c2)CN(CC3)C(=O)c2ncc(cc2F)OCCCCCCn2nnc3c(Cl)c1ccc32] |
| 214 | 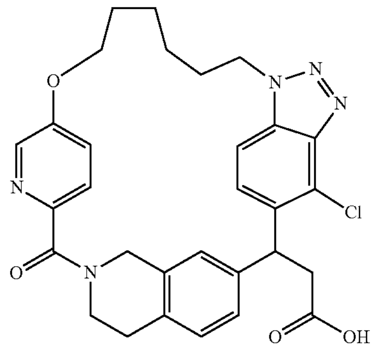 [SMILES: O=C(O)CC1c2ccc3c(c2)CN(CC3)C(=O)c2ccc(cn2)OCCCCCCn2nnc3c(Cl)c1ccc32] |
| Comp'd No | Structure |
|---|---|
| 215 | 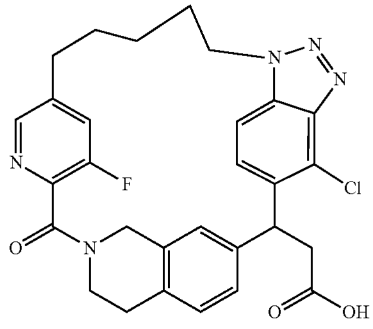 [SMILES: O=C(O)CC1c2ccc3c(c2)CN(CC3)C(=O)c2ncc(cc2F)CCCCCn2nnc3c(Cl)c1ccc32] |
| 216 | 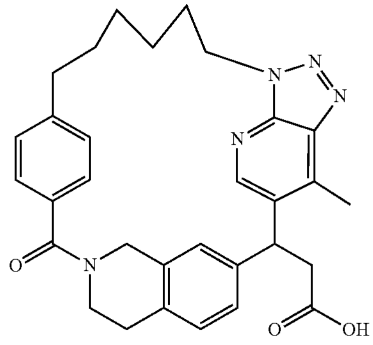 [SMILES: Cc1c2cnc3c1nnn3CCCCCCc1ccc(cc1)C(=O)N1CCc3ccc(cc3C1)C2CC(=O)O] |
| 217 | 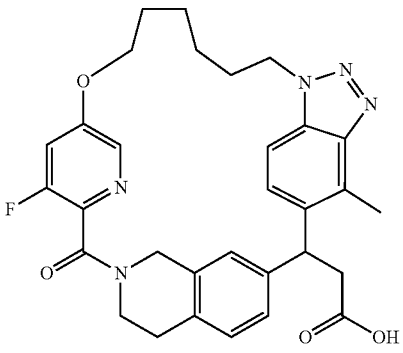 [SMILES: Cc1c2ccc3c1nnn3CCCCCCOc1cnc(c(F)c1)C(=O)N1CCc3ccc(cc3C1)C2CC(=O)O] |
| 218 | 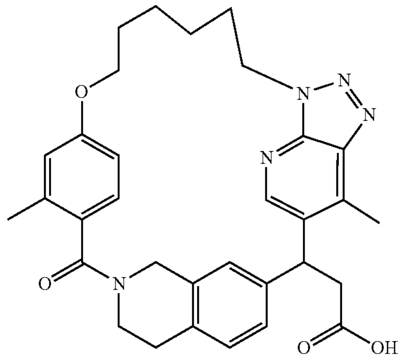 |

TABLE 2a-continued
| Comp'd No | Structure |
| --- | --- |
| 219 | 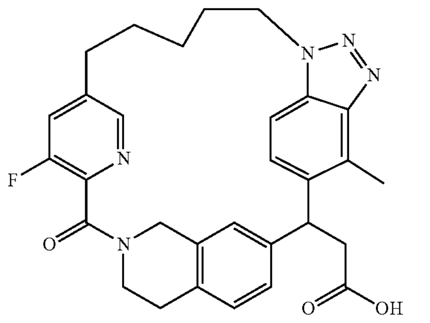 [SMILES: Cc1c2ccc3c1nnn3CCCCCc1cnc(c(F)c1)C(=O)N1CCc3ccc(cc3C1)C2CC(=O)O] |
| 220 | 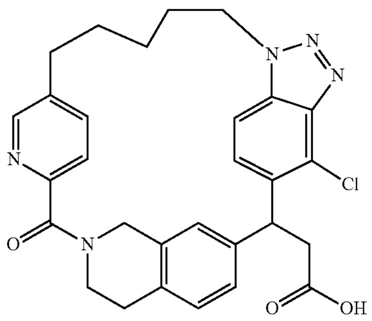 [SMILES: O=C(O)CC1c2ccc3c(c2)CN(CC3)C(=O)c2ccc(cn2)CCCCCn2nnc3c(Cl)c1ccc32] |
| 221 | 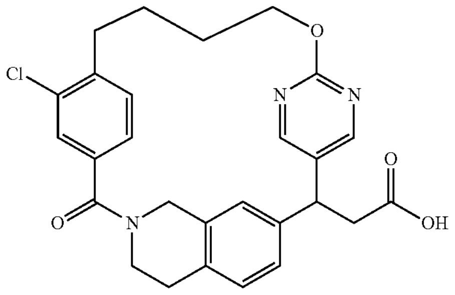 [SMILES: O=C(O)CC1c2cnc(nc2)OCCCCc2ccc(cc2Cl)C(=O)N2CCc3ccc1cc3C2] |
| 222 | 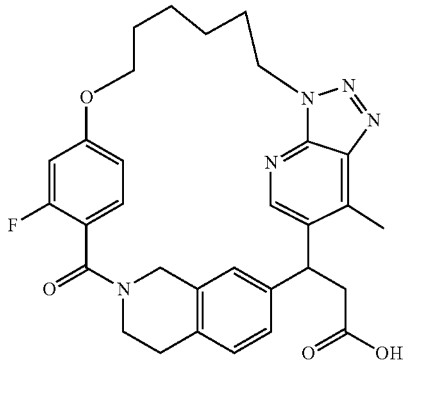 [SMILES: Cc1c2cnc3c1nnn3CCCCCCOc1ccc(c(F)c1)C(=O)N1CCc3ccc(cc3C1)C2CC(=O)O] |
| 224 | 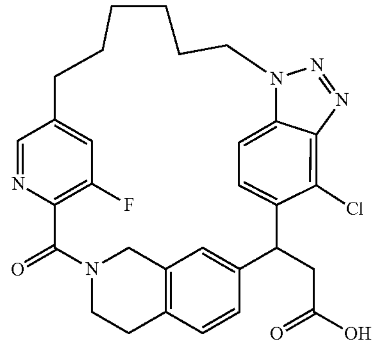 [SMILES: O=C(O)CC1c2ccc3c(c2)CN(CC3)C(=O)c2ncc(cc2F)CCCCCCn2nnc3c(Cl)c1ccc32] |
| 225 | 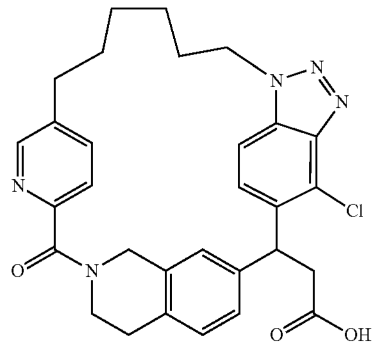 [SMILES: O=C(O)CC1c2ccc3c(c2)CN(CC3)C(=O)c2ccc(cn2)CCCCCCn2nnc3c(Cl)c1ccc32] |
| 226 | 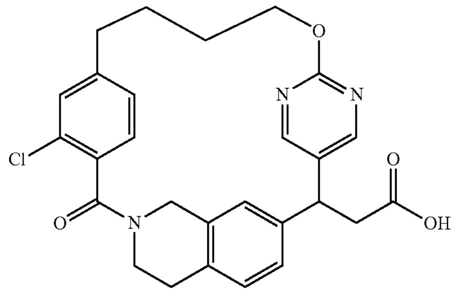 [SMILES: O=C(O)CC1c2cnc(nc2)OCCCCc2ccc(c(Cl)c2)C(=O)N2CCc3ccc1cc3C2] |
| 227 | 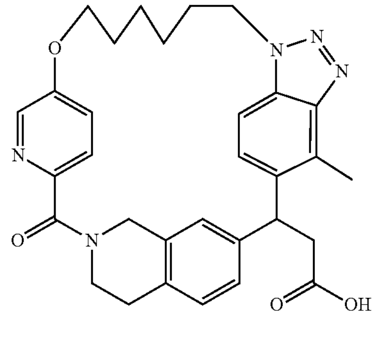 [SMILES: Cc1c2ccc3c1nnn3CCCCCCOc1ccc(nc1)C(=O)N1CCc3ccc(cc3C1)C2CC(=O)O] |

TABLE 2a-continued
| Comp'd No | Structure |
| --- | --- |
| 228 | 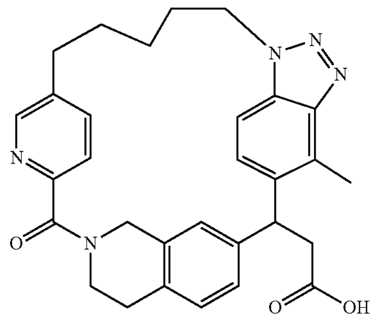 [SMILES: Cc1c2ccc3c1nnn3CCCCCc1ccc(nc1)C(=O)N1CCc3ccc(cc3C1)C2CC(=O)O] |
| 229 | 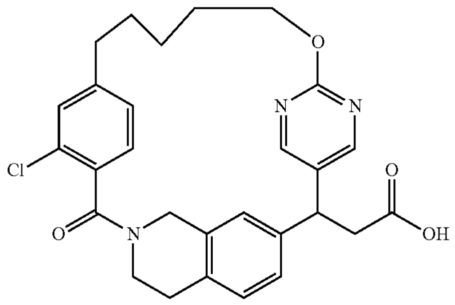 [SMILES: O=C(O)CC1c2cnc(nc2)OCCCCCc2ccc(c(Cl)c2)C(=O)N2CCc3ccc1cc3C2] |
| 230 | 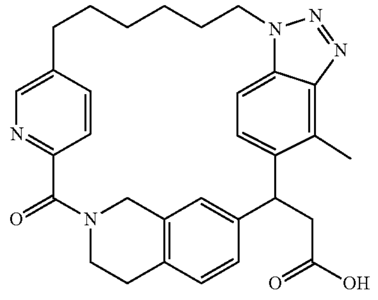 [SMILES: Cc1c2ccc3c1nnn3CCCCCCc1ccc(nc1)C(=O)N1CCc3ccc(cc3C1)C2CC(=O)O] |
| 231 | 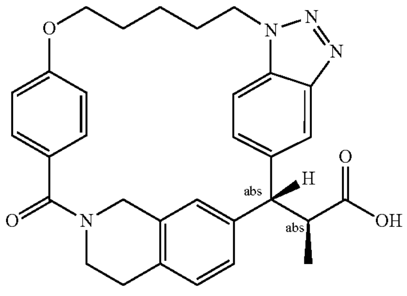 [SMILES: C[C@H](C(=O)O)[C@@H]1c2ccc3c(c2)CN(CC3)C(=O)c2ccc(cc2)OCCCCCn2nnc3cc1ccc32] |
| 232 | 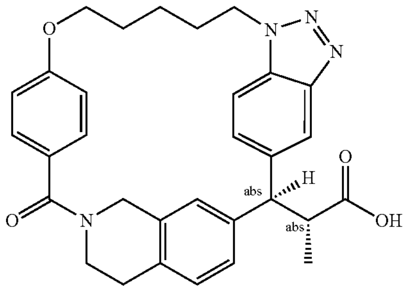 [SMILES: C[C@@H](C(=O)O)[C@H]1c2ccc3c(c2)CN(CC3)C(=O)c2ccc(cc2)OCCCCCn2nnc3cc1ccc32] |
TABLE 2a-continued
| Comp'd No | Structure |
| --- | --- |
| 233 | 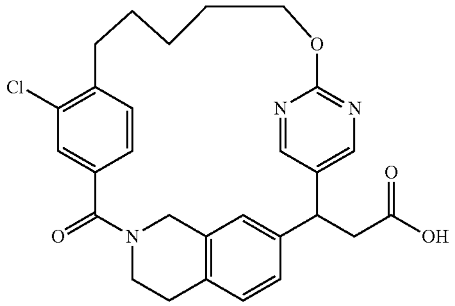 [SMILES: O=C(O)CC1c2cnc(nc2)OCCCCCc2ccc(cc2Cl)C(=O)N2CCc3ccc1cc3C2] |
| 234 | 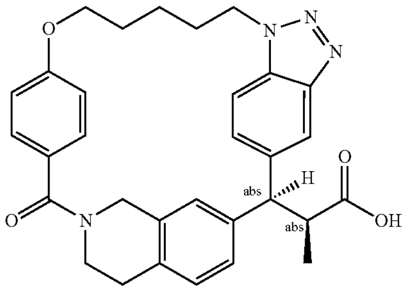 [SMILES: C[C@H](C(=O)O)[C@H]1c2ccc3c(c2)CN(CC3)C(=O)c2ccc(cc2)OCCCCCn2nnc3cc1ccc32] |
| 235 | 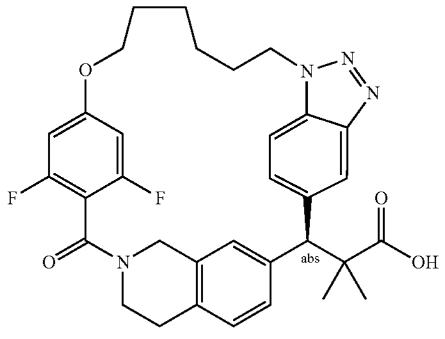 [SMILES: CC(C)(C(=O)O)[C@H]1c2ccc3c(c2)CN(CC3)C(=O)c2c(F)cc(cc2F)OCCCCCCn2nnc3cc1ccc32] |
| 236 | 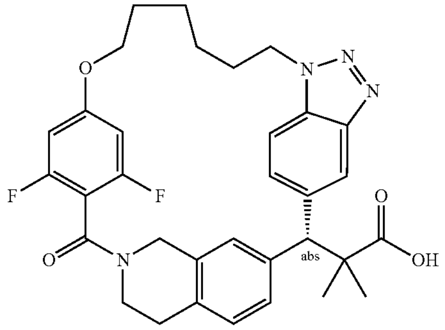 [SMILES: CC(C)(C(=O)O)[C@@H]1c2ccc3c(c2)CN(CC3)C(=O)c2c(F)cc(cc2F)OCCCCCCn2nnc3cc1ccc32] |

TABLE 2a-continued
| Comp'd No | Structure |
|---|---|
| 237 | 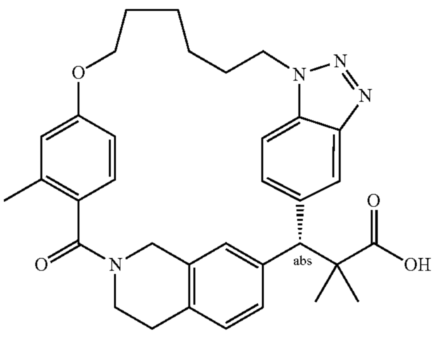 [SMILES: Cc1cc2ccc1C(=O)N1CCc3ccc(cc3C1)[C@@H](C(C)(C)C(=O)O)c1ccc3c(c1)nnn3CCCCCCO2] |
| 238 | 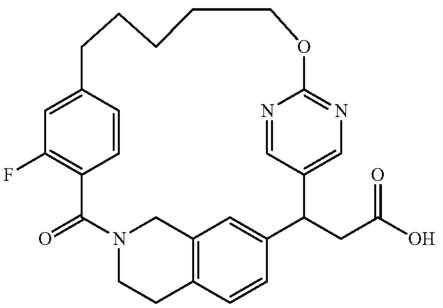 [SMILES: O=C(O)CC1c2cnc(nc2)OCCCCCc2ccc(c(F)c2)C(=O)N2CCc3ccc1cc3C2] |
| 239 | 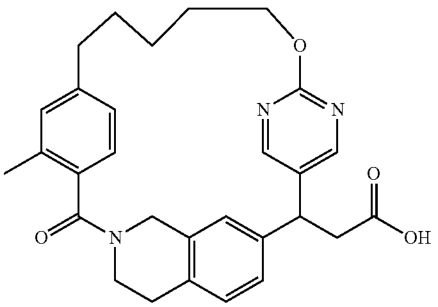 [SMILES: Cc1cc2ccc1C(=O)N1CCc3ccc(cc3C1)C(CC(=O)O)c1cnc(nc1)OCCCCC2] |
| 240 | 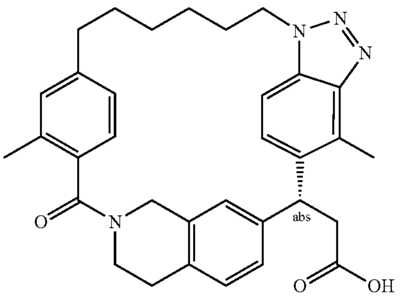 [SMILES: Cc1cc2ccc1C(=O)N1CCc3ccc(cc3C1)[C@@H](CC(=O)O)c1ccc3c(nnn3CCCCCC2)c1C] |
TABLE 2a-continued
| Comp'd No | Structure |
|---|---|
| 241 | 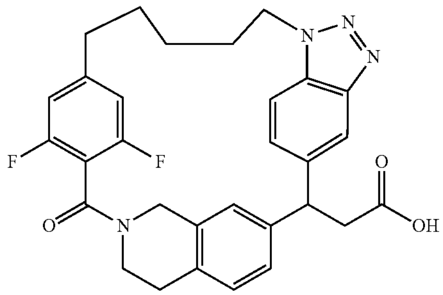 [SMILES: O=C(O)CC1c2ccc3c(c2)CN(CC3)C(=O)c2c(F)cc(cc2F)CCCCCn2nnc3cc1ccc32] |
| 242 | 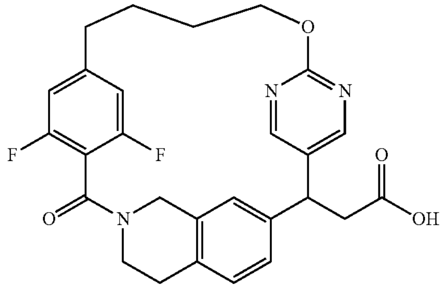 [SMILES: O=C(O)CC1c2cnc(nc2)OCCCCc2cc(F)c(c(F)c2)C(=O)N2CCc3ccc1cc3C2] |
| 243 | 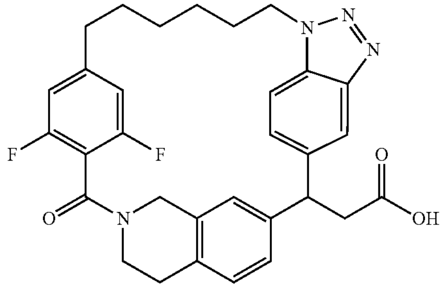 [SMILES: O=C(O)CC1c2ccc3c(c2)CN(CC3)C(=O)c2c(F)cc(cc2F)CCCCCCn2nnc3cc1ccc32] |
| 244 | 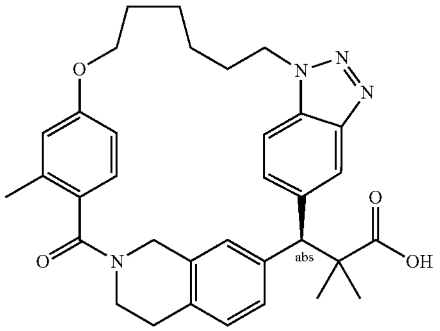 [SMILES: Cc1cc2ccc1C(=O)N1CCc3ccc(cc3C1)[C@H](C(C)(C)C(=O)O)c1ccc3c(c1)nnn3CCCCCCO2] |
| 245 | 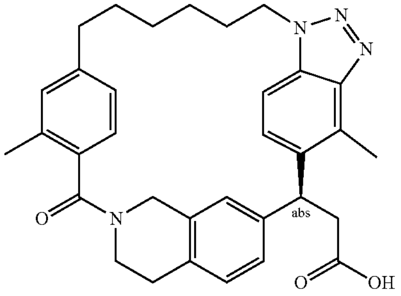 |

TABLE 2a-continued
| Comp'd No | Structure |
|---|---|
| 246 | 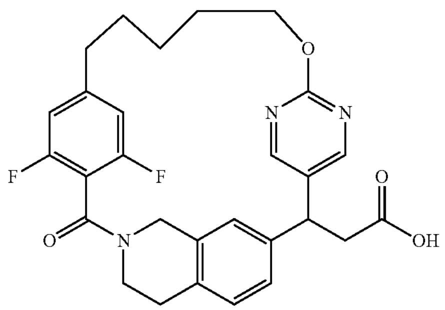 [SMILES: O=C(O)CC1c2cnc(nc2)OCCCCCc2cc(F)c(c(F)c2)C(=O)N2CCc3ccc1cc3C2] |
| 247 | 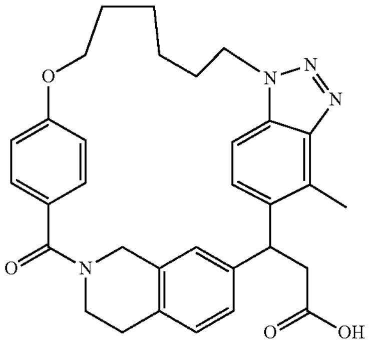 [SMILES: Cc1c2ccc3c1nnn3CCCCCCOc1ccc(cc1)C(=O)N1CCc3ccc(cc3C1)C2CC(=O)O] |
| 248 | 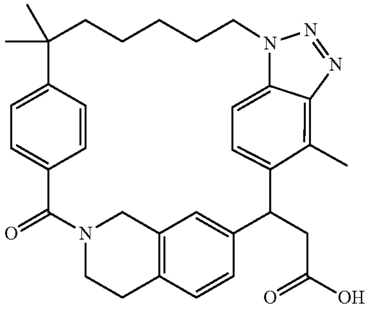 |
| 249 | 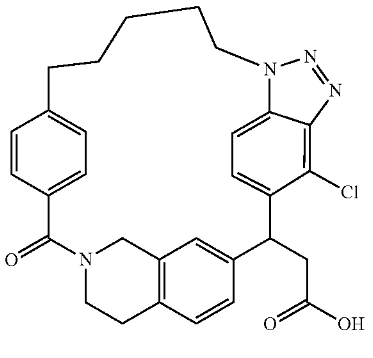 [SMILES: O=C(O)CC1c2ccc3c(c2)CN(CC3)C(=O)c2ccc(cc2)CCCCCn2nnc3c(Cl)c1ccc32] |
TABLE 2a-continued
| Comp'd No | Structure |
|---|---|
| 250 | 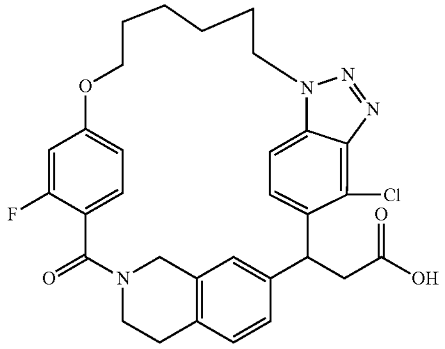 [SMILES: O=C(O)CC1c2ccc3c(c2)CN(CC3)C(=O)c2ccc(cc2F)OCCCCCCn2nnc3c(Cl)c1ccc32] |
| 251 | 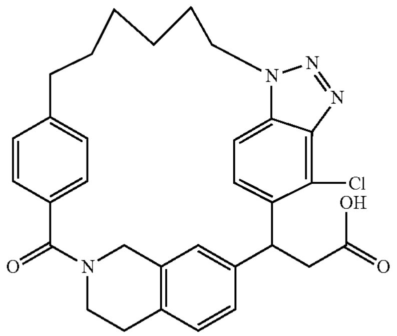 [SMILES: O=C(O)CC1c2ccc3c(c2)CN(CC3)C(=O)c2ccc(cc2)CCCCCCn2nnc3c(Cl)c1ccc32] |
| 252 | 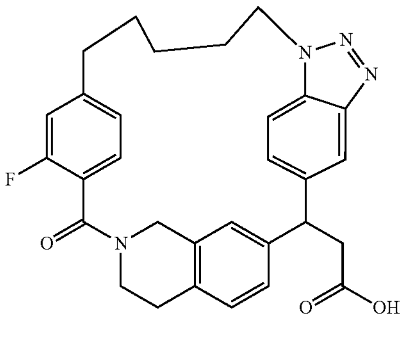 [SMILES: O=C(O)CC1c2ccc3c(c2)CN(CC3)C(=O)c2ccc(cc2F)CCCCCn2nnc3cc1ccc32] |
| 253 | 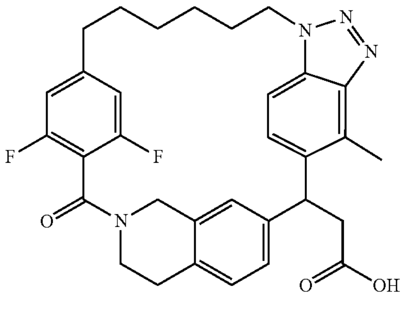 [SMILES: Cc1c2ccc3c1nnn3CCCCCCc1cc(F)c(c(F)c1)C(=O)N1CCc3ccc(cc3C1)C2CC(=O)O] |

TABLE 2a-continued
| Comp'd No | Structure |
| --- | --- |
| 254 | 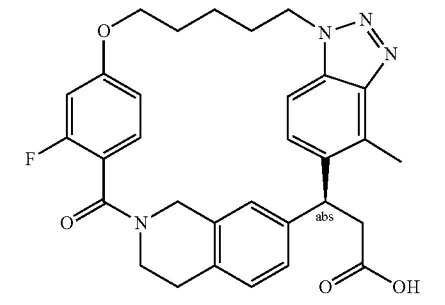 [SMILES: Cc1c2ccc3c1nnn3CCCCCOc1ccc(c(F)c1)C(=O)N1CCc3ccc(cc3C1)[C@@H]2CC(=O)O] |
| 255 | 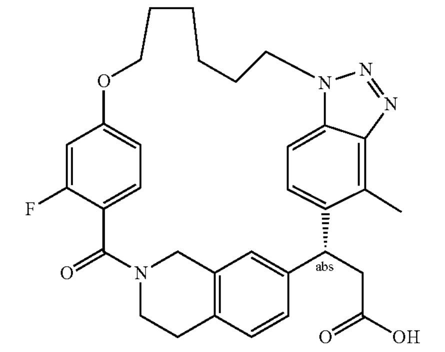 [SMILES: Cc1c2ccc3c1nnn3CCCCCCOc1ccc(c(F)c1)C(=O)N1CCc3ccc(cc3C1)[C@H]2CC(=O)O] |
| 256 | 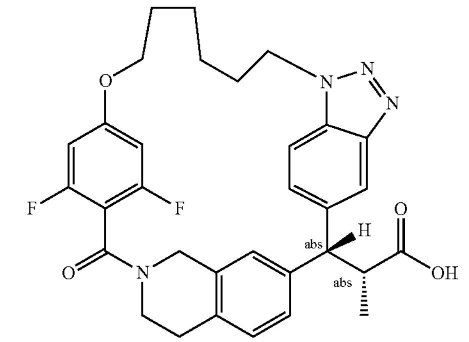 [SMILES: C[C@@H](C(=O)O)[C@@H]1c2ccc3c(c2)CN(CC3)C(=O)c2c(F)cc(cc2F)OCCCCCCn2nnc3cc1ccc32] |
| 257 | 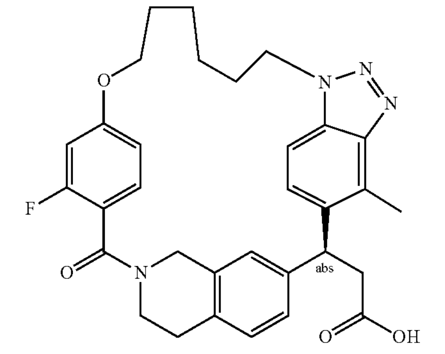 [SMILES: Cc1c2ccc3c1nnn3CCCCCCOc1ccc(c(F)c1)C(=O)N1CCc3ccc(cc3C1)[C@@H]2CC(=O)O] |
| 258 | 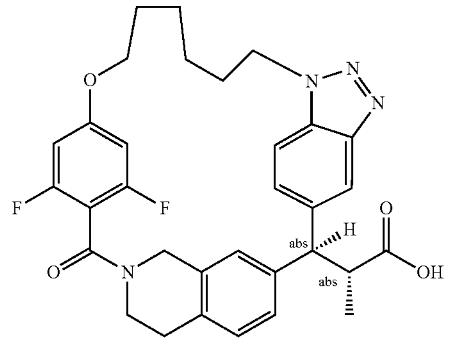 [SMILES: C[C@@H](C(=O)O)[C@H]1c2ccc3c(c2)CN(CC3)C(=O)c2c(F)cc(cc2F)OCCCCCCn2nnc3cc1ccc32] |
| 259 | 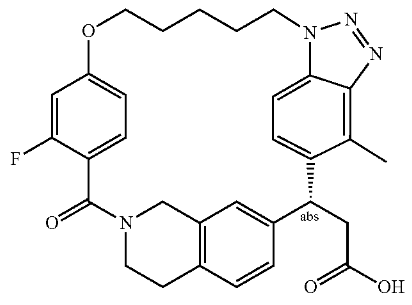 [SMILES: Cc1c2ccc3c1nnn3CCCCCOc1ccc(c(F)c1)C(=O)N1CCc3ccc(cc3C1)[C@H]2CC(=O)O] |
| 260 | 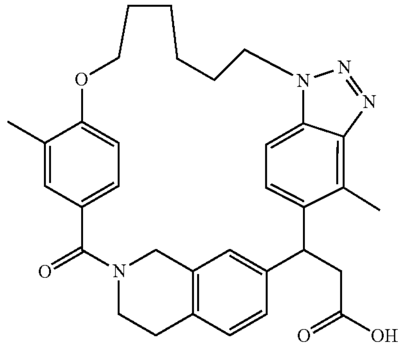 |
| 261 | 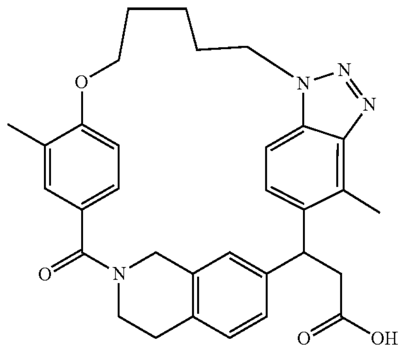 |

TABLE 2a-continued
| Comp'd No | Structure |
|---|---|
| 262 | 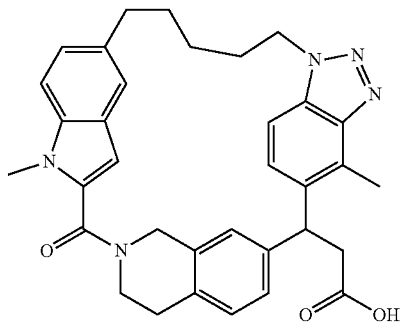 |
| 263 | 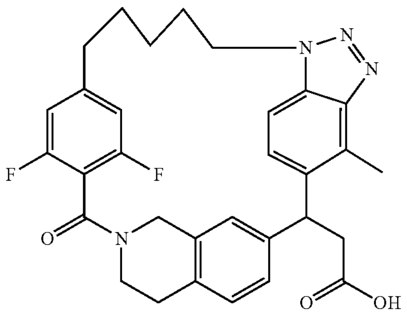 [SMILES: Cc1c2ccc3c1nnn3CCCCCc1cc(F)c(c(F)c1)C(=O)N1CCc3ccc(cc3C1)C2CC(=O)O] |
| 264 | 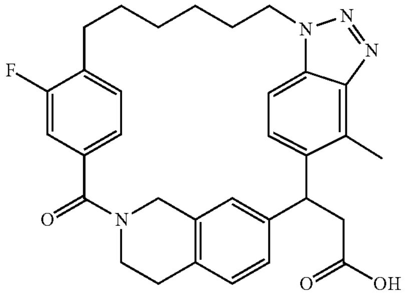 [SMILES: Cc1c2ccc3c1nnn3CCCCCCc1ccc(cc1F)C(=O)N1CCc3ccc(cc3C1)C2CC(=O)O] |
| 265 | 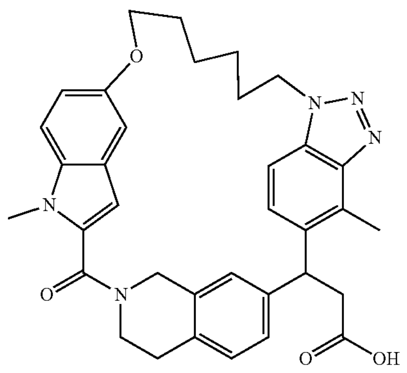 |
TABLE 2a-continued
| Comp'd No | Structure |
|---|---|
| 267 | 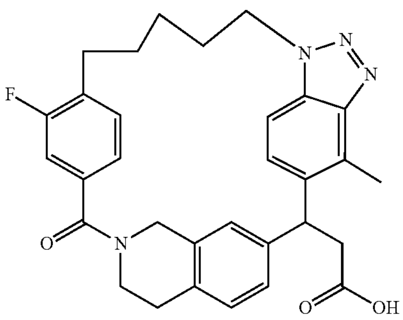 [SMILES: Cc1c2ccc3c1nnn3CCCCCc1ccc(cc1F)C(=O)N1CCc3ccc(cc3C1)C2CC(=O)O] |
| 268 | 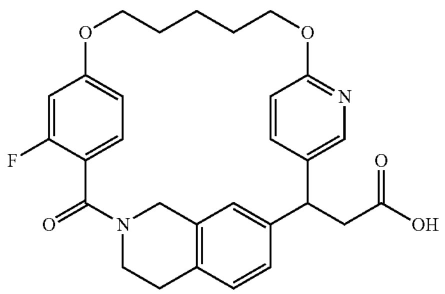 [SMILES: O=C(O)CC1c2ccc(nc2)OCCCCCOc2ccc(c(F)c2)C(=O)N2CCc3ccc1cc3C2] |
| 269 | 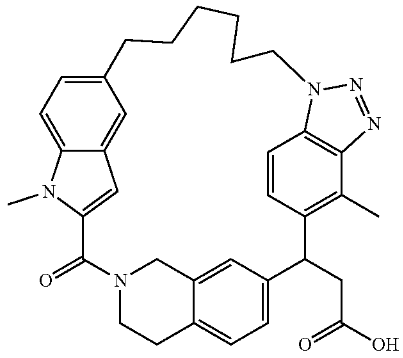 |
| 270 | 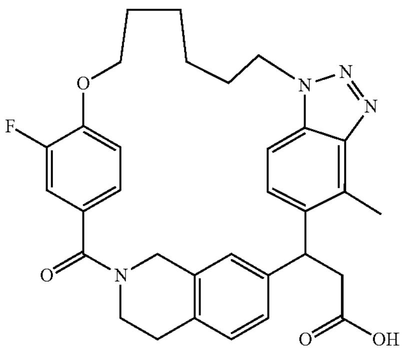 [SMILES: Cc1c2ccc3c1nnn3CCCCCCOc1ccc(cc1F)C(=O)N1CCc3ccc(cc3C1)C2CC(=O)O] |

TABLE 2a-continued
| Comp'd No | Structure |
| --- | --- |
| 271 | 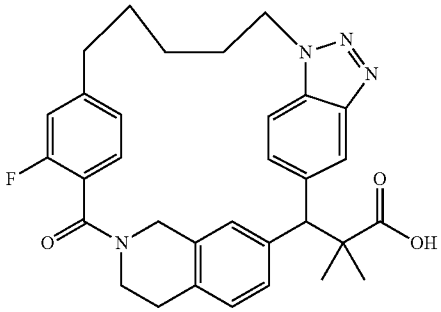 [SMILES: CC(C)(C(=O)O)C1c2ccc3c(c2)CN(CC3)C(=O)c2ccc(cc2F)CCCCCn2nnc3cc1ccc32] |
| 272 | 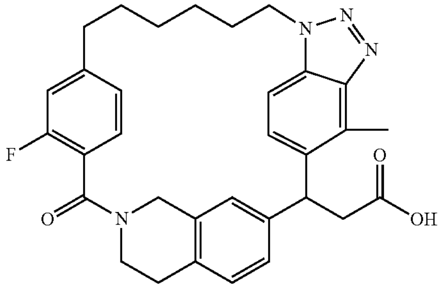 [SMILES: Cc1c2ccc3c1nnn3CCCCCCc1ccc(c(F)c1)C(=O)N1CCc3ccc(cc3C1)C2CC(=O)O] |
| 273 | 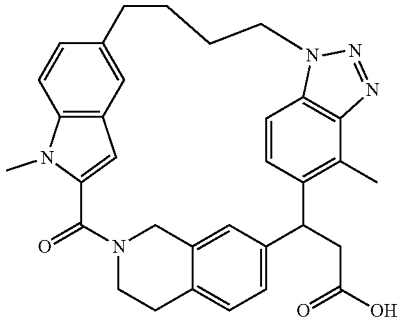 |
| 274 | 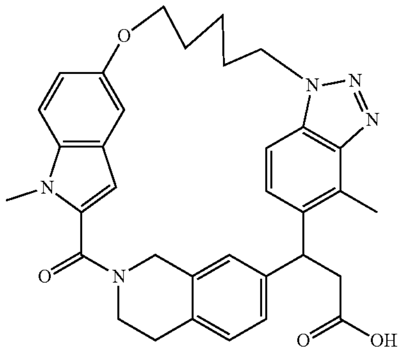 |
TABLE 2a-continued
| Comp'd No | Structure |
| --- | --- |
| 275 | 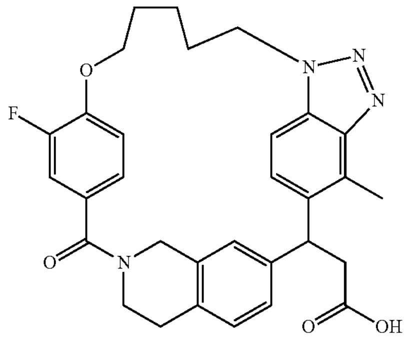 [SMILES: Cc1c2ccc3c1nnn3CCCCCOc1ccc(cc1F)C(=O)N1CCc3ccc(cc3C1)C2CC(=O)O] |
| 277 | 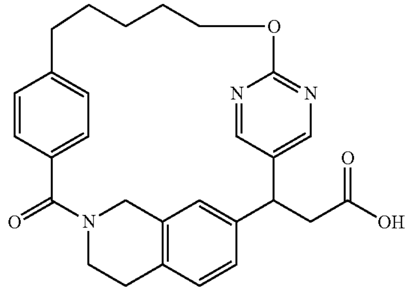 [SMILES: O=C(O)CC1c2cnc(nc2)OCCCCCc2ccc(cc2)C(=O)N2CCc3ccc1cc3C2] |
| 278 | 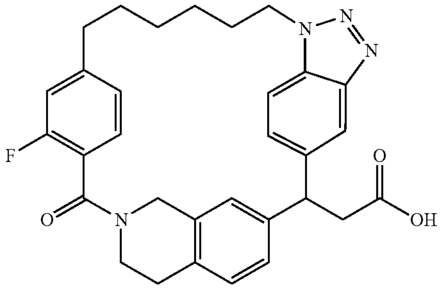 [SMILES: O=C(O)CC1c2ccc3c(c2)CN(CC3)C(=O)c2ccc(cc2F)CCCCCCn2nnc3cc1ccc32] |
| 279 | 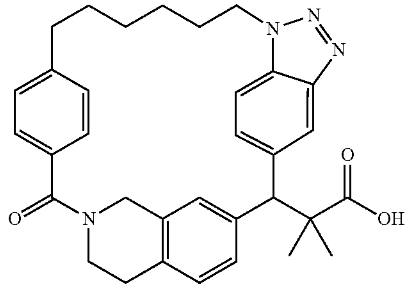 [SMILES: CC(C)(C(=O)O)C1c2ccc3c(c2)CN(CC3)C(=O)c2ccc(cc2)CCCCCCn2nnc3cc1ccc32] |
| 280 | 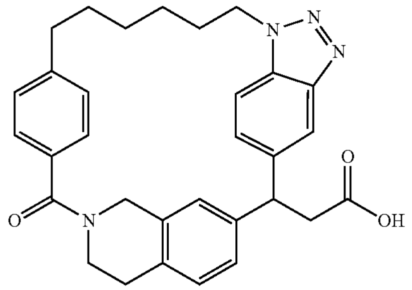 [SMILES: O=C(O)CC1c2ccc3c(c2)CN(CC3)C(=O)c2ccc(cc2)CCCCCCn2nnc3cc1ccc32] |

TABLE 2a-continued
| Comp’d No | Structure |
| --- | --- |
| 281 | 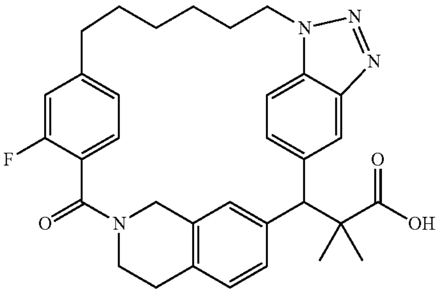 [SMILES: CC(C)(C(=O)O)C1c2ccc3c(c2)CN(CC3)C(=O)c2ccc(cc2F)CCCCCCn2nnc3cc1ccc32] |
| 282 | 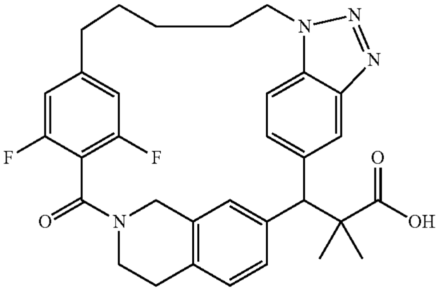 [SMILES: CC(C)(C(=O)O)C1c2ccc3c(c2)CN(CC3)C(=O)c2c(F)cc(cc2F)CCCCCn2nnc3cc1ccc32] |
| 283 | 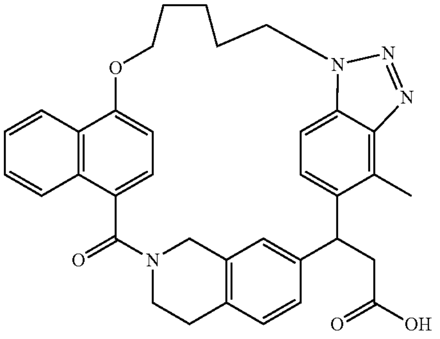 [SMILES: Cc1c2ccc3c1nnn3CCCCCOc1ccc(c3ccccc13)C(=O)N1CCc3ccc(cc3C1)C2CC(=O)O] |
| 284 | 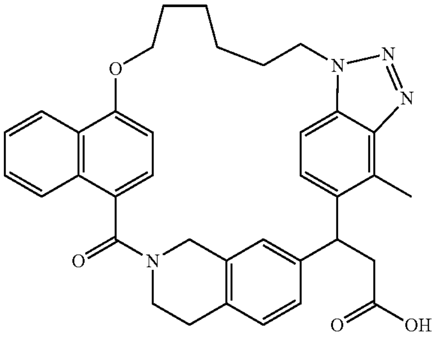 [SMILES: Cc1c2ccc3c1nnn3CCCCCCOc1ccc(c3ccccc13)C(=O)N1CCc3ccc(cc3C1)C2CC(=O)O] |
TABLE 2a-continued
| Comp’d No | Structure |
| --- | --- |
| 287 | 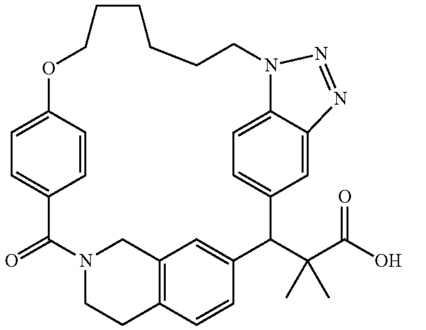 [SMILES: CC(C)(C(=O)O)C1c2ccc3c(c2)CN(CC3)C(=O)c2ccc(cc2)OCCCCCCn2nnc3cc1ccc32] |
| 288 | 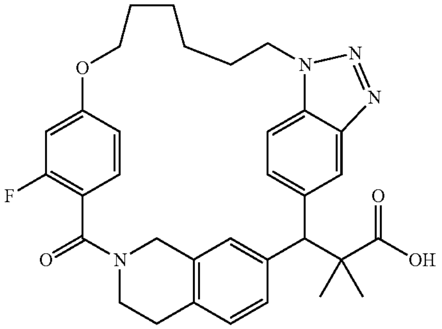 [SMILES: CC(C)(C(=O)O)C1c2ccc3c(c2)CN(CC3)C(=O)c2ccc(cc2F)OCCCCCCn2nnc3cc1ccc32] |
| 289 | 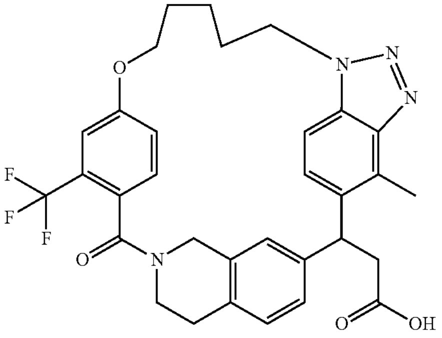 [SMILES: Cc1c2ccc3c1nnn3CCCCCOc1ccc(c(C(F)(F)F)c1)C(=O)N1CCc3ccc(cc3C1)C2CC(=O)O] |
| 290 | 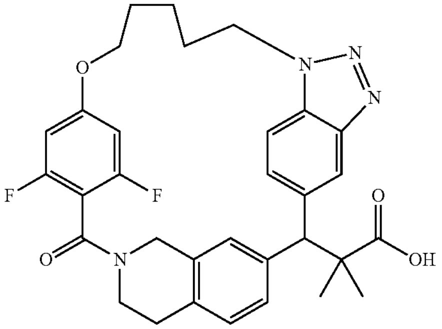 [SMILES: CC(C)(C(=O)O)C1c2ccc3c(c2)CN(CC3)C(=O)c2c(F)cc(cc2F)OCCCCCn2nnc3cc1ccc32] |

TABLE 2a-continued
| Comp'd No | Structure |
|---|---|
| 291 | 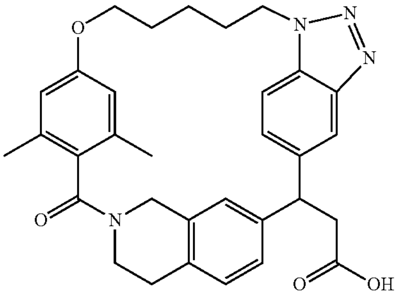 [SMILES: Cc1cc2cc(C)c1C(=O)N1CCc3ccc(cc3C1)C(CC(=O)O)c1ccc3c(c1)nnn3CCCCCO2] |
| 292 | 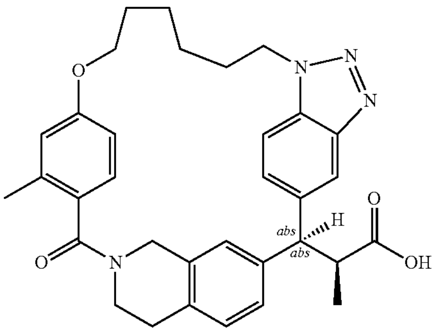 [SMILES: Cc1cc2ccc1C(=O)N1CCc3ccc(cc3C1)[C@H]([C@H](C)C(=O)O)c1ccc3c(c1)nnn3CCCCCCO2] |
| 293 | 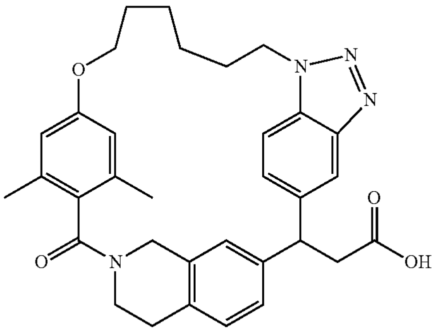 [SMILES: Cc1cc2cc(C)c1C(=O)N1CCc3ccc(cc3C1)C(CC(=O)O)c1ccc3c(c1)nnn3CCCCCCO2] |
| 294 | 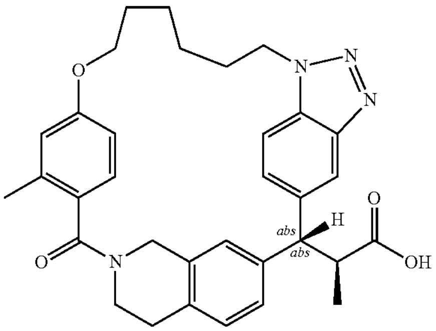 [SMILES: Cc1cc2ccc1C(=O)N1CCc3ccc(cc3C1)[C@@H]([C@H](C)C(=O)O)c1ccc3c(c1)nnn3CCCCCCO2] |
TABLE 2a-continued
| Comp'd No | Structure |
|---|---|
| 295 | 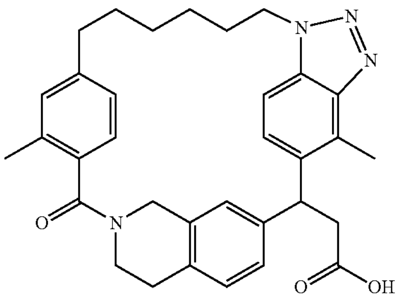 [SMILES: Cc1cc2ccc1C(=O)N1CCc3ccc(cc3C1)C(CC(=O)O)c1ccc3c(nnn3CCCCCC2)c1C] |
| 296 | 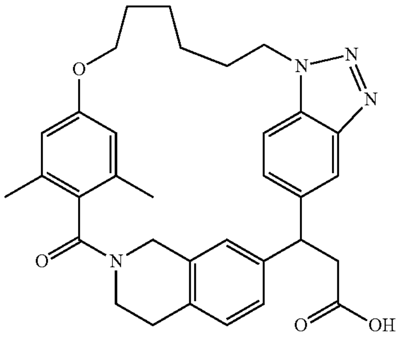 [SMILES: Cc1cc2cc(C)c1C(=O)N1CCc3ccc(cc3C1)C(CC(=O)O)c1ccc3c(c1)nnn3CCCCCCO2] |
| 297 | 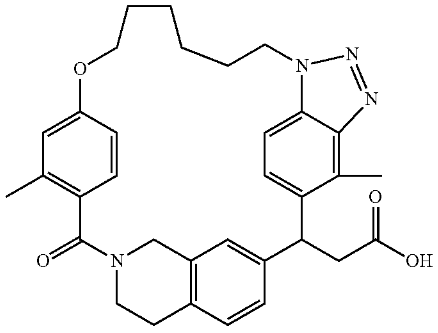 [SMILES: Cc1cc2ccc1C(=O)N1CCc3ccc(cc3C1)C(CC(=O)O)c1ccc3c(nnn3CCCCCCO2)c1C] |
| 298 | 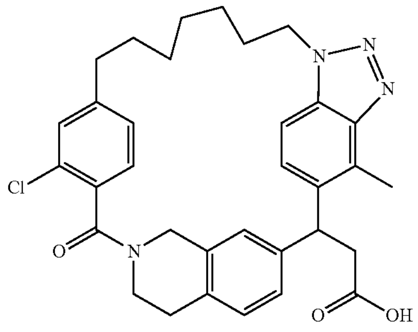 [SMILES: Cc1c2ccc3c1nnn3CCCCCCCc1ccc(c(Cl)c1)C(=O)N1CCc3ccc(cc3C1)C2CC(=O)O] |

TABLE 2a-continued
| Comp'd No | Structure |
|---|---|
| 299 | 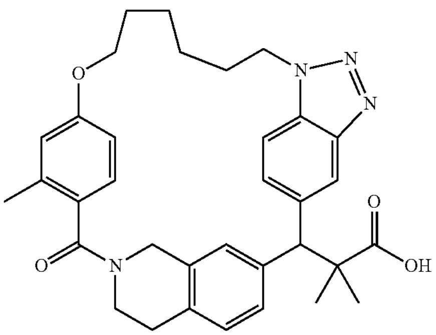 [SMILES: Cc1cc2ccc1C(=O)N1CCc3ccc(cc3C1)C(C(C)(C)C(=O)O)c1ccc3c(c1)nnn3CCCCCCO2] |
| 300 | 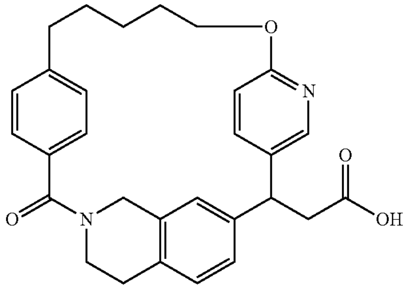 |
| 301 | 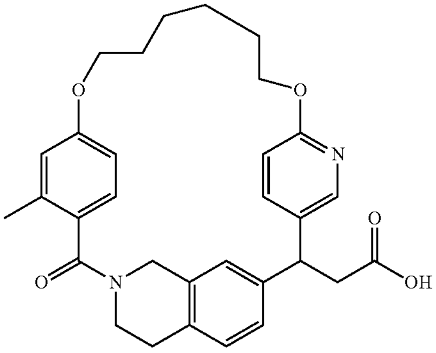 [SMILES: Cc1cc2ccc1C(=O)N1CCc3ccc(cc3C1)C(CC(=O)O)c1ccc(nc1)OCCCCCCO2] |
| 302 | 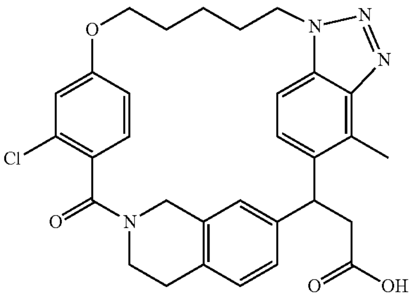 [SMILES: Cc1c2ccc3c1nnn3CCCCCOc1ccc(c(Cl)c1)C(=O)N1CCc3ccc(cc3C1)C2CC(=O)O] |
TABLE 2a-continued
| Comp'd No | Structure |
|---|---|
| 303 | 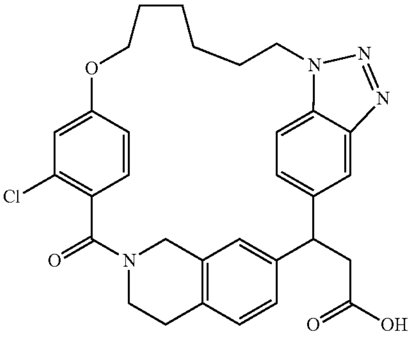 [SMILES: O=C(O)CC1c2ccc3c(c2)CN(CC3)C(=O)c2ccc(cc2Cl)OCCCCCCn2nnc3cc1ccc32] |
| 304 | 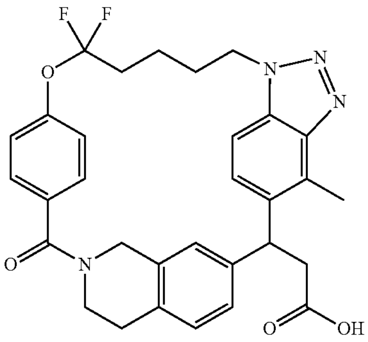 [SMILES: Cc1c2ccc3c1nnn3CCCCC(F)(F)Oc1ccc(cc1)C(=O)N1CCc3ccc(cc3C1)C2CC(=O)O] |
| 305 | 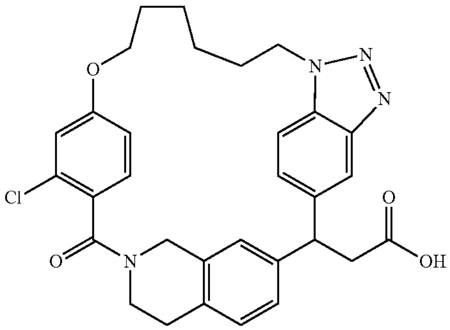 [SMILES: O=C(O)CC1c2ccc3c(c2)CN(CC3)C(=O)c2ccc(cc2Cl)OCCCCCCn2nnc3cc1ccc32] |
| 306 | 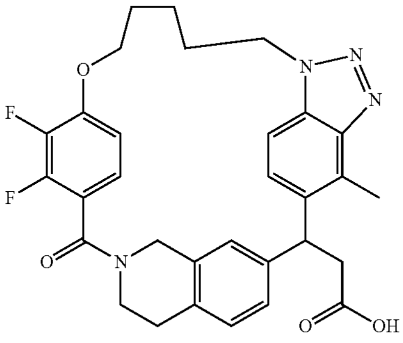 [SMILES: Cc1c2ccc3c1nnn3CCCCCOc1ccc(c(F)c1F)C(=O)N1CCc3ccc(cc3C1)C2CC(=O)O] |

TABLE 2a-continued
| Comp'd No | Structure |
| --- | --- |
| 308 | 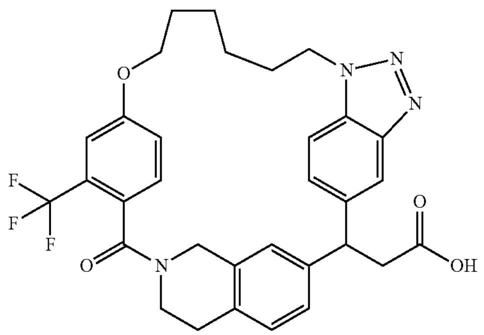 [SMILES: O=C(O)CC1c2ccc3c(c2)CN(CC3)C(=O)c2ccc(cc2C(F)(F)F)OCCCCCCn2nnc3cc1ccc32] |
| 309 | 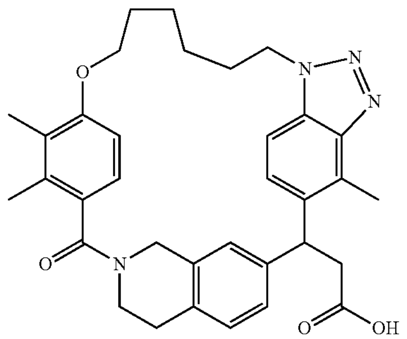 |
| 310 | 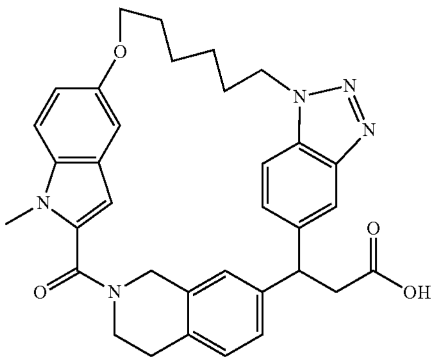 [SMILES: Cn1c2cc3cc(ccc31)OCCCCCCn1nnc3cc(ccc31)C(CC(=O)O)c1ccc3c(c1)CN(CC3)C2=O] |
| 311 | 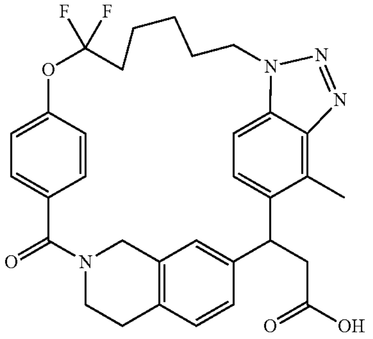 [SMILES: Cc1c2ccc3c1nnn3CCCCCC(F)(F)Oc1ccc(cc1)C(=O)N1CCc3ccc(cc3C1)C2CC(=O)O] |
TABLE 2a-continued
| Comp'd No | Structure |
| --- | --- |
| 312 | 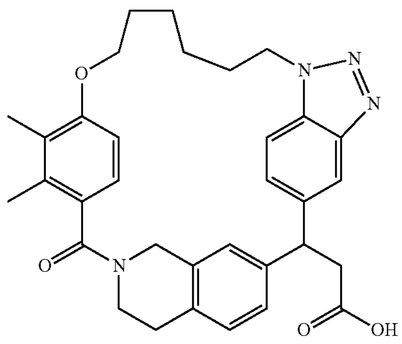 [SMILES: Cc1c2ccc(c1C)C(=O)N1CCc3ccc(cc3C1)C(CC(=O)O)c1ccc3c(c1)nnn3CCCCCCO2] |
| 313 | 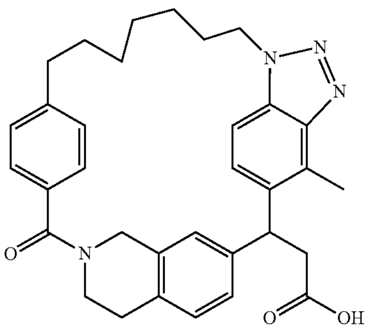 [SMILES: Cc1c2ccc3c1nnn3CCCCCCCc1ccc(cc1)C(=O)N1CCc3ccc(cc3C1)C2CC(=O)O] |
| 314 | 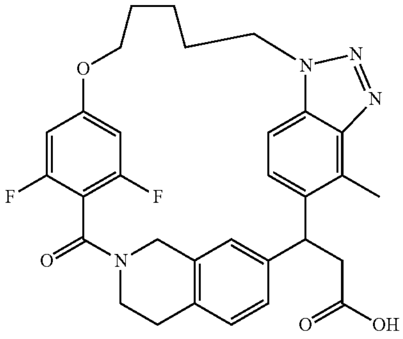 [SMILES: Cc1c2ccc3c1nnn3CCCCCOc1cc(F)c(c(F)c1)C(=O)N1CCc3ccc(cc3C1)C2CC(=O)O] |
| 315 | 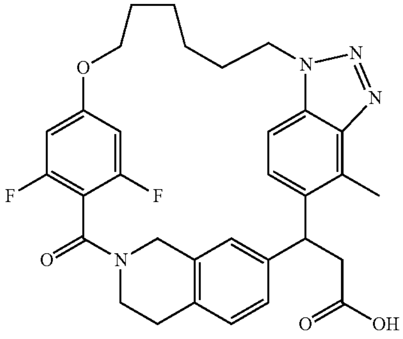 [SMILES: Cc1c2ccc3c1nnn3CCCCCCOc1cc(F)c(c(F)c1)C(=O)N1CCc3ccc(cc3C1)C2CC(=O)O] |

TABLE 2a-continued
| Comp'd No | Structure |
|---|---|
| 316 | 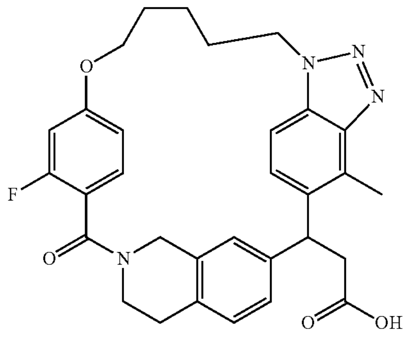 [SMILES: Cc1c2ccc3c1nnn3CCCCCOc1ccc(c(F)c1)C(=O)N1CCc3ccc(cc3C1)C2CC(=O)O] |
| 317 | 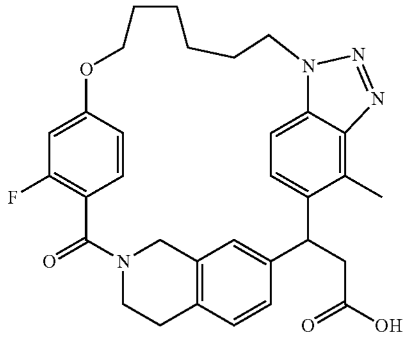 [SMILES: Cc1c2ccc3c1nnn3CCCCCCOc1ccc(c(F)c1)C(=O)N1CCc3ccc(cc3C1)C2CC(=O)O] |
| 318 | 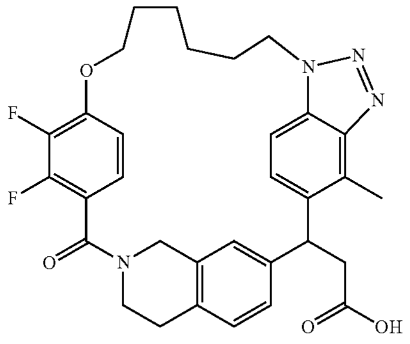 [SMILES: Cc1c2ccc3c1nnn3CCCCCCOc1ccc(c(F)c1F)C(=O)N1CCc3ccc(cc3C1)C2CC(=O)O] |
| 319 | 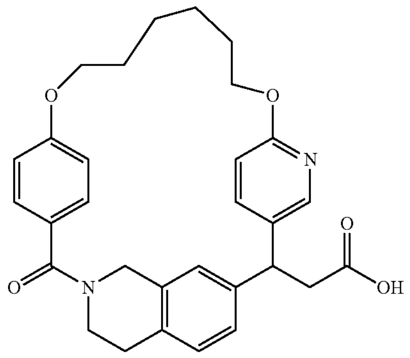 [SMILES: O=C(O)CC1c2ccc(nc2)OCCCCCCOc2ccc(cc2)C(=O)N2CCc3ccc1cc3C2] |
TABLE 2a-continued
| Comp'd No | Structure |
|---|---|
| 320 | 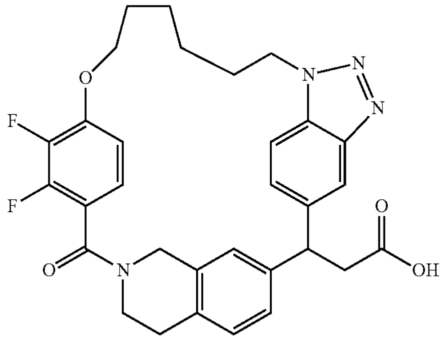 [SMILES: O=C(O)CC1c2ccc3c(c2)CN(CC3)C(=O)c2ccc(c(F)c2F)OCCCCCCn2nnc3cc1ccc32] |
| 321 | 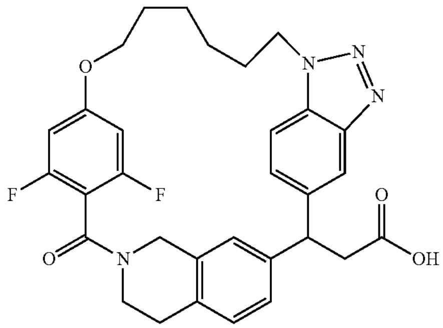 [SMILES: O=C(O)CC1c2ccc3c(c2)CN(CC3)C(=O)c2c(F)cc(cc2F)OCCCCCCn2nnc3cc1ccc32] |
| 322 | 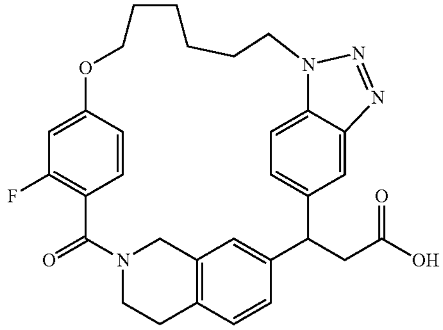 [SMILES: O=C(O)CC1c2ccc3c(c2)CN(CC3)C(=O)c2ccc(cc2F)OCCCCCCn2nnc3cc1ccc32] |
| 323 | 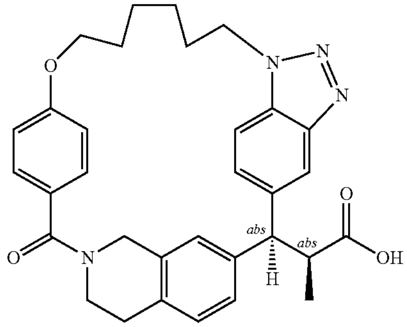 [SMILES: C[C@H](C(=O)O)[C@H]1c2ccc3c(c2)CN(CC3)C(=O)c2ccc(cc2)OCCCCCCn2nnc3cc1ccc32] |

TABLE 2a-continued
| Comp'd No | Structure |
| --- | --- |
| 324 | 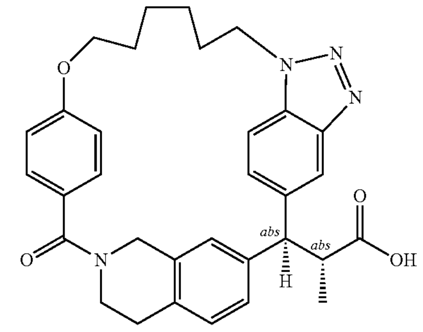 [SMILES: C[C@@H](C(=O)O)[C@H]1c2ccc3c(c2)CN(CC3)C(=O)c2ccc(cc2)OCCCCCCn2nnc3cc1ccc32] |
| 325 | 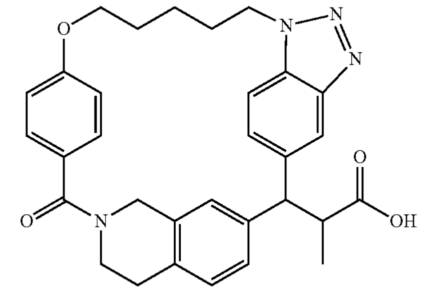 [SMILES: CC(C(=O)O)C1c2ccc3c(c2)CN(CC3)C(=O)c2ccc(cc2)OCCCCCn2nnc3cc1ccc32] |
| 326 | 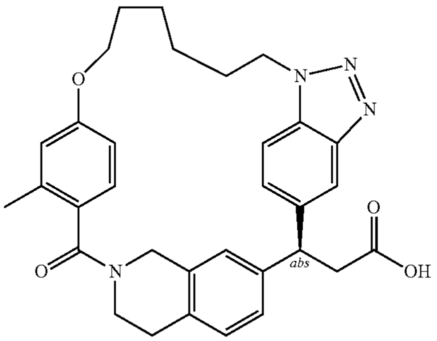 [SMILES: Cc1cc2ccc1C(=O)N1CCc3ccc(cc3C1)[C@H](CC(=O)O)c1ccc3c(c1)nnn3CCCCCCO2] |
| 327 | 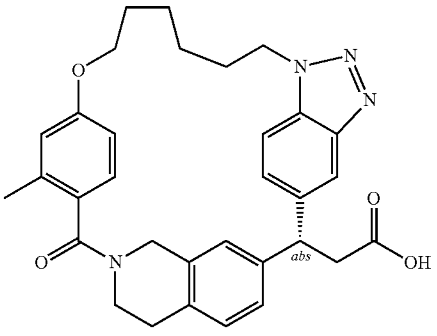 [SMILES: Cc1cc2ccc1C(=O)N1CCc3ccc(cc3C1)[C@@H](CC(=O)O)c1ccc3c(c1)nnn3CCCCCCO2] |
TABLE 2a-continued
| Comp'd No | Structure |
| --- | --- |
| 328 | 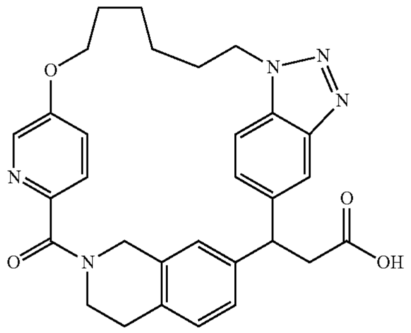 [SMILES: O=C(O)CC1c2ccc3c(c2)CN(CC3)C(=O)c2ccc(cn2)OCCCCCCn2nnc3cc1ccc32] |
| 329 | 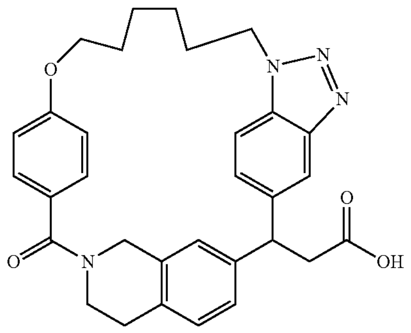 [SMILES: O=C(O)CC1c2ccc3c(c2)CN(CC3)C(=O)c2ccc(cc2)OCCCCCCn2nnc3cc1ccc32] |
| 330 | 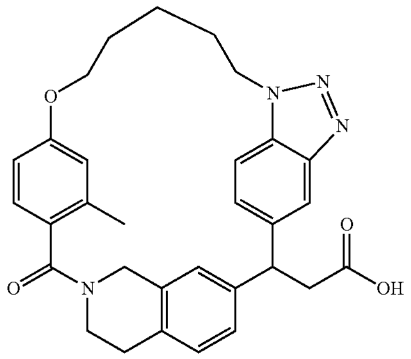 [SMILES: Cc1cc2ccc1C(=O)N1CCc3ccc(cc3C1)C(CC(=O)O)c1ccc3c(c1)nnn3CCCCCO2] |
| 331 | 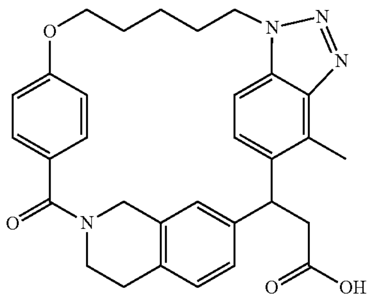 [SMILES: Cc1c2ccc3c1nnn3CCCCCOc1ccc(cc1)C(=O)N1CCc3ccc(cc3C1)C2CC(=O)O] |

TABLE 2a-continued
| Comp'd No | Structure |
|---|---|
| 332 | 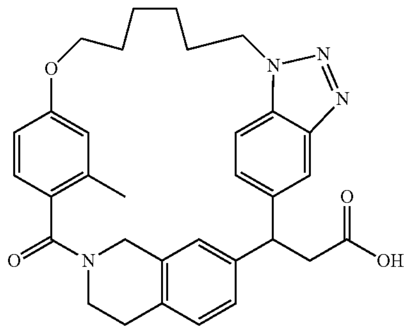 [SMILES: Cc1cc2ccc1C(=O)N1CCc3ccc(cc3C1)C(CC(=O)O)c1ccc3c(c1)nnn3CCCCCCO2] |
| 333 | 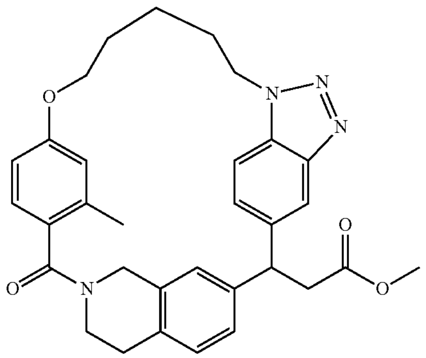 [SMILES: COC(=O)CC1c2ccc3c(c2)CN(CC3)C(=O)c2ccc(cc2C)OCCCCCn2nnc3cc1ccc32] |
| 334 | 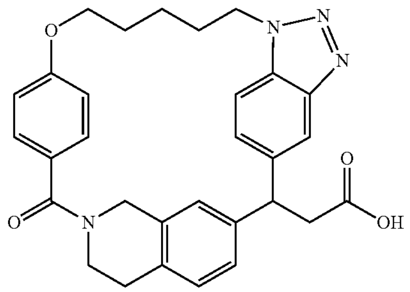 [SMILES: O=C(O)CC1c2ccc3c(c2)CN(CC3)C(=O)c2ccc(cc2)OCCCCCn2nnc3cc1ccc32] |
| 335 | 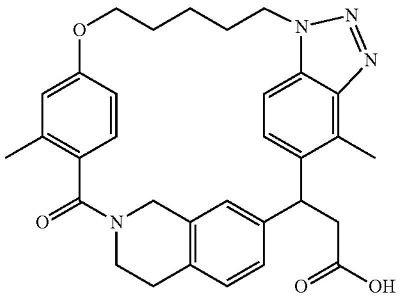 |
| 336 | 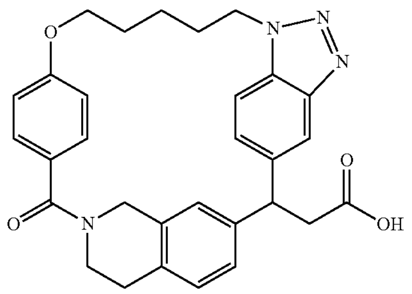 [SMILES: O=C(O)CC1c2ccc3c(c2)CN(CC3)C(=O)c2ccc(cc2)OCCCCCn2nnc3cc1ccc32] |
| 337 | 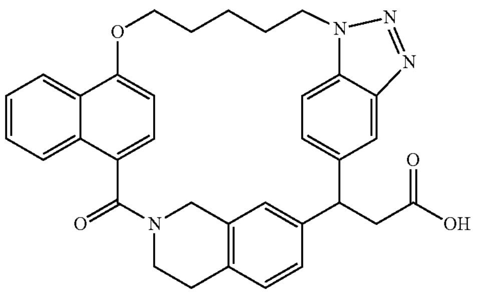 [SMILES: O=C(O)CC1c2ccc3c(c2)CN(CC3)C(=O)c2ccc(c3ccccc23)OCCCCCn2nnc3cc1ccc32] |
| 338 | 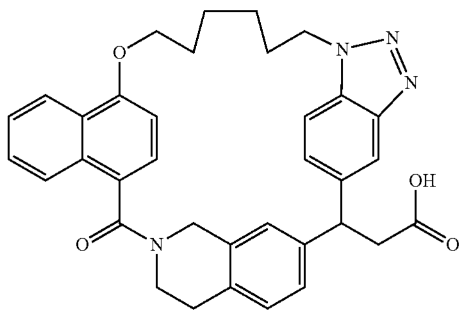 [SMILES: O=C(O)CC1c2ccc3c(c2)CN(CC3)C(=O)c2ccc(c3ccccc23)OCCCCCCn2nnc3cc1ccc32] |
| 344 | 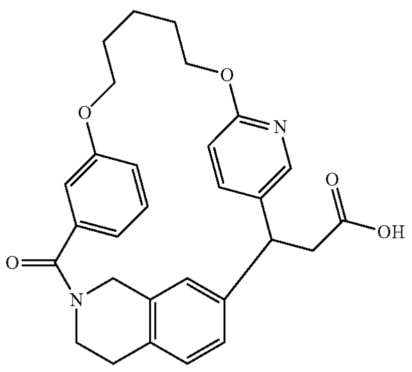 [SMILES: O=C(O)CC1c2ccc(nc2)OCCCCCOc2cccc(c2)C(=O)N2CCc3ccc1cc3C2] |

TABLE 2a-continued
| Comp'd No | Structure |
|---|---|
| 345 | 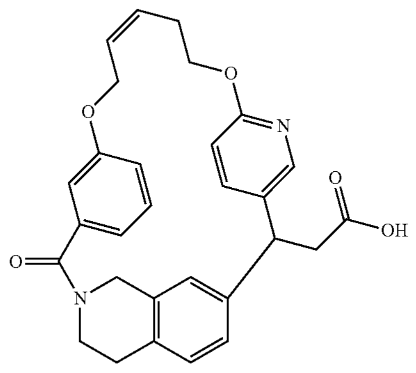 [SMILES: O=C(O)CC1c2ccc(nc2)OCC/C=C\COc2cccc(c2)C(=O)N2CCc3ccc1cc3C2] |
| 346 | 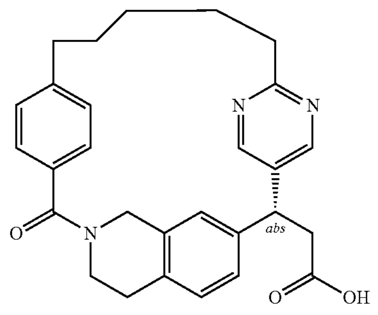 [SMILES: O=C(O)C[C@H]1c2cnc(nc2)CCCCCc2ccc(cc2)C(=O)N2CCc3ccc1cc3C2] |
| 347 | 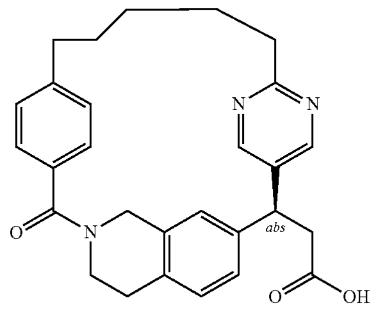 [SMILES: O=C(O)C[C@@H]1c2cnc(nc2)CCCCCc2ccc(cc2)C(=O)N2CCc3ccc1cc3C2] |
| 348 | 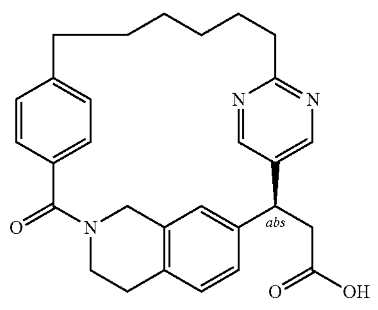 [SMILES: O=C(O)C[C@@H]1c2cnc(nc2)CCCCCCc2ccc(cc2)C(=O)N2CCc3ccc1cc3C2] |
TABLE 2a-continued
| Comp'd No | Structure |
|---|---|
| 349 | 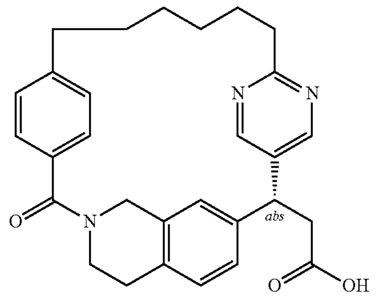 [SMILES: O=C(O)C[C@H]1c2cnc(nc2)CCCCCCc2ccc(cc2)C(=O)N2CCc3ccc1cc3C2] |
| 350 | 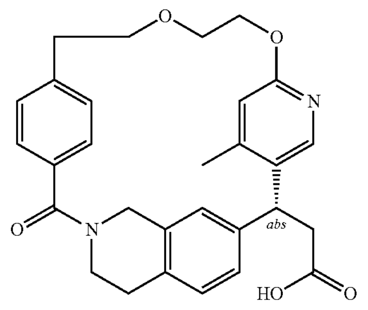 [SMILES: Cc1cc2ncc1[C@H](CC(=O)O)c1ccc3c(c1)CN(CC3)C(=O)c1ccc(cc1)CCOCCO2] |
| 351 | 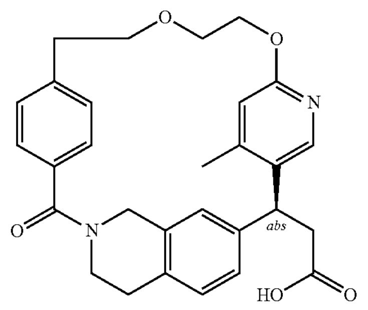 [SMILES: Cc1cc2ncc1[C@@H](CC(=O)O)c1ccc3c(c1)CN(CC3)C(=O)c1ccc(cc1)CCOCCO2] |
| 352 | 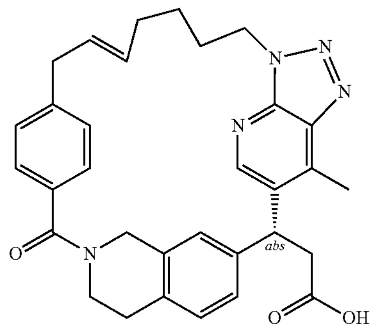 [SMILES: Cc1c2cnc3c1nnn3CCCC/C=C/Cc1ccc(cc1)C(=O)N1CCc3ccc(cc3C1)[C@H]2CC(=O)O] |

TABLE 2a-continued
| Comp'd No | Structure |
| --- | --- |
| 353 | 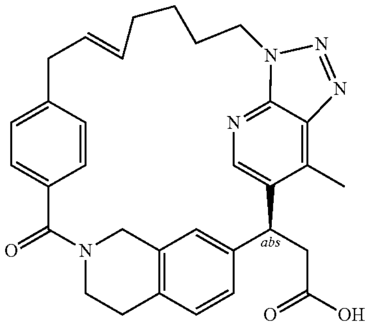 [SMILES: Cc1c2cnc3c1nnn3CCCC/C=C/Cc1ccc(cc1)C(=O)N1CCc3ccc(cc3C1)[C@@H]2CC(=O)O] |
| 354 | 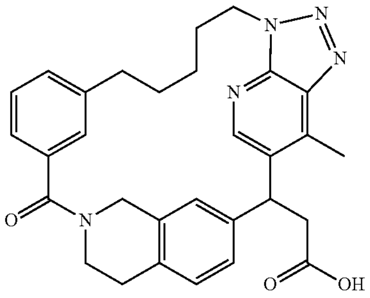 [SMILES: Cc1c2cnc3c1nnn3CCCCCc1cccc(c1)C(=O)N1CCc3ccc(cc3C1)C2CC(=O)O] |
| 355 | 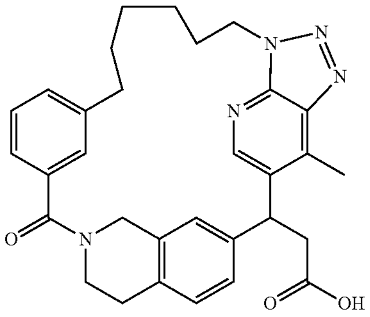 [SMILES: Cc1c2cnc3c1nnn3CCCCCCc1cccc(c1)C(=O)N1CCc3ccc(cc3C1)C2CC(=O)O] |
| 356 | 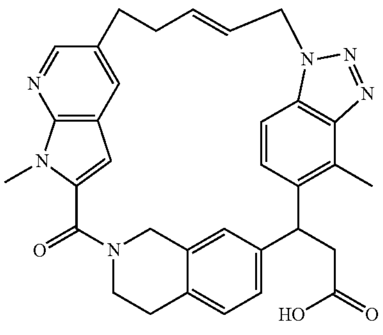 |
TABLE 2a-continued
| Comp'd No | Structure |
| --- | --- |
| 357 | 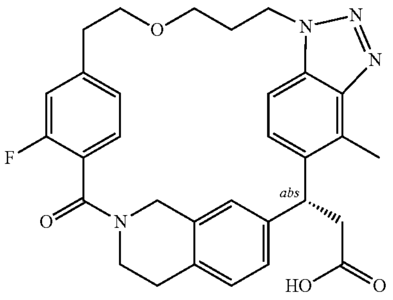 [SMILES: Cc1c2ccc3c1nnn3CCCOCCc1ccc(c(F)c1)C(=O)N1CCc3ccc(cc3C1)[C@H]2CC(=O)O] |
| 358 | 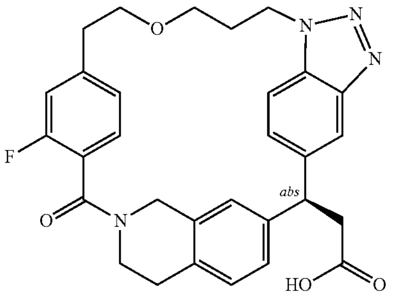 [SMILES: O=C(O)C[C@H]1c2ccc3c(c2)CN(CC3)C(=O)c2ccc(cc2F)CCOCCCn2nnc3cc1ccc32] |
| 359 | 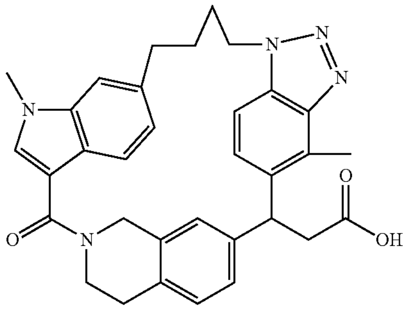 [SMILES: Cc1c2ccc3c1nnn3CCCCc1ccc3c(cn(C)c3c1)C(=O)N1CCc3ccc(cc3C1)C2CC(=O)O] |
| 360 | 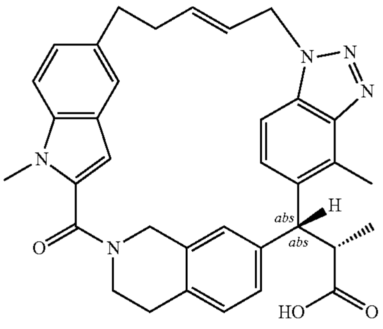 [SMILES: Cc1c2ccc3c1nnn3C/C=C/CCc1ccc3c(c1)cc(n3C)C(=O)N1CCc3ccc(cc3C1)[C@H]2[C@H](C)C(=O)O] |

TABLE 2a-continued
| Comp'd No | Structure |
|---|---|
| 361 | 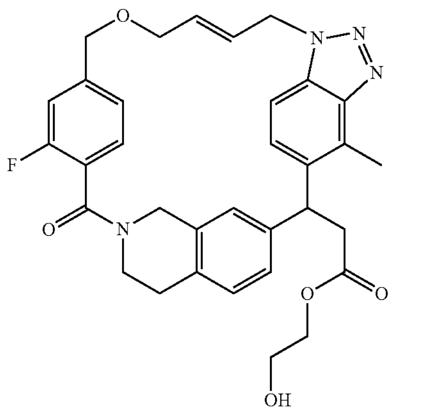 [SMILES: Cc1c2ccc3c1nnn3C/C=C/COCc1ccc(c(F)c1)C(=O)N1CCc3ccc(cc3C1)C2CC(=O)OCCO] |
| 362 | 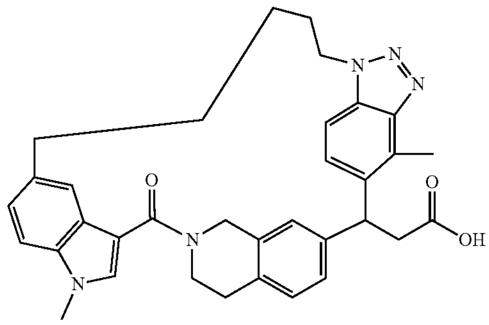 [SMILES: Cc1c2ccc3c1nnn3CCCCCc1ccc3c(c1)c(cn3C)C(=O)N1CCc3ccc(cc3C1)C2CC(=O)O] |
| 363 | 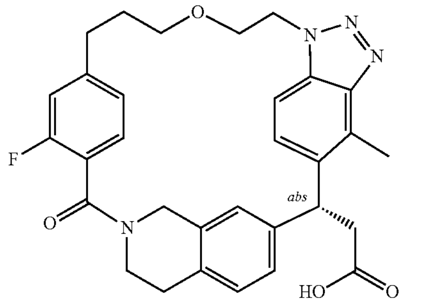 [SMILES: Cc1c2ccc3c1nnn3CCOCCCc1ccc(c(F)c1)C(=O)N1CCc3ccc(cc3C1)[C@H]2CC(=O)O] |
| 364 | 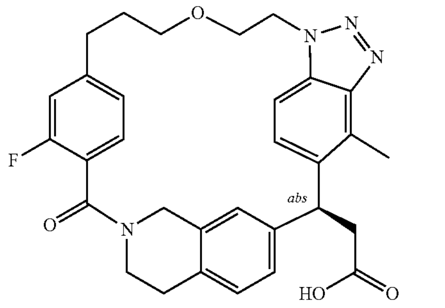 [SMILES: Cc1c2ccc3c1nnn3CCOCCCc1ccc(c(F)c1)C(=O)N1CCc3ccc(cc3C1)[C@@H]2CC(=O)O] |
TABLE 2a-continued
| Comp'd No | Structure |
|---|---|
| 365 | 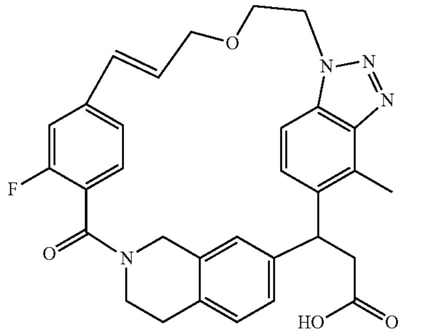 [SMILES: Cc1c2ccc3c1nnn3CCOC/C=C/c1ccc(c(F)c1)C(=O)N1CCc3ccc(cc3C1)C2CC(=O)O] |
| 366 | 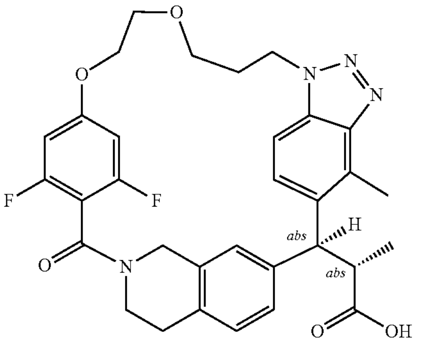 [SMILES: Cc1c2ccc3c1nnn3CCCOCCOc1cc(F)c(c(F)c1)C(=O)N1CCc3ccc(cc3C1)[C@@H]2[C@H](C)C(=O)O] |
| 367 | 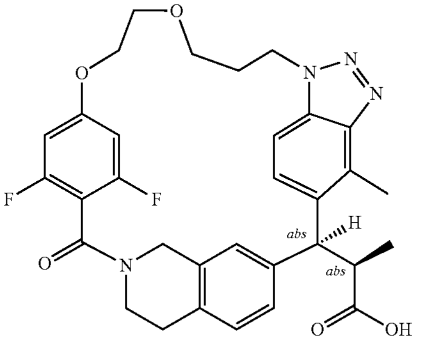 [SMILES: Cc1c2ccc3c1nnn3CCCOCCOc1cc(F)c(c(F)c1)C(=O)N1CCc3ccc(cc3C1)[C@@H]2[C@@H](C)C(=O)O] |
| 368 | 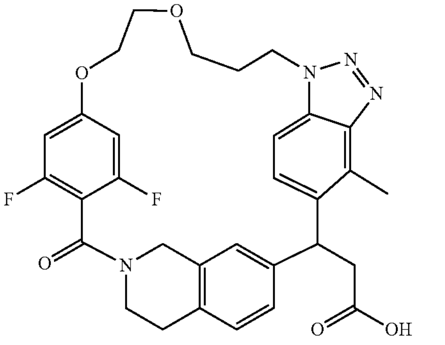 [SMILES: Cc1c2ccc3c1nnn3CCCOCCOc1cc(F)c(c(F)c1)C(=O)N1CCc3ccc(cc3C1)C2CC(=O)O] |

TABLE 2a-continued
| Comp'd No | Structure |
| --- | --- |
| 369 | 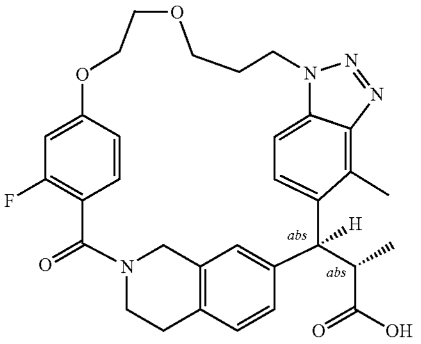 [SMILES: Cc1c2ccc3c1nnn3CCCOCCOc1ccc(c(F)c1)C(=O)N1CCc3ccc(cc3C1)[C@@H]2[C@H](C)C(=O)O] |
| 370 | 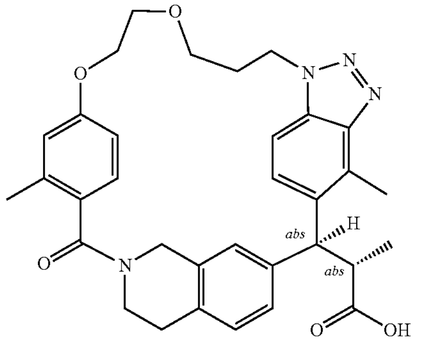 [SMILES: Cc1cc2ccc1C(=O)N1CCc3ccc(cc3C1)[C@H]([C@H](C)C(=O)O)c1ccc3c(nnn3CCCOCCO2)c1C] |
| 371 | 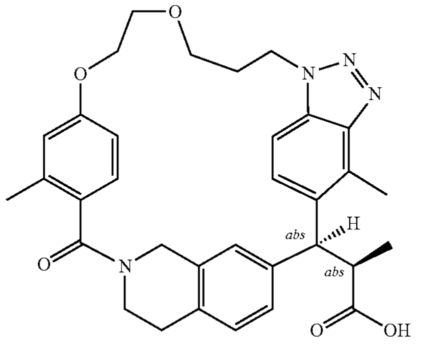 [SMILES: Cc1cc2ccc1C(=O)N1CCc3ccc(cc3C1)[C@H]([C@@H](C)C(=O)O)c1ccc3c(nnn3CCCOCCO2)c1C] |
| 372 | 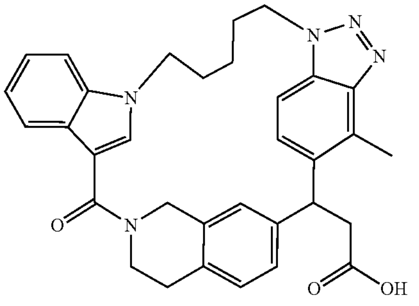 [SMILES: Cc1c2ccc3c1nnn3CCCCCn1cc(c3ccccc31)C(=O)N1CCc3ccc(cc3C1)C2CC(=O)O] |
TABLE 2a-continued
| Comp'd No | Structure |
| --- | --- |
| 373 | 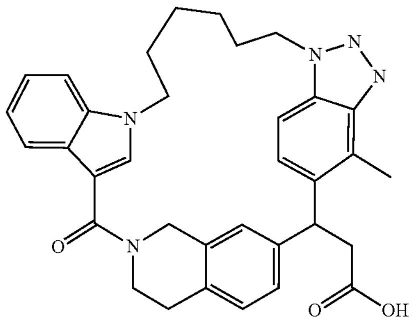 |
| 374 | 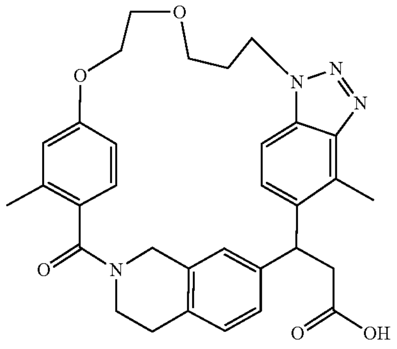 |
| 375 | 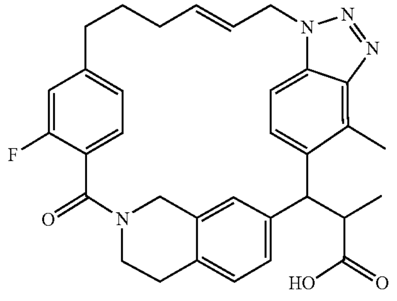 [SMILES: Cc1c2ccc3c1nnn3C/C=C/CCCc1ccc(c(F)c1)C(=O)N1CCc3ccc(cc3C1)C2C(C)C(=O)O] |
| 376 | 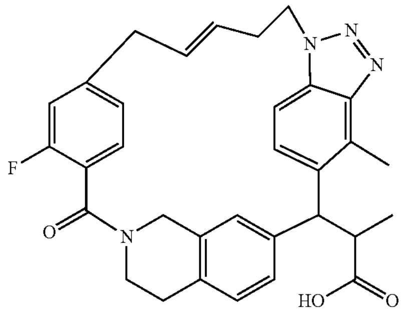 [SMILES: Cc1c2ccc3c1nnn3CC/C=C/Cc1ccc(c(F)c1)C(=O)N1CCc3ccc(cc3C1)C2C(C)C(=O)O] |

TABLE 2a-continued
| Comp'd No | Structure |
| --- | --- |
| 377 | 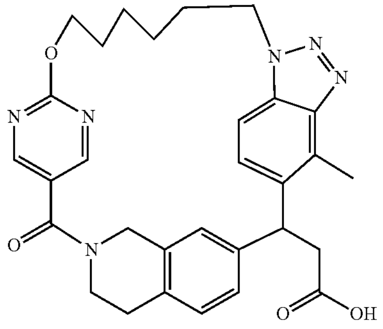 [SMILES: Cc1c2ccc3c1nnn3CCCCCCOc1ncc(cn1)C(=O)N1CCc3ccc(cc3C1)C2CC(=O)O] |
| 378 | 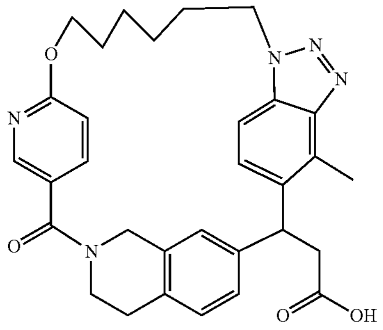 [SMILES: Cc1c2ccc3c1nnn3CCCCCCOc1ccc(cn1)C(=O)N1CCc3ccc(cc3C1)C2CC(=O)O] |
| 379 | 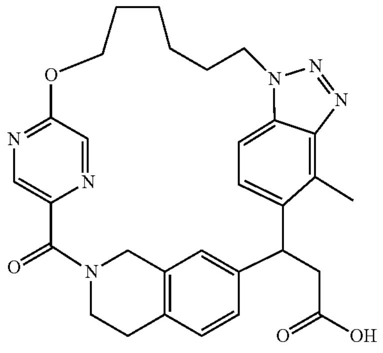 [SMILES: Cc1c2ccc3c1nnn3CCCCCCOc1cnc(cn1)C(=O)N1CCc3ccc(cc3C1)C2CC(=O)O] |
| 380 | 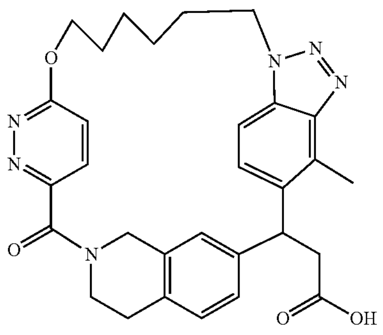 [SMILES: Cc1c2ccc3c1nnn3CCCCCCOc1ccc(nn1)C(=O)N1CCc3ccc(cc3C1)C2CC(=O)O] |
TABLE 2a-continued
| Comp'd No | Structure |
| --- | --- |
| 381 | 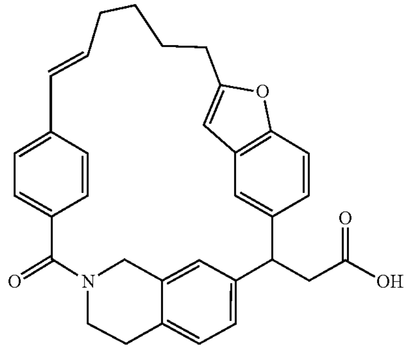 [SMILES: O=C(O)CC1c2ccc3c(c2)CN(CC3)C(=O)c2ccc(cc2)/C=C/CCCCc2cc3cc1ccc3o2] |
| 382 | 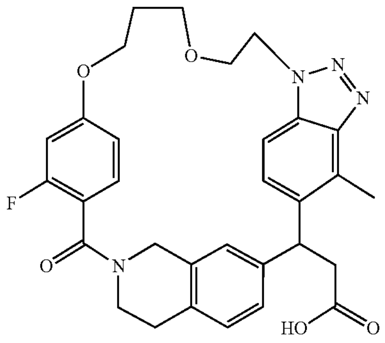 [SMILES: Cc1c2ccc3c1nnn3CCOCCCOc1ccc(c(F)c1)C(=O)N1CCc3ccc(cc3C1)C2CC(=O)O] |
| 383 | 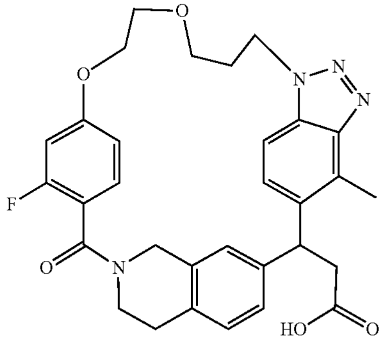 [SMILES: Cc1c2ccc3c1nnn3CCCOCCOc1ccc(c(F)c1)C(=O)N1CCc3ccc(cc3C1)C2CC(=O)O] |
| 384 | 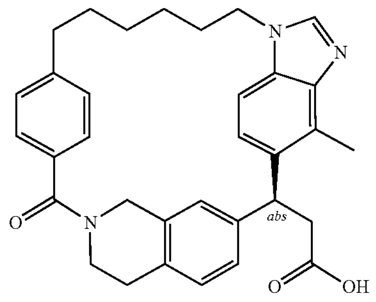 [SMILES: Cc1c2ccc3c1ncn3CCCCCCc1ccc(cc1)C(=O)N1CCc3ccc(cc3C1)[C@@H]2CC(=O)O] |

TABLE 2a-continued
| Comp'd No | Structure |
|---|---|
| 385 | 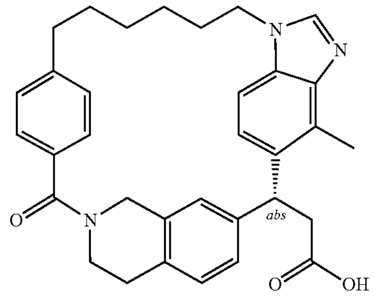 [SMILES: Cc1c2ccc3c1ncn3CCCCCCc1ccc(cc1)C(=O)N1CCc3ccc(cc3C1)[C@H]2CC(=O)O] |
| 386 | 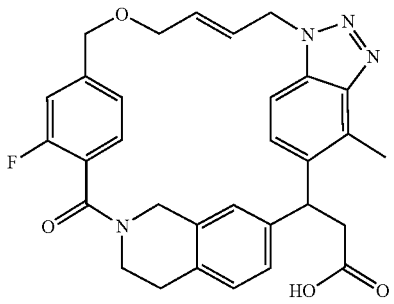 |
| 387 | 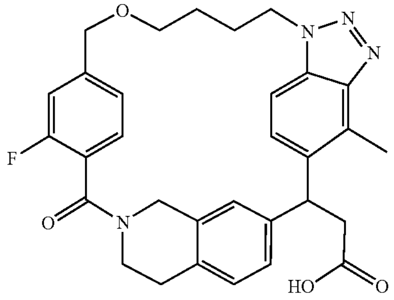 [SMILES: Cc1c2ccc3c1nnn3C/C=C/COCc1ccc(c(F)c1)C(=O)N1CCc3ccc(cc3C1)C2CC(=O)O] |
| 388 | 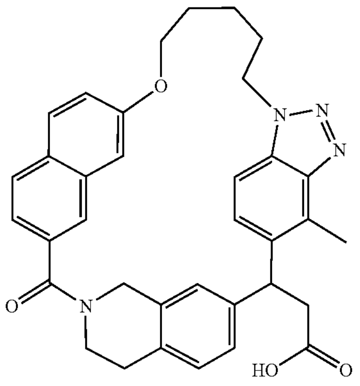 [SMILES: Cc1c2ccc3c1nnn3CCCCCOc1ccc3ccc(cc3c1)C(=O)N1CCc3ccc(cc3C1)C2CC(=O)O] |
TABLE 2a-continued
| Comp'd No | Structure |
|---|---|
| 389 | 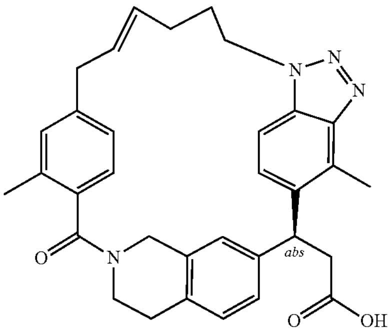 |
| 390 | 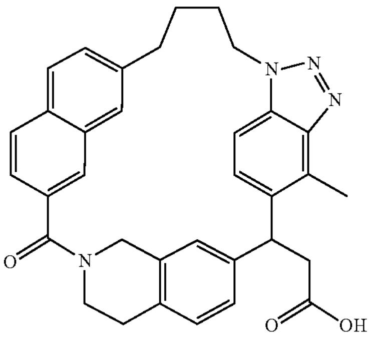 [SMILES: Cc1c2ccc3c1nnn3CCCCc1ccc3ccc(cc3c1)C(=O)N1CCc3ccc(cc3C1)C2CC(=O)O] |
| 391 | 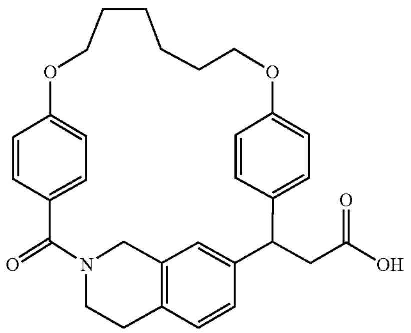 [SMILES: O=C(O)CC1c2ccc(cc2)OCCCCCCOc2ccc(cc2)C(=O)N2CCc3ccc1cc3C2] |
| 392 | 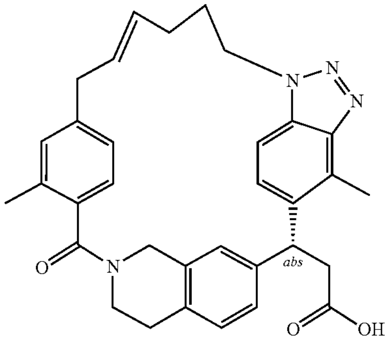 |

TABLE 2a-continued
| Comp'd No | Structure |
|---|---|
| 393 | 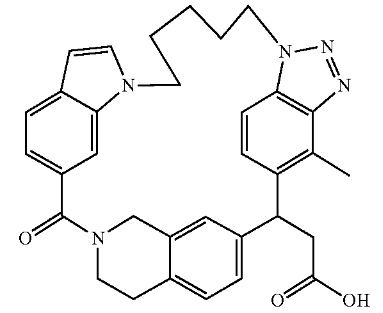 [SMILES: Cc1c2ccc3c1nnn3CCCCCn1ccc3ccc(cc31)C(=O)N1CCc3ccc(cc3C1)C2CC(=O)O] |
| 394 | 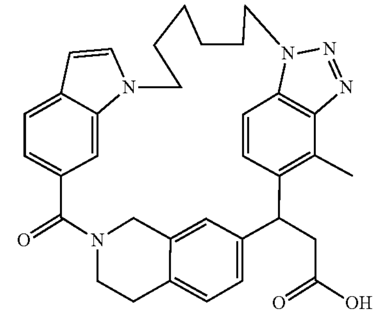 |
| 395 | 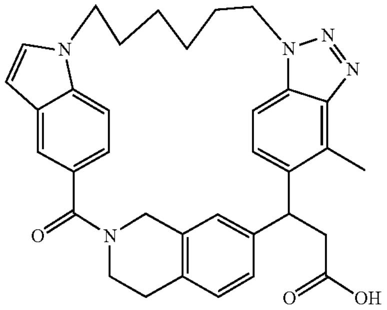 [SMILES: Cc1c2ccc3c1nnn3CCCCCCn1ccc3cc(ccc31)C(=O)N1CCc3ccc(cc3C1)C2CC(=O)O] |
| 396 | 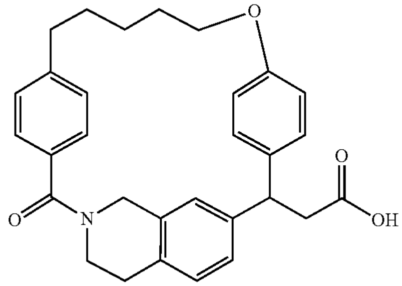 [SMILES: O=C(O)CC1c2ccc(cc2)OCCCCCc2ccc(cc2)C(=O)N2CCc3ccc1cc3C2] |
| 397 | 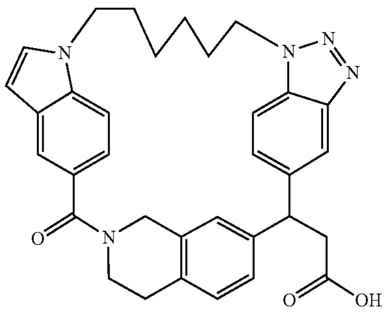 [SMILES: O=C(O)CC1c2ccc3c(c2)CN(CC3)C(=O)c2ccc3c(ccn3CCCCCCn3nnc4cc1ccc43)c2] |
TABLE 2a-continued
| Comp'd No | Structure |
|---|---|
| 398 | 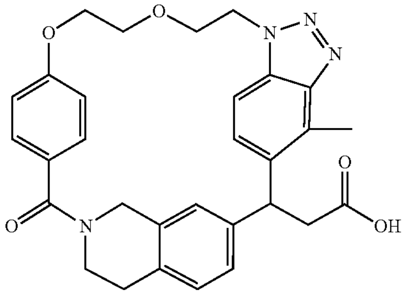 [SMILES: Cc1c2ccc3c1nnn3CCOCCOc1ccc(cc1)C(=O)N1CCc3ccc(cc3C1)C2CC(=O)O] |
| 399 | 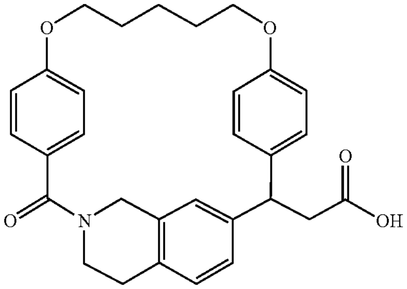 [SMILES: O=C(O)CC1c2ccc(cc2)OCCCCCOc2ccc(cc2)C(=O)N2CCc3ccc1cc3C2] |
| 400 | 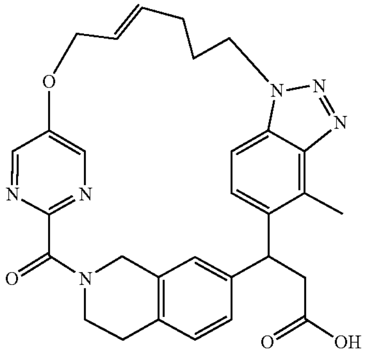 [SMILES: Cc1c2ccc3c1nnn3CCC/C=C/COc1cnc(nc1)C(=O)N1CCc3ccc(cc3C1)C2CC(=O)O] |
| 401 | 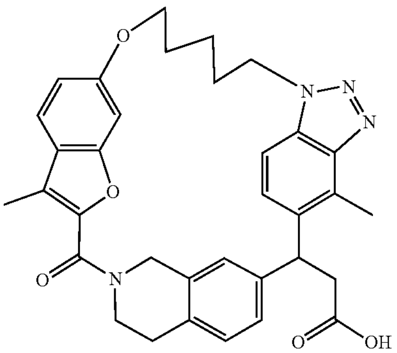 |

TABLE 2a-continued
| Comp'd No | Structure |
|---|---|
| 402 | 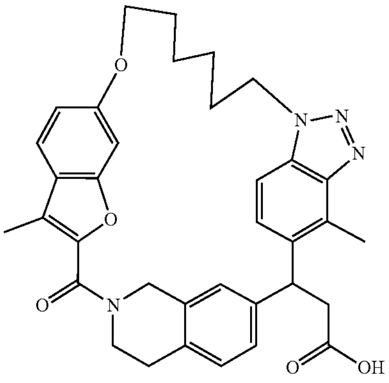 |
| 403 | 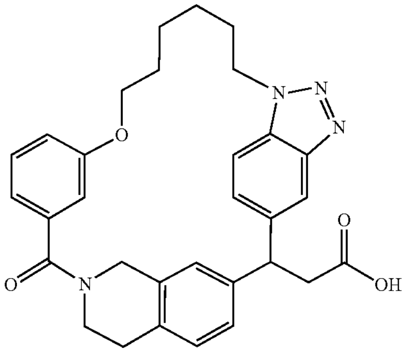 [SMILES: O=C(O)CC1c2ccc3c(c2)CN(CC3)C(=O)c2cccc(c2)OCCCCCCn2nnc3cc1ccc32] |
| 408 | 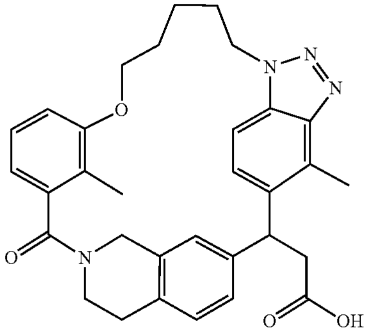 [SMILES: Cc1c2cccc1C(=O)N1CCc3ccc(cc3C1)C(CC(=O)O)c1ccc3c(nnn3CCCCCO2)c1C] |
| 409 | 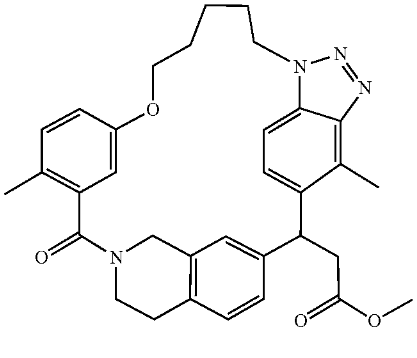 |
TABLE 2a-continued
| Comp'd No | Structure |
|---|---|
| 410 | 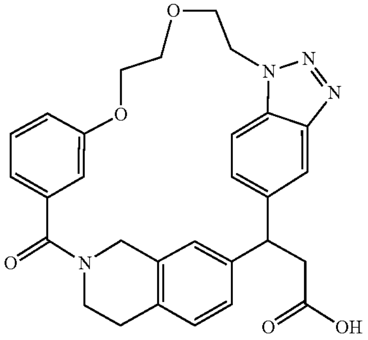 [SMILES: O=C(O)CC1c2ccc3c(c2)CN(CC3)C(=O)c2cccc(c2)OCCOCCn2nnc3cc1ccc32] |
| 411 | 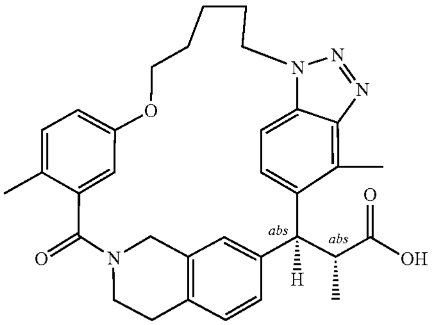 [SMILES: Cc1ccc2cc1C(=O)N1CCc3ccc(cc3C1)[C@H]([C@@H](C)C(=O)O)c1ccc3c(nnn3CCCCCO2)c1C] |
| 412 | 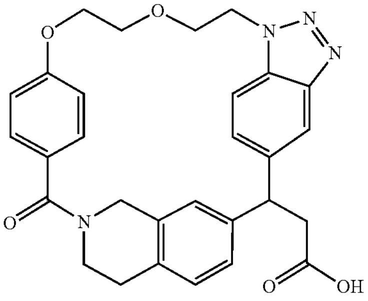 [SMILES: O=C(O)CC1c2ccc3c(c2)CN(CC3)C(=O)c2ccc(cc2)OCCOCCn2nnc3cc1ccc32] |
| 413 | 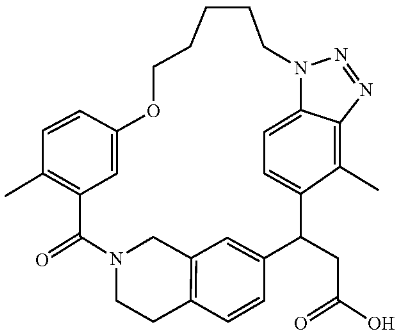 |

TABLE 2a-continued
| Comp'd No | Structure |
|---|---|
| 414 | 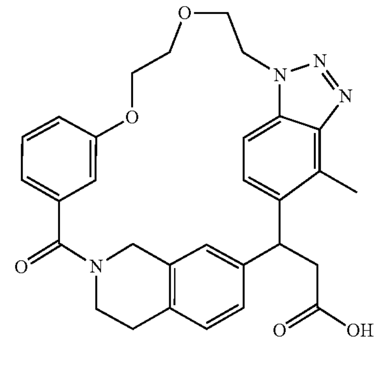 [SMILES: Cc1c2ccc3c1nnn3CCOCCOc1cccc(c1)C(=O)N1CCc3ccc(cc3C1)C2CC(=O)O] |
| 415 | 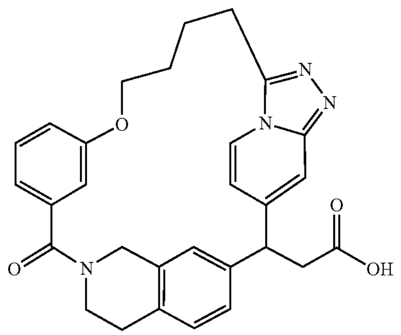 [SMILES: O=C(O)CC1c2ccc3c(c2)CN(CC3)C(=O)c2cccc(c2)OCCCCc2nnc3cc1ccn23] |
| 416 | 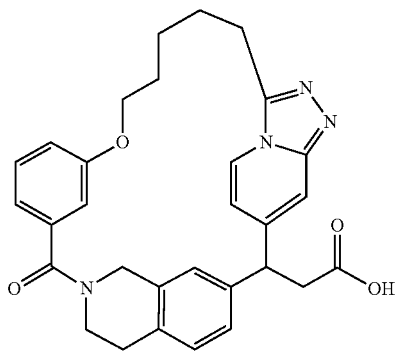 [SMILES: O=C(O)CC1c2ccc3c(c2)CN(CC3)C(=O)c2cccc(c2)OCCCCCc2nnc3cc1ccn23] |
| 417 | 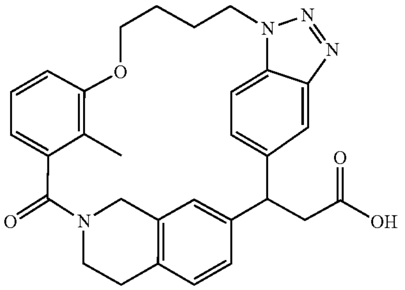 [SMILES: Cc1c2cccc1C(=O)N1CCc3ccc(cc3C1)C(CC(=O)O)c1ccc3c(c1)nnn3CCCCO2] |
TABLE 2a-continued
| Comp'd No | Structure |
|---|---|
| 418 | 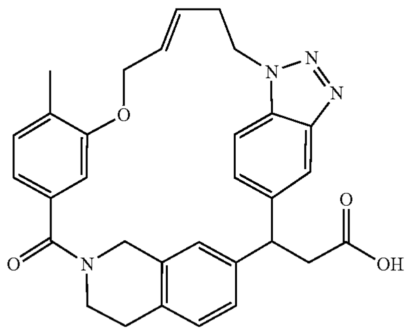 [SMILES: Cc1ccc2cc1OC/C=C/CCn1nnc3cc(ccc31)C(CC(=O)O)c1ccc3c(c1)CN(CC3)C2=O] |
| 419 | 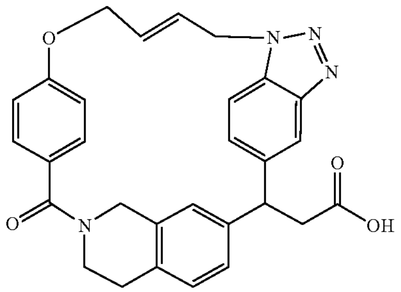 |
| 420 | 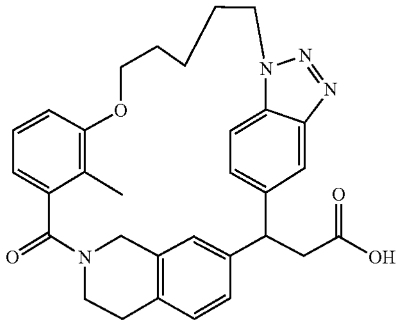 [SMILES: Cc1c2cccc1C(=O)N1CCc3ccc(cc3C1)C(CC(=O)O)c1ccc3c(c1)nnn3CCCCCO2] |
| 421 | 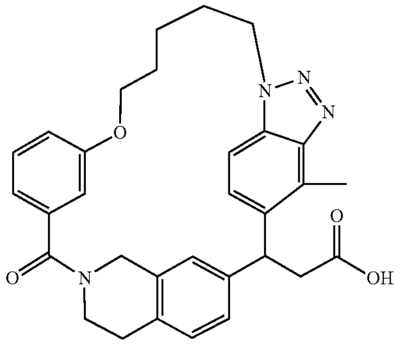 [SMILES: Cc1c2ccc3c1nnn3CCCCCOc1cccc(c1)C(=O)N1CCc3ccc(cc3C1)C2CC(=O)O] |

TABLE 2a-continued
| Comp'd No | Structure |
| --- | --- |
| 422 | 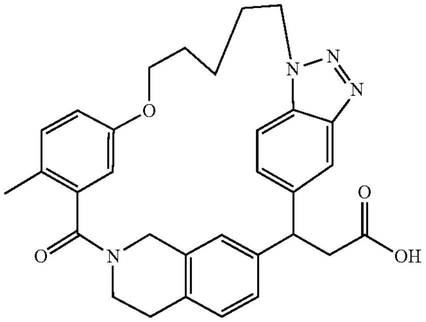 [SMILES: Cc1ccc2cc1C(=O)N1CCc3ccc(cc3C1)C(CC(=O)O)c1ccc3c(c1)nnn3CCCCCO2] |
| 423 | 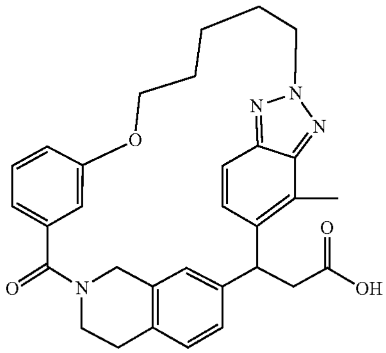 [SMILES: Cc1c2ccc3nn(nc13)CCCCCOc1cccc(c1)C(=O)N1CCc3ccc(cc3C1)C2CC(=O)O] |
| 424 | 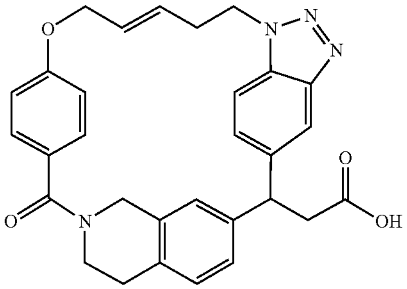 |
| 425 | 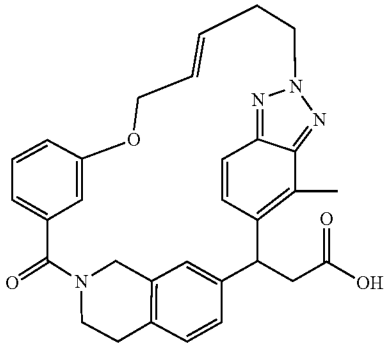 [SMILES: Cc1c2ccc3nn(nc13)CC/C=C/COc1cccc(c1)C(=O)N1CCc3ccc(cc3C1)C2CC(=O)O] |
TABLE 2a-continued
| Comp'd No | Structure |
| --- | --- |
| 426 | 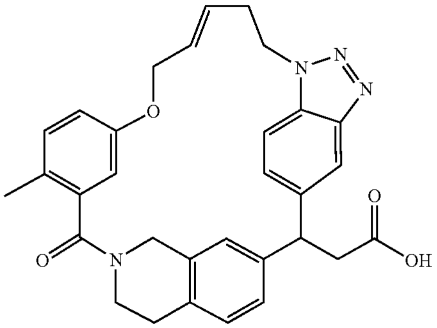 [SMILES: Cc1ccc2cc1C(=O)N1CCc3ccc(cc3C1)C(CC(=O)O)c1ccc3c(c1)nnn3CC/C=C/CO2] |
| 427 | 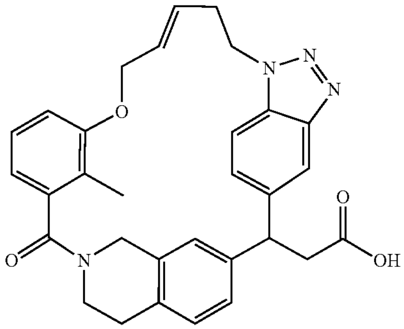 [SMILES: Cc1c2cccc1C(=O)N1CCc3ccc(cc3C1)C(CC(=O)O)c1ccc3c(c1)nnn3CC/C=C/CO2] |
| 428 | 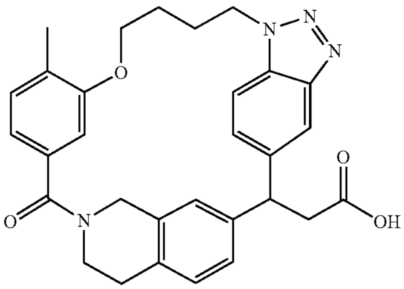 [SMILES: Cc1ccc2cc1OCCCCn1nnc3cc(ccc31)C(CC(=O)O)c1ccc3c(c1)CN(CC3)C2=O] |
| 429 | 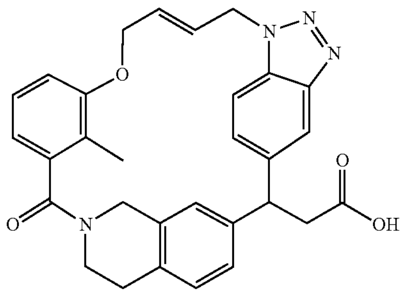 [SMILES: Cc1c2cccc1C(=O)N1CCc3ccc(cc3C1)C(CC(=O)O)c1ccc3c(c1)nnn3C/C=C/CO2] |
| 430 | 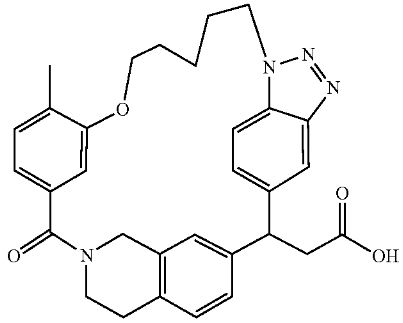 [SMILES: Cc1ccc2cc1OCCCCCn1nnc3cc(ccc31)C(CC(=O)O)c1ccc3c(c1)CN(CC3)C2=O] |

TABLE 2a-continued
| Comp'd No | Structure |
| --- | --- |
| 431 | 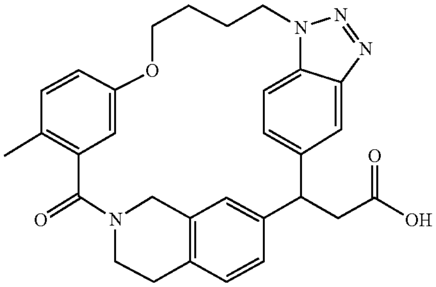 [SMILES: Cc1ccc2cc1C(=O)N1CCc3ccc(cc3C1)C(CC(=O)O)c1ccc3c(c1)nnn3CCCCO2] |
| 432 | 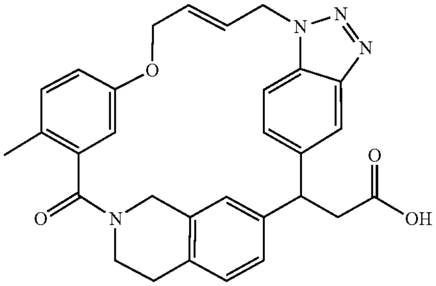 [SMILES: Cc1ccc2cc1C(=O)N1CCc3ccc(cc3C1)C(CC(=O)O)c1ccc3c(c1)nnn3C/C=C/CO2] |
| 433 | 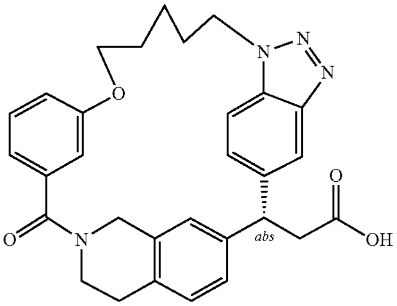 [SMILES: O=C(O)C[C@@H]1c2ccc3c(c2)CN(CC3)C(=O)c2cccc(c2)OCCCCCn2nnc3cc1ccc32] |
| 434 | 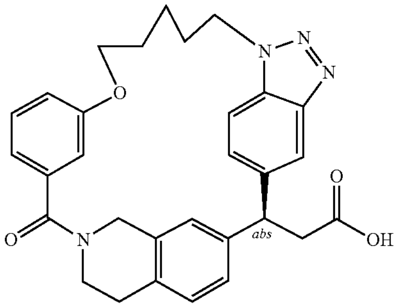 [SMILES: O=C(O)C[C@H]1c2ccc3c(c2)CN(CC3)C(=O)c2cccc(c2)OCCCCCn2nnc3cc1ccc32] |
| 435 | 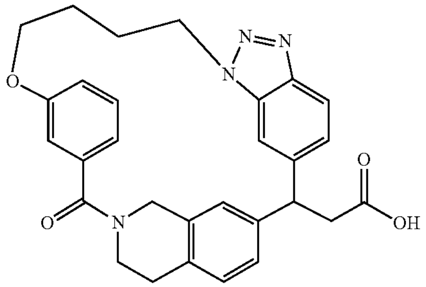 [SMILES: O=C(O)CC1c2ccc3c(c2)CN(CC3)C(=O)c2cccc(c2)OCCCCn2nnc3ccc1cc32] |
TABLE 2a-continued
| Comp'd No | Structure |
| --- | --- |
| 436 | 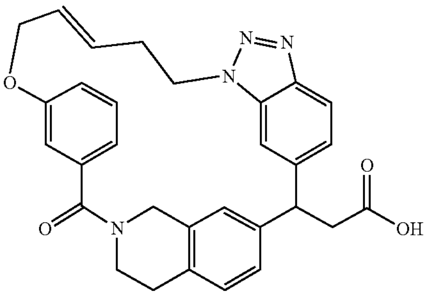 [SMILES: O=C(O)CC1c2ccc3c(c2)CN(CC3)C(=O)c2cccc(c2)OC/C=C/CCn2nnc3ccc1cc32] |
| 437 | 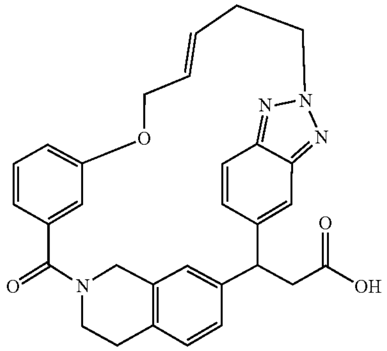 [SMILES: O=C(O)CC1c2ccc3c(c2)CN(CC3)C(=O)c2cccc(c2)OC/C=C/CCn2nc3ccc1cc3n2] |
| 438 | 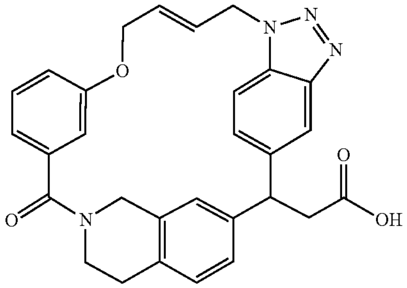 [SMILES: O=C(O)CC1c2ccc3c(c2)CN(CC3)C(=O)c2cccc(c2)OC/C=C/Cn2nnc3cc1ccc32] |
| 439 | 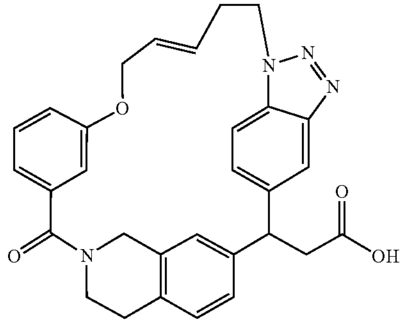 [SMILES: O=C(O)CC1c2ccc3c(c2)CN(CC3)C(=O)c2cccc(c2)OC/C=C/CCn2nnc3cc1ccc32] |

TABLE 2a-continued
| Comp'd No | Structure |
|---|---|
| 440 | 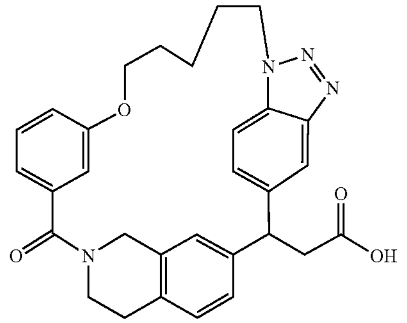 |
or a pharmaceutically acceptable salt thereof.
TABLE 3
| Comp'd No | Structure |
|---|---|
| 1 | 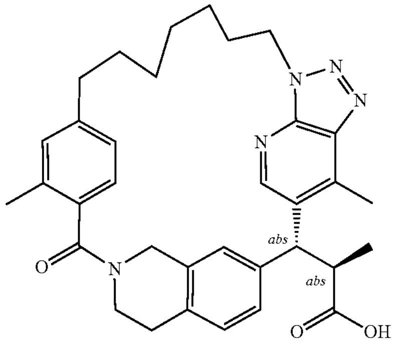 |
| 2 | 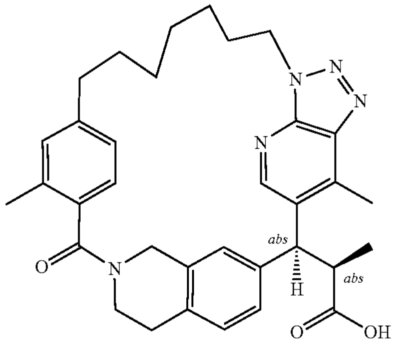 |
| 3 | 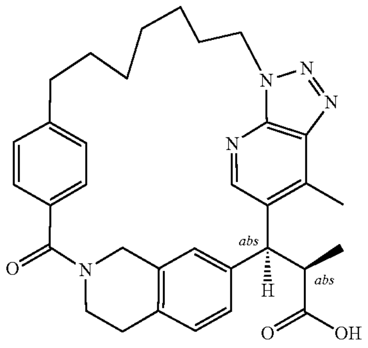 [SMILES: Cc1c2cnc3c1nnn3CCCCCCCc1ccc(cc1)C(=O)N1CCc3ccc(cc3C1)[C@@H]2[C@@H](C)C(=O)O] |
TABLE 3-continued
| Comp'd No | Structure |
|---|---|
| 4 | 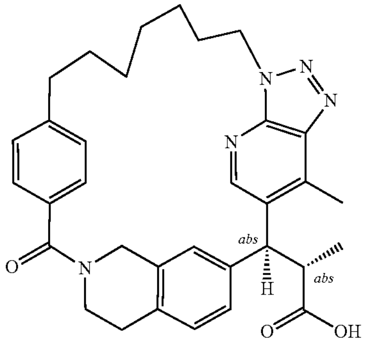 [SMILES: Cc1c2cnc3c1nnn3CCCCCCCc1ccc(cc1)C(=O)N1CCc3ccc(cc3C1)[C@@H]2[C@H](C)C(=O)O] |
| 5 | 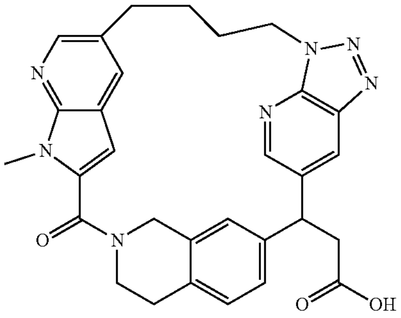 [SMILES: Cn1c2cc3cc(cnc31)CCCCn1nnc3cc(cnc31)C(CC(=O)O)c1ccc3c(c1)CN(CC3)C2=O] |
| 6 | 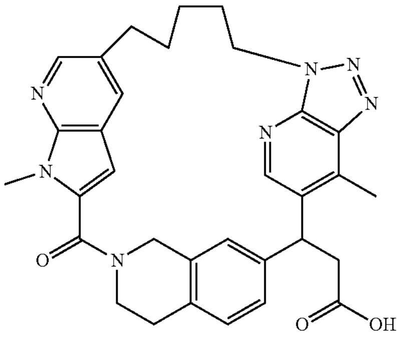 |
| 8 | 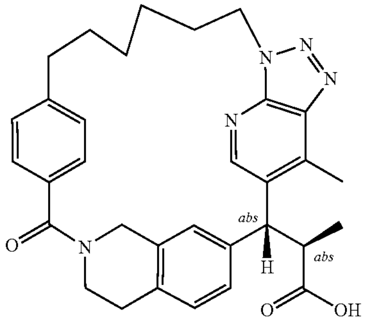 [SMILES: Cc1c2cnc3c1nnn3CCCCCCc1ccc(cc1)C(=O)N1CCc3ccc(cc3C1)[C@H]2[C@@H](C)C(=O)O] |

TABLE 3-continued
| Comp'd No | Structure |
|---|---|
| 11 | 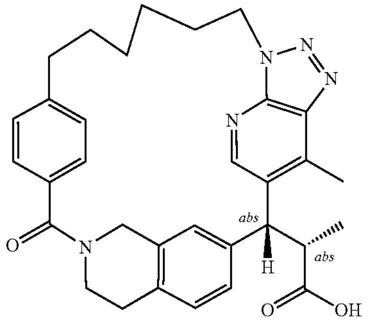 [SMILES: Cc1c2cnc3c1nnn3CCCCCCc1ccc(cc1)C(=O)N1CCc3ccc(cc3C1)[C@H]2[C@H](C)C(=O)O] |
| 12 | 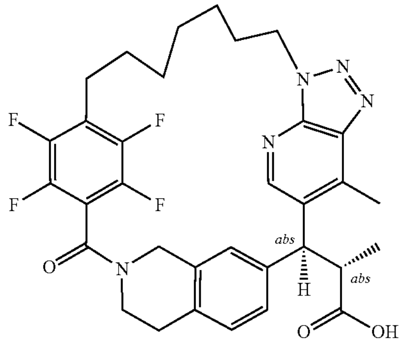 [SMILES: Cc1c2cnc3c1nnn3CCCCCCCc1c(F)c(F)c(c(F)c1F)C(=O)N1CCc3ccc(cc3C1)[C@@H]2[C@H](C)C(=O)O] |
| 13 | 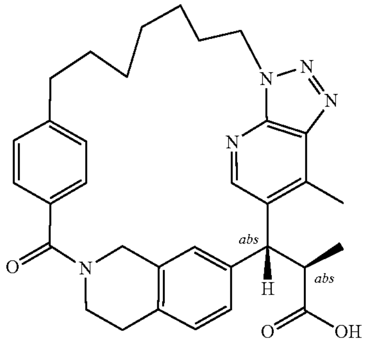 [SMILES: Cc1c2cnc3c1nnn3CCCCCCCc1ccc(cc1)C(=O)N1CCc3ccc(cc3C1)[C@H]2[C@@H](C)C(=O)O] |
| 14 | 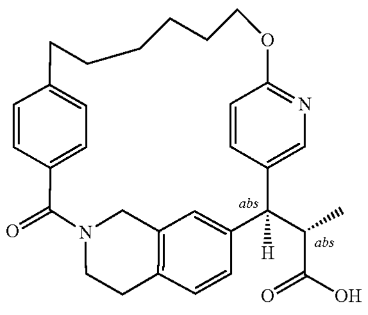 [SMILES: C[C@H](C(=O)O)[C@@H]1c2ccc(nc2)OCCCCCCc2ccc(cc2)C(=O)N2CCc3ccc1cc3C2] |
TABLE 3-continued
| Comp'd No | Structure |
|---|---|
| 15 | 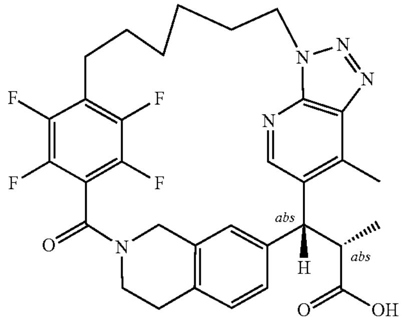 [SMILES: Cc1c2cnc3c1nnn3CCCCCCc1c(F)c(F)c(c(F)c1F)C(=O)N1CCc3ccc(cc3C1)[C@H]2[C@H](C)C(=O)O] |
| 17 | 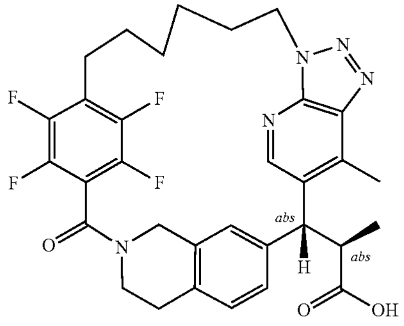 [SMILES: Cc1c2cnc3c1nnn3CCCCCCc1c(F)c(F)c(c(F)c1F)C(=O)N1CCc3ccc(cc3C1)[C@H]2[C@@H](C)C(=O)O] |
| 18 | 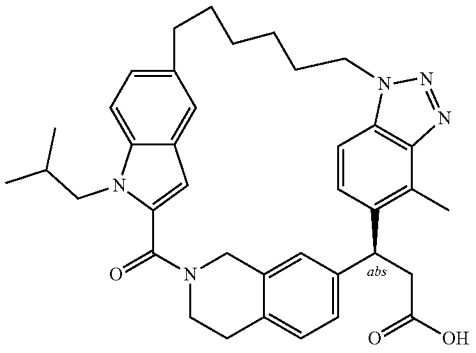 [SMILES: Cc1c2ccc3c1nnn3CCCCCCc1ccc3c(c1)cc(n3CC(C)C)C(=O)N1CCc3ccc(cc3C1)[C@@H]2CC(=O)O] |
| 19 | 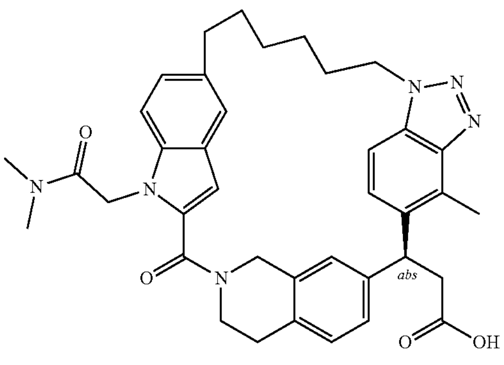 |

TABLE 3-continued
TABLE 3-continued
| Comp'd No | Structure |
| --- | --- |
| 20 | 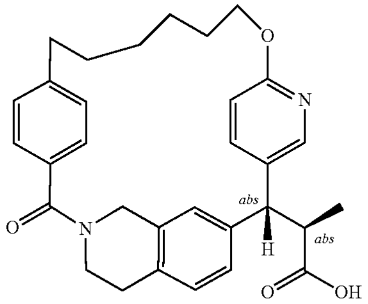 [SMILES: C[C@@H](C(=O)O)[C@H]1c2ccc(nc2)OCCCCCCc2ccc(cc2)C(=O)N2CCc3ccc1cc3C2] |
| 21 | 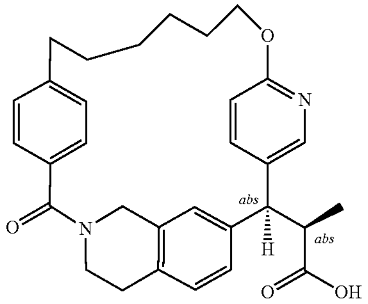 [SMILES: C[C@@H](C(=O)O)[C@@H]1c2ccc(nc2)OCCCCCCc2ccc(cc2)C(=O)N2CCc3ccc1cc3C2] |
| 22 | 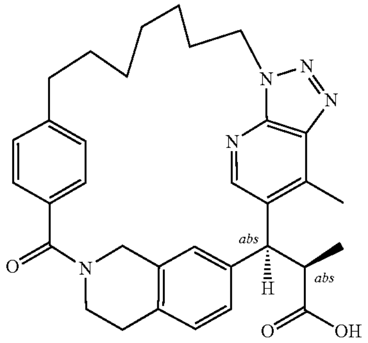 [SMILES: Cc1c2cnc3c1nnn3CCCCCCCc1ccc(cc1)C(=O)N1CCc3ccc(cc3C1)[C@@H]2[C@@H](C)C(=O)O] |
| 23 | 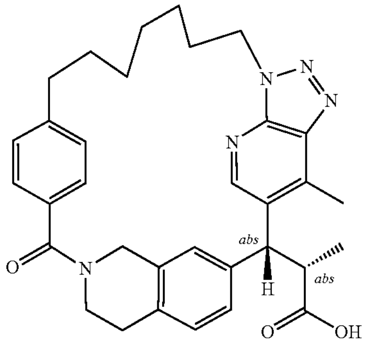 [SMILES: Cc1c2cnc3c1nnn3CCCCCCCc1ccc(cc1)C(=O)N1CCc3ccc(cc3C1)[C@H]2[C@H](C)C(=O)O] |
| 24 | 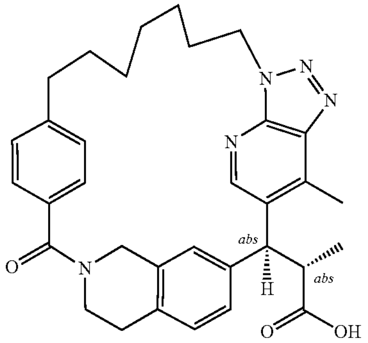 [SMILES: Cc1c2cnc3c1nnn3CCCCCCCc1ccc(cc1)C(=O)N1CCc3ccc(cc3C1)[C@@H]2[C@H](C)C(=O)O] |
| 25 | 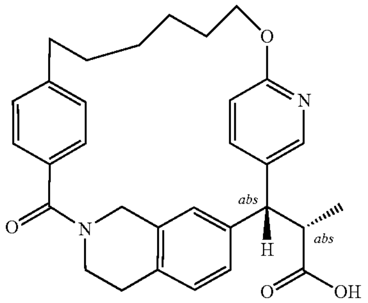 [SMILES: C[C@H](C(=O)O)[C@H]1c2ccc(nc2)OCCCCCCc2ccc(cc2)C(=O)N2CCc3ccc1cc3C2] |
| 26 | 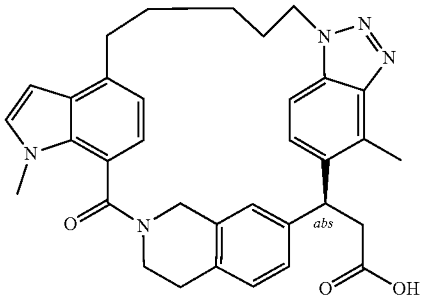 [SMILES: Cc1c2ccc3c1nnn3CCCCCc1ccc(c3c1ccn3C)C(=O)N1CCc3ccc(cc3C1)[C@@H]2CC(=O)O] |
| 28 | 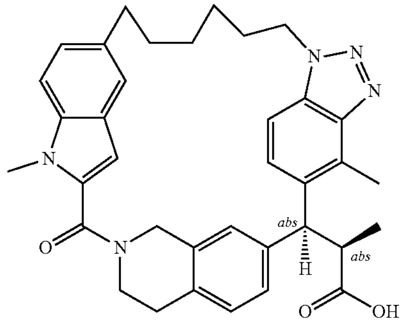 [SMILES: Cc1c2ccc3c1nnn3CCCCCCc1ccc3c(c1)cc(n3C)C(=O)N1CCc3ccc(cc3C1)[C@@H]2[C@@H](C)C(=O)O] |

TABLE 3-continued
| Comp'd No | Structure |
|---|---|
| 29 | 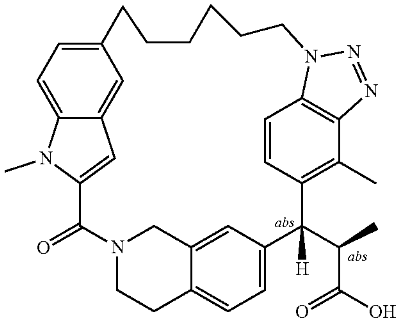 [SMILES: Cc1c2ccc3c1nnn3CCCCCCc1ccc3c(c1)cc(n3C)C(=O)N1CCc3ccc(cc3C1)[C@H]2[C@@H](C)C(=O)O] |
| 30 | 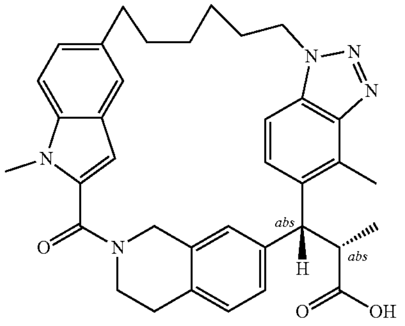 [SMILES: Cc1c2ccc3c1nnn3CCCCCCc1ccc3c(c1)cc(n3C)C(=O)N1CCc3ccc(cc3C1)[C@H]2[C@H](C)C(=O)O] |
| 31 | 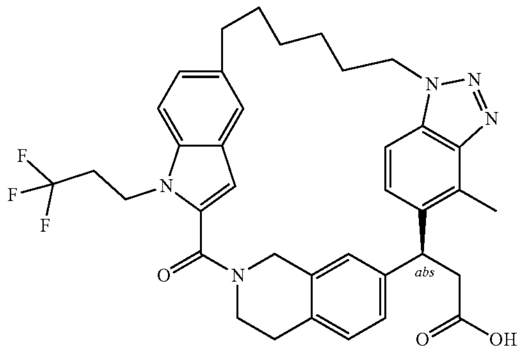 [SMILES: Cc1c2ccc3c1nnn3CCCCCCc1ccc3c(c1)cc(n3CCC(F)(F)F)C(=O)N1CCc3ccc(cc3C1)[C@@H]2CC(=O)O] |
| 34 | 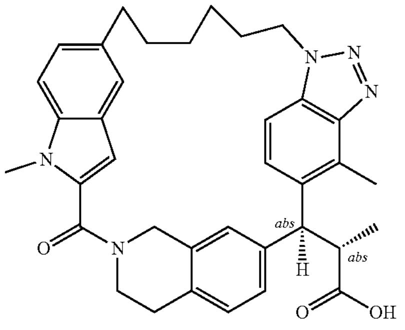 [SMILES: Cc1c2ccc3c1nnn3CCCCCCc1ccc3c(c1)cc(n3C)C(=O)N1CCc3ccc(cc3C1)[C@@H]2[C@H](C)C(=O)O] |
TABLE 3-continued
| Comp'd No | Structure |
|---|---|
| 35 | 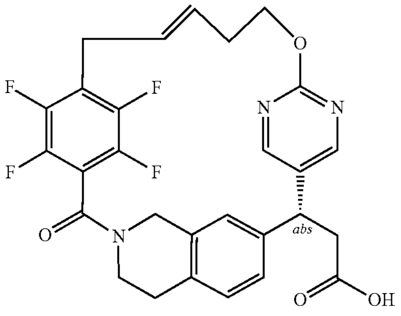 [SMILES: O=C(O)C[C@H]1c2cnc(nc2)OCC/C=C/Cc2c(F)c(F)c(c(F)c2F)C(=O)N2CCc3ccc1cc3C2] |
| 36 | 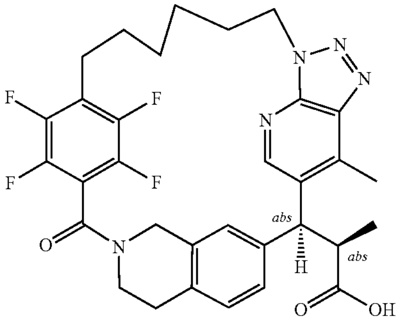 [SMILES: Cc1c2cnc3c1nnn3CCCCCCc1c(F)c(F)c(c(F)c1F)C(=O)N1CCc3ccc(cc3C1)[C@@H]2[C@@H](C)C(=O)O] |
| 39 | 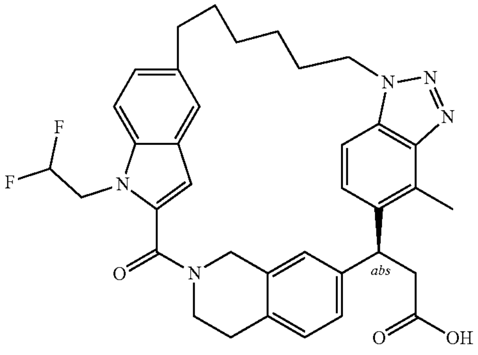 [SMILES: Cc1c2ccc3c1nnn3CCCCCCc1ccc3c(c1)cc(n3CC(F)F)C(=O)N1CCc3ccc(cc3C1)[C@@H]2CC(=O)O] |
| 40 | 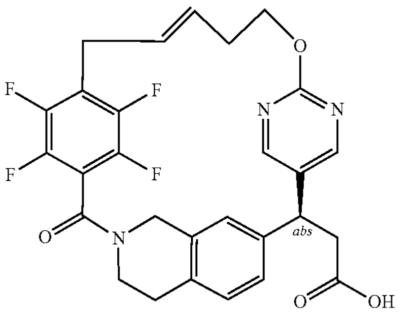 [SMILES: O=C(O)C[C@@H]1c2cnc(nc2)OCC/C=C/Cc2c(F)c(F)c(c(F)c2F)C(=O)N2CCc3ccc1cc3C2] |

TABLE 3-continued
| Comp'd No | Structure |
|---|---|
| 43 | 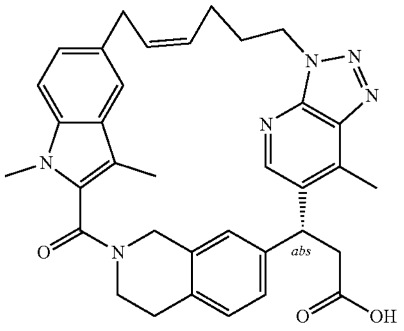 |
| 44 | 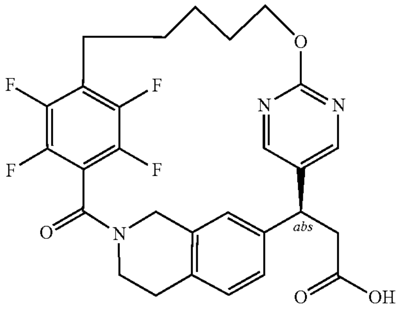 [SMILES: O=C(O)C[C@@H]1c2cnc(nc2)OCCCCCc2c(F)c(F)c(c(F)c2F)C(=O)N2CCc3ccc1cc3C2] |
| 45 | 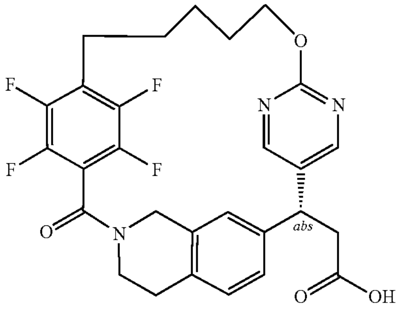 [SMILES: O=C(O)C[C@H]1c2cnc(nc2)OCCCCCc2c(F)c(F)c(c(F)c2F)C(=O)N2CCc3ccc1cc3C2] |
| 46 | 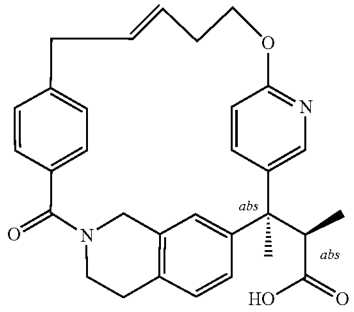 [SMILES: C[C@@H](C(=O)O)[C@]1(C)c2ccc(nc2)OCC/C=C/Cc2ccc(cc2)C(=O)N2CCc3ccc1cc3C2] |
| 47 | 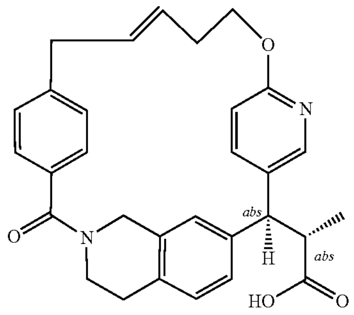 [SMILES: C[C@H](C(=O)O)[C@@H]1c2ccc(nc2)OCC/C=C/Cc2ccc(cc2)C(=O)N2CCc3ccc1cc3C2] |
TABLE 3-continued
| Comp'd No | Structure |
|---|---|
| 49 | 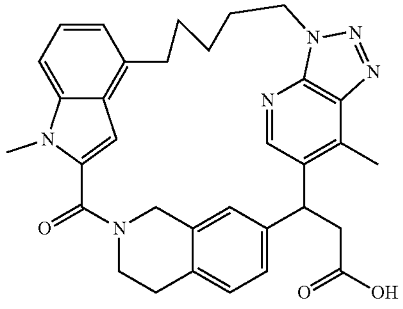 |
| 52 | 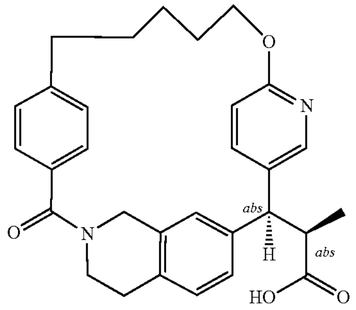 [SMILES: C[C@@H](C(=O)O)[C@@H]1c2ccc(nc2)OCCCCCc2ccc(cc2)C(=O)N2CCc3ccc1cc3C2] |
| 53 | 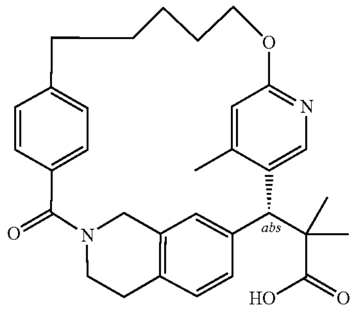 [SMILES: Cc1cc2ncc1[C@H](C(C)(C)C(=O)O)c1ccc3c(c1)CN(CC3)C(=O)c1ccc(cc1)CCCCCO2] |
| 54 | 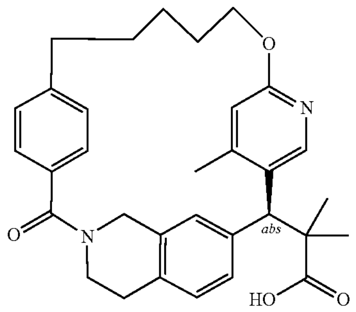 [SMILES: Cc1cc2ncc1[C@@H](C(C)(C)C(=O)O)c1ccc3c(c1)CN(CC3)C(=O)c1ccc(cc1)CCCCCO2] |
| 55 | 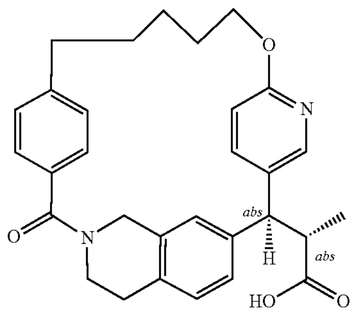 [SMILES: C[C@H](C(=O)O)[C@@H]1c2ccc(nc2)OCCCCCc2ccc(cc2)C(=O)N2CCc3ccc1cc3C2] |

TABLE 3-continued
| Comp'd No | Structure |
|---|---|
| 56 | 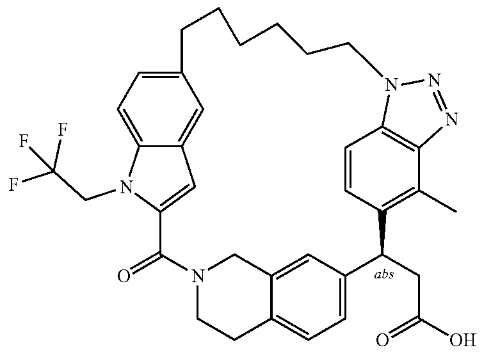 [SMILES: Cc1c2ccc3c1nnn3CCCCCCc1ccc3c(c1)cc(n3CC(F)(F)F)C(=O)N1CCc3ccc(cc3C1)[C@@H]2CC(=O)O] |
| 57 | 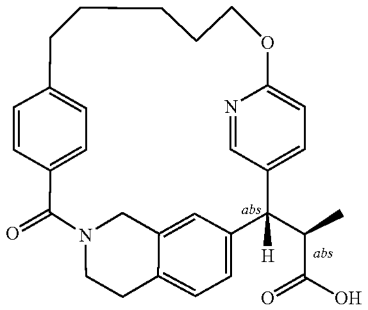 [SMILES: C[C@@H](C(=O)O)[C@H]1c2ccc(nc2)OCCCCCc2ccc(cc2)C(=O)N2CCc3ccc1cc3C2] |
| 58 | 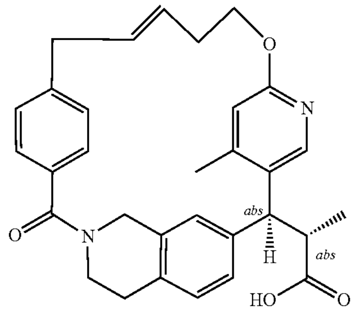 [SMILES: Cc1cc2ncc1[C@@H]([C@H](C)C(=O)O)c1ccc3c(c1)CN(CC3)C(=O)c1ccc(cc1)C/C=C/CCO2] |
| 59 | 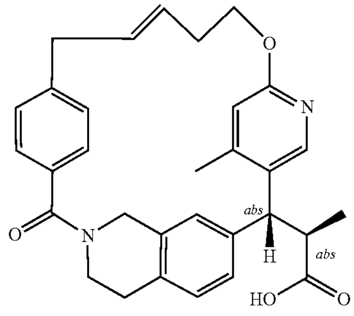 [SMILES: Cc1cc2ncc1[C@H]([C@@H](C)C(=O)O)c1ccc3c(c1)CN(CC3)C(=O)c1ccc(cc1)C/C=C/CCO2] |
TABLE 3-continued
| Comp'd No | Structure |
|---|---|
| 60 | 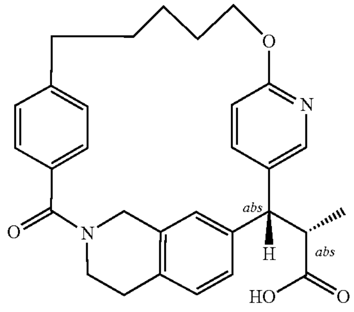 [SMILES: C[C@H](C(=O)O)[C@H]1c2ccc(nc2)OCCCCCc2ccc(cc2)C(=O)N2CCc3ccc1cc3C2] |
| 61 | 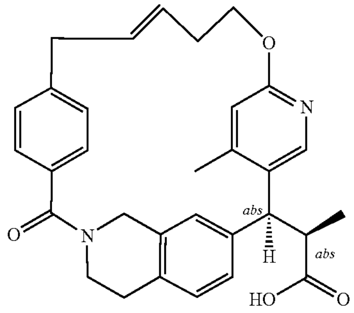 [SMILES: Cc1cc2ncc1[C@@H]([C@@H](C)C(=O)O)c1ccc3c(c1)CN(CC3)C(=O)c1ccc(cc1)C/C=C/CCO2] |
| 62 | 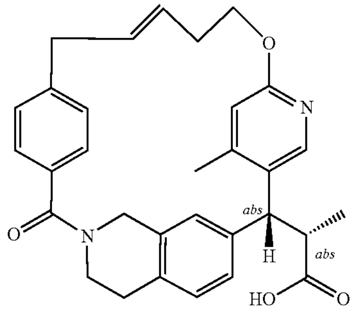 [SMILES: Cc1cc2ncc1[C@H]([C@H](C)C(=O)O)c1ccc3c(c1)CN(CC3)C(=O)c1ccc(cc1)C/C=C/CCO2] |
| 63 | 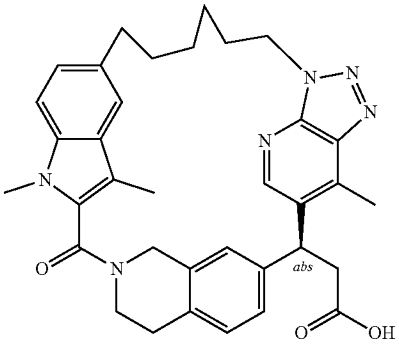 |

TABLE 3-continued
| Comp'd No | Structure |
|---|---|
| 64 | 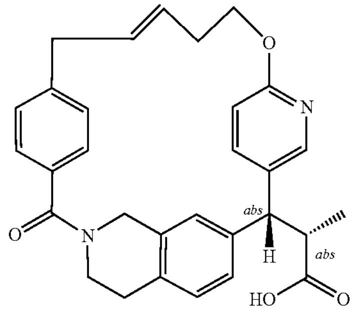 [SMILES: C[C@H](C(=O)O)[C@H]1c2ccc(nc2)OCC/C=C/Cc2ccc(cc2)C(=O)N2CCc3ccc1cc3C2] |
| 65 | 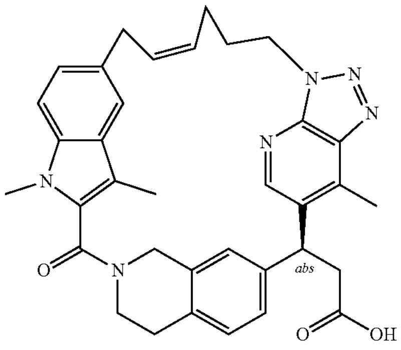 |
| 66 | 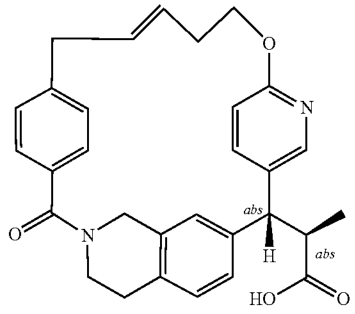 [SMILES: C[C@@H](C(=O)O)[C@H]1c2ccc(nc2)OCC/C=C/Cc2ccc(cc2)C(=O)N2CCc3ccc1cc3C2] |
| 67 | 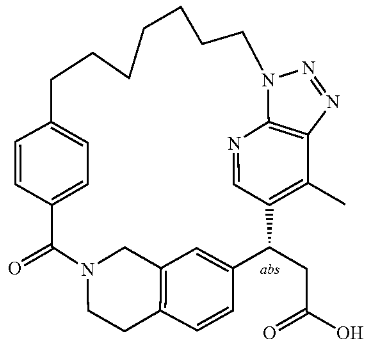 [SMILES: Cc1c2cnc3c1nnn3CCCCCCCc1ccc(cc1)C(=O)N1CCc3ccc(cc3C1)[C@H]2CC(=O)O] |
TABLE 3-continued
| Comp'd No | Structure |
|---|---|
| 68 | 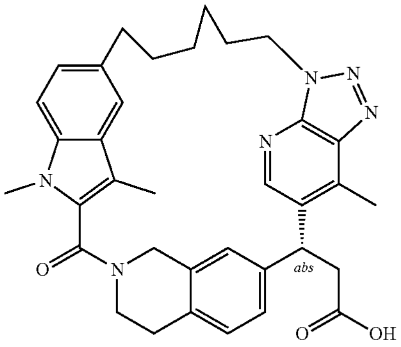 |
| 69 | 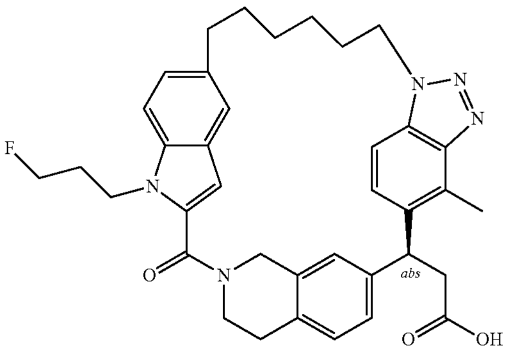 [SMILES: Cc1c2ccc3c1nnn3CCCCCCc1ccc3c(c1)cc(n3CCCF)C(=O)N1CCc3ccc(cc3C1)[C@@H]2CC(=O)O] |
| 70 | 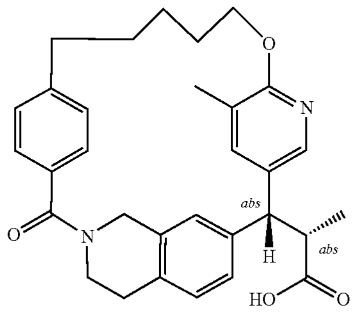 [SMILES: Cc1cc2cnc1OCCCCCc1ccc(cc1)C(=O)N1CCc3ccc(cc3C1)[C@H]2[C@H](C)C(=O)O] |
| 71 | 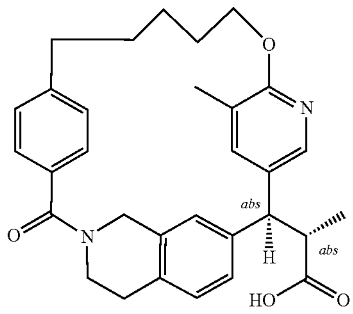 [SMILES: Cc1cc2cnc1OCCCCCc1ccc(cc1)C(=O)N1CCc3ccc(cc3C1)[C@@H]2[C@H](C)C(=O)O] |

TABLE 3-continued
| Comp'd No | Structure |
|---|---|
| 72 | 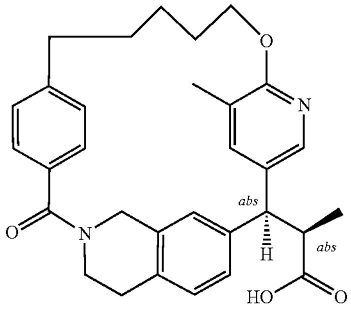 [SMILES: Cc1cc2cnc1OCCCCCc1ccc(cc1)C(=O)N1CCc3ccc(cc3C1)[C@@H]2[C@@H](C)C(=O)O] |
| 73 | 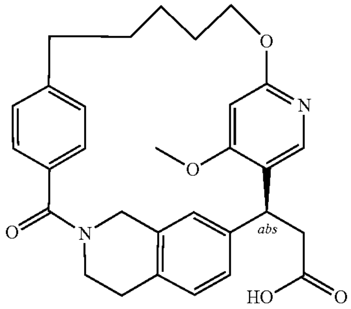 [SMILES: COc1cc2ncc1[C@@H](CC(=O)O)c1ccc3c(c1)CN(CC3)C(=O)c1ccc(cc1)CCCCCO2] |
| 74 | 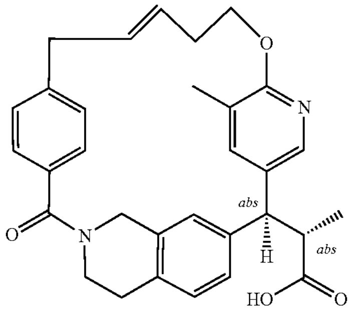 [SMILES: Cc1cc2cnc1OCC/C=C/Cc1ccc(cc1)C(=O)N1CCc3ccc(cc3C1)[C@@H]2[C@H](C)C(=O)O] |
| 75 | 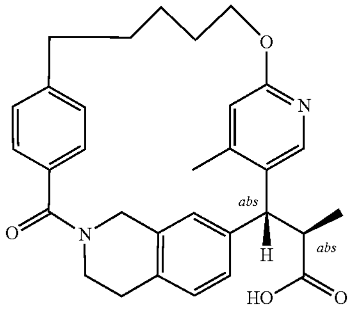 [SMILES: Cc1cc2ncc1[C@H]([C@@H](C)C(=O)O)c1ccc3c(c1)CN(CC3)C(=O)c1ccc(cc1)CCCCCO2] |
| 76 | 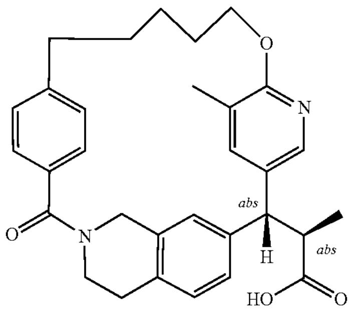 [SMILES: Cc1cc2cnc1OCCCCCc1ccc(cc1)C(=O)N1CCc3ccc(cc3C1)[C@H]2[C@@H](C)C(=O)O] |
TABLE 3-continued
| Comp'd No | Structure |
|---|---|
| 77 | 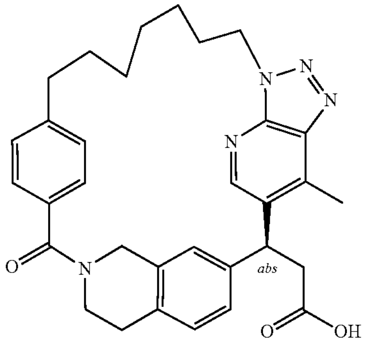 [SMILES: Cc1c2cnc3c1nnn3CCCCCCCc1ccc(cc1)C(=O)N1CCc3ccc(cc3C1)[C@@H]2CC(=O)O] |
| 78 | 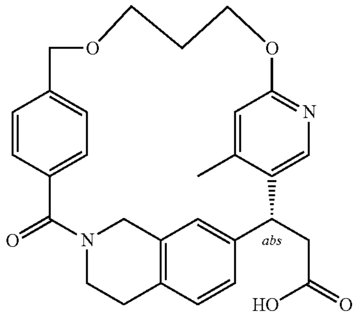 [SMILES: Cc1cc2ncc1[C@H](CC(=O)O)c1ccc3c(c1)CN(CC3)C(=O)c1ccc(cc1)COCCCO2] |
| 79 | 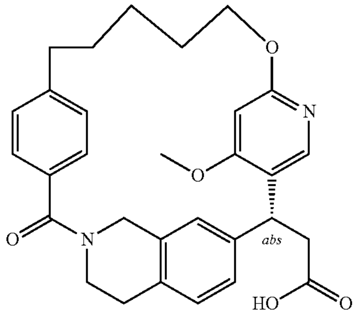 [SMILES: COc1cc2ncc1[C@H](CC(=O)O)c1ccc3c(c1)CN(CC3)C(=O)c1ccc(cc1)CCCCCO2] |
| 80 | 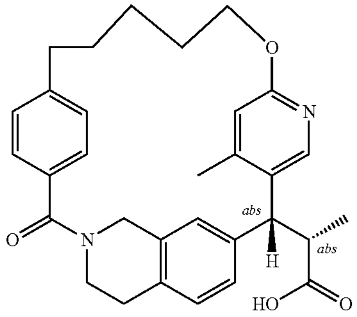 [SMILES: Cc1cc2ncc1[C@H]([C@H](C)C(=O)O)c1ccc3c(c1)CN(CC3)C(=O)c1ccc(cc1)CCCCCO2] |

TABLE 3-continued
| Comp'd No | Structure |
| --- | --- |
| 81 | 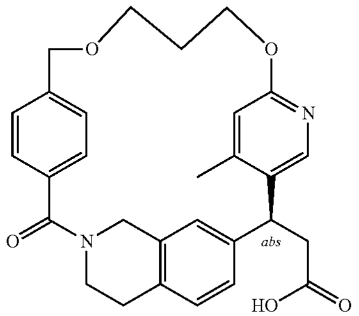 [SMILES: Cc1cc2ncc1[C@@H](CC(=O)O)c1ccc3c(c1)CN(CC3)C(=O)c1ccc(cc1)COCCCO2] |
| 82 | 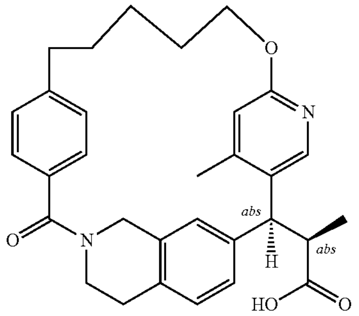 [SMILES: Cc1cc2ncc1[C@@H]([C@@H](C)C(=O)O)c1ccc3c(c1)CN(CC3)C(=O)c1ccc(cc1)CCCCCO2] |
| 83 | 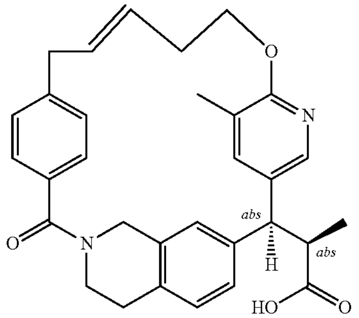 [SMILES: Cc1cc2cnc1OCC/C=C/Cc1ccc(cc1)C(=O)N1CCc3ccc(cc3C1)[C@@H]2[C@@H](C)C(=O)O] |
| 84 | 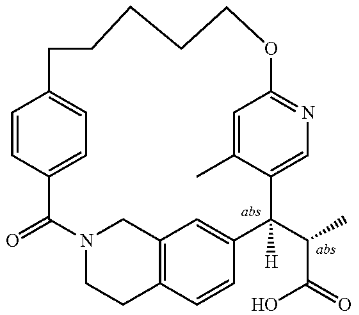 [SMILES: Cc1cc2ncc1[C@@H]([C@H](C)C(=O)O)c1ccc3c(c1)CN(CC3)C(=O)c1ccc(cc1)CCCCCO2] |
TABLE 3-continued
| Comp'd No | Structure |
| --- | --- |
| 85 | 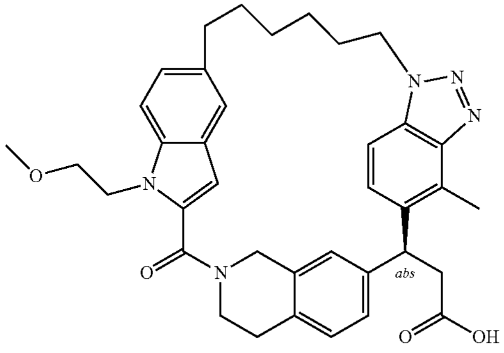 |
| 86 | 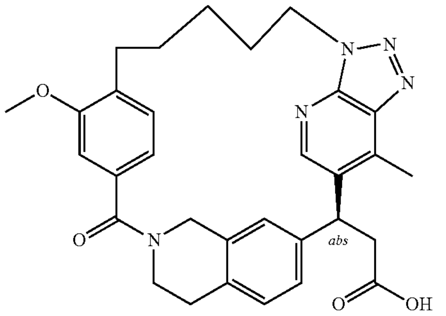 |
| 87 | 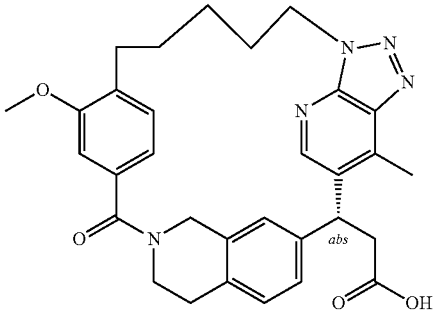 |
| 88 | 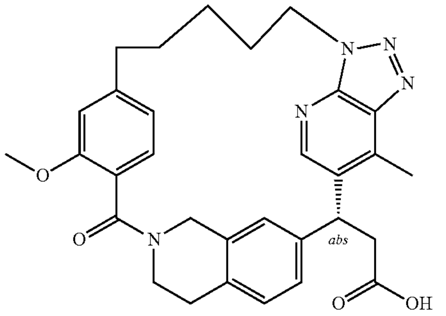 |

TABLE 3-continued
| Comp'd No | Structure |
|---|---|
| 89 | 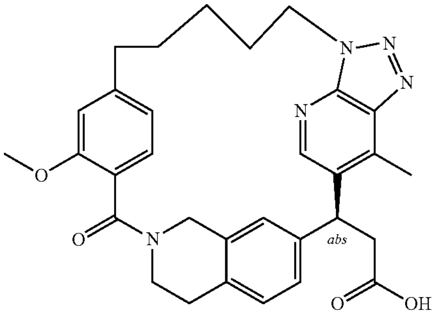 |
| 91 | 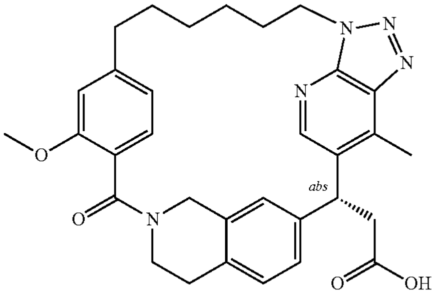 |
| 92 | 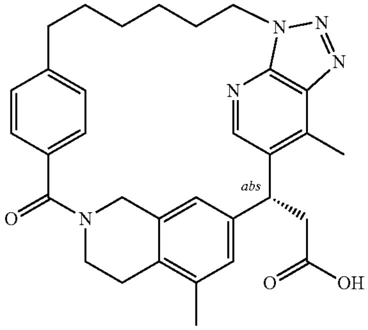 [SMILES: Cc1cc2cc3c1CCN(C3)C(=O)c1ccc(cc1)CCCCCCn1nnc3c(C)c(cnc31)[C@@H]2CC(=O)O] |
| 93 | 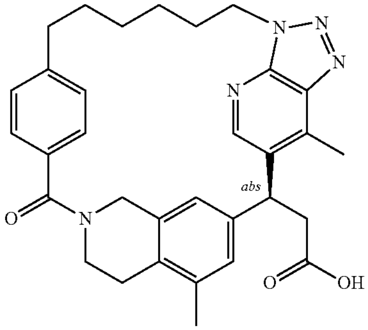 [SMILES: Cc1cc2cc3c1CCN(C3)C(=O)c1ccc(cc1)CCCCCCn1nnc3c(C)c(cnc31)[C@H]2CC(=O)O] |
| 94 | 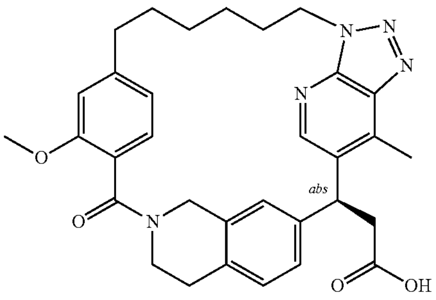 |
TABLE 3-continued
| Comp'd No | Structure |
|---|---|
| 95 | 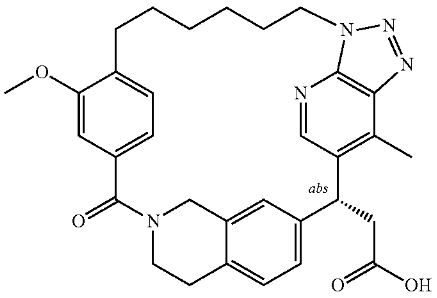 |
| 96 | 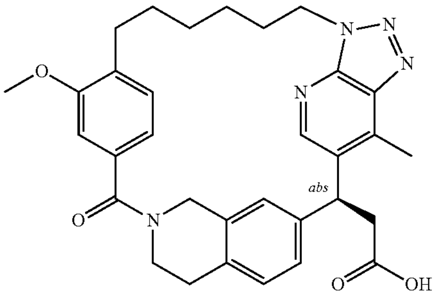 |
| 97 | 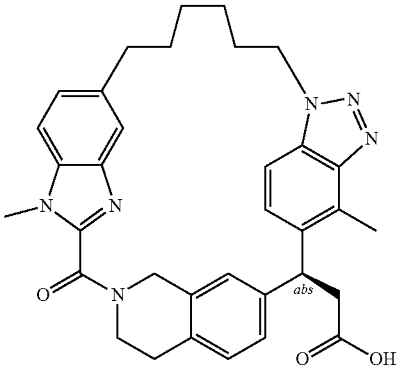 |
| 98 | 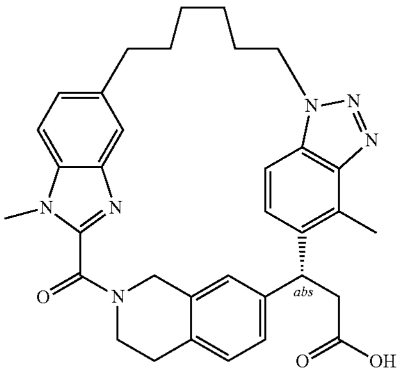 |

TABLE 3-continued
| Comp'd No | Structure |
|---|---|
| 99 | 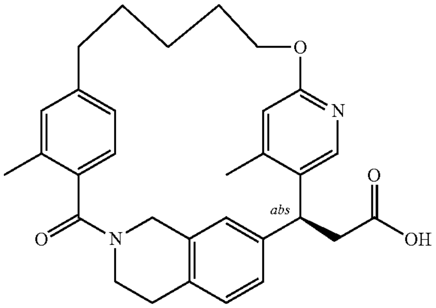 [SMILES: Cc1cc2ccc1C(=O)N1CCc3ccc(cc3C1)[C@H](CC(=O)O)c1cnc(cc1C)OCCCCC2] |
| 100 | 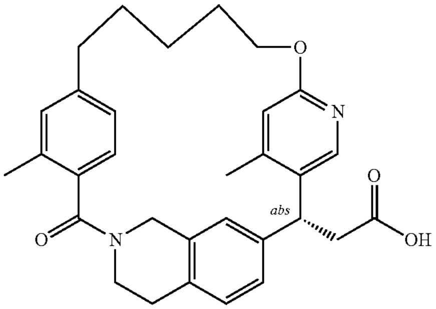 [SMILES: Cc1cc2ccc1C(=O)N1CCc3ccc(cc3C1)[C@@H](CC(=O)O)c1cnc(cc1C)OCCCCC2] |
| 103 | 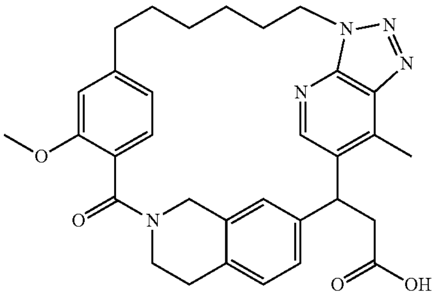 |
| 104 | 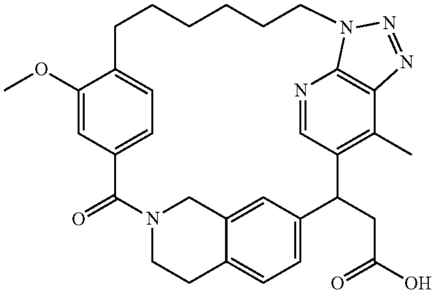 |
| 105 | 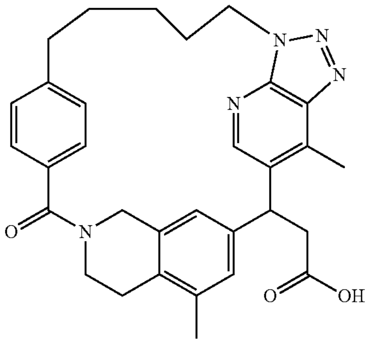 [SMILES: Cc1cc2cc3c1CCN(C3)C(=O)c1ccc(cc1)CCCCCn1nnc3c(C)c(cnc31)C2CC(=O)O] |
TABLE 3-continued
| Comp'd No | Structure |
|---|---|
| 106 | 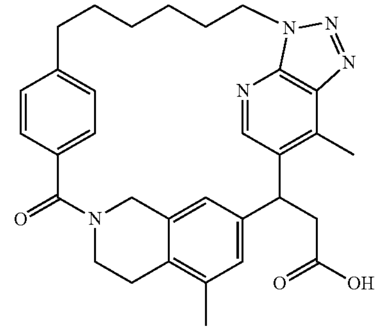 [SMILES: Cc1cc2cc3c1CCN(C3)C(=O)c1ccc(cc1)CCCCCCn1nnc3c(C)c(cnc31)C2CC(=O)O] |
| 110 | 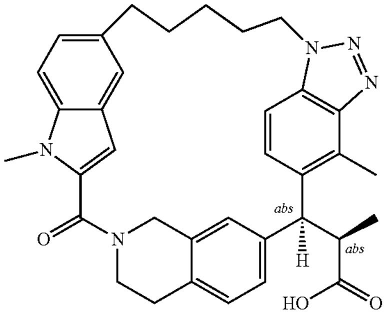 [SMILES: Cc1c2ccc3c1nnn3CCCCCc1ccc3c(c1)cc(n3C)C(=O)N1CCc3ccc(cc3C1)[C@@H]2[C@@H](C)C(=O)O] |
| 111 | 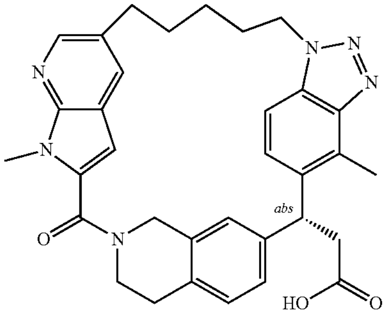 |
| 112 | 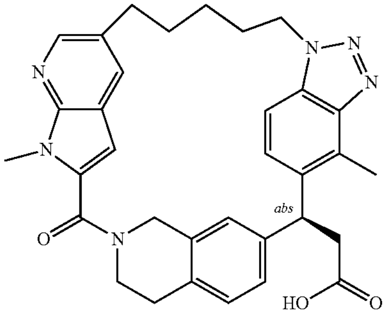 |

TABLE 3-continued
| Comp'd No | Structure |
|---|---|
| 113 | 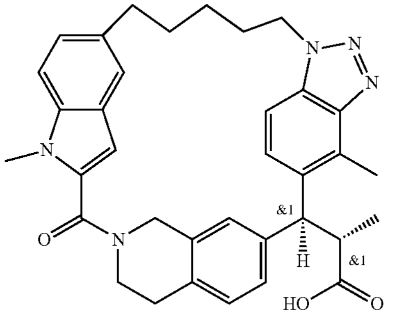 [SMILES: Cc1c2ccc3c1nnn3CCCCCc1ccc3c(c1)cc(n3C)C(=O)N1CCc3ccc(cc3C1)[C@@H]2[C@H](C)C(=O)O] |
| 114 | 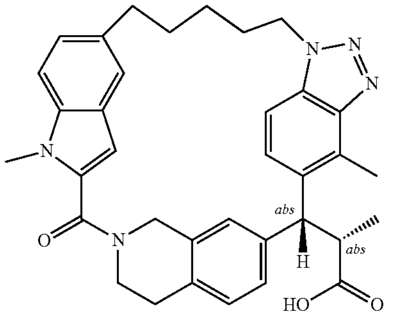 [SMILES: Cc1c2ccc3c1nnn3CCCCCc1ccc3c(c1)cc(n3C)C(=O)N1CCc3ccc(cc3C1)[C@H]2[C@H](C)C(=O)O] |
| 117 | 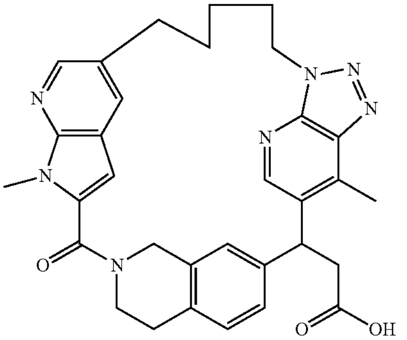 |
| 119 | 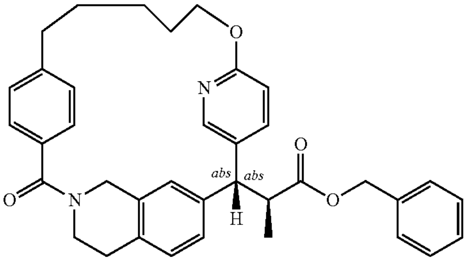 [SMILES: C[C@H](C(=O)OCc1ccccc1)[C@H]1c2ccc(nc2)OCCCCCc2ccc(cc2)C(=O)N2CCc3ccc1cc3C2] |
| 120 | 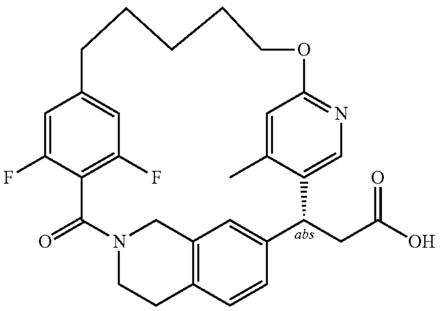 [SMILES: Cc1cc2ncc1[C@H](CC(=O)O)c1ccc3c(c1)CN(CC3)C(=O)c1c(F)cc(cc1F)CCCCCO2] |
TABLE 3-continued
| Comp'd No | Structure |
|---|---|
| 121 | 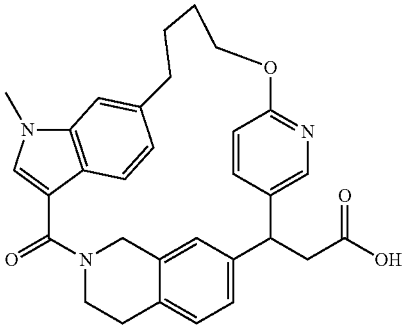 [SMILES: Cn1cc2c3ccc(cc31)CCCCOc1ccc(cn1)C(CC(=O)O)c1ccc3c(c1)CN(CC3)C2=O] |
| 122 | 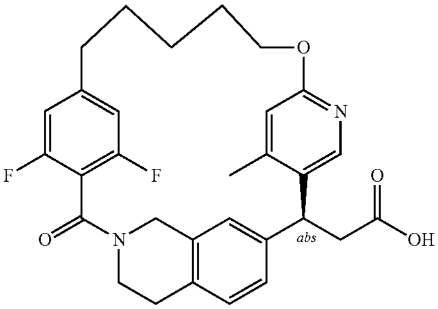 [SMILES: Cc1cc2ncc1[C@@H](CC(=O)O)c1ccc3c(c1)CN(CC3)C(=O)c1c(F)cc(cc1F)CCCCCO2] |
| 123 | 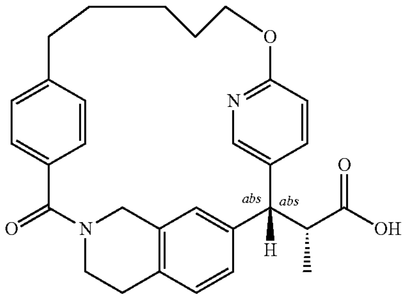 [SMILES: C[C@@H](C(=O)O)[C@H]1c2ccc(nc2)OCCCCCc2ccc(cc2)C(=O)N2CCc3ccc1cc3C2] |
| 124 | 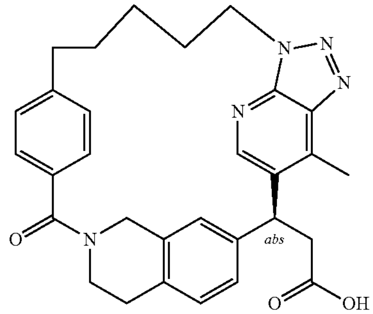 [SMILES: Cc1c2cnc3c1nnn3CCCCCc1ccc(cc1)C(=O)N1CCc3ccc(cc3C1)[C@@H]2CC(=O)O] |
| 125 | 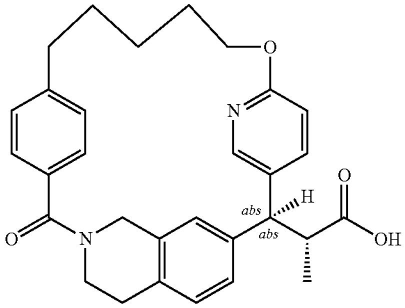 [SMILES: C[C@@H](C(=O)O)[C@@H]1c2ccc(nc2)OCCCCCc2ccc(cc2)C(=O)N2CCc3ccc1cc3C2] |

TABLE 3-continued
| Comp'd No | Structure |
|---|---|
| 126 | 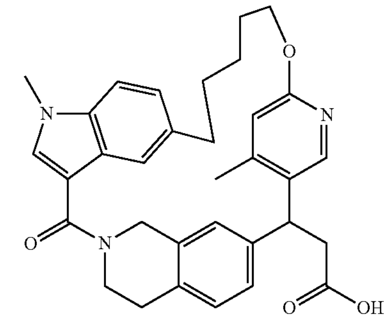 [SMILES: Cc1cc2ncc1C(CC(=O)O)c1ccc3c(c1)CN(CC3)C(=O)c1cn(C)c3ccc(cc13)CCCCCO2] |
| 127 | 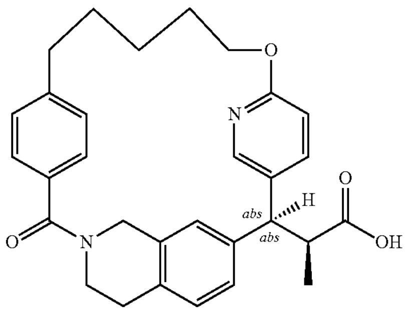 [SMILES: C[C@H](C(=O)O)[C@@H]1c2ccc(nc2)OCCCCCc2ccc(cc2)C(=O)N2CCc3ccc1cc3C2] |
| 128 | 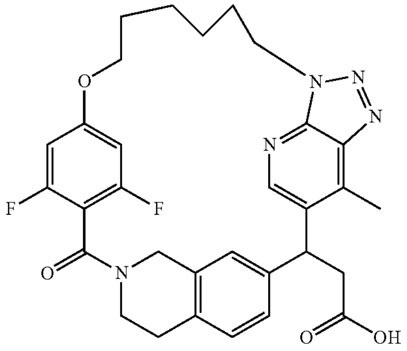 [SMILES: Cc1c2cnc3c1nnn3CCCCCCOc1cc(F)c(c(F)c1)C(=O)N1CCc3ccc(cc3C1)C2CC(=O)O] |
| 135 | 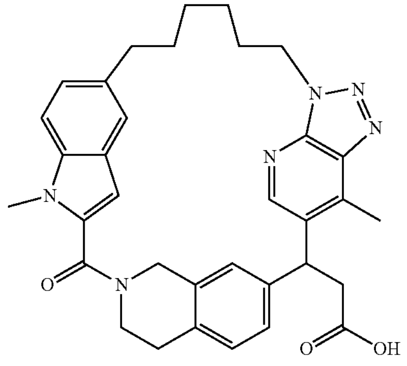 |
TABLE 3-continued
| Comp'd No | Structure |
|---|---|
| 136 | 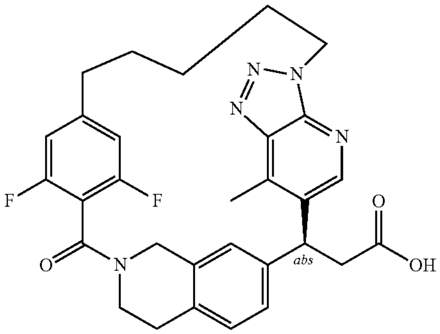 [SMILES: Cc1c2cnc3c1nnn3CCCCCc1cc(F)c(c(F)c1)C(=O)N1CCc3ccc(cc3C1)[C@@H]2CC(=O)O] |
| 137 | 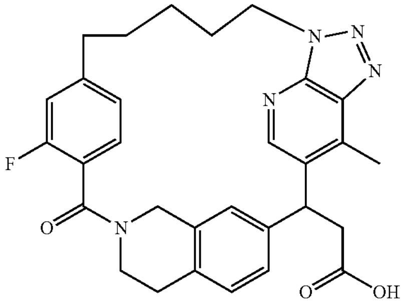 [SMILES: Cc1c2cnc3c1nnn3CCCCCc1ccc(c(F)c1)C(=O)N1CCc3ccc(cc3C1)C2CC(=O)O] |
| 138 | 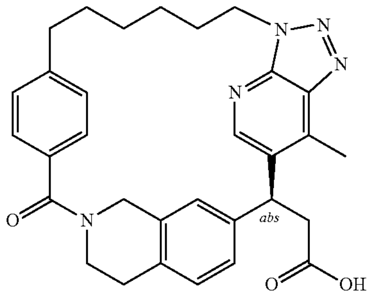 [SMILES: Cc1c2cnc3c1nnn3CCCCCCc1ccc(cc1)C(=O)N1CCc3ccc(cc3C1)[C@@H]2CC(=O)O] |
| 139 | 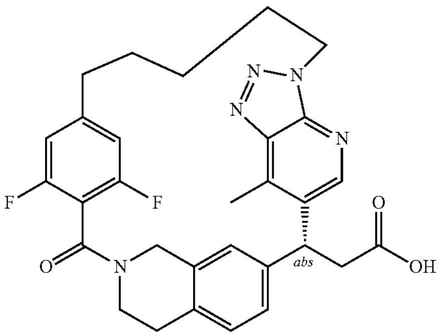 [SMILES: Cc1c2cnc3c1nnn3CCCCCc1cc(F)c(c(F)c1)C(=O)N1CCc3ccc(cc3C1)[C@H]2CC(=O)O] |
| 140 | 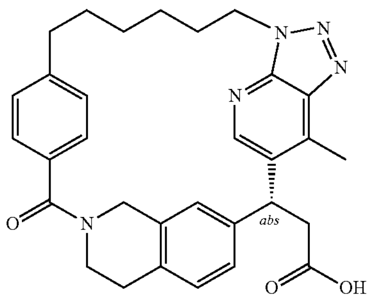 [SMILES: Cc1c2cnc3c1nnn3CCCCCCc1ccc(cc1)C(=O)N1CCc3ccc(cc3C1)[C@H]2CC(=O)O] |

TABLE 3-continued
| Comp'd No | Structure |
|---|---|
| 143 | 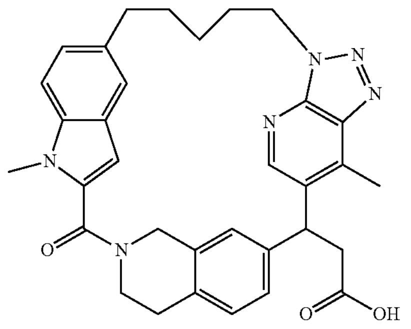 |
| 144 | 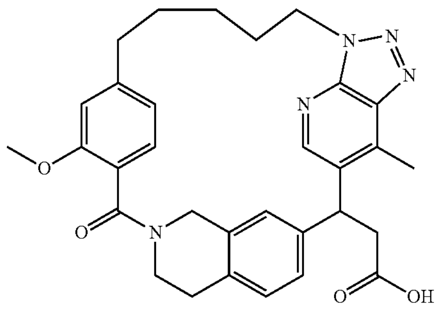 |
| 146 | 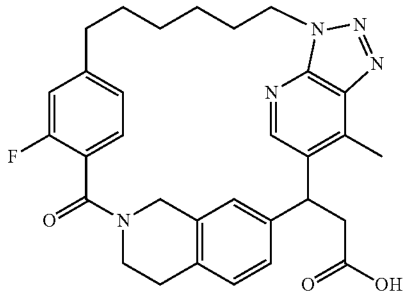 [SMILES: Cc1c2cnc3c1nnn3CCCCCCc1ccc(c(F)c1)C(=O)N1CCc3ccc(cc3C1)C2CC(=O)O] |
| 149 | 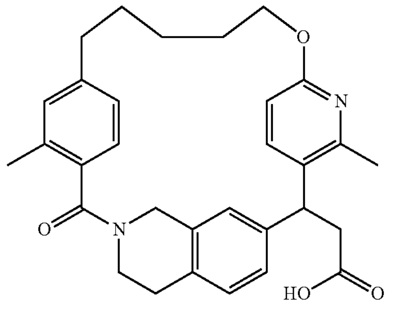 |
| 150 | 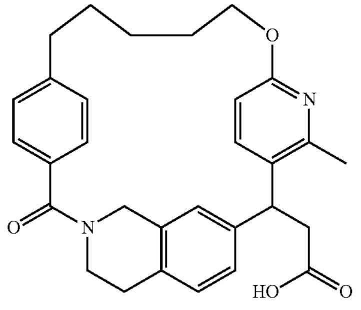 [SMILES: Cc1nc2ccc1C(CC(=O)O)c1ccc3c(c1)CN(CC3)C(=O)c1ccc(cc1)CCCCCO2] |
TABLE 3-continued
| Comp'd No | Structure |
|---|---|
| 151 | 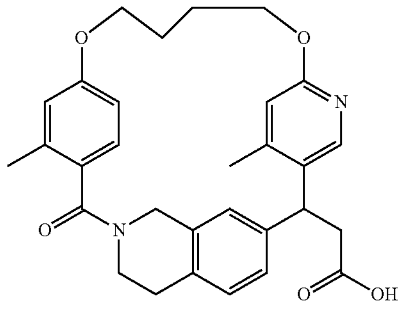 [SMILES: Cc1cc2ccc1C(=O)N1CCc3ccc(cc3C1)C(CC(=O)O)c1cnc(cc1C)OCCCCO2] |
| 154 | 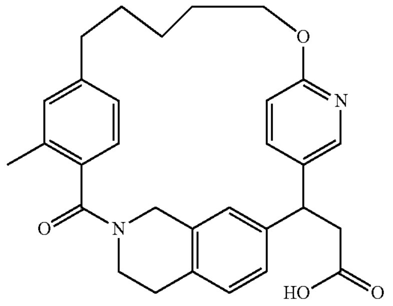 [SMILES: Cc1cc2ccc1C(=O)N1CCc3ccc(cc3C1)C(CC(=O)O)c1ccc(nc1)OCCCCC2] |
| 157 | 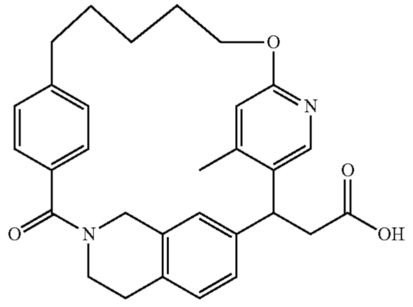 [SMILES: Cc1cc2ncc1C(CC(=O)O)c1ccc3c(c1)CN(CC3)C(=O)c1ccc(cc1)CCCCCO2] |
| 158 | 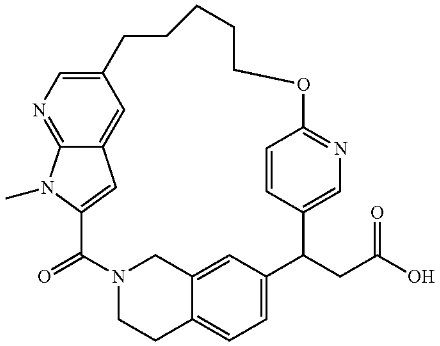 [SMILES: Cn1c2cc3cc(cnc31)CCCCCOc1ccc(cn1)C(CC(=O)O)c1ccc3c(c1)CN(CC3)C2=O] |
| 161 | 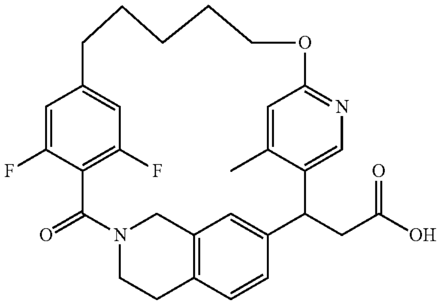 [SMILES: Cc1cc2ncc1C(CC(=O)O)c1ccc3c(c1)CN(CC3)C(=O)c1c(F)cc(cc1F)CCCCCO2] |

TABLE 3-continued
| Comp'd No | Structure |
|---|---|
| 162 | 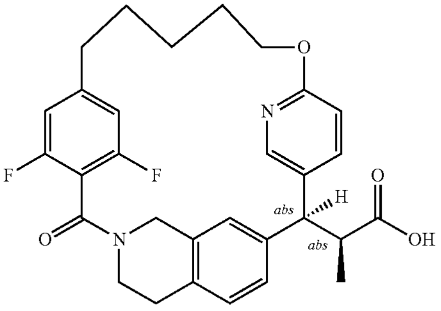 [SMILES: C[C@H](C(=O)O)[C@@H]1c2ccc(nc2)OCCCCCc2cc(F)c(c(F)c2)C(=O)N2CCc3ccc1cc3C2] |
| 163 | 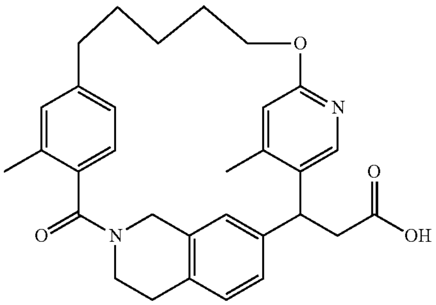 [SMILES: Cc1cc2ccc1C(=O)N1CCc3ccc(cc3C1)C(CC(=O)O)c1cnc(cc1C)OCCCCC2] |
| 164 | 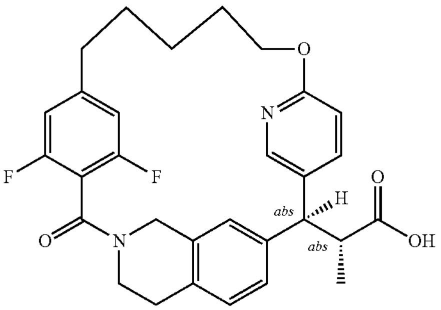 [SMILES: C[C@@H](C(=O)O)[C@@H]1c2ccc(nc2)OCCCCCc2cc(F)c(c(F)c2)C(=O)N2CCc3ccc1cc3C2] |
| 165 | 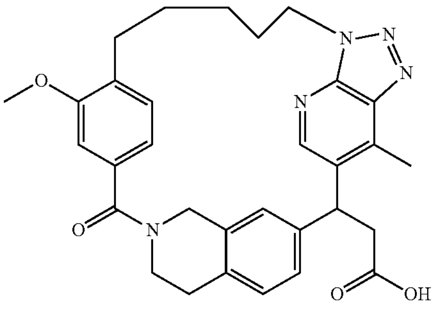 |
| 168 | 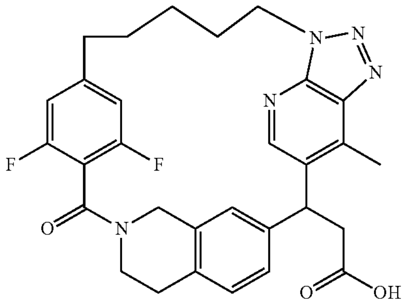 [SMILES: Cc1c2cnc3c1nnn3CCCCCc1cc(F)c(c(F)c1)C(=O)N1CCc3ccc(cc3C1)C2CC(=O)O] |
TABLE 3-continued
| Comp'd No | Structure |
|---|---|
| 169 | 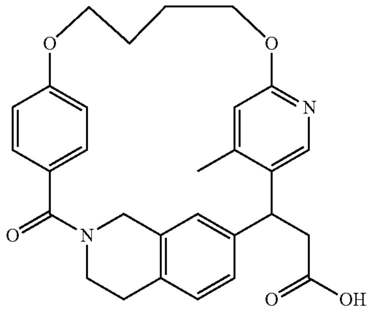 [SMILES: Cc1cc2ncc1C(CC(=O)O)c1ccc3c(c1)CN(CC3)C(=O)c1ccc(cc1)OCCCCO2] |
| 170 | 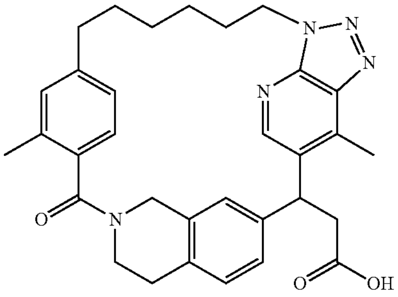 |
| 172 | 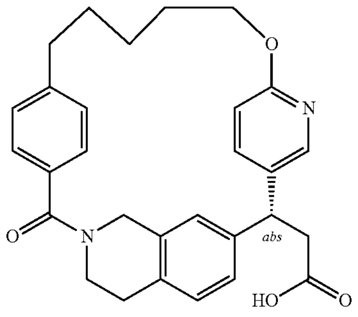 [SMILES: O=C(O)C[C@H]1c2ccc(nc2)OCCCCCc2ccc(cc2)C(=O)N2CCc3ccc1cc3C2] |
| 173 | 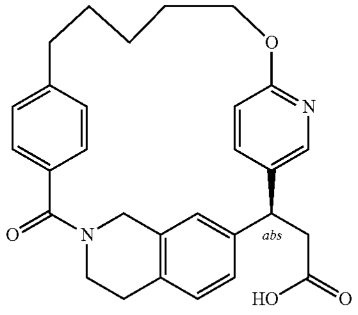 [SMILES: O=C(O)C[C@@H]1c2ccc(nc2)OCCCCCc2ccc(cc2)C(=O)N2CCc3ccc1cc3C2] |

TABLE 3-continued
| Comp'd No | Structure |
| --- | --- |
| 174 | 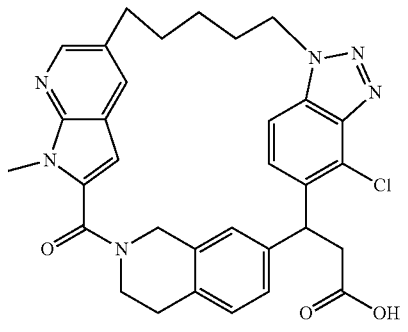 [SMILES: Cn1c2cc3cc(cnc31)CCCCCn1nnc3c(Cl)c(ccc31)C(CC(=O)O)c1ccc3c(c1)CN(CC3)C2=O] |
| 178 | 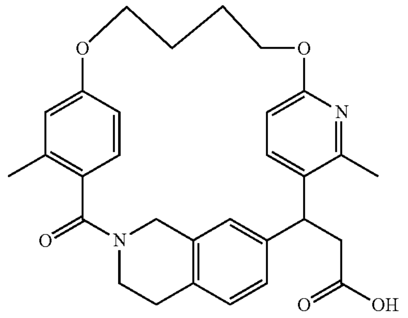 [SMILES: Cc1cc2ccc1C(=O)N1CCc3ccc(cc3C1)C(CC(=O)O)c1ccc(nc1C)OCCCCO2] |
| 180 | 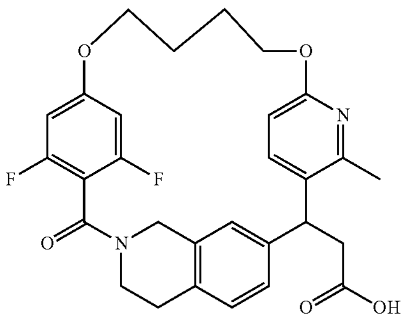 [SMILES: Cc1nc2ccc1C(CC(=O)O)c1ccc3c(c1)CN(CC3)C(=O)c1c(F)cc(cc1F)OCCCCO2] |
| 182 | 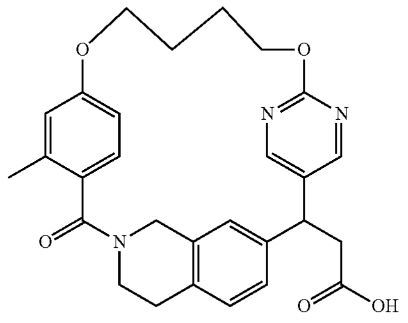 [SMILES: Cc1cc2ccc1C(=O)N1CCc3ccc(cc3C1)C(CC(=O)O)c1cnc(nc1)OCCCCO2] |
TABLE 3-continued
| Comp'd No | Structure |
| --- | --- |
| 183 | 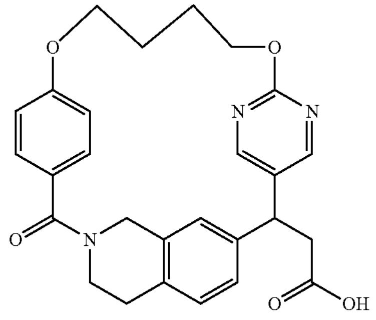 [SMILES: O=C(O)CC1c2cnc(nc2)OCCCCOc2ccc(cc2)C(=O)N2CCc3ccc1cc3C2] |
| 184 | 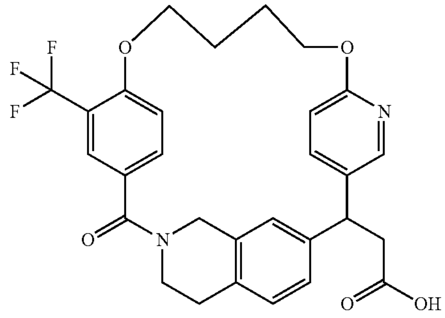 [SMILES: O=C(O)CC1c2ccc(nc2)OCCCCOc2ccc(cc2C(F)(F)F)C(=O)N2CCc3ccc1cc3C2] |
| 185 | 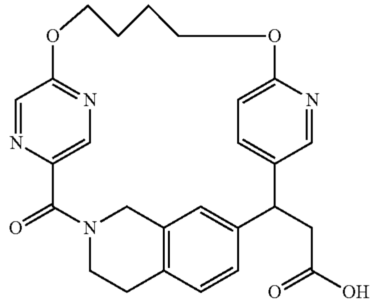 [SMILES: O=C(O)CC1c2ccc(nc2)OCCCCOc2cnc(cn2)C(=O)N2CCc3ccc1cc3C2] |
| 186 | 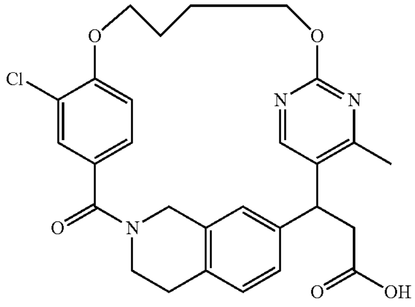 [SMILES: Cc1nc2ncc1C(CC(=O)O)c1ccc3c(c1)CN(CC3)C(=O)c1ccc(c(Cl)c1)OCCCCO2] |
| 187 | 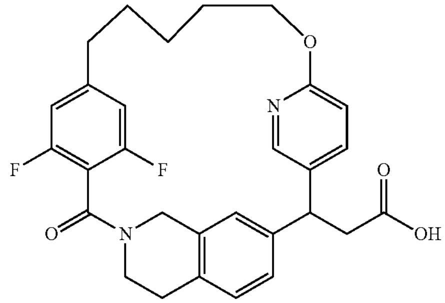 [SMILES: O=C(O)CC1c2ccc(nc2)OCCCCCc2cc(F)c(c(F)c2)C(=O)N2CCc3ccc1cc3C2] |

TABLE 3-continued
| Comp'd No | Structure |
|---|---|
| 192 | 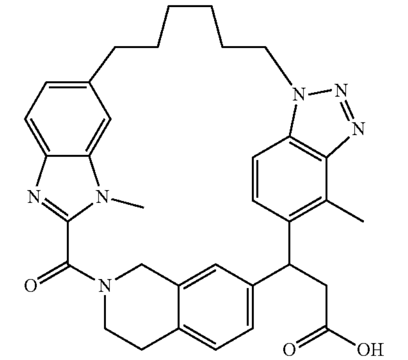 [SMILES: Cc1c2ccc3c1nnn3CCCCCCc1ccc3nc(n(C)c3c1)C(=O)N1CCc3ccc(cc3C1)C2CC(=O)O] |
| 193 | 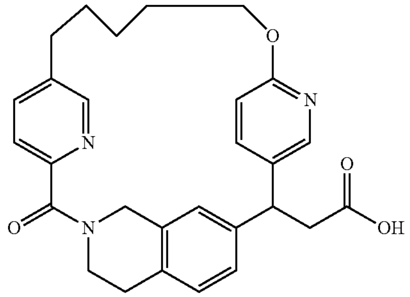 [SMILES: O=C(O)CC1c2ccc(nc2)OCCCCCc2ccc(nc2)C(=O)N2CCc3ccc1cc3C2] |
| 194 | 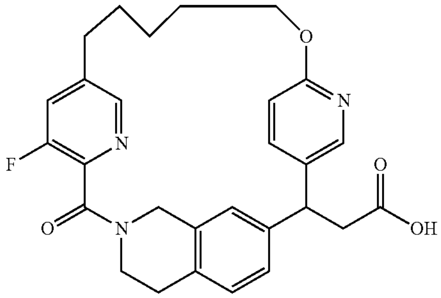 [SMILES: O=C(O)CC1c2ccc(nc2)OCCCCCc2cnc(c(F)c2)C(=O)N2CCc3ccc1cc3C2] |
| 195 | 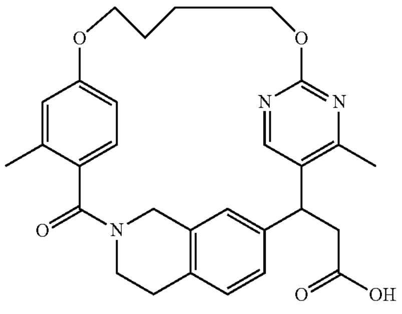 |
| 196 | 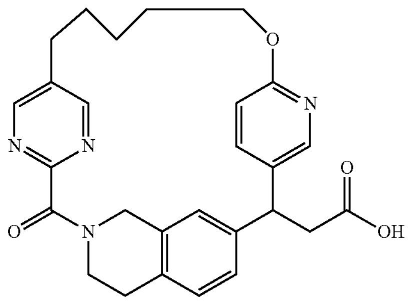 [SMILES: O=C(O)CC1c2ccc(nc2)OCCCCCc2cnc(nc2)C(=O)N2CCc3ccc1cc3C2] |
TABLE 3-continued
| Comp'd No | Structure |
|---|---|
| 197 | 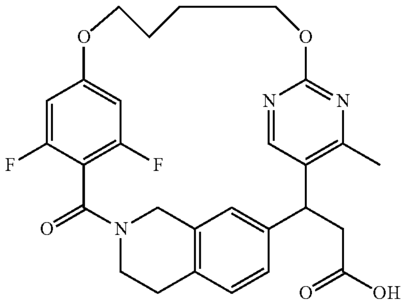 [SMILES: Cc1nc2ncc1C(CC(=O)O)c1ccc3c(c1)CN(CC3)C(=O)c1c(F)cc(cc1F)OCCCCO2] |
| 199 | 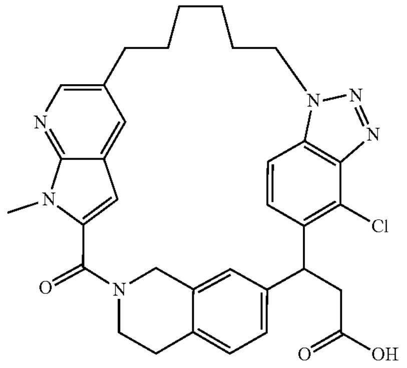 |
| 205 | 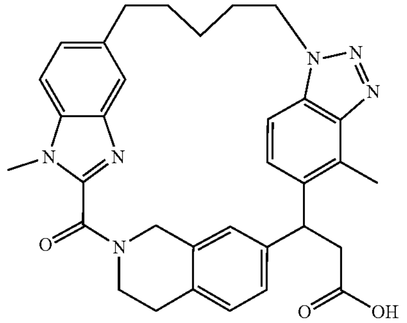 |
| 206 | 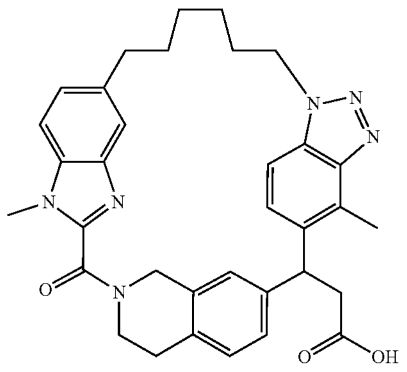 |

TABLE 3-continued
| Comp'd No | Structure |
|---|---|
| 207 | 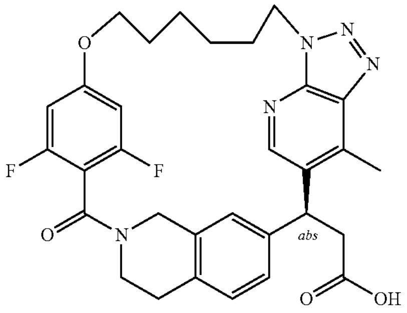 [SMILES: Cc1c2cnc3c1nnn3CCCCCCOc1cc(F)c(c(F)c1)C(=O)N1CCc3ccc(cc3C1)[C@@H]2CC(=O)O] |
| 208 | 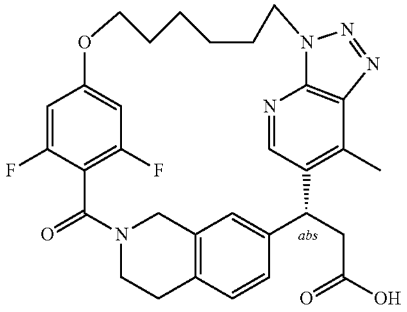 [SMILES: Cc1c2cnc3c1nnn3CCCCCCOc1cc(F)c(c(F)c1)C(=O)N1CCc3ccc(cc3C1)[C@H]2CC(=O)O] |
| 209 | 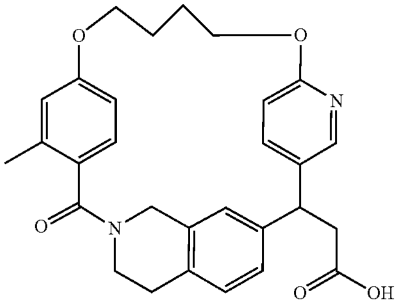 [SMILES: Cc1cc2ccc1C(=O)N1CCc3ccc(cc3C1)C(CC(=O)O)c1ccc(nc1)OCCCCO2] |
| 210 | 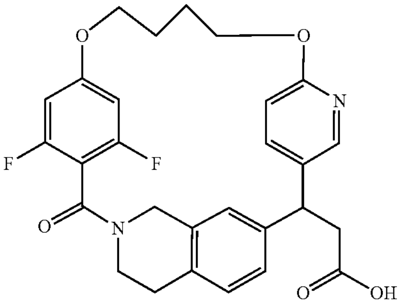 [SMILES: O=C(O)CC1c2ccc(nc2)OCCCCOc2cc(F)c(c(F)c2)C(=O)N2CCc3ccc1cc3C2] |
| 211 | 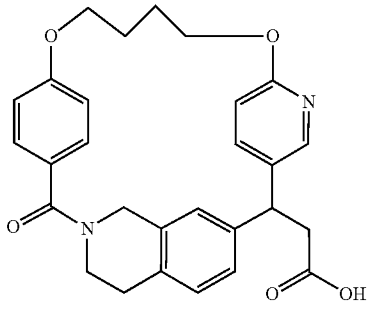 [SMILES: O=C(O)CC1c2ccc(nc2)OCCCCOc2ccc(cc2)C(=O)N2CCc3ccc1cc3C2] |
TABLE 3-continued
| Comp'd No | Structure |
|---|---|
| 212 | 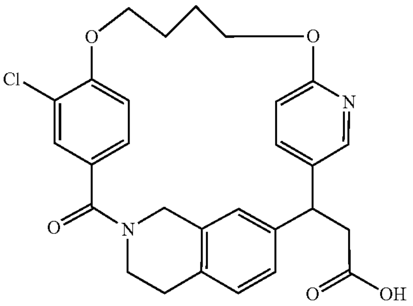 [SMILES: O=C(O)CC1c2ccc(nc2)OCCCCOc2ccc(cc2Cl)C(=O)N2CCc3ccc1cc3C2] |
| 216 | 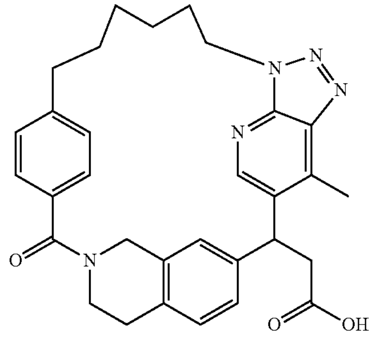 [SMILES: Cc1c2cnc3c1nnn3CCCCCCc1ccc(cc1)C(=O)N1CCc3ccc(cc3C1)C2CC(=O)O] |
| 218 | 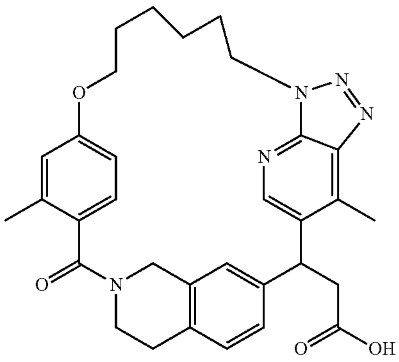 |
| 221 | 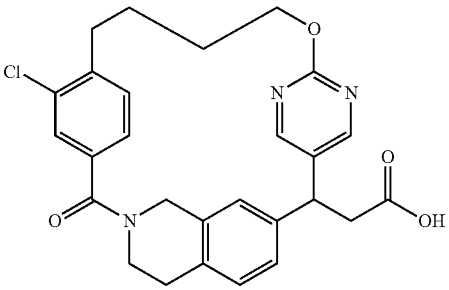 [SMILES: O=C(O)CC1c2cnc(nc2)OCCCCc2ccc(cc2Cl)C(=O)N2CCc3ccc1cc3C2] |

TABLE 3-continued
| Comp'd No | Structure |
|---|---|
| 222 | 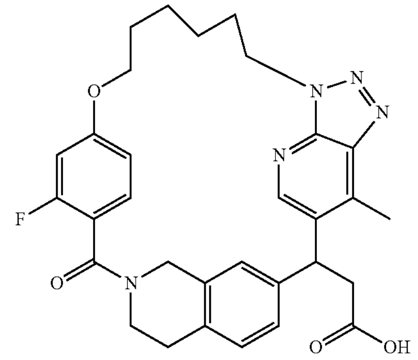 [SMILES: Cc1c2cnc3c1nnn3CCCCCCOc1ccc(c(F)c1)C(=O)N1CCc3ccc(cc3C1)C2CC(=O)O] |
| 226 | 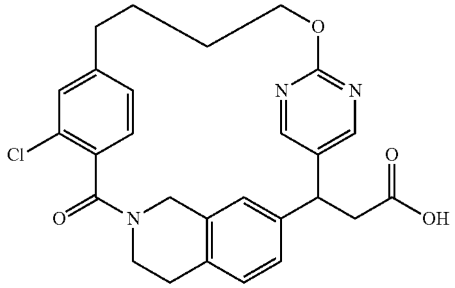 [SMILES: O=C(O)CC1c2cnc(nc2)OCCCCc2ccc(c(Cl)c2)C(=O)N2CCc3ccc1cc3C2] |
| 229 | 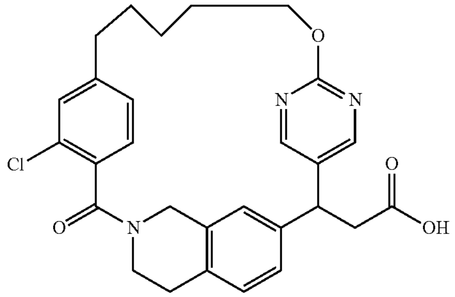 [SMILES: O=C(O)CC1c2cnc(nc2)OCCCCCc2ccc(c(Cl)c2)C(=O)N2CCc3ccc1cc3C2] |
| 233 | 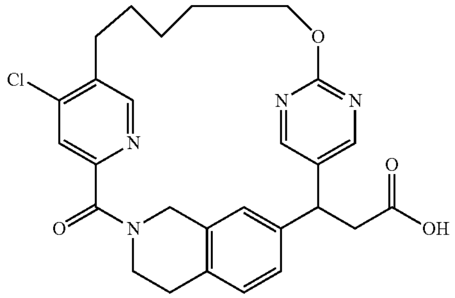 [SMILES: O=C(O)CC1c2cnc(nc2)OCCCCCc2cnc(cc2Cl)C(=O)N2CCc3ccc1cc3C2] |
| 238 | 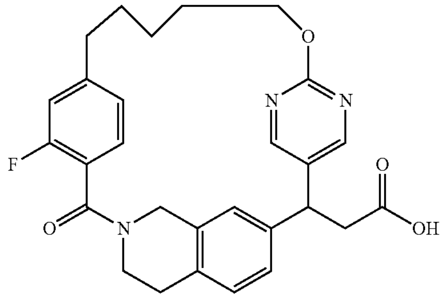 |
TABLE 3-continued
| Comp'd No | Structure |
|---|---|
| 239 | 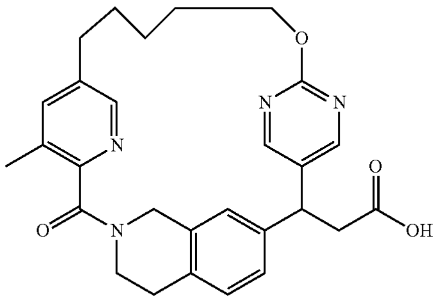 [SMILES: Cc1cc2cnc1C(=O)N1CCc3ccc(cc3C1)C(CC(=O)O)c1cnc(nc1)OCCCCC2] |
| 242 | 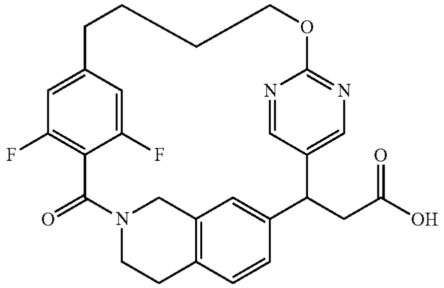 [SMILES: O=C(O)CC1c2cnc(nc2)OCCCCc2cc(F)c(c(F)c2)C(=O)N2CCc3ccc1cc3C2] |
| 246 | 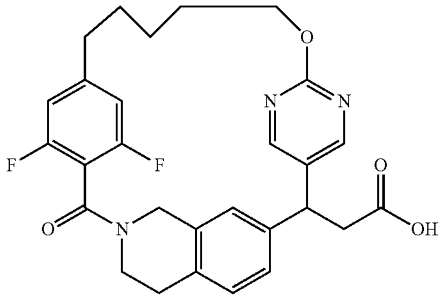 [SMILES: O=C(O)CC1c2cnc(nc2)OCCCCCc2cc(F)c(c(F)c2)C(=O)N2CCc3ccc1cc3C2] |
| 262 | 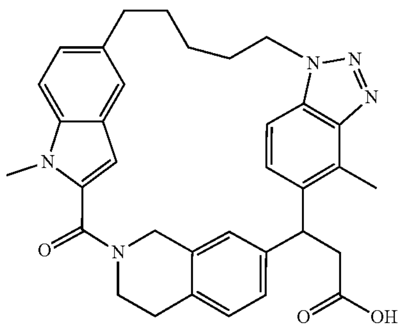 [SMILES: Cc1c2ccc3c1nnn3CCCCCc1ccc3c(c1)cc(n3C)C(=O)N1CCc3ccc(cc3C1)C2CC(=O)O] |

TABLE 3-continued
| Comp'd No | Structure |
| --- | --- |
| 265 | 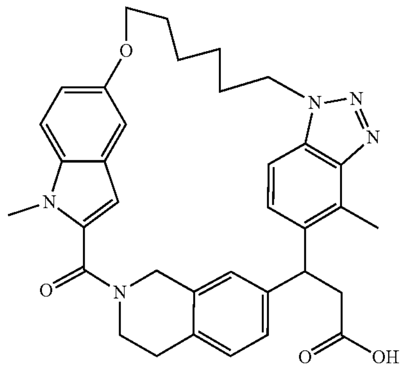 [SMILES: Cc1c2ccc3c1nnn3CCCCCCOc1ccc3c(c1)cc(n3C)C(=O)N1CCc3ccc(cc3C1)C2CC(=O)O] |
| 268 | 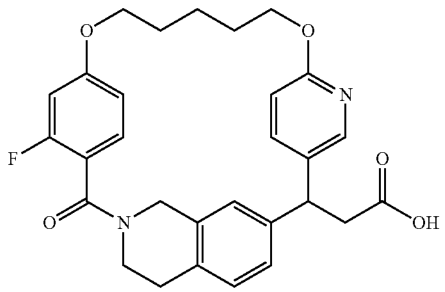 [SMILES: O=C(O)CC1c2ccc(nc2)OCCCCCOc2ccc(c(F)c2)C(=O)N2CCc3ccc1cc3C2] |
| 272 | 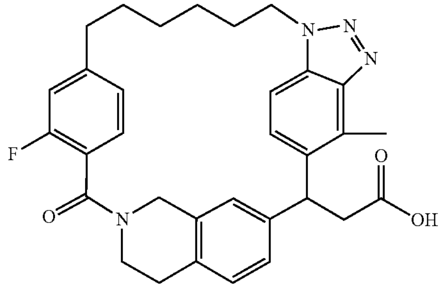 [SMILES: Cc1c2ccc3c1nnn3CCCCCCc1ccc(c(F)c1)C(=O)N1CCc3ccc(cc3C1)C2CC(=O)O] |
| 273 | 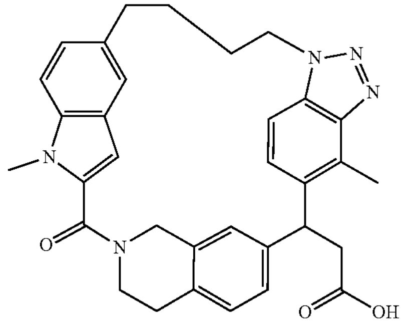 [SMILES: Cc1c2ccc3c1nnn3CCCCc1ccc3c(c1)cc(n3C)C(=O)N1CCc3ccc(cc3C1)C2CC(=O)O] |
TABLE 3-continued
| Comp'd No | Structure |
| --- | --- |
| 274 | 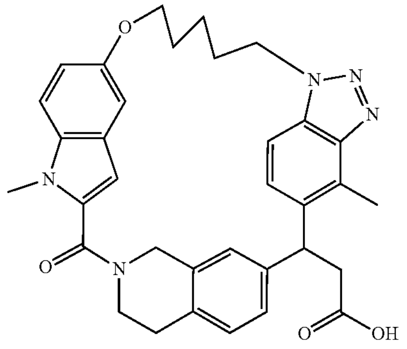 [SMILES: Cc1c2ccc3c1nnn3CCCCCOc1ccc3c(c1)cc(n3C)C(=O)N1CCc3ccc(cc3C1)C2CC(=O)O] |
| 277 | 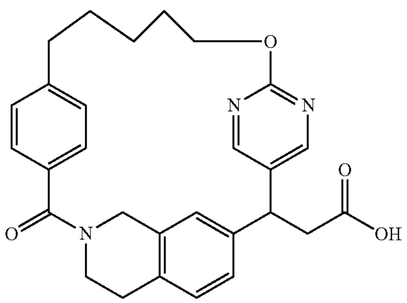 [SMILES: O=C(O)CC1c2cnc(nc2)OCCCCCc2ccc(cc2)C(=O)N2CCc3ccc1cc3C2] |
| 300 | 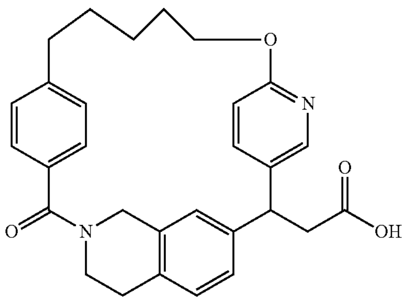 [SMILES: O=C(O)CC1c2ccc(nc2)OCCCCCc2ccc(cc2)C(=O)N2CCc3ccc1cc3C2] |
| 301 | 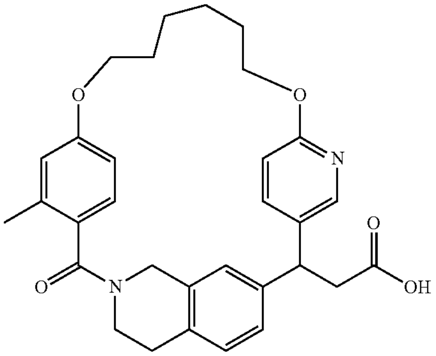 [SMILES: Cc1cc2ccc1C(=O)N1CCc3ccc(cc3C1)C(CC(=O)O)c1ccc(nc1)OCCCCCCO2] |

TABLE 3-continued
| Comp'd No | Structure |
|---|---|
| 310 | 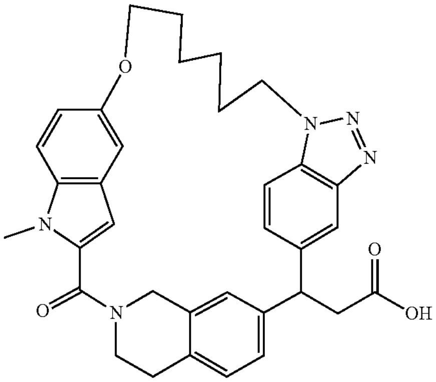 |
| 319 | 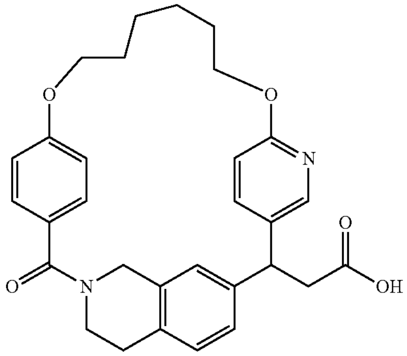 [SMILES: O=C(O)CC1c2ccc(nc2)OCCCCCCOc2ccc(cc2)C(=O)N2CCc3ccc1cc3C2] |
| 344 | 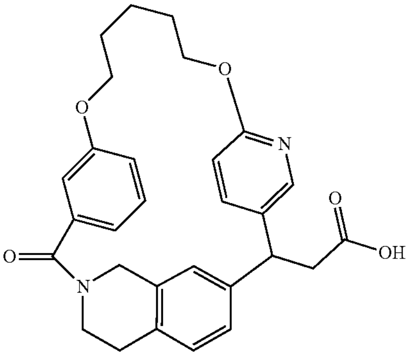 [SMILES: O=C(O)CC1c2ccc(nc2)OCCCCCOc2cccc(c2)C(=O)N2CCc3ccc1cc3C2] |
| 345 | 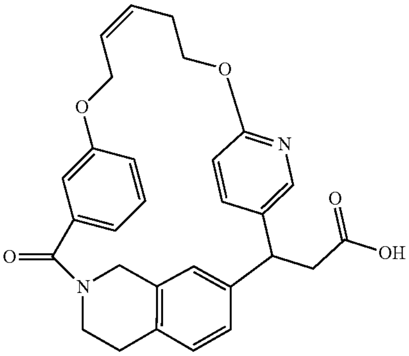 [SMILES: O=C(O)CC1c2ccc(nc2)OCC/C=C\COc2cccc(c2)C(=O)N2CCc3ccc1cc3C2] |
TABLE 3-continued
| Comp'd No | Structure |
|---|---|
| 346 | 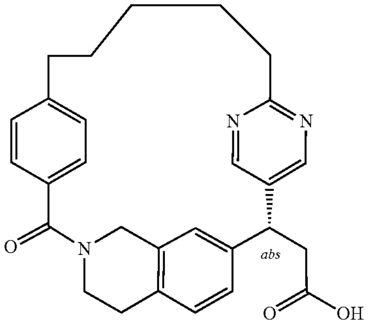 [SMILES: O=C(O)C[C@H]1c2cnc(nc2)CCCCCc2ccc(cc2)C(=O)N2CCc3ccc1cc3C2] |
| 347 | 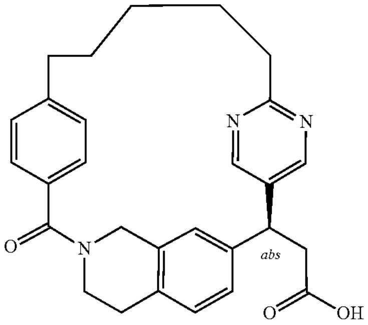 [SMILES: O=C(O)C[C@@H]1c2cnc(nc2)CCCCCc2ccc(cc2)C(=O)N2CCc3ccc1cc3C2] |
| 348 | 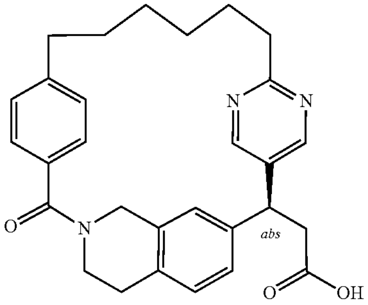 [SMILES: O=C(O)C[C@@H]1c2cnc(nc2)CCCCCCc2ccc(cc2)C(=O)N2CCc3ccc1cc3C2] |
| 349 | 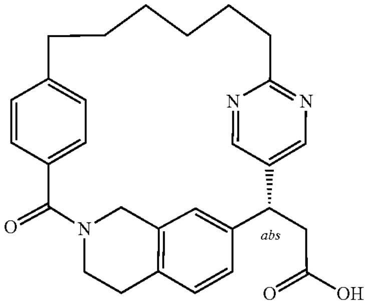 [SMILES: O=C(O)C[C@H]1c2cnc(nc2)CCCCCCc2ccc(cc2)C(=O)N2CCc3ccc1cc3C2] |
| 350 | 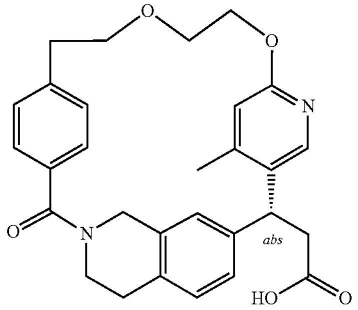 [SMILES: Cc1cc2ncc1[C@H](CC(=O)O)c1ccc3c(c1)CN(CC3)C(=O)c1ccc(cc1)CCOCCO2] |

TABLE 3-continued
| Comp'd No | Structure |
|---|---|
| 351 | 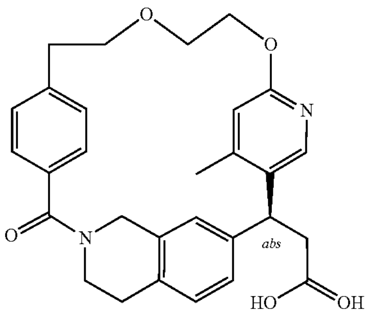 [SMILES: Cc1cc2ncc1[C@@H](CC(=O)O)c1ccc3c(c1)CN(CC3)C(=O)c1ccc(cc1)CCOCCO2] |
| 352 | 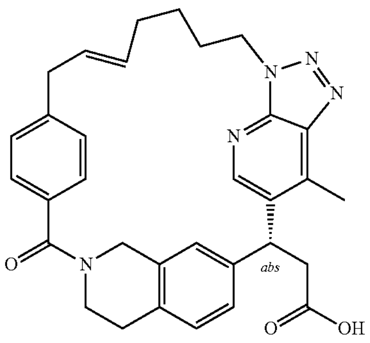 [SMILES: Cc1c2cnc3c1nnn3CCCC/C=C/Cc1ccc(cc1)C(=O)N1CCc3ccc(cc3C1)[C@H]2CC(=O)O] |
| 353 | 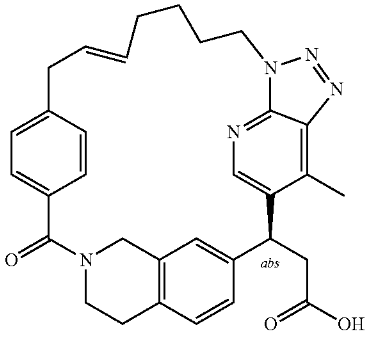 [SMILES: Cc1c2cnc3c1nnn3CCCC/C=C/Cc1ccc(cc1)C(=O)N1CCc3ccc(cc3C1)[C@@H]2CC(=O)O] |
| 354 | 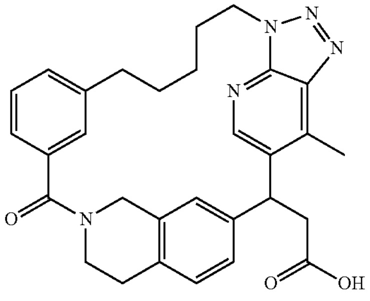 [SMILES: Cc1c2cnc3c1nnn3CCCCCc1cccc(c1)C(=O)N1CCc3ccc(cc3C1)C2CC(=O)O] |
TABLE 3-continued
| Comp'd No | Structure |
|---|---|
| 355 | 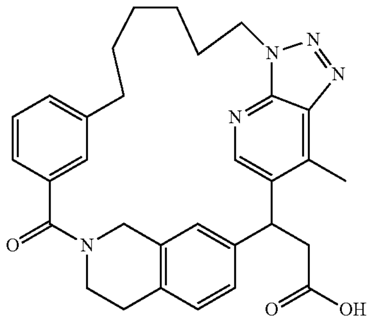 [SMILES: Cc1c2cnc3c1nnn3CCCCCCc1cccc(c1)C(=O)N1CCc3ccc(cc3C1)C2CC(=O)O] |
| 356 | 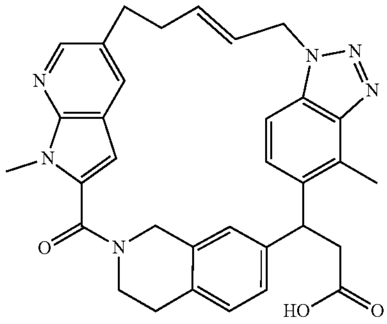 [SMILES: Cc1c2ccc3c1nnn3C/C=C/CCc1cnc3c(c1)cc(n3C)C(=O)N1CCc3ccc(cc3C1)C2CC(=O)O] |
| 359 | 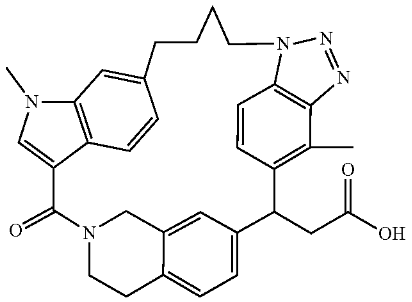 |
| 360 | 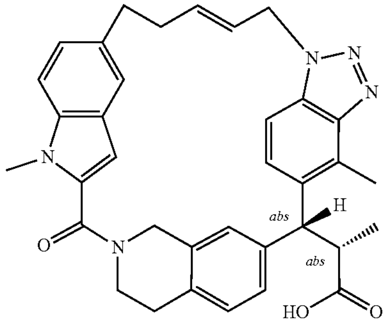 |

| Comp'd No | Structure |
| --- | --- |
| 362 | 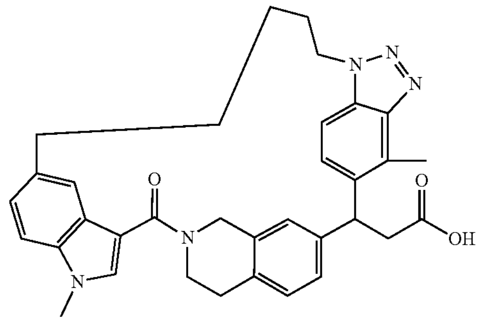 [SMILES: Cc1c2ccc3c1nnn3CCCCCc1ccc3c(c1)c(cn3C)C(=O)N1CCc3ccc(cc3C1)C2CC(=O)O] |
| 381 | 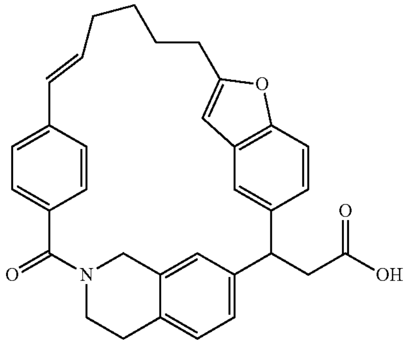 [SMILES: O=C(O)CC1c2ccc3c(c2)CN(CC3)C(=O)c2ccc(cc2)/C=C/CCCCc2cc3cc1ccc3o2] |
| 384 | 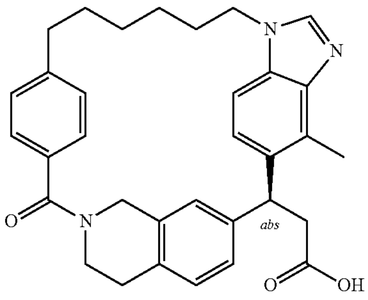 [SMILES: Cc1c2ccc3c1ncn3CCCCCCc1ccc(cc1)C(=O)N1CCc3ccc(cc3C1)[C@@H]2CC(=O)O] |
| 385 | 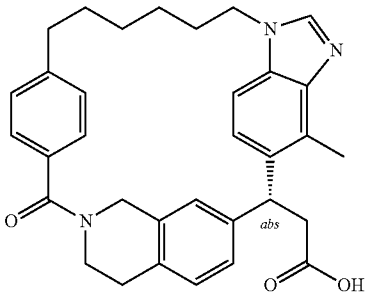 [SMILES: Cc1c2ccc3c1ncn3CCCCCCc1ccc(cc1)C(=O)N1CCc3ccc(cc3C1)[C@H]2CC(=O)O] |
| Comp'd No | Structure |
| --- | --- |
| 388 | 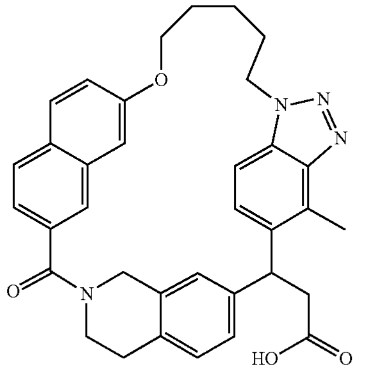 |
| 390 | 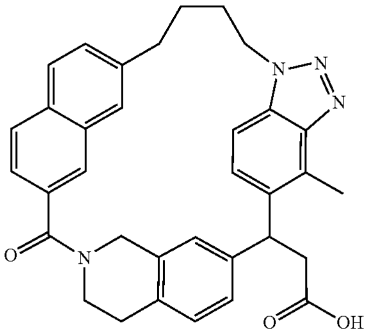 |
| 391 | 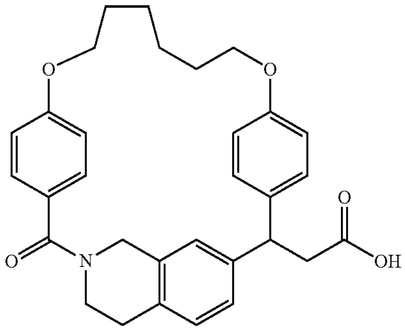 [SMILES: O=C(O)CC1c2ccc(cc2)OCCCCCCOc2ccc(cc2)C(=O)N2CCc3ccc1cc3C2] |
| 393 | 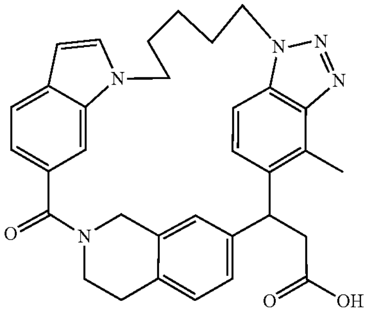 |

TABLE 3-continued
| Comp'd No | Structure |
| --- | --- |
| 394 | 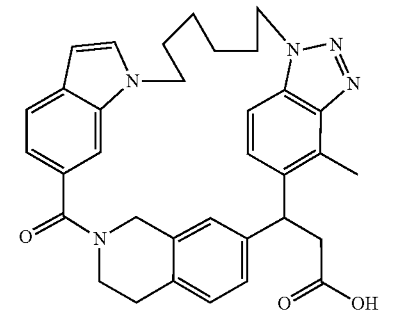 |
| 395 | 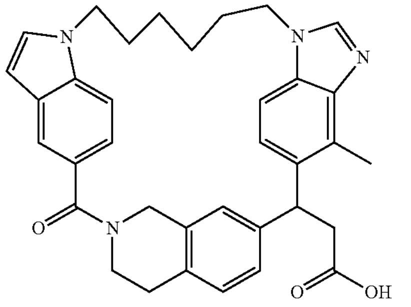 [SMILES: Cc1c2ccc3c1ncn3CCCCCCn1ccc3cc(ccc31)C(=O)N1CCc3ccc(cc3C1)C2CC(=O)O] |
| 396 | 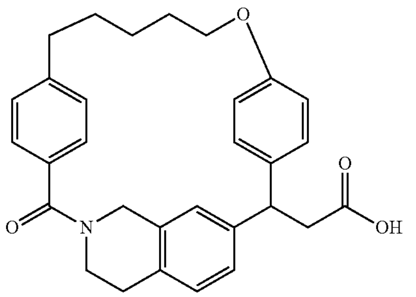 [SMILES: O=C(O)CC1c2ccc(cc2)OCCCCCc2ccc(cc2)C(=O)N2CCc3ccc1cc3C2] |
| 397 | 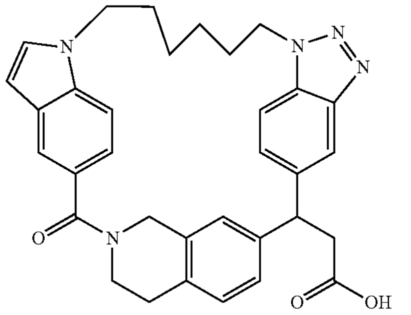 [SMILES: O=C(O)CC1c2ccc3c(c2)CN(CC3)C(=O)c2ccc3c(ccn3CCCCCCn3nnc4cc1ccc43)c2] |
| 399 | 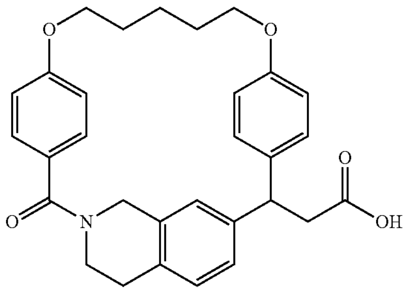 [SMILES: O=C(O)CC1c2ccc(cc2)OCCCCCOc2ccc(cc2)C(=O)N2CCc3ccc1cc3C2] |
TABLE 3-continued
| Comp'd No | Structure |
| --- | --- |
| 401 | 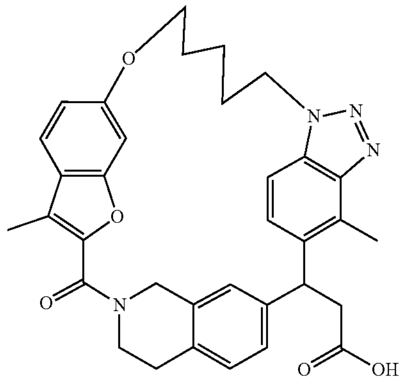 |
| 402 | 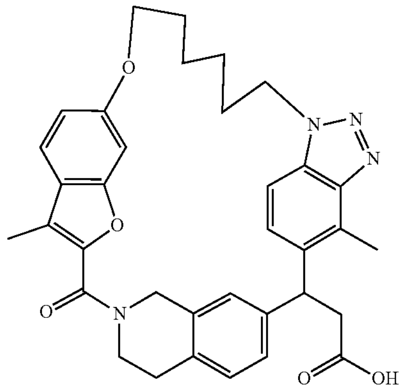 |
| 406 | 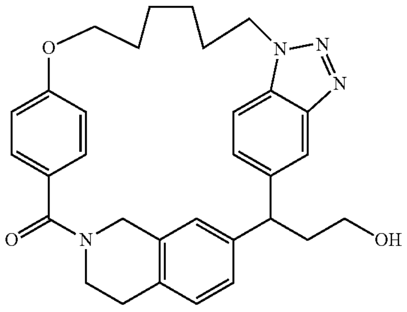 [SMILES: O=C1c2ccc(cc2)OCCCCCCn2nnc3cc(ccc32)C(CCO)c2ccc3c(c2)CN1CC3] |
| 415 | 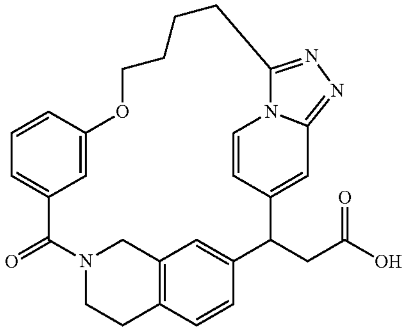 [SMILES: O=C(O)CC1c2ccc3c(c2)CN(CC3)C(=O)c2cccc(c2)OCCCCc2nnc3cc1ccn23] |

TABLE 3-continued

| Comp'd No | Structure |
| --- | --- |
| 416 | 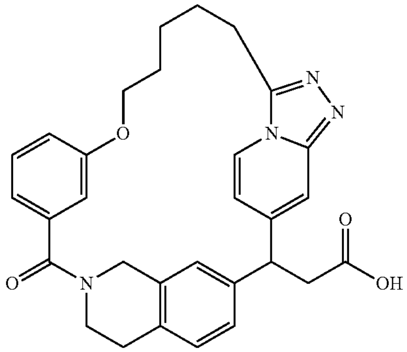 [SMILES: O=C(O)CC1c2ccc3c(c2)CN(CC3)C(=O)c2cccc(c2)OCCCCCc2nnc3cc1ccn23] |
| 423 | 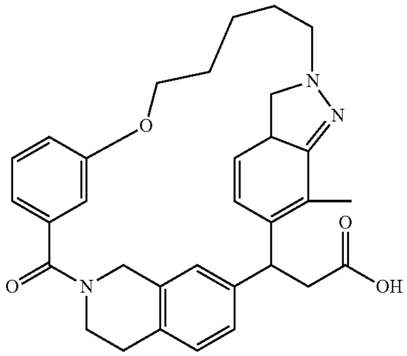 [SMILES: CC1=C2C=CC3CN(CCCCCOc4cccc(c4)C(=O)N4CCc5ccc(cc5C4)C2CC(=O)O)N=C13] |
| 425 | 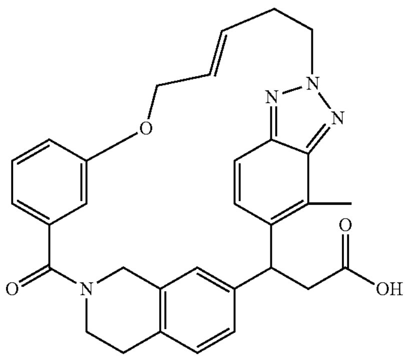 [SMILES: Cc1c2ccc3nn(nc13)CC/C=C/COc1cccc(c1)C(=O)N1CCc3ccc(cc3C1)C2CC(=O)O] |
| 437 | 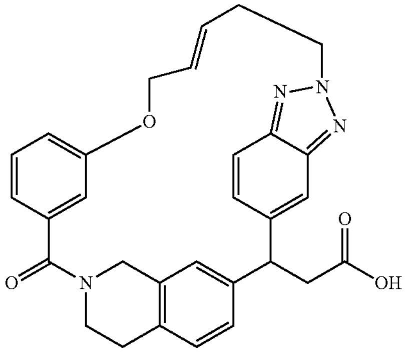 [SMILES: O=C(O)CC1c2ccc3c(c2)CN(CC3)C(=O)c2cccc(c2)OC/C=C/CCn2nc3ccc1cc3n2] |

or a pharmaceutically acceptable salt thereof.

Methods of Synthesis

Generally, compounds of Formula (I) can be prepared using known synthetic methods, and in some embodiments, using those methods shown in General Schemes 1A-4.

In General Scheme 1A, $Q^1$ and $Q^2$ are terminal alkenes that, when joined together, form a corresponding alkene substituent, $Q^3$. Building block compound 1-C can be prepared using, for example, a Miyaura 1,4-addition of a desired alkene (compound 1-B) to a dioxaborolane (compound A). In some embodiments, Ring A is coupled to compound 1-C using an amide coupling reaction after removal of the BOC protecting group under standard conditions of Compound 1-C. Once Ring A is incorporated into the molecule, the macrocycle 1-E may be prepared using, for example, a Grubbs metathesis reaction, thereby forming embodiments where the L, L', or L" group comprises one double bond (i.e. substituent Hydrogenation of the alkenylene to the alkylene provides embodiments of compounds of formula (I) where L, L', or L" comprise an alkylene group or heteroalkylene group. The final acetic acid compound (i.e. wherein R is H) is achieved by a saponification that may be performed after the hydrogenation reaction or may be performed after the metathesis reaction in embodiments where the L, L', or L" group comprise one double bond.

Building block compound C can be prepared using, for example, a Miyaura 1,4-addition of a desired alkene (compound B) to a dioxaborolane (compound A). In some embodiments, Ring A is coupled to compound C using an amide coupling reaction after removal of the BOC protecting group. Schemes 1B, 2, and 3 demonstrate a few different Ring A groups that may be coupled to compound C.

Once Ring A is incorporated into the molecule, the final macrocycle may be prepared using, for example, a Grubbs metathesis reaction to form embodiments where the L, L', or L" group comprises one double bond. Hydrogenation of the alkenylene to the alkylene provides embodiments where L, L', or L" comprise an alkylene group or heteroalkylene group. The final acetic acid compound is achieved by a saponification that may be performed after the hydrogenation reaction as shown in the schemes below, or may be performed after the metathesis reaction in embodiments where the L, L', or L" group comprise one double bond.

Scheme 4 shows that, in some embodiments, chiral compounds can be prepared in the same general manner as shown in schemes 1-3 by including chiral separation steps prior to the inclusion of Ring A.

General Scheme 1A
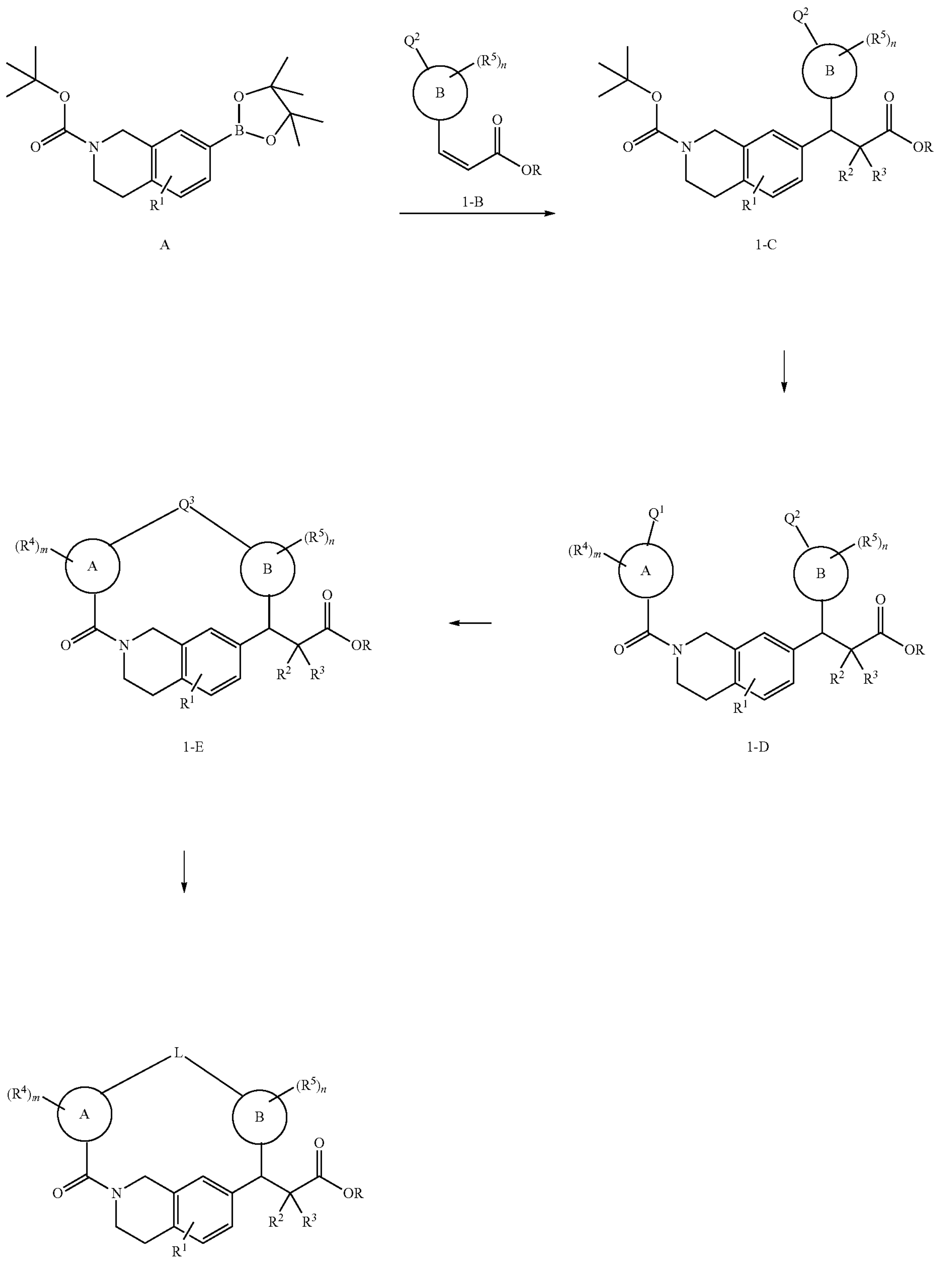

General Scheme 1B
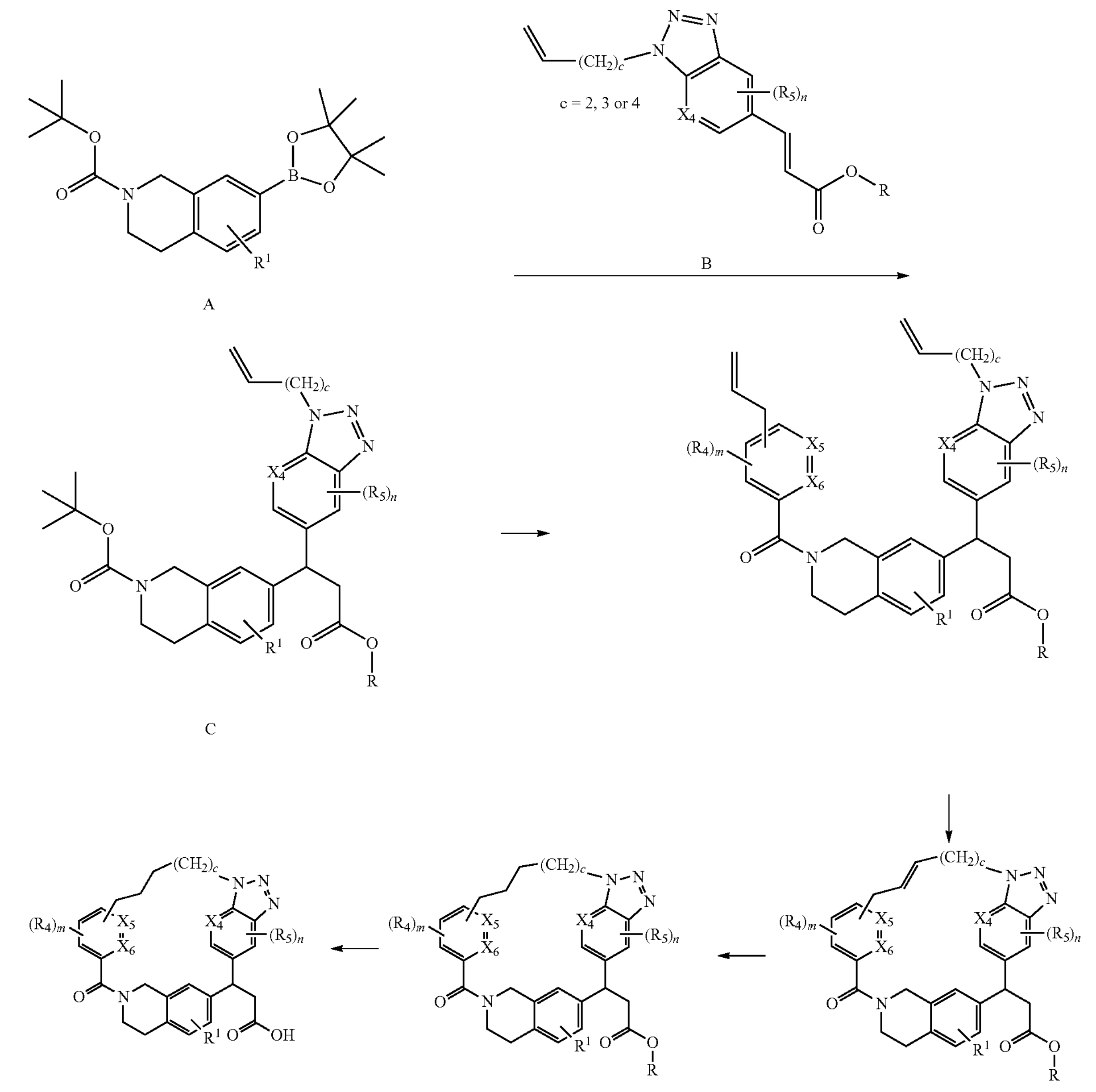
General Scheme 2
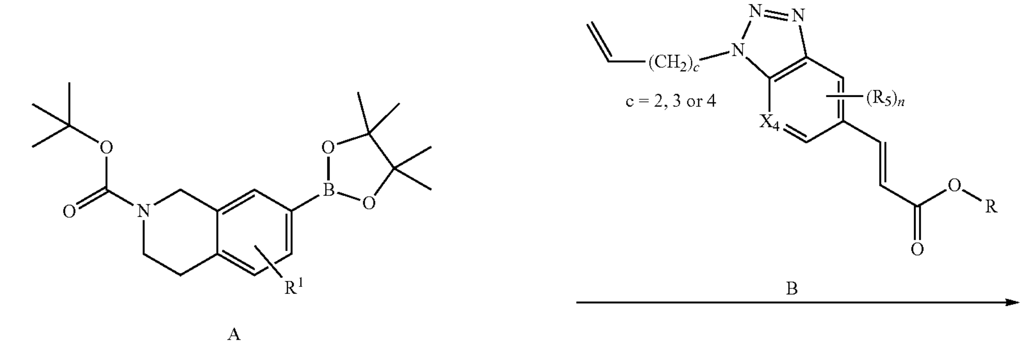

-continued
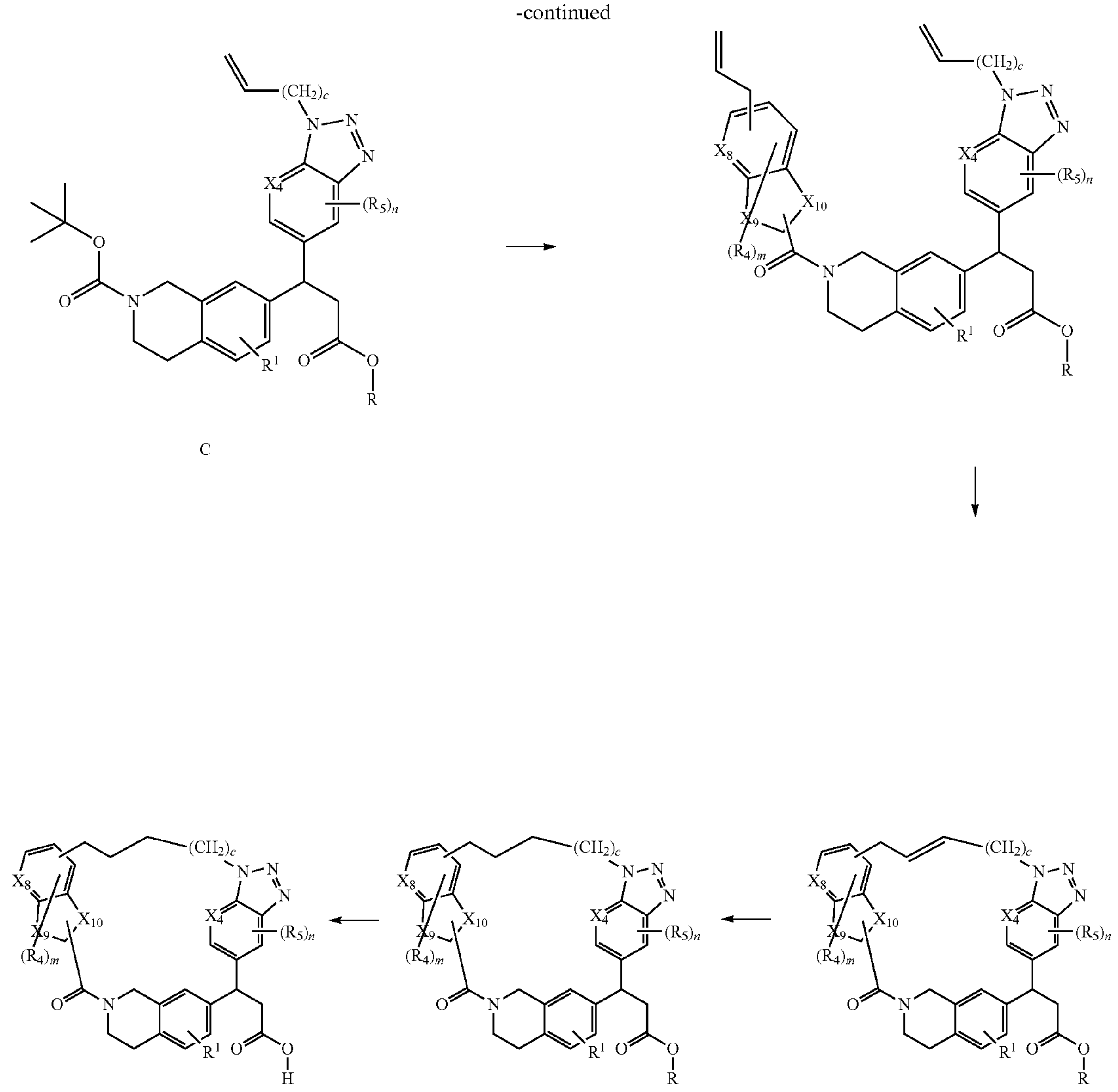
C
General Scheme 3
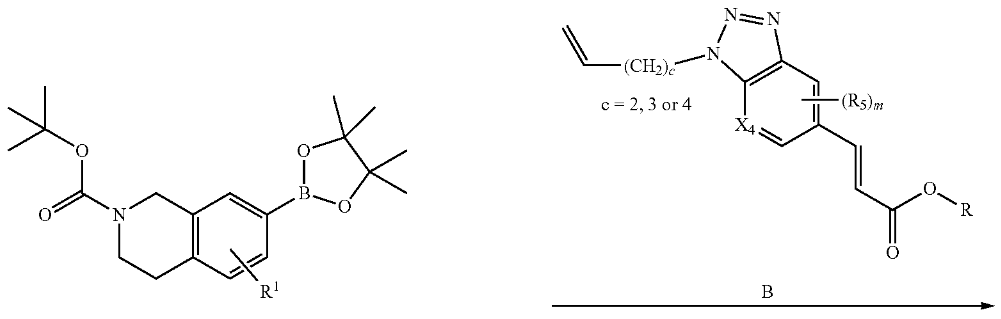
A

-continued
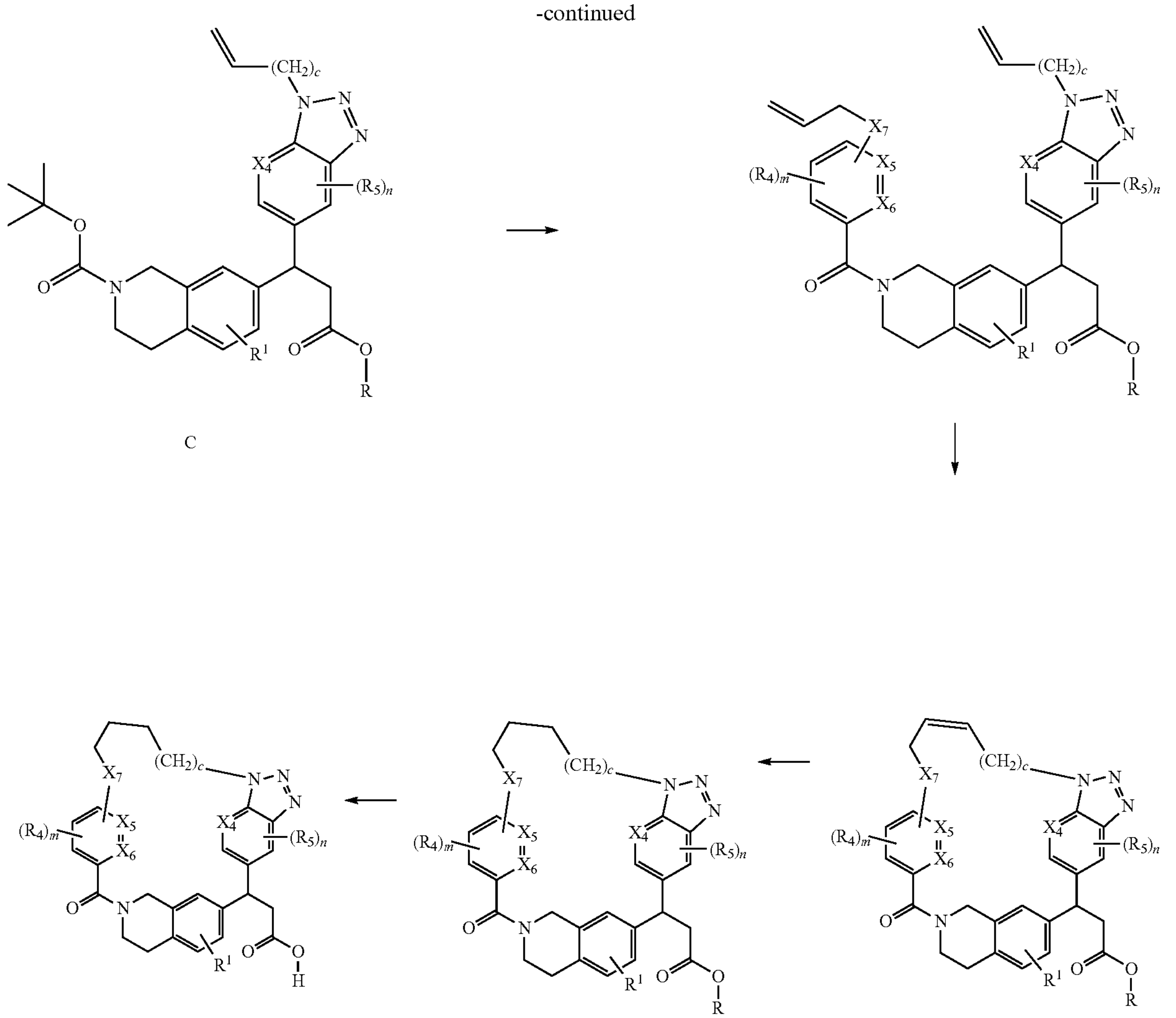
General Scheme 4
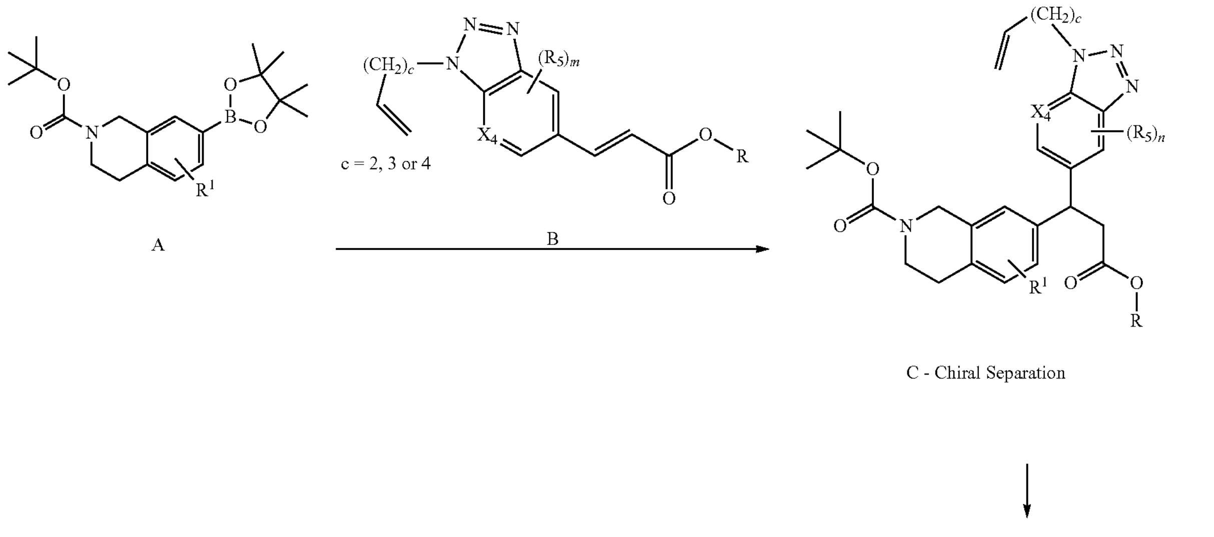

-continued

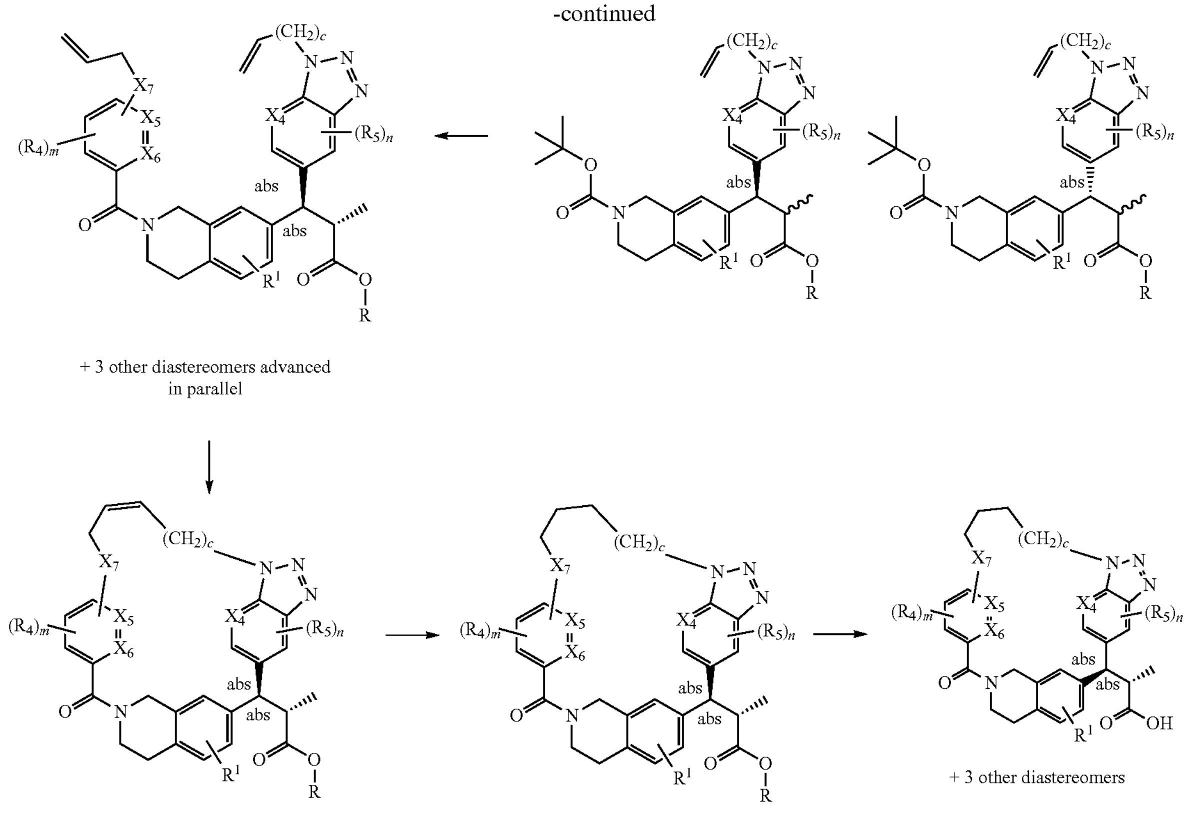

It is understood that the synthetic processes disclosed herein may be modified to arrive at various compounds of the present disclosure by selection of appropriate reagents and starting materials.

All compounds of Formula (I) or any variation thereof as described herein which exist in free base or acid form can be converted to their pharmaceutically acceptable salts by treatment with the appropriate inorganic or organic base or acid by methods known to one skilled in the art. Salts of the compounds of the disclosure can be converted to their free base or acid form by standard techniques.

Pharmaceutical Compositions and Formulations

In another aspect, provided herein are pharmaceutical compositions of any of the compounds detailed herein. Thus, the present disclosure includes pharmaceutical compositions comprising a compound disclosed herein, or a pharmaceutically acceptable salt thereof, and a pharmaceutically acceptable carrier or excipient. Pharmaceutical compositions according to the disclosure may take a form suitable for oral, buccal, parenteral, nasal, topical, or rectal administration, or a form suitable for administration by inhalation. Pharmaceutical compositions of the present disclosure comprise a compound of Formula (I), or a pharmaceutically acceptable salt thereof, and a pharmaceutically acceptable carrier, diluent, or excipient.

A compound described herein can be used in the preparation of a composition, such as a pharmaceutical composition, by combining the compound as an active ingredient with a pharmaceutically acceptable excipient. Some examples of materials which can serve as pharmaceutically acceptable excipients include: sugars, such as lactose, glucose and sucrose; starches, such as corn starch and potato starch; cellulose and its derivatives, such as sodium carboxymethyl cellulose, ethyl cellulose and cellulose acetate; surfactants, such as polysorbate 80 (i.e., Tween 80); powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; pH buffered solutions; polyesters, polycarbonates and/or polyanhydrides; and other non-toxic compatible substances employed in pharmaceutical formulations. Pharmaceutical formulations may be prepared by known pharmaceutical methods. Suitable formulations can be found in, for example, Remington: The Science and Practice of Pharmacy, Lippincott Williams & Wilkins, 21st ed. (2005), which is incorporated herein by reference.

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically-acceptable antioxidants include: water soluble antioxidants, such as ascorbic acid, cysteine hydrochloride, sodium bisulfate, sodium metabisulfite, sodium sulfite and the like; oil-soluble antioxidants, such as ascorbyl palmitate, butylated hydroxyanisole (BHA), butylated hydroxytoluene (BHT), lecithin, propyl gallate, alpha-tocopherol and the like; and metal chelating agents, such as citric acid, ethylenediamine tetraacetic acid (EDTA), sorbitol, tartaric acid, phosphoric acid and the like.

Formulations of the present disclosure include those suitable for oral, nasal, topical (including buccal and sublingual), rectal, vaginal and/or parenteral administration. The formulations may conveniently be presented in unit dosage form and may be prepared by any methods well known in the art of pharmacy. The amount of active ingredient which can be combined with a carrier material to produce a single dosage form will vary depending upon the host being treated, the particular mode of administration. The amount of active ingredient that can be combined with a carrier material to produce a single dosage form will generally be that amount of the compound which produces a therapeutic effect. Generally, this amount will range from about 1% to about 99% of active ingredient, preferably from about 5% to about 70%, most preferably from about 10% to about 30%.

In certain embodiments, a formulation of the present disclosure comprises an excipient selected from the group consisting of cyclodextrins, liposomes, micelle forming agents, e.g., bile acids and polymeric carriers, e.g., polyesters and polyanhydrides; and a compound of the present disclosure. In certain embodiments, an aforementioned formulation renders orally bioavailable a compound of the present disclosure.

Formulations of the disclosure suitable for oral administration may be in the form of capsules, cachets, pills, tablets, lozenges (using a flavored basis, usually sucrose and acacia or tragacanth), powders, granules or as a solution or a suspension in an aqueous or non-aqueous liquid or as an oil-in-water or water-in-oil liquid emulsion or as an elixir or syrup or as pastilles (using an inert base, such as gelatin and glycerin or sucrose and acacia) and/or as mouth washes and the like, each containing a predetermined amount of a compound of the present disclosure as an active ingredient. A compound of the present disclosure may also be administered as a bolus, electuary or paste.

In solid dosage forms of the disclosure for oral administration (capsules, tablets, pills, dragees, powders, granules and the like), the active ingredient is mixed with one or more pharmaceutically-acceptable carriers, such as sodium citrate or dicalcium phosphate and/or any of the following: fillers or extenders, such as starches, lactose, sucrose, glucose, mannitol and/or silicic acid; binders, such as, for example, carboxymethylcellulose, alginates, gelatin, polyvinyl pyrrolidone, sucrose and/or acacia; humectants, such as glycerol; disintegrating agents, such as agar-agar, calcium carbonate, potato or tapioca starch, alginic acid, certain silicates and sodium carbonate; solution retarding agents, such as paraffin; absorption accelerators, such as quaternary ammonium compounds; wetting agents, such as, for example, cetyl alcohol, glycerol monostearate and non-ionic surfactants; absorbents, such as kaolin and bentonite clay; lubricants, such a talc, calcium stearate, magnesium stearate, solid polyethylene glycols, sodium lauryl sulfate and mixtures thereof; and coloring agents. In the case of capsules, tablets and pills, the pharmaceutical compositions may also comprise buffering agents. Solid compositions of a similar type may also be employed as fillers in soft and hard-shelled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made in a suitable machine in which a mixture of the powdered compound is moistened with an inert liquid diluent.

The tablets and other solid dosage forms of the pharmaceutical compositions of the present disclosure, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be formulated for rapid release, e.g., freeze-dried. They may be sterilized by, for example, filtration through a bacteria-retaining filter or by incorporating sterilizing agents in the form of sterile solid compositions that can be dissolved in sterile water or some other sterile injectable medium immediately before use. These compositions may also optionally contain opacifying agents and may be of a composition that they release the active ingredient(s) only or preferentially, in a certain portion of the gastrointestinal tract, optionally, in a delayed manner. Examples of embedding compositions that can be used include polymeric substances and waxes. The active ingredient can also be in micro-encapsulated form, if appropriate, with one or more of the above-described excipients.

Liquid dosage forms for oral administration of the compounds of the disclosure include pharmaceutically acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth and mixtures thereof.

Formulations of the pharmaceutical compositions of the disclosure for rectal or vaginal administration may be presented as a suppository, which may be prepared by mixing one or more compounds of the disclosure with one or more suitable nonirritating excipients or carriers comprising, for example, cocoa butter, polyethylene glycol, a suppository wax or a salicylate and which is solid at room temperature, but liquid at body temperature and, therefore, will melt in the rectum or vaginal cavity and release the active compound.

Dosage forms for the topical or transdermal administration of a compound of this disclosure include powders, sprays, ointments, pastes, creams, lotions, gels, solutions, patches and inhalants. The active compound may be mixed under sterile conditions with a pharmaceutically-acceptable carrier and with any preservatives, buffers or propellants which may be required.

The ointments, pastes, creams and gels may contain, in addition to an active compound of this disclosure, excipients, such as animal and vegetable fats, oils, waxes, paraffins, starch, tragacanth, cellulose derivatives, polyethylene glycols, silicones, bentonites, silicic acid, talc and zinc oxide or mixtures thereof.

Powders and sprays can contain, in addition to a compound of this disclosure, excipients such as lactose, talc, silicic acid, aluminum hydroxide, calcium silicates and polyamide powder or mixtures of these substances. Sprays can additionally contain customary propellants, such as chlorofluorohydrocarbons and volatile unsubstituted hydrocarbons, such as butane and propane.

Pharmaceutical compositions of this disclosure suitable for parenteral administration comprise one or more compounds of the disclosure in combination with one or more pharmaceutically-acceptable sterile isotonic aqueous or nonaqueous solutions, dispersions, suspensions or emulsions or sterile powders which may be reconstituted into sterile injectable solutions or dispersions just prior to use, which may contain sugars, alcohols, antioxidants, buffers, bacteriostats, solutes which render the formulation isotonic with the blood of the intended recipient or suspending or thickening agents.

Examples of suitable aqueous and nonaqueous carriers, which may be employed in the pharmaceutical compositions of the disclosure include water, ethanol, polyols (such as glycerol, propylene glycol, polyethylene glycol and the like) and suitable mixtures thereof, vegetable oils, such as olive oil and injectable organic esters, such as ethyl oleate. Proper fluidity can be maintained, for example, by the use of coating materials, such as lecithin, by the maintenance of the required particle size in the case of dispersions and by the use of surfactants.

These compositions may also contain adjuvants such as preservatives, wetting agents, emulsifying agents and dispersing agents. Prevention of the action of microorganisms upon the subject compounds may be ensured by the inclusion of various antibacterial and antifungal agents, for example, paraben, chlorobutanol, phenyl sorbic acid and the like. It may also be desirable to include isotonic agents, such as sugars, sodium chloride and the like into the compositions. In addition, prolonged absorption of the injectable pharmaceutical form may be brought about by the inclusion of agents which delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution, which in turn, may depend upon crystal size and crystalline form. Alternatively, delayed absorption of a parenterally-administered drug form is accomplished by dissolving or suspending the drug in an oil vehicle.

Injectable depot forms are made by forming microencapsule matrices of the subject compounds in biodegradable polymers such as polylactide-polyglycolide. Depending on the ratio of drug to polymer and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions, which are compatible with body tissue.

Methods of Use/Treatments

Compounds and compositions detailed herein, such as a pharmaceutical composition containing a compound of any formula provided herein, or a pharmaceutically acceptable salt thereof, and a pharmaceutically acceptable carrier or excipient, may be used in methods of administration and treatment as provided herein. The compounds and compositions may also be used in in vitro methods, such as in vitro methods of administering a compound or composition to cells for screening purposes and/or for conducting quality control assays.

In some embodiments, disclosed herein are methods of activating Nrf2 comprising contacting an effective amount of a compound of Formula (I) or pharmaceutically acceptable salt thereof, or the pharmaceutical compositions thereof, with the Nrf2.

In some embodiments, disclosed herein are methods of treating sickle cell disease in a subject in need thereof, comprising administering to the subject a therapeutically effective amount of a compound of Formula (I) or pharmaceutically acceptable salt thereof, or the pharmaceutical compositions thereof.

In some embodiments, disclosed herein are methods of treating inflammatory diseases in a subject in need thereof, comprising administering to the subject a therapeutically effective amount of a compound of Formula (I) or pharmaceutically acceptable salt thereof, or the pharmaceutical compositions thereof.

In some embodiments, the subject is a mammal. In some embodiments, the subject is a primate, dog, cat, rabbit, or rodent. In some embodiments, the subject is a primate. In some embodiments, the subject is a human. In some embodiments, the human is at least about or is about any of 18, 21, 30, 50, 60, 65, 70, 80, or 85 years old. In some embodiments, the human is a child. In some embodiments, the human is less than about or about any of 21, 18, 15, 10, 5, 4, 3, 2, or 1 years old.

Dosing and Method of Administration

The phrases "parenteral administration" and "administered parenterally" as used herein mean modes of administration other than enteral and topical administration, usually by injection and includes, without limitation, intravenous, intramuscular, intraarterial, intrathecal, intracapsular, intraorbital, intracardiac, intradermal, intraperitoneal, transtracheal, subcutaneous, subcuticular, intraarticulare, subcapsular, subarachnoid, intraspinal and intrasternal injection and infusion.

The phrases "systemic administration," "administered systemically," "peripheral administration" and "administered peripherally" as used herein mean the administration of a compound, drug or other material other than directly into the central nervous system, such that it enters the patient's system and, thus, is subject to metabolism and other like processes, for example, subcutaneous administration.

These compounds may be administered to humans and other animals for therapy by any suitable route of administration, including orally, nasally, as by, for example, a spray, rectally, intravaginally, parenterally, intracistemally and topically, as by powders, ointments or drops, including buccally and sublingually.

Regardless of the route of administration selected, the compounds of the present disclosure, or the pharmaceutical compositions of the present disclosure, are formulated into pharmaceutically acceptable dosage forms by conventional methods known to those of skill in the art.

Actual dosage levels of the active ingredients in the pharmaceutical compositions of this disclosure may be varied so as to obtain an amount of the active ingredient that is effective to achieve the desired therapeutic response for a particular patient, composition and mode of administration, without being toxic to the patient.

The selected dosage level will depend upon a variety of factors including the activity of the particular compound of the present disclosure employed or the ester, salt or amide thereof, the route of administration, the time of administration, the rate of excretion or metabolism of the particular compound being employed, the duration of the treatment, other drugs, compounds and/or materials used in combination with the particular compound employed, the age, sex, weight, condition, general health and prior medical history of the patient being treated and like factors well known in the medical arts. A daily, weekly or monthly dosage (or other time interval) can be used.

A physician or veterinarian having ordinary skill in the art can readily determine and prescribe the effective amount of the pharmaceutical composition required. For example, the physician or veterinarian could start doses of the compounds of the disclosure employed in the pharmaceutical composition at levels lower than that required to achieve the desired therapeutic effect and then gradually increasing the dosage until the desired effect is achieved.

In general, a suitable daily dose of a compound of the disclosure will be that amount of the compound that is the lowest dose effective to produce a therapeutic effect (e.g., inhibit necrosis). Such an effective dose will generally depend upon the factors described above. Generally doses of the compounds of this disclosure for a patient, when used for the indicated effects, will range from about 0.0001 to about 100 mg per kg of body weight per day. Preferably the daily dosage will range from 0.001 to 50 mg of compound per kg of body weight and even more preferably from 0.01 to 10 mg of compound per kg of body weight.

If desired, the effective daily dose of the active compound may be administered as two, three, four, five, six or more sub-doses administered separately at appropriate intervals throughout the day, optionally, in unit dosage forms.

When the compounds of the present disclosure are administered as pharmaceuticals, to humans and animals, they can be given per se or as a pharmaceutical composition containing, for example, 0.1% to 99.5% (more preferably, 0.5% to 90%) of active ingredient in combination with a pharmaceutically acceptable carrier.

The compounds of the present application or the compositions thereof may be administered once, twice, three or four times daily, using any suitable mode described above. Also, administration or treatment with the compounds may be continued for a number of days; for example, commonly treatment would continue for at least 7 days, 14 days or 28 days, for one cycle of treatment. Treatment cycles are well known and are frequently alternated with resting periods of about 1 to 28 days, commonly about 7 days or about 14 days, between cycles. The treatment cycles, in certain embodiments, may also be continuous.

When administered orally, the total daily dosage for a human subject may be between 1 mg and 1,000 mg, between about 1,000-2,000 mg/day, between about 10-500 mg/day, between about 50-300 mg/day, between about 75-200 mg/day or between about 100-150 mg/day.

The daily dosage may also be described as a total amount of a compound described herein administered per dose or per day. Daily dosage of a compound may be between about 1 mg and 4,000 mg, between about 2,000 to 4,000 mg/day, between about 1 to 2,000 mg/day, between about 1 to 1,000 mg/day, between about 10 to 500 mg/day, between about 20 to 500 mg/day, between about 50 to 300 mg/day, between about 75 to 200 mg/day or between about 15 to 150 mg/day.

In certain embodiments, the method comprises administering to the subject an initial daily dose of about 1 to 800 mg of a compound described herein and increasing the dose by increments until clinical efficacy is achieved. Increments of about 5, 10, 25, 50 or 100 mg can be used to increase the dose. The dosage can be increased daily, every other day, twice per week or once per week.

In certain embodiments, a compound or pharmaceutical preparation is administered orally. In certain embodiments, the compound or pharmaceutical preparation is administered intravenously. Alternative routes of administration include sublingual, intramuscular and transdermal administrations.

The preparations of the present disclosure may be given orally, parenterally, topically or rectally. They are of course given in forms suitable for each administration route. For example, they are administered in tablets or capsule form, by injection, inhalation, eye lotion, ointment, suppository, etc. administration by injection, infusion or inhalation; topical by lotion or ointment; and rectal by suppositories. In certain embodiments, the administration is oral.

Kits/Articles of Manufacture

Also provided herein are kits that include a compound of the disclosure, or a pharmaceutically acceptable salt thereof, and suitable packaging. In certain embodiments, a kit further includes instructions for use. In one aspect, a kit includes a compound of the disclosure, or a pharmaceutically acceptable salt thereof, and a label and/or instructions for use of the compounds in the treatment of the indications, including the diseases or conditions, described herein.

Provided herein are also articles of manufacture that include a compound described herein, or a pharmaceutically acceptable salt thereof, in a suitable container. The container may be a vial, jar, ampoule, preloaded syringe and intravenous bag.

The kit can also contain instructions for using the compounds according to the disclosure. The kit can be compartmentalized to receive the containers in close confinement. As used herein, a kit such as a compartmentalized kit includes any kit in which compounds or agents are contained in separate containers. Illustrative examples of such containers include, but are not limited to, small glass containers, plastic containers or strips of plastic or paper. Particularly preferred types of containers allow the skilled worker to efficiently transfer reagents from one compartment to another compartment such that the samples and reagents are not cross-contaminated and the agents or solutions of each container can be added in a quantitative fashion from one compartment to another. Such containers include, but are not limited to, a container that will accept a compound or combination of compounds and/or other agents of the disclosure. One or more compounds or agents can be provided as a powder (e.g. lyophilized powder) or precipitate. Such compound(s) can be resuspended prior to administration in a solution that may be provided as part of the kit or separately available. A kit can contain compounds or agents in other forms such as liquids, gels, solids, as described herein. Different compounds and/or agents may be provided in different forms in a single kit.

EXAMPLES

The following examples are included to demonstrate specific embodiments of the disclosure. It should be appreciated by those of skill in the art that the techniques disclosed in the examples which follow represent techniques to function well in the practice of the disclosure, and thus can be considered to constitute specific modes for its practice. However, those of skill in the art should, in light of the present disclosure, appreciate that many changes can be made in the specific embodiments which are disclosed and still obtain a like or similar result without departing from the spirit and scope of the disclosure.

Synthetic Examples

General Procedures for Synthetic Examples.

General Procedure 6B: Amide Coupling

The variables shown in the following scheme are specific to this general procedure.

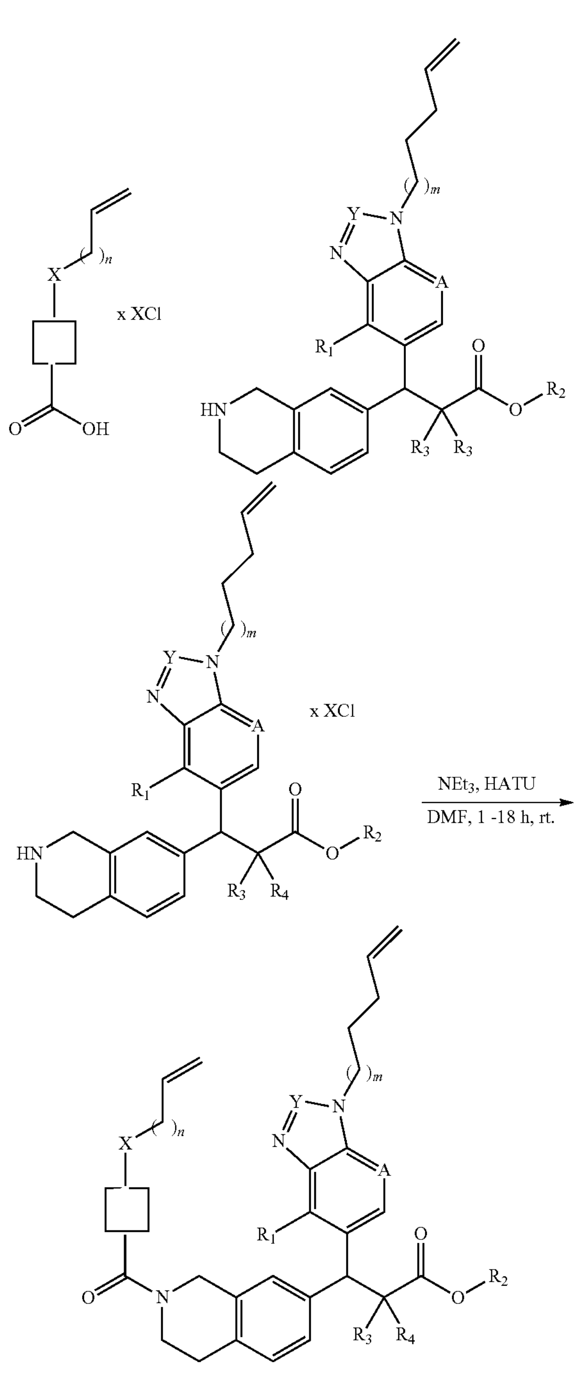

-continued

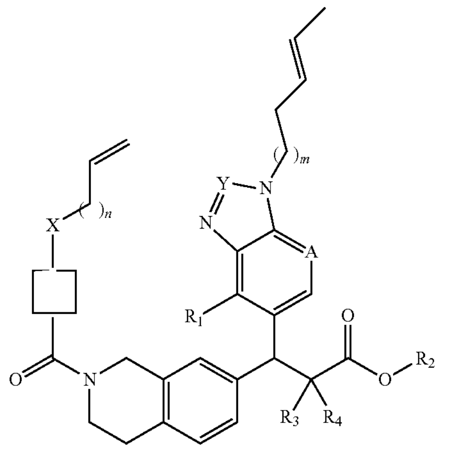

$R_1$ = H, Me, Cl, F
$R_2$ = H, Me, Bn
$R_3$, $R_4$ = H, Me X= O, $CH_2$
Y = N, CH n = 0, 1, 2
m = 0, 1 A = CH, N

The carboxylic acid (1 eq.), HATU (1 eq.) and $NEt_3$ (2-10 eq.) were dissolved in anhydrous DMF (0.05-0.2 M) and stirred for 10-60 minutes at rt. The amine HCl salt (1 eq.) (consisting of the terminal alkene and typically a minor amount of the migrated double bond isomer) was added and stirred at rt. for 1-18 hours. Water was added and the aqueous layer was extracted with EtOAc. The organic layers were combined, washed with brine (3×), dried over $Na_2SO_4$, filtered and concentrated under reduced pressure. The impure product was purified by flash column chromatography (silica, typically heptane/EtOAc=1:0→0:1) to obtain the desired amide typically the migrated double bond isomer as minor by-product.

General Procedure 7: Grubbs Metathesis

The variables shown in this scheme are specific to this general procedure.

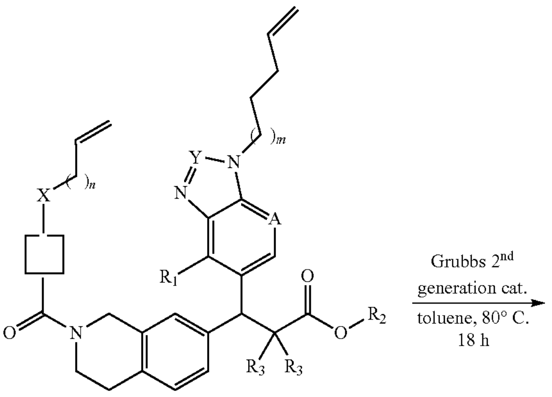

-continued

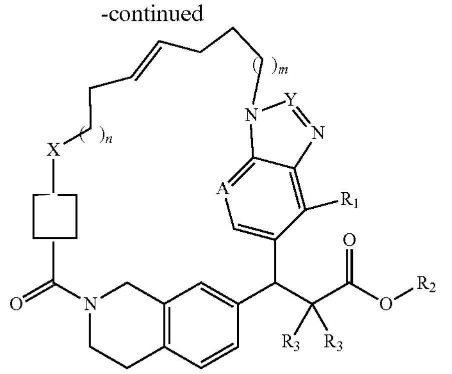

$R_1$ = H, Me, Cl, F
$R_2$ = H, Me, Bn
$R_3$, $R_4$ = H, Me
A = CH, N
n = 0, 1, 2
m = 0, 1
X = O, $CH_2$
Y = N, CH

The amide (1.0 eq.) (consisting of the terminal alkene and typically a minor amount of the migrated double bond isomer) was dissolved in anhydrous toluene (2.0-3.0 mM) and the solvent was degassed with nitrogen for 20 min. Grubbs 2$^{nd}$ generation catalyst (0.1 eq.) was added and the reaction mixture was stirred for 18 h at 80° C. The reaction mixture was concentrated under reduced pressure. The impure product was purified by flash column chromatography (silica, $CH_2Cl_2$/MeOH=1:0→9:1) to obtain the macrocycle (typically together with the one-carbon smaller analogue as by-product) as a brown foam.

General Procedure 8: Hydrogenation

The variables shown in this scheme are specific to this general procedure.

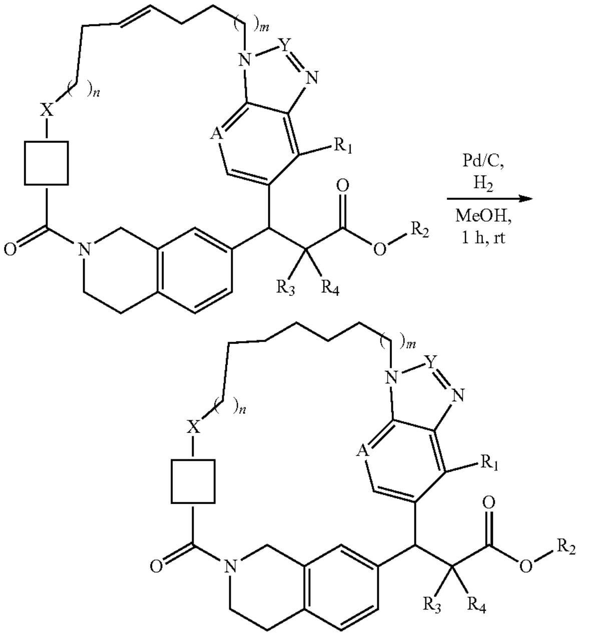

$R_1$ = H, Me, Cl $R_2$, $R_3$, $R_4$ = H, Me A = CH, N X = O, $CH_2$ Y = N, CH
n = 0, 1, 2 m = 0, 1

The unsaturated macrocycle (1.0 eq.) (typically contaminated with a minor amount of a one-carbon shorter macrocycle analogue) was dissolved in MeOH (0.05-0.2 M) under inert atmosphere. Pd/C (10% w/w, 0.1 eq.) was added and the reaction mixture was stirred under hydrogen atmosphere at rt. for 1-24 hours. The reaction mixture was filtered (nylon filter or celite) and the filtrate was concentrated under reduced pressure to obtain the saturated macrocycle (typically together with the one-carbon smaller analogue as by-product) as a brown oil.

General Procedure 9: Saponification

The variables shown in this scheme are specific to this general procedure.

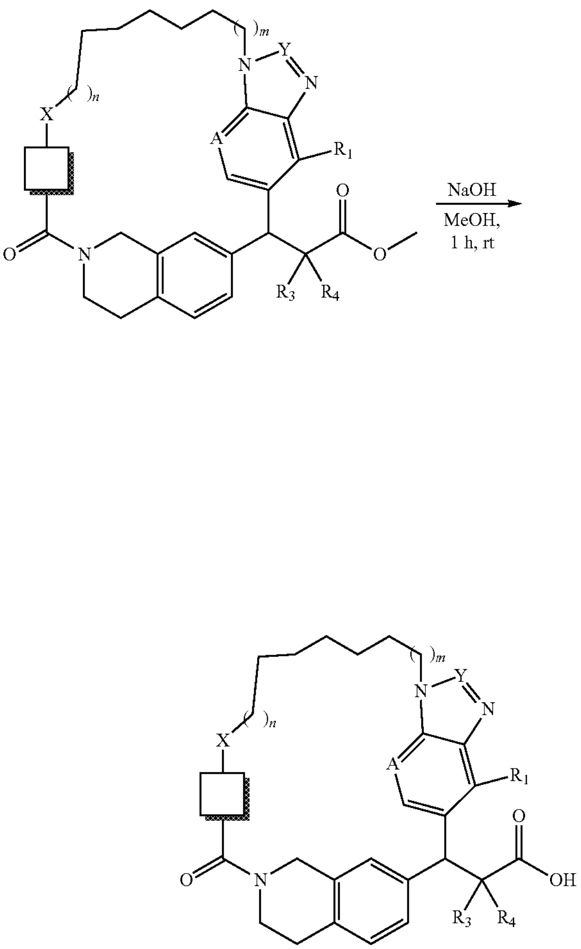

$R_1$ = H, Me, Cl X = O, $CH_2$ m = 0, 1 A = CH, N $R_2$, $R_3$, = H, Me Y = N, CH n = 0, 1, 2

The methyl ester (typically contaminated with a minor amount of a one-carbon shorter macrocycle analogue) was dissolved in MeOH (0.05-0.2 M) and aqueous NaOH (1 N; 3-10 eq.) was added and the reaction mixture was stirred at rt. for 1-18 hours. The reaction mixture was acidified with aqueous HCl (2N) until pH<5 and purified by preparative LC (acid or base) to obtain typically both the desired macrocycle carboxylic acids. The major and minor (one-carbon shorter) macrocycle analogues were separable by preparative LC and obtained as two different final compounds.

General Procedure 14: Amide Coupling

The variables shown in this scheme are specific to this general procedure.

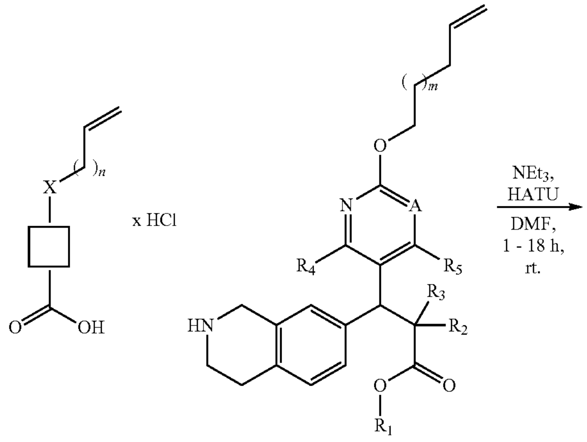

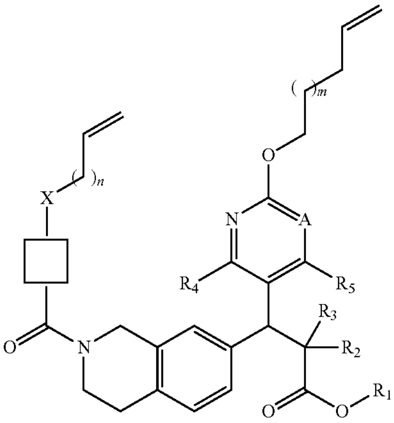

X = O, $CH_2$ $R_1$ = Me, Bn $R_2$, $R_3$, $R_4$, $R_5$ = H, Me A = CH or N m = 0 or 1 n = 0, 1, 2

The carboxylic acid (1.2 eq.), HATU (1.2 eq.) and $Et_3N$ (3-10 eq.) were dissolved in anhydrous DMF (0.05-0.2 M) and stirred for 10-60 minutes at room temperature. The amine HCl salt (1 eq.) (consisting of the terminal alkene and typically a minor amount of the migrated double bond isomer) was added and stirred at room temperature for 1-18 hours. Water was added and the aqueous layer was extracted with EtOAc. The organic layers were combined, washed with brine (3×), dried over $Na_2SO_4$, filtered and concentrated under reduced pressure. The impure product was purified by flash column chromatography (silica, typically heptane/EtOAc=1:0→0:1) to obtain the desired amide typically the migrated double bond isomer as minor by-product.

General Procedure 15: Grubbs Metathesis

The variables shown in this scheme are specific to this general procedure.

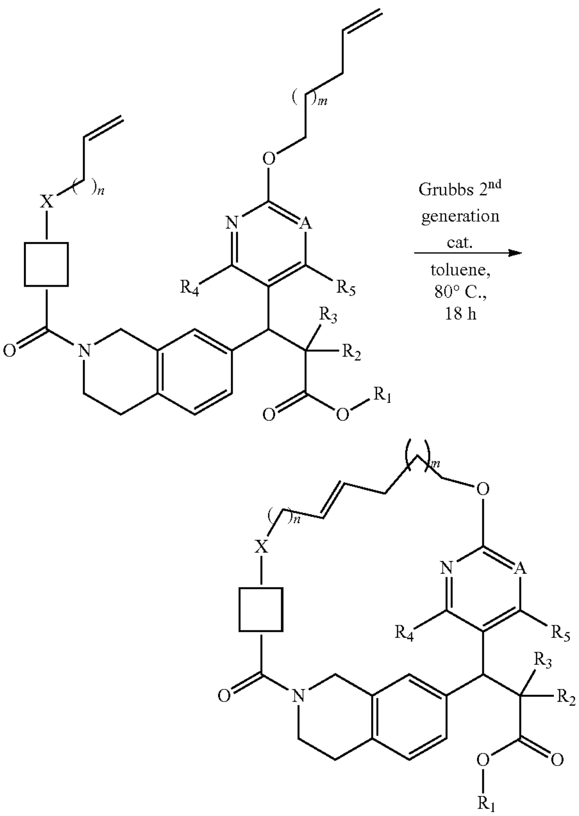

$R_2$, $R_3$, $R_4$, $R_5$ = H, Me X = O, $CH_2$ m = 0 or 1 $R_1$ = Me, Bn A = CH or N n = 0, 1, 2

The amide (1.0 eq.) (consisting of the terminal alkene and typically a minor amount of the migrated double bond isomer) was dissolved in anhydrous toluene (2.0-3.0 mM) and the solvent was degassed with nitrogen for 20 min. Grubbs $2^{nd}$ generation catalyst (0.1 eq.) was added and the reaction mixture was stirred for 18 h at 80° C. The reaction mixture was concentrated under reduced pressure. The impure product was purified by flash column chromatography (silica, $CH_2Cl_2$/MeOH=1:0→9:1) to obtain the macrocycle (typically together with the one-carbon smaller analogue as by-product) as a brown foam.

General Procedure 16: Hydrogenation

The variables shown in this scheme are specific to this general procedure.

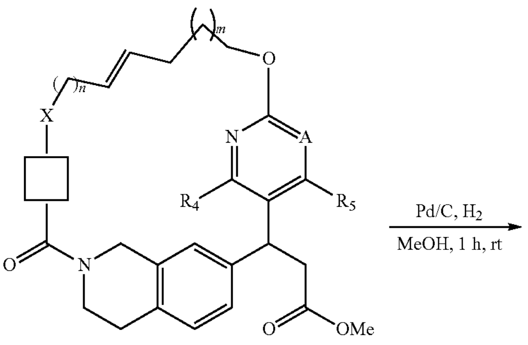

-continued

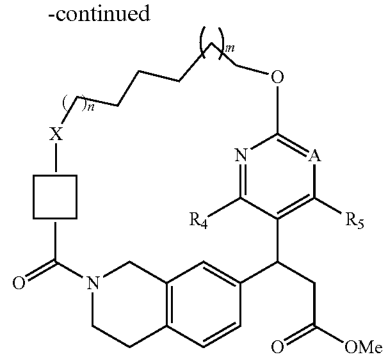

$R_4$, $R_5$ = H, Me X = O, $CH_2$ A = CH or N m = 0 or 1 n = 0, 1, 2

The unsaturated macrocycle (1.0 eq.) (typically contaminated with a minor amount of a one-carbon shorter macrocycle analogue) was dissolved in MeOH (0.05-0.2 M) under inert atmosphere. Pd/C (10% w/w, 0.1 eq.) was added and the reaction mixture was stirred under hydrogen atmosphere at room temperature for 1-5 hours. The reaction mixture was filtered (nylon filter or celite) and the filtrate was concentrated under reduced pressure to obtain the saturated macrocycle (typically together with the one-carbon smaller analogue as by-product) as a brown oil.

General Procedure 17: Saponification

The variables shown in this scheme are specific to this general procedure.

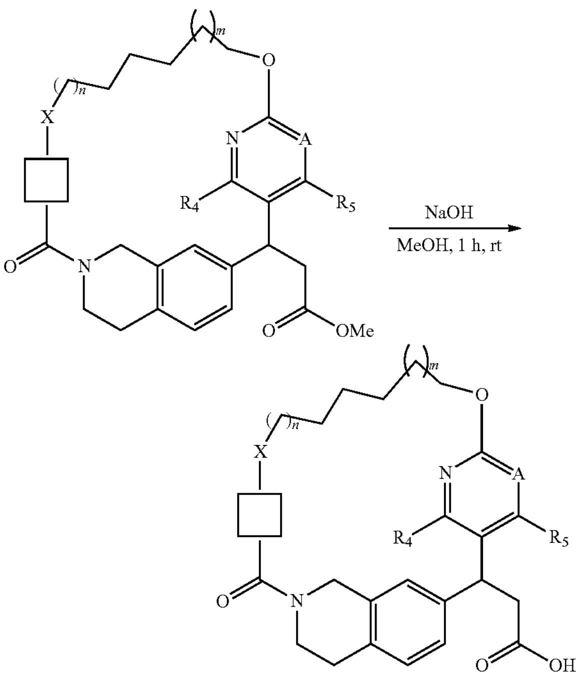

$R_4$, $R_5$ = H, Me X = O, $CH_2$ A = CH or N m = 0 or 1 n = 0, 1, 2

The methyl ester (typically contaminated with a minor amount of a one-carbon shorter macrocycle analogue) was dissolved in MeOH (0.05-0.2 M) and aqueous NaOH (1 N; 3-10 eq.) was added and the reaction mixture was stirred at room temperature for 1-18 hours. The reaction mixture was acidified with aqueous HCl (2 N) until pH<5 and purified by preparative LC (acid or base) to obtain typically both the desired macrocycle carboxylic acids. Note: The major and minor (one-carbon shorter) macrocycle analogues were separable by preparative LC and obtained as two different final compounds.

General Procedure 24: Mitsunobu Reaction

The variables shown in this scheme are specific to this general procedure.

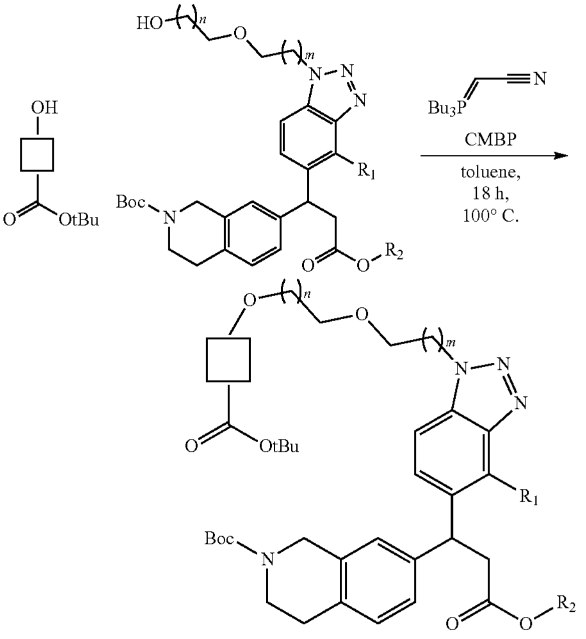

$R_1$ = H, Me $R_2$ = Me, Bn m, n = 1, 2

The benzotriazole alcohol (1.0 eq.) and hydroxy tert-butylbenzoate (1.1 eq.) were dissolved in anhydrous toluene (0.05-0.2 M) and degassed with argon for 20 min. Then cyanomethylenetributylphosphorane (1.4 eq.) was added and the mixture was stirred at reflux (115° C.) for 16 h. The reaction mixture was concentrated under reduced pressure. The impure product was purified using preparative HPLC (method: prep base) or flash column chromatography (silica, $CH_2Cl_2$/MeOH=1:0→9:1) obtain the di-ether.

General Procedure 39: Debenzylation and Alkene Reduction

The variables shown in this scheme are specific to this general procedure.

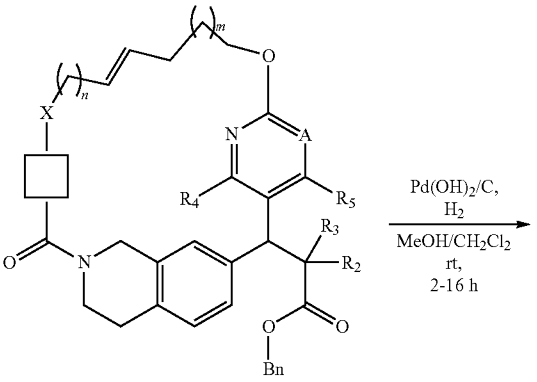

-continued

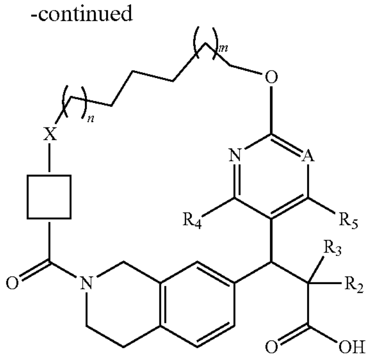

X = O, $CH_2$ $R_2$, $R_3$, $R_4$, $R_5$ = H, Me A = CH or N n = 0, 1, 2 m = 0 or 1

The unsaturated macrocycle (1.0 eq.) was dissolved in $MeOH/CH_2Cl_2$ (4:1, 0.05-0.2 M) and the solution was degassed with nitrogen. $Pd(OH)_2$ on carbon (0.1 eq.) was added and $H_2$ was bubbled through the suspension for 5 min. The reaction mixture was stirred for 2-16 h under hydrogen atmosphere at rt. The reaction mixture was filtered over celite and the filter was rinsed with $CH_2Cl_2$ and MeOH. The filtrate was concentrated and the residue was dissolved in a mixture of DMSO, MeOH and aqueous HCl (2M) and purified by preparative LC (acid or base) to obtain the desired macrocycle carboxylic acids.

General Procedure 70: Mitsunobu Reaction

The variables shown in this scheme are specific to this general procedure.

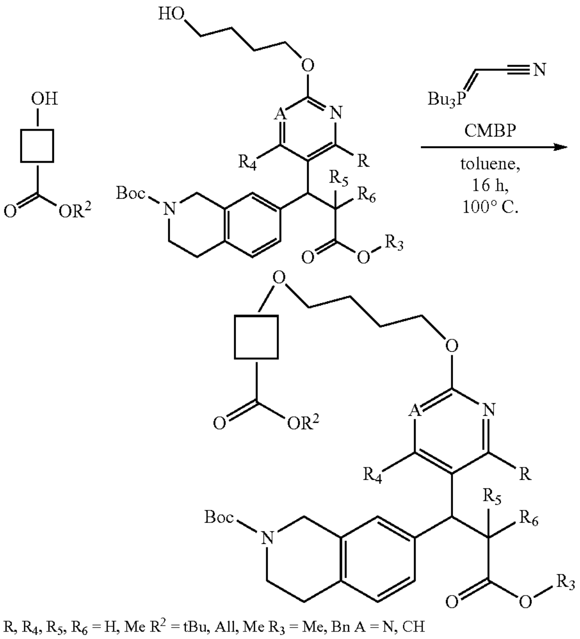

R, $R_4$, $R_5$, $R_6$ = H, Me $R^2$ = tBu, All, Me $R_3$ = Me, Bn A = N, CH

The Boc-protected THIQ core (1 eq.) and hydroxy tert-butylbenzoate (1.1 eq.) were dissolved in anhydrous toluene (0.05-0.2 M) and degassed with argon for 20 min. Then cyanomethylenetributylphosphorane (1.4 eq.) was added and the mixture was stirred at 100° C. for 16 h. The reaction mixture was concentrated under reduced pressure, then the crude was purified by flash column chromatography (silica, heptanes:EtOAc=1:0 to 0:1) to give, after evaporation, the product as a white solid.

General Procedure 71: Deprotection, Amide Coupling-Macrocyclization and Saponification The variables shown in this scheme are specific to this general procedure.

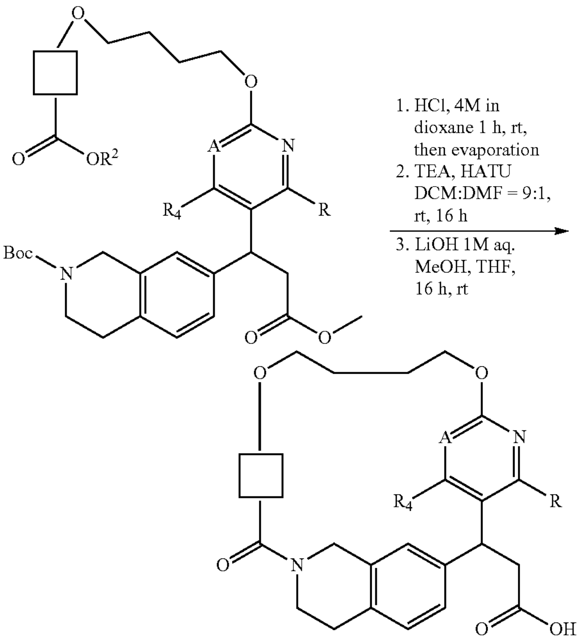

R, $R_4$, = H, Me $R^2$ = tBu, All, Me A = N, CH

Reactions were performed in the same reaction vessel, and the intermediates were not isolated.

Step 1: Simultaneous Deprotection of the Boc-Amine and $R^2$ ($R^2$=tBu, OAll, Me)-Carboxylate.

To the Boc-amine and tBu-carboxylate containing product in $CH_2Cl_2$ (0.1M) was added HCl (4 M in dioxane, 10-40 eq.) and the mixture was stirred at room temperature for 1 hour. The mixture was then concentrated under reduced pressure. In the case where $R^2$=All, the carboxylate was deprotected before the Boc, using $Pd(PPh_3)_4$ (0.15 eq.) and morpholine (10 eq.) in THF (0.1M). The reaction was run under nitrogen for 16 hours. The intermediate was purified via flash column chromatography (silica, DCM:MeOH=1:0 to 9:1). In the case where $R^2$=Me, the carboxylate was saponified before the Boc, using NaOH aq. (2.5 eq.) in MeOH (0.1M). The reaction was run at rt for 5 min. The intermediate mixture was then neutralized with HCl 2M (2.5 eq.), then evaporated and redissolved in DCM before Boc deprotection.

Step 2: Macrocyclization Via Amide Coupling.

The above mixture containing both the carboxylic acid and amine in the same substrate (1 eq.) was redissolved in $CH_2Cl_2$:DMF (20:1, 0.001M), and $NEt_3$ (3-10 eq.) was added. Then, HATU (1.1 eq.) was added and the mixture was stirred at rt for 16 hours. The reaction mixture was concentrated under reduced pressure, then the crude was used as such.

Step 3: Saponification

The above mixture was dissolved in MeOH:THF (4:1, 0.05-0.2 M) and was treated with aqueous LiOH (1M, 3-10 eq) and the mixture was stirred at rt for 1-18 hours. The reaction mixture was acidified with aqueous HCl (2 M) until pH<5 and purified by preparative HPLC (method: prep acid or prep base) to obtain the desired macrocyclic carboxylic acids.

General Procedure 86: Deprotection

The variables shown in this scheme are specific to this general procedure.

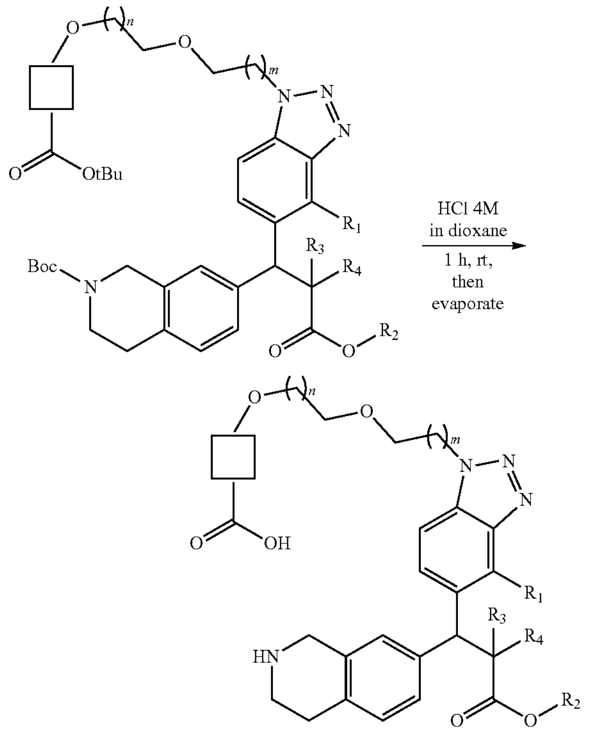

$R_1$, $R_3$, $R_4$ = H, Me $R_2$ = Me, Bn m, n = 1, 2

Simultaneous deprotection of the Boc-amine and tBu-carboxylate: To the Boc-amine and tBu-carboxylate containing input dissolved in $CH_2Cl_2$ (0.05-0.20 M) was added HCl (4 M in dioxane, 10-70 eq.) and the mixture was stirred at room temperature for 1-24 hours. The mixture was then concentrated under reduced pressure and twice stripped with $CH_2Cl_2$ to give the free amine and carboxylic acid.

General Procedure 90: Amide Coupling-Macrocyclization

The variables shown in this scheme are specific to this general procedure.

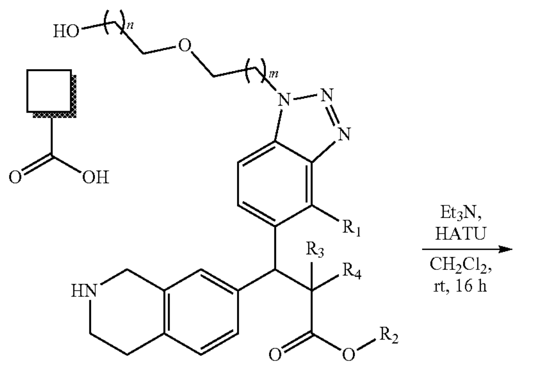

-continued

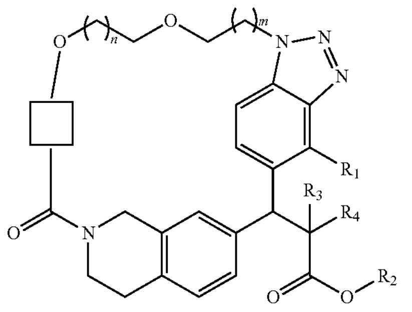

$R_1$, $R_3$, $R_4$ = H, Me $R_2$ = Me, Bn m, n = 1, 2

The carboxylic acid and amine in the same substrate (1 eq.) was dissolved in $CH_2Cl_2$ (0.01-0.05M), $NEt_3$ (3-10 eq.) and HATU (1 eq.) were added, and the formed reaction mixture was stirred at rt for 16 hours. Reaction mixture was concentrated under reduced pressure and the residue was purified by flash column chromatography (silica, $CH_2Cl_2$/MeOH=1:0→95:5). Desired fractions were combined and concentrated under reduced pressure to give the amide.

General Procedure 91: De-Benzylation

The variables shown in this scheme are specific to this general procedure.

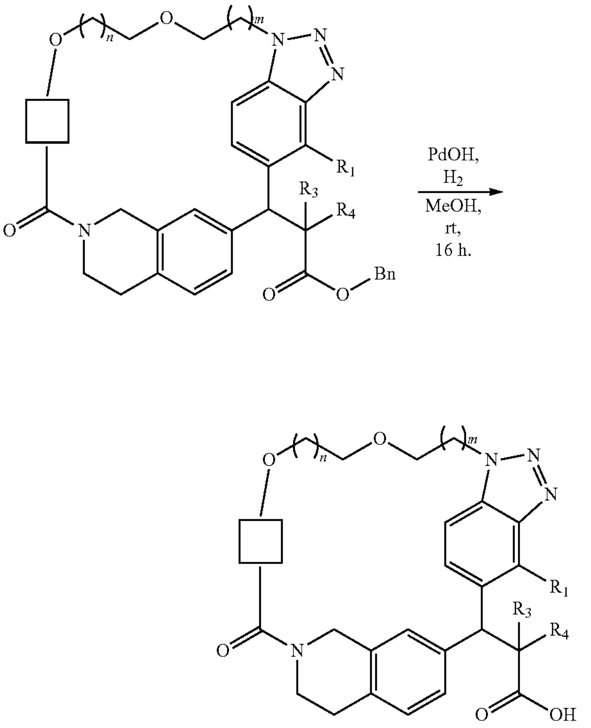

$R_1$, $R_3$, $R_4$ = H, Me m, n = 1, 2

The Amide (1 eq.) was dissolved in MeOH (0.01-0.2M) and flushed with $N_2$. PdOH (20%, 0.1 eq.) was added and the formed reaction mixture was stirred for 1-16 hours at rt. under $H_2$ atmosphere. The reaction mixture was filtered and purified by preparative HPLC (method: prep acid or prep base) to obtain the desired macrocyclic carboxylic acid.

Synthetic Example 1

2-(5,33-dimethyl-2-oxo-1,5,15,16,17-pentazaheptacyclo[22.5.3.26,9.118,22.03,7.015,19.027,31]pentatriaconta-3,6,8,16,18(33),19,21,24(32),25,27(31),34-undecaen-23-yl)acetic Acid (Compound 362)

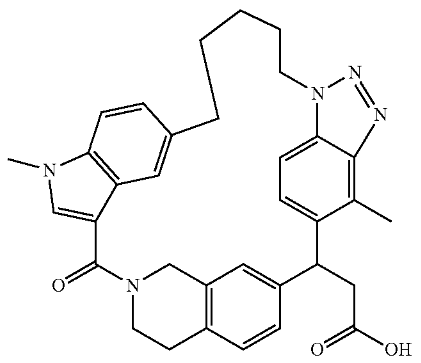 [SMILES: Cc1c2ccc3c1nnn3CCCCCc1ccc3c(c1)c(cn3C)C(=O)N1CCc3ccc(cc3C1)C2CC(=O)O]

Details: The title compound was prepared in 4 steps:

Step 1: Starting from methyl 3-(4-methyl-1-(pent-4-en-1-yl)-1H-benzo[d][1,2,3]triazol-5-yl)-3-(1,2,3,4-tetrahydroisoquinolin-7-yl)propanoate dihydrochloride (200 mg, 0.407 mmol) and 1-methyl-5-vinyl-1H-indole-3-carboxylic acid (98 mg, 0.488 mmol) following procedure General procedure 6B: Amide coupling to obtain the corresponding amide (250 mg, 0.253 mmol, 95%).

Step 2: Following General procedure 7: Grubbs metathesis to obtain the unsaturated macrocycle (100 mg, 0.163 mmol, y: 65%, py: 93.6%).

Step 3: Following General procedure 8: Hydrogenation to obtain the corresponding saturated macrocycle (100 mg, 0.162 mmol, y: 93%, py: 93.2%).

Step 4: Following General procedure 9: Saponification to obtain the title compound (15.0 mg, 0.027 mmol, 15%) as a white solid.

Yield: The final compound was isolated as a white solid (15.0 mg, 0.027 mmol, 8.6% over 4 steps)

Analysis: LCMS (Method N): $t_R$=1.49 min; m/z calculated for $[M+H]^+$=562.2. found=562.4. $^1$H NMR (400 MHz, DMSO-d6) δ 12.17 (bs, 1H), 7.62 (s, 1H), 7.49 (d, J=8.7 Hz, 1H), 7.38-7.29 (m, 2H), 7.26-7.12 (m, 2H), 7.02 (dd, J=8.4, 1.6 Hz, 1H), 6.95 (s, 1H), 6.15 (bs, 1H), 4.80-4.55 (m, 3H), 4.55-4.35 (m, 2H), 3.83-3.71 (m, 4H), 3.70-3.59 (m, 1H), 3.11 (dd, J=16.0, 6.9 Hz, 1H), 2.95 (dd, J=16.0, 8.8 Hz, 1H), 2.83 (q, J=5.6 Hz, 2H), 2.65 (s, 3H), 2.48-2.30 (m, 2H), 2.11-1.85 (m, 2H), 1.68-1.34 (m, 2H), 0.88-0.61 (m, 2H).

Synthetic Example 2

2-(34-methyl-22-oxo-17-oxa-8,9,10,19,23,32-hexazahexacyclo[21.5.3.218,21.13,7.06,10.026,30]tetratriaconta-1(29),3,5,7(34),8,18,20,26(30),27,32-decaen-2-yl)acetic Acid (Compound 379)

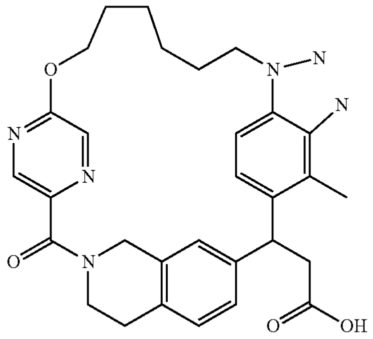 [SMILES: Cc1c2ccc(c1N)N(N)CCCCCCOc1cnc(cn1)C(=O)N1CCc3ccc(cc3C1)C2CC(=O)O]

Details: The title compound was prepared in 4 steps:

Step 1: Starting from methyl 3-(1-(but-3-en-1-yl)-4-methyl-1H-benzo[d][1,2,3]triazol-5-yl)-3-(1,2,3,4-tetrahydroisoquinolin-7-yl)propanoate dihydrochloride (200 mg, 0.419 mmol and 5-(but-3-en-1-yloxy)pyrazine-2-carboxylic acid following procedure General procedure 6B: Amide coupling to obtain the corresponding amide (158 mg, 0.272 mmol, 65%).

Step 2: Following General procedure 7: Grubbs metathesis to obtain the corresponding (major) crude unsaturated macrocycle (64 mg, 0.12 mmol, 42%).

Step 3: Following General procedure 8: Hydrogenation to obtain the corresponding saturated crude macrocycle. Product was used as if 100% conversion was reached.

Step 4: Following General procedure 9: Saponification to obtain the title compound (23.1 mg, 0.042 mmol, 55%) as a white solid.

Yield: The final compound was isolated as a white solid (23.1 mg, 0.042 mmol, 10% over 4 steps)

Analysis: LCMS (Method T): $t_R$=0.967 min; m/z calculated for $[M+H]^+$=540.3. found=541.4; 1H NMR (400 MHz, DMSO) δ 8.19-8.14 (m, 2H), 7.60 (q, J=8.7 Hz, 2H), 7.31 (dd, J=8.0, 1.8 Hz, 1H), 7.10 (d, J=7.8 Hz, 1H), 6.40 (d, J=1.9 Hz, 1H), 4.78-4.62 (m, 3H), 4.62-4.54 (m, 1H), 4.39 (d, J=16.8 Hz, 1H), 4.30-4.21 (m, 1H), 4.21-4.12 (m, 1H), 4.09 (d, J=16.8 Hz, 1H), 3.42-3.34 (m, OH), 3.03-2.89 (m, 2H), 2.84-2.76 (m, 2H), 2.55-2.51 (m, 4H), 1.89-1.67 (m, 2H), 1.56-1.35 (m, 2H), 1.32-1.07 (m, 3H), 0.87-0.72 (m, 1H).

Synthetic Example 3

2-(20,32-difluoro-34-methyl-22-oxo-14,17-dioxa-8,9,10,23-tetrazahexacyclo[21.5.3.218,21.13,7.06,10.026,30]tetratriaconta-1(29),3(34),4,6,8,18(33),19,21(32),26(30),27-decaen-2-yl)acetic Acid (Compound 368)

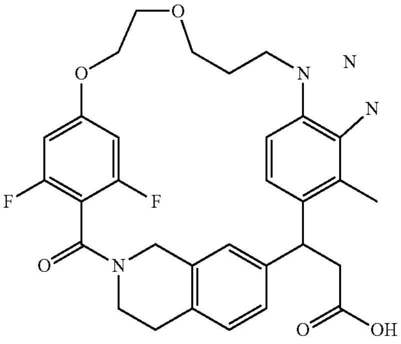

Details: The title compound was prepared in 4 steps:

Step 1: Starting from tert-butyl 7-(3-(benzyloxy)-1-(1-(3-(2-hydroxyethoxy)propyl)-4-methyl-1H-benzo[d][1,2,3]triazol-5-yl)-3-oxopropyl)-3,4-dihydroisoquinoline-2(1H)-carboxylate (1.5 g, 2.386 mmol) and tert-butyl 2,6-difluoro-4-hydroxybenzoate following General procedure 24: Mitsunobu reaction with flash column chromatography purification ($CH_2Cl_2$/MeOH=1: 0→97:3) to obtain the corresponding di-ether (1.73 g, 1.646 mmol, py: 80%, y: 69%).

Step 2: Following General procedure 86: Deprotection starting with 100 mg, 0.119 mmol of the di-ether to obtain the free amino acid (81 mg, 0.119 mmol, 100%).

Step 3: Following General procedure 90: Amide coupling-macrocyclization. Some extra $Et_3N$ (5.0 eq.) and HATU (0.5 eq.) were added to obtain the amide (26 mg, 0.035 mmol, py: 90%, y: 30%) as a beige oil.

Step 4: Following General procedure 91: De-benzylation with a total of 0.7 eq. of palladium hydroxide on carbon with prep acid to obtain the title macrocycle (3.45 mg, 0.006 mmol, 15%) as a white solid.

Yield: The final compound was isolated as a white solid (3.45 mg, 0.006 mmol, 3.1% over 4 steps) Analysis: LCMS (Method R): $t_R$=1.38 min; m/z calculated for $[M+H]^+$ =577.2. found=577.4. $^1$H NMR (400 MHz, DMSO) δ 7.62 (d, J=8.7 Hz, 1H), 7.39 (d, J=8.7 Hz, 1H), 7.34 (d, J=7.8 Hz, 1H), 7.14 (d, J=7.8 Hz, 1H), 6.71 (d, J=10.9 Hz, 1H), 6.42 (d, J=10.8 Hz, 1H), 6.23 (s, 1H), 4.79-4.66 (m, 3H), 4.20-4.08 (m, 3H), 4.05-3.90 (m, 2H), 3.74-3.62 (m, 2H), 3.63-3.52 (m, 3H), 3.05-2.85 (m, 2H), 2.83 (t, J=6.4 Hz, 2H), 2.53 (s, 3H), 2.14 (p, J=6.8 Hz, 2H).

Synthetic Example 4

2-[(12E)-20-oxo-15-oxa-8,9,10,21-tetrazahexacyclo[19.5.3.216,19.13,7.06,10.024,28] dotriaconta-1(27),3,5,7(32),8,12,16(31),17,19(30),24(28),25-undecaen-2-yl]acetic Acid (Compound 419)

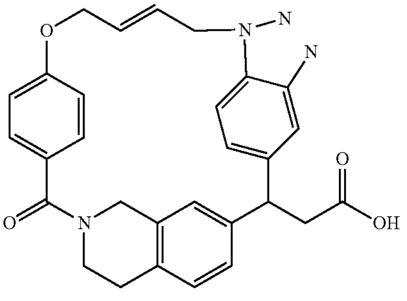 [SMILES: Nc1cc2ccc1N(N)C/C=C/COc1ccc(cc1)C(=O)N1CCc3ccc(cc3C1)C2CC(=O)O]

Details: The title compound was prepared in 3 steps:

Step 1: Starting from methyl 3-(1-(but-3-en-1-yl)-1H-benzo[d][1,2,3]triazol-5-yl)-3-(1,2,3,4-tetrahydroisoquinolin-7-yl)propanoate dihydrochloride (287 mg, 0.62 mmol) and 4-(allyloxy)benzoic acid following procedure General procedure 6B: Amide coupling to obtain the corresponding amide (240 mg, 0.62 mmol, 100%).

Step 2: Following General procedure 7: Grubbs metathesis to obtain the unsaturated macrocycle (150 mg, 0.29 mmol, 47%).

Step 3: Following General procedure 9: Saponification in MeCN instead of MeOH to obtain the title compound (minor macrocycle, 7.8 mg, 0.016 mmol, 12%) as a white solid as a 3:1 mixture of the E and Z isomers.

Yield: The final compound was isolated as a white solid (7.8 mg, 0.016 mmol, 5.6% over 3 steps). Analysis: LCMS (Method J): $t_R$=2.32 min; m/z calculated for $[M+H]^+$=495.2. found=495.1. $^1$H NMR (400 MHz, DMSO-$d_6$) δ 12.25 (s, 1H), 7.90 (s, 1H), 7.70 (d, J=8.6 Hz, 1H), 7.31 (d, J=7.7 Hz, 1H), 7.25 (d, J=9.0 Hz, 1H), 7.12 (d, J=7.9 Hz, 1H), 6.81 (d, J=8.6 Hz, 2H), 6.67 (d, J=8.6 Hz, 2H), 5.98 (d, J=1.9 Hz, 1H), 5.94-5.79 (m, 2H), 5.52-5.35 (m, 2H), 4.72 (q, J=16.8 Hz, 2H), 4.60 (t, J=7.8 Hz, 1H), 4.17-4.04 (m, 2H), 3.99 (d, J=16.4 Hz, 1H), 3.51 (dt, J=13.9, 7.3 Hz, 1H), 3.03 (qd, J=15.7, 7.6 Hz, 2H), 2.92-2.76 (m, 2H).

Synthetic Example 5

2-[(2R)-33-methyl-21-oxo-8,10,22-triazahexacyclo[20.5.3.217,20.13,7.06,10.025,29] tritriaconta-1(28),3,5,7(33),8,17(32),18,20(31),25(29),26-decaen-2-yl] acetic Acid (Compound 385)

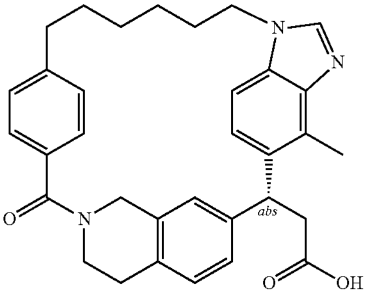 [SMILES: Cc1c2ccc3c1ncn3CCCCCCc1ccc(cc1)C(=O)N1CCc3ccc(cc3C1)[C@H]2CC(=O)O]

Details: The title compound was prepared in 4 steps:

Step 1: Starting from rel-methyl (R)-3-(1-(hex-5-en-1-yl)-4-methyl-1H-benzo[d]imidazol-5-yl)-3-(1,2,3,4-tetrahydroisoquinolin-7-yl)propanoate trihydrochloride (obtain from the second eluting enantiomer of the building block, 0.285 g, 0.527 mmol) and 4-vinylbenzoic acid following procedure General procedure 6B: Amide coupling to obtain the corresponding amide (90 mg, 0.146 mmol, 27%).

Step 2: Following General procedure 7: Grubbs metathesis, with an extra portion of Grubbs $2^{nd}$ generation catalyst and 2 days of stirring, to obtain the unsaturated macrocycle (25 mg, 0.044 mmol, 27%).

Step 3: Following General procedure 8: Hydrogenation to obtain the corresponding saturated macrocycle (27 mg, 0.048 mmol, 100%).

Step 4: Following General procedure 9: Saponification, with 4N aqeuous NaOH and 5 days of stirring to obtain the title compound (minor analogue, 7.8 mg, 0.013 mmol, 27%) as a white solid.

Yield: The final compound was isolated as a white solid (7.8 mg, 0.013 mmol, 2.0% over 4 steps). Analysis: LCMS (Method R): $t_R$=1.06 min; m/z calculated for $[M+H]^+$=522.3. found=522.4; 1H NMR (400 MHz, DMSO-d6) δ 8.06 (s, 1H), 7.35-7.24 (m, 2H), 7.18-7.04 (m, 4H), 7.01 (d, J=7.9 Hz, 2H), 6.05 (s, 1H), 4.70 (t, 1H), 4.35-4.24 (m, 2H), 4.16-4.02 (m, 3H), 3.51 (dt, J=13.0, 6.7 Hz, 1H), 2.98-2.82 (m, 2H), 2.77 (t, J=6.0 Hz, 2H), 2.69-2.58 (m, 1H), 2.39 (s, 3H), 1.73-1.48 (m, 3H), 1.28-1.00 (m, 3H), 0.74-0.61 (m, 1H), 0.57-0.42 (m, 1H).

Synthetic Example 6

2-(4-oxo-31,32,33,34-tetrahydro-6,11-dioxa-3(7,2)-isoquinolina-1(5,2)-pyridina-5(1,4)-benzenacycloundecaphane-2-yl)acetic Acid (compound 211)

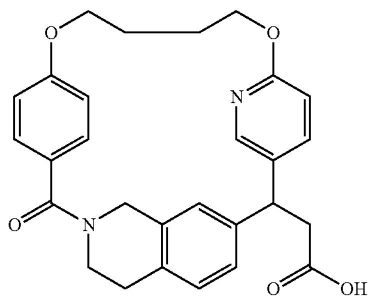 [SMILES: O=C(O)CC1c2ccc(nc2)OCCCCOc2ccc(cc2)C(=O)N2CCc3ccc1cc3C2]

Details: The title compound was prepared in 2 steps:

Step 1: Starting from tert-butyl 7-(1-(6-(4-(4-(tert-butoxycarbonyl)phenoxy)butoxy)pyridin-3-yl)-3-methoxy-3-oxopropyl)-3,4-dihydroisoquinoline-2(1H)-carboxylate (200 mg, 0.413 mmol) and tert-butyl 4-hydroxybenzoate following General procedure 70: Mitsunobu reaction to obtain the corresponding product (260 mg, 0.390 mmol, 94%).

Step 2: Following General procedure 71: Deprotection, amide coupling-macrocyclization and saponification to obtain the title macrocycle (15 mg, 0.031 mmol, 7.8%) as a white solid.

Yield: The final compound was isolated as a white solid (15 mg, 0.031 mmol, 7.3% over 2 steps) Analysis: LCMS (Method T): $t_R$=0.988 min; m/z calculated for $[M+H]^+$=473.2. found=473.4. $^1H$ NMR (400 MHz, DMSO-$d_6$) δ 12.23 (s, 1H), 8.10 (d, J=2.4 Hz, 1H), 7.44 (dd, J=8.7, 2.5 Hz, 1H), 7.28 (dd, J=7.8, 1.8 Hz, 1H), 7.13 (d, J=7.7 Hz, 1H), 6.83 (d, J=8.4 Hz, 2H), 6.72 (d, J=8.5 Hz, 1H), 6.56 (d, J=8.4 Hz, 2H), 6.43 (s, 1H), 4.48 (dp, J=21.8, 5.6 Hz, 2H), 4.36 (t, J=7.9 Hz, 1H), 4.17 (d, J=3.8 Hz, 2H), 4.12 (t, J=7.5 Hz, 2H), 3.90 (dt, J=13.0, 6.5 Hz, 1H), 3.70 (dt, J=13.2, 6.9 Hz, 1H), 2.96 (d, J=8.0 Hz, 2H), 2.88 (t, J=6.7 Hz, 2H), 1.76 (th, J=13.4, 6.9, 6.0 Hz, 4H).

Synthetic Example 7

2-(2-oxo-12-oxa-1,14,28-triazapentacyclo[16.5.3.23,6.213,16.021,25]triaconta-3,5,13(28),14,16(27),18(26),19,21(25),29-nonaen-17-yl)acetic Acid (Compound 277)

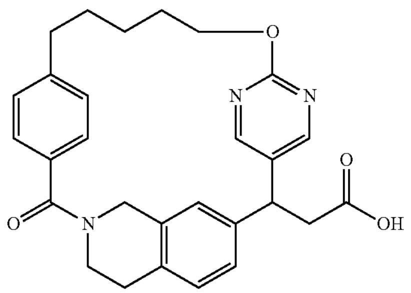

Details: The title compound was prepared in 4 steps:

Step 1: Starting from 7-(3-methoxy-3-oxo-1-(2-(pent-4-en-1-yloxy)pyrimidin-5-yl)propyl)-1,2,3,4-tetrahydroisoquinolin-2-ium chloride (350 mg, 0.837 mmol) and 4-vinylbenzoic acid following procedure General procedure 14: Amide coupling to obtain the corresponding amide (270 mg, 0.528 mmol, 63%).

Step 2: Following General procedure 15: Grubbs metathesis to obtain the corresponding (major) unsaturated macrocycle (141 mg, 0.108 mmol, 20%).

Step 3: Following General procedure 16: Hydrogenation to obtain the corresponding saturated macrocycle (130 mg, 0.088 mmol, 82%)

Step 4: Following General procedure 17: Saponification some DCM was added for solubility, with prep acid to obtain the title compound (15.5 mg, 0.033 mmol, 37%) as a white solid.

Yield: The final compound was isolated as a white solid (15.5 mg, 0.033 mmol, 3.8% over 4 steps) Analysis: LCMS (Method H): $t_R$=3.33 min; m/z calculated for $[M+H]^+$=472.2. found=472.4; 1H NMR (400 MHz, DMSO-d6) δ 12.34 (s, 1H), 8.37 (s, 2H), 7.31-7.16 (m, 1H), 7.13 (d, J=7.8 Hz, 1H), 7.03 (q, J=8.0 Hz, 4H), 6.10 (s, 1H), 4.48 (dt, J=11.0, 5.4 Hz, 1H), 4.44-4.31 (m, 2H), 4.26 (d, J=16.2 Hz, 1H), 4.12 (d, J=16.2 Hz, 1H), 4.04 (dt, J=12.3, 5.9 Hz, 1H), 3.60 (dt, J=13.5, 7.0 Hz, 1H), 2.96 (dt, J=16.4, 8.1 Hz, 2H), 2.90-2.77 (m, 2H), 2.62 (q, J=7.3, 6.9 Hz, 2H), 1.75 (t, J=7.4 Hz, 2H), 1.70-1.45 (m, 2H), 1.19 (td, J=15.3, 14.2, 6.3 Hz, 2H).

Synthetic Example 8

2-(33-methyl-2-oxo-15-oxa-1,7,17,33-tetrazahexacyclo[19.5.3.216,19.13,6.15,9.024,28] tritriaconta-3,5,7,9(32),16,18,21(29),22,24(28),30-decaen-20-yl) acetic Acid (Compound 158)

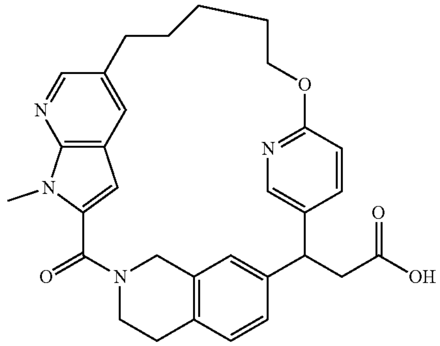 [SMILES: Cn1c2cc3cc(cnc31)CCCCCOc1ccc(cn1)C(CC(=O)O)c1ccc3c(c1)CN(CC3)C2=O]

Details: The title compound was prepared in 3 steps:

Step 1: Starting from benzyl 3-(6-(pent-4-en-1-yloxy) pyridin-3-yl)-3-(1,2,3,4-tetrahydroisoquinolin-7-yl) propanoate hydrochloride (192 mg, 0.363 mmol) and 1-methyl-5-vinyl-1H-pyrrolo[2,3-b]pyridine-2-carboxylic acid (88 mg, 0.435 mmol) following procedure General procedure 14: Amide coupling to obtain the corresponding amide (86 mg, 0.134 mmol, 37%).

Step 2: Following General procedure 15: Grubbs metathesis to obtain the corresponding (major) unsaturated macrocycle (63 mg, 0.068 mmol, y: 51%).

Step 3: Following General procedure 39: Debenzylation and alkene reduction with Pd/C and purification via preparative HPLC (method: prep acid) to yield the compound as a racemic mixture (4.63 mg, 0.0086 mmol, 8%).

Yield: The final compound was isolated as a white solid (4.63 mg, 0.0086 mmol, 2% over 3 steps). Analysis: LCMS (Method T): $t_R$=1.08 min; m/z calculated for $[M+H]^+$=525.2. found=525.4. $^1H$ NMR (400 MHz, DMSO) δ 8.18 (d, J=2.0 Hz, 1H), 8.06 (d, J=2.5 Hz, 1H), 7.49 (d, J=2.0 Hz, 1H), 7.39 (dd, J=8.5, 2.5 Hz, 1H), 7.30 (d, J=7.8 Hz, 1H), 7.18 (d, J=7.8 Hz, 1H), 6.72 (d, J=8.5 Hz, 1H), 6.54 (s, 1H), 5.85 (s, 1H), 4.49 (s, 2H), 4.44-4.31 (m, 2H), 4.24-4.15 (m, 1H), 4.14-4.04 (m, 1H), 3.81-3.71 (m, 5H), 2.96-2.82 (m, 4H), 2.72 (t, J=6.2 Hz, 2H), 1.84-1.63 (m, 4H), 1.33-1.25 (m, 2H).

Synthetic Example 9

2-[(2S)-33-methyl-21-oxo-8,9,10,22-tetrazahexacyclo[20.5.3.217,20.13,7.06,10.025,29] tritriaconta-1(28),3,5,7(33),8,17(32),18,20(31),25(29),26-decaen-2-yl]acetic Acid (Compound 223)

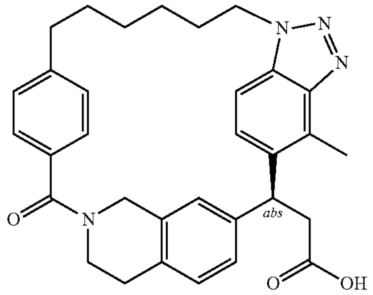 [SMILES: Cc1c2ccc3c1nnn3CCCCCCc1ccc(cc1)C(=O)N1CCc3ccc(cc3C1)[C@@H]2CC(=O)O]

Details: The title compound was prepared in 4 steps:

Step 1: Starting from rel-methyl (S)-3-(4-methyl-1-(pent-4-en-1-yl)-1H-benzo[d][1,2,3]triazol-5-yl)-3-(1,2,3,4-tetrahydroisoquinolin-7-yl)propanoate dihydrochloride (obtain from the first eluting enantiomer of the building block, 564 mg, 1.15 mmol) and 4-allylbenzoic acid following procedure General procedure 6B: Amide coupling to obtain the corresponding amide (510 mg, 0.91 mmol, 79%).

Step 2: Following General procedure 7: Grubbs metathesis to obtain the unsaturated macrocycle (480 mg, 0.90 mmol, 99%).

Step 3: Following General procedure 8: Hydrogenation to obtain the corresponding saturated macrocycle (480 mg, 0.89 mmol, 100%).

Step 4: Following General procedure 9: Saponification to obtain the title compound (major analogue, 126 mg, 0.24 mmol, 27%) as a white solid.

Yield: The final compound was isolated as a white solid (126 mg, 0.24 mmol, 21% over 4 steps). Analysis: LCMS (Method H): $t_R$=3.12 min; m/z calculated for $[M+H]^+$=523.3, found=523.4; chiral SFC method IC isocratic: ee=100%; $t_{R(major)}$=6.15 min, $t_{R(minor)}$=8.31 min; 1H NMR (400 MHz, DMSO-d6) δ 12.30 (s, 1H), 7.58 (d, J=8.6 Hz, 1H), 7.35-7.28 (m, 2H), 7.18-7.06 (m, 3H), 6.96 (d, J=7.8 Hz, 2H), 6.04 (d, J=1.9 Hz, 1H), 4.80-4.69 (m, 2H), 4.64 (ddd, J=14.3, 11.4, 3.2 Hz, 1H), 4.23 (d, J=16.7 Hz, 1H), 4.13 (d, J=16.6 Hz, 1H), 3.89 (dt, J=11.8, 5.7 Hz, 1H), 3.70 (dt, J=12.7, 6.3 Hz, 1H), 3.06 (dd, J=15.8, 6.8 Hz, 1H), 2.91 (dd, J=15.7, 8.8 Hz, 1H), 2.79 (t, J=6.1 Hz, 2H), 2.64-2.54 (m, 4H), 2.37-2.23 (m, 1H), 1.86-1.76 (m, 1H), 1.73-1.59 (m, 1H), 1.59-1.43 (m, 1H), 1.33-1.00 (m, 3H), 0.75-0.59 (m, 1H), 0.56-0.40 (m, 1H).

Synthetic Example 10

(2S)-2-[(17S)-2-oxo-12-oxa-1,14-diazapentacyclo[16.5.3.23,6.213,16.021,25]triaconta-3,5,13,15,18(26),19,21(25),27,29-nonaen-17-yl]propanoic acid (Compound 127)

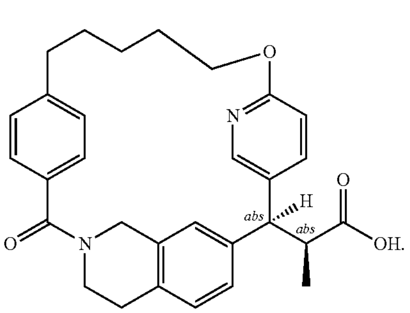 [SMILES: C[C@H](C(=O)O)[C@@H]1c2ccc(nc2)OCCCCCc2ccc(cc2)C(=O)N2CCc3ccc1cc3C2]

Details: The title compound was prepared in 3 steps:

Step 1: Starting from benzyl 2-methyl-3-(6-(pent-4-en-1-yloxy)pyridin-3-yl)-3-(1,2,3,4-tetrahydroisoquinolin-7-yl)propanoate hydrochloride (444 mg, 0.876 mmol) and 4-vinylbenzoic acid following procedure General Procedure 14: Amide coupling to obtain the corresponding amide (440 mg, 0.718 mmol, 82%).

Step 2: Following General Procedure 15: Grubbs metathesis to obtain the corresponding (major) unsaturated macrocycle (520 mg, 0.908 mmol, py unknown, y: 124%).

Step 3: Following General procedure 39: Debenzylation and alkene reduction with Pd/C and purification via preparative HPLC (method: prep acid) to obtain the diastereoisomeric mixture. With preparative HPLC (method: prep acid 2) the syn- and anti-product were separated giving the corresponding macrocycle carboxylic acid (4.41 mg, 0.0087 mmol, 1%) as first eluting product.

Yield: The final compound was isolated as a white solid (4.41 mg, 0.0087 mmol, 10% over 3 steps). Structure is assumed, based on separation as the first eluting product. Analysis: LCMS (Method H): $t_R$=3.72 min; m/z calculated for $[M+H]^+$=485.2. found=485.4. $^1H$ NMR (400 MHz, DMSO) δ 8.10 (d, J=2.6 Hz, 1H), 7.29-7.18 (m, 2H), 7.09 (d, J=7.8 Hz, 1H), 6.98 (q, J=8.0 Hz, 4H), 6.56 (d, J=8.4 Hz, 1H), 6.30 (s, 1H), 4.62-4.52 (m, 1H), 4.34 (d, J=16.3 Hz, 1H), 4.30-4.20 (m, 1H), 4.18-4.05 (m, 2H), 3.94 (d, J=11.4 Hz, 1H), 3.47-3.42 (m, 1H), 3.09-2.99 (m, 1H), 2.92-2.76 (m, 2H), 2.70-2.61 (m, 1H), 2.61-2.53 (m, 1H), 1.85-1.47 (m, 4H), 1.20 (p, J=7.5 Hz, 2H), 1.01 (d, J=6.8 Hz, 3H).

Synthetic Example 11

2-(27-methyl-2-oxo-12-oxa-1,14-diazapentacyclo[16.5.3.23,6.213,16.021,25]triaconta-3,5,13,15,18(26),19,21(25),27,29-nonaen-17-yl)acetic Acid (Compound 80)

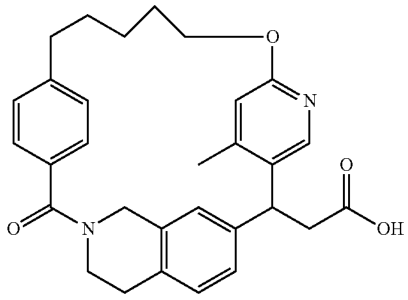 [SMILES: Cc1cc2ncc1C(CC(=O)O)c1ccc3c(c1)CN(CC3)C(=O)c1ccc(cc1)CCCCCO2]

Details: The title compound was prepared in 4 steps:

Step 1: Starting from methyl 3-(4-methyl-6-(pent-4-en-1-yloxy)pyridin-3-yl)-3-(1,2,3,4-tetrahydroisoquinolin-7-yl)propanoate dihydrochloride (200 mg, 0.428 mmol) and 4-vinylbenzoic acid following procedure General Procedure 14: Amide coupling to obtain the corresponding amide (114 mg, 0.217 mmol, 51%).

Step 2: Following General Procedure 15: Grubbs metathesis to obtain the unsaturated macrocycle (69 mg, 0.139 mmol, 64%).

Step 3: Following General Procedure 16: Hydrogenation to obtain the corresponding saturated macrocycle (55 mg, 0.110 mmol, 79%)

Step 4: Following General Procedure 17: Saponification in MeOH/DMSO instead of MeOH to obtain the title compound (39 mg, 0.080 mmol, 72%) as a white solid.

Yield: The final compound was isolated as a white solid (39 mg, 0.080 mmol, 19% over 4 steps). Analysis: LCMS (Method R): $t_R$=1.60 min; m/z calculated for $[M+H]^+$=485.2. found=485.4; 1H NMR (400 MHz, DMSO) δ 12.24 (s, 1H), 8.00 (s, 1H), 7.27 (dd, J=7.8, 1.9 Hz, 1H), 7.10 (d, J=7.8 Hz, 1H), 7.06 (d, J=7.9 Hz, 2H), 6.99 (d, J=7.9 Hz, 2H), 6.51 (s, 1H), 6.11 (d, J=1.8 Hz, 1H), 4.79 (ddd, J=11.5, 8.3, 3.4 Hz, 1H), 4.40 (t, J=7.9 Hz, 1H), 4.26 (d, J=16.1 Hz, 1H), 4.19 (dt, J=12.1, 5.6 Hz, 1H), 4.00 (d, J=16.1 Hz, 1H), 3.94 (ddd, J=10.6, 6.3, 3.7 Hz, 1H), 3.42 (d, J=6.3 Hz, 1H), 2.99 (dd, J=15.9, 8.0 Hz, 1H), 2.93-2.76 (m, 3H), 2.72-2.62 (m, 1H), 2.59-2.52 (m, 1H), 1.96 (s, 3H), 1.85-1.74 (m, 1H), 1.73-1.58 (m, 2H), 1.58-1.42 (m, 1H), 1.21 (p, J=7.7 Hz, 2H).

Synthetic Example 12

The remaining compounds of Tables 1 and 2 were prepared in accordance with the synthetic procedures described above using suitable reagents and modifications as would be known by a person of skill in the art. Compounds described herein were characterized using standard techniques known in the art, such as $^1H$ NMR and mass spectra.

Biological Examples

Nrf2-Keap1 Biochemical Assay Protocol

Materials

Pf-BSA (protease free): Sigma: A3059

Streptavidin labeled with XL665: CisBio: 610SAXLA
Anti-6HIS antibody labelled with Terbium: CisBio: 61HI2TLA
Biotin-Nrf2 (16-mer): Biosyntan: custom synthesis
HIS-Keap1 full length: Biosyntan: custom synthesis
Proxiplate-384 Plus, White 384 Microplate: Perkin Elmer: 6008280

Assay Buffer
10 mM Hepes pH 7.4 (sigma $H_{3375}$)
150 mM NaCl (sigma 57653)
0.005% Tween-20 (sigma P1379)
0.01% pf-BSA (sigma A3059)

Final Assay Concentrations
HIS-Keap1 full length 4.1 nM
Biotin-Nrf2 (16-mer) 4.1 nM
Anti-6HIS Terbium 0.18 nM
Streptavidin XL665 10.4 nM Assay Protocol In a first step, the Keap1/compound complex was prepared by addition of 100 nL of the compound by ECHO 555, followed by 5 µL aliquots of 2×Keap1. This mixture was incubated for 15 minutes at room temperature. In a second step, the Keap1/Nrf2 complex was prepared by adding 5 µL aliquots of 2×Nrf2 to the same mixture and incubating again for 15 minutes at room temperature. 5 µL of anti HIS-Tb was then added, followed by the addition of 5 µL of 4× streptavidin-XL665. After incubation at 4° C. for 2 hours, TR-FRET measurements were made on Pherastar FS (optic module HTRF 337/620/665 nM).

Cellular Assay Protocols

BEAS-2B Cell Culture

The growth rate of the BEAS-2B cells changed based on the lot of BEGM SingleQuots in the BEGM media. The cell growth rate was determined for each lot of SingleQuots. Ideally, cells were thawed into media with the new lot of SingleQuots and grown for two passages before testing; however, growing an active culture in the new lot of media for two to three passages before testing was also acceptable. Until the cell growth rate was determined, cells were seeded at different densities (cells/$cm^2$) in multiple tissue culture flasks in order to avoid the cells becoming more than 70% confluent. Cells should not go above 70% confluent as the cells differentiate when they become confluent. After the cells were grown in the new lot of media as described above, the number of cells per well needed to seed in the collagen plates was determined by seeding different numbers of cells per well and incubating for 48 hours. Cell confluency was checked after 48 hours and a cell number that results in just below to just above confluency was chosen for future plate seeding. Cell confluency in the assay plate was 95-100% confluent after 48 hours. 70% confluency in the assay plate after 48 hours resulted in more variability in MTT signal and failing Z'.

BEAS-2B Cell Media:

Cell media consists of BEBM basal media with the BEGM SingleQuots added. SingleQuots vials were thawed in the tissue culture hood, and GA-1000 (Gentamicin-Amphotericin) was not added.

If complete media was to be used immediately, BEBM basal media was warmed to room temperature in the hood, but not as high as 37° C. When the media was made for future use, SingleQuots were added to cold BEBM. One at a time, the SingleQuots components (except GA-1000) were added to the BEBM media. After removal of each component from the vial, the vial was rinsed with 0.5-1 mL of BEBM (depending on the volume the vial could hold) and added to the bottle of BEBM. Once all components were added, the label that comes with the SingleQuots kit was put on the bottle of media and the date was recorded. The bottle of media was mixed by gentle shaking. The media was not filtered. This media was stored at 4° C., with any leftover media disposed of one month after the date the SingleQuots were added.

BEAS-2B Cell Splitting Protocol:

First, Trypsin was warmed to 37° C. in the water bath. The media was then warmed to room temperature by letting it sit in the tissue culture hood, but not as high as 37° C. The media was aspirated from flask(s) and the flask(s) were washed with PBS. From 1 to 1.5 mL of warm trypsin were added to each flask and incubated at 37° C. until cells came off the flask on their own (~8-10 minutes), with no vigorous tapping on the flask to detach the cells.

Media was added to each flask to a total volume of 8-10 mL per flask and transferred to 15 mL conical tube(s). The cells were spun down at 120 g for 5 minutes, level 5 brake. The cells can be spun down between 100 and 150 g. Next the media was aspirated and the cell pellet was resuspended in fresh media by pipetting up and down and flicking the tube side to side. Any clumps of cells that remained were allowed to settle to the bottom of the tube before the top suspension was transferred into another tube, leaving about 1 mL of media in the original tube. The 1 mL of media and cell clumps were mixed with a single channel p1000 pipette, and any remaining clumps were removed before adding the cells in suspension to the other tube. The suspension was mixed with a pipette, an aliquot was removed, and the cells were counted. The amount of cells/$cm^2$ desired was calculated and the required volume of cells was added to tissue culture flasks. For example, use of SingleQuots with ~6000 cells/$cm^2$ was appropriate for a three day incubation and ~3000 cells/$cm^2$ for a five day incubation. Optimal cell density differed depending on lot of SingleQuots. The flasks were incubated at 37° C. in 5% $CO_2$.

Day One: Seeding BEAS-2B Cells in Collagen Plates:

Plate(s) were either seeded with 0.3% or 0% HSA. While the protocol was similar for both conditions any differences are noted herein below.

Trypsin was warmed to 37° C. in a water bath. The media was warmed to room temperature by letting it sit in the tissue culture hood. (Do not warm media to 37° C.) If the collagen plates with compound had been frozen, the plates were thawed at room temperature for 1 hour. Two multidrop standard cassettes were used: one was used to dispense media and cells without Human Serum Albumin (HSA) and the other one was used to dispense media with HSA.

Once everything was brought to temperature, the seals were removed from the collagen plates. Using the no HSA multidrop cassette, 20 µL of media were added to each well and the plates sat covered at room temperature.

In this example a single injection of 20 µL was used for 0.3% HSA plates and two injections of 20 µL were used for 0% HSA plates.

Next the BEAS-2B cells were split according to the BEAS-2B Cell Splitting Protocol. First the cells were counted, then the switch from the multidrop cassette to the +HSA cassette was made.

For 0.3% HSA plates only: 20 µL each of media, HSA in media, and cells were combined and the HSA was added at three times the concentration. Because the final HSA concentration on cells was 0.3%, 0.9% HSA was added to the plate. To prepare the 0.9% HSA solution, 0.9 mL of an HSA stock (10%) was added to 9.1 mL of media to obtain 10 mL of 0.9% HSA.

Using the HSA multidrop cassette, 20 μL of 0.9% HSA in media (for 0.3% HSA plates only) was added to each well, and the switch from the multidrop cassette to the no HSA cassette was made. Cells were prepared to the desired concentration in media. In an example of SingleQuots with 2500 cells/well, 20 μL were added per well, resulting in $1.25\times10^5$ cells/mL. The cell number per well was adjusted depending on the lot of SingleQuots.

Using the no HSA multidrop cassette, 20 μL of cells were added to each well of both 0.3 and 0% HSA plates. The plates sat at room temperature for about 15-30 minutes before the plates were incubated at 37° C. and 5% $CO_2$ for 48 hours.

Day Three: MTT Assay

Because this assay is time-dependent, one plate was started at a time. Two clear bottom, white-walled plates were labeled as DMSO and DIC, then placed in a darker room. The Biotek washer was primed with PBS−/− (minimum 200 mL prime). The Protocol involved the following: Prime A—100 mL (twice) or Prime A—250 mL.

The lysis buffer was prepared immediately before use. The BioTek was used to aspirate the media, which was washed twice with 75 μL of PBS−/−. The Beas Wash protocol involved a W-Wash 75 μL of Buffer A for 2 cycles, followed by priming the BioTek twice with water to wash away the PBS.

The plates were turned upside down over an absorbent plate and pulled back, to remove as much liquid as possible, manually, before patting the plate on a clean spot on the absorbent pad (3-4 times). 50 μL of lysis buffer was added, to each well, and the plate was placed on a shaker at a setting of 8/10 for 20 minutes at room temperature.

40 mL of Reagent C was prepared in a limited-light room (with a red light), and then divided into two 19 mL volumes (one to a tube labelled DMSO, the other to a tube labelled DIC). Then 19 μL of DMSO was added to the DMSO tube and 19 μL of 1.5 mM dicoumarol ("DIC") was added into the DIC tube and the tubes were mixed.

40 μL of the DMSO+Reagent C mixture was added to each well of the DMSO plate. Once the DMSO+Reagent C mixture was added to the DMSO plate, anything with MTT was protected from light. 40 μL of the DIC+Reagent C mixture was added to each well of the DIC plate.

Each plate remained light-protected while 10 μL of lysate was added to each well of the DMSO plate first, then 10 μL of lysate was added to each well of the DIC plate.

Both the DMSO and DIC plates were incubated, while being protected from light, at room temperature for approximately 15-30 minutes. If the number of cells are increased this incubation time can be decreased. For example, 5000 cells/well may need only 15 minutes to develop. The plates were spun at 277 g (1500 RPM) for 5 minutes to remove any air bubbles. The absorbance at 570 nm of both plates was measured on the Pherastar (Settings: Settling time=0.1 seconds, 15 flashes/well). Express NQO1 activation as:

$$\Delta OD_{570}=OD_{570}DMSO-OD_{570}DIC$$

HUDEP Cells

Evaluation of the gene expression by qPCR in HUDEP cells treated with titration of novel compounds. HUDEP Compound Treatment Method HUDEP cells were plated in 96-well plates, @ 25,000 cells per well in 200 μL of maintenance media. Compounds were added in a 10-point dose response starting at 10 uM with 1/3 dilution scheme using the HP digital diluter. A DMSO control was run to all for normalization of DMSO. The compounds were incubated for 48 hours in 37° C. incubator with 5% CO. Post incubation, total RNA was isolated using Cells to Ct kit and gene expression was evaluated for genes of interest (GOI) after normalizing to a housekeeping gene. The ΔΔCT was calculated and compared to the DMSO control.

Cell Lysis, Isolation and Gene Expression Materials

Cells to Ct is a kit offered by Applied Biosystems. mRNA prepared using this kit can be directly used for cDNA conversion followed subsequently with qPCR for gene expression analysis Procedure Cell lysis and preparation of RNA: For suspension cells such as HUDEPs, 10,000-100,000 cells (as per kit guidelines) were used for making lysates. The plate was centrifuged at 1500 rpm for 5 mins and the cells were pelleted. Spent medium was removed using a multi-channel pipette. 200 μL ice-cold PBS was added to all treated wells, followed by centrifuging at 1500 rpm for 5 mins 195 μL cold PBS were aspirated from all treatment wells without disturbing the cell monolayer.

To prepare the Cells to CT lysis solution, 49.5 μL of the Cells to CT Lysis Buffer and 0.5 μL/well DNase I (returned DNase I reagent to the −20 C freezer immediately after pipetting) were added to each well. The Cells to CT lysis solution was pipetted to a reservoir and 50 μL were added per well to the treated wells. (Mix 35 μL 5 times without creating bubbles and set timer to 5 mins. At the end of the 5-minute incubation, add 5 μL of stop solution with a multichannel pipet touching the tip to the liquid. Then mix 35 μL 5 times without creating bubbles and set timer to 2 mins.)

The plates were sealed and stored at −20° C. until cDNA synthesis. Optionally they were placed on ice to allow for directly moving to the cDNA synthesis.

cDNA Synthesis: The cell lysate plates were thawed on ice if necessary and mixed 4 times with a multi-channel pipette. 4 μL of Superscript IV VILO and 6 μL of Nuclease free water were combined together for each sample. The mixture was poured into a reservoir and 10 μL was pipetted into each well of a 96-well PCR plate. 10 μL of lysate prepared previously was added and mixed 5 times. The wells were completely sealed, especially around the edges, with plate sealing film using the plate sealing paddle. The PCR plate was centrifuged to pull down the sample to the bottom of the wells. The lysate plate was sealed and returned to the −20° C. freezer as soon as possible. The PCR plate was placed in the thermal cycler and run at 20 μL at 25° C. for 10 minutes, 50° C. for 10 minutes, 85° C. for 5 minutes and then 4° C.

Real Time PCR: The cDNA plate was thawed at room temperature when necessary and 30 μL nuclease free water was added to each cell lysate, followed by mixing, up and down 4 times with a pipette. The primers were thawed for the genes of interest—both housekeeping gene (HKG) and gene(s) of interest (GOI).

A template was prepared and the number of wells needed for each gene of interest (GOI) calculated. Each sample required 2 μL of cDNA, 5 μL of Taqman Master Mix, 0.16667 μL of GOI at 60 times concentration, 0.16667 μL of HKG at 60 times concentration and 2.6667 μL of nuclease free water. If genes at 20 times concentration were used, then 2 μL cDNA, 5 μL Taqman Master Mix, 0.5 GOI, 0.5 μL HKG and 2 μL of nuclease free water were combined for each well.

After calculating the number of wells for each gene, GOI, HKG, Taqman Master Mix and Nuclease free water were combined. 8 μL were pipetted in to each well of the 384-well PCR plate as detailed in the template. 2 μL of cDNA were pipetted into the appropriate wells as detailed in the template, followed by mixing, up and down 4 times, with a change of the tips between sample additions. The wells were completely sealed, especially around the edges, with plate sealing film using the plate sealing paddle. The PCR plate was centrifuged to pull down the sample to the bottom of the wells.

RTPCR was run for 40 cycles with a sample size at 10 μL, and held at 95° C. for 10 minutes, then denatured at 95° C. for 15 secs and annealed/extended at 60° C. for 1 min. The data was analyzed by normalizing to the HKG and the ΔΔCT was calculated and compared to the control.

TABLE 4

| Compound number | ENZ IC50 (nM) | BEAS EC50 (nM) serum free | BEAS EC50 (nM) Serum Free W | BEAS+ W EC50 (nM) | BEAS+ EC50 (nM) | HUDEP HbG EC50 (μM) (Num) |
|---|---|---|---|---|---|---|
| 26 | 0.4, 0.3 | | | | | |
| 27 | 0.4, 0.3 | | | | | |
| 28 | 0.4, 0.5 | | | | | |
| 29 | 191.6, 102.6 | | | | | |
| 30 | 102.6, 158.7 | | | | | |
| 31 | 2.1, 1.2 | | | | | |
| 32 | 0.5, 0.6 | | | | | |
| 33 | 0.4, 0.3 | | | | | |
| 34 | 1.7, 0.6 | | 3.6, 3.8 | 190.3, 189.0 | | |
| 35 | 839.6, 662.1 | | >1000.0 | >10000.0 | | |
| 36 | 12.7, 2.5 | | 35.0, 36.7 | 184.4, 95.4 | | |
| 37 | 1.0, 0.8 | | 18.1, 18.2 | 100.2, 72.3 | | |
| 38 | 0.4, 0.3 | | 4.8, 4.5 | 15.0, 17.0 | | |
| 39 | 1.0, 1.1 | | 5.9, 4.2, 4.3 | 491.9, 530.9, 589.7 | | |
| 40 | 46.2, 53.6 | | >1000.0 | 3584.9 | | |
| 41 | 0.3, 0.1 | | 1.8, 2.1 | 6.5, 5.6 | | |
| 42 | 0.9, 1.4 | | 8.7, 8.7 | 35.0, 54.1 | | |
| 43 | 0.2, 0.2 | | 4.4, 4.3, 3.7 | 42.9, 43.5, 37.0 | | |
| 44 | 6.7, 5.1 | | 392.6 | 1557.8 | | |
| 45 | 228.6, 244.1 | | >1000.0 | >10000.0 | | |
| 46 | 0.4, 0.3 | | 0.7, 0.7, 0.5 | 3.3, 2.0, 2.0 | | |
| 47 | 26.4, 26.4 | | 26.2, 26.0, 28.7 | 140.2, 94.2, 96.9 | | |
| 48 | 0.1, 0.2 | | 12.0, 9.1 | 26.1, 23.9 | | |
| 49 | 0.6, 0.6, 0.4, 0.5 | | 27.0, 28.8 | 116.6, 93.2 | | |
| 50 | 0.2, 0.3 | | 57.3, 47.6 | 89.7, 137.5 | | |
| 51 | 0.3, 0.2 | | 44.9, 38.6 | 70.6, 125.2 | | |
| 52 | 0.5, 0.6, 0.5, 0.5 | | 0.4, 0.5, 0.4, 0.4 | 1.8, 1.6, 1.2, 1.1 | | |
| 53 | 44.7, 61.1, 50.0, 27.0 | | 8.7, 12.3 | 38.5, 47.8 | | |
| 54 | 0.8, 0.8, 0.4, 0.4 | | 0.2, 0.1, 0.1 | 0.9, 0.7, 0.4, 0.3 | | |
| 55 | 214.5, 226.3, 220.4, 201.0 | | 124.7, 147.2 | 482.3, 353.5 | | |
| 56 | 3.4, 3.0, 2.0, 1.9 | | 4.4, 4.9 | 103.1, 126.6 | | |
| 57 | 0.4, 0.4, 58.8, 56.7 | | 11.0, 0.3, 0.3, 8.5, 6.6 | 20.2, 0.6, 0.8, 0.6, 18.6, 21.8 | | |
| 58 | 10.9, 8.4 | | 9.7, 8.8 | 26.5, 35.1 | | |
| 59 | 8.1, 7.3 | | 1.7, 1.6 | 5.0, 4.4 | | |
| 60 | 580.1, 613.9 | | 333.1, 257.7, 226.1 | 539.0, 1662.2, 744.0 | | |
| 61 | 719.9, 651.4 | | 421.8, 244.8 | 585.1, 1288.2 | | |
| 62 | 0.4, 0.8 | | 0.2, 0.2, 0.1 | <0.5, 0.4, 0.3 | | |
| 63 | 0.5, 0.4 | | 0.7, 0.9, 0.9 | 2.8, 3.7, 3.5 | | |
| 64 | 5579.1, 4997.5 | | >1000.0, 3735.4 | >10000.0 | | |
| 65 | 1.5, 1.6 | | 3.7, 2.7 | 18.4, 23.9 | | |
| 66 | 31.9, 29.5 | | 20.6, 27.6 | 39.3, 55.6 | | |
| 67 | 14.0, 14.5 | | 23.0, 23.5 | 159.4, 166.4 | | |
| 68 | 0.3 | | 0.4, 0.3, 0.3 | 1.2, 1.1, 2.3 | | |
| 69 | 0.9, 0.7 | | 7.7, 9.0 | 494.5, 548.9 | | |
| 70 | 593.9, 763.2 | | 32.4, 29.9 | 150.1, 221.4 | | |
| 71 | | | 3.4, 3.3 | 10.5, 13.2 | | |
| 72 | | | >1000.0, 1934.8 | 9870.9, 7716.9 | | |
| 73 | 862.0, 1006.9 | | 286.8, 373.2 | 464.4, 590.5 | | |
| 74 | 24.4, 36.4 | | 4.7, 7.1 | 13.1, 28.0 | | |
| 75 | 21.7, 22.7 | | 9.1, 16.0 | 45.2, 60.0 | | |
| 76 | >9901.0 | | >1000.0, 5626.0 | >10000.0 | | |
| 77 | 0.4, 0.8 | | 11.7, 13.7 | 34.5, 45.3 | | |
| 78 | 7.6, 6.0 | | 43.0, 59.3 | 105.0, 108.3 | | |
| 79 | 1074.9, 786.6 | | 732.9, 809.5 | 1721.5, 2045.0 | | |
| 80 | 0.3, 0.4 | | 0.1, 0.1, 0.1 | <0.5, 0.2, 0.3 | | |
| 81 | 250.6, 220.0 | | >1000.0, 1836.8 | 2164.2, 1948.6 | | |
| 82 | | | 593.9, 640.8 | 1957.4, 1758.8 | | |
| 83 | 4420.6, 3909.9 | | >1000.0, 1780.7 | >10000.0, 8444.6 | | |
| 84 | | | 7.4, 6.2 | 26.3, 30.0 | | |
| 85 | 1.6, 1.2 | | 39.4, 61.3 | 249.1, 244.2 | | |
| 86 | 0.9, 0.8 | | 18.0, 19.7 | 20.4, 25.7 | | |
| 87 | 0.8, 0.9 | | 13.0, 18.2 | 40.5, 38.1 | | |
| 88 | 1.0, 1.1 | | 35.3, 40.4 | 88.5, 101.1 | | |
| 89 | 0.8, 0.9 | | 30.6, 22.8 | 38.7, 48.5 | | |

TABLE 4-continued

| Compound number | ENZ IC50 (nM) | BEAS EC50 (nM) serum free | BEAS EC50 (nM) Serum Free W | BEAS+ W EC50 (nM) | BEAS+ EC50 (nM) | HUDEP HbG EC50 (μM) (Num) |
|---|---|---|---|---|---|---|
| 90 | 1.1, 1.1 | | 1.3, 1.0 | 3.6, 3.5, 3.5 | | |
| 91 | 1.9 | | 59.0, 154.8, 87.2 | 131.3, 154.9 | | |
| 92 | 4.6, 3.9 | | 23.6, 24.8 | 115.1, 141.1 | | |
| 93 | 1.3, 1.4 | | 3.4, 2.7 | 15.4, 17.1 | | |
| 94 | 1.1, 1.3 | | 36.8, 63.2 | 51.0, 52.3 | | |
| 95 | 1.8, 1.9 | | 53.1, 64.8 | 92.0, 123.7 | | |
| 96 | 0.8, 0.8 | | 25.5, 29.4 | 42.8, 49.6 | | |
| 97 | 0.6, 0.7 | | 33.7, 30.8 | 97.4, 112.1 | | |
| 98 | 9.9, 10.0 | | 125.4, 161.0, 273.5 | 488.2, 425.5 | | |
| 99 | 8.8, 8.4 | | 23.9, 25.6 | 107.8, 79.0 | | |
| 100 | 1.1, 1.0 | | 1.7, 1.6 | 8.0, 9.1 | | |
| 101 | 2.6, 2.8 | | 4.7, 5.1 | 34.9, 31.0 | | |
| 102 | 4.5, 4.2 | | 25.1, 24.6 | 116.6, 103.8 | | |
| 103 | 1.2, 1.2 | | 22.1, 36.8 | 198.8, 76.5 | | |
| 104 | 0.2, 0.3, 1.7, 1.6 | 9.3, 7.4 | 30.0, 36.5 | 146.8, 130.4 | 16.4, 19.2 | |
| 105 | 0.8, 0.8 | | 3.9, 4.2 | 11.6, 9.1 | | |
| 106 | 0.9, 0.7 | | 4.5, 5.6 | 35.5, 44.8 | | |
| 107 | 1.6, 1.6 | 0.6, 0.4 | 3.6, 4.1 | 16.7, 32.7 | 3.2, 2.4 | 0.038 |
| 108 | 1.0, 1.0 | | 7.2, 7.9 | 200.0, 41.4, 18.4, 21.4 | | |
| 109 | 4.0, 3.6 | | 32.1, 38.0 | 172.1, 100.2 | | |
| 110 | 2.6, 3.2 | | 15.2, 12.1 | 219.7, 228.5 | | |
| 111 | 0.4, 0.2 | | 19.0, 19.5 | 121.6, 101.4 | | |
| 112 | 0.3, 0.3 | | 2.9, 2.7 | 23.0, 25.5 | | |
| 113 | 1.1, 0.9 | | 1.6, 1.8 | 62.7, 48.7 | | |
| 114 | 0.4, 0.4 | | 0.1, 0.2, 0.2, 0.2 | 9.8, 8.2 | | |
| 115 | 15.5, 13.3 | | 167.5, 162.2, 127.2 | 1055.1, 912.3 | | |
| 116 | 3.9, 2.9 | | 129.5, 84.8 | 211.6, 251.9 | | |
| 118 | 0.4, 0.4 | | 2.5, 4.2 | 3.8, 4.4, 3.6, 6.5 | | |
| 120 | 0.3, 0.4 | | 1.4, 1.4 | 7.9, 7.6, 4.6, 6.3 | | |
| 121 | >990.1 | | >1000.0 | >10000.0 | | |
| 122 | 52.8, 42.8 | | 17.6, 30.2 | 47.0, 54.2 | | |
| 124 | 0.6, 0.6 | | 7.6, 7.3 | 9.0, 12.5 | | |
| 125 | 72.5, 75.7 | 19.0, 21.1 | | | 58.1, 64.2 | |
| 126 | >990.1 | | >1000.0 | >10000.0 | | |
| 127 | 3.8, 3.9 | 0.3, 0.3 | | | 0.4, 0.6 | |
| 128 | 1.0, 1.4 | 14.2, 12.2 | 9.8, 7.1 | 31.0, 47.2 | 17.7, 20.3 | |
| 129 | 616.7, 652.4, 0.4, 0.4 | 1364.9, 1215.0 | 0.4, 1.6, 0.8 | 2.0, 2.2, 1.6, 1.9 | 2185.6, 3082.4 | 0.013 |
| 130 | 0.6, 0.4 | | 0.6, 1.5 | <0.5, 0.5, 0.7 | | 0.000 |
| 131 | 157.4, 162.1 | | >1000.0 | 4781.1, 5037.7 | | |
| 132 | 7572.7, 7939.6 | | >1000.0 | >10000.0 | | |
| 133 | 1.4, 1.3 | | 16.0, 31.0 | 39.4, 38.9 | | |
| 134 | 3.8, 3.8, 10.4, 9.8 | 22.6, 20.2 | 56.5, 90.8 | 142.7, 202.6 | 80.5, 72.8 | |
| 135 | 0.9, 1.2 | | 1.9, 1.8 | 18.9, 11.8 | | |
| 136 | 1.4, 1.3 | 10.0, 7.3 | | | 15.0, 24.3 | |
| 137 | 0.3, 0.3 | 1.9, 1.8 | | | 1.9, 2.8 | |
| 138 | 0.1, 0.1 | 0.5, 0.3 | | | 0.7, 0.3 | |
| 139 | 0.1, 0.1 | 0.2, 0.2 | | | 0.2, 0.3 | |
| 140 | 0.3, 0.5 | 11.6, 8.8 | | | 30.4, 27.3 | |
| 141 | >990.1 | | >1000.0 | 7197.4, 7038.1 | | |
| 142 | 11.3, 11.6 | | 34.5, 36.1 | 129.0, 82.2, 173.9, 169.3 | | |
| 143 | 0.7, 0.7 | | 2.2, 2.6 | 10.3, 10.6 | | |
| 144 | 0.7, 0.6 | | 19.8, 50.2 | 32.4, 60.2 | | |
| 145 | 0.1, 0.0 | 0.6, 0.5 | | | 0.4, 0.7 | |
| 146 | 0.1, 0.1 | 0.2 | | | 0.5, 1.2 | |
| 147 | 0.0, 0.0, 0.4, 0.3 | 0.6, 0.4, 3.1, 2.8 | | | 0.7, 0.6, 5.4, 6.8 | |
| 148 | 0.3, 0.4, 0.8, 0.7 | <0.1, 2.9, 2.4 | | | 0.3, 0.3, 6.4, 7.2 | |
| 149 | 9.4, 7.4 | 74.3, 67.8 | | | 103.4, 89.3 | |
| 150 | 112.8, 106.2 | 102.8, 146.6 | | | 163.6, 188.4 | |
| 151 | 2.4, 2.7 | 215.7, 170.3 | | | 230.4, 120.8 | |
| 152 | 588.7, 571.9 | >10000.0 | | | >10000.0 | |
| 153 | 0.2, 0.2, 0.0 | <0.1, 0.0 | | | <0.1, 0.0, 0.0 | |
| 154 | 3.3, 3.5 | 16.6, 13.6 | | | 37.8, 35.8 | |
| 155 | 734.5, 513.5 | >10000.0 | | | >10000.0 | |
| 156 | 1.4, 1.4 | 55.9, 44.3 | | | 200.8, 171.4 | |
| 157 | 3.8, 4.0 | 3.2, 2.1 | | | 9.2, 8.9 | |
| 158 | 3.6, 3.2 | 18.2, 22.1 | | | 403.3, 399.5 | |
| 159 | 6.9, 7.2 | 112.6, 122.3 | | | 461.0, 480.2 | |
| 160 | 0.6, 0.5 | 9.4, 7.0 | | | 12.4, 13.2 | |
| 161 | 2.5, 2.3, 1.0, 1.0 | 1.4, 0.7, 1.1 | | | 7.8, 6.0, 7.5, 5.2 | |

TABLE 4-continued

| Compound number | ENZ IC50 (nM) | BEAS EC50 (nM) serum free | BEAS EC50 (nM) Serum Free W | BEAS+ W EC50 (nM) | BEAS+ EC50 (nM) | HUDEP HbG EC50 (μM) (Num) |
|---|---|---|---|---|---|---|
| 162 | 2.1, 2.0 | 0.6, 0.6 | | | 0.8, 0.6 | |
| 163 | 2.4, 2.4 | 2.6, 3.3 | | | 10.0, 9.3 | |
| 164 | 51.2, 59.3 | 16.0, 20.3 | | | 32.6, 34.0 | |
| 165 | 1.7, 1.6 | 11.7, 13.3 | | | 26.0, 21.1 | |
| 166 | 0.7, 0.6 | | 1.1, 1.1 | 2.2, 2.7, 2.9, 4.2 | | |
| 167 | 12.3, 14.1 | | 34.7, 36.6 | 102.9, 132.8 | | |
| 168 | 2.2, 2.2 | 1.3, 1.2 | | | 3.7, 3.4 | |
| 169 | 68.9, 66.2 | 84.4, 55.9 | | | 155.1, 174.9 | |
| 170 | 6.3, 6.5 | 28.3, 20.4 | | | 50.1, 54.3 | |
| 171 | 2.5, 2.5 | 1.0, 1.6 | | | 8.3, 5.4 | |
| 172 | 215.8, 227.2 | 79.2, 73.0 | | | 188.3, 262.9 | |
| 173 | 12.5, 12.4 | 3.7, 4.3 | | | 12.8, 13.1 | |
| 174 | 2.0, 2.1 | 5.8, 7.3 | | | 29.4, 15.5 | |
| 175 | 10.4, 10.3 | 53.3, 53.7 | | | 104.4, 125.4 | |
| 176 | 2.4, 2.6 | 0.5, 0.8 | | | 0.1, 0.2 | |
| 177 | 1.7, 1.7 | 43.7, 36.1 | | | 107.1, 140.3 | |
| 178 | 112.6, 104.5 | 1161.8, 1138.6 | | | 1413.2, 933.3 | |
| 179 | 5.7, 5.7 | 113.0, 91.5 | | | 234.8, 207.8 | |
| 180 | 253.0, 296.3 | 701.1, 877.7 | | | 1297.9, 1003.1 | |
| 181 | 1.9, 2.1 | 3.6, 3.4 | | | 5.3, 6.6 | |
| 182 | 55.7, 44.0 | | >1000.0 | >10000.0 | | |
| 183 | 642.5, 570.7 | | >1000.0 | >10000.0 | | |
| 184 | 168.1, 146.8 | 471.0, 712.8 | | | 2902.1, 2571.3 | |
| 185 | >1000.0 | >10000.0 | | | >10000.0 | |
| 186 | 527.0, 289.2 | >10000.0 | | | >10000.0 | |
| 187 | 5.9, 5.6 | 9.3, 8.9 | | | 22.0, 19.1 | |
| 188 | 24.7, 26.0 | 9.4, 9.1 | | | 15.3, 14.9 | |
| 189 | 22.8, 23.3 | 4.4, 6.0 | | | 18.8, 15.9 | |
| 190 | 4.2, 4.4, 1.1, 1.1 | 1.0, 1.0, <0.1, 2.6, 3.3 | | | 1.8, 2.0, 5.4, 2.9, 8.8, 6.8 | |
| 191 | 19.5, 20.4 | 11.4, 18.0 | | | 20.5, 18.0 | |
| 192 | 7.0, 6.8 | 75.6, 63.7 | | | 113.6, 124.5 | |
| 193 | 29.1, 31.5 | 1140.0, 768.4 | | | 3150.7, 1278.6 | |
| 194 | 24.3, 22.9 | 870.3, 1099.5 | | | 1083.7, 828.9 | |
| 195 | 62.3, 69.9 | 5570.3, >10000.0 | | | >10000.0 | |
| 196 | 130.1, 116.4 | >10000.0 | | | >10000.0 | |
| 197 | 164.1, 147.9 | 2795.8, >10000.0 | | | 6614.9, 2297.5 | |
| 198 | 0.5, 1.2, 1.0 | <0.1, 0.4, 7916.2, 2532.0 | | | 8.5, 5.9, 2117.2, 2793.8 | |
| 199 | 3.7, 3.6 | 12.7, 11.9 | | | 128.2, 58.9 | |
| 200 | 87.3, 86.3 | 3.4, 6.5 | | | 9.5, 9.3 | |
| 201 | 18.2, 16.9, 0.9, 0.8 | 0.3, 0.3, 0.4, <0.1, 0.1, 0.1 | | | 0.5, 0.5, 0.2, 0.5, 0.2, 0.2 | |
| 202 | 7.2, 6.8, 7.1 | 58.2, 55.5, 69.1 | | | 200.0, 297.5, 338.5 | |
| 203 | 13.0, 11.9 | 4540.0, 2419.7 | | | 4471.2, 3616.6 | |
| 204 | 3.0, 2.7 | 2877.4, 3288.4 | | | 8306.6, 2830.3 | |
| 205 | 2.7, 3.0 | 317.9, 328.8 | | | 372.4, 506.7 | |
| 206 | 5.3, 5.7 | 64.0, 38.5 | | | 89.9, 118.6 | |
| 207 | 1.4, 1.4 | | 23.7, 32.1 | 65.4, 57.6 | | |
| 208 | 1.1, 1.1 | | 10.1, 14.9 | 25.1, 27.2 | | |
| 209 | 0.4, 0.5 | 469.3, 493.9 | | | 842.7, 903.2 | |
| 210 | 3.7, 4.0 | 481.6, 474.8 | | | 1020.3, 844.9 | |
| 211 | 10.7, 24.5 | 829.0, 573.6 | | | 2209.1, 1726.9 | |
| 212 | 7.7, 5.7 | 190.3, 254.5 | | | 606.4, 811.0 | |
| 213 | 1.5, 1.6 | 117.6, 98.4 | | | 146.6, 125.5 | |
| 214 | 2.3, 2.1 | 245.2, 132.2 | | | 233.5, 240.8 | |
| 215 | 1.0, 1.1 | 243.1, 251.2 | | | 349.4, 309.5 | |
| 216 | 2.1, 2.3 | 1.8, 2.5 | | | 35.8, 28.2 | |
| 217 | 1.9, 2.1 | 371.2, 360.2 | | | 428.6, 301.0 | |
| 218 | 0.8, 0.8 | 27.5, 39.7 | | | 29.3, 37.5 | |
| 219 | 1.3, 1.5 | 180.2, 207.6 | | | 227.8, 207.6 | |
| 220 | 1.4, 1.2 | 178.0, 181.7 | | | 313.5, 345.5 | |
| 221 | 216.4 | >10000.0, 3197.2 | | | >10000.0 | |
| 222 | 1.6, 1.5 | 17.2, 14.2 | | | 47.4, 38.6 | |
| 223 | 0.5, 0.9, 1.2, 1.2 | 6.4, 3.9, 2.0 | | | 13.6, 4.0, 2.8 | 0.015 |
| 224 | 2.1, 2.0 | 400.2, 295.7 | | | 320.5, 314.0 | |
| 225 | 2.5, 2.4 | 168.8, 174.9 | | | 302.8, 338.6 | |
| 226 | 244.7 | >10000.0 | | | >10000.0 | |
| 227 | 2.1 | 516.9, 567.5 | | | 1132.2, 931.8 | |
| 228 | 1.3 | 523.6, 471.0 | | | 771.1, 666.8 | |
| 229 | 10.4 | 1428.9, 2226.7 | | | 2983.1, 1440.2 | |
| 230 | 4.8 | 384.0, 470.6 | | | 1085.8, 960.8 | |
| 231 | 3.2 | 153.3, 227.5 | | | 272.7, 227.2 | |
| 232 | 1.4 | 7.2, 4.6 | | | 9.0, 8.3 | |
| 233 | 15.1 | 215.5, 196.8 | | | 269.3, 307.2 | |
| 234 | 49.1 | 1839.4, 1411.0 | | | 3858.6, 5839.6 | |

TABLE 4-continued

| Compound number | ENZ IC50 (nM) | BEAS EC50 (nM) serum free | BEAS EC50 (nM) Serum Free W | BEAS+ W EC50 (nM) | BEAS+ EC50 (nM) | HUDEP HbG EC50 (μM) (Num) |
|---|---|---|---|---|---|---|
| 235 | 0.5, 0.6, 0.6 | >10000.0, 0.8, 1.0 | | | 0.4, <0.1, 4.1, 3.7 | |
| 236 | 51.0, 44.4, 44.6 | 62.7, 50.3, 82.1, 84.7 | | | 286.4, 248.2, 219.5, 190.0 | |
| 237 | 22.9, 36.1, 70.2, 28.2, 29.9 | 47.6, 33.1, 360.0, 325.6, 41.2, 39.6 | | | 196.4, 268.9, 362.8, 607.9, 761.8, 754.2 | |
| 238 | 6.2 | 570.9, 376.6 | | | 572.4, 603.2 | |
| 239 | 0.3 | 147.7, 259.1 | | | 214.4, 248.3 | |
| 240 | 0.2 | 1.1, 0.6 | | | 1.0, 0.6 | 0.018 |
| 241 | 0.4 | 9.7, 2.7 | | | 12.2, 89.9 | 0.095 |
| 242 | >1000.0 | 2266.3, >10000.0 | | | >10000.0 | |
| 243 | 2.6 | 40.7, 48.7 | | | 71.8, 104.0 | |
| 244 | 37.4, 39.9, 0.3, 36.1, 37.6, 0.5, 0.5 | 233.0, 0.6, >10000.0, 0.8, 0.9 | | | 1140.0, 0.7, 0.3, 7.5, 8.6 | |
| 245 | 0.8 | 19.4, 18.5 | | | 24.8, 37.6 | |
| 246 | 5.3 | 919.3, 3110.2 | | | 991.8, 1485.3 | |
| 247 | 1.6, 1.7 | 29.4, 26.3 | | | 45.4, 47.2 | |
| 248 | 41.8, 40.4 | 288.3, 339.8 | | | 433.4, 429.8 | |
| 249 | 1.1, 1.3 | 0.4, 1.7 | | | 3.0, 13.0 | |
| 250 | 2.0, 1.9 | 16.4, 16.5 | | | | |
| 251 | 4.7, 4.8 | 1.8, 0.8 | | | 10.6, 1.0 | 0.017 |
| 252 | 1.2, 1.3, 1.3, 1.4 | 15.5 | | | 21.2 | |
| 253 | 1.3, 1.3 | 5.4 | | | 6.6 | |
| 254 | 1.8 | 16.0, 17.2 | | | 16.4, 22.6 | |
| 255 | 5.1 | 4.8, 4.0 | | | 288.0, 289.0 | |
| 256 | 86.9 | >10000.0 | | | >10000.0 | |
| 257 | 4.6 | 7.4, 4.3 | | | 227.8, 146.1 | |
| 258 | 4.9 | 9076.0, 9481.2 | | | 2635.4, 2527.6 | |
| 259 | 4.1 | 20.2, 18.7 | | | 47.6, 78.5 | |
| 260 | 6.0 | 400.0, 403.4 | | | 337.4, 484.4 | |
| 261 | 3.0 | 89.8, 93.0 | | | 198.4, 113.4 | |
| 262 | 0.9, 0.8 | 0.6 | | | 4.4 | 0.031 |
| 263 | 2.7, 3.0 | 18.3 | | | 20.4 | |
| 264 | 2.7, 2.9 | 3.7 | | | 5.4 | |
| 265 | 4.2, 3.8 | 25.1 | | | 323.0 | |
| 266 | 0.5, 0.5 | 2.1 | | | 2.6 | |
| 267 | 2.4, 2.3 | 3.9 | | | 5.3 | |
| 268 | 68.1, 70.7 | 505.0 | | | 561.0 | |
| 269 | 2.5, 1.2 | 2.8 | | | 19.9 | |
| 270 | 4.0, 3.6 | 56.5 | | | 55.9 | |
| 271 | 1.9, 1.7, 1.9 | <0.1, 1.8, 1.3 | | | 0.2, 4.3, 4.1 | |
| 272 | 1.1, 1.3 | 2.5 | | | 3.3 | |
| 273 | 3.0, 3.0 | 59.0 | | | 73.2 | |
| 274 | 1.5, 1.5 | 30.3 | | | 108.0 | |
| 275 | 1.9, 1.9 | 123.0 | | | 85.9 | |
| 276 | 2.2, 2.0, 2.1 | 88.5 | | | 49.3 | |
| 277 | 2.5, 1.9, 2.7, 1.7 | 459.0 | | | 3350.0 | |
| 278 | 1.8, 1.4, 1.8, 1.3 | 136.0 | | | 159.0 | |
| 279 | 2.3, 2.2, 2.1, 2.2 | 10.8 | | | 10.7 | |
| 280 | 2.3, 2.8, 2.8, 2.3 | 108.0 | | | 114.0 | |
| 281 | 0.4, 0.5, 1.4, 0.6, 0.4, 0.5 | 5.2, 0.4 | | | 0.9, 2.6 | |
| 282 | 0.4, 0.3, 0.3, 1.1, 0.3, 0.4 | 0.5, 0.2 | | | 1.0, 0.3 | |
| 283 | 1.1, 1.7 | 450.0 | | | 418.0 | |
| 284 | 0.4, 0.3 | 3.4 | | | 22.8 | |
| 285 | 0.3, 0.5 | 4.7 | | | 9.8 | |
| 286 | 0.7, 0.7 | 15.8 | | | 44.5 | |
| 287 | 1.8, 1.8 | 3.1 | | | 112.0 | |
| 288 | 1.8, 2.3 | 2.7 | | | 34.3 | |
| 289 | <0.1 | 74.9 | | | 69.3 | |
| 290 | 0.7, 0.8 | 0.9 | | | 5.6 | |
| 291 | 0.8, 0.8 | 217.0 | | | 165.0 | |
| 292 | 7.7, 5.9 | 349.0 | | | 637.0 | |
| 293 | <0.1 | 141.0 | | | 208.0 | |
| 294 | 22.1, 17.3 | 450.0 | | | 809.0 | |
| 295 | 0.1, 0.1 | 0.2 | | | 0.7 | |
| 296 | 3.5, 1.9 | 23.4 | | | 30.5 | |
| 297 | 0.2, 0.2 | 1.8 | | | 2.9 | |
| 298 | 3.0, 3.1 | 33.1 | | | 20.4 | |
| 299 | <0.1 | 0.6 | | | 3.6 | |
| 300 | <0.1 | 3.1, 5.4 | | | 10.8, 7.9 | |
| 301 | 6.8, 6.0 | 80.6, 144.0 | | | 317.0, 214.0 | |
| 302 | 0.8, 0.9 | 129.0, 213.0 | | | 134.0, 196.0 | |
| 303 | 0.7, 0.5 | 39.6, 70.0 | | | 97.8, 48.8 | |
| 304 | <0.1, 0.2 | 18.3 | | | 25.1, 29.0 | |
| 305 | <0.1 | 345.0 | | | 651.0, 748.0 | |

TABLE 4-continued

| Compound number | ENZ IC50 (nM) | BEAS EC50 (nM) serum free | BEAS EC50 (nM) Serum Free W | BEAS+ W EC50 (nM) | BEAS+ EC50 (nM) | HUDEP HbG EC50 (μM) (Num) |
|---|---|---|---|---|---|---|
| 306 | 0.1, <0.1 | 68.1 | | | 134.0, 90.1 | |
| 307 | 0.2, 0.2 | 0.4 | | | 3.7, 5.2 | |
| 308 | <0.1 | 910.0 | | | 3250.0, 561.0 | |
| 309 | <0.1 | 3.2 | | | 4.1, 11.5 | |
| 310 | 0.3, <0.1 | 698.0 | | | 9100.0, 9570.0 | |
| 311 | 0.1, <0.1 | 10.4 | | | 16.9, 54.6 | |
| 312 | <0.1, No Val | 40.7 | | | 93.7, 206.0 | |
| 313 | <0.1, 0.4 | 8.8 | | | 885.0, 28.9 | |
| 314 | 4.4, 1.8 | 2.6 | | | 109.0 | |
| 315 | 0.7, 0.3 | 2.2 | | | 25.9 | |
| 316 | 1.6, 0.9 | 141.0 | | | 77.9 | |
| 317 | 0.9, 1.7 | 0.6 | | | 11.9 | |
| 318 | 0.8, 0.8 | 20.4 | | | 59.2 | |
| 319 | 99.0, 106.0 | 432.0 | | | 1430.0 | |
| 320 | <0.1 | 332.0 | | | 462.0 | |
| 321 | 0.4, 0.1 | 75.7 | | | 88.9 | |
| 322 | 0.8, 1.0 | 176.0 | | | 231.0 | |
| 323 | 1.2, 1.8 | 135.0 | | | 386.0 | |
| 324 | 0.4, 0.4 | 6.0 | | | 18.1 | |
| 325 | <0.1 | 2.9 | | | 4.0 | |
| 326 | 2.7, 0.8 | 392.0, 168.0 | | | 804.0 | |
| 327 | 0.8, 2.3 | 52.9, 46.9 | | | 179.0 | |
| 328 | 0.9, <0.1 | 6710.0 | | | | |
| 329 | <0.1, 1.6 | 403.0 | | | 1230.0 | |
| 330 | 1.8, <0.1, 0.7 | 1070.0 | | | 862.0 | |
| 331 | 1.7, 4.3, 2.6, 10.9 | 47.4 | | | 40.3 | |
| 332 | <0.1, <0.0 | 27.4 | | | 62.7 | |
| 333 | 1820.0, >1000.0, 1220.0 | No Val | | | >10000.0 | |
| 334 | 5.0, 2.8, 6.4, 0.6 | 547.0 | | | 898.0 | |
| 335 | 2.5, 2.9, 6.4, 1.3 | 35.0 | | | 36.1 | |
| 336 | 7.6, 7.7 | | | | | |
| 337 | 0.7, 0.8 | 1890.0 | | | 2540.0 | |
| 338 | 0.2, 0.1 | 25.3 | | | 27.5 | 0.667 |
| 344 | 4410.0, 4850.0 | | | | | |
| 345 | 2900.0, 3360.0 | | | | | |
| 350 | 11.5, 10.1, 9.8, 10.2 | | 161.2, 145.0 | 276.3, 425.6 | | |
| 351 | 648.8, 618.8, 401.4, 416.4 | | >1000.0, 1775.0 | 3740.1, 2883.5, 2800.9 | | |
| 352 | 6.8, 7.7 | | 21.9, 33.0 | 416.6, 481.1 | | |
| 353 | 0.5, 0.5 | | 16.8, 19.1 | 72.3, 109.2 | | |
| 354 | 20.1, 13.8 | | >1000.0 | 2695.7, 2129.5 | | |
| 355 | 9.1, 9.3 | | 810.2, 1301.6 | 4700.4, 3855.5 | | |
| 356 | 0.6, 0.7 | | 11.2, 4.3 | 56.1, 67.8 | | |
| 357 | 11.4, 11.0 | | >1000.0, 969.1 | 1941.7, 1711.2 | | |
| 358 | 1.0, 1.1 | | 59.5, 57.0 | 129.5, 118.5 | | |
| 359 | 7.4, 8.1 | | >1000.0 | >10000.0 | | |
| 360 | 0.9, 0.9 | | 0.3, 1.2, 0.5 | <0.5, 1.5, 2.5, 2.0, 13.1, 28.8 | | |
| 361 | 917.8, 740.4 | | >1000.0 | 1664.6, 1276.4 | | |
| 362 | 50.0, 47.3 | 3247.9, 3756.4 | | | >10000.0 | |
| 363 | 9.0, 8.5 | | 321.1, 459.6, 649.8 | 681.6, 711.3 | | |
| 364 | 1.7, 1.6 | | 56.0, 68.3 | 98.8, 92.6 | | |
| 365 | 3.4, 3.6 | | 90.0, 171.2 | 188.1, 214.0 | | |
| 366 | 5.6, 5.3 | 580.5, 442.3 | | | 1066.2, 1181.8 | |
| 367 | 0.4, 0.4 | 10.3, 12.5 | | | 12.2, 12.3 | |
| 368 | 0.1, 0.2 | 300.8, 99.9 | | | 114.4, 139.5 | |
| 369 | 13.2, 14.0 | 2014.7, 1933.0 | | | 2078.6, 2234.1 | |
| 370 | 4.3, 4.2 | 1482.8, 1353.8 | | | 1640.6, 1709.3 | |
| 371 | 1.6, 1.7 | 21.3, 22.1 | | | 23.6, 28.8 | |
| 372 | 0.2, 0.2 | 994.3, 1025.0 | | | 1628.0, 861.1 | |
| 373 | 3.6, 3.9 | 2074.1, 2025.4 | | | 2032.3, 3143.9 | |
| 374 | 1.0, 1.0 | | 132.6, 290.0, 386.9 | 283.6, 296.9 | | |
| 375 | 1.4, 1.4 | | 2.9, 2.9 | 7.0, 8.0, 5.9, 13.0 | | |
| 376 | 1.3, 1.4 | | 2.1, 2.3 | 3.9, 4.5, 5.5, 3.9 | | |
| 377 | 5.7, 5.8 | 2941.4, 2651.8 | | | 3167.6, 3206.8 | |
| 378 | 7.7, 8.0 | 133.3, 139.1 | | | 213.1, 154.7 | |
| 379 | 5.2, 5.4 | 158.1, 146.6 | | | 205.5, 193.2 | |
| 380 | 5.9, 5.4 | 1455.7, 1387.6 | | | 1232.3, 1443.6 | |
| 381 | | | | | | |
| 382 | 0.0, 0.0 | 86.2, 124.9 | | | 169.1, 136.4 | |
| 383 | 0.9, 0.9 | 178.7, 162.1 | | | 196.4, 186.8 | |
| 384 | 65.0, 66.0 | 495.9, 510.7 | | | 413.4, 302.8 | |

TABLE 4-continued

| Compound number | ENZ IC50 (nM) | BEAS EC50 (nM) serum free | BEAS EC50 (nM) Serum Free W | BEAS+ W EC50 (nM) | BEAS+ EC50 (nM) | HUDEP HbG EC50 (μM) (Num) |
|---|---|---|---|---|---|---|
| 385 | 238.2, 243.6 | 2247.8, 2853.4 | | | >10000.0, 2407.1 | |
| 386 | 1.9, 2.0 | 90.3, 89.0 | | | 123.0, 105.0 | |
| 387 | 1.5, 1.7 | 95.9, 75.2 | | | 62.6, 90.3 | |
| 388 | 1.6 | 51.4, 44.2 | | | 464.3, 876.5 | |
| 389 | 1.8, 1.9 | 147.3, 152.7 | | | 230.7, 409.4 | |
| 390 | 5.1, 5.6 | >10000.0, 211.5 | | | 3350.5, 5768.6 | |
| 391 | 276.0, 264.8 | 8.8, 7.9 | | | 2064.2, 1948.4 | |
| 392 | 0.5, 0.5 | 10.6, 10.3 | | | 13.7, 15.5 | |
| 393 | 3.8, 4.3 | 2445.6, 2111.3 | | | 1885.8, 2249.5 | |
| 394 | 9.0, 10.4 | 3104.4, 2895.7 | | | 2693.6, 2863.7 | |
| 395 | 5.7, 6.7 | 80.9, 83.3 | | | 110.5, 89.6 | |
| 396 | 94.7, 138.1 | 80.5, 78.2 | | | 204.2, 175.9 | |
| 397 | 13.9, 14.8 | 597.0, 658.8 | | | 1523.2, 2151.5 | |
| 398 | 5.2, 17.3 | | | | | |
| 399 | >1000.0, 335.2 | 478.6, 407.2 | | | 1980.4, 2001.4 | |
| 400 | 2.0 | 54.7, 21.0 | | | 31.6, 29.3 | |
| 401 | 6.1, 6.5 | No Val | | | 7110.0 | |
| 402 | 58.7, 57.7 | No Val | | | >10000.0 | |
| 403 | 146.0, 192.0 | No Val | | | >10000.0 | |
| 404 | 662.0, 271.0 | No Val | | | No Val | |
| 405 | 2150.0, 2050.0 | | | | | |
| 406 | No Val, 8660.0 | | | | | |
| 407 | 942.0, 203.0 | | | | | |
| 408 | 1.6, 1.5, 13.2, 5.0 | | | | | |
| 409 | 259.0, 363.0 | | | | | |
| 410 | 1050.0, 1900.0 | | | | | |
| 411 | 5.2, 10.1 | | | | | |
| 412 | 28.7, 47.9 | | | | | |
| 413 | 2.9, 1.5, 7.1, 9.7 | | | | | |
| 414 | 106.0, 313.0 | | | | | |
| 415 | 13200.0, 8750.0 | | | | | |
| 416 | 2420.0, 348.0 | | | | | |
| 417 | 42.7, 35.2 | | | | | |
| 418 | 390.0, 381.0 | | | | | |
| 419 | 5.7, 19.1, 16.8, 10.8 | | | | | |
| 420 | 8.5, 8.3 | | | | | |
| 421 | 10.1, 8.4 | | | | | |
| 422 | 11.3, 12.2 | | | | | |
| 423 | 17400.0, 10700.0 | | | | | |
| 424 | 4.8, 4.7, 2.2, 0.5 | | | | | |
| 425 | 4320.0, 5390.0 | | | | | |
| 426 | 9.2, 11.6 | | | | | |
| 427 | 9.2, 9.9 | | | | | |
| 428 | 1090.0, 962.0 | | | | | |
| 429 | 112.0, 82.3 | | | | | |
| 430 | 67.5, 56.1 | | | | | |
| 431 | 102.0, 96.9 | | | | | |
| 432 | 93.1, 93.3 | | | | | |
| 433 | 287.0, 204.0 | | | | | |
| 434 | 17.8, 55.4 | | | | | |
| 435 | >30000.0 | | | | | |
| 436 | 2670.0, 3410.0 | | | | | |
| 437 | 219.0, 234.0 | | | | | |
| 438 | 565.0, 1010.0 | | | | | |
| 439 | 52.7, 121.0, 119.0, No Val, 122.0, 106.0 | | | | | |
| 440 | 64.9, 70.3, 114.0, 113.0 | | | | | |

Unless otherwise defined, all technical and scientific terms used herein have the same meaning as commonly understood by one of ordinary skill in the art to which this disclosure belongs.

The disclosure illustratively described herein may suitably be practiced in the absence of any element or elements, limitation or limitations, not specifically disclosed herein. Thus, for example, the terms “comprising”, “including,” “containing”, etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the disclosure.

It is to be understood that while the disclosure has been described in conjunction with the above embodiments, that the foregoing description and examples are intended to illustrate and not limit the scope of the disclosure. Other aspects, advantages and modifications within the scope of the disclosure will be apparent to those skilled in the art to which the disclosure pertains. The disclosures of all patent and scientific literature cited herein are expressly incorporated herein in their entirety by reference.

The invention claimed is:

1. A compound of Formula (I):

(I)

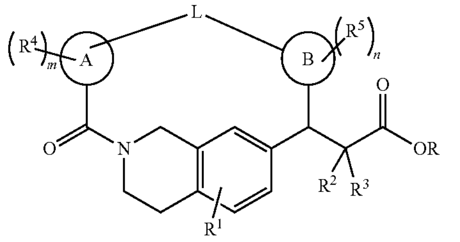

or a pharmaceutically acceptable salt thereof, wherein:

R is H or $C_{1-6}$alkyl optionally substituted with one substituent selected from —OH, $C_{1-6}$ alkyloxy, or $C_{6-12}$ aryl;

$R^1$ is H or $C_{1-6}$ alkyl;

$R^2$ is H or $C_{1-6}$ alkyl;

$R^3$ is H or $C_{1-6}$ alkyl;

Ring B is $C_{6-12}$ arylene or $C_{3-12}$ heteroarylene containing 1 to 4 heteroatoms independently selected from N and O provided that Ring B is not

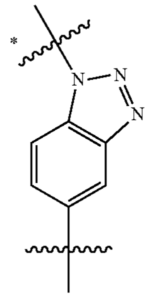 [SMILES: *c1ccc2c(c1)nnn2*]

wherein the * designates a bond to L;

n is 0, 1, 2, or 3;

each $R^5$ is independently halo, $C_{1-6}$ alkyl, or $C_{1-6}$ alkyloxy;

Ring A is $C_{6-12}$ arylene or $C_{3-12}$ heteroarylene containing 1-2 heteroatoms independently selected from N and O;

m is 1, 2, 3, or 4;

each $R^4$ is independently H, halo, $C_{1-6}$ alkyl, or $C_{1-6}$ alkoxy, wherein the $C_{1-6}$ alkyl and $C_{1-6}$ alkoxy groups are optionally substituted with 1-3 groups independently selected from halo, $C_{1-6}$ alkyloxy, amido, and N,N-dimethylamido groups; and L is $C_{4-8}$ alkylene, $C_{4-8}$ alkenylene, $C_{4-8}$ heteroalkylene, or $C_{4-8}$ heteroalkenylene, each of which is optionally substituted with 1 or 4 groups independently selected from halo and $C_{1-6}$ alkyl, and wherein the heteroalkylene and heteroalkenylene comprise 1 to 4 oxygen atoms.

2. The compound of claim 1, or a pharmaceutically acceptable salt thereof, wherein the compound of Formula (I) is a compound of Formula (IA):

(IA)

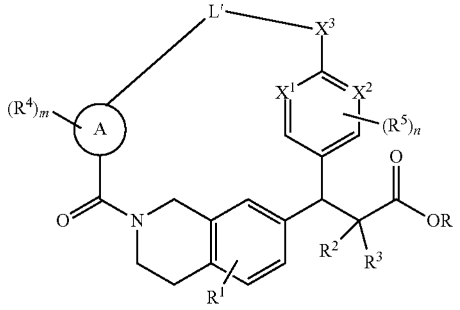

wherein:

L' is $C_{4-6}$ alkylene, $C_{4-6}$ alkenylene, $C_{4-6}$ heteroalkylene, or $C_{4-6}$ heteroalkenylene, each of which is optionally substituted with 1 or 2 groups independently selected from halo and $C_{1-6}$ alkyl, and wherein the heteroalkylene and heteroalkenylene comprise 1 or 2 oxygen atoms;

$X^3$ is $CH_2$ or O;

n is 0, 1, or 2; and $X^1$ and $X^2$ are independently CH or N.

3. The compound of claim 1, or a pharmaceutically acceptable salt thereof, wherein each $R^5$ is independently methyl or methoxy.

4. The compound of claim 2, or a pharmaceutically acceptable salt thereof, wherein the $C_{4-6}$ alkenylene or $C_{4-6}$ heteroalkenylene comprise one unsaturated bond.

5. The compound of claim 1, or a pharmaceutically acceptable salt thereof, wherein the compound of Formula (I) is a compound of Formula (IB):

(IB)

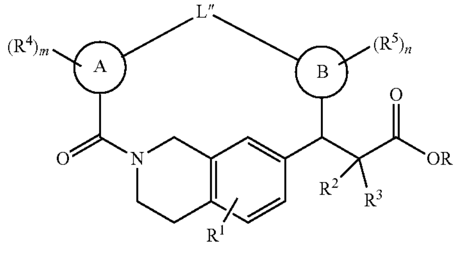

wherein:

L" is $C_{4-6}$ alkylene, $C_{4-6}$ alkenylene, $C_{4-6}$ heteroalkylene, or $C_{4-6}$ heteroalkenylene, each of which is optionally substituted with 1 or 2 groups independently selected from halo and $C_{1-6}$alkyl, and wherein the heteroalkylene and heteroalkenylene comprise 1 to 2 oxygen atoms;

Ring B" is selected from

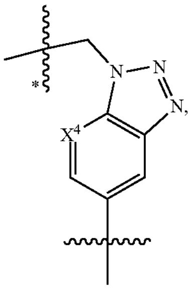

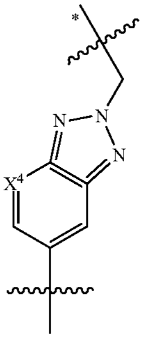

,

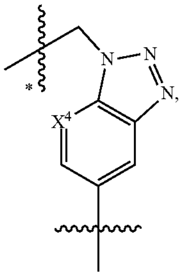

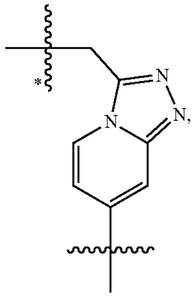

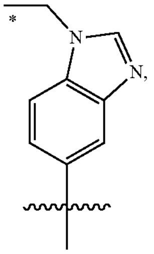

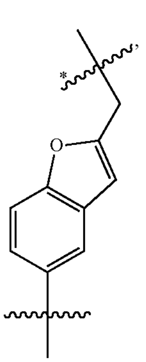

and

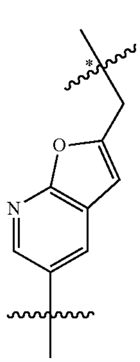

, wherein the * designates a bond to L"; $X^4$ is $CR^5$, CH or N; Ring B" is substituted with —$(R^5)_n$ where n is 0, 1, 2, or 3; and each $R^5$ is independently halo, $C_{1-4}$ alkyl, or $C_{1-4}$ alkyloxy; provided that the ring is not

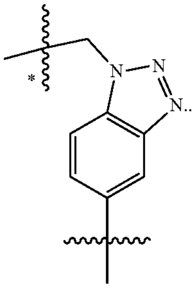 [SMILES: *Cn1nnc2cc(*)ccc21]

6. The compound of claim 5, or a pharmaceutically acceptable salt thereof, wherein each $R^5$ is independently methyl or methoxy.

7. The compound of claim 5, or a pharmaceutically acceptable salt thereof, wherein L" is $C_{4-6}$ alkenylene or $C_{4-6}$ heteroalkenylene, wherein the heteroalkenylene comprises 1 oxygen atom, and wherein the $C_{4-6}$ alkenylene and $C_{4-6}$ heteroalkylene comprise one unsaturated bond.

8. The compound of claim 5, or a pharmaceutically acceptable salt thereof, wherein each $R^5$ is independently F, Cl, or methyl.

9. The compound of claim 5, or a pharmaceutically acceptable salt thereof, wherein Ring A is phenylene, indolylene, pyrrolopyridinylene, pyridinylene, pyrazinylene, pyrimidinylene, pyridazinylene, naphthalenylene, quinolinylene, benzoimidazolylene, or benzofuranylene.

10. The compound of claim 1, or a pharmaceutically acceptable salt thereof, wherein Ring A is

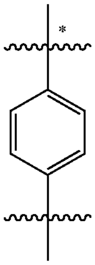

,

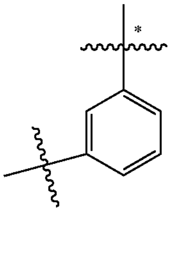

,

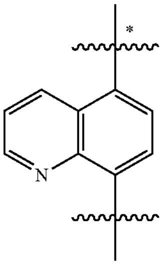

,

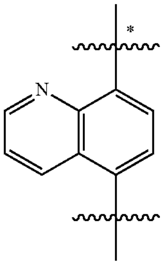

,

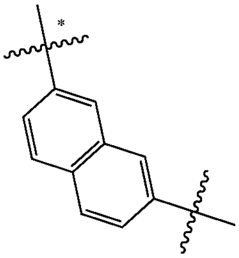

,

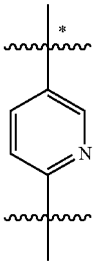

,

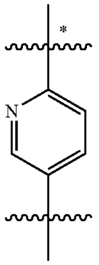

,

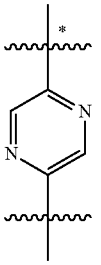

,

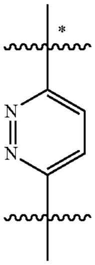

,

-continued

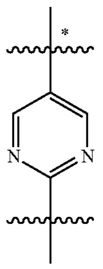 , 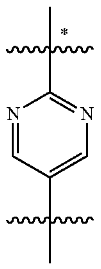 , 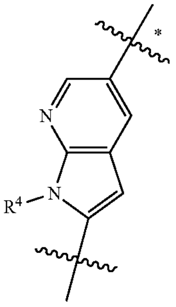 ,

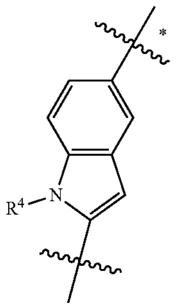 , 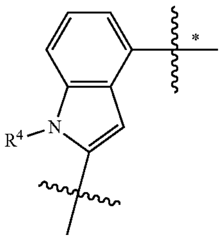 ,

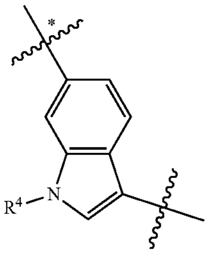 , 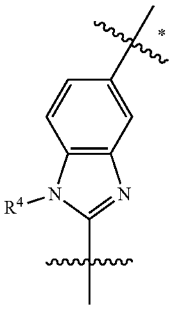 ,

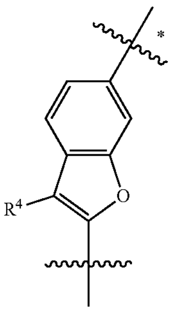 , 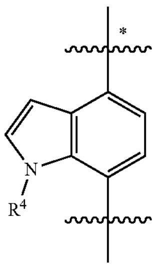 ,

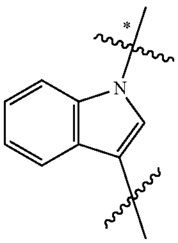 , 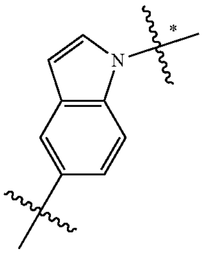 , or

-continued

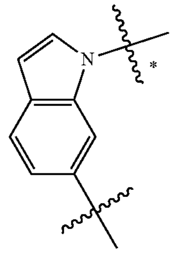 , wherein the * designates a bond to L,

Ring A is substituted with —$(R^4)_m$ where m is 1, 2, 3, or 4; and each $R^4$ is independently H, halo, $C_{1-6}$ alkyl, or $C_{1-6}$ alkoxy, wherein the $C_{1-6}$ alkyl and $C_{1-6}$ alkoxy groups are optionally substituted with 1-3 groups independently selected from halo, $C_{1-6}$ alkyloxy, amido, and N,N-dimethylamido groups.

11. The compound of claim 1, or a pharmaceutically acceptable salt thereof, wherein each $R^4$ is independently selected from H, methyl, isobutyl, F, Cl, trifluoromethyl, methoxy, difluoromethoxy, trifluoromethoxy, N,N-dimethylamido, 3,3,3-trifluoropropyl, 2,2-difluoroethyl, 3-fluoropropyl, and methoxyethyl.

12. The compound of claim 1, or a pharmaceutically acceptable salt thereof, wherein R is H, methyl, ethyl, 2-hydroxy-ethyl, or benzyl.

13. The compound of claim 1, or a pharmaceutically acceptable salt thereof, wherein $R^1$ is H or methyl.

14. The compound of claim 1, or a pharmaceutically acceptable salt thereof, wherein $R^2$ is H or methyl.

15. The compound of claim 1, or a pharmaceutically acceptable salt thereof, wherein $R^3$ is H or methyl.

16. A pharmaceutical composition comprising the compound of claim 1, or a pharmaceutically acceptable salt thereof, and a pharmaceutically acceptable excipient.

17. A method of treating sickle cell disease in a subject in need thereof, comprising administering to the subject a therapeutically effective amount of the compound of claim 1, or a pharmaceutically acceptable salt thereof.

18. The compound of claim 1, or a pharmaceutically acceptable salt thereof, which is selected from the group consisting of:

| Comp'd No | Structure |
| --- | --- |
| 1 | 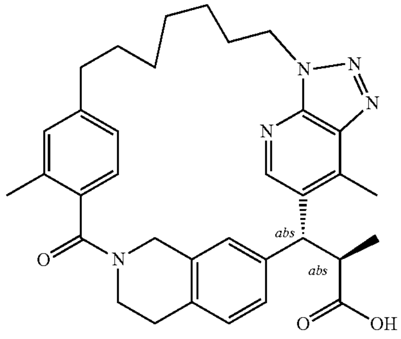 [SMILES: Cc1cc2ccc1C(=O)N1CCc3ccc(cc3C1)[C@@H]([C@@H](C)C(=O)O)c1cnc3c(nnn3CCCCCCC2)c1C] |

-continued
| Comp'd No | Structure |
|---|---|
| 2 | 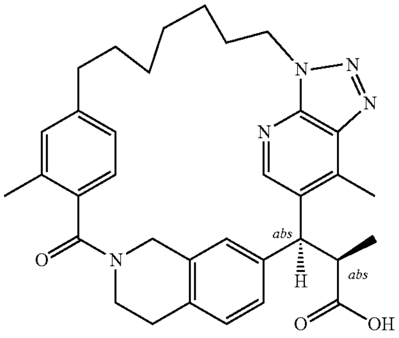 [SMILES: Cc1cc2ccc1C(=O)N1CCc3ccc(cc3C1)[C@H]([C@@H](C)C(=O)O)c1cnc3c(nnn3CCCCCCC2)c1C] |
| 3 | 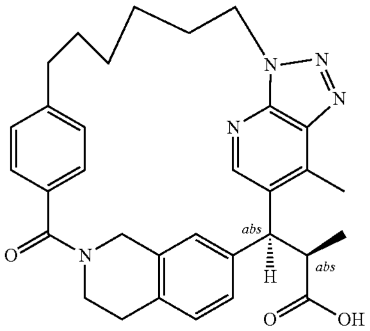 [SMILES: Cc1c2cnc3c1nnn3CCCCCCc1ccc(cc1)C(=O)N1CCc3ccc(cc3C1)[C@@H]2[C@@H](C)C(=O)O] |
| 4 | 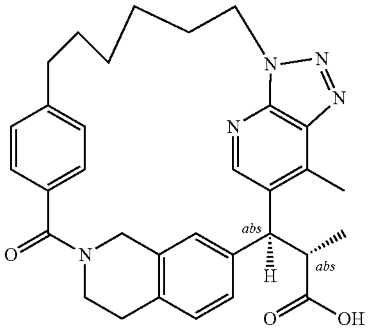 [SMILES: Cc1c2cnc3c1nnn3CCCCCCc1ccc(cc1)C(=O)N1CCc3ccc(cc3C1)[C@@H]2[C@H](C)C(=O)O] |
| 5 | 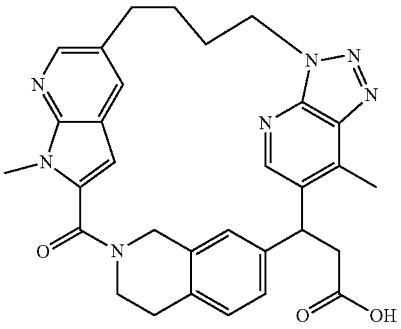 |
-continued
| Comp'd No | Structure |
|---|---|
| 6 | 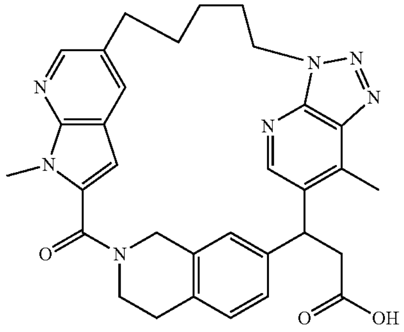 |
| 8 | 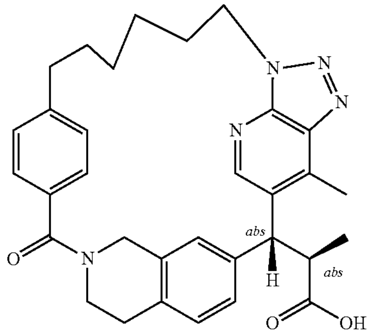 [SMILES: Cc1c2cnc3c1nnn3CCCCCCc1ccc(cc1)C(=O)N1CCc3ccc(cc3C1)[C@H]2[C@@H](C)C(=O)O] |
| 11 | 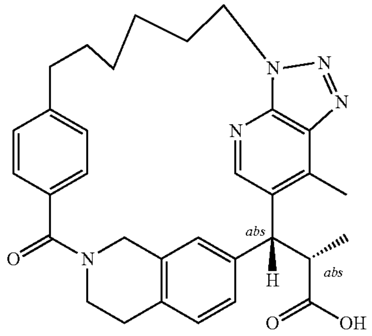 [SMILES: Cc1c2cnc3c1nnn3CCCCCCc1ccc(cc1)C(=O)N1CCc3ccc(cc3C1)[C@H]2[C@H](C)C(=O)O] |
| 12 | 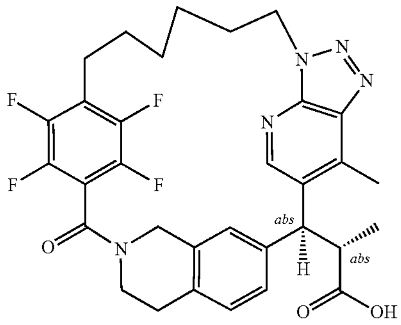 [SMILES: Cc1c2cnc3c1nnn3CCCCCCc1c(F)c(F)c(c(F)c1F)C(=O)N1CCc3ccc(cc3C1)[C@@H]2[C@H](C)C(=O)O] |

-continued
| Comp'd No | Structure |
|---|---|
| 13 | 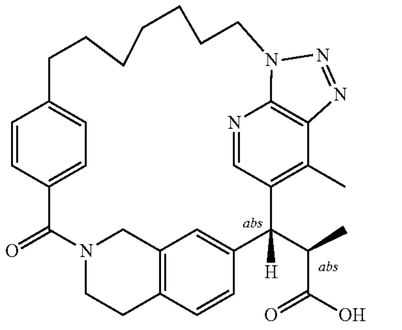 [SMILES: Cc1c2cnc3c1nnn3CCCCCCCc1ccc(cc1)C(=O)N1CCc3ccc(cc3C1)[C@H]2[C@@H](C)C(=O)O] |
| 14 | 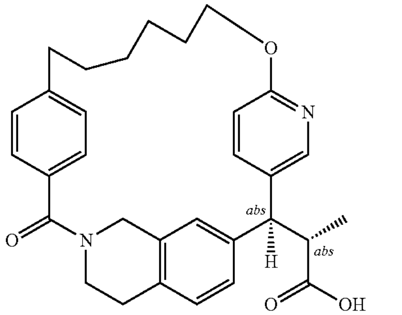 [SMILES: C[C@H](C(=O)O)[C@@H]1c2ccc(nc2)OCCCCCCc2ccc(cc2)C(=O)N2CCc3ccc1cc3C2] |
| 15 | 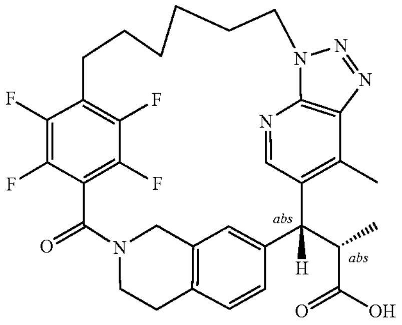 [SMILES: Cc1c2cnc3c1nnn3CCCCCCc1c(F)c(F)c(c(F)c1F)C(=O)N1CCc3ccc(cc3C1)[C@H]2[C@H](C)C(=O)O] |
| 17 | 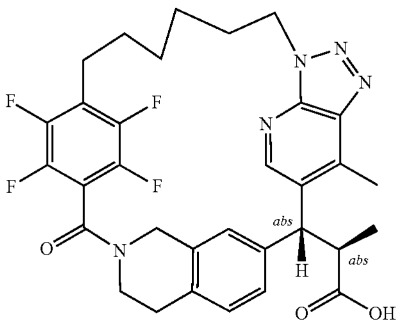 [SMILES: Cc1c2cnc3c1nnn3CCCCCCc1c(F)c(F)c(c(F)c1F)C(=O)N1CCc3ccc(cc3C1)[C@H]2[C@@H](C)C(=O)O] |
-continued
| Comp'd No | Structure |
|---|---|
| 20 | 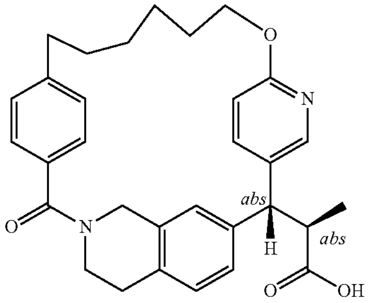 [SMILES: C[C@@H](C(=O)O)[C@H]1c2ccc(nc2)OCCCCCCc2ccc(cc2)C(=O)N2CCc3ccc1cc3C2] |
| 21 | 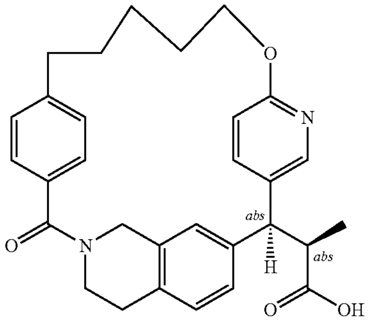 [SMILES: C[C@@H](C(=O)O)[C@@H]1c2ccc(nc2)OCCCCCc2ccc(cc2)C(=O)N2CCc3ccc1cc3C2] |
| 22 | 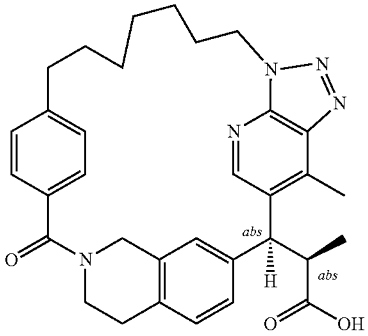 [SMILES: Cc1c2cnc3c1nnn3CCCCCCCc1ccc(cc1)C(=O)N1CCc3ccc(cc3C1)[C@@H]2[C@@H](C)C(=O)O] |
| 23 | 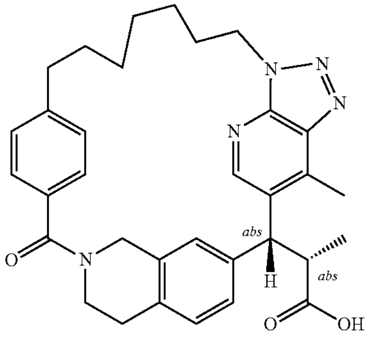 [SMILES: Cc1c2cnc3c1nnn3CCCCCCCc1ccc(cc1)C(=O)N1CCc3ccc(cc3C1)[C@H]2[C@H](C)C(=O)O] |

-continued
| Comp'd No | Structure |
| --- | --- |
| 24 | 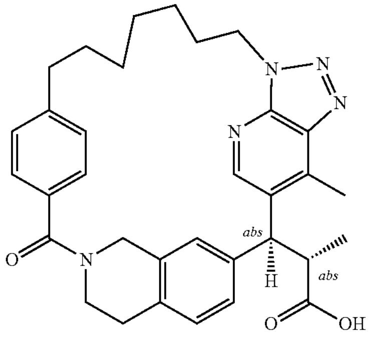 [SMILES: Cc1c2cnc3c1nnn3CCCCCCCc1ccc(cc1)C(=O)N1CCc3ccc(cc3C1)[C@@H]2[C@H](C)C(=O)O] |
| 25 | 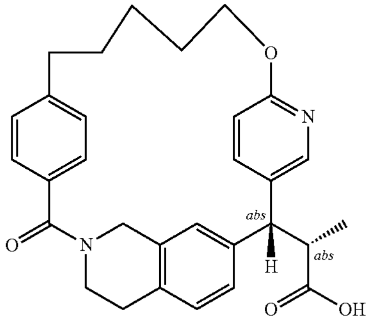 [SMILES: C[C@H](C(=O)O)[C@H]1c2ccc(nc2)OCCCCCc2ccc(cc2)C(=O)N2CCc3ccc1cc3C2] |
| 35 | 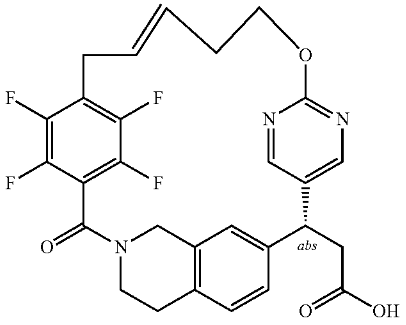 [SMILES: O=C(O)C[C@H]1c2cnc(nc2)OCC/C=C/Cc2c(F)c(F)c(c(F)c2F)C(=O)N2CCc3ccc1cc3C2] |
| 36 | 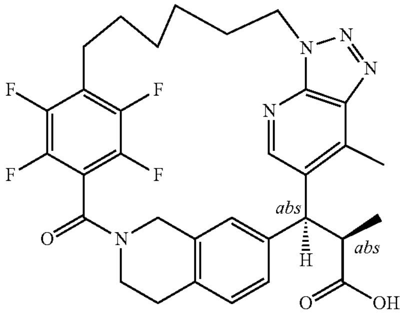 [SMILES: Cc1c2cnc3c1nnn3CCCCCCc1c(F)c(F)c(c(F)c1F)C(=O)N1CCc3ccc(cc3C1)[C@@H]2[C@@H](C)C(=O)O] |
-continued
| Comp'd No | Structure |
| --- | --- |
| 40 | 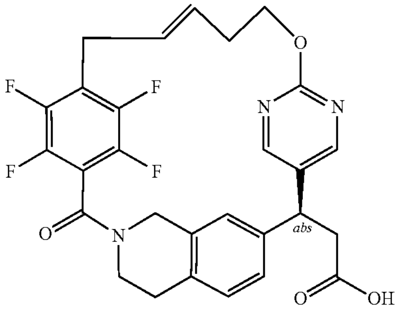 [SMILES: O=C(O)C[C@@H]1c2cnc(nc2)OCC/C=C/Cc2c(F)c(F)c(c(F)c2F)C(=O)N2CCc3ccc1cc3C2] |
| 43 | 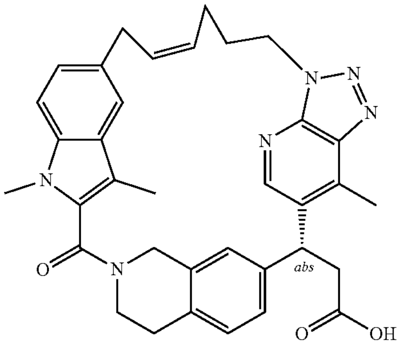 |
| 44 | 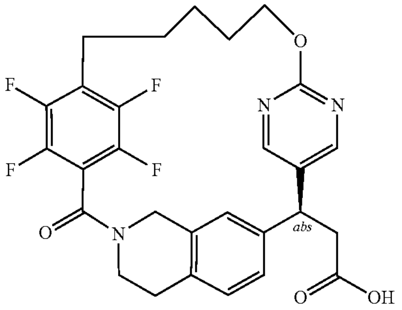 [SMILES: O=C(O)C[C@@H]1c2cnc(nc2)OCCCCCc2c(F)c(F)c(c(F)c2F)C(=O)N2CCc3ccc1cc3C2] |
| 45 | 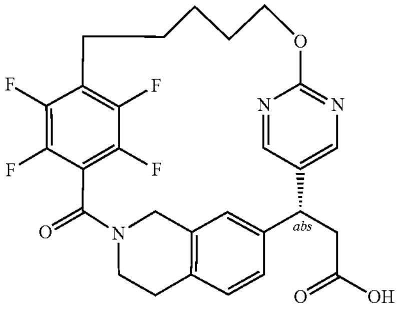 [SMILES: O=C(O)C[C@H]1c2cnc(nc2)OCCCCCc2c(F)c(F)c(c(F)c2F)C(=O)N2CCc3ccc1cc3C2] |

-continued
| Comp'd No | Structure |
|---|---|
| 46 | 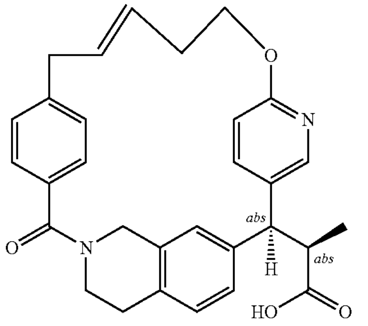 [SMILES: C[C@@H](C(=O)O)[C@@H]1c2ccc(nc2)OCC/C=C/Cc2ccc(cc2)C(=O)N2CCc3ccc1cc3C2] |
| 47 | 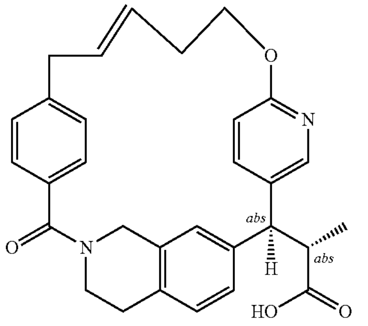 [SMILES: C[C@H](C(=O)O)[C@@H]1c2ccc(nc2)OCC/C=C/Cc2ccc(cc2)C(=O)N2CCc3ccc1cc3C2] |
| 49 | 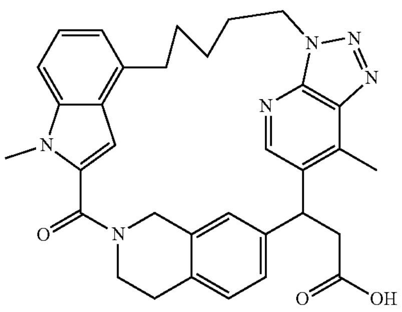 |
| 52 | 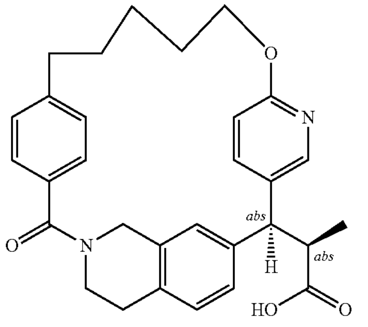 [SMILES: C[C@@H](C(=O)O)[C@@H]1c2ccc(nc2)OCCCCCc2ccc(cc2)C(=O)N2CCc3ccc1cc3C2] |
-continued
| Comp'd No | Structure |
|---|---|
| 53 | 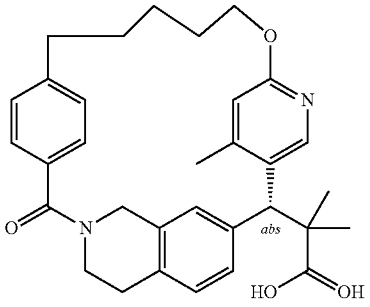 [SMILES: Cc1cc2ncc1[C@H](C(C)(C)C(=O)O)c1ccc3c(c1)CN(CC3)C(=O)c1ccc(cc1)CCCCCO2] |
| 54 | 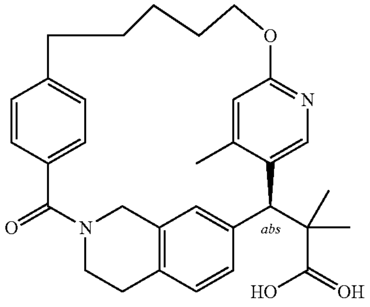 [SMILES: Cc1cc2ncc1[C@@H](C(C)(C)C(=O)O)c1ccc3c(c1)CN(CC3)C(=O)c1ccc(cc1)CCCCCO2] |
| 55 | 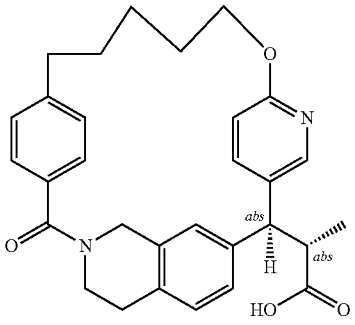 [SMILES: C[C@H](C(=O)O)[C@@H]1c2ccc(nc2)OCCCCCc2ccc(cc2)C(=O)N2CCc3ccc1cc3C2] |
| 57 | 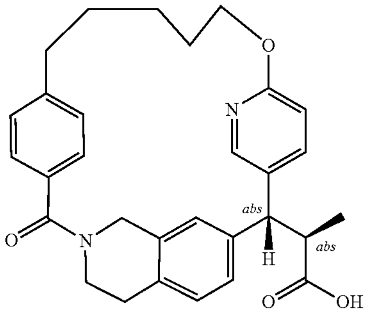 [SMILES: C[C@@H](C(=O)O)[C@H]1c2ccc(nc2)OCCCCCc2ccc(cc2)C(=O)N2CCc3ccc1cc3C2] |
| 58 | 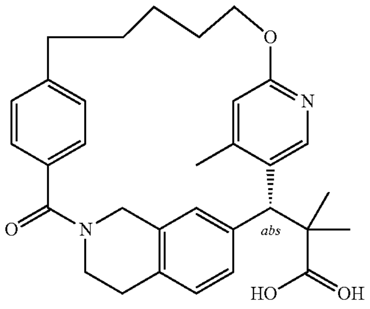 [SMILES: Cc1cc2ncc1[C@H](C(C)(C)C(=O)O)c1ccc3c(c1)CN(CC3)C(=O)c1ccc(cc1)CCCCCO2] |

Comp'd No | Structure
59
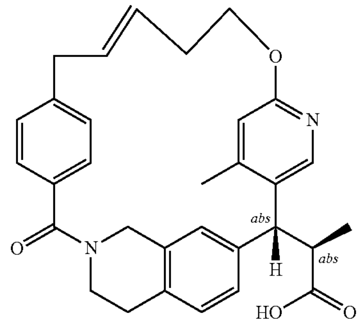 [SMILES: Cc1cc2ncc1[C@H]([C@@H](C)C(=O)O)c1ccc3c(c1)CN(CC3)C(=O)c1ccc(cc1)C/C=C/CCO2]
60
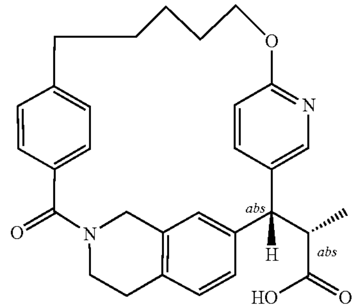 [SMILES: C[C@H](C(=O)O)[C@H]1c2ccc(nc2)OCCCCCc2ccc(cc2)C(=O)N2CCc3ccc1cc3C2]
61
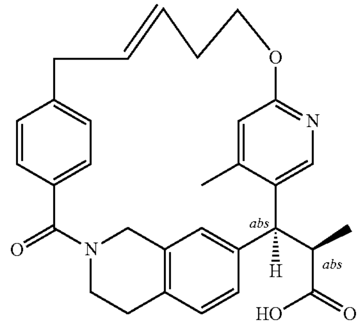 [SMILES: Cc1cc2ncc1[C@@H]([C@@H](C)C(=O)O)c1ccc3c(c1)CN(CC3)C(=O)c1ccc(cc1)C/C=C/CCO2]
62
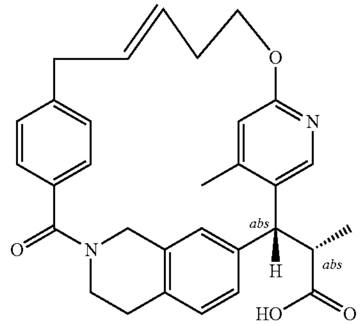 [SMILES: Cc1cc2ncc1[C@H]([C@H](C)C(=O)O)c1ccc3c(c1)CN(CC3)C(=O)c1ccc(cc1)C/C=C/CCO2]
Comp'd No | Structure
63
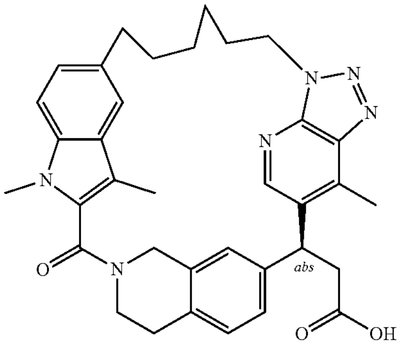
64
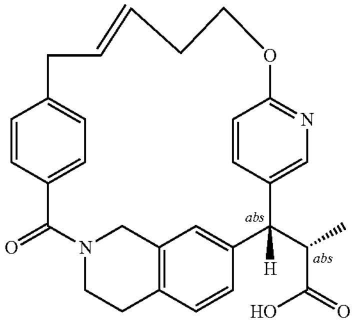 [SMILES: C[C@H](C(=O)O)[C@H]1c2ccc(nc2)OCC/C=C/Cc2ccc(cc2)C(=O)N2CCc3ccc1cc3C2]
65
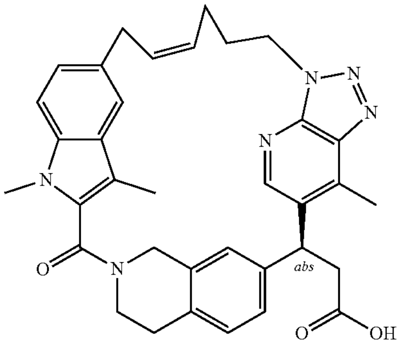
66
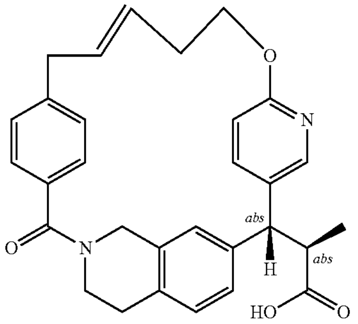 [SMILES: C[C@@H](C(=O)O)[C@H]1c2ccc(nc2)OCC/C=C/Cc2ccc(cc2)C(=O)N2CCc3ccc1cc3C2]

-continued
| Comp'd No | Structure |
| --- | --- |
| 67 | 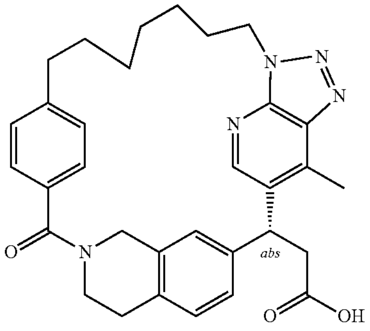 [SMILES: Cc1c2cnc3c1nnn3CCCCCCCc1ccc(cc1)C(=O)N1CCc3ccc(cc3C1)[C@H]2CC(=O)O] |
| 68 | 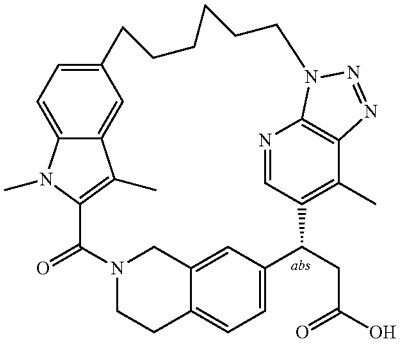 |
| 70 | 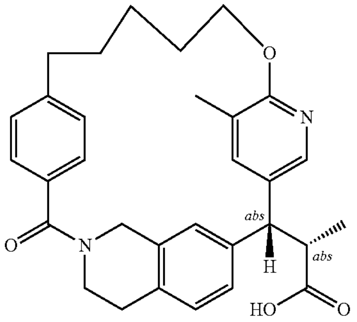 [SMILES: Cc1cc2cnc1OCCCCCc1ccc(cc1)C(=O)N1CCc3ccc(cc3C1)[C@H]2[C@H](C)C(=O)O] |
| 71 | 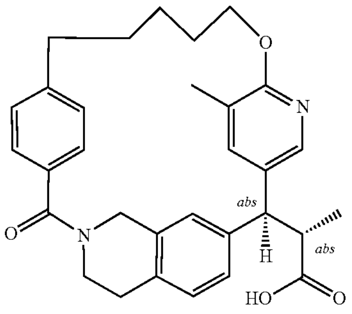 [SMILES: Cc1cc2cnc1OCCCCCc1ccc(cc1)C(=O)N1CCc3ccc(cc3C1)[C@@H]2[C@H](C)C(=O)O] |
-continued
| Comp'd No | Structure |
| --- | --- |
| 72 | 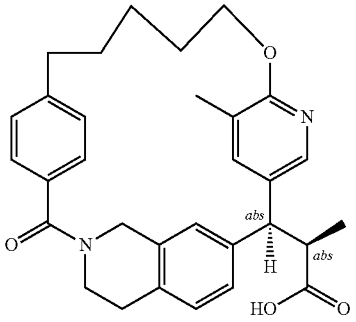 [SMILES: Cc1cc2cnc1OCCCCCc1ccc(cc1)C(=O)N1CCc3ccc(cc3C1)[C@@H]2[C@@H](C)C(=O)O] |
| 73 | 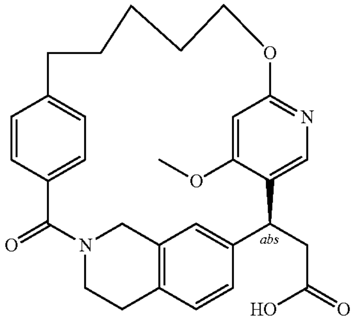 [SMILES: COc1cc2ncc1[C@@H](CC(=O)O)c1ccc3c(c1)CN(CC3)C(=O)c1ccc(cc1)CCCCCO2] |
| 74 | 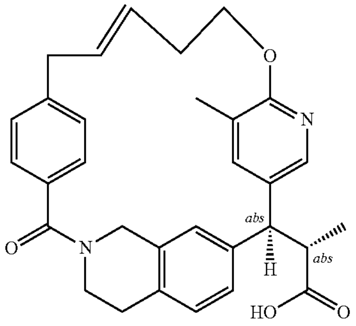 [SMILES: Cc1cc2cnc1OCC/C=C/Cc1ccc(cc1)C(=O)N1CCc3ccc(cc3C1)[C@@H]2[C@H](C)C(=O)O] |
| 75 | 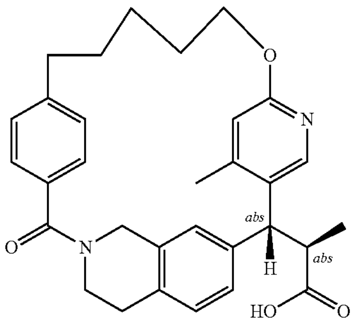 [SMILES: Cc1cc2ncc1[C@H]([C@@H](C)C(=O)O)c1ccc3c(c1)CN(CC3)C(=O)c1ccc(cc1)CCCCCO2] |

-continued
| Comp'd No | Structure |
|---|---|
| 76 | 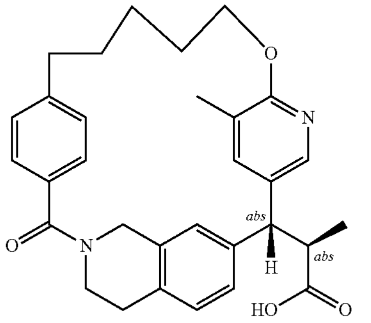 [SMILES: Cc1cc2cnc1OCCCCCc1ccc(cc1)C(=O)N1CCc3ccc(cc3C1)[C@H]2[C@@H](C)C(=O)O] |
| 77 | 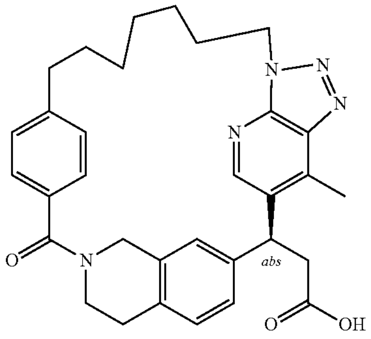 [SMILES: Cc1c2cnc3c1nnn3CCCCCCCc1ccc(cc1)C(=O)N1CCc3ccc(cc3C1)[C@@H]2CC(=O)O] |
| 78 | 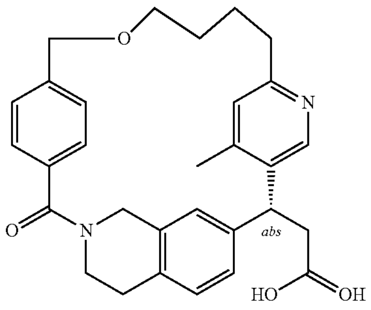 [SMILES: Cc1cc2ncc1[C@H](CC(=O)O)c1ccc3c(c1)CN(CC3)C(=O)c1ccc(cc1)COCCCC2] |
| 79 | 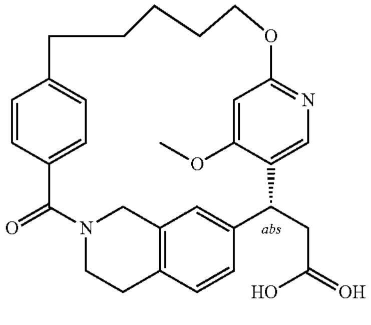 [SMILES: COc1cc2ncc1[C@H](CC(=O)O)c1ccc3c(c1)CN(CC3)C(=O)c1ccc(cc1)CCCCCO2] |
-continued
| Comp'd No | Structure |
|---|---|
| 80 | 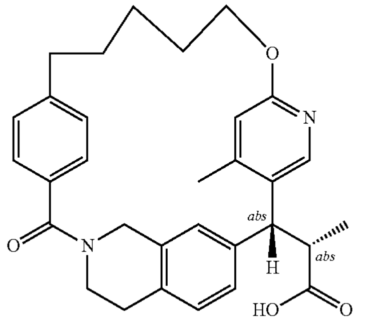 [SMILES: Cc1cc2ncc1[C@H]([C@H](C)C(=O)O)c1ccc3c(c1)CN(CC3)C(=O)c1ccc(cc1)CCCCCO2] |
| 81 | 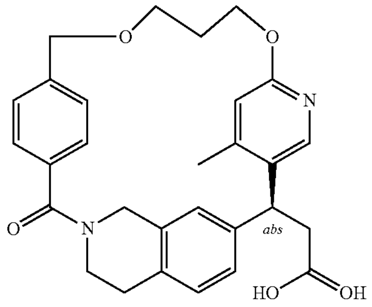 [SMILES: Cc1cc2ncc1[C@@H](CC(=O)O)c1ccc3c(c1)CN(CC3)C(=O)c1ccc(cc1)COCCCO2] |
| 82 | 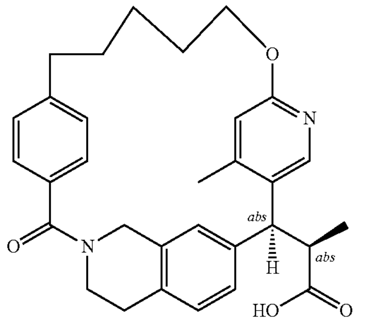 [SMILES: Cc1cc2ncc1[C@@H]([C@@H](C)C(=O)O)c1ccc3c(c1)CN(CC3)C(=O)c1ccc(cc1)CCCCCO2] |
| 83 | 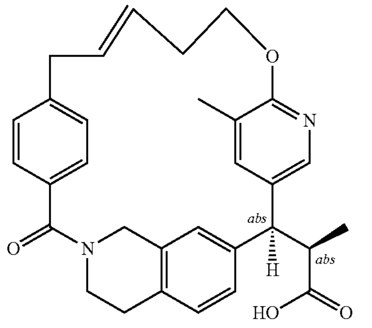 [SMILES: Cc1cc2cnc1OCC/C=C/Cc1ccc(cc1)C(=O)N1CCc3ccc(cc3C1)[C@@H]2[C@@H](C)C(=O)O] |

-continued
| Comp'd No | Structure |
| --- | --- |
| 84 | 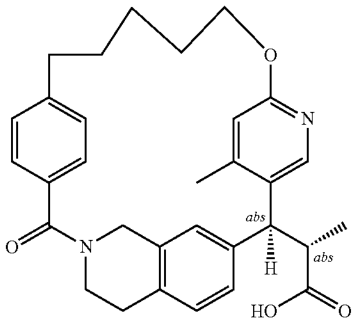 [SMILES: Cc1cc2ncc1[C@@H]([C@H](C)C(=O)O)c1ccc3c(c1)CN(CC3)C(=O)c1ccc(cc1)CCCCCO2] |
| 86 | 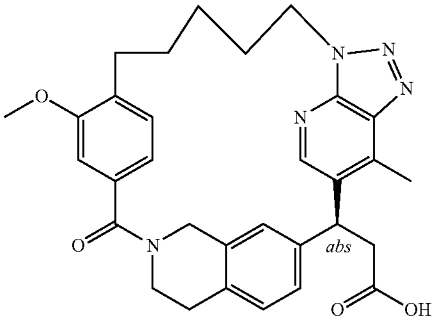 |
| 87 | 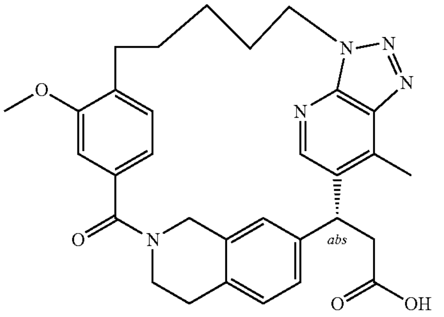 |
| 88 | 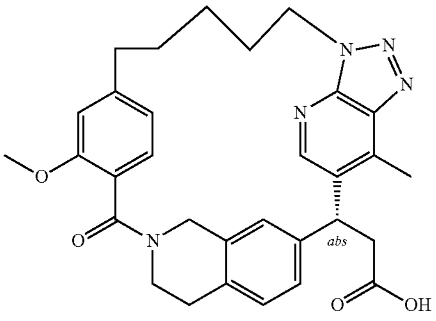 |
-continued
| Comp'd No | Structure |
| --- | --- |
| 89 | 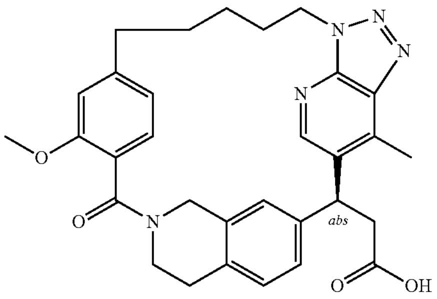 |
| 91 | 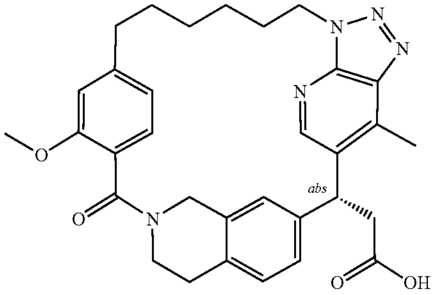 |
| 92 | 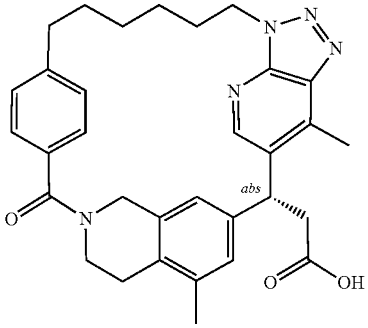 [SMILES: Cc1cc2cc3c1CCN(C3)C(=O)c1ccc(cc1)CCCCCCn1nnc3c(C)c(cnc31)[C@@H]2CC(=O)O] |
| 93 | 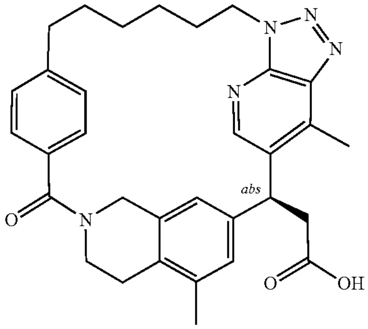 [SMILES: Cc1cc2cc3c1CCN(C3)C(=O)c1ccc(cc1)CCCCCCn1nnc3c(C)c(cnc31)[C@H]2CC(=O)O] |
| 94 | 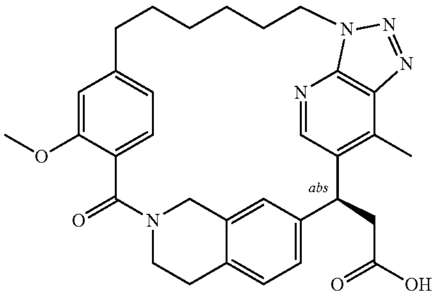 |

-continued
| Comp'd No | Structure |
|---|---|
| 95 | 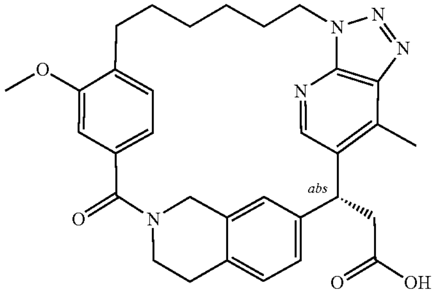 |
| 96 | 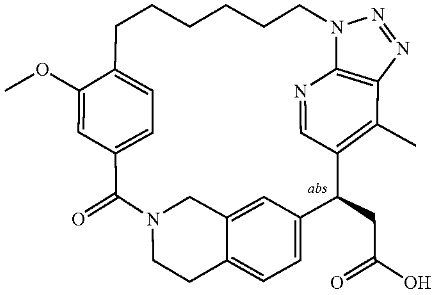 |
| 99 | 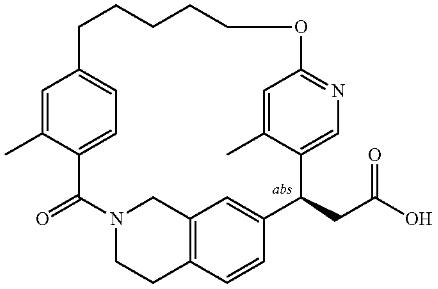 [SMILES: Cc1cc2ccc1C(=O)N1CCc3ccc(cc3C1)[C@H](CC(=O)O)c1cnc(cc1C)OCCCCC2] |
| 100 | 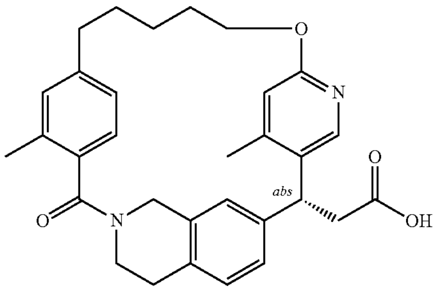 [SMILES: Cc1cc2ccc1C(=O)N1CCc3ccc(cc3C1)[C@@H](CC(=O)O)c1cnc(cc1C)OCCCCC2] |
| 103 | 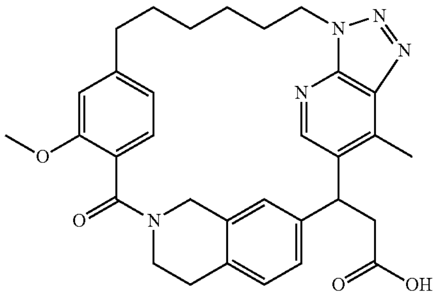 |
-continued
| Comp'd No | Structure |
|---|---|
| 104 | 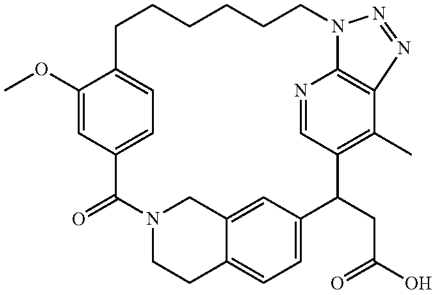 |
| 105 | 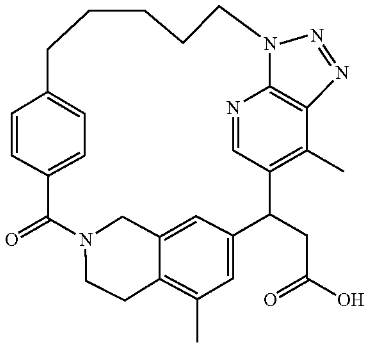 [SMILES: Cc1cc2cc3c1CCN(C3)C(=O)c1ccc(cc1)CCCCCn1nnc3c(C)c(cnc31)C2CC(=O)O] |
| 106 | 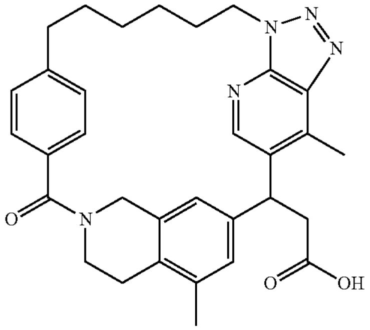 [SMILES: Cc1cc2cc3c1CCN(C3)C(=O)c1ccc(cc1)CCCCCCn1nnc3c(C)c(cnc31)C2CC(=O)O] |
| 117 | 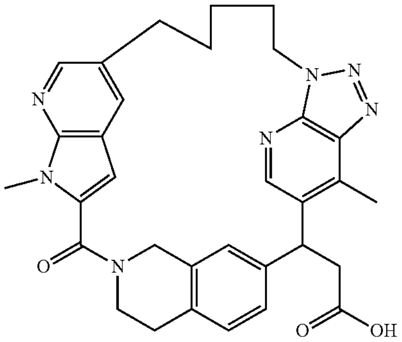 |

-continued
| Comp'd No | Structure |
|---|---|
| 119 | 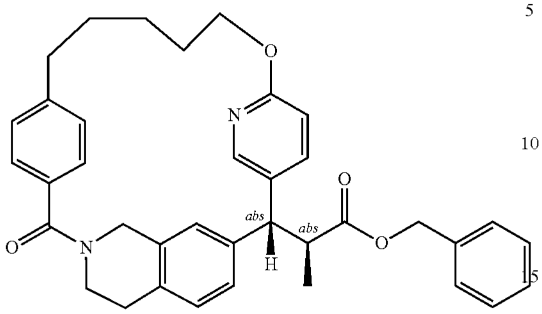 |
| 120 | 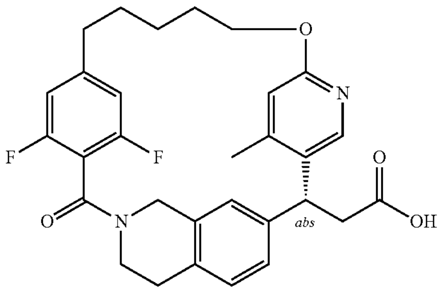 [SMILES: Cc1cc2ncc1[C@H](CC(=O)O)c1ccc3c(c1)CN(CC3)C(=O)c1c(F)cc(cc1F)CCCCCO2] |
| 121 | 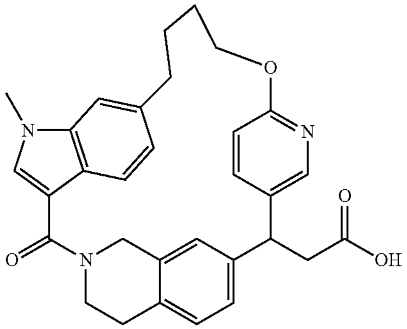 [SMILES: Cn1cc2c3ccc(cc31)CCCCOc1ccc(cn1)C(CC(=O)O)c1ccc3c(c1)CN(CC3)C2=O] |
| 122 | 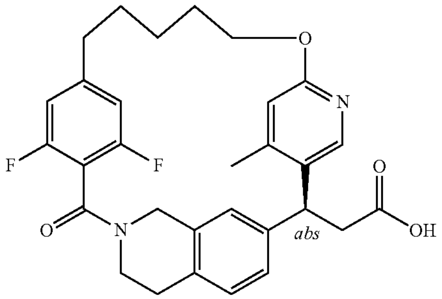 [SMILES: Cc1cc2ncc1[C@@H](CC(=O)O)c1ccc3c(c1)CN(CC3)C(=O)c1c(F)cc(cc1F)CCCCCO2] |
| 123 | 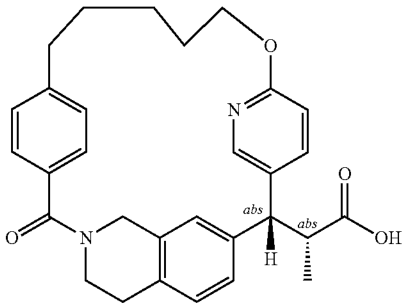 [SMILES: C[C@@H](C(=O)O)[C@H]1c2ccc(nc2)OCCCCCc2ccc(cc2)C(=O)N2CCc3ccc1cc3C2] |
-continued
| Comp'd No | Structure |
|---|---|
| 124 | 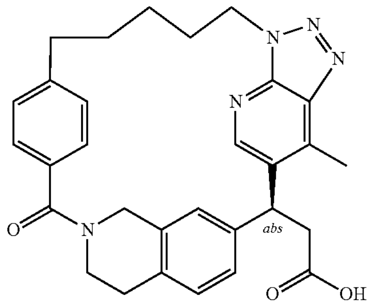 [SMILES: Cc1c2cnc3c1nnn3CCCCCc1ccc(cc1)C(=O)N1CCc3ccc(cc3C1)[C@@H]2CC(=O)O] |
| 125 | 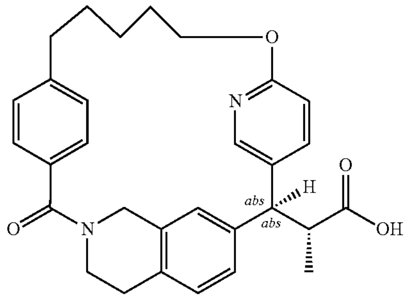 [SMILES: C[C@@H](C(=O)O)[C@@H]1c2ccc(nc2)OCCCCCc2ccc(cc2)C(=O)N2CCc3ccc1cc3C2] |
| 126 | 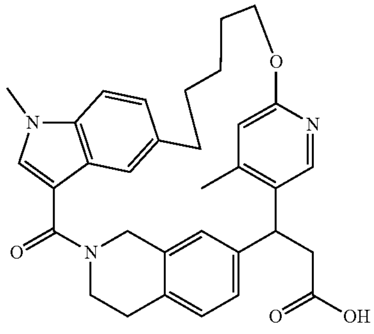 [SMILES: Cc1cc2ncc1C(CC(=O)O)c1ccc3c(c1)CN(CC3)C(=O)c1cn(C)c3ccc(cc13)CCCCCO2] |
| 127 | 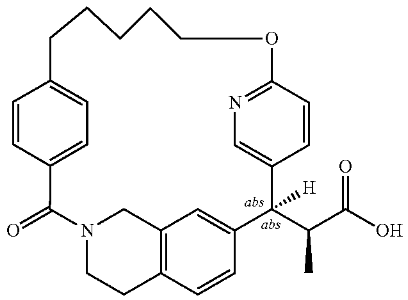 [SMILES: C[C@H](C(=O)O)[C@@H]1c2ccc(nc2)OCCCCCc2ccc(cc2)C(=O)N2CCc3ccc1cc3C2] |

-continued
| Comp'd No | Structure |
|---|---|
| 128 | 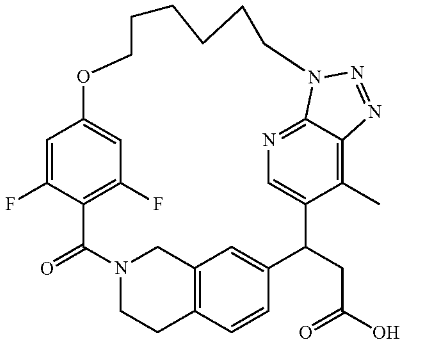 [SMILES: Cc1c2cnc3c1nnn3CCCCCCOc1cc(F)c(c(F)c1)C(=O)N1CCc3ccc(cc3C1)C2CC(=O)O] |
| 135 | 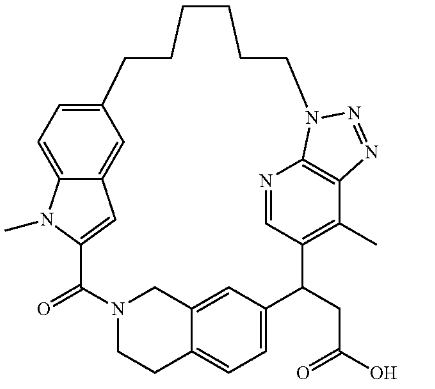 |
| 136 | 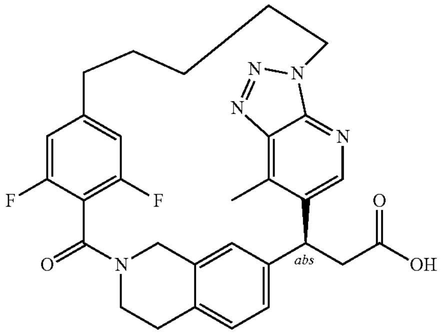 |
| 137 | 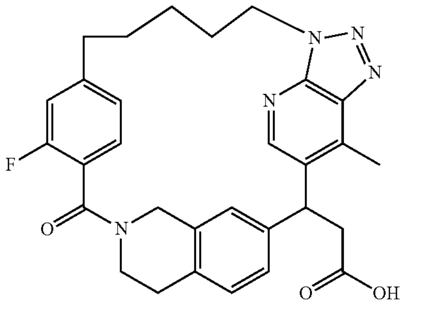 [SMILES: Cc1c2cnc3c1nnn3CCCCCc1ccc(c(F)c1)C(=O)N1CCc3ccc(cc3C1)C2CC(=O)O] |
| 138 | 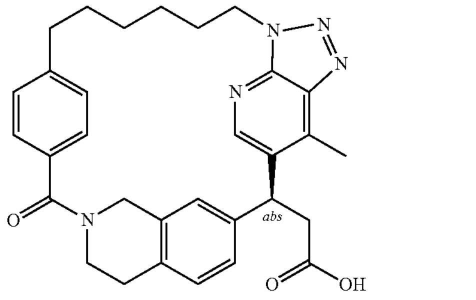 [SMILES: Cc1c2cnc3c1nnn3CCCCCCc1ccc(cc1)C(=O)N1CCc3ccc(cc3C1)[C@@H]2CC(=O)O] |
| 139 | 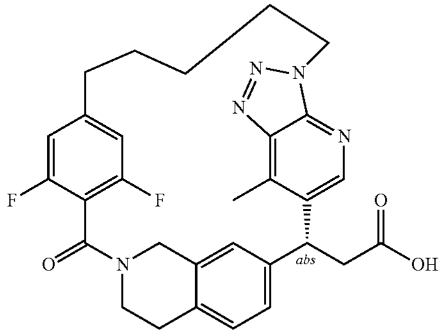 [SMILES: Cc1c2cnc3c1nnn3CCCCCc1cc(F)c(c(F)c1)C(=O)N1CCc3ccc(cc3C1)[C@H]2CC(=O)O] |
| 140 | 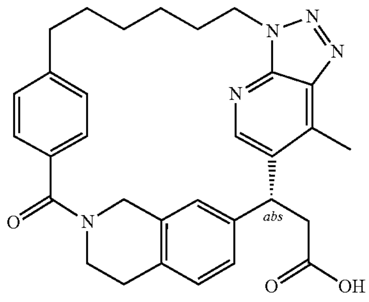 [SMILES: Cc1c2cnc3c1nnn3CCCCCCc1ccc(cc1)C(=O)N1CCc3ccc(cc3C1)[C@H]2CC(=O)O] |
| 143 | 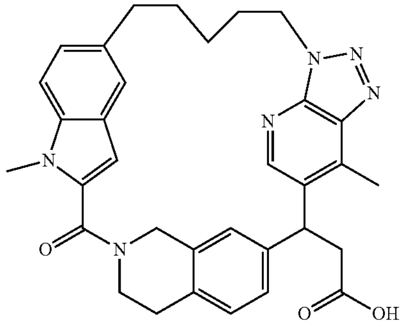 |
| 144 | 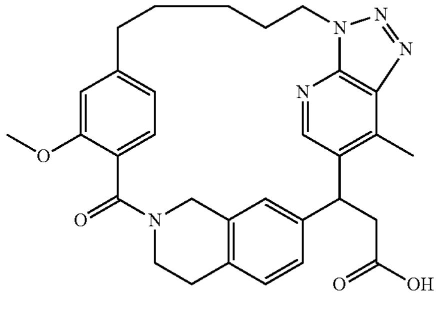 |

-continued
| Comp'd No | Structure |
|---|---|
| 146 | 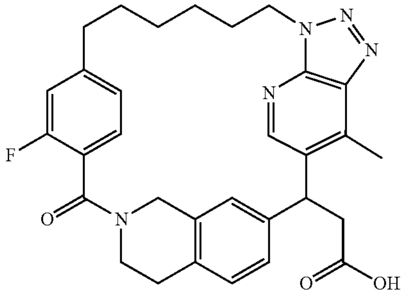 [SMILES: Cc1c2cnc3c1nnn3CCCCCCc1ccc(c(F)c1)C(=O)N1CCc3ccc(cc3C1)C2CC(=O)O] |
| 149 | 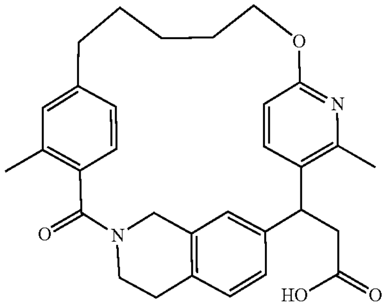 [SMILES: Cc1cc2ccc1C(=O)N1CCc3ccc(cc3C1)C(CC(=O)O)c1ccc(nc1C)OCCCCC2] |
| 150 | 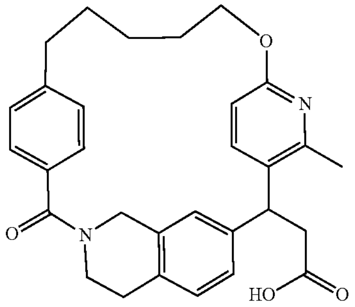 [SMILES: Cc1nc2ccc1C(CC(=O)O)c1ccc3c(c1)CN(CC3)C(=O)c1ccc(cc1)CCCCCO2] |
| 151 | 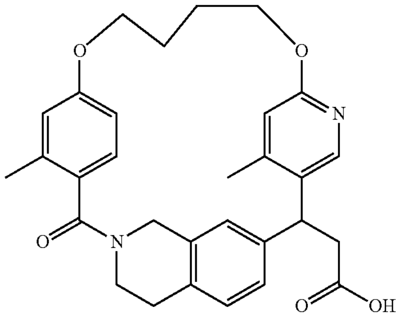 [SMILES: Cc1cc2ccc1C(=O)N1CCc3ccc(cc3C1)C(CC(=O)O)c1cnc(cc1C)OCCCCO2] |
| 154 | 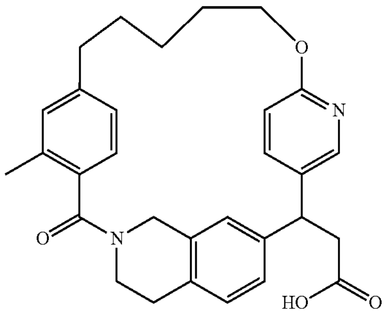 [SMILES: Cc1cc2ccc1C(=O)N1CCc3ccc(cc3C1)C(CC(=O)O)c1ccc(nc1)OCCCCC2] |
-continued
| Comp'd No | Structure |
|---|---|
| 157 | 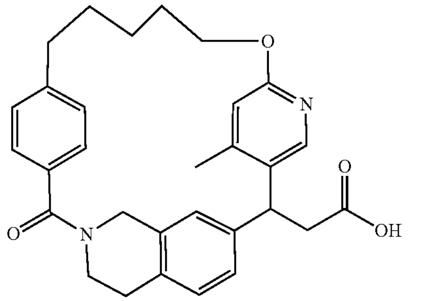 [SMILES: Cc1cc2ncc1C(CC(=O)O)c1ccc3c(c1)CN(CC3)C(=O)c1ccc(cc1)CCCCCO2] |
| 158 | 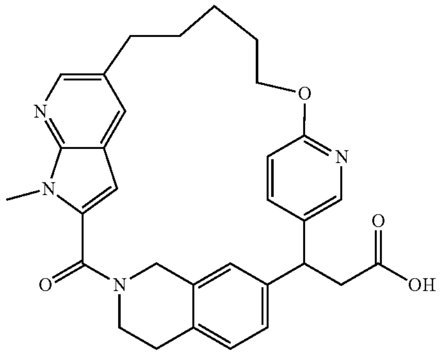 [SMILES: Cn1c2cc3cc(cnc31)CCCCCOc1ccc(cn1)C(CC(=O)O)c1ccc3c(c1)CN(CC3)C2=O] |
| 161 | 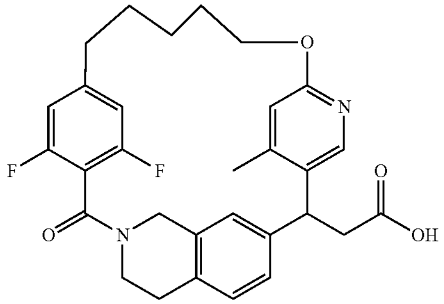 [SMILES: Cc1cc2ncc1C(CC(=O)O)c1ccc3c(c1)CN(CC3)C(=O)c1c(F)cc(cc1F)CCCCCO2] |
| 162 | 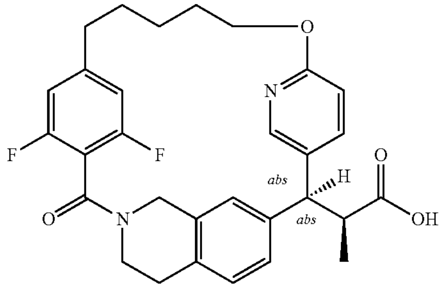 [SMILES: C[C@H](C(=O)O)[C@@H]1c2ccc(nc2)OCCCCCc2cc(F)c(c(F)c2)C(=O)N2CCc3ccc1cc3C2] |

-continued
| Comp'd No | Structure |
| --- | --- |
| 163 | 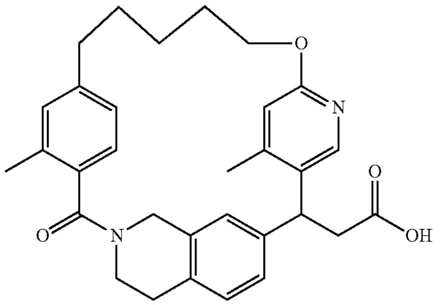 [SMILES: Cc1cc2ccc1C(=O)N1CCc3ccc(cc3C1)C(CC(=O)O)c1cnc(cc1C)OCCCCC2] |
| 164 | 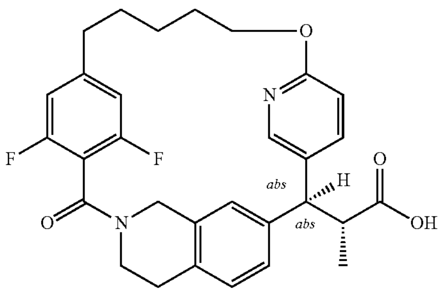 [SMILES: C[C@@H](C(=O)O)[C@@H]1c2ccc(nc2)OCCCCCc2cc(F)c(c(F)c2)C(=O)N2CCc3ccc1cc3C2] |
| 165 | 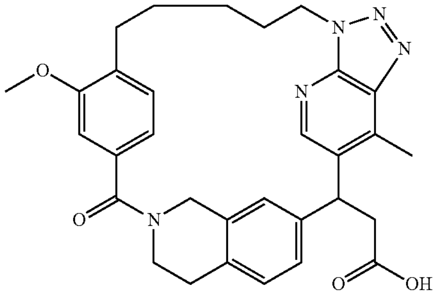 |
| 168 | 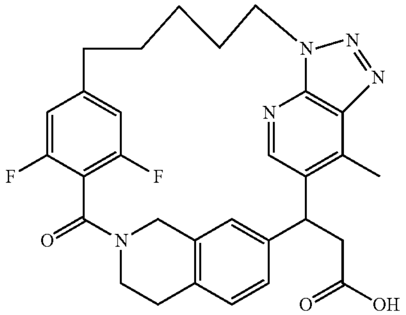 [SMILES: Cc1c2cnc3c1nnn3CCCCCc1cc(F)c(c(F)c1)C(=O)N1CCc3ccc(cc3C1)C2CC(=O)O] |
| 169 | 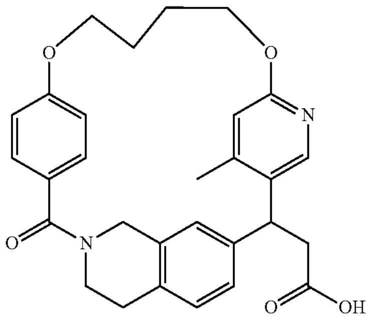 [SMILES: Cc1cc2ncc1C(CC(=O)O)c1ccc3c(c1)CN(CC3)C(=O)c1ccc(cc1)OCCCCO2] |
-continued
| Comp'd No | Structure |
| --- | --- |
| 170 | 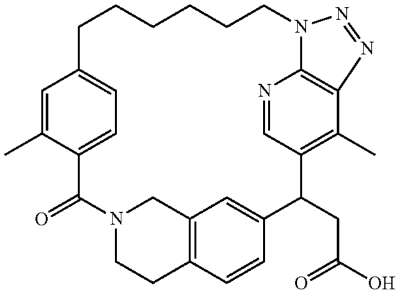 |
| 172 | 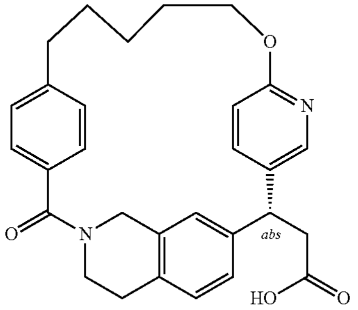 [SMILES: O=C(O)C[C@H]1c2ccc(nc2)OCCCCCc2ccc(cc2)C(=O)N2CCc3ccc1cc3C2] |
| 173 | 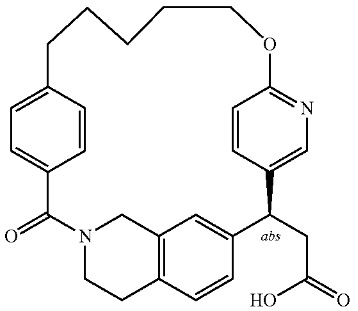 [SMILES: O=C(O)C[C@@H]1c2ccc(nc2)OCCCCCc2ccc(cc2)C(=O)N2CCc3ccc1cc3C2] |
| 178 | 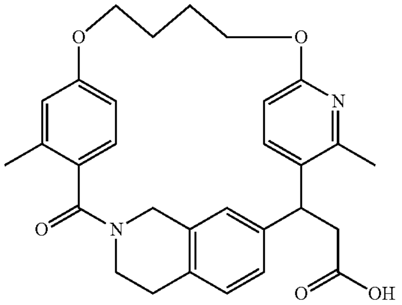 |
| 180 | 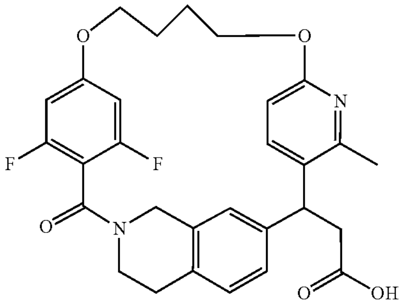 [SMILES: Cc1nc2ccc1C(CC(=O)O)c1ccc3c(c1)CN(CC3)C(=O)c1c(F)cc(cc1F)OCCCCO2] |

-continued
| Comp'd No | Structure |
|---|---|
| 182 | 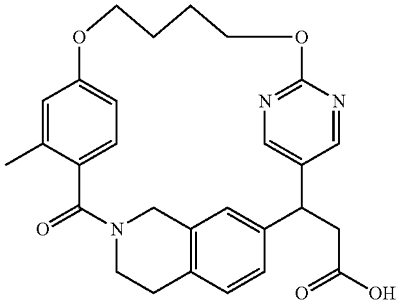 |
| 183 | 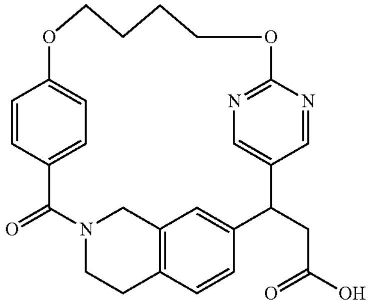 |
| 184 | 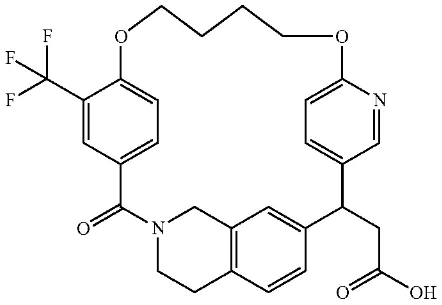 [SMILES: O=C(O)CC1c2ccc(nc2)OCCCCOc2ccc(cc2C(F)(F)F)C(=O)N2CCc3ccc1cc3C2] |
| 185 | 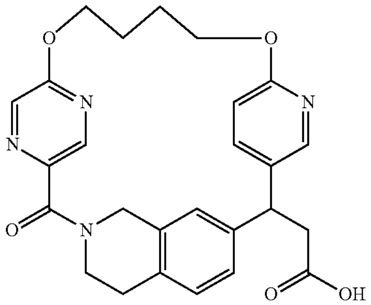 |
| 186 | 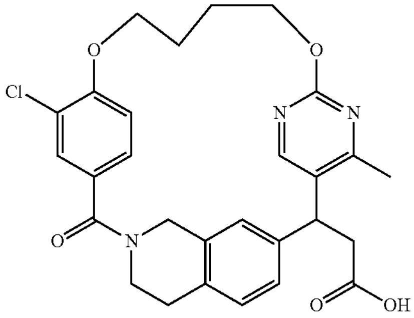 [SMILES: Cc1nc2ncc1C(CC(=O)O)c1ccc3c(c1)CN(CC3)C(=O)c1ccc(c(Cl)c1)OCCCCO2] |
-continued
| Comp'd No | Structure |
|---|---|
| 187 | 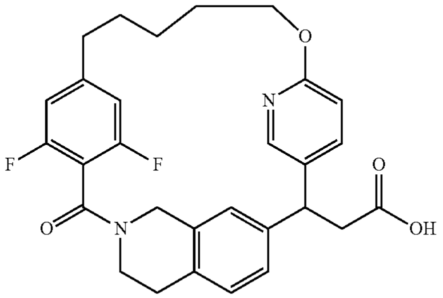 |
| 193 | 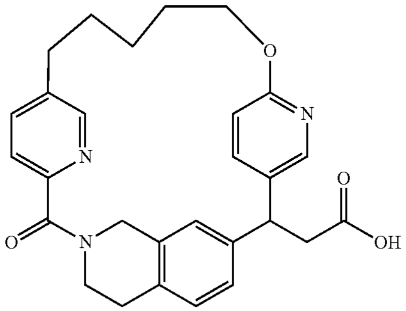 |
| 194 | 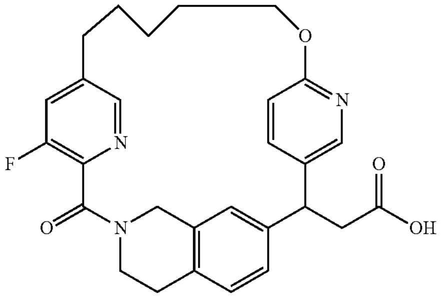 [SMILES: O=C(O)CC1c2ccc(nc2)OCCCCCc2cnc(c(F)c2)C(=O)N2CCc3ccc1cc3C2] |
| 195 | 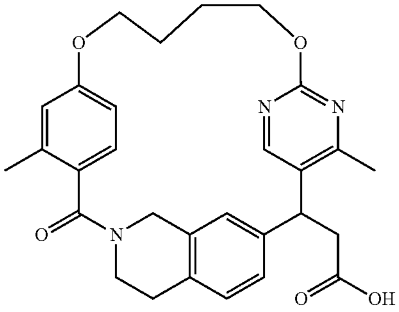 [SMILES: Cc1cc2ccc1C(=O)N1CCc3ccc(cc3C1)C(CC(=O)O)c1cnc(nc1C)OCCCCO2] |
| 196 | 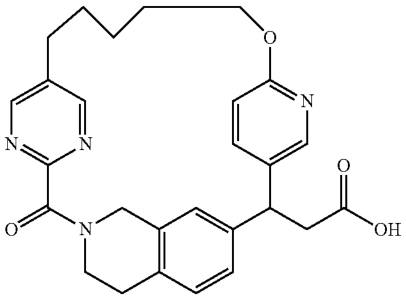 |

-continued
| Comp'd No | Structure |
| --- | --- |
| 197 | 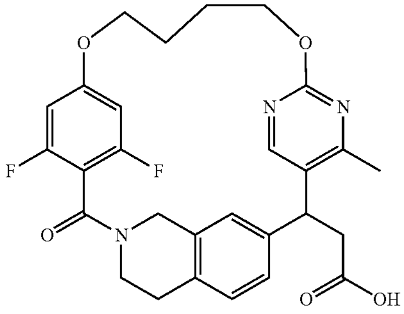 [SMILES: Cc1nc2ncc1C(CC(=O)O)c1ccc3c(c1)CN(CC3)C(=O)c1c(F)cc(cc1F)OCCCCO2] |
| 207 | 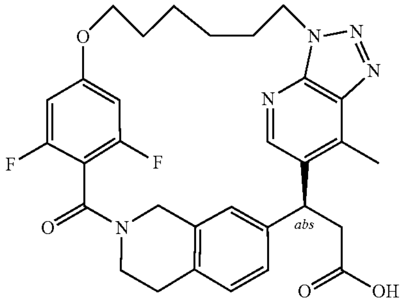 [SMILES: Cc1c2cnc3c1nnn3CCCCCCOc1cc(F)c(c(F)c1)C(=O)N1CCc3ccc(cc3C1)[C@@H]2CC(=O)O] |
| 208 | 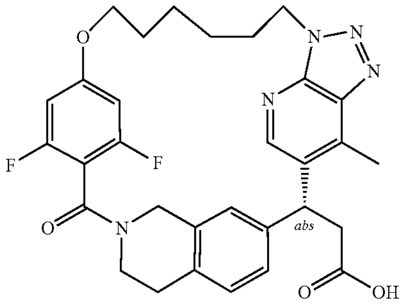 [SMILES: Cc1c2cnc3c1nnn3CCCCCCOc1cc(F)c(c(F)c1)C(=O)N1CCc3ccc(cc3C1)[C@H]2CC(=O)O] |
| 209 | 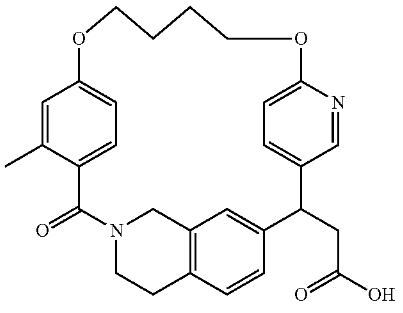 [SMILES: Cc1cc2ccc1C(=O)N1CCc3ccc(cc3C1)C(CC(=O)O)c1ccc(nc1)OCCCCO2] |
| 210 | 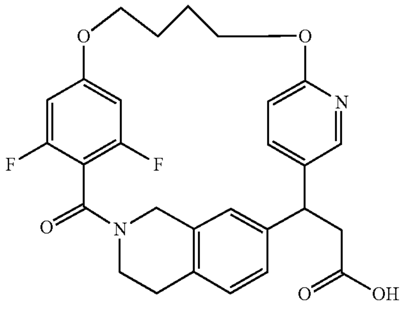 [SMILES: O=C(O)CC1c2ccc(nc2)OCCCCOc2cc(F)c(c(F)c2)C(=O)N2CCc3ccc1cc3C2] |
-continued
| Comp'd No | Structure |
| --- | --- |
| 211 | 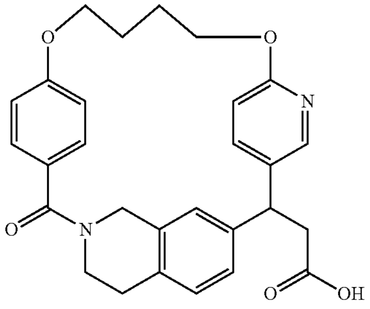 [SMILES: O=C(O)CC1c2ccc(nc2)OCCCCOc2ccc(cc2)C(=O)N2CCc3ccc1cc3C2] |
| 212 | 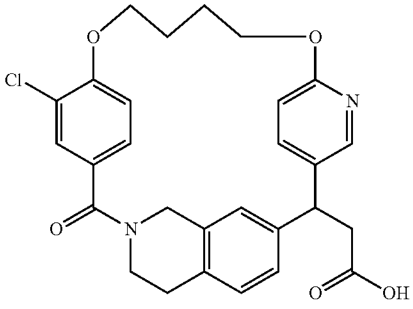 [SMILES: O=C(O)CC1c2ccc(nc2)OCCCCOc2ccc(cc2Cl)C(=O)N2CCc3ccc1cc3C2] |
| 216 | 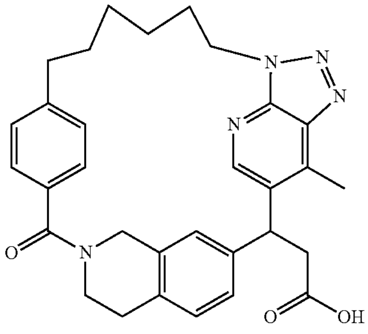 [SMILES: Cc1c2cnc3c1nnn3CCCCCCc1ccc(cc1)C(=O)N1CCc3ccc(cc3C1)C2CC(=O)O] |
| 218 | 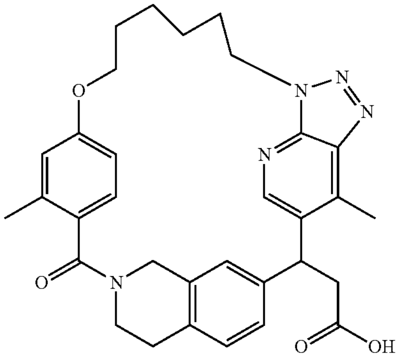 |

-continued
| Comp'd No | Structure |
|---|---|
| 221 | 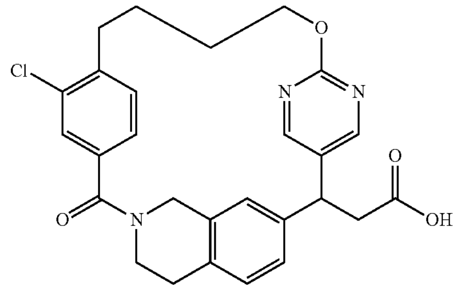 [SMILES: O=C(O)CC1c2cnc(nc2)OCCCCc2ccc(cc2Cl)C(=O)N2CCc3ccc1cc3C2] |
| 222 | 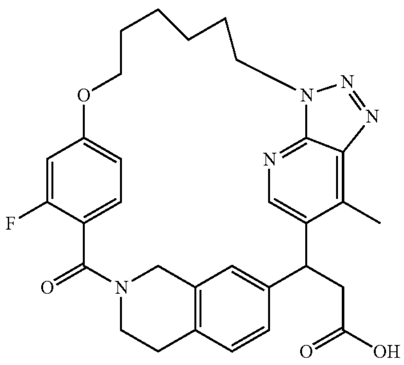 [SMILES: Cc1c2cnc3c1nnn3CCCCCCOc1ccc(c(F)c1)C(=O)N1CCc3ccc(cc3C1)C2CC(=O)O] |
| 226 | 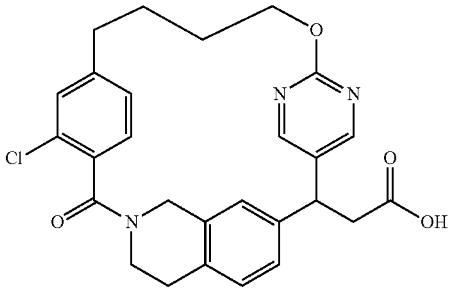 [SMILES: O=C(O)CC1c2cnc(nc2)OCCCCc2ccc(c(Cl)c2)C(=O)N2CCc3ccc1cc3C2] |
| 229 | 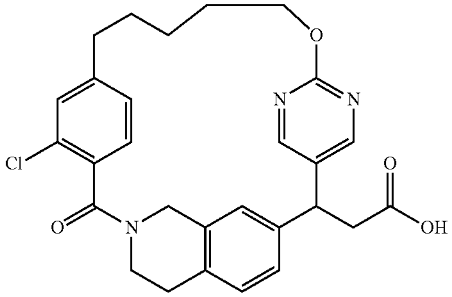 [SMILES: O=C(O)CC1c2cnc(nc2)OCCCCCc2ccc(c(Cl)c2)C(=O)N2CCc3ccc1cc3C2] |
| 233 | 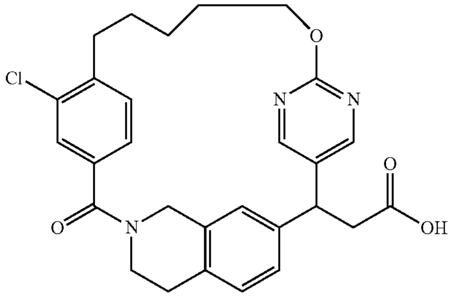 [SMILES: O=C(O)CC1c2cnc(nc2)OCCCCCc2ccc(cc2Cl)C(=O)N2CCc3ccc1cc3C2] |
-continued
| Comp'd No | Structure |
|---|---|
| 238 | 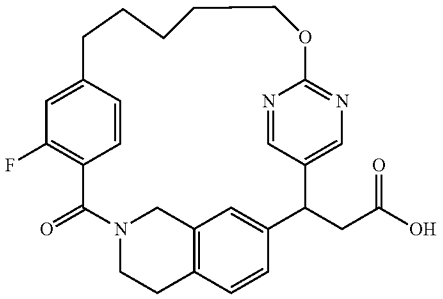 [SMILES: O=C(O)CC1c2cnc(nc2)OCCCCCc2ccc(c(F)c2)C(=O)N2CCc3ccc1cc3C2] |
| 239 | 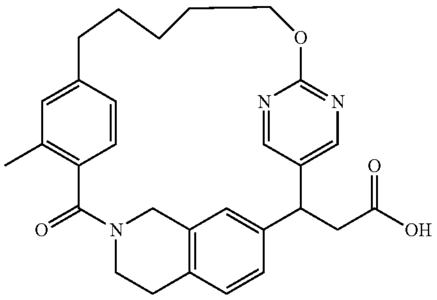 [SMILES: Cc1cc2ccc1C(=O)N1CCc3ccc(cc3C1)C(CC(=O)O)c1cnc(nc1)OCCCCC2] |
| 242 | 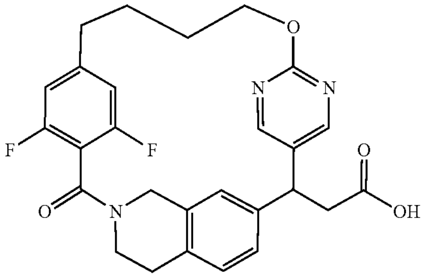 [SMILES: O=C(O)CC1c2cnc(nc2)OCCCCc2cc(F)c(c(F)c2)C(=O)N2CCc3ccc1cc3C2] |
| 246 | 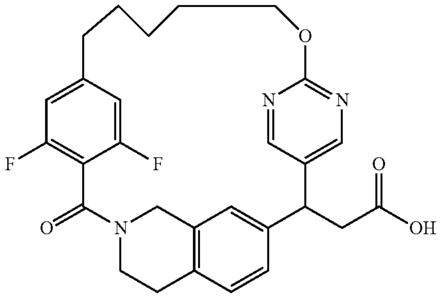 [SMILES: O=C(O)CC1c2cnc(nc2)OCCCCCc2cc(F)c(c(F)c2)C(=O)N2CCc3ccc1cc3C2] |
| 268 | 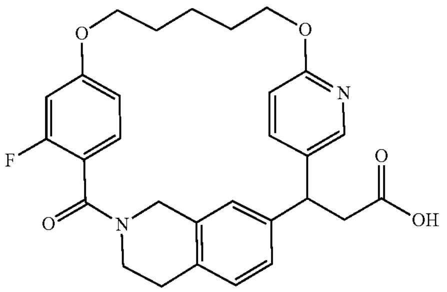 [SMILES: O=C(O)CC1c2ccc(nc2)OCCCCCOc2ccc(c(F)c2)C(=O)N2CCc3ccc1cc3C2] |

-continued
| Comp'd No | Structure |
|---|---|
| 277 | 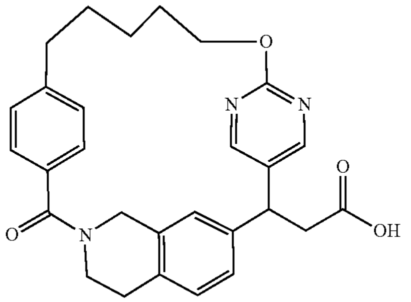 [SMILES: O=C(O)CC1c2cnc(nc2)OCCCCCc2ccc(cc2)C(=O)N2CCc3ccc1cc3C2] |
| 300 | 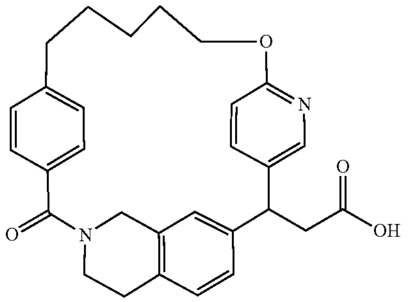 [SMILES: O=C(O)CC1c2ccc(nc2)OCCCCCc2ccc(cc2)C(=O)N2CCc3ccc1cc3C2] |
| 301 | 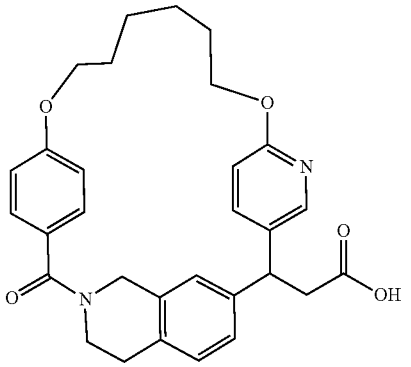 [SMILES: O=C(O)CC1c2ccc(nc2)OCCCCCCOc2ccc(cc2)C(=O)N2CCc3ccc1cc3C2] |
| 319 | 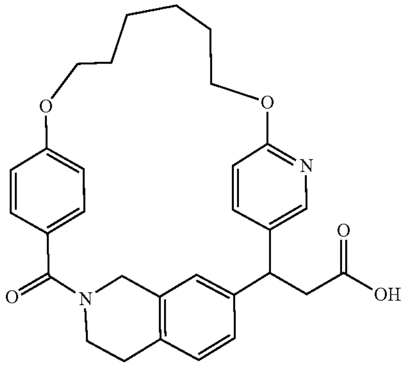 [SMILES: O=C(O)CC1c2ccc(nc2)OCCCCCCOc2ccc(cc2)C(=O)N2CCc3ccc1cc3C2] |
-continued
| Comp'd No | Structure |
|---|---|
| 344 | 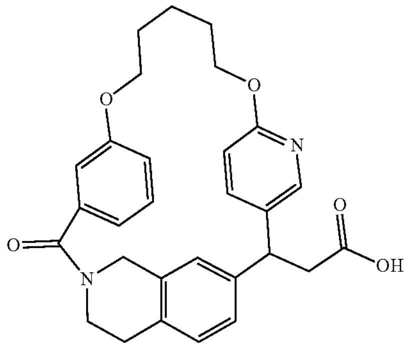 [SMILES: O=C(O)CC1c2ccc(nc2)OCCCCCOc2cccc(c2)C(=O)N2CCc3ccc1cc3C2] |
| 345 | 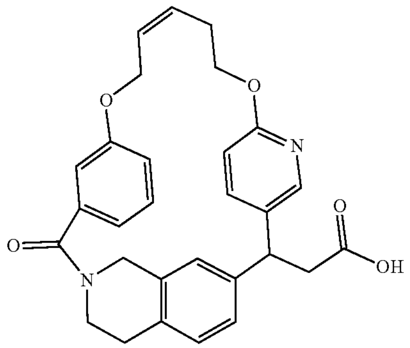 [SMILES: O=C(O)CC1c2ccc(nc2)OCC/C=C\COc2cccc(c2)C(=O)N2CCc3ccc1cc3C2] |
| 346 | 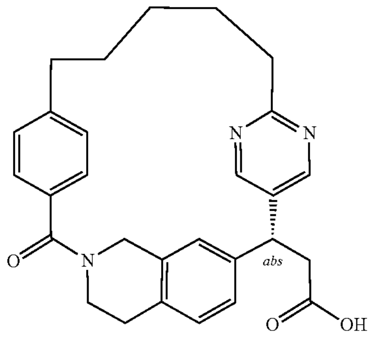 [SMILES: O=C(O)C[C@H]1c2cnc(nc2)CCCCCc2ccc(cc2)C(=O)N2CCc3ccc1cc3C2] |
| 347 | 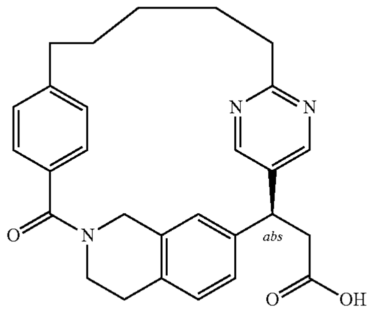 [SMILES: O=C(O)C[C@@H]1c2cnc(nc2)CCCCCc2ccc(cc2)C(=O)N2CCc3ccc1cc3C2] |

-continued
| Comp'd No | Structure |
|---|---|
| 348 | 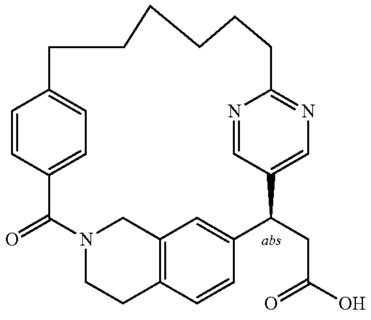 [SMILES: O=C(O)C[C@@H]1c2cnc(nc2)CCCCCCc2ccc(cc2)C(=O)N2CCc3ccc1cc3C2] |
| 349 | 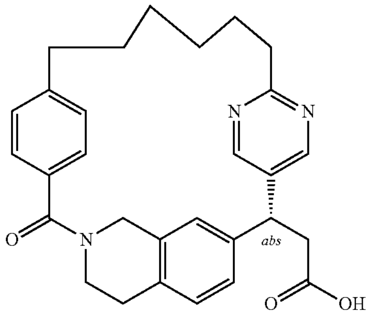 [SMILES: O=C(O)C[C@H]1c2cnc(nc2)CCCCCCc2ccc(cc2)C(=O)N2CCc3ccc1cc3C2] |
| 350 | 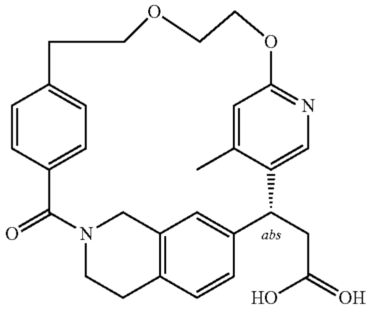 [SMILES: Cc1cc2ncc1[C@H](CC(=O)O)c1ccc3c(c1)CN(CC3)C(=O)c1ccc(cc1)CCOCCO2] |
| 351 | 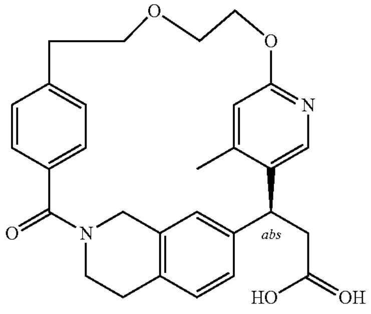 [SMILES: Cc1cc2ncc1[C@@H](CC(=O)O)c1ccc3c(c1)CN(CC3)C(=O)c1ccc(cc1)CCOCCO2] |
-continued
| Comp'd No | Structure |
|---|---|
| 352 | 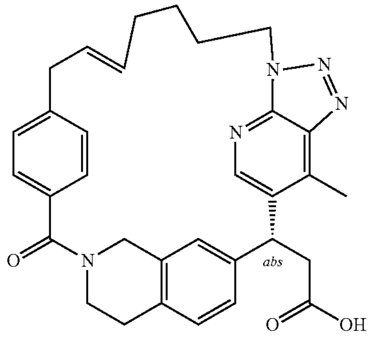 [SMILES: Cc1c2cnc3c1nnn3CCCC/C=C/Cc1ccc(cc1)C(=O)N1CCc3ccc(cc3C1)[C@H]2CC(=O)O] |
| 353 | 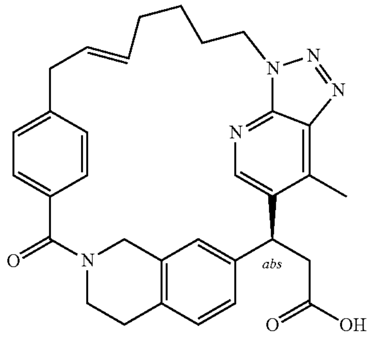 |
| 354 | 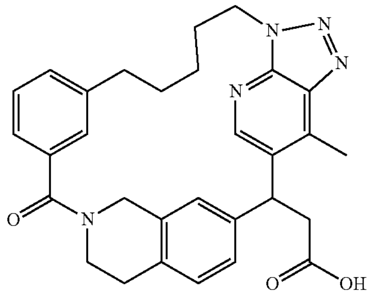 [SMILES: Cc1c2cnc3c1nnn3CCCCCc1cccc(c1)C(=O)N1CCc3ccc(cc3C1)C2CC(=O)O] |
| 355 | 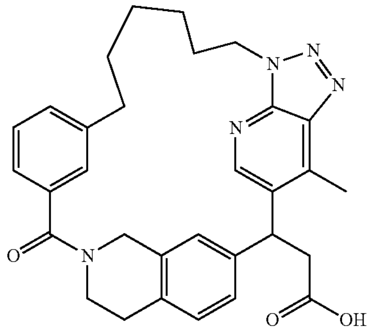 [SMILES: Cc1c2cnc3c1nnn3CCCCCCc1cccc(c1)C(=O)N1CCc3ccc(cc3C1)C2CC(=O)O] |

-continued

| Comp'd No | Structure |
|---|---|
| 381 | 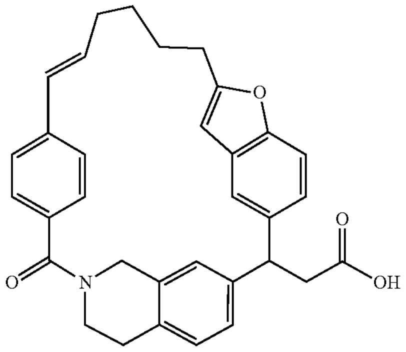 [SMILES: O=C(O)CC1c2ccc3c(c2)CN(CC3)C(=O)c2ccc(cc2)/C=C/CCCCc2cc3cc1ccc3o2] |
| 384 | 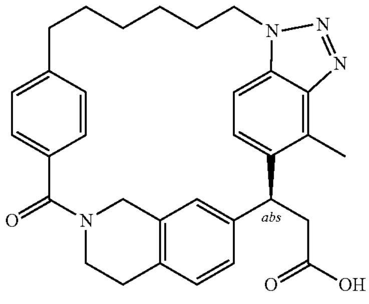 [SMILES: Cc1c2ccc3c1nnn3CCCCCCc1ccc(cc1)C(=O)N1CCc3ccc(cc3C1)[C@@H]2CC(=O)O] |
| 385 | 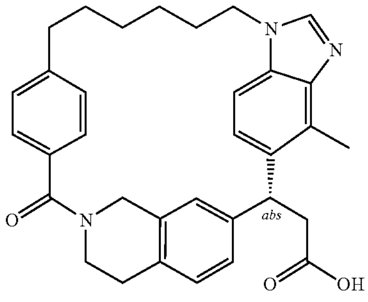 [SMILES: Cc1c2ccc3c1ncn3CCCCCCc1ccc(cc1)C(=O)N1CCc3ccc(cc3C1)[C@H]2CC(=O)O] |
| 391 | 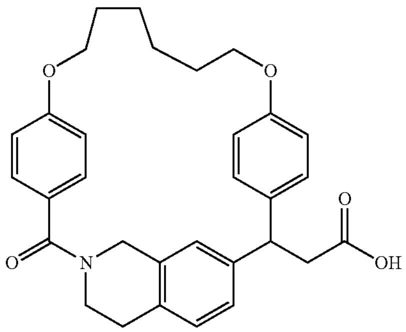 [SMILES: O=C(O)CC1c2ccc(cc2)OCCCCCCOc2ccc(cc2)C(=O)N2CCc3ccc1cc3C2] |

-continued

| Comp'd No | Structure |
|---|---|
| 396 | 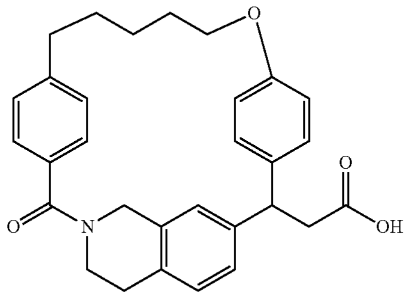 [SMILES: O=C(O)CC1c2ccc(cc2)OCCCCCc2ccc(cc2)C(=O)N2CCc3ccc1cc3C2] |
| 399 | 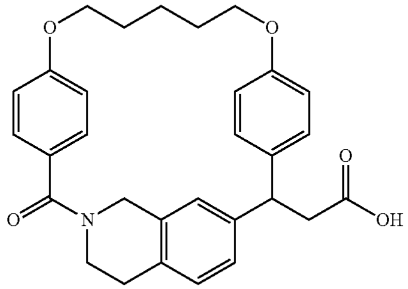 [SMILES: O=C(O)CC1c2ccc(cc2)OCCCCCOc2ccc(cc2)C(=O)N2CCc3ccc1cc3C2] |
| 415 | 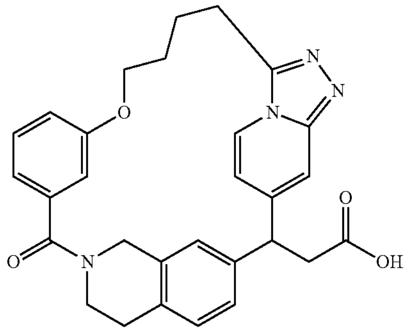 [SMILES: O=C(O)CC1c2ccc3c(c2)CN(CC3)C(=O)c2cccc(c2)OCCCCc2nnc3cc1ccn23] |
| 416 | 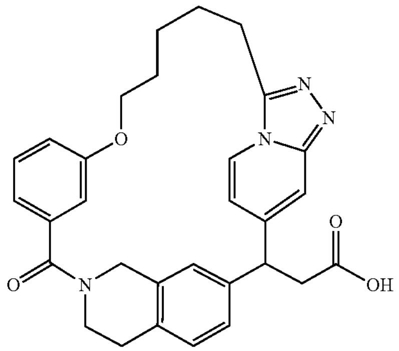 [SMILES: O=C(O)CC1c2ccc3c(c2)CN(CC3)C(=O)c2cccc(c2)OCCCCCc2nnc3cc1ccn23] |

19. A method of treating a disease or disorder in a subject in need thereof, comprising administering to the subject a therapeutically effective amount of the compound of claim 1, or a pharmaceutically acceptable salt thereof, wherein the disease or disorder is selected from anemia, hemoglobinopathies, asthma, rheumatoid arthritis, ulcerative colitis and Crohn's disease.

20. A method of treating a disease or disorder in a subject in need thereof, comprising administering to the subject a therapeutically effective amount of the compound of claim 1, or a pharmaceutically acceptable salt thereof, wherein the disease or disorder is selected from anemia, sickle cell disease, thalassemia, asthma, rheumatoid arthritis, ulcerative colitis and Crohn's disease.

* * * * *